US011760728B2

(12) United States Patent
Castro

(10) Patent No.: US 11,760,728 B2
(45) Date of Patent: Sep. 19, 2023

(54) TEAD INHIBITORS AND USES THEREOF

(71) Applicant: Ikena Oncology, Inc., Boston, MA (US)

(72) Inventor: Alfredo C. Castro, Somerville, MA (US)

(73) Assignee: IKENA ONCOLOGY, INC., Boston, MA (US)

( * ) Notice: Subject to any disclaimer, the term of this patent is extended or adjusted under 35 U.S.C. 154(b) by 0 days.

(21) Appl. No.: 17/646,787

(22) Filed: Jan. 3, 2022

(65) Prior Publication Data
US 2022/0251048 A1 Aug. 11, 2022

Related U.S. Application Data

(62) Division of application No. 16/886,926, filed on May 29, 2020, now Pat. No. 11,274,082.

(60) Provisional application No. 63/025,219, filed on May 15, 2020, provisional application No. 62/944,567, filed on Dec. 6, 2019, provisional application No. 62/928,931, filed on Oct. 31, 2019, provisional application No. 62/855,082, filed on May 31, 2019.

(51) Int. Cl.
| C07D 233/58 | (2006.01) |
| A61P 35/00 | (2006.01) |
| C07C 317/14 | (2006.01) |
| C07D 231/12 | (2006.01) |
| C07D 249/08 | (2006.01) |
| C07D 257/04 | (2006.01) |
| C07D 271/10 | (2006.01) |
| C07D 401/04 | (2006.01) |
| C07D 401/12 | (2006.01) |
| C07D 403/12 | (2006.01) |
| C07D 405/12 | (2006.01) |
| C07D 417/12 | (2006.01) |
| C07F 5/02 | (2006.01) |

(52) U.S. Cl.
CPC ............ *C07D 233/58* (2013.01); *A61P 35/00* (2018.01); *C07C 317/14* (2013.01); *C07D 231/12* (2013.01); *C07D 249/08* (2013.01); *C07D 257/04* (2013.01); *C07D 271/10* (2013.01); *C07D 401/04* (2013.01); *C07D 401/12* (2013.01); *C07D 403/12* (2013.01); *C07D 405/12* (2013.01); *C07D 417/12* (2013.01); *C07F 5/025* (2013.01)

(58) Field of Classification Search
CPC .................................................. C07D 233/58
See application file for complete search history.

(56) References Cited

U.S. PATENT DOCUMENTS

| 3,120,564 A | 2/1964 | Milionis et al. |
| 5,256,791 A | 10/1993 | Braish |
| 5,298,629 A | 3/1994 | Braish |
| 5,475,116 A | 12/1995 | Brighty et al. |
| 5,623,078 A | 4/1997 | Urata et al. |
| 5,703,091 A | 12/1997 | Steiner et al. |
| 5,968,929 A | 10/1999 | Blythin et al. |
| 6,051,575 A | 4/2000 | Blythin et al. |
| 6,184,380 B1 | 2/2001 | Chiu et al. |
| 6,590,118 B1 | 7/2003 | Kristiansen et al. |
| 7,019,142 B2 | 3/2006 | Chiu et al. |
| 7,232,835 B2 | 6/2007 | Mehta et al. |
| 7,473,787 B2 | 1/2009 | McHardy et al. |
| 7,488,748 B2 | 2/2009 | Mehta et al. |
| 7,501,443 B2 | 3/2009 | Mehta et al. |
| 7,560,551 B2 | 7/2009 | Cee et al. |
| 7,582,643 B2 | 9/2009 | Blake et al. |
| 7,750,158 B2 | 7/2010 | Shankar et al. |
| 7,902,373 B2 | 3/2011 | Blake et al. |
| 7,932,246 B2 | 4/2011 | Moffat et al. |
| 7,935,725 B2 | 5/2011 | Bembenek et al. |
| 8,022,221 B2 | 9/2011 | Cee et al. |
| 8,067,589 B2 | 11/2011 | Blake et al. |
| 8,124,639 B2 | 2/2012 | McHardy et al. |
| 8,344,008 B2 | 1/2013 | Bacani et al. |
| 8,367,719 B2 | 2/2013 | Bacani et al. |
| 8,686,155 B2 | 4/2014 | Cee et al. |
| 8,772,277 B2 | 7/2014 | Matsumoto et al. |
| 8,895,602 B1 | 11/2014 | Nam et al. |
| 9,186,354 B2 | 11/2015 | Morriello et al. |
| 9,216,993 B2 | 12/2015 | Grembecka et al. |
| 9,242,961 B2 | 1/2016 | Cee et al. |
| 9,505,782 B2 | 11/2016 | Grembecka et al. |
| 9,527,830 B2 | 12/2016 | Walsh et al. |
| 9,777,002 B2 | 10/2017 | Walsh et al. |
| 9,802,919 B1 | 10/2017 | Sutton et al. |
| 10,023,558 B2 | 7/2018 | Sutton et al. |
| 10,160,769 B2 | 12/2018 | Grembecka et al. |
| 10,314,823 B2 | 6/2019 | Blumstein et al. |
| 11,274,082 B2 | 3/2022 | Castro |

(Continued)

FOREIGN PATENT DOCUMENTS

| CN | 1944398 A | 4/2007 |
| EP | 0074768 A2 | 3/1983 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Bum-Erdene et al., "Small-Molecule Covalent Modification of Conserved Cysteine Leads to Allosteric Inhibition . . . ," Cell Chemical Biology, 2019, 26: 378-389.
Chan et al., Nature Chemical Biology, 2016, 2036:282-289.

(Continued)

*Primary Examiner* — Shawquia Jackson
(74) *Attorney, Agent, or Firm* — Dechert LLP; Andrea L. C. Reid; Gang Wang

(57) ABSTRACT

The present invention provides compounds, compositions thereof, and methods of using the same.

21 Claims, 2 Drawing Sheets

Specification includes a Sequence Listing.

(56) References Cited

U.S. PATENT DOCUMENTS

| | | |
|---|---|---|
| 11,458,149 B1 | 10/2022 | Castro |
| 2002/0119961 A1 | 8/2002 | Blumberg et al. |
| 2002/0143017 A1 | 10/2002 | Mylari |
| 2004/0034019 A1 | 2/2004 | Tomlinson et al. |
| 2004/0082641 A1 | 4/2004 | Rytved et al. |
| 2005/0054618 A1 | 3/2005 | Rytved et al. |
| 2006/0047114 A1 | 3/2006 | Wlodecki |
| 2008/0300251 A1 | 12/2008 | Sattigeri et al. |
| 2009/0124600 A1 | 5/2009 | Layton |
| 2009/0221664 A1 | 9/2009 | Ray et al. |
| 2010/0016400 A1 | 1/2010 | Kumar et al. |
| 2010/0056496 A1 | 3/2010 | Kumar et al. |
| 2011/0028478 A1 | 2/2011 | Behnke et al. |
| 2016/0039802 A1 | 2/2016 | Cho et al. |
| 2017/0158702 A1 | 6/2017 | Vacca et al. |
| 2018/0099940 A1 | 4/2018 | Crew et al. |
| 2019/0010136 A1 | 1/2019 | Danjo et al. |
| 2019/0062309 A1 | 2/2019 | Beckwith et al. |
| 2019/0276434 A1 | 9/2019 | Vacca et al. |
| 2020/0095236 A1 | 3/2020 | Teng et al. |
| 2022/0251048 A1 | 8/2022 | Castro |

FOREIGN PATENT DOCUMENTS

| | | |
|---|---|---|
| EP | 1184372 A1 | 3/2002 |
| EP | 1717225 A1 | 11/2006 |
| EP | 3479696 A1 | 5/2019 |
| EP | 3712129 A1 | 9/2020 |
| JP | S58179838 A | 10/1983 |
| WO | 1997030030 A1 | 8/1997 |
| WO | WO-2001058891 A2 | 8/2001 |
| WO | WO-2004056810 A1 | 7/2004 |
| WO | 2006122014 A2 | 11/2006 |
| WO | WO-2008010061 A2 | 1/2008 |
| WO | WO-2008010238 A2 | 1/2008 |
| WO | WO-2008117229 A1 | 10/2008 |
| WO | WO-2009152027 A1 | 12/2009 |
| WO | 2010053732 A1 | 5/2010 |
| WO | WO-2010135360 A1 | 11/2010 |
| WO | WO-2013115391 A1 | 8/2013 |
| WO | WO-2014199164 A1 | 12/2014 |
| WO | WO-2017053706 A1 | 3/2017 |
| WO | WO-2017111076 A1 | 6/2017 |
| WO | 2018039232 A1 | 3/2018 |
| WO | WO-2018204532 A1 | 11/2018 |
| WO | WO-2018235926 A1 | 12/2018 |
| WO | WO-2019040380 A1 | 2/2019 |
| WO | 2019060850 A1 | 3/2019 |
| WO | 2019079659 A1 | 4/2019 |
| WO | 2019089667 A1 | 5/2019 |
| WO | WO-2019089670 A1 | 5/2019 |
| WO | WO-2019113236 A1 | 6/2019 |
| WO | WO-2019152809 A1 | 8/2019 |
| WO | 2019196764 A1 | 10/2019 |
| WO | WO-2019204505 A2 | 10/2019 |
| WO | 2019232216 A1 | 12/2019 |
| WO | 2020051099 A1 | 3/2020 |
| WO | 2020081450 A1 | 4/2020 |
| WO | 2020087063 A1 | 4/2020 |
| WO | WO-2020073031 A1 | 4/2020 |
| WO | WO-2020081572 A1 | 4/2020 |
| WO | 2020165833 A1 | 8/2020 |
| WO | 2020190774 A1 | 9/2020 |
| WO | 2020206137 A1 | 10/2020 |
| WO | 2020219650 A1 | 10/2020 |
| WO | 2020243415 A2 | 12/2020 |
| WO | 2020243423 A1 | 12/2020 |
| WO | 2021097110 A1 | 5/2021 |
| WO | 2021133896 A1 | 7/2021 |
| WO | 2021178339 A1 | 9/2021 |
| WO | 2021247634 A1 | 12/2021 |
| WO | 2022120353 A1 | 6/2022 |
| WO | 2022120354 A1 | 6/2022 |
| WO | 2022120355 A1 | 6/2022 |
| WO | 2022159986 A1 | 7/2022 |

OTHER PUBLICATIONS

Crawford et al., "Hippo pathway inhibition by blocking the YAP/TAZ-TEAD interface: a patent review," Expert Opin Ther Pat. 2018;28(12):867-873.

De Amici et al., "Analogues of the Low-Efficacy Partial GABA A Agonist 4-PIOL. Syntheses and In Vitro Pharmacological Studies," European Journal of Medicinal Chemistry, Elsevier, Amsterdam, NL, vol. 26, No. 6, 1991, pp. 625-631.

Gibault et al., "Targeting Transcriptional Enhanced Associate Domains (TEADs)," Journal of Medicinal Chemistry, 2018, 61: 5057-5072.

Holden et al., "Small Molecule Dysregulation of TEAD Lipidation Induces a Dominant-Negative Inhibition of Hippo Pathway Signaling," Cell Rep. 2020;31(12):107809.

Kaneda et al., "The novel potent TEAD inhibitor, K-975, inhibits YAP1/TAZ-TEAD protein-protein interactions and exerts an anti-tumor effect on malignant pleural mesothelioma," Am J Cancer Res. 2020;10(12):4399-4415.

Kirin, "Discovery of First in Class TEAD Inhibitor . . . ," AACR Annual Meeting 2019.

Lu et al., "Discovery and biological evaluation of vinylsulfonamide derivatives as highly potent, covalent TEAD autopalmitoylation inhibitors," Eur J Med Chem. 2019;184:111767.

Noland et al., "Palmitoylation of TEAD Transcription Factors is Required for Their Stability . . . ," Structure, 2016, 24: 1-8.

Nouri et al., "Identification of Celastrol as Novel YAP-TEAD Inhibitor for Cancer Therapy . . . ," Cancers (Basel), 2019, 11: 1-18.

PCT International Search Report and Written Opinion for PCT Application No. PCT/US2020/035098, ISA/EP, dated Nov. 23, 2020.

Pobbati and Rubin, "Protein-Protein Interaction Disruptors of the YAP/TAZ-TEAD Transcriptional Complex," Molecules. 2020;25(24):6001.

Pobbati et al., "Targeting the Central Pocket in Human Transcription Factor TEAD as a Potential Cancer Therapeutic Strategy," Nov. 2015; 23: 2076-2086.

Tang, Vivace, "AACR Hippo-YAP Pathway with Small Molecule Inhibitors," 2019.

White et al., "The Complex Entanglement o fHippo-Yap/Taz Signaling in Tumor Immunity," Oncogene 2019, 38: 2899-2909.

Amidon et al., "Abstract 2474: Potent small molecule TEAD inhibitors targeting the Hippo pathway exhibit antiproliferation in vitro and anti-tumor effect in vivo," Cancer Research. 2020; 80(16):2474.

PCT International Search Report and Written Opinion for PCT Application No. PCT/US2020/035111, ISA/EP, dated Nov. 18, 2020.

Eggenweiler, et al., Document No. 144:254124, retrieved from STN; Feb. 23, 2006.

Crosby et al., "YAP vs. TAZ: differences in expression revealed through rigorous validation of target-specific monoclonal antibodies," 2020;43(4):182-195.

Dey et al., "Targeting the Hippo pathway in cancer, fibrosis, wound healing and regenerative medicine," Nat Rev Drug Discov. 2020;19(7):480-494.

Gibault et al., "Toward the Discovery of a Novel Class of YAP-TEAD Interaction Inhibitors by Virtual Screening Approach Targeting YAP-TEAD Protein?Protein Interface," Cancers (Basel). May 8, 2018;10(5):140.

Golub et al., "Molecular classification of cancer: class discovery and class prediction by gene expression monitoring," Science. Oct. 15, 1999;286(5439):531-7.

Ip et al., "Immunohistochemical validation of overexpressed genes identified by global expression microarrays in adrenocortical carcinoma reveals potential predictive and prognostic biomarkers," 2015;20(3):247-56.

Ito et al., "Exploiting ubiquitin ligase cereblon as a target for small-molecule compounds in medicine and chemical biology," Cell Chem Biol. Jul. 15, 2021;28(7):987-999.

Lala and Orucevic, "Role of nitric oxide in tumor progression: lessons from experimental tumors," Cancer Metastasis Rev. Mar. 1998;17(1):91-106.

Lodge et al., "Homeostatic and tumourigenic activity of SOX2+ pituitary stem cells is controlled by the LATS/YAP/TAZ cascade," 2019;8:e43996.

(56) References Cited

OTHER PUBLICATIONS

Medlineplus, "Cancer," Health Topics. Updated May 18, 2017; Accessed Dec. 15, 2022: https://medlineplus.gov/cancer.html#.
PCT International Search Report and Written Opinion from PCT/US2020/035098, dated Nov. 16, 2020.
PCT International Search Report and Written Opinion from PCT/US2020/035111, dated Sep. 15, 2020.
PCT International Search Report and Written Opinion from PCT/US2021/072683, dated Apr. 7, 2022.
PCT International Search Report and Written Opinion from PCT/US2021/072684, dated May 5, 2022.
PCT International Search Report and Written Opinion from PCT/US2021/072685, dated May 11, 2022.
PCT International Search Report and Written Opinion from PCT/US2022/070330, dated Apr. 5, 2022.
PCT International Search Report and Written Opinion from PCT/US2022/077747, dated Jan. 26, 2023.
Teng et al., "Development of CDK2 and CDK5 Dual Degrader TMX-2172," Angew Chem Int Ed Engl. Aug. 10, 2020;59(33):13865-13870.
U.S. Appl. No. 17/816,859, filed Aug. 2, 2022.
Zambaldo et al., "Selective affinity-based probe for oncogenic kinases suitable for live cell imaging," Chem Sci. Mar. 13, 2013;4:2088-92.

\* cited by examiner

SEQUENCE LISTING

<160> NUMBER OF SEQ ID NOS: 9

<210> SEQ ID NO 1
<211> LENGTH: 426
<212> TYPE: PRT
<213> ORGANISM: Homo sapiens

<400> SEQUENCE: 1

```
Met Glu Pro Ser Ser Trp Ser Gly Ser Glu Ser Pro Ala Glu Asn Met
1               5                   10                  15

Glu Arg Met Ser Asp Ser Ala Asp Lys Pro Ile Asp Asn Asp Ala Glu
            20                  25                  30

Gly Val Trp Ser Pro Asp Ile Glu Gln Ser Phe Gln Glu Ala Leu Ala
        35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Arg Lys Gln Val Ser Ser His Ile Gln Val
                85                  90                  95

Leu Ala Arg Arg Lys Ser Arg Asp Phe His Ser Lys Leu Lys Asp Gln
```

```
                100             105              110
Thr Ala Lys Asp Lys Ala Leu Gln His Met Ala Ala Met Ser Ser Ala
            115                 120                 125
Gln Ile Val Ser Ala Thr Ala Ile His Asn Lys Leu Gly Leu Pro Gly
            130                 135                 140
Ile Pro Arg Pro Thr Phe Pro Gly Ala Pro Gly Phe Trp Pro Gly Met
145                 150                 155                 160
Ile Gln Thr Gly Gln Pro Gly Ser Ser Gln Asp Val Lys Pro Phe Val
            165                 170                 175
Gln Gln Ala Tyr Pro Ile Gln Pro Ala Val Thr Ala Pro Ile Pro Gly
            180                 185                 190
Phe Glu Pro Ala Ser Ala Pro Ala Pro Ser Val Pro Ala Trp Gln Gly
            195                 200                 205
Arg Ser Ile Gly Thr Thr Lys Leu Arg Leu Val Glu Phe Ser Ala Phe
            210                 215                 220
Leu Glu Gln Gln Arg Asp Pro Asp Ser Tyr Asn Lys His Leu Phe Val
225                 230                 235                 240
His Ile Gly His Ala Asn His Ser Tyr Ser Asp Pro Leu Leu Glu Ser
            245                 250                 255
Val Asp Ile Arg Gln Ile Tyr Asp Lys Phe Pro Glu Lys Lys Gly Gly
            260                 265                 270
Leu Lys Glu Leu Phe Gly Lys Gly Pro Gln Asn Ala Phe Phe Leu Val
            275                 280                 285
Lys Phe Trp Ala Asp Leu Asn Cys Asn Ile Gln Asp Asp Ala Gly Ala
            290                 295                 300
Phe Tyr Gly Val Thr Ser Gln Tyr Glu Ser Ser Glu Asn Met Thr Val
305                 310                 315                 320
Thr Cys Ser Thr Lys Val Cys Ser Phe Gly Lys Gln Val Val Glu Lys
            325                 330                 335
Val Glu Thr Glu Tyr Ala Arg Phe Glu Asn Gly Arg Phe Val Tyr Arg
            340                 345                 350
Ile Asn Arg Ser Pro Met Cys Glu Tyr Met Ile Asn Phe Ile His Lys
            355                 360                 365
Leu Lys His Leu Pro Glu Lys Tyr Met Met Asn Ser Val Leu Glu Asn
            370                 375                 380
Phe Thr Ile Leu Leu Val Val Thr Asn Arg Asp Thr Gln Glu Thr Leu
385                 390                 395                 400
Leu Cys Met Ala Cys Val Phe Glu Val Ser Asn Ser Glu His Gly Ala
            405                 410                 415
Gln His His Ile Tyr Arg Leu Val Lys Asp
            420                 425

<210> SEQ ID NO 2
<211> LENGTH: 447
<212> TYPE: PRT
<213> ORGANISM: Homo sapiens

<400> SEQUENCE: 2

Met Gly Glu Pro Arg Ala Gly Ala Ala Leu Asp Asp Gly Ser Gly Trp
1               5                   10                  15
Thr Gly Ser Glu Glu Gly Ser Glu Gly Thr Gly Gly Ser Glu Gly
            20                  25                  30
Ala Gly Gly Asp Gly Gly Pro Asp Ala Glu Gly Val Trp Ser Pro Asp
            35                  40                  45
```

```
Ile Glu Gln Ser Phe Gln Glu Ala Leu Ala Ile Tyr Pro Pro Cys Gly
 50                  55                  60

Arg Arg Lys Ile Ile Leu Ser Asp Glu Gly Lys Met Tyr Gly Arg Asn
 65                  70                  75                  80

Glu Leu Ile Ala Arg Tyr Ile Lys Leu Arg Thr Gly Lys Thr Arg Thr
                 85                  90                  95

Arg Lys Gln Val Ser Ser His Ile Gln Val Leu Ala Arg Arg Lys Ser
                100                 105                 110

Arg Glu Ile Gln Ser Lys Leu Lys Asp Gln Val Ser Lys Asp Lys Ala
            115                 120                 125

Phe Gln Thr Met Ala Thr Met Ser Ser Ala Gln Leu Ile Ser Ala Pro
130                 135                 140

Ser Leu Gln Ala Lys Leu Gly Pro Thr Gly Pro Gln Ala Ser Glu Leu
145                 150                 155                 160

Phe Gln Phe Trp Ser Gly Ser Gly Pro Pro Trp Asn Val Pro Asp
                165                 170                 175

Val Lys Pro Phe Ser Gln Thr Pro Phe Thr Leu Ser Leu Thr Pro Pro
                180                 185                 190

Ser Thr Asp Leu Pro Gly Tyr Glu Pro Pro Gln Ala Leu Ser Pro Leu
                195                 200                 205

Pro Pro Pro Thr Pro Ser Pro Pro Ala Trp Gln Ala Arg Gly Leu Gly
210                 215                 220

Thr Ala Arg Leu Gln Leu Val Glu Phe Ser Ala Phe Val Glu Pro Pro
225                 230                 235                 240

Asp Ala Val Asp Ser Tyr Gln Arg His Leu Phe Val His Ile Ser Gln
                245                 250                 255

His Cys Pro Ser Pro Gly Ala Pro Pro Leu Glu Ser Val Asp Val Arg
                260                 265                 270

Gln Ile Tyr Asp Lys Phe Pro Glu Lys Lys Gly Gly Leu Arg Glu Leu
            275                 280                 285

Tyr Asp Arg Gly Pro Pro His Ala Phe Phe Leu Val Lys Phe Trp Ala
    290                 295                 300

Asp Leu Asn Trp Gly Pro Ser Gly Glu Glu Ala Gly Ala Gly Gly Ser
305                 310                 315                 320

Ile Ser Ser Gly Gly Phe Tyr Gly Val Ser Ser Gln Tyr Glu Ser Leu
                325                 330                 335

Glu His Met Thr Leu Thr Cys Ser Ser Lys Val Cys Ser Phe Gly Lys
                340                 345                 350

Gln Val Val Glu Lys Val Glu Thr Glu Arg Ala Gln Leu Glu Asp Gly
            355                 360                 365

Arg Phe Val Tyr Arg Leu Leu Arg Ser Pro Met Cys Glu Tyr Leu Val
    370                 375                 380

Asn Phe Leu His Lys Leu Arg Gln Leu Pro Glu Arg Tyr Met Met Asn
385                 390                 395                 400

Ser Val Leu Glu Asn Phe Thr Ile Leu Gln Val Val Thr Asn Arg Asp
                405                 410                 415

Thr Gln Glu Leu Leu Leu Cys Thr Ala Tyr Val Phe Glu Val Ser Thr
                420                 425                 430

Ser Glu Arg Gly Ala Gln His His Ile Tyr Arg Leu Val Arg Asp
            435                 440                 445

<210> SEQ ID NO 3
<211> LENGTH: 435
<212> TYPE: PRT
```

<213> ORGANISM: Homo sapiens

<400> SEQUENCE: 3

Met Ala Ser Asn Ser Trp Asn Ala Ser Ser Pro Gly Glu Ala Arg
1               5                   10                  15

Glu Asp Gly Pro Glu Gly Leu Asp Lys Gly Leu Asp Asn Asp Ala Glu
            20                  25                  30

Gly Val Trp Ser Pro Asp Ile Glu Gln Ser Phe Gln Glu Ala Leu Ala
        35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Arg Lys Gln Val Ser Ser His Ile Gln Val
                85                  90                  95

Leu Ala Arg Lys Lys Val Arg Glu Tyr Gln Val Gly Ile Lys Ala Met
                100                 105                 110

Asn Leu Asp Gln Val Ser Lys Asp Lys Ala Leu Gln Ser Met Ala Ser
            115                 120                 125

Met Ser Ser Ala Gln Ile Val Ser Ala Ser Val Leu Gln Asn Lys Phe
130                 135                 140

Ser Pro Pro Ser Pro Leu Pro Gln Ala Val Phe Ser Thr Ser Ser Arg
145                 150                 155                 160

Phe Trp Ser Ser Pro Pro Leu Leu Gly Gln Gln Pro Gly Pro Ser Gln
                165                 170                 175

Asp Ile Lys Pro Phe Ala Gln Pro Ala Tyr Pro Ile Gln Pro Pro Leu
            180                 185                 190

Pro Pro Thr Leu Ser Ser Tyr Glu Pro Leu Ala Pro Leu Pro Ser Ala
        195                 200                 205

Ala Ala Ser Val Pro Val Trp Gln Asp Arg Thr Ile Ala Ser Ser Arg
    210                 215                 220

Leu Arg Leu Leu Glu Tyr Ser Ala Phe Met Glu Val Gln Arg Asp Pro
225                 230                 235                 240

Asp Thr Tyr Ser Lys His Leu Phe Val His Ile Gly Gln Thr Asn Pro
                245                 250                 255

Ala Phe Ser Asp Pro Pro Leu Glu Ala Val Asp Val Arg Gln Ile Tyr
                260                 265                 270

Asp Lys Phe Pro Glu Lys Lys Gly Gly Leu Lys Glu Leu Tyr Glu Lys
            275                 280                 285

Gly Pro Pro Asn Ala Phe Phe Leu Val Lys Phe Trp Ala Asp Leu Asn
290                 295                 300

Ser Thr Ile Gln Glu Gly Pro Gly Ala Phe Tyr Gly Val Ser Ser Gln
305                 310                 315                 320

Tyr Ser Ser Ala Asp Ser Met Thr Ile Ser Val Ser Thr Lys Val Cys
                325                 330                 335

Ser Phe Gly Lys Gln Val Val Glu Lys Val Glu Thr Glu Tyr Ala Arg
                340                 345                 350

Leu Glu Asn Gly Arg Phe Val Tyr Arg Ile His Arg Ser Pro Met Cys
            355                 360                 365

Glu Tyr Met Ile Asn Phe Ile His Lys Leu Lys His Leu Pro Glu Lys
        370                 375                 380

Tyr Met Met Asn Ser Val Leu Glu Asn Phe Thr Ile Leu Gln Val Val
385                 390                 395                 400

```
Thr Ser Arg Asp Ser Gln Glu Thr Leu Leu Val Ile Ala Phe Val Phe
            405                 410                 415

Glu Val Ser Thr Ser Glu His Gly Ala Gln His His Val Tyr Lys Leu
            420                 425                 430

Val Lys Asp
        435

<210> SEQ ID NO 4
<211> LENGTH: 434
<212> TYPE: PRT
<213> ORGANISM: Homo sapiens

<400> SEQUENCE: 4

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Ala Glu Gly Val Trp Ser Pro Asp Ile Glu
            35                  40                  45

Gln Ser Phe Gln Glu Ala Leu Ala Ile Tyr Pro Pro Cys Gly Arg Arg
        50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Asp Gln Ala Ala Lys Asp Lys Ala Leu Gln
        115                 120                 125

Ser Met Ala Ala Met Ser Ser Ala Gln Ile Ile Ser Ala Thr Ala Phe
130                 135                 140

His Ser Ser Met Ala Leu Ala Arg Gly Pro Gly Arg Pro Ala Val Ser
145                 150                 155                 160

Gly Phe Trp Gln Gly Ala Leu Pro Gly Gln Ala Gly Thr Ser His Asp
                165                 170                 175

Val Lys Pro Phe Ser Gln Gln Thr Tyr Ala Val Gln Pro Pro Leu Pro
            180                 185                 190

Leu Pro Gly Phe Glu Ser Pro Ala Gly Pro Ala Pro Ser Pro Ser Ala
        195                 200                 205

Pro Pro Ala Pro Pro Trp Gln Gly Arg Ser Val Ala Ser Ser Lys Leu
210                 215                 220

Trp Met Leu Glu Phe Ser Ala Phe Leu Glu Gln Gln Asp Pro Asp
225                 230                 235                 240

Thr Tyr Asn Lys His Leu Phe Val His Ile Gly Gln Ser Ser Pro Ser
                245                 250                 255

Tyr Ser Asp Pro Tyr Leu Glu Ala Val Asp Ile Arg Gln Ile Tyr Asp
            260                 265                 270

Lys Phe Pro Glu Lys Lys Gly Gly Leu Lys Asp Leu Phe Glu Arg Gly
        275                 280                 285

Pro Ser Asn Ala Phe Phe Leu Val Lys Phe Trp Ala Asp Leu Asn Thr
290                 295                 300

Asn Ile Glu Asp Glu Gly Ser Ser Phe Tyr Gly Val Ser Ser Gln Tyr
305                 310                 315                 320

Glu Ser Pro Glu Asn Met Ile Ile Thr Cys Ser Thr Lys Val Cys Ser
                325                 330                 335
```

```
Phe Gly Lys Gln Val Val Glu Lys Val Glu Thr Glu Tyr Ala Arg Tyr
                340                 345                 350

Glu Asn Gly His Tyr Ser Tyr Arg Ile His Arg Ser Pro Leu Cys Glu
            355                 360                 365

Tyr Met Ile Asn Phe Ile His Lys Leu Lys His Leu Pro Glu Lys Tyr
        370                 375                 380

Met Met Asn Ser Val Leu Glu Asn Phe Thr Ile Leu Gln Val Val Thr
385                 390                 395                 400

Asn Arg Asp Thr Gln Glu Thr Leu Leu Cys Ile Ala Tyr Val Phe Glu
                405                 410                 415

Val Ser Ala Ser Glu His Gly Ala Gln His His Ile Tyr Arg Leu Val
            420                 425                 430

Lys Glu

<210> SEQ ID NO 5
<211> LENGTH: 221
<212> TYPE: PRT
<213> ORGANISM: Homo sapiens

<400> SEQUENCE: 5

Trp Gln Gly Arg Ser Ile Gly Thr Thr Lys Leu Arg Leu Val Glu Phe
1               5                   10                  15

Ser Ala Phe Leu Glu Gln Gln Arg Asp Pro Asp Ser Tyr Asn Lys His
            20                  25                  30

Leu Phe Val His Ile Gly His Ala Asn His Ser Tyr Ser Asp Pro Leu
        35                  40                  45

Leu Glu Ser Val Asp Ile Arg Gln Ile Tyr Asp Lys Phe Pro Glu Lys
    50                  55                  60

Lys Gly Gly Leu Lys Glu Leu Phe Gly Lys Gly Pro Gln Asn Ala Phe
65                  70                  75                  80

Phe Leu Val Lys Phe Trp Ala Asp Leu Asn Cys Asn Ile Gln Asp Asp
                85                  90                  95

Ala Gly Ala Phe Tyr Gly Val Thr Ser Gln Tyr Glu Ser Ser Glu Asn
            100                 105                 110

Met Thr Val Thr Cys Ser Thr Lys Val Cys Ser Phe Gly Lys Gln Val
        115                 120                 125

Val Glu Lys Val Glu Thr Glu Tyr Ala Arg Phe Glu Asn Gly Arg Phe
    130                 135                 140

Val Tyr Arg Ile Asn Arg Ser Pro Met Cys Glu Tyr Met Ile Asn Phe
145                 150                 155                 160

Ile His Lys Leu Lys His Leu Pro Glu Lys Tyr Met Met Asn Ser Val
                165                 170                 175

Leu Glu Asn Phe Thr Ile Leu Leu Val Val Thr Asn Arg Asp Thr Gln
            180                 185                 190

Glu Thr Leu Leu Cys Met Ala Cys Val Phe Glu Val Ser Asn Ser Glu
        195                 200                 205

His Gly Ala Gln His His Ile Tyr Arg Leu Val Lys Asp
    210                 215                 220

<210> SEQ ID NO 6
<211> LENGTH: 230
<212> TYPE: PRT
<213> ORGANISM: Homo sapiens

<400> SEQUENCE: 6
```

Trp Gln Ala Arg Gly Leu Gly Thr Ala Arg Leu Gln Leu Val Glu Phe
1               5                   10                  15

Ser Ala Phe Val Glu Pro Pro Asp Ala Val Asp Ser Tyr Gln Arg His
                20                  25                  30

Leu Phe Val His Ile Ser Gln His Cys Pro Ser Pro Gly Ala Pro Pro
            35                  40                  45

Leu Glu Ser Val Asp Val Arg Gln Ile Tyr Asp Lys Phe Pro Glu Lys
50                  55                  60

Lys Gly Gly Leu Arg Glu Leu Tyr Asp Arg Pro Pro His Ala Phe
65                  70                  75                  80

Phe Leu Val Lys Phe Trp Ala Asp Leu Asn Trp Gly Pro Ser Gly Glu
                85                  90                  95

Glu Ala Gly Ala Gly Gly Ser Ile Ser Ser Gly Gly Phe Tyr Gly Val
                100                 105                 110

Ser Ser Gln Tyr Glu Ser Leu Glu His Met Thr Leu Thr Cys Ser Ser
            115                 120                 125

Lys Val Cys Ser Phe Gly Lys Gln Val Val Glu Lys Val Glu Thr Glu
130                 135                 140

Arg Ala Gln Leu Glu Asp Gly Arg Phe Val Tyr Arg Leu Leu Arg Ser
145                 150                 155                 160

Pro Met Cys Glu Tyr Leu Val Asn Phe Leu His Lys Leu Arg Gln Leu
                165                 170                 175

Pro Glu Arg Tyr Met Met Asn Ser Val Leu Glu Asn Phe Thr Ile Leu
                180                 185                 190

Gln Val Val Thr Asn Arg Asp Thr Gln Glu Leu Leu Leu Cys Thr Ala
                195                 200                 205

Tyr Val Phe Glu Val Ser Thr Ser Glu Arg Gly Ala Gln His His Ile
                210                 215                 220

Tyr Arg Leu Val Arg Asp
225                 230

<210> SEQ ID NO 7
<211> LENGTH: 221
<212> TYPE: PRT
<213> ORGANISM: Homo sapiens

<400> SEQUENCE: 7

Trp Gln Asp Arg Thr Ile Ala Ser Ser Arg Leu Arg Leu Leu Glu Tyr
1               5                   10                  15

Ser Ala Phe Met Glu Val Gln Arg Asp Pro Asp Thr Tyr Ser Lys His
                20                  25                  30

Leu Phe Val His Ile Gly Gln Thr Asn Pro Ala Phe Ser Asp Pro Pro
            35                  40                  45

Leu Glu Ala Val Asp Val Arg Gln Ile Tyr Asp Lys Phe Pro Glu Lys
50                  55                  60

Lys Gly Gly Leu Lys Glu Leu Tyr Glu Lys Gly Pro Pro Asn Ala Phe
65                  70                  75                  80

Phe Leu Val Lys Phe Trp Ala Asp Leu Asn Ser Thr Ile Gln Glu Gly
                85                  90                  95

Pro Gly Ala Phe Tyr Gly Val Ser Ser Gln Tyr Ser Ser Ala Asp Ser
                100                 105                 110

Met Thr Ile Ser Val Ser Thr Lys Val Cys Ser Phe Gly Lys Gln Val
            115                 120                 125

Val Glu Lys Val Glu Thr Glu Tyr Ala Arg Leu Glu Asn Gly Arg Phe
130                 135                 140

Val Tyr Arg Ile His Arg Ser Pro Met Cys Glu Tyr Met Ile Asn Phe
145                 150                 155                 160

Ile His Lys Leu Lys His Leu Pro Glu Lys Tyr Met Met Asn Ser Val
                165                 170                 175

Leu Glu Asn Phe Thr Ile Leu Gln Val Val Thr Ser Arg Asp Ser Gln
            180                 185                 190

Glu Thr Leu Leu Val Ile Ala Phe Val Phe Glu Val Ser Thr Ser Glu
        195                 200                 205

His Gly Ala Gln His His Val Tyr Lys Leu Val Lys Asp
    210                 215                 220

<210> SEQ ID NO 8
<211> LENGTH: 221
<212> TYPE: PRT
<213> ORGANISM: Homo sapiens

<400> SEQUENCE: 8

Trp Gln Gly Arg Ser Val Ala Ser Ser Lys Leu Trp Met Leu Glu Phe
1               5                   10                  15

Ser Ala Phe Leu Glu Gln Gln Gln Asp Pro Asp Thr Tyr Asn Lys His
            20                  25                  30

Leu Phe Val His Ile Gly Gln Ser Ser Pro Ser Tyr Ser Asp Pro Tyr
        35                  40                  45

Leu Glu Ala Val Asp Ile Arg Gln Ile Tyr Asp Lys Phe Pro Glu Lys
    50                  55                  60

Lys Gly Gly Leu Lys Asp Leu Phe Glu Arg Gly Pro Ser Asn Ala Phe
65                  70                  75                  80

Phe Leu Val Lys Phe Trp Ala Asp Leu Asn Thr Asn Ile Glu Asp Glu
                85                  90                  95

Gly Ser Ser Phe Tyr Gly Val Ser Ser Gln Tyr Glu Ser Pro Glu Asn
            100                 105                 110

Met Ile Ile Thr Cys Ser Thr Lys Val Cys Ser Phe Gly Lys Gln Val
        115                 120                 125

Val Glu Lys Val Glu Thr Glu Tyr Ala Arg Tyr Glu Asn Gly His Tyr
    130                 135                 140

Ser Tyr Arg Ile His Arg Ser Pro Leu Cys Glu Tyr Met Ile Asn Phe
145                 150                 155                 160

Ile His Lys Leu Lys His Leu Pro Glu Lys Tyr Met Met Asn Ser Val
                165                 170                 175

Leu Glu Asn Phe Thr Ile Leu Gln Val Val Thr Asn Arg Asp Thr Gln
            180                 185                 190

Glu Thr Leu Leu Cys Ile Ala Tyr Val Phe Glu Val Ser Ala Ser Glu
        195                 200                 205

His Gly Ala Gln His His Ile Tyr Arg Leu Val Lys Glu
    210                 215                 220

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid

```
<220> FEATURE:
<221> NAME/KEY: MOD_RES
<222> LOCATION: (4)..(5)
<223> OTHER INFORMATION: Any amino acid

<400> SEQUENCE: 9

His Xaa Arg Xaa Xaa Ser
1               5
```

TEAD INHIBITORS AND USES THEREOF

CROSS-REFERENCE TO RELATED APPLICATIONS

This application is a divisional of U.S. application Ser. No. 16/886,926, filed May 29, 2020, which claims the benefit under 35 U.S.C. § 119(e) of U.S. Provisional Patent Application No. 62/855,082, filed May 31, 2019; U.S. Provisional Patent Application No. 62/928,931, filed Oct. 31, 2019; U.S. Provisional Patent Application No. 62/944,567, filed Dec. 6, 2019; and U.S. Provisional Patent Application No. 63/025,219, filed May 15, 2020, the contents of each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jan. 3, 2021, is named 187989_SL.txt and is 23,666 bytes in size.

TECHNICAL FIELD OF THE INVENTION

The present invention relates to compounds and methods useful for inhibition of Transcriptional Enhancer Associate Domain (TEAD). The invention also provides pharmaceutically acceptable compositions comprising compounds of the present invention and methods of using said compositions in the treatment of various diseases, disorders, and conditions as described herein.

BACKGROUND OF THE INVENTION

Yes-associated protein (YAP) and transcriptional co-activator with PDZ-binding motif (TAZ) are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with TEAD transcription factors and coactivate the expression of target genes and promote cell proliferation. Hyperactivation of YAP and TAZ and/or mutations in one or more members of the Hippo pathway network have been implicated in numerous cancers.

SUMMARY OF THE INVENTION

The Hippo signaling cascade is an important pathway for cancer biogenesis and tumor maintenance. The Hippo pathway is heavily mutated across many cancer indications through loss of function mutations in genes such as NF2. These pro-tumor mutations lead to the constitutive activation of the downstream transcriptional coactivators YAP and TAZ that drive the expression of many pro-survival and proliferation genes through the essential interaction with a TEAD protein family member. In addition, this unrestrained transcriptional program drives enhanced immune suppression in the tumor microenvironment. As described herein, to target this oncogenic pathway novel small molecule inhibitors were identified that selectively bind to TEAD and disrupt their interaction with YAP and TAZ, thereby downregulating YAP- and TAZ-dependent transcription. As demonstrated herein, these TEAD inhibitors prevent TEAD palmitoylation, which is critical for the interaction between YAP and TEAD. Furthermore, the TEAD inhibitors described herein inhibit in vitro proliferation of YAP-dependent (i.e., Hippo pathway-deficient cancer cell lines), but not Hippo pathway wild type cancer cell lines. Importantly, as shown herein, the TEAD inhibitor compounds of the present invention did not affect survival of a differentiated mouse podocyte cell line or compromise mouse kidney histology. Subsequent experiments in vivo demonstrate the TEAD inhibitors described herein downregulate YAP-dependent genes in human tumor xenografts after oral dosing. In addition, the TEAD inhibitors described herein exhibit single agent tumor growth inhibition of human tumor xenografts in mice at well tolerated oral doses. The data described herein demonstrate the ability of the small molecule TEAD inhibitors provided herein for targeting the Hippo pathway in cancers.

It has now been found that compounds of the present invention, and pharmaceutically acceptable compositions thereof, are effective as TEAD inhibitors. In one aspect, the present invention provides a compound of Formula I':

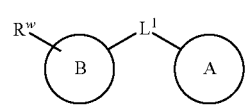

or a pharmaceutically acceptable salt thereof, wherein each variable is as defined and described herein. In one aspect, the present invention provides a compound of Formula I:

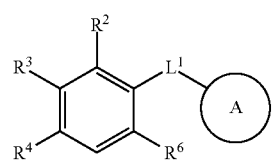

or a pharmaceutically acceptable salt thereof, wherein each variable is as defined and described herein.

Compounds of the present invention, and pharmaceutically acceptable salts and compositions thereof, are useful for treating a variety of diseases, disorders or conditions associated with TEAD. Such diseases, disorders, or conditions include cellular proliferative disorders (e.g., cancer as described herein).

DETAILED DESCRIPTION OF CERTAIN EMBODIMENTS

Figure 1:
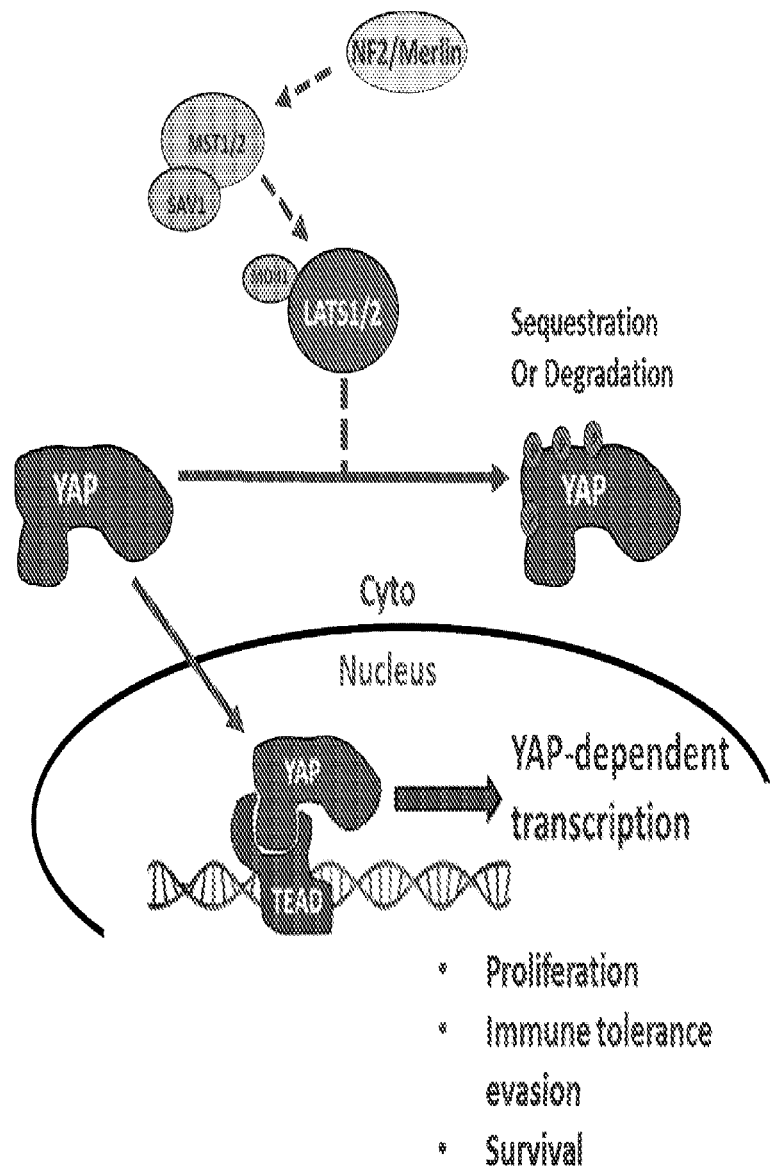
FIG. 1 depicts a schematic of Hippo pathway signaling.

1. General Description of Certain Embodiments of the Invention

Compounds of the present invention, and pharmaceutical salts and compositions thereof, are useful as inhibitors of TEAD. Without wishing to be bound by any particular theory, it is believed that compounds of the present invention, and pharmaceutical compositions thereof, inhibit the activity of TEAD and thus treat diseases, disorders, or conditions associated with TEAD, such as cancer.

In one aspect, the present invention provides a compound of Formula I':

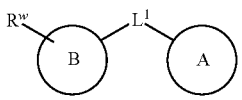

I' or a pharmaceutically acceptable salt thereof, wherein:

$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur;

Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur;

$R^w$ is an optionally substituted 4-, 5-, or 6-membered ring having 1, 2, 3, or 4 heteroatoms independently selected from nitrogen, oxygen, or sulfur; and each R is independently —H or optionally substituted —C$_{1-6}$ aliphatic.

In one aspect, the present invention provides a compound of Formula I:

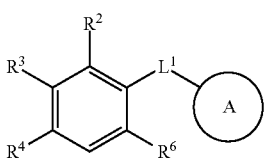

I or a pharmaceutically acceptable salt thereof, wherein:

$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by -halogen, —CN, —NO$_2$, or —C$_{1-6}$ aliphatic substituted 0-6 times by -halogen, —CN, or —NO$_2$;

$R^2$ is —H, or an optionally substituted 4-, 5-, or 6-membered ring having 1, 2, 3, or 4 heteroatoms independently selected from nitrogen, oxygen, or sulfur;

$R^3$ is —H;

$R^4$ is —H, halogen, —S(O)$_2$N(R)$_2$, —S(O)N(R)$_2$, or —C(O)N(R)$_2$;

$R^6$ is —H or —C$_{1-6}$ aliphatic substituted 0-6 times by -halogen, —CN, or —NO$_2$; and each R is independently —H or optionally substituted —C$_{1-6}$ aliphatic.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

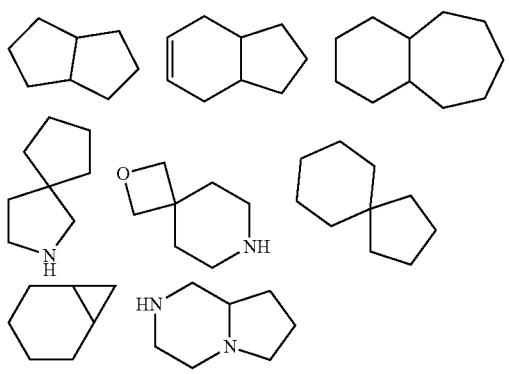

Exemplary bridged bicyclics include:

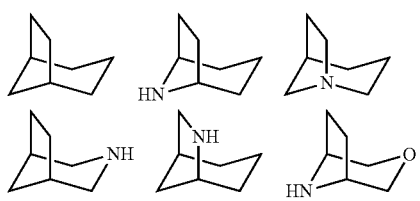

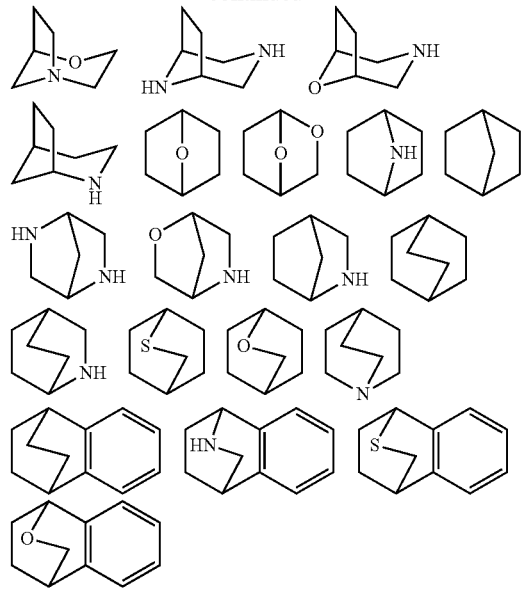

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

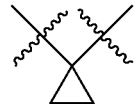

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —S(O)(NR°)R°; —S(O)$_2$N=C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$.

Each $R^\circ$ is independently hydrogen, $C_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from =O and =S; or each $R^\circ$ is optionally substituted with a monovalent substituent independently selected from halogen, —(CH$_2$)$_{0-2}R^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$.

Each $R^\bullet$ is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*2))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each $R^\bullet$ is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R$^\dagger$ is $C_{1-6}$ aliphatic, R is optionally substituted with halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each $R^\bullet$ is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C— or $^{14}$C-enriched carbon are within the scope of this invention. Such compounds are useful, for example, as analytical tools, as probes in biological assays, or as therapeutic agents in accordance with the present invention.

As used herein, the terms "inhibitor" or "TEAD inhibitor" or "TEAD antagonist" are defined as a compound that binds to and/or inhibits TEAD with measurable affinity. In some embodiments, inhibition in the presence of the inhibitor is observed in a dose-dependent manner. In some embodiments, the measured signal (e.g., signaling activity or biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% lower than the signal measured with a negative control under comparable conditions. The potency of an inhibitor is usually defined by its $IC_{50}$ value (half maximal inhibitory concentration or concentration required to inhibit 50% of the agonist response). The lower the $IC_{50}$ value the greater the potency of the antagonist and the lower the concentration that is required to inhibit the maximum biological response. In certain embodiments, an inhibitor has an $IC_{50}$ and/or binding constant of less than about 100 µM, less than about 50 µM, less than about 1 µM, less than about 500 nM, less than about 100 nM, less than about 10 nM, or less than about 1 nM.

The terms "measurable affinity" and "measurably inhibit," as used herein, means a measurable change or inhibition in TEAD activity between a sample comprising a compound of the present invention, or composition thereof, and TEAD, and an equivalent sample comprising TEAD, in the absence of said compound, or composition thereof.

3. Description of Exemplary Embodiments

In one aspect, the present invention provides a compound of Formula I':

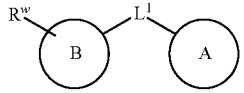

I' or a pharmaceutically acceptable salt thereof, wherein:
$L^1$ is a covalent bond, or a $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur;

Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur;

$R^w$ is an optionally substituted 4-, 5-, or 6-membered ring having 1, 2, 3, or 4 heteroatoms independently selected from nitrogen, oxygen, or sulfur; and each R is independently —H or optionally substituted —$C_{1-6}$ aliphatic.

In one aspect, the present invention provides a compound of Formula I:

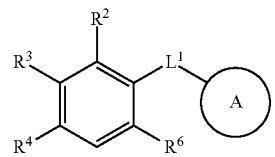

I or a pharmaceutically acceptable salt thereof, wherein:
$L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N(R)—, —(R)NSO$_2$—, —C(S)—, —C(S)O—, —OC(S)—, —C(S)N(R)—, —(R)NC(S)—, or —(R)NC(S)N(R)—;

Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by halogen, —CN, —NO$_2$, or —C$_{1-6}$ aliphatic substituted 0-6 times by halogen, —CN, or —NO$_2$;

$R^2$ is —H, or an optionally substituted 4-, 5-, or 6-membered ring having 1, 2, 3, or 4 heteroatoms independently selected from nitrogen, oxygen, or sulfur;

$R^3$ is —H;

$R^4$ is —H, halogen, —S(O)$_2$N(R)$_2$, —S(O)N(R)$_2$, or —C(O)N(R)$_2$;

$R^6$ is —H or —C$_{1-6}$ aliphatic substituted 0-6 times by halogen, —CN, or —NO$_2$; and each R is independently —H or optionally substituted —C$_{1-6}$ aliphatic.

As defined generally above, $L^1$ is $C_{1-6}$ bivalent straight or branched hydrocarbon chain wherein 1, 2, or 3 methylene units of the chain are independently and optionally replaced with —O—, —CH(OR)—, —CH(SR)—, —CH(N(R)$_2$)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO$_2$—, —SO$_2$N (R)—, —(R)NSO₂—, —C(S)—, —C(S)O—, —OC(S)—, —C(S)N(R)—, —(R)NC(S)—, or —(R)NC(S)N(R)—.

In some embodiments, L¹ is a covalent bond, or a C₁₋₆ bivalent straight or branched hydrocarbon chain wherein 1, 2, or 3 methylene units of the chain are independently and optionally replaced with —O—, —CH(OR)—, —CH(SR)—, —CH(N(R)₂)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO₂—, —SO₂N(R)—, —(R)NSO₂—, —C(S)—, —C(S)O—, —OC(S)—, —C(S)N(R)—, —(R)NC(S)—, or —(R)NC(S)N(R)—.

In some embodiments, L¹ is a covalent bond.

In some embodiments, L¹ is C₁₋₆ bivalent straight or branched hydrocarbon chain wherein 1, 2, or 3 methylene units of the chain are independently and optionally replaced with —O—, —CH(OR)—, —CH(N(R)₂)—, —C(O)—, —C(O)O—, —OC(O)—, —N(R)—, —C(O)N(R)—, —(R)NC(O)—, —OC(O)N(R)—, —(R)NC(O)O—, or —N(R)C(O)N(R)—.

In some embodiments, L¹ is C₁₋₆ bivalent straight or branched hydrocarbon chain wherein 1, 2, or 3 methylene units of the chain are optionally replaced with —CH(SR)—, —S—, —SO—, —SO₂—, —SO₂N(R)—, —(R)NSO₂—, —C(S)—, —C(S)O—, —OC(S)—, —C(S)N(R)—, —(R)NC(S)—, or —(R)NC(S)N(R)—.

In some embodiments, L¹ is C₁₋₆ bivalent straight or branched hydrocarbon chain wherein 1, 2, or 3 methylene units of the chain are independently and optionally replaced with —O—, —S—, or —N(R)—.

In some embodiments, L¹ is C₁₋₆ bivalent straight or branched hydrocarbon chain wherein 1, 2, or 3 methylene units of the chain are independently and optionally replaced with —CH(OR)—, —CH(SR)—, or —CH(N(R)₂)—.

In some embodiments, L¹ is C₁₋₆ bivalent straight or branched hydrocarbon chain wherein 1, 2, or 3 methylene units of the chain are independently and optionally replaced with —C(O)—, —C(O)O—, —OC(O)—, —SO—, —SO₂—, —C(S)—, —C(S)O—, or —OC(S)—.

In some embodiments, L¹ is C₁₋₆ bivalent straight or branched hydrocarbon chain wherein 1, 2, or 3 methylene units of the chain are independently and optionally replaced with —C(O)N(R)—, —(R)NC(O)—, —OC(O)N(R)—, —(R)NC(O)O—, —N(R)C(O)N(R)—, —SO₂N(R)—, —(R)NSO₂—, —C(S)N(R)—, —(R)NC(S)—, or —(R)NC(S)N(R)—.

In some embodiments, L¹ is —O—, —CH(OR)—, —CH(SR)—, —CH(N(R)₂)—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO₂—, —SO₂N(R)—, —(R)NSO₂—, —C(S)—, —C(S)O—, —OC(S)—, —C(S)N(R)—, —(R)NC(S)—, or —(R)NC(S)N(R)—.

In some embodiments, L¹ is —O—, —CH(OR)—, —CH(N(R)₂)—, —C(O)—, —C(O)O—, —OC(O)—, —N(R)—, —C(O)N(R)—, —(R)NC(O)—, —OC(O)N(R)—, —(R)NC(O)O—, or —N(R)C(O)N(R)—.

In some embodiments, L¹ is —CH(SR)—, —S—, —SO—, —SO₂—, —SO₂N(R)—, —(R)NSO₂—, —C(S)—, —C(S)O—, —OC(S)—, —C(S)N(R)—, —(R)NC(S)—, or —(R)NC(S)N(R)—.

In some embodiments, L¹ is —O—, —S—, or —N(R)—. In some embodiments, L¹ is —O—. In some embodiments, L¹ is —S—. In some embodiments, L¹ is —N(R)—. In some embodiments, L¹ is —NH—.

In some embodiments, L¹ is —CH(OR)—, —CH(SR)—, or —CH(N(R)₂)—. In some embodiments, L¹ is —CH(OR)—. In some embodiments, L¹ is —CH(SR)—. In some embodiments, L¹ is —CH(N(R)₂)—.

In some embodiments, L¹ is —C(O)—, —C(O)O—, —OC(O)—, —SO—, —SO₂—, —C(S)—, —C(S)O—, or —OC(S)—. In some embodiments, L¹ is —C(O)—. In some embodiments, L¹ is —C(O)O—. In some embodiments, L¹ is —OC(O)—. In some embodiments, L¹ is —SO—. In some embodiments, L¹ is —SO₂—. In some embodiments, L¹ is —C(S)—. In some embodiments, L¹ is —C(S)O—. In some embodiments, L¹ is —OC(S)—.

In some embodiments, L¹ is —C(O)N(R)—, —(R)NC(O)—, —OC(O)N(R)—, —(R)NC(O)O—, —N(R)C(O)N(R)—, —SO₂N(R)—, —(R)NSO₂—, —C(S)N(R)—, —(R)NC(S)—, or —(R)NC(S)N(R)—. In some embodiments, L¹ is —C(O)N(R)—. In some embodiments, L¹ is —(R)NC(O)—. In some embodiments, L¹ is —OC(O)N(R)—. In some embodiments, L¹ is —(R)NC(O)O—. In some embodiments, L¹ is —N(R)C(O)N(R)—. In some embodiments, L¹ is —SO₂N(R)—. In some embodiments, L¹ is —(R)NSO₂—. In some embodiments, L¹ is —C(S)N(R)—. In some embodiments, L¹ is —(R)NC(S)—. or In some embodiments, L¹ is —(R)NC(S)N(R)—.

In some embodiments, L¹ is —CH₂—, —CH(CH₃)—, —NH—CH₂—, —NH—CH(CH₃)—, —C(O)—NH—, or —N(CH₃)—.

In some embodiments, L¹ is

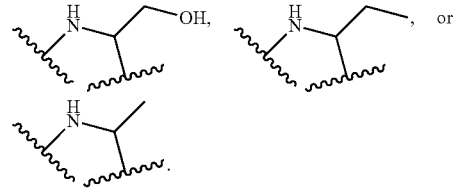

In some embodiments, L¹ is selected from those depicted in Table 1, below.

As defined generally above, Ring A is a 4-, 5-, or 6-membered saturated or partially unsaturated monocyclic carbocyclic ring, phenyl, a 4-, 5-, or 6-membered saturated or partially unsaturated monocyclic heterocyclic ring having 1-2 heteroatoms independently selected from nitrogen, oxygen, or sulfur, or a 5-6 membered monocyclic heteroaromatic ring having 1, 2, 3, or 4 heteroatoms independently selected from nitrogen, oxygen, or sulfur, wherein Ring A is optionally substituted 1-2 times by halogen, —CN, —NO₂, or —C₁₋₆ aliphatic substituted 0-6 times by halogen, —CN, or —NO₂.

In some embodiments, Ring A is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, or a 8-10 membered bicyclic heteroaromatic ring having 1-5 heteroatoms independently selected from nitrogen, oxygen, or sulfur.

In some embodiments, Ring A is optionally substituted phenyl. In some embodiments, Ring A is optionally substituted 4-, 5-, or 6-membered saturated or partially unsaturated monocyclic carbocyclic ring. In some embodiments, Ring A is optionally substituted 4-, 5-, or 6-membered saturated or partially unsaturated monocyclic heterocyclic ring having 1-2 heteroatoms independently selected from nitrogen, oxygen, or sulfur. In some embodiments, Ring A is optionally substituted 5-6 membered monocyclic heteroaromatic ring having 1, 2, 3, or 4 heteroatoms independently selected from nitrogen, oxygen, or sulfur. In some embodiments, Ring A is optionally substituted 8-10 membered bicyclic aromatic ring. In some embodiments, Ring A is optionally substituted 8-10 membered bicyclic heteroaromatic ring having 1-5 heteroatoms independently selected from nitrogen, oxygen, or sulfur.

In some embodiments, Ring A is optionally substituted phenyl, a 6-membered monocyclic heteroaromatic ring having 1 or 2 nitrogen, or a 10-membered bicyclic heteroaromatic ring having 1-2 nitrogen.

In some embodiments, Ring A is optionally substituted N

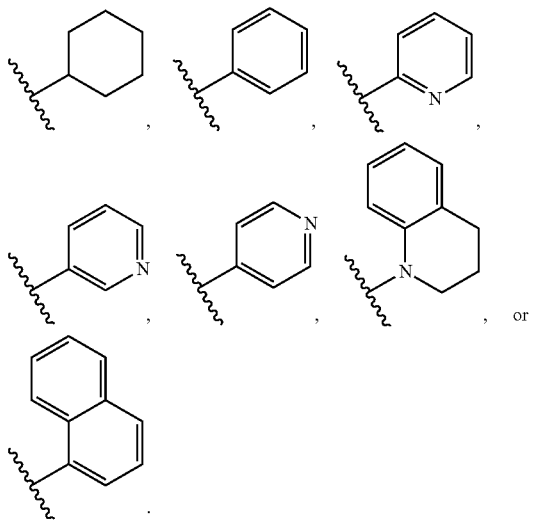

In some embodiments, Ring A is optionally substituted 1-2 times by -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is independently substituted 0-6 times by -halogen, —CN, or —NO$_2$. In some embodiments, Ring A is optionally substituted 1-2 times by halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is independently substituted 0, 1, 2, 3, 4, 5, or 6 times by halogen, —CN, or —NO$_2$. In some embodiments, Ring A is optionally substituted 1-2 times by halogen, —C$_{1-6}$ aliphatic, or —O—C$_{1-6}$ aliphatic, wherein each of —C$_{1-6}$ aliphatic and —O—C$_{1-6}$ aliphatic is independently substituted 1, 2, 3, 4, 5, or 6 times by halogen.

In some embodiments, Ring A is a 4-, 5-, or 6-membered saturated or partially unsaturated monocyclic carbocyclic ring. In some embodiments, Ring A is cyclohexyl. In some embodiments, Ring A is phenyl. In some embodiments, Ring A is a 4-, 5-, or 6-membered saturated or partially unsaturated monocyclic heterocyclic ring having 1-2 heteroatoms independently selected from nitrogen, oxygen, or sulfur. In some embodiments, Ring A is a 5-6 membered monocyclic heteroaromatic ring having 1, 2, 3, or 4 heteroatoms independently selected from nitrogen, oxygen, or sulfur.

In some embodiments, Ring A is a 8-10 membered bicyclic aromatic ring. In some embodiments, Ring A is a 8-10 membered bicyclic heteroaromatic ring having 1-5 heteroatoms independently selected from nitrogen, oxygen, or sulfur.

In some embodiments, Ring A is optionally substituted 1-2 times by halogen, —CN, —NO$_2$, or —C$_{1-6}$ aliphatic substituted 0, 1, 2, 3, 4, 5, or 6 times by halogen, —CN, or —NO$_2$. In some embodiments, Ring A is optionally substituted 1-2 times by halogen, or —C$_{1-6}$ aliphatic substituted 0, 1, 2, 3, 4, 5, or 6 times by halogen.

In some embodiments, Ring A is selected from

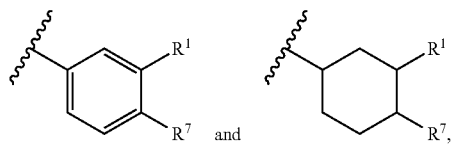

wherein each of R$^1$ and R$^7$ is independently as described herein.

In some embodiments, Ring A is selected from

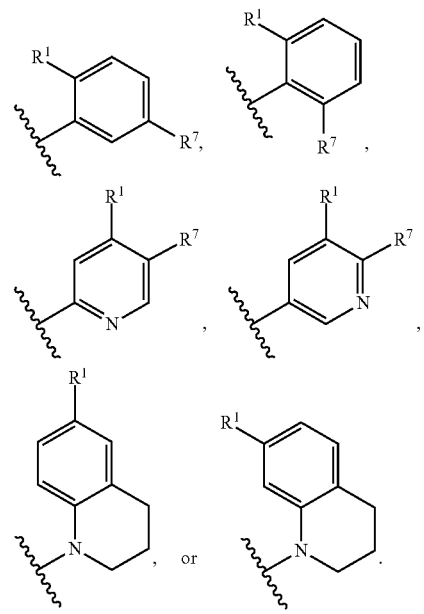

In some embodiments, R$^1$ is —H, -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is substituted 0, 1, 2, 3, 4, 5, or 6 times by -halogen, —CN, or —NO$_2$. In some embodiments, R$^1$ is unsubstituted —O—C$_{1-6}$ aliphatic. In some embodiments, R$^1$ is —OCH$_3$. In some embodiments, R$^1$ is —O—C$_{1-6}$ aliphatic substituted 1, 2, 3, 4, 5, or 6 times by -halogen. In some embodiments, R$^1$ is —O—C$_{1-3}$ aliphatic substituted 1, 2, 3, 4, 5, or 6 times by -halogen. In some embodiments, R$^1$ is —O—C$_{1-6}$ aliphatic substituted 1, 2, 3, 4, 5, or 6 times by —F. In some embodiments, R$^1$ is —OCF$_3$. In some embodiments, R$^1$ is

In some embodiments, $R^1$ is —H, -halogen, —CN, —NO$_2$, or —C$_{1-6}$ aliphatic substituted 0, 1, 2, 3, 4, 5, or 6 times by -halogen, —CN, or —NO$_2$. In some embodiments, $R^1$ is —H. In some embodiments, $R^1$ is -halogen. In some embodiments, $R^1$ is —F. In some embodiments, $R^1$ is —Cl. In some embodiments, $R^1$ is —Br. In some embodiments, $R^1$ is —CN. In some embodiments, $R^1$ is —NO$_2$. In some embodiments, $R^1$ is unsubstituted —C$_{1-6}$ aliphatic. In some embodiments, $R^1$ is —CH$_3$. In some embodiments, $R^1$ is —C$_{1-6}$ aliphatic substituted 1, 2, 3, 4, 5, or 6 times by -halogen. In some embodiments, $R^1$ is —C$_{1-3}$ aliphatic substituted 1, 2, 3, 4, 5, or 6 times by -halogen. In some embodiments, $R^1$ is —C$_{1-6}$ aliphatic substituted 1, 2, 3, 4, 5, or 6 times by —F. In some embodiments, $R^1$ is —C$_{1-3}$ aliphatic substituted 1, 2, 3, 4, 5, or 6 times by —F. In some embodiments, $R^1$ is —CF$_3$. In some embodiments, $R^1$ is —C$_{1-6}$ aliphatic substituted 1, 2, 3, 4, 5, or 6 times by —CN. In some embodiments, $R^1$ is —C$_{1-6}$ aliphatic substituted 1, 2, 3, 4, 5, or 6 times by —NO$_2$.

In some embodiments, $R^7$ is —H, -halogen, —CN, —NO$_2$, —C$_{1-6}$ aliphatic, or —O—C$_{1-6}$ aliphatic, wherein each of —C$_{1-6}$ aliphatic and —O—C$_{1-6}$ aliphatic is substituted 0, 1, 2, 3, 4, 5, or 6 times by -halogen, —CN, or —NO$_2$. In some embodiments, $R^7$ is unsubstituted —O—C$_{1-6}$ aliphatic. In some embodiments, $R^7$ is —OCH$_3$. In some embodiments, $R^7$ is —O—C$_{1-6}$ aliphatic substituted 1, 2, 3, 4, 5, or 6 times by -halogen. In some embodiments, $R^7$ is —O—C$_{1-3}$ aliphatic substituted 1, 2, 3, 4, 5, or 6 times by -halogen. In some embodiments, $R^7$ is —O—C$_{1-6}$ aliphatic substituted 1, 2, 3, 4, 5, or 6 times by —F. In some embodiments, $R^7$ is —OCF$_3$. In some embodiments, $R^7$ is

In some embodiments, $R^7$ is —H, -halogen, —CN, —NO$_2$, or —C$_{1-6}$ aliphatic substituted 0, 1, 2, 3, 4, 5, or 6 times by -halogen, —CN, or —NO$_2$. In some embodiments, $R^7$ is —H. In some embodiments, $R^7$ is -halogen. In some embodiments, $R^7$ is —F. In some embodiments, $R^7$ is —Cl. In some embodiments, $R^7$ is —Br. In some embodiments, $R^7$ is —CN. In some embodiments, $R^7$ is —NO$_2$. In some embodiments, $R^7$ is unsubstituted —C$_{1-6}$ aliphatic. In some embodiments, $R^1$ is —CH$_3$. In some embodiments, $R^7$ is —C$_{1-6}$ aliphatic substituted 1, 2, 3, 4, 5, or 6 times by -halogen. In some embodiments, $R^7$ is —C$_{1-3}$ aliphatic substituted 1, 2, 3, 4, 5, or 6 times by -halogen. In some embodiments, $R^7$ is —C$_{1-6}$ aliphatic substituted 1, 2, 3, 4, 5, or 6 times by —F. In some embodiments, $R^7$ is —C$_{1-3}$ aliphatic substituted 1, 2, 3, 4, 5, or 6 times by —F. In some embodiments, $R^7$ is —CF$_3$. In some embodiments, $R^7$ is —C$_{1-6}$ aliphatic substituted 1, 2, 3, 4, 5, or 6 times by —CN. In some embodiments, $R^7$ is —C$_{1-6}$ aliphatic substituted 1, 2, 3, 4, 5, or 6 times by —NO$_2$.

In some embodiments, Ring A is

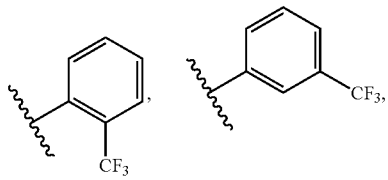

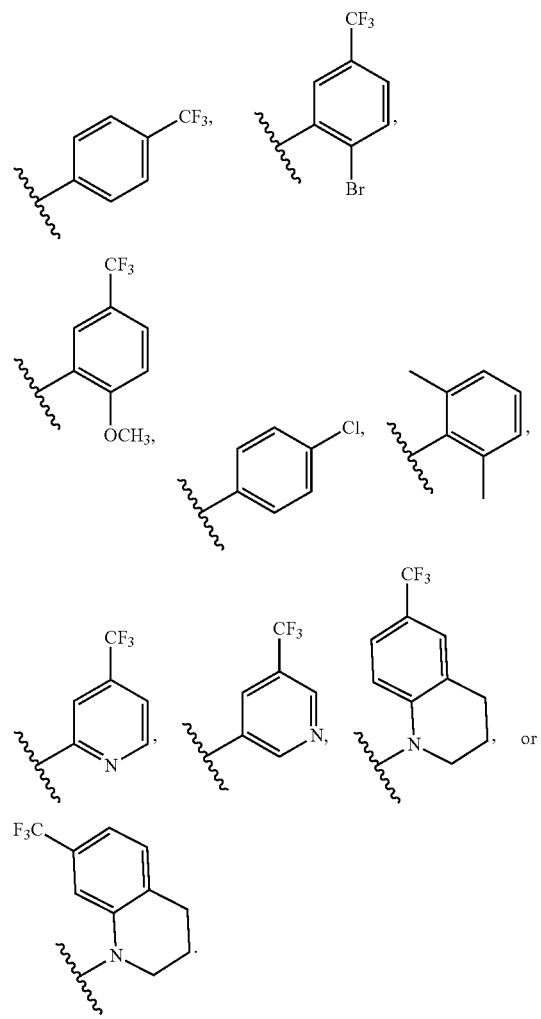

In some embodiments, Ring A is

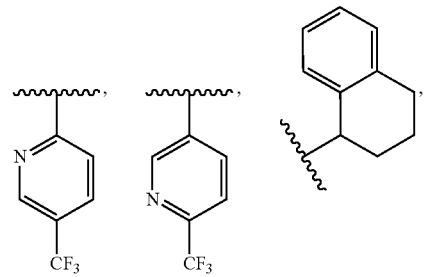

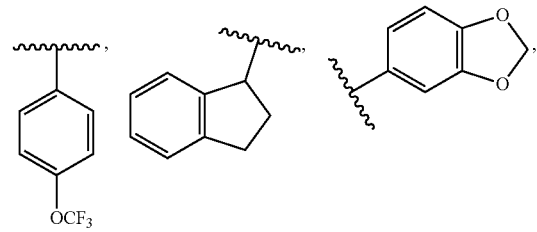

-continued

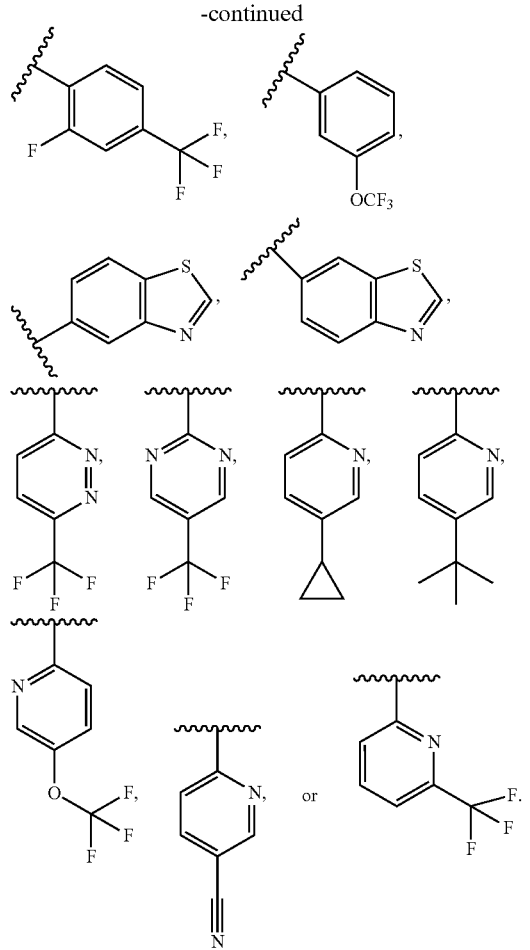

In some embodiments, Ring A is selected from those depicted in Table 1, below.

As defined generally above, Ring B is an optionally substituted ring selected from phenyl, a 4-, 5-, or 6-membered saturated or partially unsaturated monocyclic carbocyclic ring, a 4-, 5-, or 6-membered saturated or partially unsaturated monocyclic heterocyclic ring having 1-2 heteroatoms independently selected from nitrogen, oxygen, or sulfur, a 5-6 membered monocyclic heteroaromatic ring having 1, 2, 3, or 4 heteroatoms independently selected from nitrogen, oxygen, or sulfur, a 8-10 membered bicyclic aromatic ring, a 8-10 membered bicyclic heteroaromatic ring having 1-5 heteroatoms independently selected from nitrogen, oxygen, or sulfur.

In some embodiments, Ring B is optionally substituted phenyl. In some embodiments, Ring B is optionally substituted 4-, 5-, or 6-membered saturated or partially unsaturated monocyclic carbocyclic ring. In some embodiments, Ring B is optionally substituted 4-, 5-, or 6-membered saturated or partially unsaturated monocyclic heterocyclic ring having 1-2 heteroatoms independently selected from nitrogen, oxygen, or sulfur. In some embodiments, Ring B is optionally substituted 5-6 membered monocyclic heteroaromatic ring having 1, 2, 3, or 4 heteroatoms independently selected from nitrogen, oxygen, or sulfur. In some embodiments, Ring B is optionally substituted 8-10 membered bicyclic aromatic ring. In some embodiments, Ring B is optionally substituted 8-10 membered bicyclic heteroaromatic ring having 1-5 heteroatoms independently selected from nitrogen, oxygen, or sulfur.

In some embodiments, Ring B is optionally substituted phenyl or a 6-membered monocyclic heteroaromatic ring having 1 or 2 nitrogen.

In some embodiments, Ring B is optionally substituted

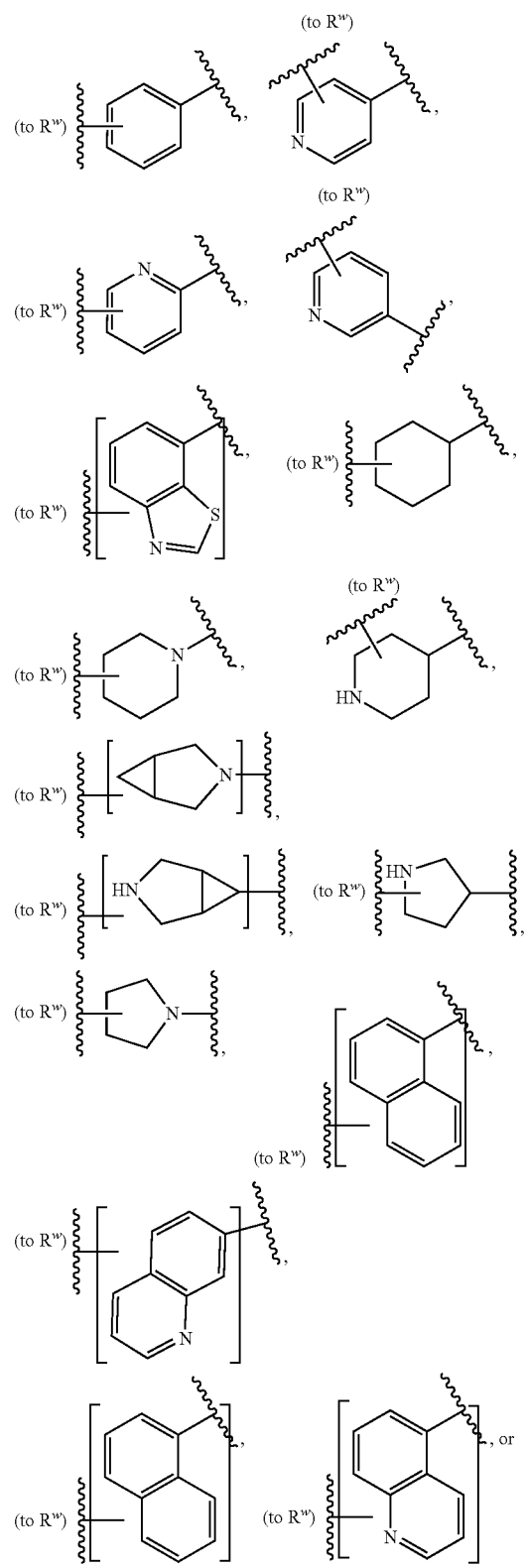

-continued

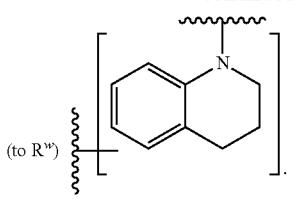

In some embodiments, Ring B is optionally substituted 1-4 times by halogen, —S(O)$_2$N(R)$_2$, —S(O)N(R)$_2$, —C(O)N(R)$_2$, —C(O)OR, —C$_{1-6}$ aliphatic, or —O—C$_{1-6}$ aliphatic, wherein each of —C$_{1-6}$ aliphatic and —O—C$_{1-6}$ aliphatic is independently substituted 0-6 times by halogen, —CN, or —NO$_2$.

In some embodiments, Ring B is optionally substituted 1-4 times by —F, —Cl, —Br—, —S(O)$_2$NHCH$_3$, —S(O)NHCH$_3$, —C(O)N(CH$_3$)$_2$, —C(O)NHCH$_3$, —C(O)OH, —C(O)OCH$_3$, —CH$_3$, —OCH$_3$, or —C(CH$_3$)$_3$.

In some embodiments, Ring B is

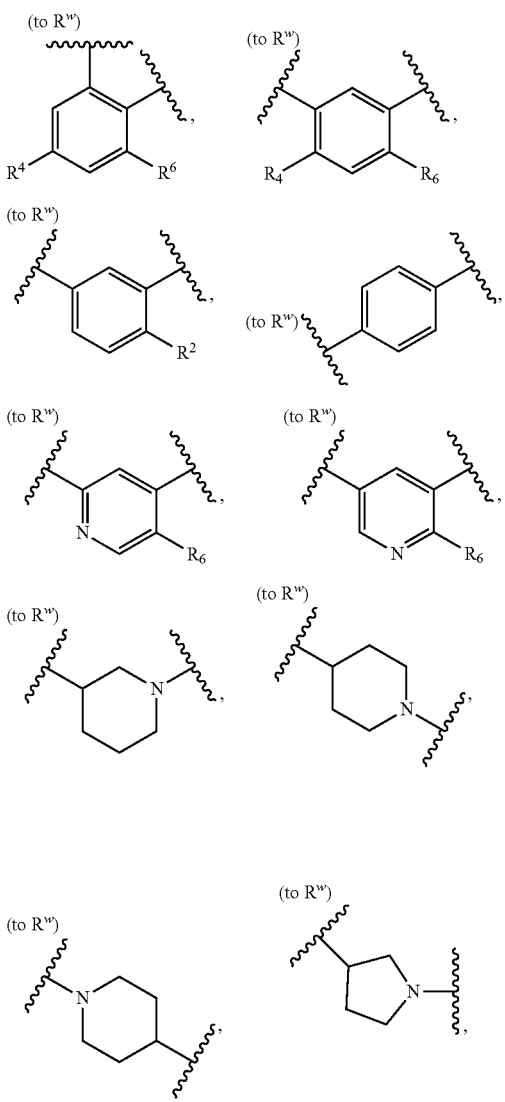

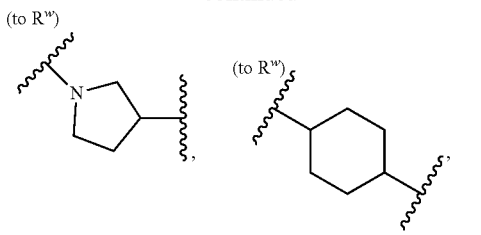

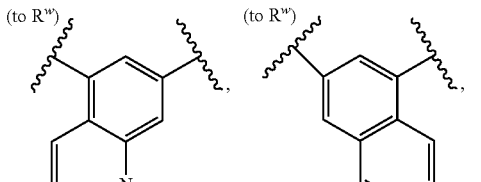

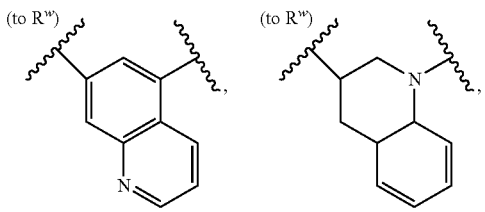

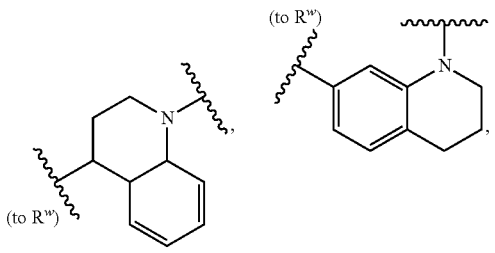

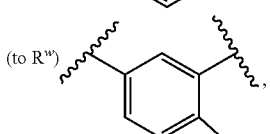

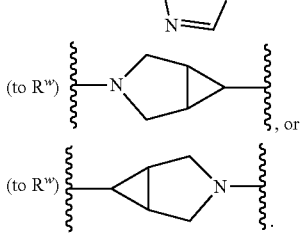

In some embodiments, Ring B is selected from those depicted in Table 1, below.

As defined generally above, R$^2$ is —H, or an optionally substituted 4-, 5-, or 6-membered ring having 1, 2, 3, or 4 heteroatoms independently selected from nitrogen, oxygen, or sulfur.

In some embodiments, R$^2$ is —H.

In some embodiments, R$^2$ is an optionally substituted 4-, 5-, or 6-membered ring having 1, 2, 3, or 4 heteroatoms independently selected from nitrogen, oxygen, or sulfur. In some embodiments, R$^2$ is a 4-, 5-, or 6-membered ring having 1, 2, 3, or 4 heteroatoms independently selected from nitrogen, oxygen, or sulfur, optionally substituted 1-3 times by —C$_{1-6}$ alkyl.

In some embodiments, $R^2$ is

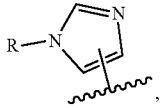, wherein R is as described herein. In some embodiments, $R^2$ is

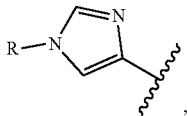, wherein R is as described herein.

In some embodiments, $R^2$ is

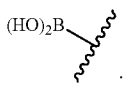.

In some embodiments, $R^2$ is

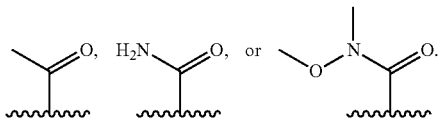

In some embodiments, $R^2$ is an optionally substituted 5-membered ring having 1, 2, 3, or 4 nitrogen. In some embodiments, $R^2$ is selected from

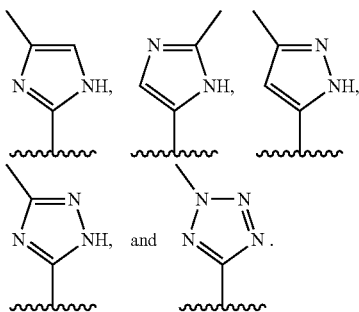

In some embodiments, $R^2$ is

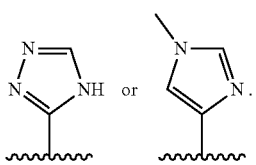

In some embodiments, $R^2$ is

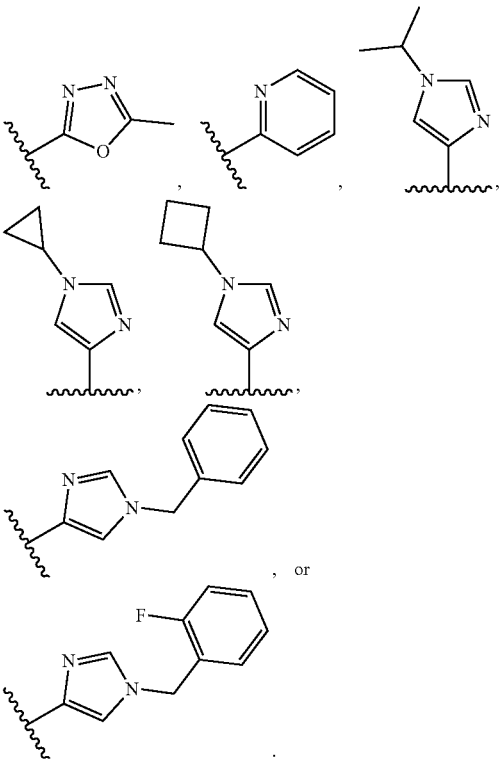

In some embodiments, $R^2$ is selected from those depicted in Table 1, below.

As defined generally above, in some embodiments, $R^3$ is —H.

In some embodiments, $R^3$ is

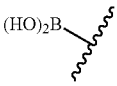.

In some embodiments, $R^3$ is

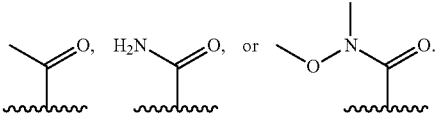

In some embodiments, $R^3$ is selected from those depicted in Table 1, below.

As defined generally above, $R^4$ is —H, halogen, —S(O)$_2$N(R)$_2$, —S(O)N(R)$_2$, or —C(O)N(R)$_2$.

In some embodiments, $R^4$ is —H, halogen, —S(O)$_2$N(R)$_2$, —S(O)N(R)$_2$, —C(O)N(R)$_2$, or —C(O)OR.

In some embodiments, $R^4$ is —H.

In some embodiments, $R^4$ is halogen. In some embodiments, $R^4$ is —F. In some embodiments, $R^4$ is —Cl. In some embodiments, $R^4$ is —Br.

In some embodiments, $R^4$ is —S(O)$_2$N(R)$_2$, —S(O)N(R)$_2$, or —C(O)N(R)$_2$. In some embodiments, $R^4$ is —S(O)$_2$N(R)$_2$. In some embodiments, $R^4$ is —S(O)N(R)$_2$. In some embodiments, $R^4$ is —C(O)N(R)$_2$. In some embodiments, $R^4$ is —S(O)$_2$NHCH$_3$.

In some embodiments, R⁴ is —S(O)NHCH₃, —C(O)N(CH₃)₂, —C(O)NHCH₃, —C(O)OH, or —C(O)OCH₃.

In some embodiments, R⁴ is

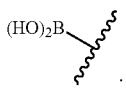

In some embodiments, R⁴ is

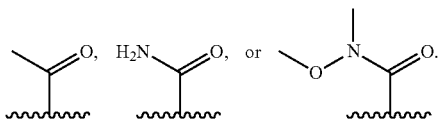

In some embodiments, R⁴ is selected from those depicted in Table 1, below.

As defined generally above, R⁶ is —H or —C₁₋₆ aliphatic substituted 0, 1, 2, 3, 4, 5, or 6 times by -halogen, —CN, or —NO₂.

In some embodiments, R⁶ is —H, -halogen, —CN, —NO₂, —C₁₋₆ aliphatic, —OC₁₋₆ aliphatic, or a 4-, 5-, or 6-membered ring having 1, 2, 3, or 4 heteroatoms independently selected from nitrogen, oxygen, or sulfur optionally substituted 1-3 times by —C₁₋₆ aliphatic or —OC₁₋₆ aliphatic, wherein each of —C₁₋₆ aliphatic and —OC₁₋₆ aliphatic is independently substituted 0, 1, 2, 3, 4, 5, or 6 times by -halogen, —CN, or —NO₂.

In some embodiments, R⁶ is —H. In some embodiments, R⁶ is —F. In some embodiments, R⁶ is —Cl. In some embodiments, R⁶ is —Br. In some embodiments, R⁶ is —CN. In some embodiments, R⁶ is —NO₂.

In some embodiments, R⁶ is —C₁₋₆ aliphatic, substituted 0, 1, 2, 3, 4, 5, or 6 times by -halogen, —CN, or —NO₂. In some embodiments, R⁶ is unsubstituted —C₁₋₆ aliphatic. In some embodiments, R⁶ is —CH₃. In some embodiments, R⁶ is —C₁₋₆ aliphatic substituted 1, 2, 3, 4, 5, or 6 times by -halogen, —CN, or —NO₂. In some embodiments, R⁶ is —C₁₋₆ aliphatic substituted 1, 2, 3, 4, 5, or 6 times by —F. In some embodiments, R⁶ is —C₁₋₃ aliphatic substituted 1, 2, 3, 4, 5, or 6 times by —F. In some embodiments, R⁶ is —CF₃.

In some embodiments, R⁶ is —OC₁₋₆ aliphatic, substituted 0, 1, 2, 3, 4, 5, or 6 times by -halogen, —CN, or —NO₂. In some embodiments, R⁶ is unsubstituted —OC₁₋₆ aliphatic. In some embodiments, R⁶ is —OCH₃. In some embodiments, R⁶ is —OC₁₋₆ aliphatic substituted 1, 2, 3, 4, 5, or 6 times by -halogen, —CN, or —NO₂. In some embodiments, R⁶ is —OC₁₋₆ aliphatic substituted 1, 2, 3, 4, 5, or 6 times by —F. In some embodiments, R⁶ is —OC₁₋₃ aliphatic substituted 1, 2, 3, 4, 5, or 6 times by —F. In some embodiments, R⁶ is —OCF₃.

In some embodiments, R⁶ is a 4-, 5-, or 6-membered ring having 1, 2, 3, or 4 heteroatoms independently selected from nitrogen, oxygen, or sulfur optionally substituted 1-3 times by —C₁₋₆ aliphatic or —OC₁₋₆ aliphatic, wherein each of —C₁₋₆ aliphatic and —OC₁₋₆ aliphatic is independently substituted 0, 1, 2, 3, 4, 5, or 6 times by -halogen, —CN, or —NO₂. In some embodiments, R⁶ is a 5-membered ring having 1, 2, 3, or 4 nitrogen optionally substituted 1-3 times by —C₁₋₆ aliphatic. In some embodiments, R⁶ is

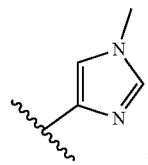

In some embodiments, R⁶ is selected from those depicted in Table 1, below.

As defined generally above, R^w is an optionally substituted 4-, 5-, or 6-membered ring having 1, 2, 3, or 4 heteroatoms independently selected from nitrogen, oxygen, or sulfur.

In some embodiments, R^w is an optionally substituted 4-, 5-, or 6-membered ring having 1, 2, 3, or 4 heteroatoms independently selected from nitrogen, oxygen, or sulfur. In some embodiments, R^w is a 4-, 5-, or 6-membered ring having 1, 2, 3, or 4 heteroatoms independently selected from nitrogen, oxygen, or sulfur, optionally substituted 1-3 times by —C₁₋₆ alkyl.

In some embodiments, R^w is

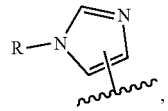

wherein R is as described herein. In some embodiments, R^w is

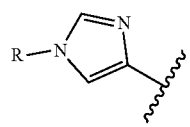

wherein R is as described herein.

In some embodiments, R^w is a 4-, 5-, or 6-membered ring having 1, 2, 3, or 4 heteroatoms independently selected from nitrogen, oxygen, or sulfur, optionally substituted 1-3 times by —C₁₋₆ alkyl. In some embodiments, R^w is an optionally substituted 5-membered ring having 1, 2, 3, or 4 nitrogen. In some embodiments, R^w is

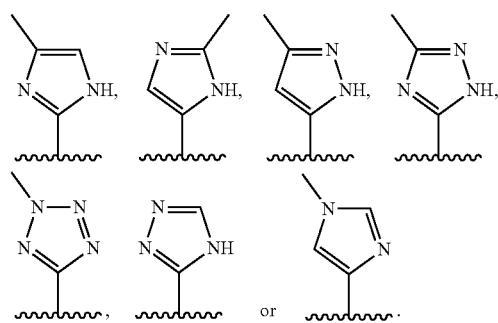

In some embodiments, $R^w$ is

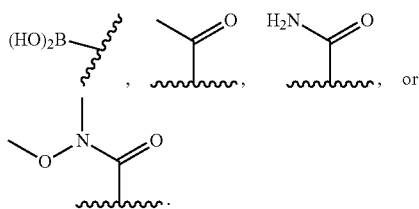

In some embodiments, $R^w$ is

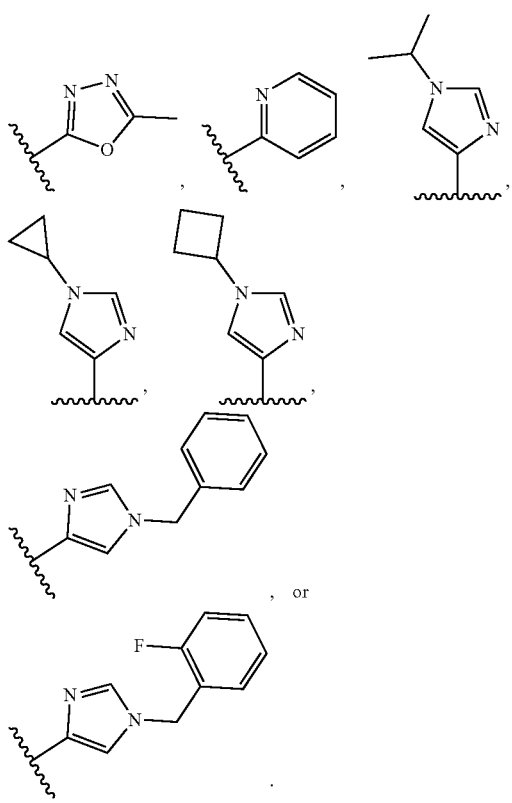

In some embodiments, $R^w$ is selected from those depicted in Table 1, below.

As defined generally above, R is independently —H or optionally substituted —$C_{1-6}$ aliphatic.

In some embodiments, R is —H.

In some embodiments, R is optionally substituted —$C_{1-6}$ aliphatic. In some embodiments, R is unsubstituted —$C_{1-6}$ aliphatic. In some embodiments, R is —$CH_3$. In some embodiments, R is —$C_{1-6}$ aliphatic substituted 1, 2, 3, 4, 5, or 6 times by -halogen, —CN, or —$NO_2$. In some embodiments, R is —$C_{1-6}$ aliphatic substituted 1, 2, 3, 4, 5, or 6 times by —F. In some embodiments, R is —$C_{1-3}$ aliphatic substituted 1, 2, 3, 4, 5, or 6 times by —F. In some embodiments, R is —$CF_3$.

In some embodiments, R is selected from those depicted in Table 1, below.

In some embodiments, a compound provided herein is capable of reversibly inhibiting a target protein, for example, TEAD, by interacting with an amino acid residue (such as cysteine, lysine, and histidine) present in the binding pocket of the protein. In some embodiments, a compound provided herein is capable of interacting with cysteine. In some embodiments, a compound provided herein is capable of interacting with serine. In some embodiments, a compound provided herein is capable of interacting with lysine. In some embodiments, a compound provided herein is capable of interacting with Cys359 of hTEAD1, Cys380 of hTEAD2, Cys368 of hTEAD3, and/or Cys367 of hTEAD4. In some embodiments, a compound provided herein is capable of interacting with Ser356 of hTEAD1, Ser345 and/or Ser377 of hTEAD2, Ser365 of hTEAD3, and/or Ser364 of hTEAD4. In some embodiments, a compound provided herein is capable of interacting with Lys336 of hTEAD1, Lys357 of hTEAD2, Lys345 of hTEAD3, and/or Lys344 of hTEAD4. Representative reference amino acid sequences of human TEAD1, human TEAD2, human TEAD3, and human TEAD4 include UniProt KB ID P28347-1 (SEQ ID NO: 1), UniProtKB ID Q15562 (SEQ ID NO: 2), UniProtKB ID Q99594 (SEQ ID NO: 3), and UniProtKB ID Q15561 (SEQ ID NO: 4), respectively. Below is the sequence alignments of TEAD coactivator binding domains, which is shown in Table 1 of "Targeting Transcriptional Enhanced Associate Domains (TEADs)," *J. Med. Chem.* 2018, 61, 5057-5072, the entire content of which is incorporated herein reference.

```
SEQ ID   hTEAD1  206WQGRSIGTTKLRLVEFSAFLEQQRDPDSYNKHLFVHIGHANHSYSDPLLESVDIRQIYDKFPEKKGGLKE275
NO: 5

SEQ ID   hTEAD2  218WQARGLGTARLQLVEFSAFVEPPDANDSYQRHLFVHISQHCPSPGAPPLESVDVRQIYDKFPEKKGGLRE287
NO: 6

SEQ ID   hTEAD3  215WQDRTIASSRLRLLEYSAFMEVQRDPDTYSKHLFVHIGQTNPAFSDPPLEANDVRQIYDKFPEKKGGLKE284
NO: 7

SEQ ID   hTEAD4  214WQGRSVASSKLWMLEFSAFLEQQQDPDTYNKHLFVHIGQSSPSYSDPYLEAVDIRQIYDKFPEKKGGLKD283
NO: 8

SEQ ID   hTEAD1  276LFGKGPQNAFFLVKFWADLNCNIQ-DDAGA--------FYGVTSQYESSENMTVTCSTKVCSFGKQVVEK336
NO: 5

SEQ ID   hTEAD2  288LYDRGPPHAFFLVKFWADLNWGPSGEEAGAGGSISSGGFYGVSSQYESLEHMTLTCSSKVCSFGKQVVEK357
NO: 6

SEQ ID   hTEAD3  285LYEKGPPNAFFLVKFWADLNSTIQ-EGPGA--------FYGVSSQYSSADSMTISVSTKVCSFGKQVVEK345
NO: 7
```

```
SEQ ID     hTEAD4  ²⁸⁴LFERGPSNAFFLVKFWADLNTNIE-DEGSS--------FYGVSSQYESPENMIITCSTKVCSFGKQVVEK³⁴⁴
NO: 8

SEQ ID     hTEAD1  ³³⁷VETEYARFENGRFVYRINRSPMCEYMINHFIHKLKHLPEKYMMNSVLENFTILLVVTNRDTQETLLCMACV⁴⁹⁶
NO: 5

SEQ ID     hTEAD2  ³⁵⁸VETERAQLEDGRFVYRLLRSPMCEYLVNFLHKLRQLPERYMMNSVLENFTILQVVTNRDTQELLLCTAYV⁴²⁷
NO: 6

SEQ ID     hTEAD3  ³⁴⁶VETEYARLENGRFVYRIHRSPMCEYMINFIHKLKHLPEKYMMNSVLENFTILQVVTSRDSQETLLVIAFV⁴¹⁵
NO: 7

SEQ ID     hTEAD4  ³⁴⁵VETEYARYENGHYSYRIHRSPLCEYMINFIHKLKHLPEKYMMNSVLENFTILQVVTNRDTQETLLCIAYV⁴¹⁴
NO: 8

SEQ ID     hTEAD1  ⁴⁰⁷FEVSNSEHGAQHHIYRLVKD⁴²⁶
NO: 5

SEQ ID     hTEAD2  ⁴²⁸FEVSTSERGAQHHIYRLVRD⁴⁴⁷
NO: 6

SEQ ID     hTEAD3  ⁴¹⁶FEVSTSEHGAQHHVYKLVKD⁴³⁵
NO: 7

SEQ ID     hTEAD4  ⁴¹⁵FEVSASEHGAQHHIYRLVKE⁴³⁴
NO: 8
```

In some embodiments, the present invention provides a compound of Formula (II):

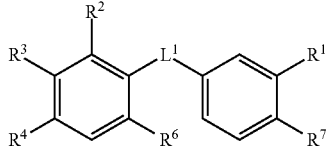

(II)

or a pharmaceutically acceptable salt thereof, wherein the variables are as described herein.

In some embodiments, the present invention provides a compound of Formula (II), or a pharmaceutically acceptable salt thereof, wherein:
$L^1$ is —O— or —S—;
$R^1$ is —$C_{1-6}$ aliphatic substituted 0, 1, 2, 3, 4, 5, or 6 times by halogen;
$R^2$ is an optionally substituted 5-membered aromatic ring having 1, 2, 3, or 4 nitrogen;
$R^3$ is —H;
$R^4$ is —$S(O)_2N(R)_2$; —$S(O)N(R)_2$, or —$C(O)N(R)_2$, each R independently is selected —H and optionally substituted —$C_{1-6}$ aliphatic;
$R^6$ is —H or —$C_{1-6}$ aliphatic substituted 0, 1, 2, 3, 4, 5, or 6 times by halogen; and
$R^7$ is —H.

In some embodiments, the present invention provides a compound of Formula (II), or a pharmaceutically acceptable salt thereof, wherein:
$L^1$ is —NH—;
$R^1$ is —$C_{1-6}$ aliphatic substituted 1, 2, 3, 4, 5, or 6 times by halogen;
$R^2$ is an optionally substituted 5-membered aromatic ring having 1, 2, 3, or 4 nitrogen;
$R^3$ is —H;
$R^4$ is —$S(O)_2N(R)_2$, —$S(O)N(R)_2$, or —$C(O)N(R)_2$, each R independently is selected from —H and optionally substituted —$C_{1-6}$ aliphatic;
$R^6$ is —$C_{1-6}$ aliphatic; and
$R^7$ is —H.

In some embodiments, the present invention provides a compound of Formula III:

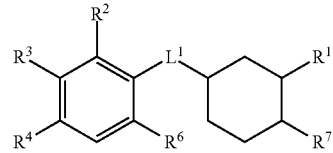

III or a pharmaceutically acceptable salt thereof, wherein the variables are as described herein.

In some embodiments, the present invention provides a compound of Formula (IV):

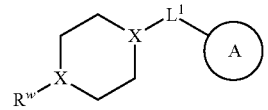

IV or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (IVa) or (IVb):

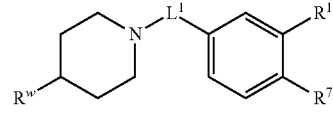

IVa

-continued

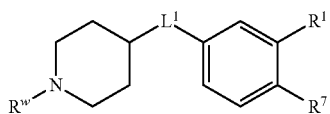
IVb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (V):

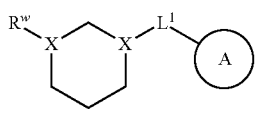
V or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (Va) or (Vb):

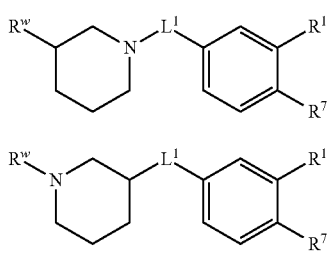
Va

Vb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VI):

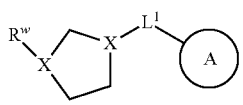
VI or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIa) or (VIb):

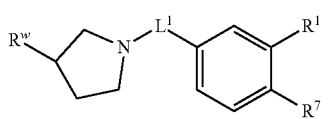
VIa

-continued

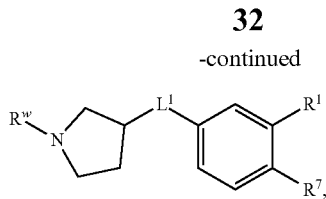
VIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VII):

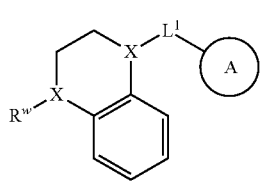
VII or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIIa) or (VIIb):

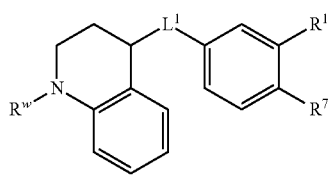
VIIa

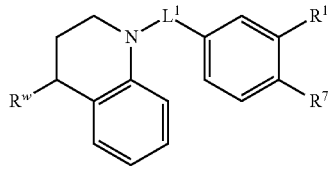
VIIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (VIII):

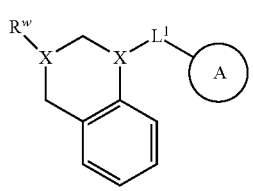
VIII or a pharmaceutically acceptable salt thereof, wherein each of X is independently C or N; and each of Ring A, $R^w$, and $L^1$ is as defined above and described in embodiments herein, both singly and in combination.

In some embodiments, the present invention provides a compound of Formula (VIIIa) or (VIIIb):

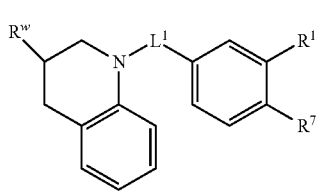

VIIIa

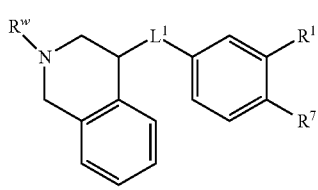

VIIIb or a pharmaceutically acceptable salt thereof, wherein each of $R^1$, $R^7$, $R^w$, and $L^1$ is as defined above and described in embodiments herein, both singly and in combination.

In some embodiments, the present invention provides a compound of Formula (I'), or a pharmaceutically acceptable salt thereof, wherein Ring A is phenyl, a 6-membered monocyclic heteroaromatic ring having 1 or 2 nitrogen, or a 10-membered bicyclic heteroaromatic ring having 1-2 nitrogen; Ring B is phenyl or a 6-membered monocyclic heteroaromatic ring having 1 or 2 nitrogen; and each of $R^w$ and $L^1$ is as defined above and described in embodiments herein, both singly and in combination.

In some embodiments, the present invention provides a compound of Formula (IXa-1) or (IXa-2):

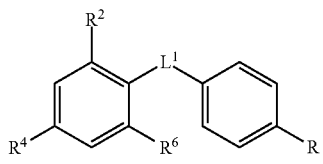

IXa-1

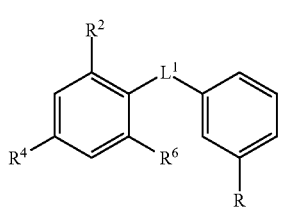

IXa-2 or a pharmaceutically acceptable salt thereof, wherein $L^1$ is a $C_{2-6}$ bivalent straight or branched hydrocarbon chain wherein 1 methylene unit of the chain is replaced with —N(R)—, and each of $R^2$, $R^4$, $R^6$, and R is as defined above and described in embodiments herein, both singly and in combination.

In some embodiments, the present invention provides a compound of Formula (Xa-1) or (Xa-2):

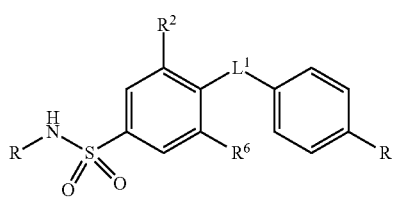

Xa-1

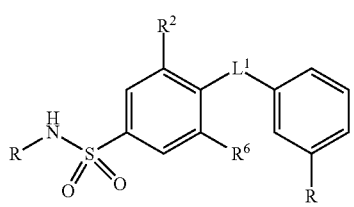

Xa-2 or a pharmaceutically acceptable salt thereof, wherein $L^1$ is a $C_{2-6}$ bivalent straight or branched hydrocarbon chain wherein 1 methylene unit of the chain is replaced with —N(R)—, and each of $R^2$, $R^6$, and R is as defined above and described in embodiments herein, both singly and in combination.

In some embodiments, the present invention provides a compound of Formula (XIa-1) or (XIa-2):

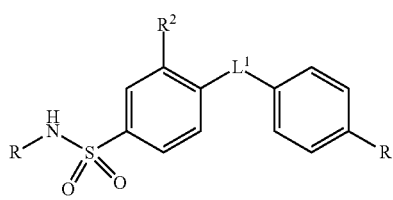

XIa-1

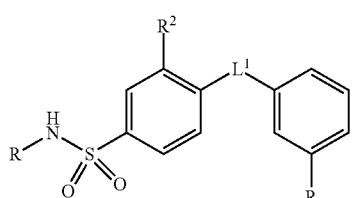

XIa-2 or a pharmaceutically acceptable salt thereof, wherein $L^1$ is a $C_{2-6}$ bivalent straight or branched hydrocarbon chain wherein 1 methylene unit of the chain is replaced with —NH—, each of $R^2$ and R is as defined above and described in embodiments herein, both singly and in combination.

In some embodiments, the present invention provides a compound of Formula (XIIa-1) or (XIIa-2):

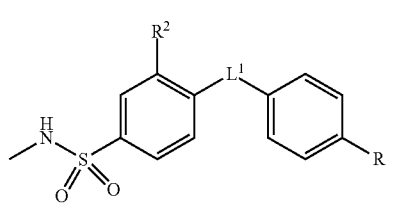

XIIa-1

-continued

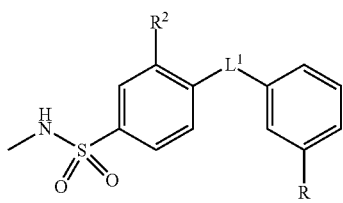

XIIa-2 or a pharmaceutically acceptable salt thereof, wherein $L^1$ is a $C_{2-6}$ bivalent straight or branched hydrocarbon chain wherein 1 methylene unit of the chain is replaced with —NH—, R is —$C_{1-3}$ aliphatic substituted 1, 2, 3, 4, 5, or 6 times by —F, and $R^2$ is as defined above and described in embodiments herein.

In some embodiments, the present invention provides a compound of Formula (XIIIa-1) or (XIIIa-2):

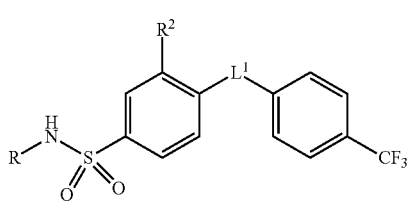

XIIIa-1

XIIIa-2 or a pharmaceutically acceptable salt thereof, wherein $L^1$ is a $C_{2-6}$ bivalent straight hydrocarbon chain wherein 1 methylene unit of the chain is replaced with —NH—, R is optionally substituted —$C_{1-6}$ aliphatic, and $R^2$ is as defined above and described in embodiments herein.

In some embodiments, the present invention provides a compound of Formula (XIVa-1) or (XIVa-2):

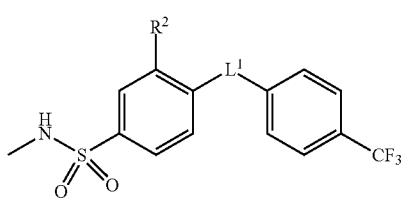

XIVa-1

XIVa-2 or a pharmaceutically acceptable salt thereof, wherein $L^1$ is a $C_{2-6}$ bivalent straight hydrocarbon chain wherein 1 methylene unit of the chain is replaced with —NH—, and $R^2$ is as defined above and described in embodiments herein.

In some embodiments, the present invention provides a compound of Formula (XVa-1) or (XVa-2):

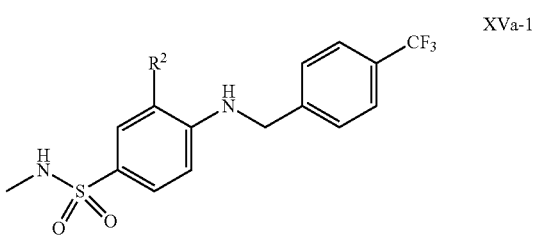

XVa-1

XVa-2 or a pharmaceutically acceptable salt thereof, wherein $R^2$ is an optionally substituted 5-membered ring having 1, 2, 3, or 4 nitrogen.

In some embodiments, the present invention provides a compound of Formula (XVIa-1) or (XVIa-2):

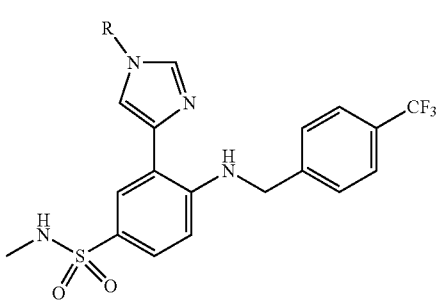

(XVIa-1)

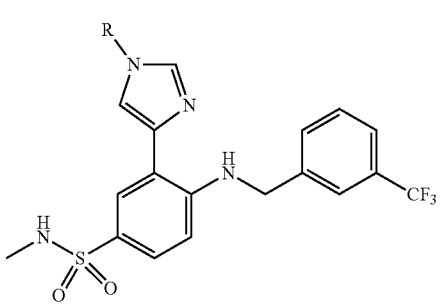

(XVIa-2)

or a pharmaceutically acceptable salt thereof, wherein R is as defined above and described in embodiments herein.

In some embodiments, the present invention provides a compound of Formula (IXb) or (IXc):

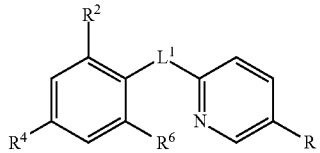

IXb

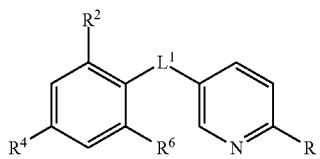

IXc or a pharmaceutically acceptable salt thereof, wherein $L^1$ is a $C_{1-6}$ bivalent straight or branched hydrocarbon chain wherein 1 methylene unit of the chain is replaced with —N(R)—, and each of $R^2$, $R^4$, $R^6$, and R is as defined above and described in embodiments herein, both singly and in combination.

In some embodiments, the present invention provides a compound of Formula (Xb) or (Xc):

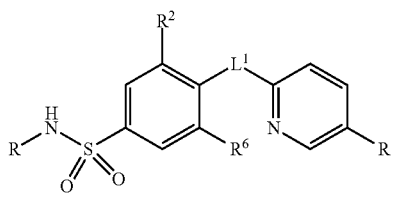

Xb

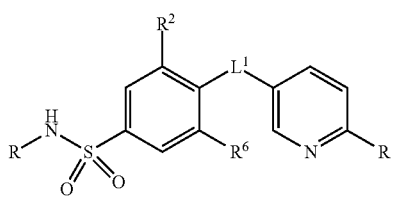

Xc or a pharmaceutically acceptable salt thereof, wherein $L^1$ is a $C_{1-6}$ bivalent straight or branched hydrocarbon chain wherein 1 methylene unit of the chain is replaced with —N(R)—, and each of $R^2$, $R^6$, and R is as defined above and described in embodiments herein, both singly and in combination.

In some embodiments, the present invention provides a compound of Formula (XIb) or (XIc):

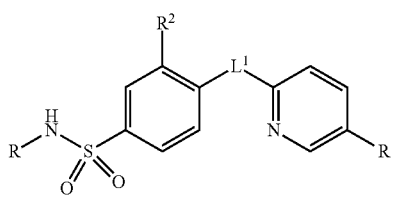

XIb

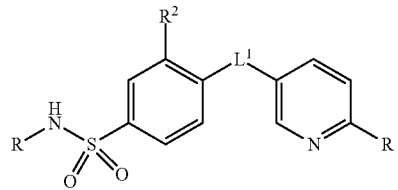

XIc or a pharmaceutically acceptable salt thereof, wherein $L^1$ is a $C_{1-6}$ bivalent straight or branched hydrocarbon chain wherein 1 methylene unit of the chain is replaced with —NH—, each of $R^2$ and R is as defined above and described in embodiments herein, both singly and in combination.

In some embodiments, the present invention provides a compound of Formula (XIIb) or (XIIc):

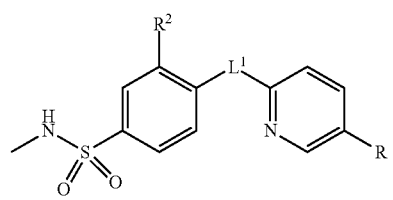

XIIb

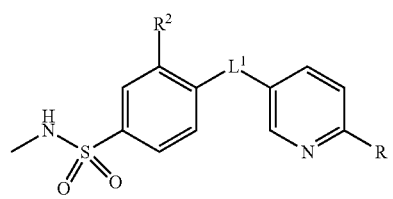

XIIc or a pharmaceutically acceptable salt thereof, wherein $L^1$ is a $C_{1-6}$ bivalent straight or branched hydrocarbon chain wherein 1 methylene unit of the chain is replaced with —NH—, R is —$C_{1-3}$ aliphatic substituted 1, 2, 3, 4, 5, or 6 times by —F, and $R^2$ is as defined above and described in embodiments herein.

In some embodiments, the present invention provides a compound of Formula (XIIIb) or (XIIIc):

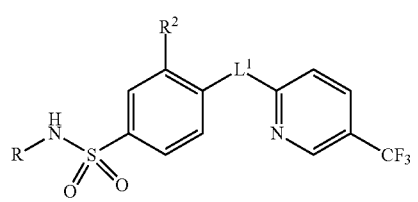

XIIIb

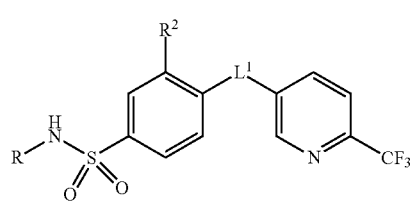

XIIIc or a pharmaceutically acceptable salt thereof, wherein $L^1$ is a $C_{1-6}$ bivalent straight hydrocarbon chain wherein 1 methylene unit of the chain is replaced with —NH—, R is optionally substituted —C$_{1-6}$ aliphatic, and R$^2$ is as defined above and described in embodiments herein.

In some embodiments, the present invention provides a compound of Formula (XIVb) or (XIVc):

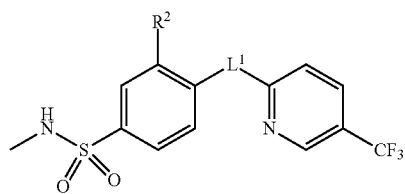

XIVb

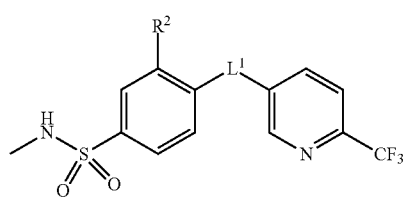

XIVc or a pharmaceutically acceptable salt thereof, wherein L is a C$_{1-6}$ bivalent straight hydrocarbon chain wherein 1 methylene unit of the chain is replaced with —NH—, and R$^2$ is as defined above and described in embodiments herein.

In some embodiments, the present invention provides a compound of Formula (XVb) or (XVc):

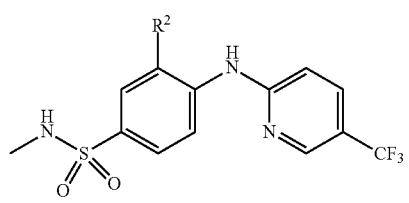

XVb

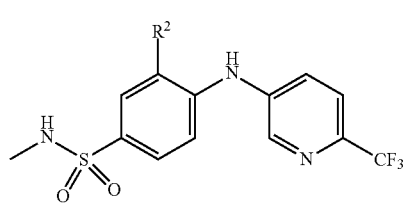

XVc or a pharmaceutically acceptable salt thereof, wherein R$^2$ is an optionally substituted 5-membered ring having 1, 2, 3, or 4 nitrogen.

In some embodiments, the present invention provides a compound of Formula (XVIb) or (XVIc):

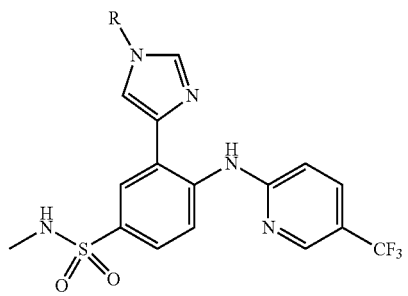

XVIb

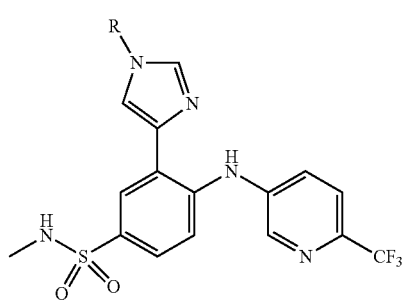

XVIc or a pharmaceutically acceptable salt thereof, wherein R is as defined above and described in embodiments herein.

Exemplary compounds of the invention are set forth in Table 1, below.

TABLE 1

Exemplary Compounds

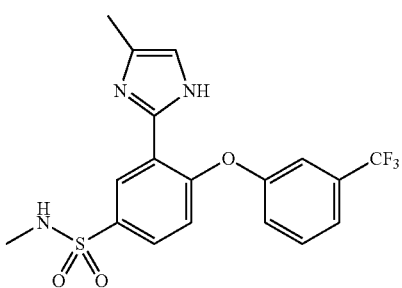 [SMILES: CNS(=O)(=O)c1ccc(Oc2cccc(C(F)(F)F)c2)c(-c2nc(C)c[nH]2)c1]

I-1

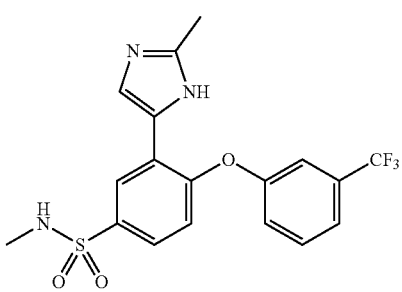 [SMILES: CNS(=O)(=O)c1ccc(Oc2cccc(C(F)(F)F)c2)c(-c2cnc(C)[nH]2)c1]

I-2

TABLE 1-continued
Exemplary Compounds
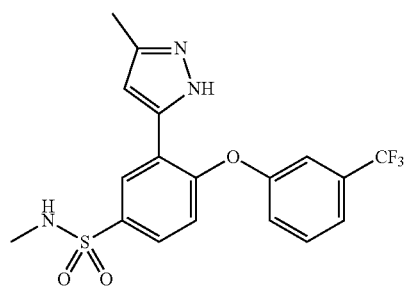 [SMILES: CNS(=O)(=O)c1ccc(Oc2cccc(C(F)(F)F)c2)c(-c2cc(C)n[nH]2)c1] I-3
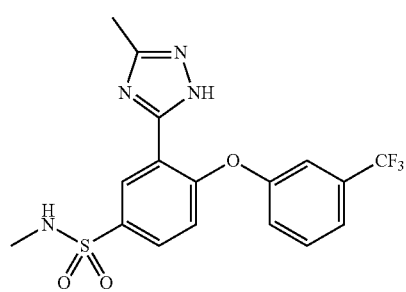 [SMILES: CNS(=O)(=O)c1ccc(Oc2cccc(C(F)(F)F)c2)c(-c2nc(C)n[nH]2)c1] I-4
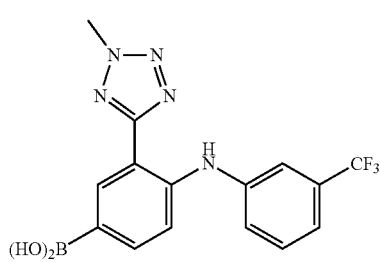 [SMILES: Cn1nnc(-c2cc(B(O)O)ccc2Nc2cccc(C(F)(F)F)c2)n1] I-5
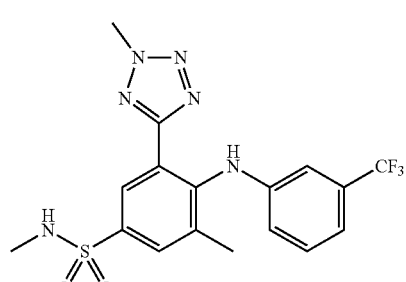 I-6
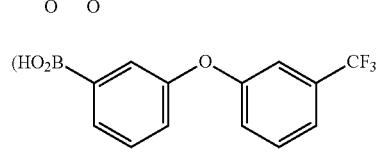 I-7
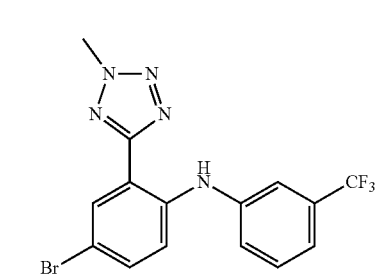 [SMILES: Cn1nnc(-c2cc(Br)ccc2Nc2cccc(C(F)(F)F)c2)n1] I-8
TABLE 1-continued
Exemplary Compounds
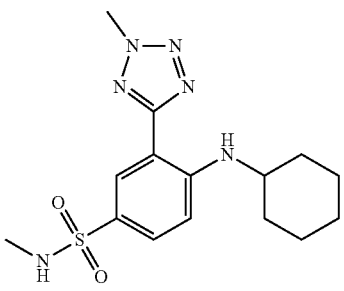 [SMILES: CNS(=O)(=O)c1ccc(NC2CCCCC2)c(-c2nnn(C)n2)c1] I-9
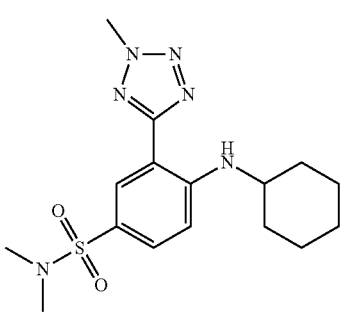 [SMILES: CN(C)S(=O)(=O)c1ccc(NC2CCCCC2)c(-c2nnn(C)n2)c1] I-10
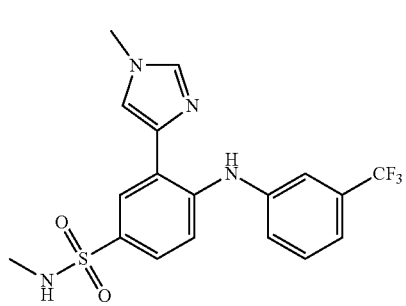 [SMILES: CNS(=O)(=O)c1ccc(Nc2cccc(C(F)(F)F)c2)c(-c2cn(C)cn2)c1] I-11
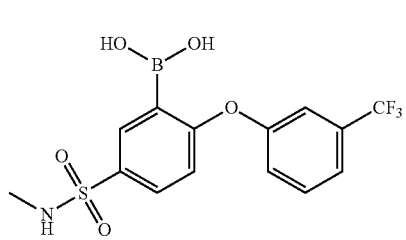 [SMILES: CNS(=O)(=O)c1ccc(Oc2cccc(C(F)(F)F)c2)c(B(O)O)c1] I-12
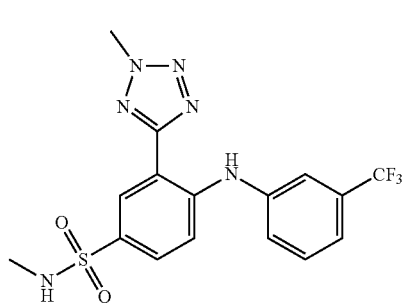 [SMILES: CNS(=O)(=O)c1ccc(Nc2cccc(C(F)(F)F)c2)c(-c2nnn(C)n2)c1] I-13

TABLE 1-continued

Exemplary Compounds

I-14, I-15, I-16, I-17, I-18, I-19, I-20, I-21, I-22, I-23, I-24

TABLE 1-continued
Exemplary Compounds
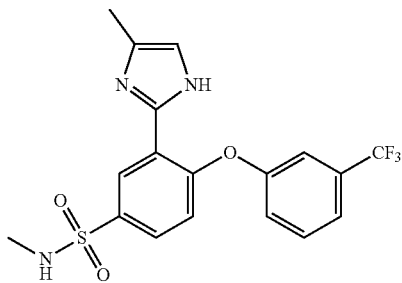 [SMILES: CNS(=O)(=O)c1ccc(Oc2cccc(C(F)(F)F)c2)c(-c2nc(C)c[nH]2)c1]
I-25
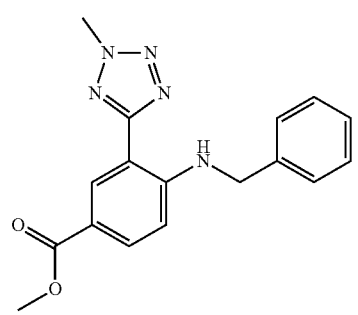 [SMILES: COC(=O)c1ccc(NCc2ccccc2)c(-c2nnn(C)n2)c1]
I-26
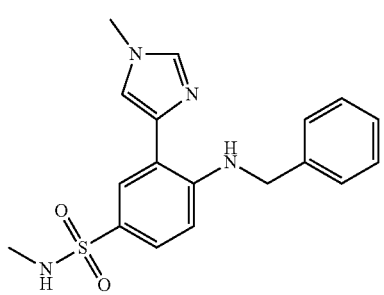 [SMILES: CNS(=O)(=O)c1ccc(NCc2ccccc2)c(-c2cn(C)cn2)c1]
I-27
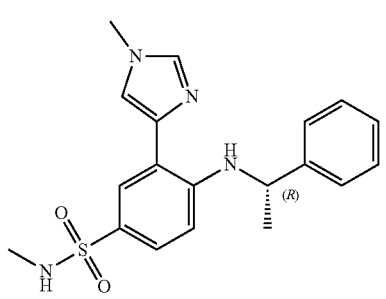
I-28
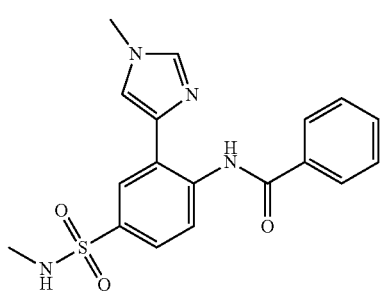 [SMILES: CNS(=O)(=O)c1ccc(NC(=O)c2ccccc2)c(-c2cn(C)cn2)c1]
I-29
TABLE 1-continued
Exemplary Compounds
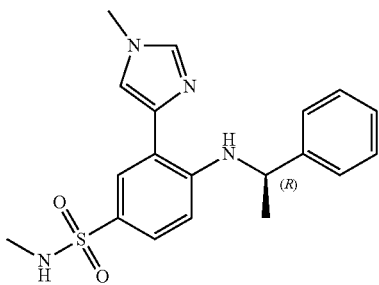
I-30
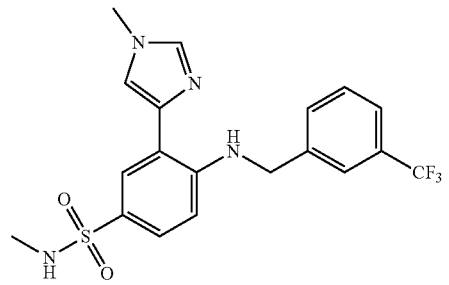 [SMILES: CNS(=O)(=O)c1ccc(NCc2cccc(C(F)(F)F)c2)c(-c2cn(C)cn2)c1]
I-31
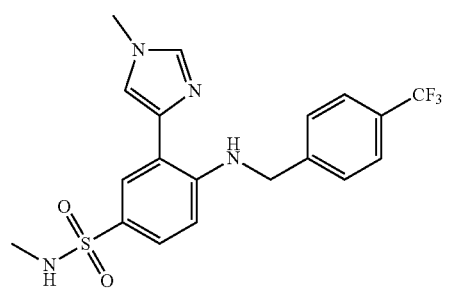 [SMILES: CNS(=O)(=O)c1ccc(NCc2ccc(C(F)(F)F)cc2)c(-c2cn(C)cn2)c1]
I-32
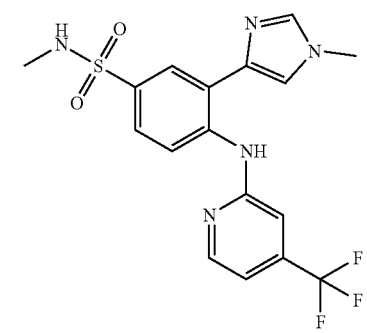 [SMILES: CNS(=O)(=O)c1ccc(Nc2cc(C(F)(F)F)ccn2)c(-c2cn(C)cn2)c1]
I-33
I-34

TABLE 1-continued

Exemplary Compounds

I-35, I-36, I-37, I-38, I-39, I-40, I-41, I-42, I-43, I-44

TABLE 1-continued
Exemplary Compounds

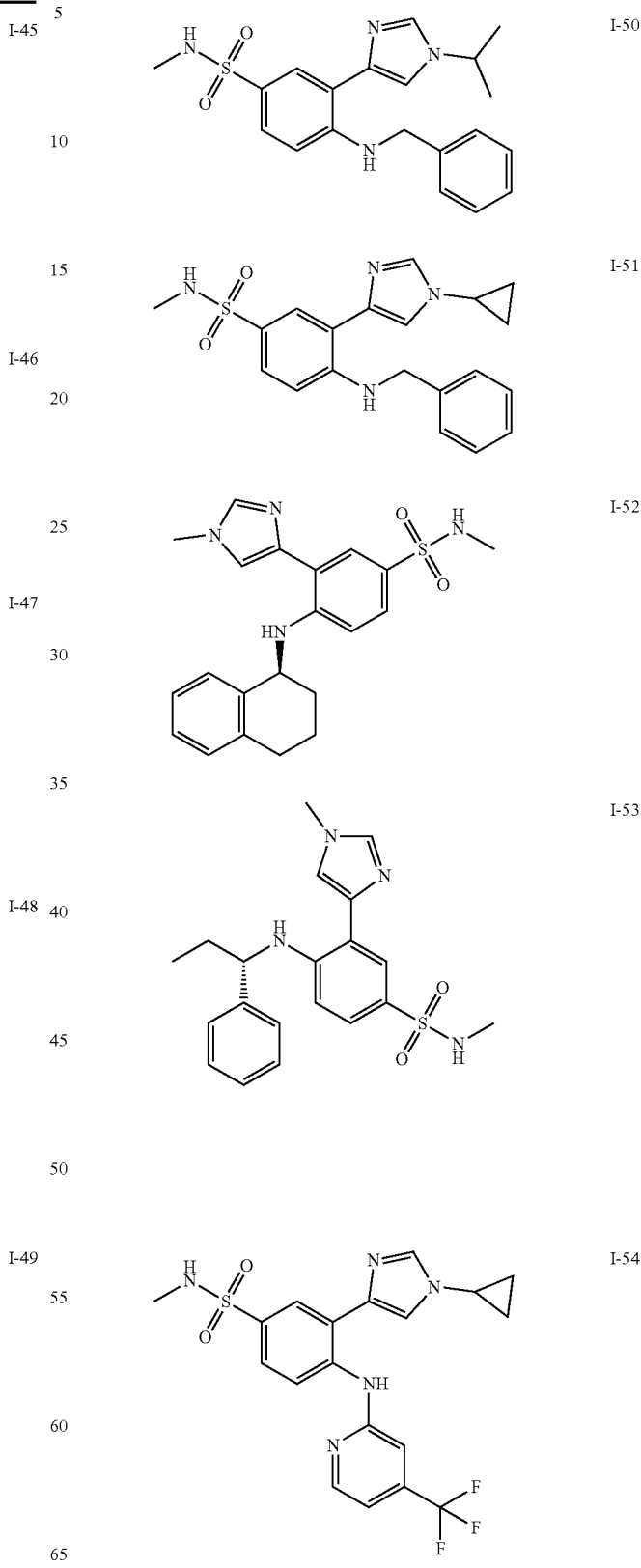

TABLE 1-continued

Exemplary Compounds

I-55, I-56, I-57, I-58, I-59, I-60, I-61, I-62, I-63, I-64

TABLE 1-continued
Exemplary Compounds
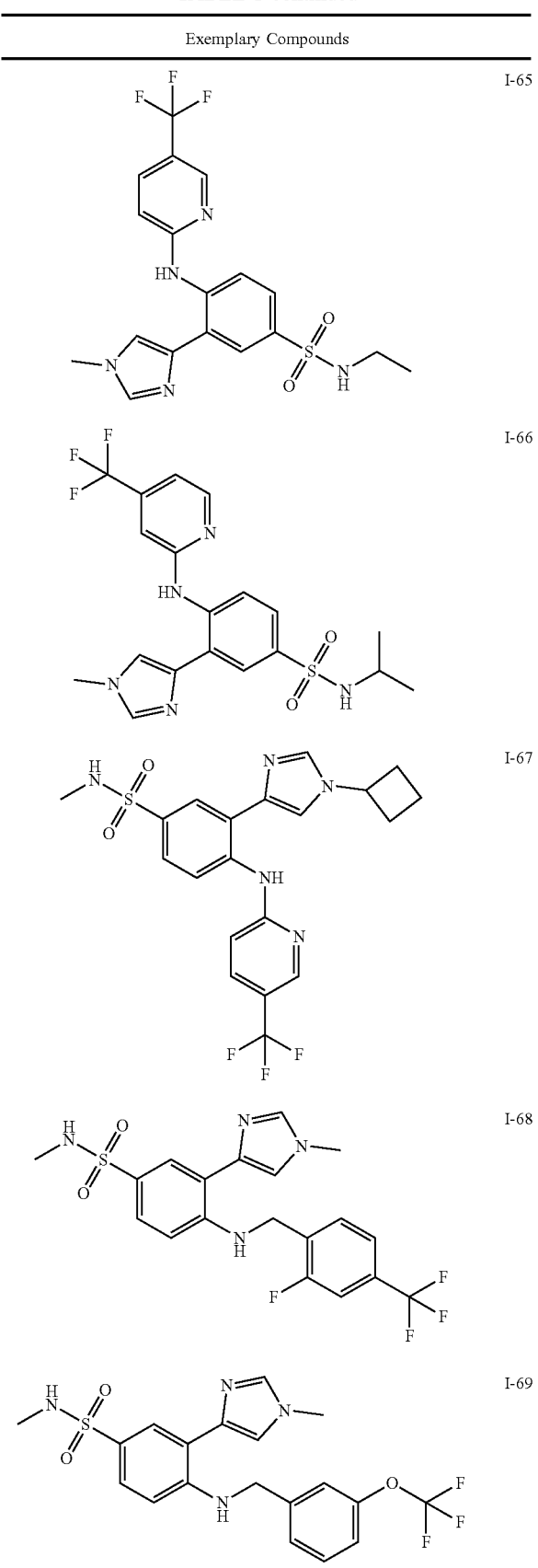
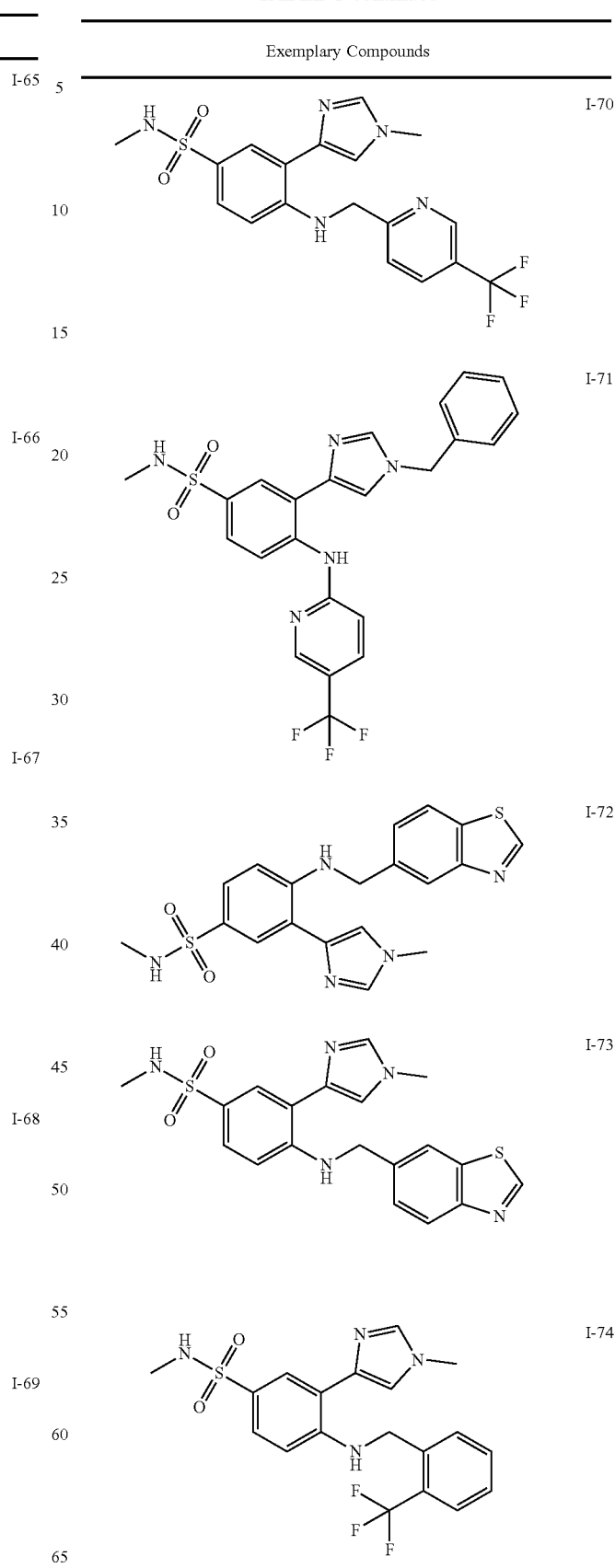

TABLE 1-continued
Exemplary Compounds
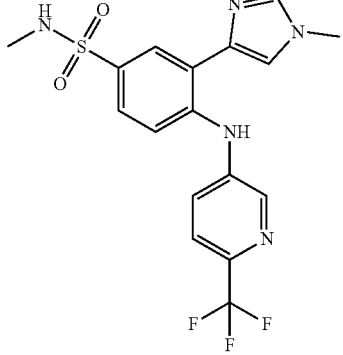 I-75
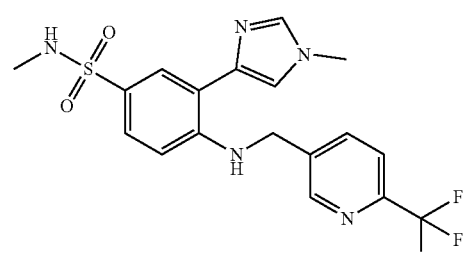 I-76
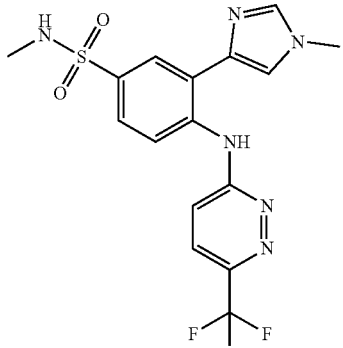 I-77
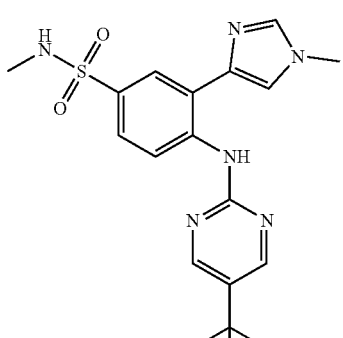 I-78
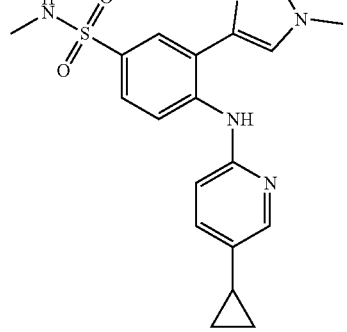 I-79
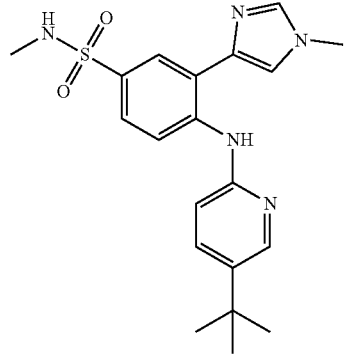 I-80
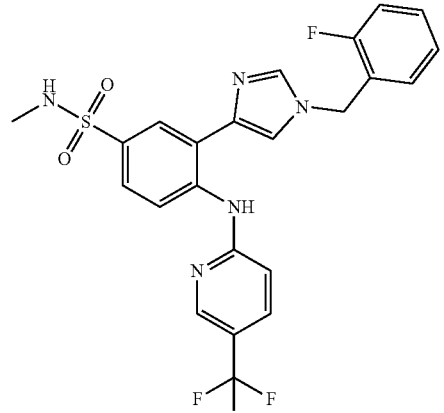 I-81
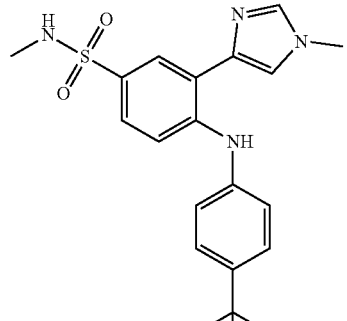 I-82

TABLE 1-continued

Exemplary Compounds

I-83, I-84, I-85, I-86, I-87, I-88, I-89, I-90

TABLE 1-continued
Exemplary Compounds
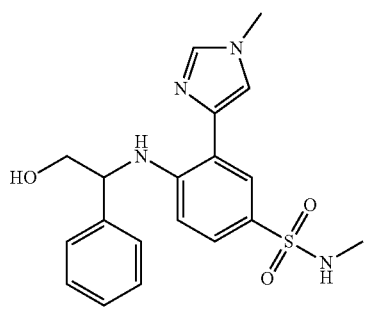 [SMILES: CNS(=O)(=O)c1ccc(N[C@@H](CO)c2ccccc2)c(-c2cn(C)cn2)c1]
I-91
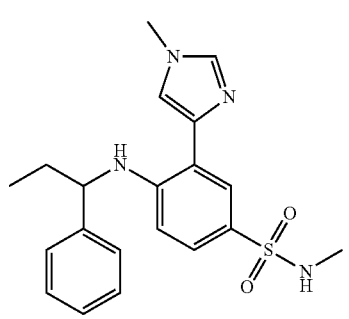 [SMILES: CC[C@H](Nc1ccc(S(=O)(=O)NC)cc1-c1cn(C)cn1)c1ccccc1]
I-92
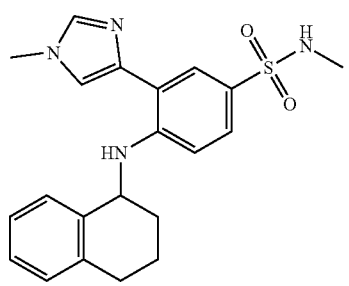 [SMILES: CNS(=O)(=O)c1ccc(NC2CCCc3ccccc32)c(-c2cn(C)cn2)c1]
I-93
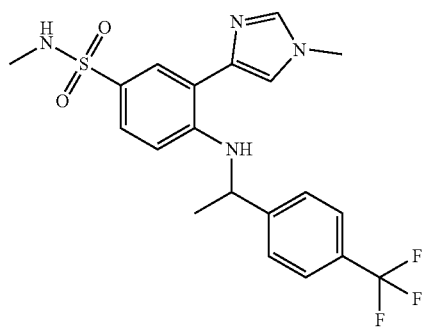 [SMILES: CNS(=O)(=O)c1ccc(NC(C)c2ccc(C(F)(F)F)cc2)c(-c2cn(C)cn2)c1]
I-94
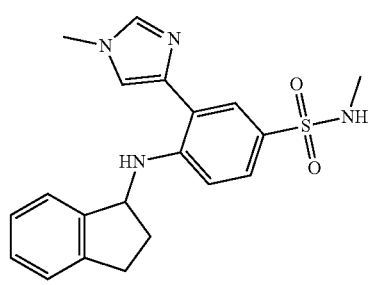 [SMILES: CNS(=O)(=O)c1ccc(NC2CCc3ccccc32)c(-c2cn(C)cn2)c1]
I-95
TABLE 1-continued
Exemplary Compounds
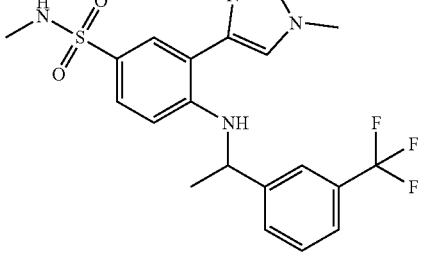
I-96
In some embodiments, the present invention provides a compound set forth in Table 1, above, or a pharmaceutically acceptable salt thereof.
In some embodiments, a compound of the present invention is not a compound selected from:
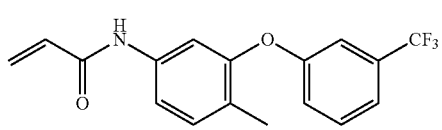
P-1
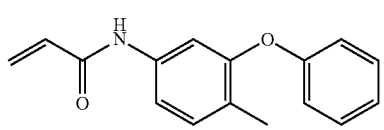
P-2
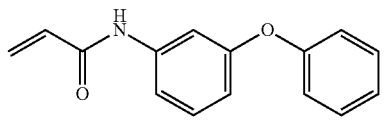
P-3
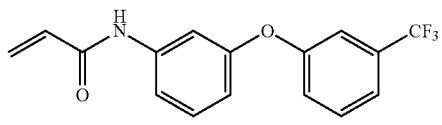
P-4
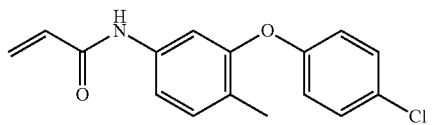
P-5
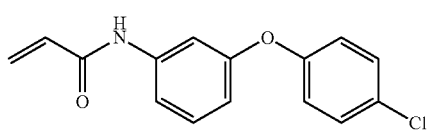
P-6
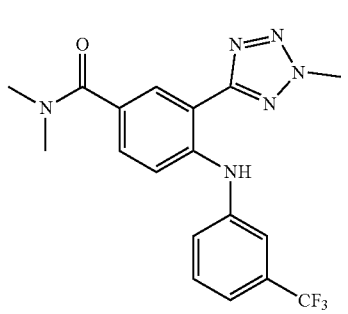
P-7

-continued
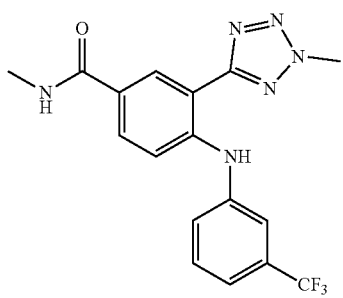
P-8
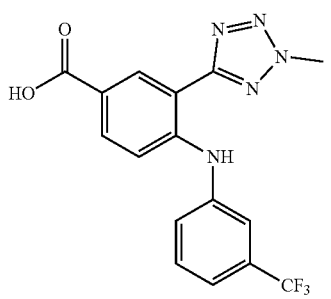
P-9
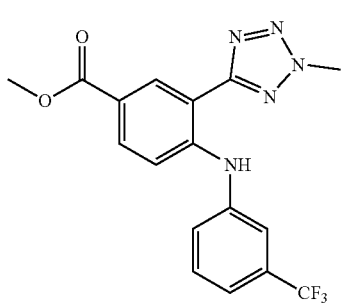
P-10
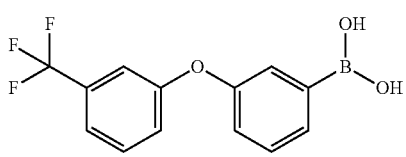
P-11
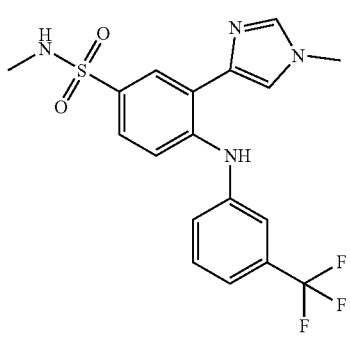
P-12
-continued
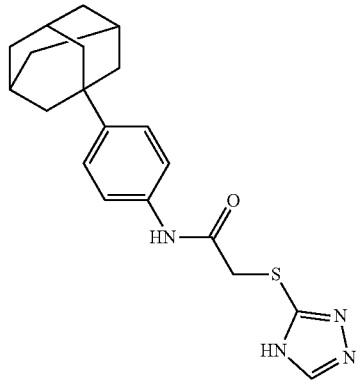
P-13
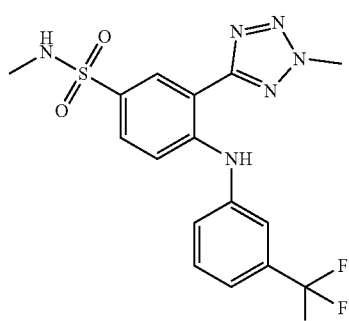
P-14
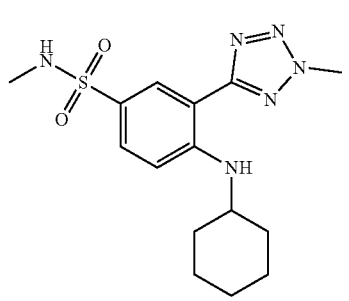
P-15
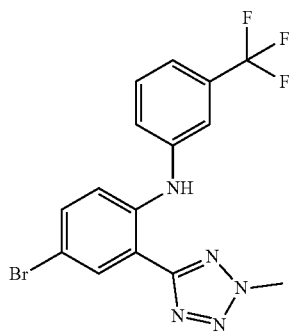
P-16
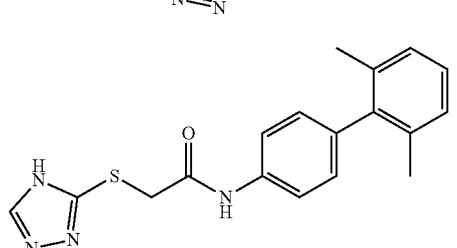
P-17
The compounds of this invention can be prepared or isolated in general by synthetic and/or semi-synthetic methods known to those skilled in the art for analogous compounds and by methods described in detail in the Examples, herein. In some embodiments, the present invention provides an intermediate compound described in the Examples, or a salt thereof.

4. Uses, Formulation and Administration

Pharmaceutically Acceptable Compositions

According to another embodiment, the invention provides a pharmaceutical composition comprising a compound of this invention or a pharmaceutically acceptable derivative thereof and a pharmaceutically acceptable carrier, adjuvant, or vehicle. The amount of compound in compositions of this invention is such that is effective to measurably inhibit TEAD, or a variant or mutant thereof, in a biological sample or in a patient. In certain embodiments, the amount of compound in compositions of this invention is such that is effective to measurably inhibit TEAD, or a variant or mutant thereof, in a biological sample or in a patient. In certain embodiments, a composition of this invention is formulated for administration to a patient in need of such composition. In some embodiments, a composition of this invention is formulated for oral administration to a patient.

The terms "patient" or "subject" as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of TEAD, or a variant or mutant thereof.

Compositions of the present invention can be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention can be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium.

For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

Pharmaceutically acceptable compositions of this invention can be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, pharmaceutically acceptable compositions of this invention can be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, provided pharmaceutically acceptable compositions can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations can be administered with or without food. In some embodiments, pharmaceutically acceptable compositions of this invention are administered without food. In other embodiments, pharmaceutically acceptable compositions of this invention are administered with food.

The amount of compounds of the present invention that can be combined with the carrier materials to produce a composition in a single dosage form varies depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient depends upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition also depends upon the particular compound in the composition.

Uses of Compounds and Pharmaceutically Acceptable Compositions

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in *Drosophila*), Lats1/2 (homologues of Warts/Wts), and their adaptor proteins Sav1 (homologue of Salvador/Sav) and Mob (MOBKL1A and MOBKL1B; homologues of Mats), respectively. In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] (SEQ ID NO: 9) consensus motifs. YAP comprises five [HXRXXS] (SEQ ID NO: 9) consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK16/F in the degradation motif, which then signals for interaction with the β-TRCP E3 ubiquitin ligase, leading to polyubiquitination and degradation of YAP.

In some instances, Lats1/2 phosphorylates TAZ at the [HXRXXS] (SEQ ID NO: 9) consensus motifs. TAZ comprises four [HXRXXS] (SEQ ID NO: 9) consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta-TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxw1, hsSlimb, plkappaBalpha-E3 receptor subunit) and S-phase kinase-associated proteins 2 (SKP2). In some embodiments, the SCF complex (e.g. $SCF^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2O, UBE2Q1, UBE2Q2, UBE2R1, UBE2R2, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators. In some instances, the Hippo pathway is regulated by the G-protein and its coupled receptors, the Crumbs complex, regulators upstream of the MST kinases, and the adherens junction.
YAP/TAZ Interaction with TEAD In some embodiments, un-phosphorylated and/or dephosphorylated YAP/TAZ accumulates in the nucleus. Within the nucleus, YAP/TAZ interacts with the TEAD family of transcription factors (e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4)) to activate genes involved in anti-apoptosis and proliferation, such as for example CTFG, Cyr61, and FGF1.

Proteomic and biochemical studies have shown that the TEAD (TEA Domain) transcription factors are palmitoylated at evolutionarily conserved cysteine residues. Three cysteine residues were found that are evolutionarily conserved and mutated to serine in human TEAD1 (C53S, C327S and C359S) to test whether the mutation affects TEAD1 palmitoylation. The C359S mutant showed the greatest loss of palmitoylation, and C327S and C53S also showed decreased palmitoylation. These results suggest that C359 plays a critical role in TEAD1 palmitoylation. Furthermore, combination mutation of all three cysteine residues, C53/327/359S (3CS), completely ablated TEAD1 palmitoylation, indicating that these residues are involved in TEAD1 palmitoylation. It has been found that TEADs undergo PAT-independent autopalmitoylation, under physiological concentrations of palmitoy 1-CoA. Furthermore, autopalmitoylation plays critical roles in regulating TEAD-YAP association and their physiological functions in vitro and in vivo. Chan, et al. Nature Chem. Biol. 12, pages 282-289 (2016); Noland, et al. Structure, 24, 1-8 (2016); Gibault et al. J. Med. Chem. 61, 5057-5072 (2018). Therefore, palmitoylation of TEADs play important roles in regulating Hippo pathway transcriptional complexes.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

In some embodiments, the compounds described herein reversibly inhibit a TEAD transcription factor. In some embodiments, the transcription factor is TEAD1. In some embodiments, the transcription factor is TEAD2. In some embodiments, the transcription factor is TEAD3. In some embodiments, the transcription factor is TEAD4. In some embodiments, the compounds described herein reversibly inhibit the activity of a TEAD transcription factor (e.g., TEAD1, TEAD2, TEAD3, and/or TEAD4).

In some embodiments, the compounds disclosed herein bind to TEAD1 and disrupt or inhibit the interaction between YAP and TEAD1. In some embodiments, the compounds disclosed herein bind to TEAD2 and disrupt or inhibit the interaction between YAP and TEAD2. In some embodiments, the compounds disclosed herein bind to TEAD3 and disrupt or inhibit the interaction between YAP and TEAD3. In some embodiments, the compounds disclosed herein bind to TEAD4 and disrupt or inhibit the interaction between YAP and TEAD4.

In some embodiments, the compounds disclosed herein bind to TEAD1 and disrupt or inhibit the interaction between YAP and TEAD1. In some embodiments, the compounds disclosed herein bind to TEAD1 at C359, and disrupt or inhibit the interaction between YAP and TEAD1. In some embodiments, the compounds disclosed herein bind to TEAD1 at C53, and disrupt or inhibit the interaction between YAP and TEAD1. In some embodiments, the compounds disclosed herein bind to TEAD1 at C327, and disrupt or inhibit the interaction between YAP and TEAD1. In some embodiments, the compounds disclosed herein bind to TEAD1 at C405, and disrupt or inhibit the interaction between YAP and TEAD1. In some embodiments, the compounds disclosed herein bind to TEAD1 at C359 and C327, and disrupt or inhibit the interaction between YAP and TEAD1. In some embodiments, the compounds disclosed herein bind to TEAD1 at C359 and C53, and disrupt or inhibit the interaction between YAP and TEAD1. In some embodiments, the compounds disclosed herein bind to TEAD1 at C53 and C327, and disrupt or inhibit the interaction between YAP and TEAD1. In some embodiments, the compounds disclosed herein bind to TEAD1 at C359 and C405, and disrupt or inhibit the interaction between YAP and TEAD1. In some embodiments, the compounds disclosed herein bind to TEAD1 at C53 and C405, and disrupt or inhibit the interaction between YAP and TEAD1. In some embodiments, the compounds disclosed herein bind to TEAD1 at C327 and C405, and disrupt or inhibit the interaction between YAP and TEAD1. In some embodiments, the compounds disclosed herein bind to TEAD1 at C359, C327, and C53, and disrupt or inhibit the interaction between YAP and TEAD1. In some embodiments, the compounds disclosed herein bind to TEAD1 at C359, C327, and C405, and disrupt or inhibit the interaction between YAP and TEAD1. In some embodiments, the compounds disclosed herein bind to TEAD1 at C359, C353, and C405, and disrupt or inhibit the interaction between YAP and TEAD1. In some embodiments, the compounds disclosed herein bind to TEAD1 at C327, C53, and C405, and disrupt or inhibit the interaction between YAP and TEAD1. In some embodiments, the compounds disclosed herein bind to TEAD1 at C359, C327, C53, and C405, and disrupt or inhibit the interaction between YAP and TEAD1.

In some embodiments, the compounds disclosed herein bind to TEAD1 and prevent TEAD1 palmitoylation. In some embodiments, the compounds disclosed herein bind to TEAD1 and prevent TEAD1 palmitoylation at C359. In some embodiments, the compounds disclosed herein bind to TEAD1 and prevent TEAD1 palmitoylation at C53. In some embodiments, the compounds disclosed herein bind to TEAD1 and prevent TEAD1 palmitoylation at C327. In some embodiments, the compounds disclosed herein bind to TEAD1 and prevent TEAD1 palmitoylation at C405. In some embodiments, the compounds disclosed herein bind to TEAD1 and prevent TEAD1 palmitoylation at C359 and C327. In some embodiments, the compounds disclosed herein bind to TEAD1 and prevent TEAD1 palmitoylation at C359 and C53. In some embodiments, the compounds disclosed herein bind to TEAD1 and prevent TEAD1 palmitoylation at C53 and C327. In some embodiments, the compounds disclosed herein bind to TEAD1 and prevent TEAD1 palmitoylation at C359 and C405. In some embodiments, the compounds disclosed herein bind to TEAD1 and prevent TEAD1 palmitoylation at C53 and C405. In some embodiments, the compounds disclosed herein bind to TEAD1 and prevent TEAD1 palmitoylation at C327 and C405. In some embodiments, the compounds disclosed herein bind to TEAD1 and prevent TEAD1 palmitoylation at C359, C327, and C53. In some embodiments, the compounds disclosed herein bind to TEAD1 and prevent TEAD1 palmitoylation at C359, C327, and C405. In some embodiments, the compounds disclosed herein bind to TEAD1 and prevent TEAD1 palmitoylation at C359, C353, and C405. In some embodiments, the compounds disclosed herein bind to TEAD1 and prevent TEAD1 palmitoylation at C327, C53, and C405. In some embodiments, the compounds disclosed herein bind to TEAD1 and prevent TEAD1 palmitoylation at C359, C327, C53, and C405.

In some embodiments, the compounds disclosed herein bind to TEAD, prevent TEAD palmitoylation, and disrupt or inhibit the interaction between YAP and TEAD. In some embodiments, the compounds disclosed herein bind to TEAD1 and prevent TEAD1 palmitoylation at C359, and disrupt or inhibit the interaction between YAP and TEAD1. In some embodiments, the compounds disclosed herein bind to TEAD1 and prevent TEAD1 palmitoylation at C53, and disrupt or inhibit the interaction between YAP and TEAD1. In some embodiments, the compounds disclosed herein bind to TEAD1 and prevent TEAD1 palmitoylation at C327, and disrupt or inhibit the interaction between YAP and TEAD1. In some embodiments, the compounds disclosed herein bind to TEAD1 and prevent TEAD1 palmitoylation at C405, and disrupt or inhibit the interaction between YAP and TEAD1. In some embodiments, the compounds disclosed herein bind to TEAD1 and prevent TEAD1 palmitoylation at C359 and C327, and disrupt or inhibit the interaction between YAP and TEAD1. In some embodiments, the compounds disclosed herein bind to TEAD1 and prevent TEAD1 palmitoylation at C359 and C53, and disrupt or inhibit the interaction between YAP and TEAD1. In some embodiments, the compounds disclosed herein bind to TEAD1 and prevent TEAD1 palmitoylation at C53 and C327, and disrupt or inhibit the interaction between YAP and TEAD1. In some embodiments, the compounds disclosed herein bind to TEAD1 and prevent TEAD1 palmitoylation at C359 and C405, and disrupt or inhibit the interaction between YAP and TEAD1. In some embodiments, the compounds disclosed herein bind to TEAD1 and prevent TEAD1 palmitoylation at C53 and C405, and disrupt or inhibit the interaction between YAP and TEAD1. In some embodiments, the compounds disclosed herein bind to TEAD1 and prevent TEAD1 palmitoylation at C327 and C405, and disrupt or inhibit the interaction between YAP and TEAD1. In some embodiments, the compounds disclosed herein bind to TEAD1 and prevent TEAD1 palmitoylation at C359, C327, and C53, and disrupt or inhibit the interaction between YAP and TEAD1. In some embodiments, the compounds disclosed herein bind to TEAD1 and prevent TEAD1 palmitoylation at C359, C327, and C405, and disrupt or inhibit the interaction between YAP and TEAD1. In some embodiments, the compounds disclosed herein bind to TEAD1 and prevent TEAD1 palmitoylation at C359, C353, and C405, and disrupt or inhibit the interaction between YAP and TEAD1. In some embodiments, the compounds disclosed herein bind to TEAD1 and prevent TEAD1 palmitoylation at C327, C53, and C405, and disrupt or inhibit the interaction between YAP and TEAD1. In some embodiments, the compounds disclosed herein bind to TEAD1 and prevent TEAD1 palmitoylation at C359, C327, C53, and C405, and disrupt or inhibit the interaction between YAP and TEAD1.

In some embodiments, the compounds disclosed herein bind to TEAD2 at C380, and disrupt or inhibit the interaction between YAP and TEAD2.

In some embodiments, the compounds disclosed herein bind to TEAD2 and prevent TEAD2 palmitoylation. In some embodiments, the compounds disclosed herein bind to TEAD2 and prevent TEAD2 palmitoylation at C380.

In some embodiments, the compounds disclosed herein bind to TEAD2, prevent TEAD2 palmitoylation, and disrupt or inhibit the interaction between YAP and TEAD2. In some embodiments, the compounds disclosed herein bind to TEAD2 and prevent TEAD2 palmitoylation at C380, and disrupt or inhibit the interaction between YAP and TEAD2.

In some embodiments, the compounds disclosed herein bind to TEAD3 at C371, and disrupt or inhibit the interaction between YAP and TEAD3. In some embodiments, the compounds disclosed herein bind to TEAD3 at C368, and disrupt or inhibit the interaction between YAP and TEAD3. In some embodiments, the compounds disclosed herein bind to TEAD3 at C371 and C368, and disrupt or inhibit the interaction between YAP and TEAD3.

In some embodiments, the compounds disclosed herein bind to TEAD3 and prevent TEAD3 palmitoylation. In some embodiments, the compounds disclosed herein bind to TEAD3 and prevent TEAD3 palmitoylation at C371. In some embodiments, the compounds disclosed herein bind to TEAD3 and prevent TEAD3 palmitoylation at C368. In some embodiments, the compounds disclosed herein bind to TEAD3 and prevent TEAD3 palmitoylation at C368 and C371.

In some embodiments, the compounds disclosed herein bind to TEAD3, prevent TEAD3 palmitoylation, and disrupt or inhibit the interaction between YAP and TEAD3. In some embodiments, the compounds disclosed herein bind to TEAD3 and prevent TEAD3 palmitoylation at C371, and disrupt or inhibit the interaction between YAP and TEAD3. In some embodiments, the compounds disclosed herein bind to TEAD3 and prevent TEAD3 palmitoylation at C368, and disrupt or inhibit the interaction between YAP and TEAD3. In some embodiments, the compounds disclosed herein bind to TEAD3 and prevent TEAD3 palmitoylation at C371 and C368, and disrupt or inhibit the interaction between YAP and TEAD3.

In some embodiments, the compounds disclosed herein bind to TEAD4 at C367, and disrupt or inhibit the interaction between YAP and TEAD4.

In some embodiments, the compounds disclosed herein bind to TEAD4 and prevent TEAD4 palmitoylation. In some embodiments, the compounds disclosed herein bind to TEAD4 and prevent TEAD4 palmitoylation at C367.

In some embodiments, the compounds disclosed herein bind to TEAD4, prevent TEAD4 palmitoylation, and disrupt or inhibit the interaction between YAP and TEAD4. In some embodiments, the compounds disclosed herein bind to TEAD4 and prevent TEAD4 palmitoylation at C367, and disrupt or inhibit the interaction between YAP and TEAD4.

YAP/TAZ Regulation Mediated by G-Proteins/GPCRs

In some embodiments, the Hippo pathway is regulated by the G protein-coupled receptor (GPCR) and G protein (also known as guanine nucleotide-binding proteins) family of proteins. G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, Giα (G inhibitory), $G_o\alpha$ (G other), $G_q/11\alpha$, and G12/13α coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s$a, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q\alpha$ include, but are not limited to, 5-hydroxytryptamine receptor (5-HT receptor) types $5-HT_2$ and $5-HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g., Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g., $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g., $S1P_2$, $S1P_3$, $S1P_4$ and $S1P_5$); lysophosphatidic acid (e.g., $LPA_1$, $LPA_2$, $LPA_3$); angiotensin II (AT1); serotonin ($5-HT_{2c}$ and $5-HT_4$); somatostatin ($sst_5$); endothelin ($ET_A$ and $ET_B$); cholecystokinin ($CCK_1$); $V_{1a}$ vasopressin receptors; $D_5$ dopamine receptors; fMLP formyl peptide receptors; $GAL_2$ galanin receptors; $EP_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_o$ or $G_i$ protein) suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_{i\alpha}$ include, but are not limited to, 5-hydroxytryptamine receptor (5-HT receptor) types $5-HT_1$ and $5-HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors $sst_1$, $sst_2$, $sst_3$, $sst_4$, and $sst_5$; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$, and $G_z$. $G_i\alpha1$ is encoded by GNAI1. $G_i\alpha2$ is encoded by GNAI2. $G_i\alpha3$ is encoded by GNAI3. $G_o\alpha$, the $\alpha_o$ subunit, is encoded by GNAO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5-HT_4$, $5-HT_6$, and $5-HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $β_1$, $β_2$, and $β_3$; calcitonin receptor; calcitonin gene-related peptide receptor; corticotropin-releasing hormone receptor; dopamine receptor D1-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein a-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of Guns. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of G.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g., 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

In some embodiments, the present invention provides a use of a compound, or a pharmaceutical salt or composition thereof, for treating one or more disorders, diseases, and/or conditions wherein the disorder, disease, or condition includes, but is not limited to, a cellular proliferative disorder.

The activity of a compound utilized in this invention as an inhibitor of TEAD (e.g., TEAD1, TEAD2, TEAD3, and/or TEAD4), or a variant or mutant thereof, can be assayed in vitro, in vivo or in a cell line. In vitro assays include assays that determine inhibition of TEAD (e.g., TEAD1, TEAD2, TEAD3, and/or TEAD4), or a variant or mutant thereof. Alternate in vitro assays quantitate the ability of the inhibitor to bind to TEAD (e.g., TEAD1, TEAD2, TEAD3, and/or TEAD4) or a variant or mutant thereof. Detailed conditions for assaying a compound utilized in this invention as an inhibitor of TEAD (e.g., TEAD1, TEAD2, TEAD3, and/or TEAD4), or a variant or mutant thereof, are set forth in the Examples below. See, for example, Examples 2 and 5.

As used herein, the terms "treatment," "treat," and "treating" refer to reversing, alleviating, delaying the onset of, or inhibiting the progress of a disease or disorder, or one or more symptoms thereof, as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

The provided compounds are inhibitors of TEAD (e.g., TEAD1, TEAD2, TEAD3, and/or TEAD4) and are therefore useful for treating one or more disorders associated with activity of TEAD (e.g., TEAD1, TEAD2, TEAD3, and/or TEAD4). Thus, in certain aspects and embodiments, the present invention provides a method for treating a TEAD-mediated disorder comprising the step of administering to a patient in need thereof a therapeutically effective compound of the present invention, or pharmaceutically acceptable composition thereof.

As used herein, the term "TEAD-mediated" disorders, diseases, and/or conditions as used herein means any disease or other deleterious condition in which TEAD (e.g., TEAD1, TEAD2, TEAD3, and/or TEAD4), or a variant or mutant thereof, is known to play a role. Accordingly, another aspect or embodiment of the present invention relates to treating or lessening the severity of one or more diseases in which TEAD (e.g., TEAD1, TEAD2, TEAD3, and/or TEAD4), or a variant or mutant thereof, are known to play a role.

As used herein, the term "a therapeutically effective amount of" refers to the amount of a TEAD inhibitor or a pharmaceutically acceptable salt thereof, which is effective to reduce or attenuate the biological activity of TEAD (e.g., TEAD1, TEAD2, TEAD3, and/or TEAD4) or a variant or mutant thereof, provide a therapeutic benefit in the treatment of a condition, or to delay or minimize one or more symptoms associated with the condition in a biological sample or in a patient. In some embodiments, "a therapeutically effective amount of" refers to the amount of a TEAD inhibitor or a pharmaceutically acceptable salt thereof that measurably decreases the binding or signaling activity of TEAD (e.g., TEAD1, TEAD2, TEAD3, and/or TEAD4), or a variant or mutant thereof, or any TEAD-mediated activity. The term "therapeutically effective amount" can encompass, in some embodiments, an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibition of a TEAD transcription factor. In certain embodiments, a therapeutically effective amount is an amount sufficient for treating a proliferative disease.

In some aspects and embodiments, provided herein are methods of treating, reducing the severity of, delaying the onset of, or inhibiting the progress of a disease or disorder, or one or more symptoms thereof of a disease or disorder characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity comprising the step of administering to a patient in need thereof a therapeutically effective compound of the present invention, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of TEAD (e.g., TEAD1, TEAD2, TEAD3, and/or TEAD4) activity is beneficial comprising the step of administering to a patient in need thereof a therapeutically effective compound of the present invention, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of the Hippo pathway is beneficial comprising the step of administering to a patient in need thereof a therapeutically effective compound of the present invention, or pharmaceutically acceptable composition thereof.

In some aspects and embodiments, the present invention provides a method for treating one or more disorders, diseases, and/or conditions wherein the disorder, disease, or condition includes, but is not limited to, a cellular proliferative disorder, comprising administering to a patient in need thereof, a TEAD inhibitor compound as described herein, or a pharmaceutical salt or composition thereof. In some embodiments, a cellular proliferative disorder is cancer. In some embodiments, the cancer is characterized by increased TEAD (e.g., TEAD1, TEAD2, TEAD3, and/or TEAD4) expression and/or increased TEAD (e.g., TEAD1, TEAD2, TEAD3, and/or TEAD4) activity.

As used herein, the terms "increased," "elevated," or "enhanced," are used interchangeably and encompass any measurable increase in a biological function and/or biological activity and/or a concentration. For example, an increase can be by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to a control or baseline amount of a function, or activity, or concentration.

As used herein, the terms "increased expression" and/or "increased activity" of a substance, such as TEAD, in a sample or cancer or patient, refers to an increase in the amount of the substance, such as TEAD, of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to the amount of the substance, such as TEAD, in a control sample or control samples, such as an individual or group of individuals who are not suffering from the disease or disorder (e.g., cancer) or an internal control, as determined by techniques known in the art. A subject can also be determined to have an "increased expression" or "increased activity" of TEAD if the expression and/or activity of TEAD is increased by one standard deviation, two standard deviations, three standard deviations, four standard deviations, five standard deviations, or more, relative to the mean (average) or median amount of TEAD in a control group of samples or a baseline group of samples or a retrospective analysis of patient samples. As practiced in the art, such control or baseline expression levels can be previously determined, or measured prior to the measurement in the sample or cancer or subject, or can be obtained from a database of such control samples.

As used herein, a "proliferative disease" refers to a disease that occurs due to abnormal growth or extension by the multiplication of cells (Walker, Cambridge Dictionary of Biology, Cambridge University Press: Cambridge, UK, 1990). A proliferative disease can be associated with: 1) the pathological proliferation of normally quiescent cells; 2) the pathological migration of cells from their normal location (e.g., metastasis of neoplastic cells); 3) the pathological expression of proteolytic enzymes, such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

Cancer

The cancer or proliferative disorder or tumor to be treated using the compounds and methods and uses described herein include, but are not limited to, a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer.

In some embodiments of the methods and uses described herein, a cancer is mediated by activation of transcriptional coactivator with PDZ binding motif/Yes-associated protein transcription coactivator (TAZ/YAP). In some embodiments of the methods and uses described herein, a cancer is mediated by modulation of the interaction of YAP/TAZ with TEAD (e.g., TEAD1, TEAD2, TEAD3, and/or TEAD4). In some embodiments of the methods and uses described herein, the cancer is characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity. In some embodiments of the methods and uses described herein, the cancer is a cancer in which YAP is localized in the nucleus of the cancer cells.

In some embodiments, a cancer is characterized by a mutant Gα-protein. In some embodiments, a mutant Gα-protein is selected from G12, G13, Gq, G11, Gi, Go, and Gs. In some embodiments, a mutant Gα-protein is G12. In some embodiments, a mutant Gα-protein is G13. In some embodiments, a mutant Gα-protein is $G_q$. In some embodiments, a mutant Gα-protein is G11. In some embodiments, a mutant Gα-protein is $G_i$. In some embodiments, a mutant Gα-protein is Go. In some embodiments, a mutant Gα-protein is $G_s$.

In some embodiments of the methods and uses described herein, a cancer is treated by inhibiting or reducing or decreasing or arresting further growth or spread of the cancer or tumor. In some embodiments of the methods and uses described herein, a cancer is treated by inhibiting or reducing the size (e.g., volume or mass) of the cancer or tumor by at least 5%, at least 10%, at least 25%, at least 50%, at least 75%, at least 90% or at least 99% relative to the size of the cancer or tumor prior to treatment. In some embodiments of the methods and uses described herein, a cancer is treated by reducing the quantity of the cancers or tumors in the patient by at least 5%, at least 10%, at least 25%, at least 50%, at least 75%, at least 90% or at least 99% relative to the quantity of the cancers or tumors prior to treatment.

In some embodiments of the methods and uses described herein, the cancer is lung cancer, thyroid cancer, ovarian cancer, colorectal cancer, prostate cancer, cancer of the pancreas, cancer of the esophagus, liver cancer, breast cancer, skin cancer, or mesothelioma. In some embodiments, the cancer is mesothelioma, such as malignant mesothelioma. In some embodiments, cancer includes, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g., Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, a cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, a cancer is a viral-associated cancer, including human immunodeficiency virus (HIV)

associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, a cancer is melanoma cancer. In some embodiments, a cancer is breast cancer. In some embodiments, a cancer is lung cancer. In some embodiments, a cancer is small cell lung cancer (SCLC). In some embodiments, a cancer is non-small cell lung cancer (NSCLC).

The compounds and compositions, according to the method of the present invention, can be administered using any amount and any route of administration effective for treating or lessening the severity of a cancer. The exact amount required varies from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention is decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The terms "patient" or "subject," as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention can be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Co-Administration with One or More Other Therapeutic Agent(s)

Depending upon the particular condition, or disease, to be treated, additional therapeutic agents that are normally administered to treat that condition, can also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention can also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides, or in addition, be administered especially for tumor therapy in combination with chemotherapy, radiotherapy, immunotherapy, phototherapy, surgical intervention, or a combination of these. Long-term therapy is equally possible, as is adjuvant therapy in the context of other treatment strategies, as described above. Other possible treatments are therapy to maintain the patient's status after tumor regression, or even chemopreventive therapy, for example in patients at risk.

One or more other therapeutic agent(s) can be administered separately from a compound or composition of the invention, as part of a multiple dosage regimen. Alternatively, one or more other therapeutic agents can be part of a single dosage form, mixed together with a compound of this invention in a single composition. If administered as a multiple dosage regime, one or more other therapeutic agent(s) and a compound or composition of the invention can be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent(s) and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention can be administered with one or more other therapeutic agent(s) simultaneously or sequentially in separate unit dosage forms or together in a single unit dosage form. Accordingly, the present invention provides a single unit dosage form comprising a compound of the current invention, one or more other therapeutic agent(s), and a pharmaceutically acceptable carrier, adjuvant, or vehicle.

The amount of a compound of the invention and one or more other therapeutic agent(s) (in those compositions which comprise an additional therapeutic agent as described above) that can be combined with the carrier materials to produce a single dosage form varies depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent(s), the one or more other therapeutic agent(s) and a compound of the invention can act synergistically. Therefore, the amount of the one or more other therapeutic agent(s) in such compositions may be less than that required in a monotherapy utilizing only that therapeutic agent. In such compositions a dosage of between 0.01-1,000 µg/kg body weight/day of the one or more other therapeutic agent(s) can be administered.

The amount of one or more other therapeutic agent(s) present in the compositions of this invention may be no more than the amount that would normally be administered in a composition comprising that therapeutic agent as the only active agent. Preferably the amount of one or more other therapeutic agent(s) in the presently disclosed compositions ranges from about 50% to 100% of the amount normally present in a composition comprising that agent as the only therapeutically active agent. In some embodiments, one or more other therapeutic agent(s) is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

The compounds of this invention, or pharmaceutical compositions thereof, can also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (LYNPARZA®, AstraZeneca); rucaparib (RUBRACA®, Clovis Oncology); niraparib (ZEJULA®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (ZOLINZA®, Merck); romidepsin (ISTODAX®, Celgene); panobinostat (FARYDAK®, Novartis); belinostat (BELEODAQ®, Spectrum Pharmaceuticals); entinostat (SNDX-275, Syndax Pharmaceuticals) (NCT00866333); and chidamide (EPIDAZA®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (IBRANCE®, Pfizer); ribociclib (KISQALI®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (ZYDELIG®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (PLATINOL®, Bristol-Myers Squibb); carboplatin (PARAPLATIN®, Bristol-Myers Squibb; also, Teva; Pfizer); oxaliplatin (ELOXITIN® Sanofi-Aventis); nedaplatin (AQUPLA®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (TAXOL®, Bristol-Myers Squibb), docetaxel (TAXOTERE®, Sanofi-Aventis; DOCEFREZ®, Sun Pharmaceutical), albumin-bound paclitaxel (ABRAXANE®; Abraxis/Celgene), cabazitaxel (JEVTANA®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, YONDELIS®, Janssen Oncology), mechlorethamine (alkylating agent, VALCHLOR®, Aktelion Pharmaceuticals); vincristine (ONCOVIN®, Eli Lilly; VINCASAR®, Teva Pharmaceuticals; MARQIBO®, Talon Therapeutics); temozolomide (prodrug to alkylating agent 5-(3-methyltriazen-1-yl)-imidazole-4-carboxamide (MTIC) TEMODAR®, Merck); cytarabine injection (ara-C, antimetabolic cytidine analog, Pfizer); lomustine (alkylating agent, CEENU®, Bristol-Myers Squibb; GLEOSTINE®, NextSource Biotechnology); azacitidine (pyrimidine nucleoside analog of cytidine, VIDAZA®, Celgene); omacetaxine mepesuccinate (cephalotaxine ester) (protein synthesis inhibitor, SYNRIBO®; Teva Pharmaceuticals); asparaginase *Erwinia chrysanthemi* (enzyme for depletion of asparagine, ELSPAR®, Lundbeck; ERWINAZE®, EUSA Pharma); eribulin mesylate (microtubule inhibitor, tubulin-based antimitotic, HALAVEN®, Eisai); cabazitaxel (microtubule inhibitor, tubulin-based antimitotic, JEVTANA®, Sanofi-Aventis); capacetrine (thymidylate synthase inhibitor, XELODA®, Genentech); bendamustine (bifunctional mechlorethamine derivative, believed to form interstrand DNA cross-links, TREANDA®, Cephalon/Teva); ixabepilone (semi-synthetic analog of epothilone B, microtubule inhibitor, tubulin-based antimitotic, IXEMPRA®, Bristol-Myers Squibb); nelarabine (prodrug of deoxyguanosine analog, nucleoside metabolic inhibitor, ARRANON®, Novartis); clorafabine (prodrug of ribonucleotide reductase inhibitor, competitive inhibitor of deoxycytidine, CLOLAR®, Sanofi-Aventis); and trifluridine and tipiracil (thymidine-based nucleoside analog and thymidine phosphorylase inhibitor, LONSURF®, Taiho Oncology).

In some embodiments, one or more other therapeutic agent is a kinase inhibitor or VEGF-R antagonist. Approved VEGF inhibitors and kinase inhibitors useful in the present invention include: bevacizumab (AVASTIN®, Genentech/Roche) an anti-VEGF monoclonal antibody; ramucirumab (CYRAMZA®, Eli Lilly), an anti-VEGFR-2 antibody and ziv-aflibercept, also known as VEGF Trap (ZALTRAP®; Regeneron/Sanofi). VEGFR inhibitors, such as regorafenib (STIVARGA®, Bayer); vandetanib (CAPRELSA®, AstraZeneca); axitinib (INLYTA®, Pfizer); and lenvatinib (LENVIMA®, Eisai); Raf inhibitors, such as sorafenib (NEXAVAR®, Bayer AG and Onyx); dabrafenib (TAFINLAR®, Novartis); and vemurafenib (ZELBORAF®, Genentech/Roche); MEK inhibitors, such as cobimetanib (COTELLIC®, Exelexis/Genentech/Roche); trametinib (MEKINIST®, Novartis); Bcr-Abl tyrosine kinase inhibitors, such as imatinib (GLEEVEC®, Novartis); nilotinib (TASIGNA®, Novartis); dasatinib (SPRYCEL®, BristolMyersSquibb); bosutinib (BOSULIF®, Pfizer); and ponatinib (INCLUSIG®, Ariad Pharmaceuticals); Her2 and EGFR inhibitors, such as gefitinib (IRESSA®, AstraZeneca); erlotinib (TARCEEVA®, Genentech/Roche/Astellas); lapatinib (TYKERB®, Novartis); afatinib (GILOTRIF®, Boehringer Ingelheim); osimertinib (targeting activated EGFR, TAGRISSO®, AstraZeneca); and brigatinib (ALUNBRIG®, Ariad Pharmaceuticals); c-Met and VEGFR2 inhibitors, such as cabozanitib (COMETRIQ®, Exelexis); and multi-kinase inhibitors, such as sunitinib (SUTENT®, Pfizer); pazopanib (VOTRIENT®, Novartis); ALK inhibitors, such as crizotinib (XALKORI®, Pfizer); ceritinib (ZYKADIA®, Novartis); and alectinib (ALECENZa®, Genentech/Roche); Bruton's tyrosine kinase inhibitors, such as ibrutinib (IMBRUVICA®, Pharmacyclics/Janssen); and Flt3 receptor inhibitors, such as midostaurin (RYDAPT®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (SUPECT®, IY5511, Il-Yang Pharmaceuticals, S. Korea); ruxolitinib (JAKAFI®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (AFINITOR®, Novartis); temsirolimus (TORISEL®, Pfizer); and sirolimus (RAPAMUNE®, Pfizer).

In some embodiments, one or more other therapeutic agent is a proteasome inhibitor. Approved proteasome inhibitors useful in the present invention include bortezomib (VELCADE®, Takeda); carfilzomib (KYPROLIS®, Amgen); and ixazomib (NINLARO®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (LARTRUVO®; Eli Lilly). Approved EGFR antagonists which may be used in the present invention include cetuximab (ERBITUX®, Eli Lilly); necitumumab (PORTRAZZA®, Eli Lilly), panitumumab (VECTIBIX®, Amgen); and osimertinib (targeting activated EGFR, TAGRISSO®, AstraZeneca).

In some embodiments, one or more other therapeutic agent is an aromatase inhibitor. In some embodiments, an aromatase inhibitor is selected from exemestane (AROMASIN®, Pfizer); anastazole (ARIMIDEX®, AstraZeneca) and letrozole (FEMARA®, Novartis).

In some embodiments, one or more other therapeutic agent is an antagonist of the hedgehog pathway. Approved hedgehog pathway inhibitors which may be used in the present invention include sonidegib (ODOMZO®, Sun Pharmaceuticals); and vismodegib (ERIVEDGE®, Genentech), both for treatment of basal cell carcinoma.

In some embodiments, one or more other therapeutic agent is a folic acid inhibitor. Approved folic acid inhibitors useful in the present invention include pemetrexed (ALIMTA®, Eli Lilly).

In some embodiments, one or more other therapeutic agent is a CC chemokine receptor 4 (CCR4) inhibitor. CCR4 inhibitors being studied that may be useful in the present invention include mogamulizumab (POTELIGEO®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (RITUXAN®, Genentech/BiogenIdec); ofatumumab (anti-CD20, ARZERRA®, GlaxoSmithKline); obinutuzumab (anti-CD20, GAZYVA®, Genentech), ibritumomab (anti-CD20 and Yttrium-90, ZEVALIN®, Spectrum Pharmaceuticals); daratumumab (anti-CD38, DARZALEX®, Janssen Biotech), dinutuximab (anti-glycolipid GD2, UNITUXIN®, United Therapeutics); trastuzumab (anti-HER2, HERCEPTIN®, Genentech); ado-trastuzumab emtansine (anti-HER2, fused to emtansine, KADCYLA®, Genentech); and pertuzumab (anti-HER2, PERJETA®, Genentech); and brentuximab vedotin (anti-CD30-drug conjugate, ADCETRIS®, Seattle Genetics).

In some embodiments, one or more other therapeutic agent is a topoisomerase inhibitor. Approved topoisomerase inhibitors useful in the present invention include irinotecan (ONIVYDE®, Merrimack Pharmaceuticals); topotecan (HYCAMTIN®, GlaxoSmithKline). Topoisomerase inhibitors being studied which may be used in the present invention include pixantrone (PIXUVRI®, CTI Biopharma).

In some embodiments, one or more other therapeutic agent is an inhibitor of anti-apoptotic proteins, such as BCL-2. Approved anti-apoptotics which may be used in the present invention include venetoclax (VENCLEXTA®, AbbVie/Genentech); and blinatumomab (BLINCYTO®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (XTANDI®, Astellas/Medivation); approved inhibitors of androgen synthesis include abiraterone (ZYTIGA®, Centocor/Ortho); approved antagonist of gonadotropin-releasing hormone (GnRH) receptor (degaralix, FIRMAGON®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (EVISTA®, Eli Lilly).

In some embodiments, one or more other therapeutic agent is an inhibitor of bone resorption. An approved therapeutic which inhibits bone resorption is Denosumab (XGEVA®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (ZOMETA®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβtrap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agents is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, TEMODAL CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name AROMASIN™. Formestane is marketed under the trade name LENTARON™. Fadrozole is marketed under the trade name AFEMA™. Anastrozole is marketed under the trade name ARIMIDEX™. Letrozole is marketed under the trade names FEMARA™ or FEMAr™ Aminoglutethimide is marketed under the trade name ORIMETEN™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name NOLVADEX™. Raloxifene hydrochloride is marketed under the trade name EVISTA™ Fulvestrant can be administered under the trade name FASLODEX™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (CASODEX™). The term "gonadorelin agonist" as used herein includes, but is not limited to abarelix, goserelin, and goserelin acetate. Goserelin can be administered under the trade name ZOLADEX™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark CAMPTOSAR™. Topotecan is marketed under the trade name HYCAMPTIN™

The term "topoisomerase II inhibitor" as used herein includes, but is not limited to, the anthracyclines such as doxorubicin (including liposomal formulation, such as CAELYX™) daunorubicin, epirubicin, idarubicin and nemorubicin, the anthraquinones mitoxantrone and losoxantrone, and the podophillotoxines etoposide and teniposide. Etoposide is marketed under the trade name ETOPOPHOS™. Teniposide is marketed under the trade name VM 26-Bristol Doxorubicin is marketed under the trade name ACRIBLASTIN™ or ADRIAMYCIN™ Epirubicin is marketed under the trade name FARMORUBICIN™. Idarubicin is marketed. under the trade name ZAVEDOS™. Mitoxantrone is marketed under the trade name NOVANTRON™.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name TAXOL™ Docetaxel is marketed under the trade name TAXOTERE™. Vinblastine sulfate is marketed under the trade name VINBLASTIN R.P™. Vincristine sulfate is marketed under the trade name FARMISTIN™

The term "alkylating agent" as used herein includes, but is not limited to, cyclophosphamide, ifosfamide, melphalan or nitrosourea (BCNU or Gliadel). Cyclophosphamide is marketed under the trade name CYCLOSTIN™. Ifosfamide is marketed under the trade name HOLOXAN™

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name XELODA™. Gemcitabine is marketed under the trade name GEMZAR™

The term "platin compound" as used herein includes, but is not limited to, carboplatin, cis-platin, cisplatinum and oxaliplatin. Carboplatin can be administered, e.g., in the form as it is marketed, e.g., under the trademark CARBOPLAT™. Oxaliplatin can be administered, e.g., in the form as it is marketed, e.g. under the trademark ELOXATIN™

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (HERCEPTIN™), cetuximab (ERBITUX™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p10$^1$, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g., unrelated to protein or lipid kinase inhibition e.g., thalidomide (THALOMID™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name DIDRONEL™. Clodronic acid is marketed under the trade name BONEFOS™. Tiludronic acid is marketed under the trade name Skelid™. Pamidronic acid is marketed under the trade name AREDIA™. Alendronic acid is marketed under the trade name FOSAMAX™. Ibandronic acid is marketed under the trade name BONDRANAT™. Risedronic acid is marketed under the trade name ACTONEL™. Zoledronic acid is marketed under the trade name ZOMETA™. The term "mTOR inhibitors" relates to compounds which inhibit the mammalian target of rapamycin (mTOR) and which possess antiproliferative activity such as sirolimus (RAPAMUNE®), everolimus (CERTICAN™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (ZARNESTRA™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (VELCADE™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (HERCEPTIN™), Trastuzumab-DM1, erbitux, bevacizumab (AVASTIN™) rituximab (RITUXAN©), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; ANGIOSTATIN™; ENDOSTATIN™; anthranilic acid amides; ZD4190; $Zd_6474$; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (AVASTIN™)

Photodynamic therapy as used herein refers to therapy which uses certain chemicals known as photosensitizing compounds to treat or prevent cancers. Examples of photodynamic therapy include treatment with compounds, such as VISUDYNE™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO09/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO©, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-lh68/GLV-lh153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCTO2124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, T6, and memory CD8+(ap) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Example 1: Synthesis of Exemplary Compounds

Certain exemplary compounds are prepared following the following schemes.
Synthesis of I-13, I-14, & I-15

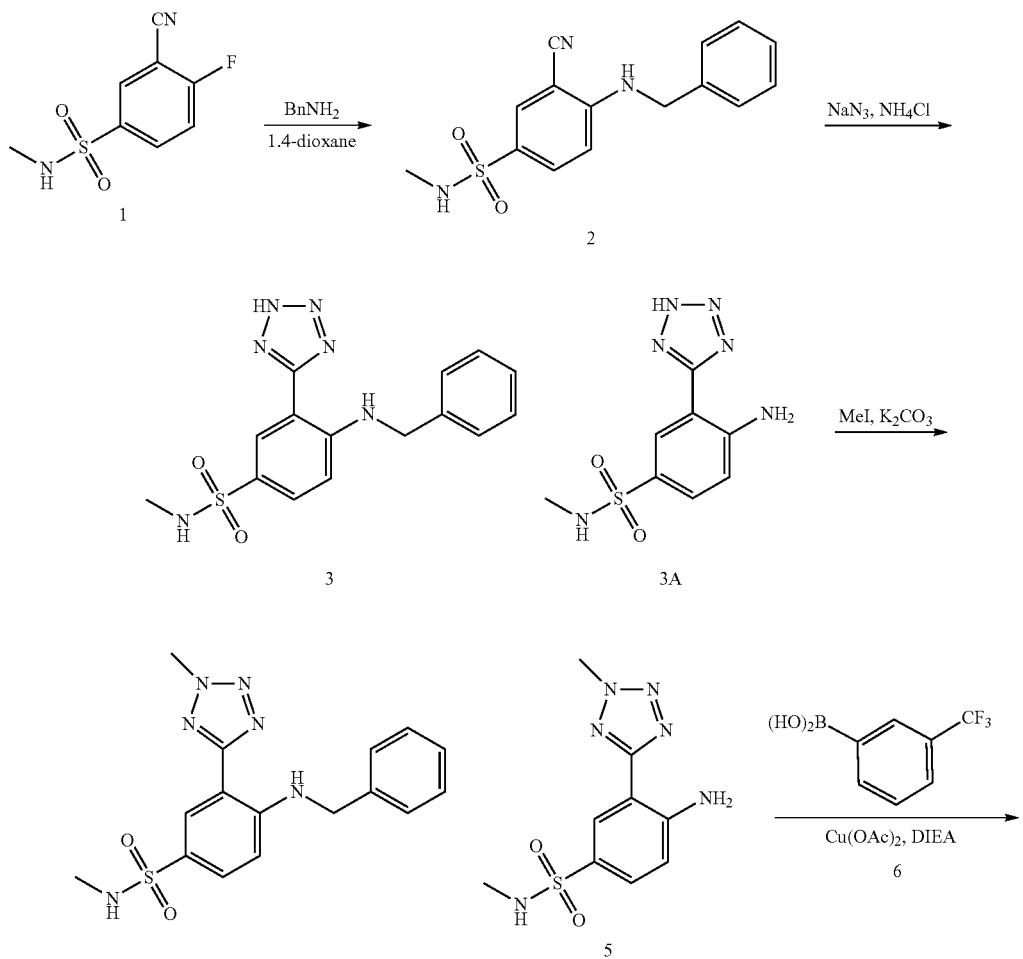

109
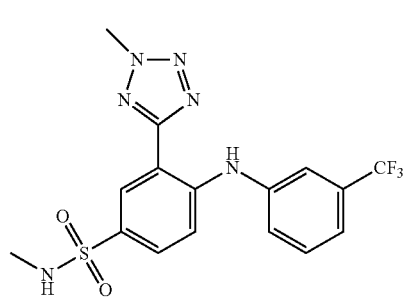
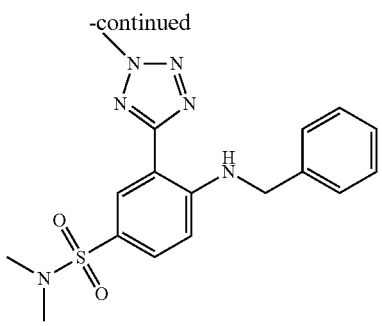
4A
110
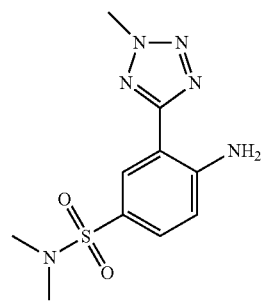
4B
Synthesis of I-1, I-2, & I-12
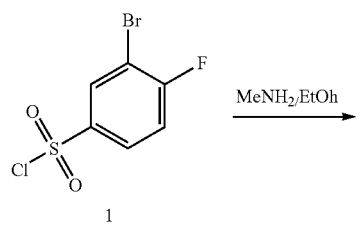
1
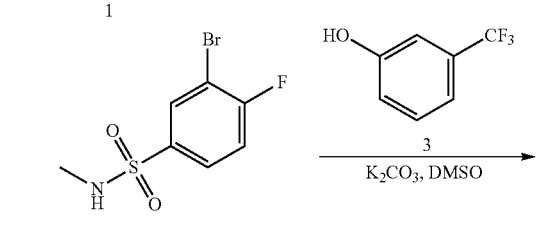
2
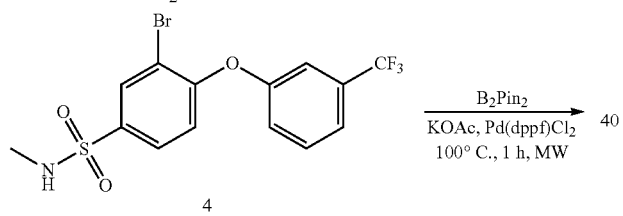
4
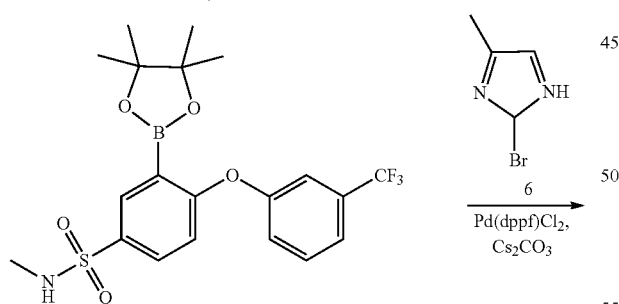
5
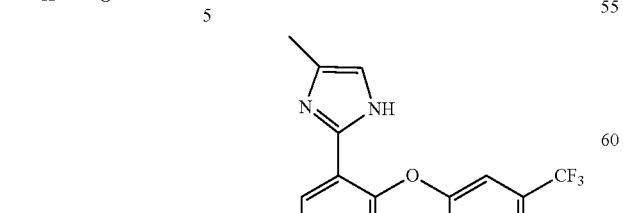
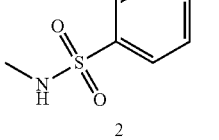
2
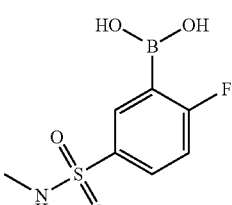
9
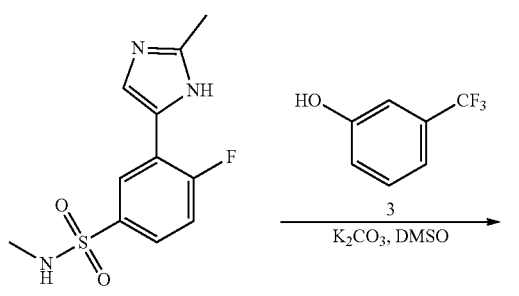
11
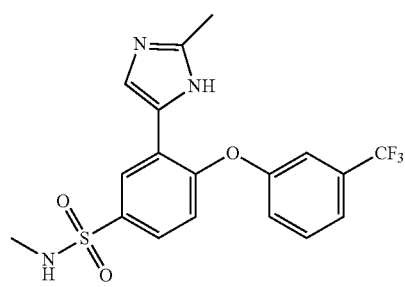

111
-continued
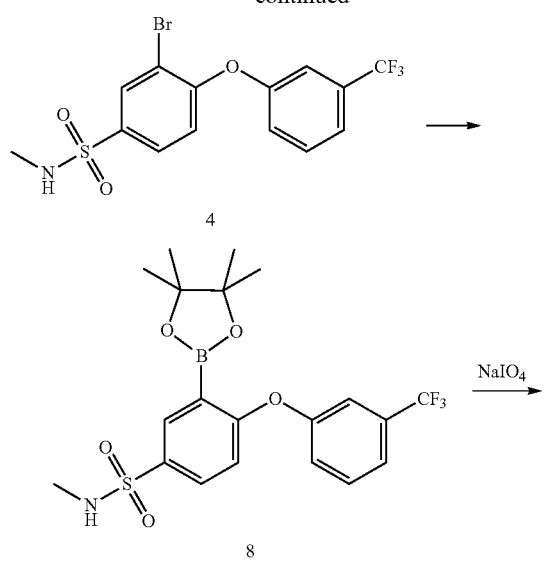
Synthesis of I-4
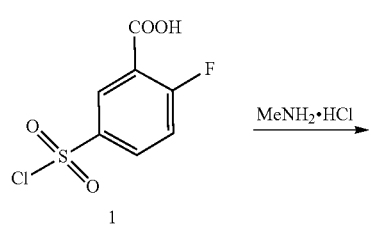
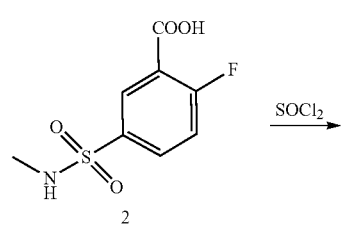
112
-continued
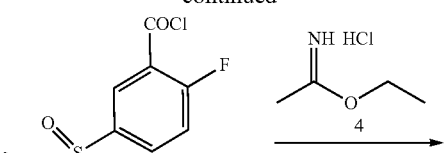
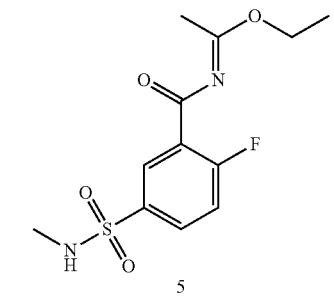
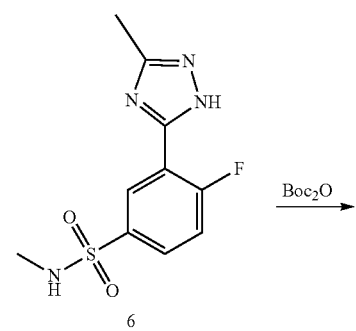
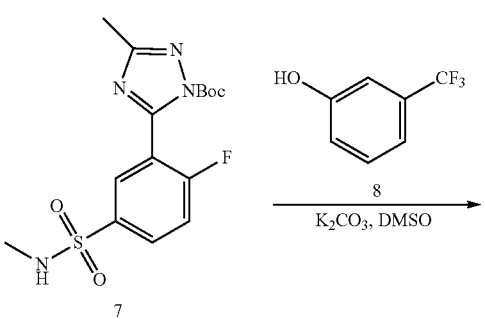
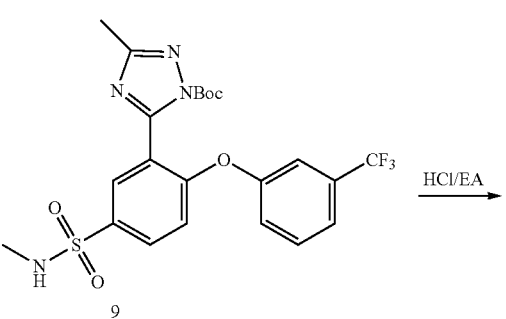

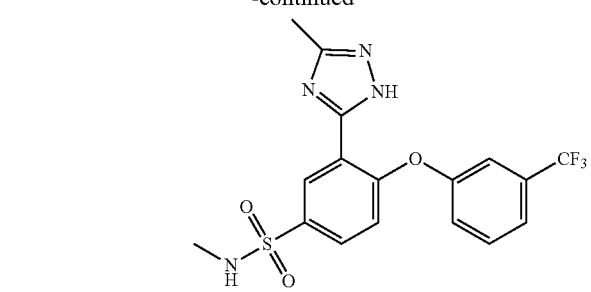
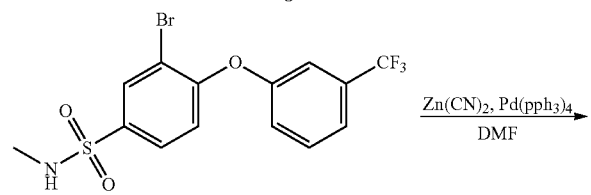
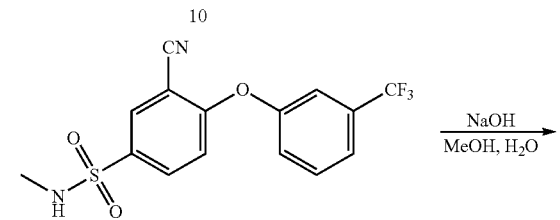
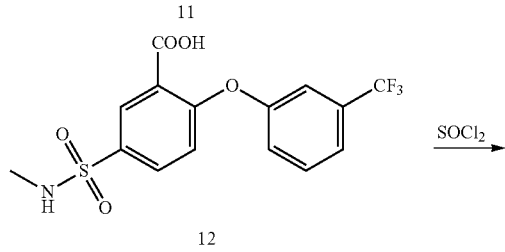
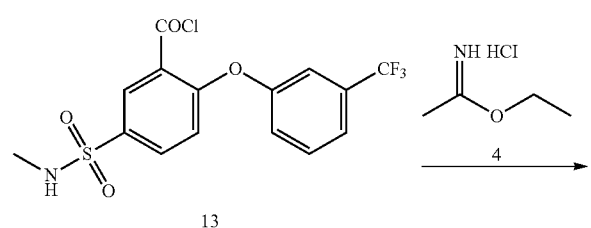
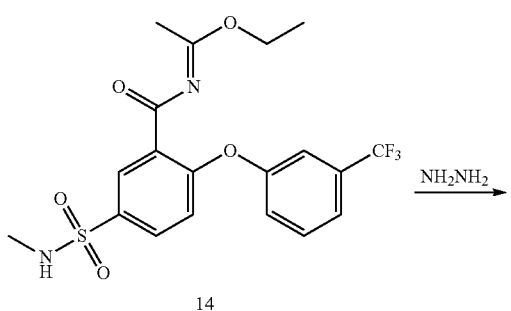
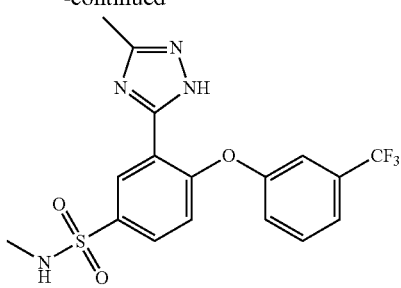
Synthesis of 1-6
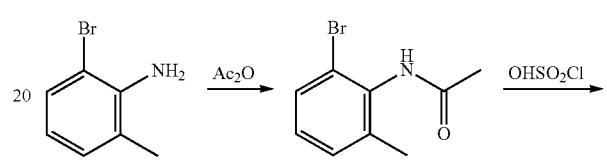
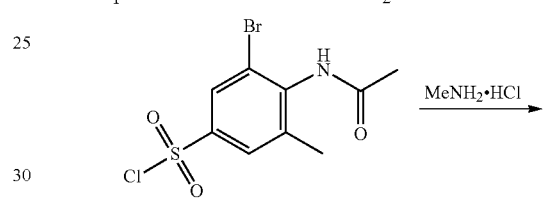
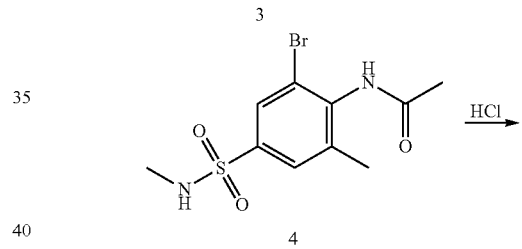
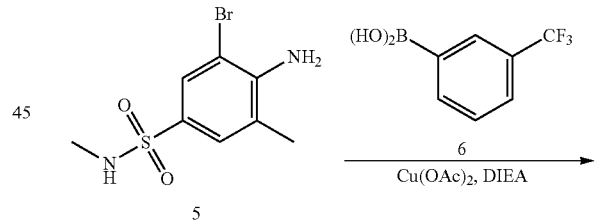
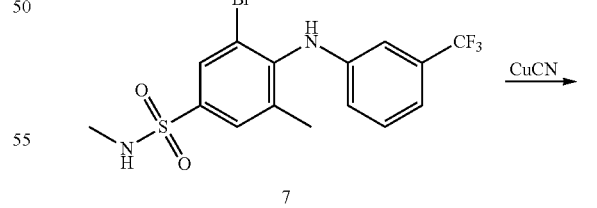
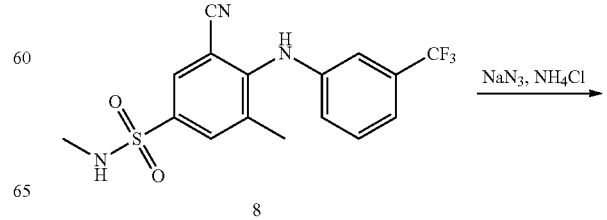

115
-continued
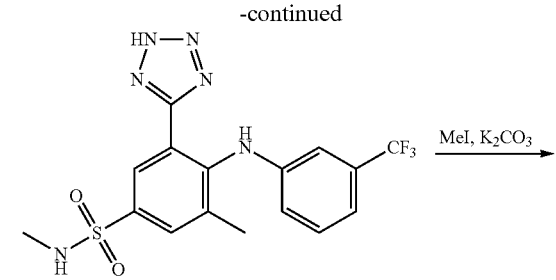
9
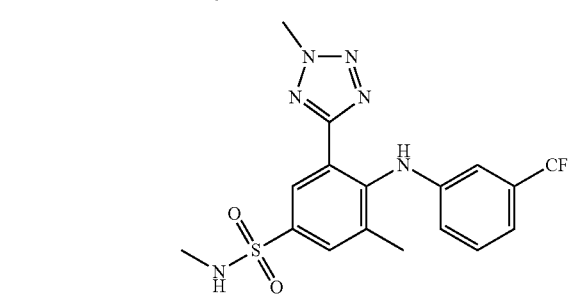
10
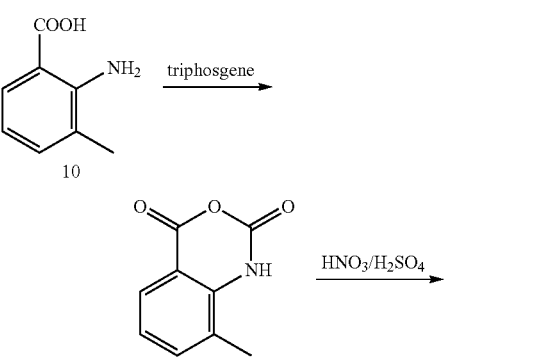
10
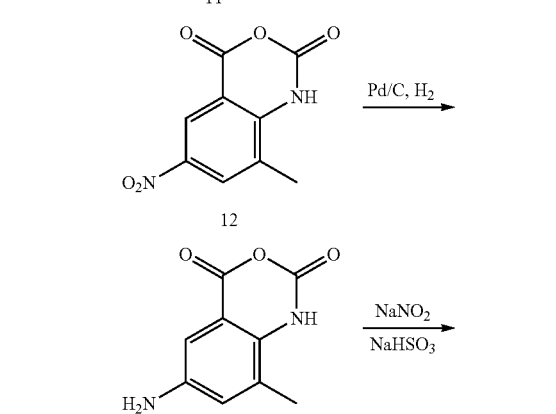
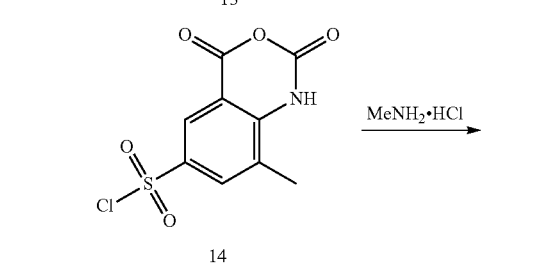
14
116
-continued
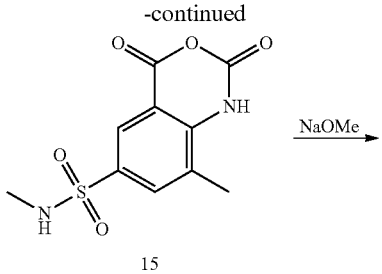
15
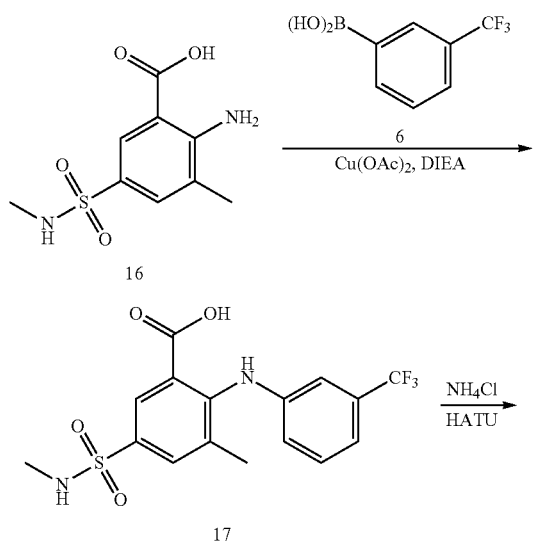
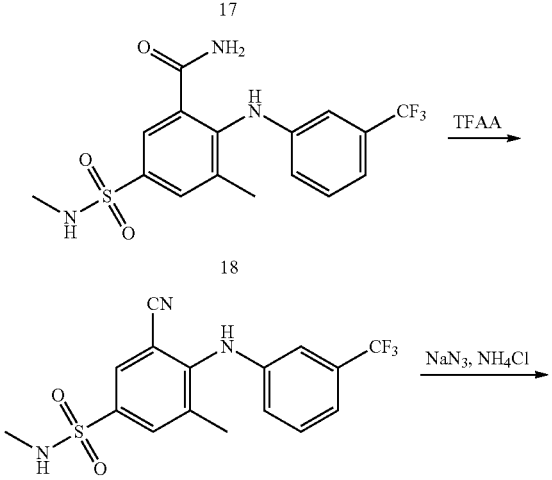
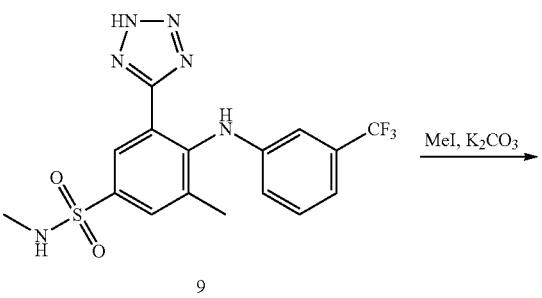
9

117
-continued
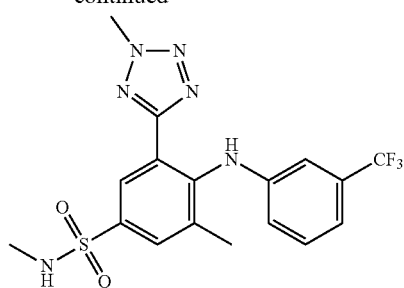
118
-continued
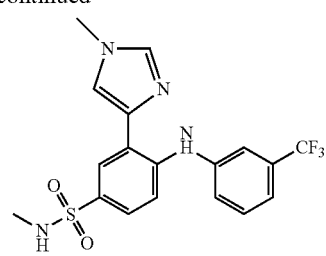
Synthesis of I-7
Synthesis of I-9 and I-10
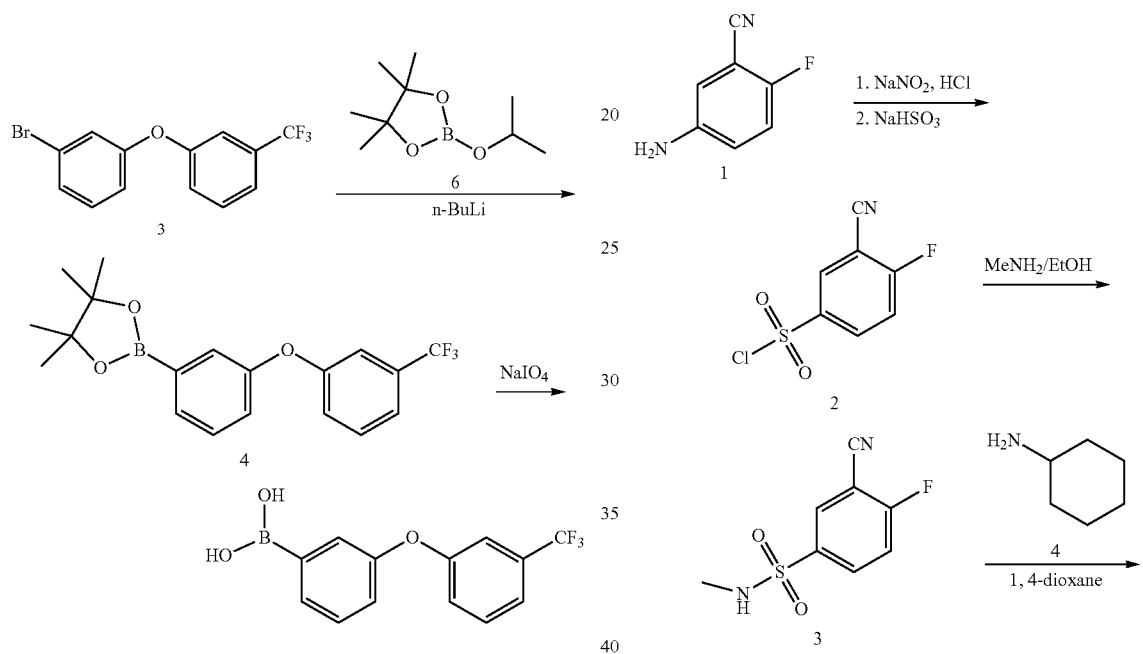
Synthesis of I-11
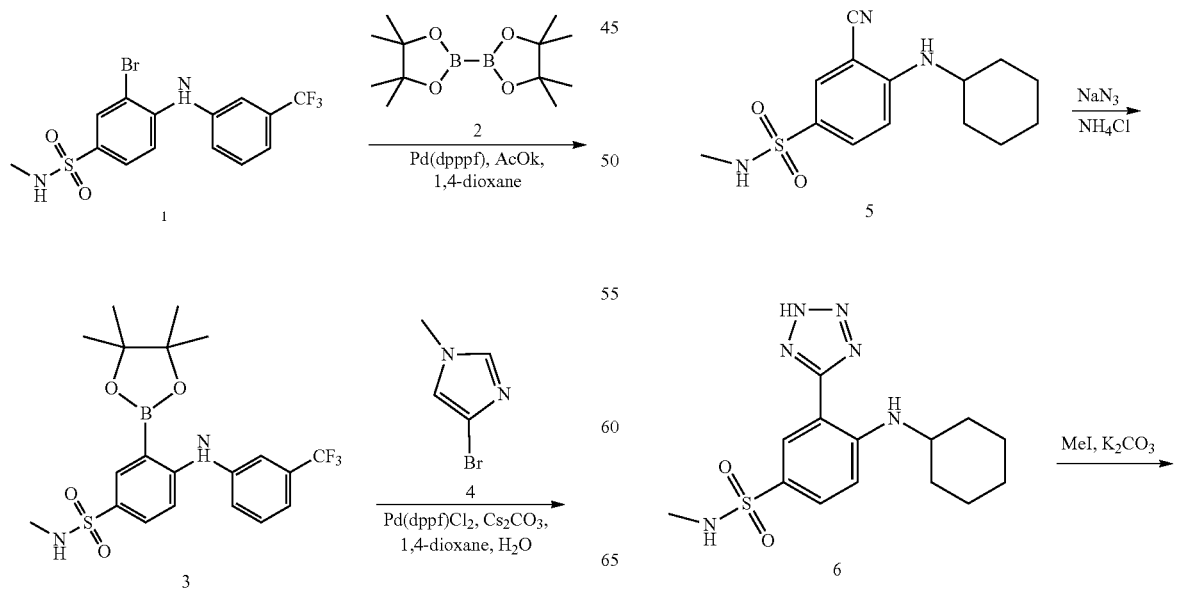

119

-continued

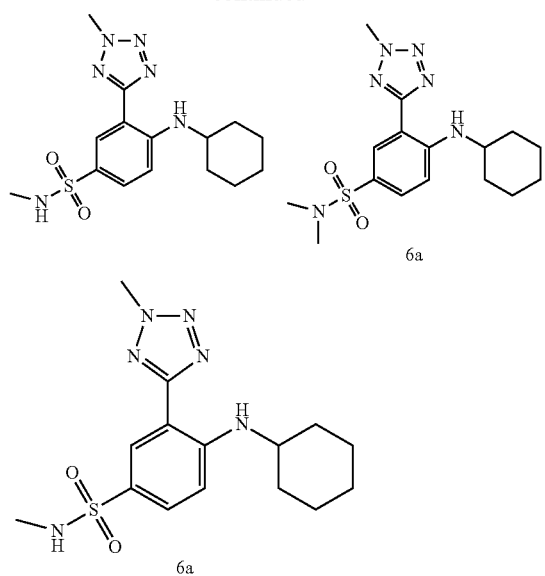

Synthesis of I-5 & I-8

120

-continued

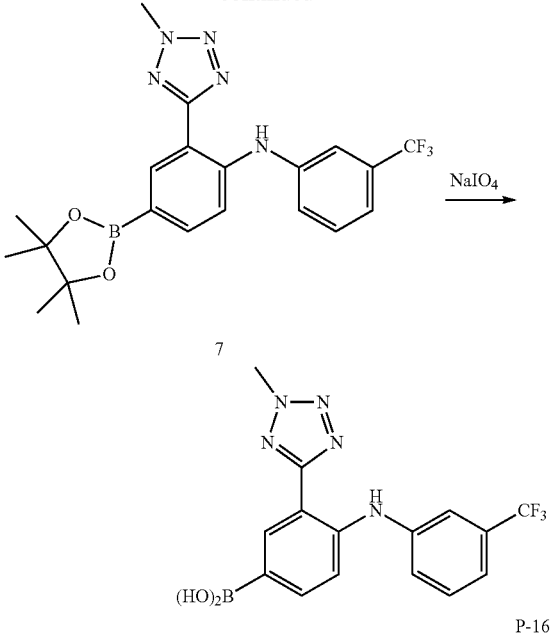

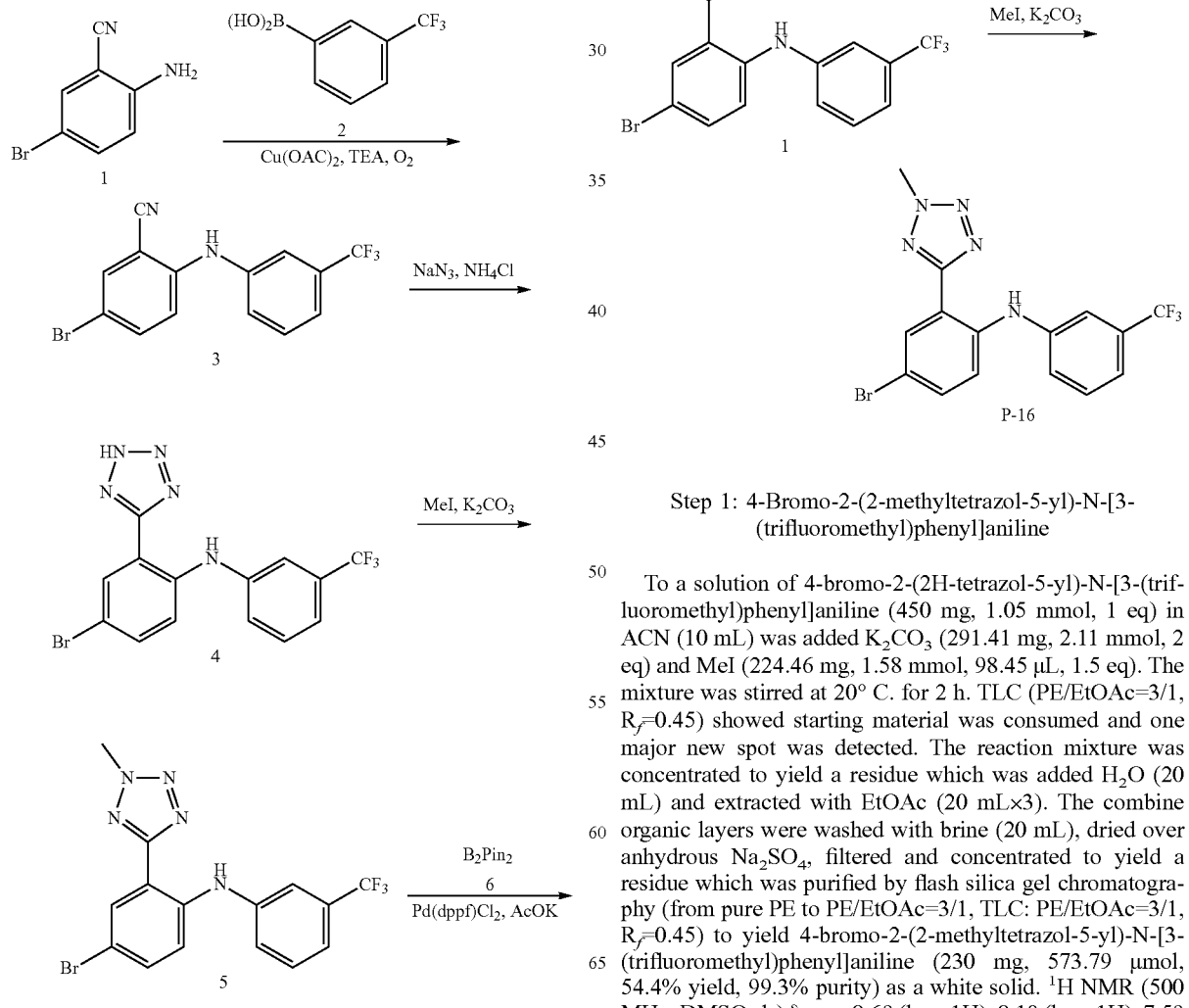

Step 1: 4-Bromo-2-(2-methyltetrazol-5-yl)-N-[3-(trifluoromethyl)phenyl]aniline

To a solution of 4-bromo-2-(2H-tetrazol-5-yl)-N-[3-(trifluoromethyl)phenyl]aniline (450 mg, 1.05 mmol, 1 eq) in ACN (10 mL) was added $K_2CO_3$ (291.41 mg, 2.11 mmol, 2 eq) and MeI (224.46 mg, 1.58 mmol, 98.45 µL, 1.5 eq). The mixture was stirred at 20° C. for 2 h. TLC (PE/EtOAc=3/1, $R_f$=0.45) showed starting material was consumed and one major new spot was detected. The reaction mixture was concentrated to yield a residue which was added $H_2O$ (20 mL) and extracted with EtOAc (20 mL×3). The combine organic layers were washed with brine (20 mL), dried over anhydrous $Na_2SO_4$, filtered and concentrated to yield a residue which was purified by flash silica gel chromatography (from pure PE to PE/EtOAc=3/1, TLC: PE/EtOAc=3/1, $R_f$=0.45) to yield 4-bromo-2-(2-methyltetrazol-5-yl)-N-[3-(trifluoromethyl)phenyl]aniline (230 mg, 573.79 µmol, 54.4% yield, 99.3% purity) as a white solid. $^1$H NMR (500 MHz, DMSO-$d_6$) δ ppm 8.69 (br s, 1H), 8.10 (br s, 1H), 7.59

(d, J=8.9 Hz, 1H), 7.54-7.48 (m, 1H), 7.47-7.41 (m, 2H), 7.36 (d, J=8.7 Hz, 1H), 7.28 (d, J=7.3 Hz, 1H), 4.45 (s, 3H); ES-LCMS m/z 399.4 [M+H]+.

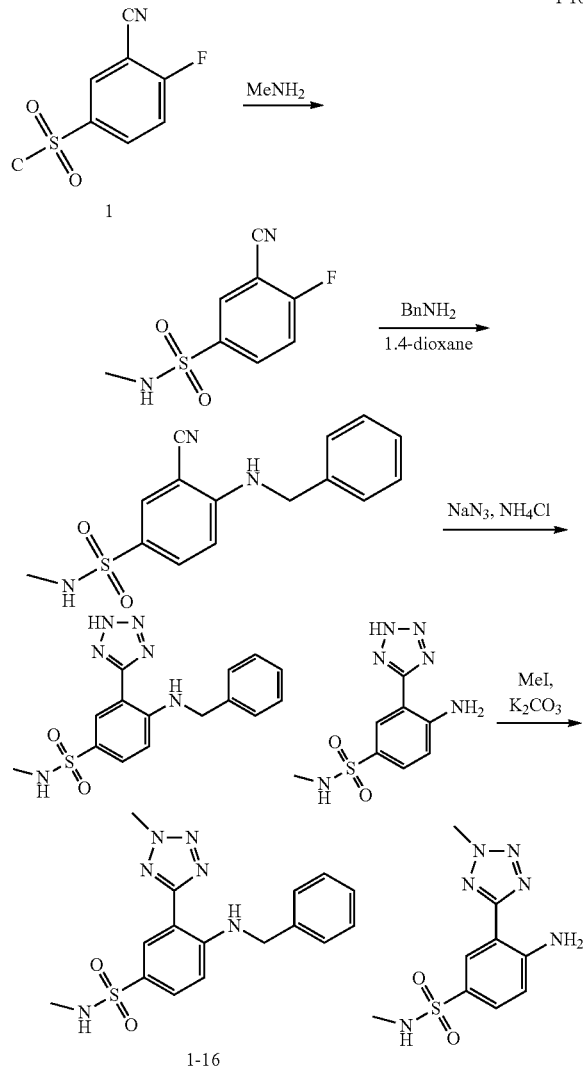

Step 1: 3-Cyano-4-fluoro-N-methyl-benzenesulfonamide

To a solution of 3-cyano-4-fluoro-benzenesulfonyl chloride (1.2 g, 5.46 mmol, 1 eq) in THF (20 mL) was added MeNH$_2$ (1.8 g, 19.13 mmol, 33% purity, 3.50 eq) at −70° C. The mixture was stirred at −70° C. for 1 h. TLC (PE/EtOAc=10/1, R$_f$=0.06) showed the starting material was consumed completely. The reaction mixture was quenched with aqueous HCl (10 mL, 1M), diluted with water (20 mL) and extracted with EtOAc (50 mL×3). The organic layer was dried over Na$_2$SO$_4$, filtered and concentrated under reduced pressure to yield 3-cyano-4-fluoro-N-methyl-benzenesulfonamide (1.1 g, 5.13 mmol, 94.0% yield, N/A purity) as a brown gum, which was used in the next step without further purification. $^1$H NMR (400 MHz, CDCl$_3$) δ ppm 8.15 (td, J=2.2, 5.6 Hz, 1H), 8.12-8.07 (m, 1H), 7.39 (dt, J=2.1, 8.5 Hz, 1H), 4.51 (s, 1H), 2.71 (d, J=1.5 Hz, 3H).

Step 2: 4-(Benzylamino)-3-cyano-N-methyl-benzenesulfonamide

A mixture of 3-cyano-4-fluoro-N-methyl-benzenesulfonamide (1.1 g, 5.13 mmol, 1 eq), BnNH$_2$ (850 mg, 7.93 mmol, 864.70 μL, 1.54 eq) and K$_2$CO$_3$ (2.13 g, 15.40 mmol, 3 eq) in 1,4-dioxane (20 mL) was stirred at 90° C. for 3 h. TLC (PE/EtOAc=1/1, R$_f$=0.50) showed the starting material was consumed completely. The reaction mixture was diluted with H$_2$O (50 mL) and extracted with EtOAc (50 mL×3). The organic layer was washed with aqueous citric acid (10 mL, 2M) and brine (20 mL), dried over Na$_2$SO$_4$, filtered and concentrated under reduced pressure to yield a residue which was purified by flash silica gel chromatography (from PE/EtOAc=20/1 to 3/1, TLC: PE/EtOAc=1/1, R$_f$=0.50) to yield 4-(benzylamino)-3-cyano-N-methyl-benzenesulfonamide (1.1 g, 3.57 mmol, 69.6% yield, 97.9% purity) as a yellow solid. $^1$H NMR (400 MHz, DMSO-d$_6$) δ ppm 7.80 (d, J=2.0 Hz, 1H), 7.70 (t, J=6.0 Hz, 1H), 7.61 (dd, J=2.0, 9.0 Hz, 1H), 7.39-7.32 (m, 4H), 7.28-7.18 (m, 2H), 6.77 (d, J=9.0 Hz, 1H), 4.50 (d, J=6.1 Hz, 2H), 2.35 (d, J=5.1 Hz, 3H); ES-LCMS m/z 302.1 [M+H]+.

Step 3: 4-(Benzylamino)-N-methyl-3-(2H-tetrazol-5-yl)benzenesulfonamide and 4-amino-N-methyl-3-(2H-tetrazol-5-yl)benzenesulfonamide A mixture of 4-(benzylamino)-3-cyano-N-methyl-benzenesulfonamide (500 mg, 1.66 mmol, 1 eq), NaN$_3$ (375 mg, 5.77 mmol, 3.48 eq) and NH$_4$Cl (450 mg, 8.41 mmol, 5.07 eq) in DMF (10 mL) was stirred at 120° C. for 6 h. TLC (PE/EtOAc, R$_f$=0.03) showed the starting material was consumed completely. The reaction mixture was filtered. The filtrate was purified by flash silica gel chromatography (from PE/EtOAc=10/1 to 0/1 and then EtOAc/MeOH=20/1, TLC: PE/EtOAc=1/1, R$_f$=0.03) to yield a mixture of 4-(benzylamino)-N-methyl-3-(2H-tetrazol-5-yl)benzenesulfonamide (550 mg, 843.23 μmol, 50.8% yield, 52.8% purity) and 4-amino-N-methyl-3-(2H-tetrazol-5-yl)benzenesulfonamide (550 mg, 906.33 μmol, 54.6% yield, 41.9% purity) as a colorless gum. $^1$H NMR (400 MHz, CD$_3$OD) δ ppm 8.34 (d, J=2.2 Hz, 1H), 7.65 (dd, J=2.3, 8.9 Hz, 1H), 7.42-7.37 (m, 2H), 7.36-7.30 (m, 2H), 7.28-7.21 (m, 1H), 6.89 (d, J=9.0 Hz, 1H), 4.61 (s, 2H), 2.50 (s, 3H); ES-LCMS m/z 345.0 [M+H]+. $^1$H NMR (400 MHz, CD$_3$OD) δ ppm 8.26 (d, J=2.2 Hz, 1H), 7.60 (dd, J=2.2, 8.8 Hz, 1H), 6.97 (d, J=8.8 Hz, 1H), 2.51 (s, 3H); ES-LCMS m/z 255.0 [M+H]+.

Step 4: 4-(Benzylamino)-N-methyl-3-(2-methyltetrazol-5-yl)benzenesulfonamide and 4-amino-N-methyl-3-(2-methyltetrazol-5-yl)benzenesulfonamide To a mixture of 4-(benzylamino)-N-methyl-3-(2H-tetrazol-5-yl)benzenesulfonamide (250 mg, 383.29 μmol, 1 eq), 4-amino-N-methyl-3-(2H-tetrazol-5-yl)benzenesulfonamide (250 mg, 411.97 μmol, 1.07 eq) and K$_2$CO$_3$ (160 mg, 1.16 mmol, 3.02 eq) in THF (20 mL) was added MeI (38.76 mg, 273.08 μmol, 17 μL, 7.12e-1 eq) at −70° C. The mixture was warmed to 20° C. slowly and stirred at 20° C. for 12 h. TLC (PE/EtOAc=1/1, R$_f$=0.50, 0.34) showed two major spots formed. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by preparative HPLC (column: Agela DuraShell C18 150*25 mm*5 um; mobile phase: [water (0.04% NH$_3$.H$_2$O+

10 mM NH$_4$HCO$_3$)-ACN]; B %: 36%-66%, 10 min) to yield peak 1 and peak 2. Peak 2 was lyophilized to yield 4-(benzylamino)-N-methyl-3-(2-methyltetrazol-5-yl)benzenesulfonamide (50 mg, 138.17 μmol, 36.1% yield, 99.0% purity) as a yellow solid. $^1$H NMR (500 MHz, DMSO-d$_6$) δ ppm 8.40 (d, J=2.3 Hz, 1H), 8.09 (t, J=5.7 Hz, 1H), 7.62 (dd, J=2.1, 8.9 Hz, 1H), 7.43-7.35 (m, 4H), 7.31-7.26 (m, 1H), 7.24 (d, J=5.0 Hz, 1H), 6.94 (d, J=8.9 Hz, 1H), 4.66 (d, J=5.8 Hz, 2H), 4.49 (s, 3H), 2.37 (d, J=4.9 Hz, 3H); ES-LCMS m/z 358.6 [M+H]$^+$. Peak 1 was lyophilized to yield 4-amino-N-methyl-3-(2-methyltetrazol-5-yl)benzenesulfonamide (35 mg, 130.45 μmol, 34.0% yield, 100.0% purity) as a white solid. $^1$H NMR (500 MHz, DMSO-d$_6$) δ ppm 8.35 (d, J=2.1 Hz, 1H), 7.56 (dd, J=2.1, 8.7 Hz, 1H), 7.20 (q, J=4.8 Hz, 1H), 7.05 (s, 2H), 7.00 (d, J=8.7 Hz, 1H), 4.48 (s, 3H), 2.38 (d, J=5.0 Hz, 3H); ES-LCMS m/z 268.5 [M+H]$^+$.

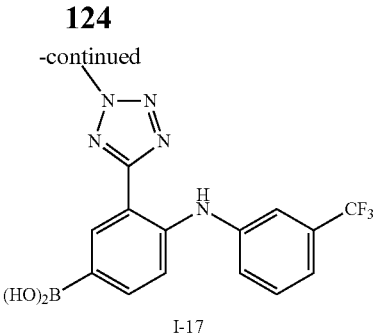

I-17

Step 1: 5-Bromo-2-[3-(trifluoromethyl)anilino]benzonitrile

To a mixture of 2-amino-5-bromo-benzonitrile (2 g, 10.15 mmol, 1 eq) and [3-(trifluoromethyl)phenyl]boronic acid (2.89 g, 15.23 mmol, 1.5 eq) in DCM (40 mL) was added Cu(OAc)$_2$ (2.21 g, 12.18 mmol, 1.2 eq) and DIEA (2.62 g, 20.30 mmol, 3.54 mL, 2 eq). The mixture was stirred under oxygen (30 psi) atmosphere at 25° C. for 12 h. TLC (PE/EtOAc=3:1, R$_f$=0.6) showed starting material was consumed completely and one major new spot was detected. The mixture was filtered and the filtrate was concentrated to yield a residue which was purified by flash silica gel chromatography (from pure PE to PE/EtOAc=4/1, TLC: PE/EtOAc=3/1, R$_f$=0.6) to yield 5-bromo-2-[3-(trifluoromethyl)anilino]benzonitrile (1.8 g, 4.75 mmol, 46.8% yield, 90.0% purity) as a yellow solid. $^1$H NMR (400 MHz, DMSO-d$_6$) δ ppm 8.95 (s, 1H), 8.00 (d, J=2.4 Hz, 1H), 7.71 (dd, J=2.4, 9.0 Hz, 1H), 7.54-7.49 (m, 1H), 7.41-7.37 (m, 2H), 7.30-7.24 (m, 2H).

Step 2: 4-Bromo-2-(2H-tetrazol-5-yl)-N-[3-(trifluoromethyl)phenyl]aniline

To a mixture of 5-bromo-2-[3-(trifluoromethyl)anilino]benzonitrile (500 mg, 1.32 mmol, 1 eq) in DMF (20 mL) was added NaN$_3$ (970 mg, 14.92 mmol, 11.31 eq) and NH$_4$Cl (705.64 mg, 13.19 mmol, 10 eq). The mixture was stirred at 120° C. for 10 h. TLC (DCM/MeOH=5:1, R$_f$=0.5) showed starting material was consumed completely and one major new spot was detected. The residue was diluted with H$_2$O (100 mL) and extracted with EtOAc (80 mL×2). The combined organic layers were dried over Na$_2$SO$_4$, filtered and concentrated under reduced pressure to yield a residue which was purified by flash silica gel chromatography (from pure DCM to DCM/MeOH=20/1, TLC: DCM/MeOH=5/1, R$_f$=0.5) to yield 4-bromo-2-(2H-tetrazol-5-yl)-N-[3-(trifluoromethyl)phenyl]aniline (650 mg, 1.27 mmol, 96.2% yield, 75.0% purity) as a yellow solid. $^1$H NMR (400 MHz, DMSO-d$_6$) δ ppm 9.14 (s, 1H), 8.08 (d, J=2.4 Hz, 1H), 7.63 (dd, J=2.4, 8.8 Hz, 1H), 7.56-7.48 (m, 1H), 7.48-7.43 (m, 2H), 7.42-7.35 (m, 1H), 7.30 (d, J=7.6 Hz, 1H).

Step 3: 4-Bromo-2-(2-methyltetrazol-5-yl)-N-[3-(trifluoromethyl)phenyl]aniline

To a solution of 4-bromo-2-(2H-tetrazol-5-yl)-N-[3-(trifluoromethyl)phenyl]aniline (200 mg, 390.47 μmol, 1 eq) in ACN (5 mL) was added K$_2$CO$_3$ (107.93 mg, 780.94 μmol, 2 eq) and MeI (83.13 mg, 585.70 μmol, 36.46 μL, 1.5 eq). The mixture was stirred at 20° C. for 2 h. The reaction mixture was concentrated to yield a residue which was added H$_2$O (20 mL) and extracted with EtOAc (20 mL×3).

The combine organic layers were washed with brine (20 mL), dried over anhydrous Na₂SO₄, filtered and concentrated to yield a residue which was purified by flash silica gel chromatography (from pure PE to PE/EtOAc=3/1, TLC: PE/EtOAc=3/1, $R_f$=0.45) to yield 4-bromo-2-(2-methyltetrazol-5-yl)-N-[3-(trifluoromethyl)phenyl]aniline (150 mg, 339.04 μmol, 86.8% yield, 90.0% purity) as a white solid. ¹H NMR (500 MHz, DMSO-d₆) δ ppm 8.70 (s, 1H), 8.09 (d, J=2.4 Hz, 1H), 7.59 (dd, J=2.4, 8.9 Hz, 1H), 7.54-7.49 (m, 1H), 7.46-7.42 (m, 2H), 7.37 (d, J=8.9 Hz, 1H), 7.28 (d, J=7.6 Hz, 1H), 4.45 (s, 3H); ES-LCMS m/z 398.0, 400.0 [M+H]⁺.

Step 4: 2-(2-Methyltetrazol-5-yl)-4-(4,4,5,5-tetramethyl-1,3,2-dioxaborolan-2-yl)-N-[3-(trifluoromethyl)phenyl]aniline To a solution of 4-bromo-2-(2-methyltetrazol-5-yl)-N-[3-(trifluoromethyl)phenyl]aniline (150 mg, 339.04 μmol, 1 eq) in 1,4-dioxane (2 mL) was added Pd(dppf)Cl₂ (24.81 mg, 33.90 μmol, 0.1 eq), B₂Pin₂ (129.14 mg, 508.56 μmol, 1.5 eq) and AcOK (99.82 mg, 1.02 mmol, 3 eq) under N₂ atmosphere. The mixture was stirred at 80° C. for 2 h under N₂ atmosphere. TLC (PE/EtOAc=5/1, $R_f$=0.55) showed starting material was consumed completely and one major new spot was detected. The mixture was added H₂O (20 mL) and extracted with EtOAc (20 mL×3). The combine organic layers were dried over anhydrous Na₂SO₄, filtered and concentrated to yield a residue which was purified by flash silica gel chromatography (from pure PE to PE/EtOAc=4/1, TLC: PE/EtOAc=5/1, $R_f$=0.55) to yield 2-(2-methyltetrazol-5-yl)-4-(4,4,5,5-tetramethyl-1,3,2-dioxaborolan-2-yl)-N-[3-(trifluoromethyl)phenyl]aniline (150 mg, 303.20 μmol, 89.4% yield, 90.0% purity) as a white solid. ¹H NMR (400 MHz, DMSO-d₆) δ ppm 8.98 (s, 1H), 8.38 (d, J=1.5 Hz, 1H), 7.67 (dd, J=1.7, 8.3 Hz, 1H), 7.57-7.52 (m, 3H), 7.39-7.33 (m, 2H), 4.46 (s, 3H), 1.31 (s, 12H).

Step 5: [3-(2-Methyltetrazol-5-yl)-4-[3-(trifluoromethyl)anilino]phenyl]boronic acid To a solution of 2-(2-methyltetrazol-5-yl)-4-(4,4,5,5-tetramethyl-1,3,2-dioxaborolan-2-yl)-N-[3-(trifluoromethyl)phenyl]aniline (60 mg, 121.28 μmol, 1 eq) in acetone (3 mL) was added NaIO₄ (259.41 mg, 1.21 mmol, 10 eq) and NH₄OAc (1 M, 1.21 mL, 10 eq). The mixture was stirred at 20° C. for 12 h. TLC (PE/EtOAc=1/1, $R_f$=0.5) showed starting material was consumed and one major new spot was detected. The mixture was filtered and the filtrate was concentrated to yield a residue which was purified by preparative HPLC (column: Welch Xtimate C18 150*30 mm*5 μm; mobile phase: [water (10 mM NH₄HCO₃)-ACN]; B %: 40%-70%, 10 min) and lyophilized to yield [3-(2-methyltetrazol-5-yl)-4-[3-(trifluoromethyl)anilino]phenyl]boronic acid (11.17 mg, 30.76 μmol, 25.4% yield, 100.0% purity) as a brown solid. ¹H NMR (400 MHz, CD₃OD) δ ppm 8.64-8.44 (m, 1H), 7.81-7.63 (m, 1H), 7.49 (s, 3H), 7.43-7.34 (m, 1H), 7.29 (s, 1H), 4.46 (s, 3H); ES-LCMS m/z 364.0 [M+H]⁺.

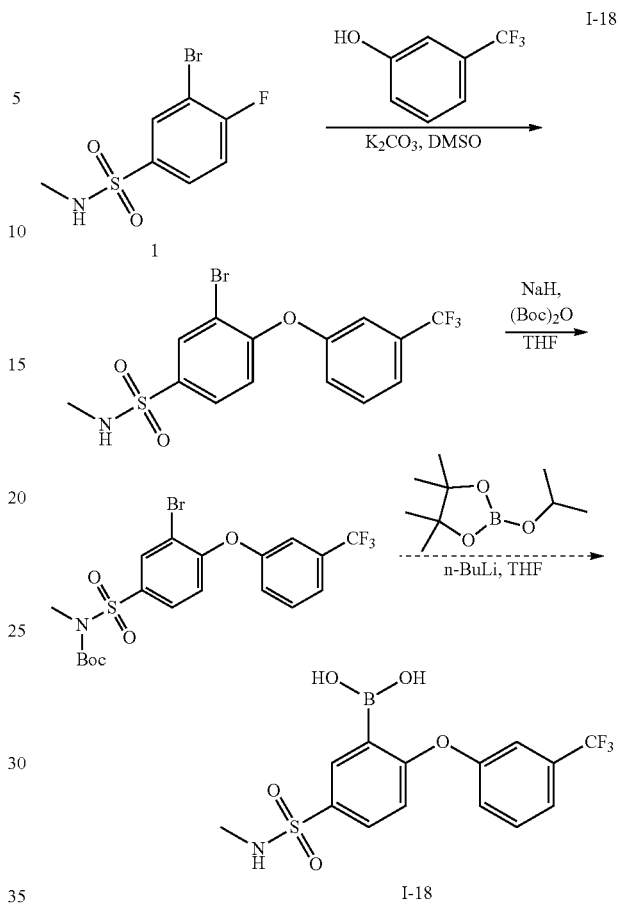

I-18

Step 1: 3-Bromo-N-methyl-4-[3-(trifluoromethyl)phenoxy]benzenesulfonamide

To a stirred solution of 3-bromo-4-fluoro-N-methyl-benzenesulfonamide (1.5 g, 5.32 mmol, 1 eq) in DMSO (30 mL) was added K₂CO₃ (2.20 g, 15.95 mmol, 3 eq) and 3-(trifluoromethyl)phenol (1.72 g, 10.63 mmol, 1.28 mL, 2 eq). The reaction mixture was stirred at 140° C. for 4 h. TLC (PE/EtOAc=3/1, $R_f$=0.10) showed starting material was consumed completely and one new spot was detected. The reaction mixture was added to water (300 mL) then extracted with EtOAc (150 mL×3). The combined organic layers were dried over Na₂SO₄, filtered and the filtrate was concentrated to yield a residue which was purified by flash silica gel chromatography (from PE/EtOAc=100/1 to 3/1, TLC: PE/EtOAc=3/1, $R_f$=0.10) to yield 3-bromo-N-methyl-4-[3-(trifluoromethyl)phenoxy]benzenesulfonamide (1.6 g, 3.71 mmol, 69.7% yield, 95.0% purity) as yellow solid. ¹H NMR (500 MHz, CDCl₃) δ ppm 8.18 (d, J=2.1 Hz, 1H), 7.77 (dd, J=2.1, 8.5 Hz, 1H), 7.58-7.53 (m, 1H), 7.52-7.47 (m, 1H), 7.32 (s, 1H), 7.22 (d, J=8.1 Hz, 1H), 6.97 (d, J=8.7 Hz, 1H), 4.41 (q, J=5.2 Hz, 1H), 2.74 (d, J=5.3 Hz, 3H).

Step 2: tert-Butyl N-[3-bromo-4-[3-(trifluoromethyl)phenoxy]phenyl]sulfonyl-N-methyl-carbamate To a stirred solution of 3-bromo-N-methyl-4-[3-(trifluoromethyl)phenoxy]benzenesulfonamide (200 mg, 463.18 μmol, 1 eq) in THF (8 mL) was cooled to 0° C. then added NaH (22.23 mg, 555.82 µmol, 60% in mineral oil, 1.2 eq). The reaction mixture was stirred at 0° C. for 30 min. (Boc)₂O (151.63 mg, 694.77 µmol, 159.61 µL, 1.5 eq) was added to the above mixture then stirred at 28° C. for 2 h. TLC (PE/EtOAc=3/1, R$_f$=0.35) showed starting material was consumed completely and one new spot was detected. The reaction mixture was added to water (5 mL) then extracted with EtOAc (30 mL×3). The combined organic layers were dried over Na₂SO₄, filtered and the filtrate was concentrated to yield a residue which was purified by flash silica gel chromatography (from PE/EtOAc=100/1 to 3/1, TLC: PE/EtOAc=3/1, R$_f$=0.35) to yield tert-butyl N-[3-bromo-4-[3-(trifluoromethyl)phenoxy]phenyl]sulfonyl-N-methyl-carbamate (230 mg, 428.16 µmol, 92.4% yield, 95.0% purity) as colorless oil. ¹H NMR (400 MHz, CDCl₃) δ ppm 8.23 (d, J=2.2 Hz, 1H), 7.81 (dd, J=2.2, 8.6 Hz, 1H), 7.58-7.49 (m, 2H), 7.29 (s, 1H), 7.23 (d, J=7.8 Hz, 1H), 6.97 (d, J=8.6 Hz, 1H), 3.36 (s, 3H), 1.43 (s, 9H).

Step 3: N-[4-(1-Adamantyl)phenyl]-2-(4H-1,2,4-triazol-3-ylsulfanyl)acetamide

To a stirred solution of tert-butyl N-[3-bromo-4-[3-(trifluoromethyl)phenoxy]phenyl]sulfonyl-N-methyl-carbamate (100 mg, 186.16 µmol, 1 eq) in THF (5 mL) was cooled to −75° C. then added n-BuLi (2.5 M in hexane, 148.93 µL, 2 eq). The reaction mixture was degassed and purged with N₂ for three times then stirred at −75° C. for 30 min under N₂ atmosphere. 2-Isopropoxy-4,4,5,5-tetramethyl-1,3,2-dioxaborolane (103.91 mg, 558.47 µmol, 113.93 µL, 3 eq) was added to the above mixture then stirred at −75° C. for 1.5 h under N₂ atmosphere. Water (1 mL) was added to the above reaction mixture then stirred for 5 min at 28° C. The mixture was concentrated to remove THF then purified by preparative HPLC (column: Phenomenex Synergi C18 150*30 mm*4 um; mobile phase: [water (0.05% HCl)-ACN]; B %: 37%-57%, 10 min). The desired fraction was lyophilized to yield [5-(methylsulfamoyl)-2-[3-(trifluoromethyl)phenoxy]phenyl]boronic acid (5.41 mg, 14.42 µmol, 7.8% yield, 100.0% purity) as white solid. ¹H NMR (400 MHz, CD₃OD) δ ppm 7.91 (s, 1H), 7.85 (dd, J=2.3, 8.7 Hz, 1H), 7.64-7.58 (m, 1H), 7.50 (d, J=7.8 Hz, 1H), 7.39-7.25 (m, 2H), 7.04 (d, J=7.3 Hz, 1H), 2.55 (s, 3H); ES-LCMS m/z 375.9 [M+H]⁺.

I-19

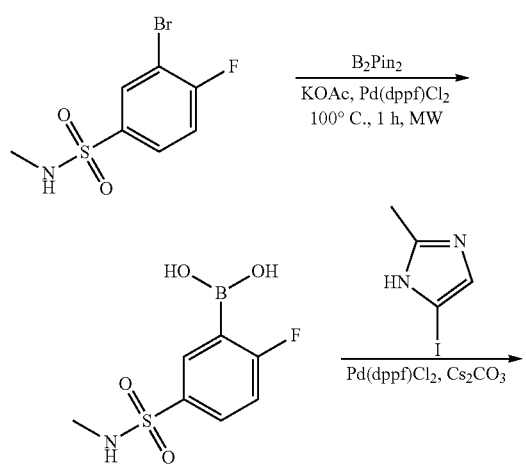

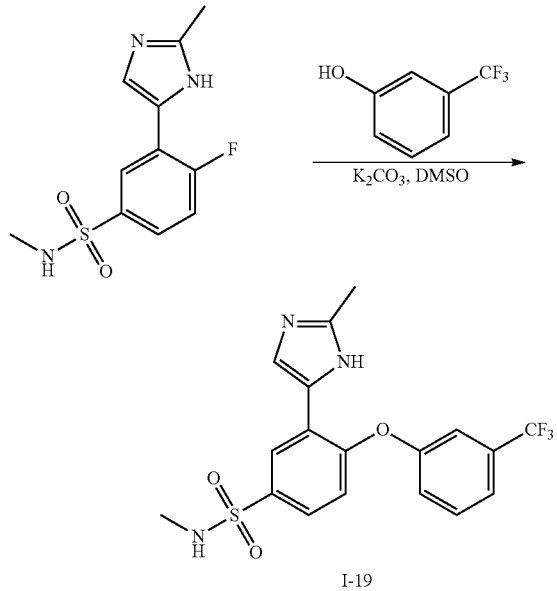

I-19

Step 1: 4-Fluoro-N-methyl-3-(2-methyl-1H-imidazol-5-yl)benzenesulfonamide

To a stirred solution of 3-bromo-4-fluoro-N-methyl-benzenesulfonamide (400 mg, 1.42 mmol, 1 eq) in 1,4-dioxane (5 mL) was added KOAc (278.20 mg, 2.83 mmol, 2 eq), Pd(dppf)Cl₂ (103.71 mg, 141.74 µmol, 0.1 eq) and 4,4,5,5-tetramethyl-2-(4,4,5,5-tetramethyl-1,3,2-dioxaborolan-2-yl)-1,3,2-dioxaborolane (467.90 mg, 1.84 mmol, 1.3 eq). The reaction mixture was degassed and purged with N₂ for three times then stirred at 80° C. for 2 h. The reaction mixture was cooled to 25° C. Pd(dppf)Cl₂ (103.71 mg, 144.74 µmol, 1.3 eq) Cs₂CO₃ (923.61 mg, 2.83 mmol, 2 eq), water (1 mL) and 5-iodo-2-methyl-1H-imidazole (383.25 mg, 1.84 mmol, 1.3 eq) were added to the above reaction mixture then bubbled with N₂ for 3 min then stirred at 100° C. for 2 h under N₂ atmosphere. The reaction mixture was concentrated to yield a residue which was purified by flash silica gel chromatography (from PE/EtOAc=100/1 to 0/1, TLC: PE/EtOAc=0/1, R$_f$=0.50) to yield 4-fluoro-N-methyl-3-(2-methyl-1H-imidazol-5-yl)benzenesulfonamide (130 mg, 434.47 µmol, 30.7% yield, 90.0% purity) as yellow solid. H NMR (400 MHz, DMSO-d₆) δ ppm 12.12 (s, 1H), 8.47 (d, J=5.9 Hz, 1H), 7.62-7.56 (m, 1H), 7.51 (d, J=4.9 Hz, 1H), 7.48-7.39 (m, 2H), 2.41 (d, J=4.9 Hz, 3H), 2.35 (s, 3H).

Step 2: N-Methyl-3-(2-methyl-1H-imidazol-5-yl)-4-[3-(trifluoromethyl)phenoxy]benzenesulfonamide To a stirred solution of 4-fluoro-N-methyl-3-(2-methyl-1H-imidazol-5-yl)benzenesulfonamide (130 mg, 434.47 µmol, 1 eq) and 3-(trifluoromethyl)phenol (176.08 mg, 1.09 mmol, 130.43 µL, 2.5 eq) in DMSO (5 mL) was added K₂CO₃ (180.14 mg, 1.30 mmol, 3 eq). The reaction mixture was stirred at 140° C. for 4 h. The reaction mixture was diluted with water (30 mL) then extracted with EtOAc (20 mL×3). The combined organic layers were dried over Na₂SO₄, filtered and the filtrate was concentrated to yield a residue which was purified by preparative HPLC (column: Agela DuraShell C18 150*25 mm*5 um; mobile phase: [water (0.04% NH₃.H₂O+10 mM NH₄HCO₃)-ACN]; B %:

20%-50%, 10 min). The desired fraction was lyophilized to yield N-methyl-3-(2-methyl-1H-imidazol-5-yl)-4-[3-(trifluoromethyl)phenoxy]benzenesulfonamide (26.01 mg, 63.22 μmol, 14.6% yield, 100.0% purity) as yellow solid. $^1$H NMR (500 MHz, DMSO-d$_6$) δ ppm 10.49 (s, 1H), 7.73 (d, J=7.8 Hz, 1H), 7.65 (t, J=7.7 Hz, 1H), 7.60-7.55 (m, 2H), 7.49 (dd, J=2.4, 8.5 Hz, 1H), 7.41 (d, J=2.3 Hz, 1H), 7.11 (q, J=5.0 Hz, 1H), 7.06 (s, 1H), 6.86 (d, J=8.5 Hz, 1H), 2.27 (s, 3H), 2.18 (d, J=5.2 Hz, 3H); ES-LCMS m/z 411.9 [M+H]$^+$.

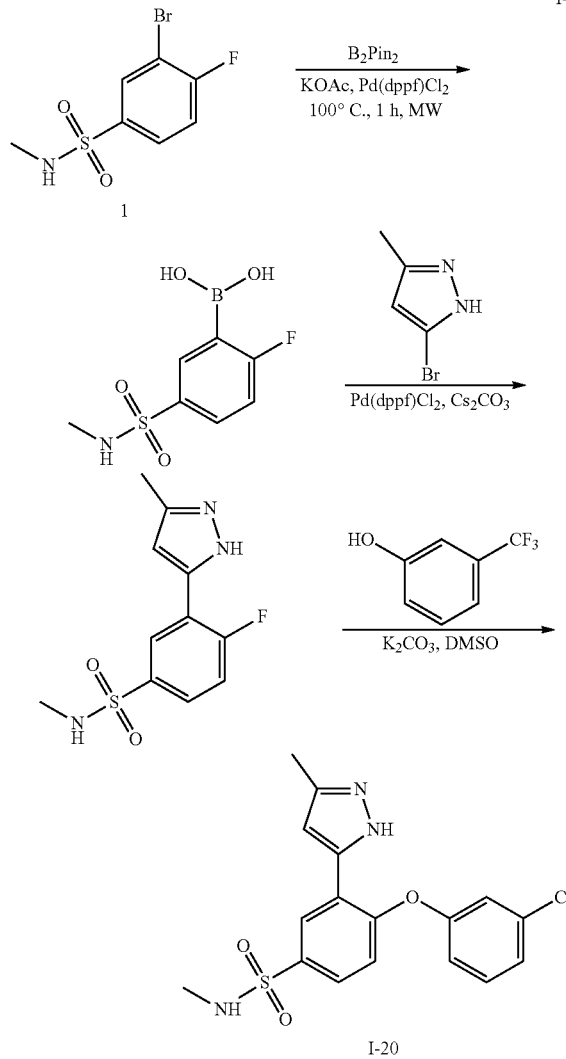

Step 1: 4-Fluoro-N-methyl-3-(3-methyl-1H-pyrazol-5-yl)benzenesulfonamide

To a stirred solution of 3-bromo-4-fluoro-N-methyl-benzenesulfonamide (400 mg, 1.42 mmol, 1 eq) in 1,4-dioxane (6 mL) was added KOAc (278.20 mg, 2.83 mmol, 2 eq), Pd(dppf)Cl$_2$ (103.71 mg, 141.74 μmol, 0.1 eq) and 4,4,5,5-tetramethyl-2-(4,4,5,5-tetramethyl-1,3,2-dioxaborolan-2-yl)-1,3,2-dioxaborolane (467.90 mg, 1.84 mmol, 1.3 eq). The reaction mixture was degassed and purged with N$_2$ for three times then stirred at 80° C. for 1.5 h. Pd(dppf)Cl$_2$ (103.71 mg, 141.74 μmol, 0.1 eq), Cs$_2$CO$_3$ (923.61 mg, 2.83 mmol, 2 eq), water (2 mL) and 5-bromo-3-methyl-1H-pyrazole (296.65 mg, 1.84 mmol, 1.3 eq) was added to the above reaction mixture then bubbled with N$_2$ for 3 min then stirred at 100° C. for 2 h under N$_2$ atmosphere. The reaction mixture was concentrated to yield a residue which was purified by flash silica gel chromatography (from PE/EtOAc=100/1 to 0/1, TLC: PE/EtOAc=1/2, R$_f$=0.35) to yield 4-fluoro-N-methyl-3-(3-methyl-1H-pyrazol-5-yl)benzenesulfonamide (321 mg, 611.50 μmol, 43.1% yield, 51.3% purity) as yellow solid. $^1$H NMR (500 MHz, DMSO-d) ppm 12.95 (s, 1H), 8.42-8.35 (m, 1H), 7.94 (s, 1H), 7.73-7.69 (m, 1H), 7.58-7.51 (m, 2H), 2.41 (d, J=5.0 Hz, 3H), 2.30 (s, 3H); ES-LCMS m/z 270.0 [M+H]$^+$.

Step 2: N-methyl-3-(3-methyl-1H-pyrazol-5-yl)-4-[3-(trifluoromethyl)phenoxy]benzenesulfonamide To a stirred solution of 4-fluoro-N-methyl-3-(3-methyl-1H-pyrazol-5-yl)benzenesulfonamide (321 mg, 611.50 μmol, 1 eq) and 3-(trifluoromethyl)phenol (247.82 mg, 1.53 mmol, 183.57 μL, 2.5 eq) in DMSO (10 mL) was added K$_2$CO$_3$ (253.55 mg, 1.83 mmol, 3 eq). The reaction mixture was stirred at 140° C. for 4 h. The reaction mixture was diluted with water (50 mL) then extracted with EtOAc (50 mL×3). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 24%-54%, 10 min). The desired fraction was lyophilized to yield N-methyl-3-(3-methyl-1H-pyrazol-5-yl)-4-[3-(trifluoromethyl)phenoxy]benzenesulfonamide (27.95 mg, 67.94 μmol, 11.1% yield, 100.0% purity) as white solid. $^1$H NMR (500 MHz, DMSO-d$_6$) δ ppm 7.64-7.56 (m, 4H), 7.55-7.52 (m, 1H), 7.46 (s, 1H), 7.20 (d, J=5.2 Hz, 1H), 6.91 (d, J=8.5 Hz, 1H), 6.43 (s, 1H), 2.31-2.28 (m, 6H); ES-LCMS m/z 411.9 [M-I$^-$]$^+$.

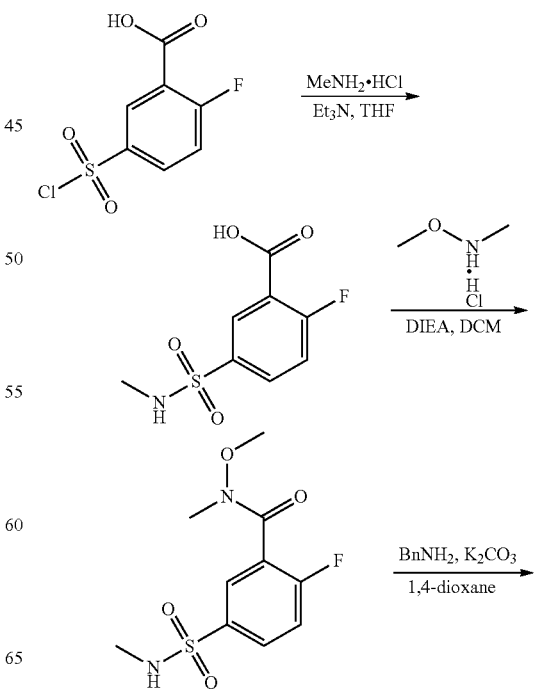

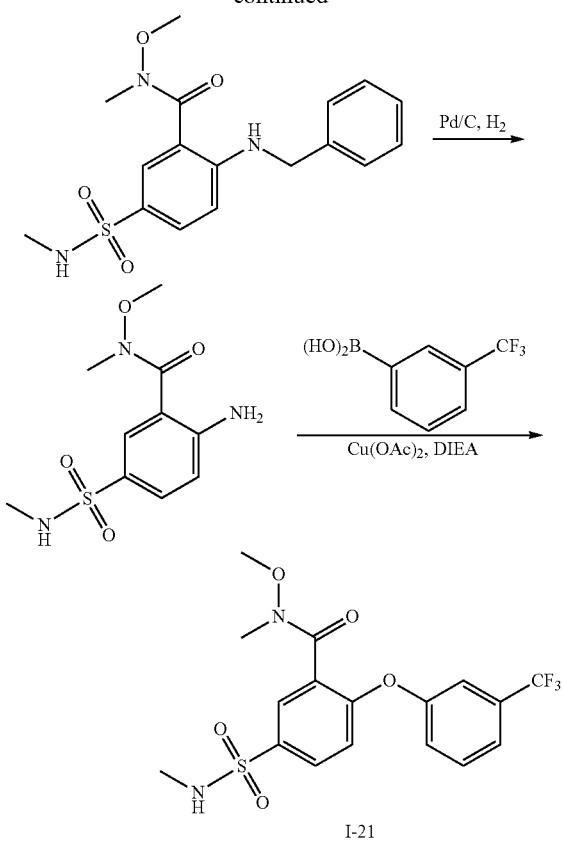

Step 1: 2-Fluoro-5-(methylsulfamoyl)benzoic acid

To a solution of 5-chlorosulfonyl-2-fluoro-benzoic acid (10 g, 41.91 mmol, 1 eq) in THF (100 mL) was added MeNH$_2$/EtOH (12 g, 127.51 mmol, 33% purity, 3.04 eq) at −78° C. The mixture was stirred at −78° C. for 2 h. The reaction mixture was quenched with aqueous HCl (100 mL, 2 M) at −78° C. The mixture was warmed to 20° C. and extracted with EtOAc (150 mL×3). The organic layer was dried over Na$_2$SO$_4$, filtered and concentrated under reduced pressure to yield 2-fluoro-5-(methylsulfamoyl)benzoic acid (9.5 g, 39.02 mmol, 93.1% yield, 95.8% purity) as an off white solid, which was used in the next step without further purification. $^1$H NMR (400 MHz, DMSO-d$_6$) δ ppm 8.26 (dd, J=2.3, 6.7 Hz, 1H), 8.01 (ddd, J=2.4, 4.3, 8.6 Hz, 1H), 7.65 (q, J=4.6 Hz, 1H), 7.58 (dd, J=8.8, 10.5 Hz, 1H), 2.42 (d, J=4.9 Hz, 3H); ES-LCMS m/z 233.9 [M+H]$^+$.

Step 2: 2-Fluoro-N-methoxy-N-methyl-5-(methylsulfamoyl)benzamide

A mixture of 2-fluoro-5-(methylsulfamoyl)benzoic acid (5 g, 20.54 mmol, 1 eq), N-methoxymethanamine (2.40 g, 24.65 mmol, 1.2 eq, HCl), HATU (9.37 g, 24.65 mmol, 1.2 eq) and DIEA (10.66 g, 82.50 mmol, 14.37 mL, 4.02 eq) in DCM (100 mL) was stirred at 25° C. for 3 h. TLC (PE/EtOAc=1/1, R$_f$=0.35) showed the starting material was consumed completely. The reaction mixture was diluted with H$_2$O (50 mL) and extracted with DCM (50 mL×3). The organic layer was dried over Na$_2$SO$_4$, filtered and concentrated under reduced pressure to yield a residue which was purified by flash silica gel chromatography (from PE/EtOAc=20/1 to 1/1, TLC: PE/EtOAc=1/1, R$_f$=0.35) to yield 2-fluoro-N-methoxy-N-methyl-5-(methylsulfamoyl)benzamide (5 g, 17.92 mmol, 87.2% yield, 99.0% purity) as a colorless gum. $^1$H NMR (400 MHz, DMSO-d$_6$) δ ppm 7.98-7.84 (m, 2H), 7.65-7.49 (m, 2H), 3.29 (s, 3H), 2.69 (s, 3H), 2.43 (d, J=4.9 Hz, 3H); ES-LCMS m/z 276.9 [M+H]$^+$.

Step 3: 2-(Benzylamino)-N-methoxy-N-methyl-5-(methylsulfamoyl)benzamide

A mixture of 2-fluoro-N-methoxy-N-methyl-5-(methylsulfamoyl)benzamide (1 g, 3.58 mmol, 1 eq), phenylmethanamine (575 mg, 5.37 mmol, 584.94 µL, 1.5 eq) and K$_2$CO$_3$ (1.5 g, 10.85 mmol, 3.03 eq) in 1,4-dioxane (20 mL) was stirred at 135° C. for 12 h. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by flash silica gel chromatography (from PE/EtOAc=20/1 to 2/1, TLC: PE/EtOAc=1/1, R$_f$=0.29) to yield 2-(benzylamino)-N-methoxy-N-methyl-5-(methylsulfamoyl)benzamide (740 mg, 2.04 mmol, 56.8% yield, 100.0% purity) as a colorless gum. $^1$H NMR (400 MHz, CDCl$_3$) δ ppm 7.99 (s, 1H), 7.66 (d, J=8.8 Hz, 1H), 7.40-7.29 (m, 5H), 6.99 (s, 1H), 6.70 (d, J=8.8 Hz, 1H), 4.43 (d, J=5.4 Hz, 2H), 4.21-4.15 (m, 1H), 3.62 (d, J=1.2 Hz, 3H), 3.37 (d, J=1.2 Hz, 3H), 2.65-2.60 (m, 3H); ES-LCMS m/z 364.0 [M+H]$^+$.

Step 4: 2-Amino-N-methoxy-N-methyl-5-(methylsulfamoyl)benzamide

A mixture of 2-(benzylamino)-N-methoxy-N-methyl-5-(methylsulfamoyl)benzamide (740 mg, 2.04 mmol, 1 eq) and Pd/C (100 mg, 10% purity) in MeOH (30 mL) was stirred under H$_2$ (45 psi) at 25° C. for 12 h. TLC (PE/EtOAc=1/1, R$_f$=0.10) showed the starting material was consumed completely. The reaction mixture was filtered. The filtrate was concentrated under reduced pressure to yield 2-amino-N-methoxy-N-methyl-5-(methylsulfamoyl)benzamide (510 mg, 1.49 mmol, 73.3% yield, 80.0% purity) as a colorless gum, which was used in the next step without further purification. $^1$H NMR (400 MHz, CD$_3$OD) δ ppm 7.85 (d, J=2.2 Hz, 1H), 7.68 (dd, J=2.2, 8.8 Hz, 1H), 7.05 (d, J=8.8 Hz, 1H), 3.59 (s, 3H), 3.35 (s, 3H), 2.49 (s, 3H); ES-LCMS m/z 274.0 [M+H]$^+$.

Step 5: N-Methoxy-N-methyl-5-(methylsulfamoyl)-2-[3-(trifluoromethyl)anilino]benzamide A mixture of 2-amino-N-methoxy-N-methyl-5-(methylsulfamoyl)benzamide (100 mg, 365.89 µmol, 1 eq), [3-(trifluoromethyl)phenyl]boronic acid (200 mg, 1.05 mmol, 2.88 eq), DIEA (200 mg, 1.55 mmol, 269.54 µL, 4.23 eq) and Cu(OAc)$_2$ (165 mg, 908.42 µmol, 2.48 eq) in DCM (3 mL) was stirred under O$_2$ (15 psi) at 25° C. for 12 h. The reaction mixture was diluted with H$_2$O (20 mL) and extracted with EtOAc (20 mL×3). The organic layer was dried over Na$_2$SO$_4$, filtered and concentrated under reduced pressure to yield a residue which was purified by flash silica gel chromatography (from PE/EtOAc=100/1 to 3/1, TLC: PE/EtOAc=1/1, R$_f$=0.40). The desired fraction was concentrated under reduced pressure to yield a residue which was purified by preparative HPLC (column: Welch Xtimate C18 150*30 mm*5 um; mobile phase: [water (10 mM NH$_4$HCO$_3$)-ACN]; B %: 36%-66%, 10 min). The desired fraction was lyophilized to yield N-methoxy-N-methyl-5-

(methylsulfamoyl)-2-[3-(trifluoromethyl)anilino]benzamide (19.19 mg, 45.97 μmol, 12.6% yield, 100.0% purity) as a white solid. $^1$H NMR (400 MHz, CD$_3$OD) δ ppm 7.89 (d, J=2.1 Hz, 1H), 7.77 (dd, J=2.1, 8.8 Hz, 1H), 7.55-7.50 (m, 1H), 7.47-7.43 (m, 2H), 7.38 (d, J=8.9 Hz, 1H), 7.35 (d, J=7.8 Hz, 1H), 3.61 (s, 3H), 3.35 (s, 3H), 2.57 (s, 3H); ES-LCMS m/z 418.0 [M+H]$^+$.

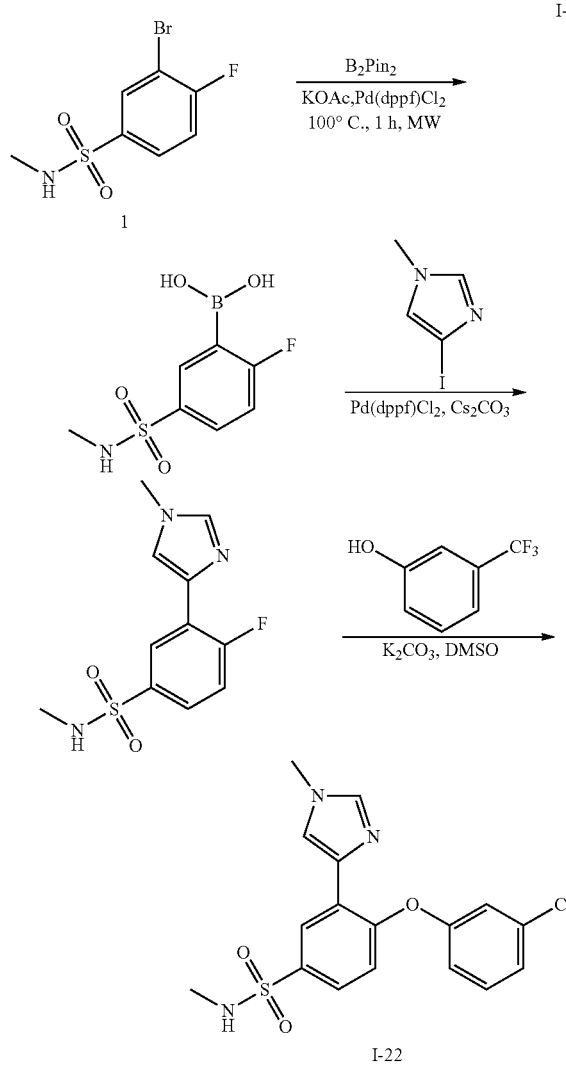

I-22

Step 1: 4-Fluoro-N-methyl-3-(1-methyl-1H-imidazol-4-yl)benzenesulfonamide

To a solution of 3-bromo-4-fluoro-N-methyl-benzenesulfonamide (500 mg, 1.77 mmol, 1 eq) in 1,4-dioxane (6 mL) was added potassium; acetate (347.76 mg, 3.54 mmol, 2.0 eq), Pd(dppf)Cl$_2$ (129.64 mg, 177.17 μmol, 0.1 eq) and 4,4,5,5-tetramethyl-2-(4,4,5,5-tetramethyl-1,3,2-dioxaborolan-2-yl)-1,3,2-dioxaborolane (584.87 mg, 2.30 mmol, 1.3 eq). The mixture was stirred under N$_2$ atmosphere at 90° C. for 3 h. 4-iodo-1-methyl-imidazole (479.07 mg, 2.30 mmol, 1.3 eq) and Cs$_2$CO$_3$ (1.15 g, 3.54 mmol, 2.0 eq), H$_2$O (1 mL) were added. The mixture was stirred under N$_2$ atmosphere at 130° C. for 5 h. After filtration, the filtrate was concentrated. The residue was diluted with water (10 mL) and extracted with EtOAc (10 mL×3). The combined organic layers were washed with brine (10 mL), dried over Na$_2$SO$_4$, filtered and concentrated to yield a residue which was purified by flash silica gel chromatography (from PE/EtOAc=10/1 to 0/1, TLC: PE/EtOAc=0/1, R$_f$=0.4) to yield 4-fluoro-N-methyl-3-(1-methylimidazol-4-yl)benzenesulfonamide (70 mg, 233.94 μmol, 13.2% yield, 90.0% purity) as yellow oil. $^1$H NMR (400 MHz, CDCl$_3$) δ ppm 8.62-8.60 (m, 1H), 7.71-7.69 (m, 1H), 7.50-7.49 (m, 1H), 7.19-7.12 (m, 2H), 4.54 (s, 1H), 3.75 (s, 3H), 2.65 (d, J=4.0, Hz, 3H); ES-LCMS m/z 270.1 [M+H]$^+$.

Step 2: N-Methyl-3-(1-methyl-1H-imidazol-4-yl)-4-(3-(trifluoromethyl)phenoxy)benzenesulfonamide To a solution of 4-fluoro-N-methyl-3-(1-methylimidazol-4-yl)benzenesulfonamide (70 mg, 233.94 μmol, 1 eq) in DMSO (5 mL) was added K$_2$CO$_3$ (97.00 mg, 701.83 μmol, 3.0 eq), 3-(trifluoromethyl)phenol (113.77 mg, 701.83 μmol, 84.28 μL, 3.0 eq). The mixture was stirred under N$_2$ atmosphere at 140° C. for 16 h. The mixture was filtered which was purified by preparative HPLC (column: Welch Xtimate C18 150*30 mm*5 um; mobile phase: [water (10 mM NH$_4$HCO$_3$)-ACN]; B %: 36%-66%, 10 min), followed by lyophilization to yield N-methyl-3-(1-methylimidazol-4-yl)-4-[3-(trifluoromethyl)phenoxy]benzenesulfonamide (26.69 mg, 63.77 μmol, 27.3% yield, 98.3% purity) as a white solid. $^1$H NMR (400 MHz, CD$_3$OD) δ ppm 8.54-8.52 (m, 1H), 7.70-7.69 (m, 2H), 7.68-7.67 (m, 2H), 7.62-7.61 (m, 1H), 7.41-7.40 (m, 1H), 7.39-7.38 (m, 1H), 7.05 (d, J=8.8 Hz, 1H), 3.75 (s, 3H), 2.58 (s, 3H); ES-LCMS m/z 412.0 [M+H]$^+$.

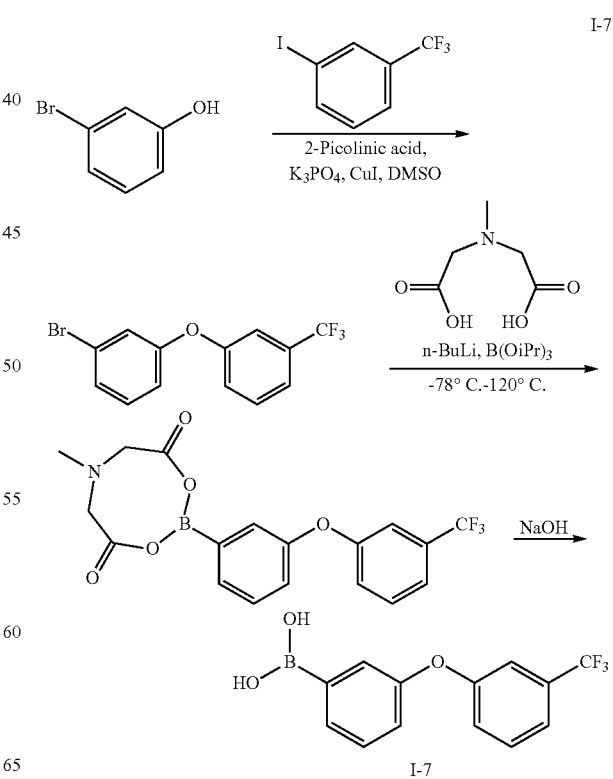

I-7

Step 1:
1-Bromo-3-(3-(trifluoromethyl)phenoxy)benzene

To a solution of 1-iodo-3-(trifluoromethyl)benzene (1.0 g, 3.68 mmol, 529.10 μL, 1.0 eq) in DMSO (20 mL) was added 2-Picolinic acid (45.26 mg, 367.64 μmol, 0.1 eq), CuI (35.01 mg, 183.82 μmol, 0.05 eq), K$_3$PO$_4$ (1.56 g, 7.35 mmol, 2.0 eq) and 3-bromophenol (667.84 mg, 3.86 mmol, 644.02 μL, 1.05 eq). The mixture was stirred at 120° C. for 16 h. TLC (PE/EtOAc=100/1, R$_f$=0.6) showed the reaction was completed. Water (20 mL) was added. The mixture was extracted with EtOAc (30 mL×3). The combined organic layers were washed with brine (50 mL), dried over Na$_2$SO$_4$, filtered and concentrated to yield a residue which was purified by flash silica gel chromatography (from PE/EtOAc=1/0 to 100/1, TLC: PE/EtOAc=100/1, R$_f$=0.6) to yield 1-bromo-3-[3-(trifluoromethyl)phenoxy]benzene (600 mg, 1.70 mmol, 46.3% yield, 90.0% purity) as yellow oil. $^1$H NMR (400 MHz, CDCl$_3$) δ ppm 7.52-7.43 (m, 1H), 7.39 (d, J=8.6 Hz, 1H), 7.35-7.20 (m, 3H), 7.20-7.07 (m, 2H), 7.01-6.92 (m, 1H); ES-LCMS m/z 479.1 [M+H]$^+$.

Step 2: 6-Methyl-2-(3-(3-(trifluoromethyl)phenoxy)phenyl)-1,3,6,2-dioxazaborocane-4,8-dione To a solution of 1-bromo-3-[3-(trifluoromethyl)phenoxy]benzene (111.11 mg, 315.36 μmol, 1 eq) in THF (5 mL) was added triisopropyl borate (71.17 mg, 378.43 μmol, 87.01 μL, 1.2 eq) and n-BuLi (2.5 M, 236.52 μL, 1.5 eq) under N$_2$ atmosphere at −78° C. The mixture was stirred under N$_2$ atmosphere at −78° C. for 1 h and then stirred at 20° C. for 10 h to yield a solution A. Separately, a solution of 2-[carboxymethyl(methyl)amino]acetic acid (92.80 mg, 630.71 μmol, 2.0 eq) in DMSO (5 mL) was heated with stirring to an internal temperature of 115° C. Above solution A was added. The mixture was stirred at 120° C. for 1 h. The mixture was quenched with water (10 mL) and extracted with EtOAc (10 mL×3). The combined organic layers were washed with brine (20 mL), dried over Na$_2$SO$_4$, filtered and concentrated to yield a residue which was purified with preparative TLC (PE/EtOAc=1/1, R$_f$=0.1) to yield 6-methyl-2-[3-[3-(trifluoromethyl)phenoxy]phenyl]-1,3,6,2-dioxazaborocane-4,8-dione (10 mg, 22.89 μmol, 7.3% yield, 90.0% purity) as yellow oil. $^1$H NMR (400 MHz, CDCl$_3$) δ ppm 7.27 (td, J=8.0, 12.8 Hz, 2H), 7.21-7.13 (m, 2H), 7.09 (s, 1H), 7.04-6.95 (m, 2H), 6.91 (d, J=7.8 Hz, 1H), 4.11-3.85 (m, 2H), 3.72-3.56 (m, 2H), 2.43 (s, 3H); ES-LCMS m/z 411.1 [M+NH$_4$]$^+$.

Step 3:
(3-(3-(Trifluoromethyl)phenoxy)phenyl)boronic acid

To a solution of 6-methyl-2-[3-[3-(trifluoromethyl)phenoxy]phenyl]-1,3,6,2-dioxazaborocane-4,8-dione (10 mg, 22.89 μmol, 1 eq) in THF (5 mL) was added NaOH (1 M, 45.79 μL, 2.0 eq). The mixture was stirred at 20° C. for 16 h. The mixture was adjusted pH=4 with 2 N HCl, extracted with EtOAc (10 mL×3). The combined organic layers were washed with brine (10 mL), dried over Na$_2$SO$_4$, filtered and concentrated to yield a residue which was purified by preparative HPLC (column: Phenomenex Synergi C18 150*30 mm*4 um; mobile phase: [water (0.05% HCl)-ACN]; B %: 53%-73%, 10 min), followed by lyophilization to yield [3-[3-(trifluoromethyl)phenoxy]phenyl]boronic acid (5.2 mg, 18.4 μmol, 80.3% yield, 99.7% purity) as yellow oil. $^1$H NMR (400 MHz, CD$_3$OD) δ ppm 7.65-7.48 (m, 2H), 7.48-7.30 (m, 3H), 7.18 (br s, 2H), 7.09 (dd, J=2.6, 9.2 Hz, 1H); ES-LCMS m/z 280.8 [M−H]−.

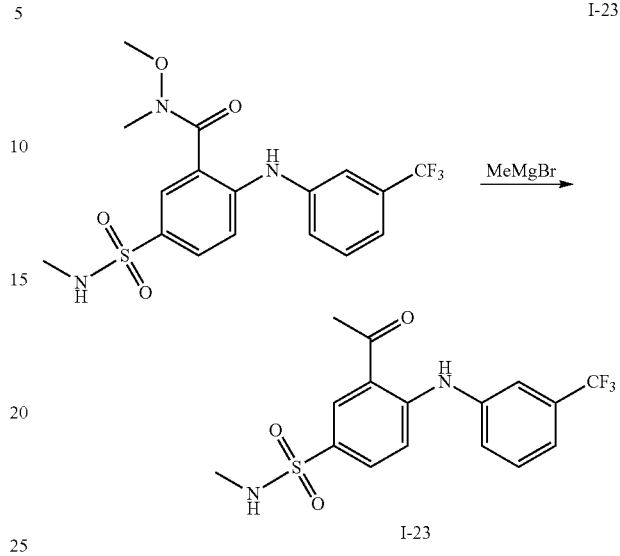

I-23

Step 1: 3-Acetyl-N-methyl-4-[3-(trifluoromethyl)anilino]benzenesulfonamide

To a solution of N-methoxy-N-methyl-5-(methylsulfamoyl)-2-[3-(trifluoromethyl)anilino]benzamide (100 mg, 239.58 μmol, 1 eq) in THF (3 mL) was added MeMgBr (3 M, 800 μL, 10.02 eq) under N$_2$ atmosphere at −30° C. The mixture was stirred under N$_2$ atmosphere at −30° C. for 2 h and then at 25° C. for 10 h. The reaction mixture was quenched with saturated aqueous NH$_4$Cl (10 mL) and extracted with EtOAc (10 mL×3). The organic layer was dried over Na$_2$SO$_4$, filtered and concentrated under reduced pressure to yield a residue which was purified by preparative HPLC (column: Phenomenex Synergi C18 150*30 mm*4 um; mobile phase: [water (0.05% HCl)-ACN]; B %: 52%-72%, 10 min). The desired fraction was basified with saturated aqueous NaHCO$_3$ until pH=8 and extracted with EtOAc (50 mL×3). The organic layer was dried over Na$_2$SO$_4$, filtered and concentrated under reduced pressure to yield a residue which was dissolved in MeCN (5 mL) and water (5 mL) and lyophilized to yield 3-acetyl-N-methyl-4-[3-(trifluoromethyl)anilino]benzenesulfonamide (50 mg, 134.28 μmol, 56.1% yield, 100.0% purity) as a white solid. $^1$H NMR (500 MHz, CDCl$_3$) δ ppm 11.06 (s, 1H), 8.37 (d, J=2.1 Hz, 1H), 7.75 (dd, J=2.1, 9.0 Hz, 1H), 7.58-7.52 (m, 2H), 7.50-7.44 (m, 2H), 7.21 (d, J=9.0 Hz, 1H), 4.44 (q, J=5.2 Hz, 1H), 2.73 (s, 3H), 2.70 (d, J=5.5 Hz, 3H); ES-LCMS m/z 373.0 [M+H]$^+$. I-24

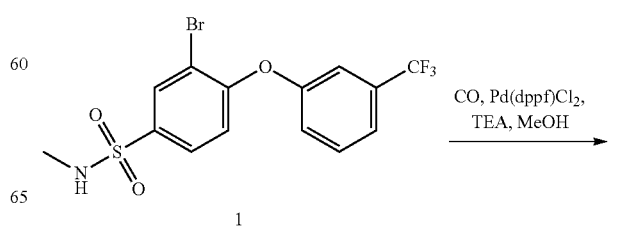

I-24

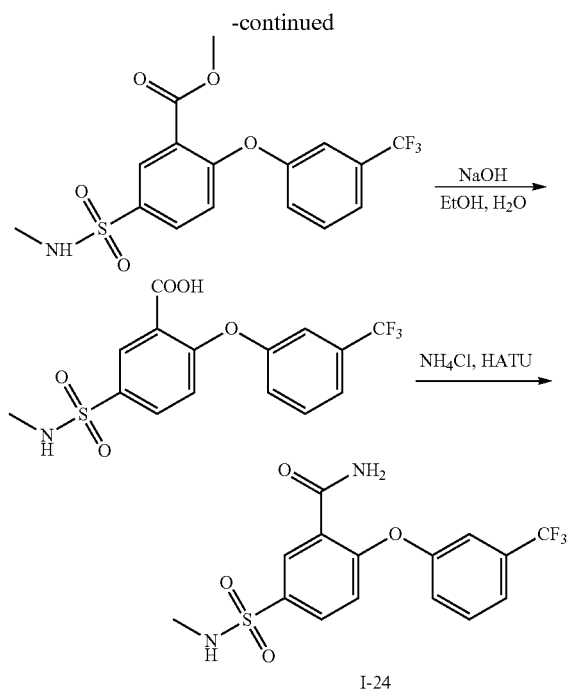

Step 1: Methyl 5-(methylsulfamoyl)-2-[3-(trifluoromethyl)phenoxy]benzoate

A solution of 3-bromo-N-methyl-4-[3-(trifluoromethyl)phenoxy]benzenesulfonamide (210.53 mg, 487.56 μmol, 1 eq), Pd(dppf)Cl$_2$ (35.68 mg, 48.76 μmol, 0.1 eq) and TEA (148.01 mg, 1.46 mmol, 203.59 μL, 3 eq) in MeOH (10 mL) was stirred at 60° C. under CO (50 Psi) for 24 h in a 50 mL of sealed tube. The mixture was stirred at 80° C. under CO (50 Psi) for 24 h in a 50 mL of sealed tube. The reaction mixture was concentrated under reduced pressure to yield a residue which was purified by flash silica gel chromatography (from PE/EtOAc=200/1 to 3/1, TLC: PE/EtOAc=3/1, R$_f$=0.25) to yield methyl 5-(methylsulfamoyl)-2-[3-(trifluoromethyl)phenoxy]benzoate (180 mg, 457.69 μmol, 93.9% yield, 99.0% purity) as a white solid. $^1$H NMR (400 MHz, CDCl$_3$) δ ppm 8.44 (d, J=2.3 Hz, 1H), 7.95 (dd, J=2.5, 8.8 Hz, 1H), 7.56-7.46 (m, 2H), 7.32 (s, 1H), 7.22 (d, J=8.2 Hz, 1H), 7.04 (d, J=9.0 Hz, 1H), 4.40 (d, J=5.5 Hz, 1H), 3.89 (s, 3H), 2.73 (d, J=5.5 Hz, 3H); ES-LCMS m/z 390.0 [M+H]$^+$.

Step 2: 5-(Methylsulfamoyl)-2-[3-(trifluoromethyl)phenoxy]benzoic acid

To a solution of methyl 5-(methylsulfamoyl)-2-[3-(trifluoromethyl)phenoxy]benzoate (170 mg, 432.26 μmol, 1 eq) in EtOH (5 mL) and H$_2$O (5 mL) was added LiOH·H$_2$O (90.70 mg, 2.16 mmol, 5 eq). The mixture was stirred at 25° C. for 1 h. The reaction mixture was concentrated under reduced pressure to yield 5-(methylsulfamoyl)-2-[3-(trifluoromethyl)phenoxy]benzoic acid (150 mg, 391.67 μmol, 90.6% yield, 98.0% purity) as a white solid which was used in the next step without further purification. $^1$H NMR (500 MHz, DMSO-d$_6$) δ ppm 7.77 (d, J=2.1 Hz, 1H), 7.51-7.45 (m, 1H), 7.40 (dd, J=2.2, 8.2 Hz, 1H), 7.34-7.24 (m, 1H), 7.11-7.03 (m, 2H), 6.80 (d, J=8.2 Hz, 1H), 2.32 (s, 3H); ES-LCMS m/z 375.9 [M+H]$^+$.

Step 3: 5-(Methylsulfamoyl)-2-[3-(trifluoromethyl)phenoxy]benzamide

To a solution of 5-(methylsulfamoyl)-2-[3-(trifluoromethyl)phenoxy]benzoic acid (15 mg, 39.17 μmol, 1 eq) in DMF (1 mL) was added NH$_4$Cl (10.48 mg, 195.83 μmol, 5 eq), HATU (26.81 mg, 70.50 μmol, 1.8 eq) and DIEA (15.19 mg, 117.50 μmol, 20.47 μL, 3 eq). The mixture was stirred at 25° C. for 1 h. To the mixture was added water (30 mL) and extracted with ethyl acetate (30 mL×3). The combined organic phase was washed with brine (20 mL), dried with anhydrous Na$_2$SO$_4$, filtered and concentrated in vacuum to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B%: 30%-60%, 10 min), followed by lyophilization to yield 5-(methylsμLfamoyl)-2-[3-(trifluoromethyl)phenoxy]benzamide (3.02 mg, 7.95 μmol, 20.3% yield, 98.6% purity) as a white solid. $^1$H NMR (500 MHz, CD$_3$OD) δ ppm 8.31 (d, J=2.3 Hz, 1H), 7.90 (dd, J=2.4, 8.8 Hz, 1H), 7.69-7.63 (m, 1H), 7.58 (d, J=7.9 Hz, 1H), 7.51 (s, 1H), 7.40 (d, J=7.9 Hz, 1H), 7.04 (d, J=8.7 Hz, 1H), 2.56 (s, 3H); ES-LCMS m/z 374.9 [M+H]$^+$.

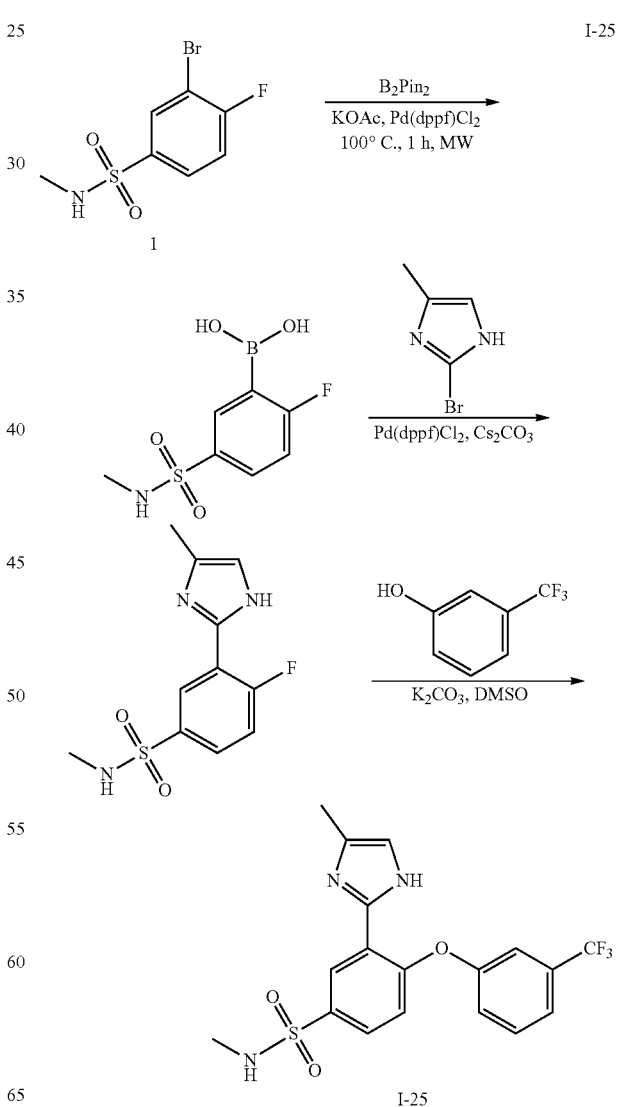

Step 1: 4-Fluoro-N-methyl-3-(4-methyl-1H-imidazol-2-yl)benzenesulfonamide

To a stirred solution of 3-bromo-4-fluoro-N-methyl-benzenesulfonamide (300 mg, 1.06 mmol, 1 eq) in 1,4-dioxane (5 mL) was added KOAc (208.65 mg, 2.13 mmol, 2 eq), Pd(dppf)Cl$_2$ (77.78 mg, 106.30 μmol, 0.1 eq) and 4,4,5,5-tetramethyl-2-(4,4,5,5-tetramethyl-1,3,2-dioxaborolan-2-yl)-1,3,2-dioxaborolane (404.91 mg, 1.59 mmol, 1.5 eq). The reaction mixture was degassed and purged with N$_2$ for three times then stirred at 80° C. for 2 h. Pd(dppf)Cl$_2$ (77.78 mg, 106.30 umol, 0.1 eq), Cs$_2$CO$_3$ (692.71 mg, 2.13 mmol, 2 eq), water (1 mL) and 2-bromo-4-methyl-1H-imidazole (222.49 mg, 1.38 mmol, 1.3 eq) was added to the above reaction mixture the bubbled with N$_2$ for 3 min then stirred at 100° C. for 1 h under N$_2$ atmosphere. The reaction mixture was concentrated to yield a residue which was purified by flash silica gel chromatography (from PE/EtOAc=100/1 to 0/1, TLC: PE/EtOAc=1/1, R$_f$=0.35) to yield 4-fluoro-N-methyl-3-(4-methyl-1H-imidazol-2-yl)benzenesulfonamide (60 mg, 108.28 μmol, 10.2% yield, 48.6% purity) as yellow oil. ES-LCMS m/z 269.9 [M+H]$^+$.

Step 2: N-Methyl-3-(4-methyl-1H-imidazol-2-yl)-4-[3-(trifluoromethyl)phenoxy]benzenesulfonamide To a stirred solution of 4-fluoro-N-methyl-1H-imidazol-2-yl)benzenesulfonamide (100 mg, 371.34 μmol, 1 eq) and 3-(trifluoromethyl)phenol (180.59 mg, 1.11 mmol, 133.77 μL, 3 eq) in DMSO (3 mL) was added K$_2$CO$_3$ (153.97 mg, 1.11 mmol, 3 eq). The reaction mixture was stirred at 140° C. for 12 h. The reaction mixture was diluted with water (30 mL) then extracted with EtOAc (20 mL×3). The combined organic layers were dried over Na$_2$SO$_4$, filtered and the filtrate was concentrated to yield a residue which was purified by flash silica gel chromatography (from PE/EtOAc=100/1 to 1/1, TLC: PE/EtOAc=1/1, R$_f$=0.65). The residue was purified by preparative HPLC column: Welch Xtimate C18 150*30 mm*5 um; mobile phase: [water (10 mM NH$_4$HCO$_3$)-ACN]; B %: 40%-70%, 10 min) then re-purified by preparative TLC (PE/EtOAc=1/1, TLC: PE/EtOAc=1/1, R$_f$=0.65) to yield a residue. The residue was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 27%-57%, 10 min). The desired fraction was lyophilized to yield N-methyl-3-(4-methyl-1H-imidazol-2-yl)-4-[3-(trifluoromethyl)phenoxy]benzenesulfonamide (5.92 mg, 14.39 μmol, 3.9% yield, 100.0% purity) as yellow solid. $^1$H NMR (500 MHz, CDCl$_3$) δ ppm 7.91-7.81 (m, 1H), 7.76 (t, J=7.8 Hz, 1H), 7.65-7.55 (m, 3H), 7.18-7.04 (m, 2H), 6.86 (s, 1H), 3.91 (s, 1H), 2.54-2.20 (m, 6H); ES-LCMS m/z 411.9 [M+H]$^+$.

I-26

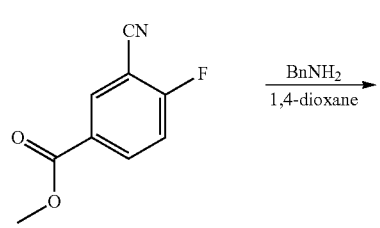

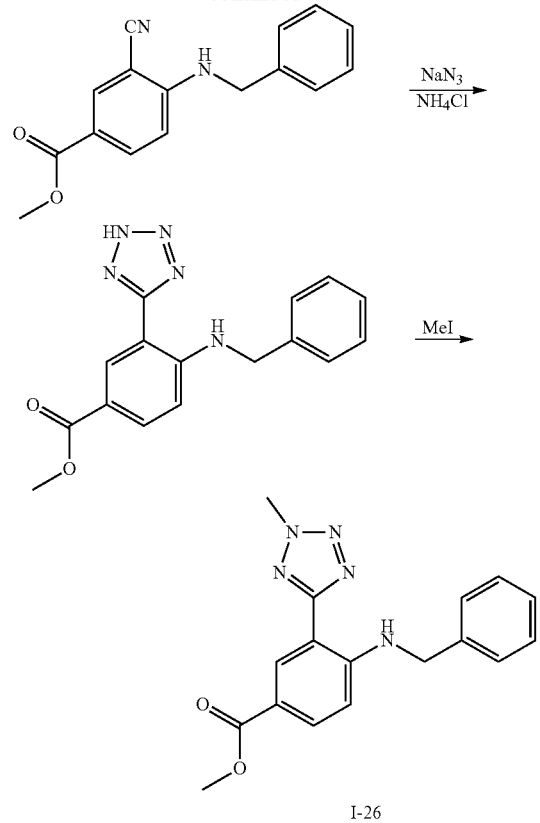

I-26

Step 1: Methyl 4-(benzylamino)-3-cyano-benzoate

To a stirred solution of methyl 3-cyano-4-fluoro-benzoate (300 mg, 1.59 mmol, 1 eq) in 1,4-dioxane (5 mL) was added K$_2$CO$_3$ (659.62 mg, 4.77 mmol, 3 eq) and phenylmethanamine (272.75 mg, 2.55 mmol, 277.46 μL, 1.6 eq). The reaction mixture was stirred at 90° C. for 12 h. The reaction mixture was added to water (30 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 3/1, TLC: PE/EtOAc=3/1, R$_f$=0.30) to yield methyl 4-(benzylamino)-3-cyano-benzoate (400 mg, 1.43 mmol, 89.7% yield, 95.0% purity) as yellow oil. $^1$H NMR (400 MHz, DMSO-d$_6$) δ ppm 8.01 (d, J=2.0 Hz, 1H), 7.82 (dd, J=1.7, 9.0 Hz, 1H), 7.68 (t, J=6.0 Hz, 1H), 7.33 (d, J=4.4 Hz, 4H), 7.28-7.21 (m, 1H), 6.70 (d, J=9.0 Hz, 1H), 4.51 (d, J=6.1 Hz, 2H), 3.76 (s, 3H); ES-LCMS m/z 267.0 [M+H]$^+$.

Step 2: Methyl 4-(benzylamino)-3-(2H-tetrazol-5-yl)benzoate

To a stirred solution of methyl 4-(benzylamino)-3-cyano-benzoate (400 mg, 1.43 mmol, 1 eq) in DMF (10 mL) was added NaN$_3$ (218.50 mg, 3.36 mmol, 2.36 eq) and NH$_4$Cl (381.66 mg, 7.13 mmol, 5 eq). The reaction mixture was stirred at 120° C. for 4 h. TLC (PE/EtOAc=1/1, R$_f$=0.10) showed starting material was consumed completely and one new spot was detected. The reaction mixture was diluted with water (100 mL) and adjusted pH to 10 by 15% NaOH solution then extracted with DCM (50 mL×4). The combine organic layers were dried over Na₂SO₄, filtered and the filtrate was concentrated to yield a residue which was purified by flash silica gel chromatography (from PE/EtOAc=100/1 to 2/3, TLC: PE/EtOAc=1/1, R$_f$=0.10) to yield methyl 4-(benzylamino)-3-(2H-tetrazol-5-yl)benzoate (370 mg, 1.19 mmol, 83.5% yield, 99.6% purity) as yellow solid. ¹H NMR (500 MHz, DMSO-d₆) δ ppm 8.66 (s, 1H), 8.55 (d, J=1.8 Hz, 1H), 7.86 (dd, J=1.9, 8.9 Hz, 1H), 7.40-7.33 (m, 4H), 7.31-7.25 (m, 1H), 6.90 (d, J=9.0 Hz, 1H), 4.65 (s, 2H), 3.86-3.78 (m, 3H); ES-LCMS m/z 310.0 [M+H]⁺.

Step 3: Methyl 4-(benzylamino)-3-(2-methyltetrazol-5-yl)benzoate

To a stirred solution of methyl 4-(benzylamino)-3-(2H-tetrazol-5-yl)benzoate (370 mg, 1.19 mmol, 1 eq) in THF (20 mL) was cooled to −70° C. then added K₂CO₃ (493.97 mg, 3.57 mmol, 3 eq) and MeI (135.28 mg, 953.10 μmol, 59.33 μL, 0.8 eq). The reaction mixture was stirred at 25° C. for 12 h. The reaction mixture was diluted with water (100 mL) then extracted with EtOAc (50 mL×3). The combine organic layers were dried over Na₂SO₄, filtered and the filtrate was concentrated to yield a residue which was purified by preparative HPLC (column: Agela DuraShell C18 150*25 mm*5 um; mobile phase: [water (0.04% NH₃.H₂O+10 mM NH₄HCO₃)-ACN]; B %: 45%-75%, 10 min). The desired fraction was lyophilized to yield methyl 4-(benzylamino)-3-(2-methyltetrazol-5-yl)benzoate (215.92 mg, 667.76 μmol, 56.1% yield, 100.0% purity) as white solid. ¹H NMR (400 MHz, DMSO-d₆) δ ppm 8.63 (d, J=2.2 Hz, 1H), 8.10 (t, J=5.7 Hz, 1H), 7.82 (dd, J=2.0, 8.8 Hz, 1H), 7.41-7.32 (m, 4H), 7.30-7.24 (m, 1H), 6.86 (d, J=9.0 Hz, 1H), 4.65 (d, J=5.6 Hz, 2H), 4.47 (s, 3H), 3.80 (s, 3H); ES-LCMS m/z 324.0 [M+H]⁺.

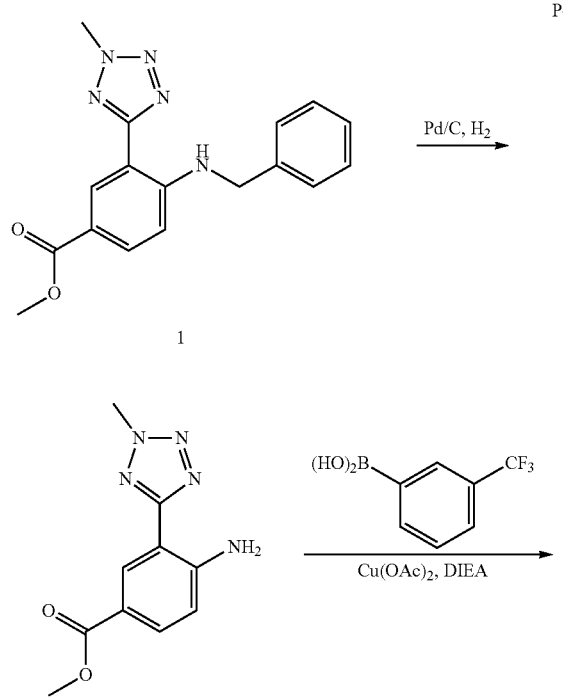

P-10

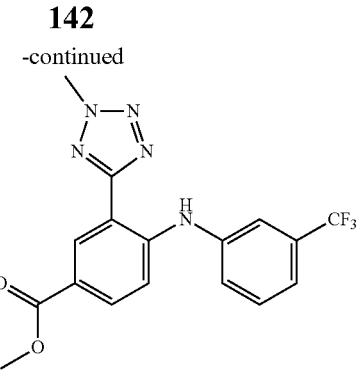

P-10

Step 1: Methyl 4-amino-3-(2-methyltetrazol-5-yl)benzoate

To a stirred solution of methyl 4-(benzylamino)-3-(2-methyltetrazol-5-yl)benzoate (400 mg, 1.24 mmol, 1 eq) in MeOH (50 mL) was added Pd/C (0.4 g, 10% Pd in C in 50% water) slowly. The reaction mixture was stirred at 25° C. for 12 h under H₂ atmosphere (45 psi). TLC (PE/EtOAc=1/1, R$_f$=0.30) showed starting material was remained and one new spot was detected. The reaction mixture was filtered through a pad of celite. The filtrate was concentrated under reduced pressure to give a residue which was purified by flash silica gel chromatography (from PE/EtOAc=100/1 to 1/1, TLC: PE/EtOAc=1/1, R$_f$=0.30) to yield methyl 4-amino-3-(2-methyltetrazol-5-yl)benzoate (200 mg, 857.54 μmol, 69.3% yield, 100.0% purity) as white solid. ¹H NMR (400 MHz, DMSO-d₆) δ ppm 8.58 (d, J=2.0 Hz, 1H), 7.76 (dd, J=2.0, 8.6 Hz, 1H), 7.07 (s, 2H), 6.92 (d, J=8.8 Hz, 1H), 4.46 (s, 3H), 3.80 (s, 3H).

Step 2: N-Methyl-3-(4-methyl-1H-imidazol-2-yl)-4-[3-(trifluoromethyl)phenoxy]benzenesulfonamide To a stirred solution of methyl 4-amino-3-(2-methyltetrazol-5-yl)benzoate (180 mg, 771.78 umol, 1 eq) and [3-(trifluoromethyl)phenyl]boronic acid (366.46 mg, 1.93 mmol, 2.5 eq) in DCM (10 mL) was added Cu(OAc)₂ (280.36 mg, 1.54 mmol, 2 eq) and DIEA (299.24 mg, 2.32 mmol, 403.29 μL, 3 eq). The reaction mixture was stirred at 25° C. for 48 h under oxygen atmosphere (15 psi). The reaction mixture was diluted with water (50 mL) then extracted with DCM (30 mL×3). The combined organic layers were dried over Na₂SO₄, filtered and the filtrate was concentrated to yield a residue which was purified by preparative HPLC (column: Agela DuraShell C18 150*25 mm*5 um; mobile phase: [water (0.04% NH₃.H₂O+10 mM NH₄HCO₃)-ACN]; B %: 55%-85%, 10 min). The desired fraction was lyophilized to yield methyl 3-(2-methyltetrazol-5-yl)-4-[3-(trifluoromethyl)anilino]benzoate (215.65 mg, 571.53 μmol, 74.1% yield, 100.0% purity) as white solid. ¹H NMR (400 MHz, DMSO-d₆) δ ppm 9.20 (s, 1H), 8.64 (d, J=2.0 Hz, 1H), 7.94 (dd, J=2.0, 8.8 Hz, 1H), 7.66-7.58 (m, 3H), 7.45 (d, J=6.8 Hz, 1H), 7.39 (d, J=8.8 Hz, 1H), 4.49 (s, 3H), 3.85 (s, 3H); ES-LCMS m/z 378.0 [M+H]⁺.

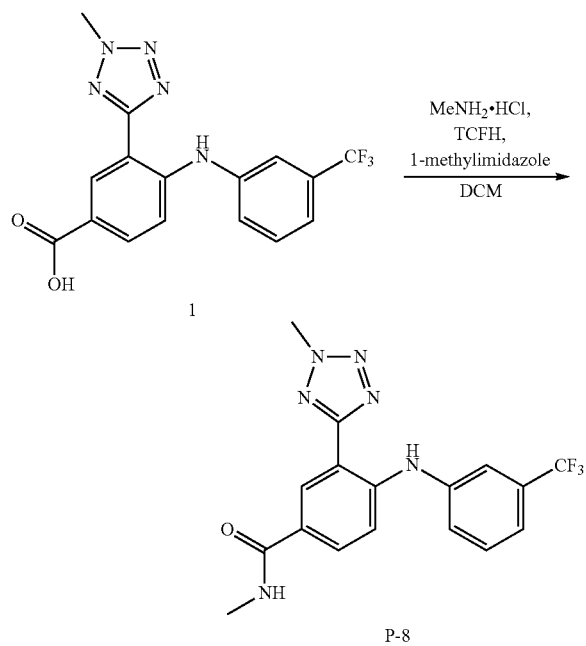

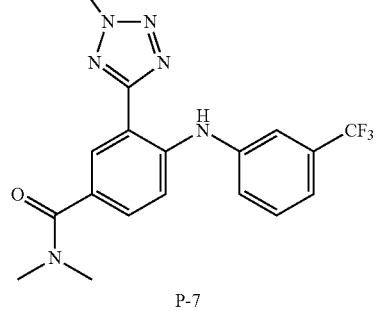

Step 1: N-Methyl-3-(2-methyltetrazol-5-yl)-4-[3-(trifluoromethyl)anilino]benzamide To a stirred solution of 3-(2-methyltetrazol-5-yl)-4-[3-(trifluoromethyl)anilino]benzoic acid (100 mg, 247.73 μmol, 1 eq) in DCM (10 mL) was added methanamine; hydrochloride (25.09 mg, 371.60 μmol, 1.5 eq), [chloro(dimethylamino)methylene]-dimethyl-ammonium; hexafluorophosphate (104.26 mg, 371.60 μmol, 1.5 eq) and 1-methylimidazole (61.02 mg, 743.20 μmol, 59.24 μL, 3 eq). The reaction mixture was stirred at 29° C. for 6 h. The reaction mixture was concentrated to yield a residue which was purified by preparative HPLC (column: Agela DuraShell C18 150*25 mm*5 um; mobile phase: [water (0.04% NH$_3$H$_2$O+10 mM NH$_4$HCO$_3$)-ACN]; B %: 40%-70%, 10 min). The desired fraction was lyophilized to yield N-methyl-3-(2-methyltetrazol-5-yl)-4-[3-(trifluoromethyl)anilino]benzamide (18.78 mg, 49.90 μmol, 20.1% yield, 100.0% purity) as white solid. $^1$H NMR (500 MHz, CD$_3$OD) δ ppm 8.74-8.67 (m, 1H), 7.81 (dd, J=2.1, 8.9 Hz, 1H), 7.59-7.51 (m, 3H), 7.42-7.35 (m, 1H), 7.39 (d, J=8.9 Hz, 1H), 4.51-4.45 (m, 3H), 2.96-2.90 (m, 3H); ES-LCMS m/z 377.0 [M+H]$^+$.

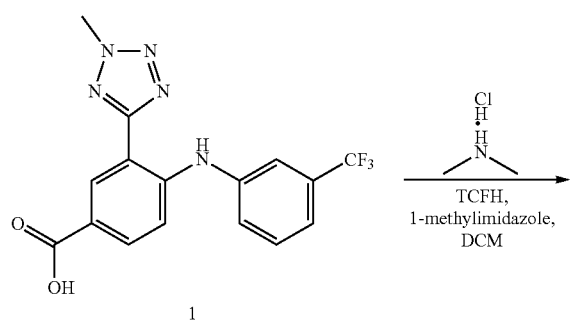

Step 1: N,N-Dimethyl-3-(2-methyltetrazol-5-yl)-4-[3-(trifluoromethyl)anilino]benzamide To a stirred solution of 3-(2-methyltetrazol-5-yl)-4-[3-(trifluoromethyl)anilino]benzoic acid (100 mg, 247.73 μmol, 1 eq) in DCM (10 mL) was added [chloro(dimethylamino)methylene]-dimethyl-ammonium; hexafluorophosphate (104.26 mg, 371.60 μmol, 1.5 eq), 1-methylimidazole (61.02 mg, 743.20 μmol, 3 eq) and N-methylmethanamine; hydrochloride (30.30 mg, 371.60 μmol, 1.5 eq). The reaction mixture was stirred at 29° C. for 6 h. The reaction mixture was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 43%-73%, 10 min). The desired fraction was lyophilized to yield N,N-dimethyl-3-(2-methyltetrazol-5-yl)-4-[3-(trifluoromethyl)anilino]benzamide (21.49 mg, 55.05 μmol, 22.2% yield, 100.0% purity) as white solid. $^1$H NMR (500 MHz, CD$_3$OD) δ ppm 8.31 (d, J=2.0 Hz, 1H), 7.57-7.52 (m, 3H), 7.51-7.47 (m, 1H), 7.45-7.41 (m, 1H), 7.38-7.33 (m, 1H), 4.47 (s, 3H), 3.13 (s, 6H); ES-LCMS m/z 391.0 [M+H]$^+$.

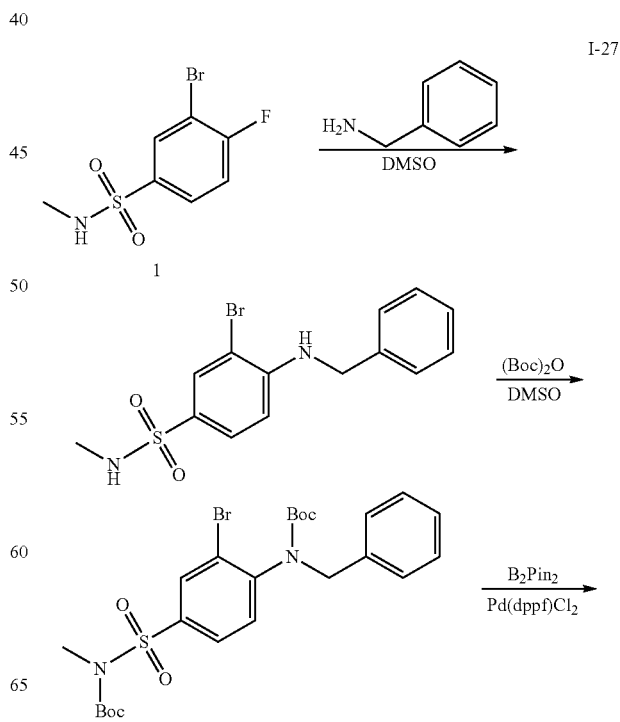

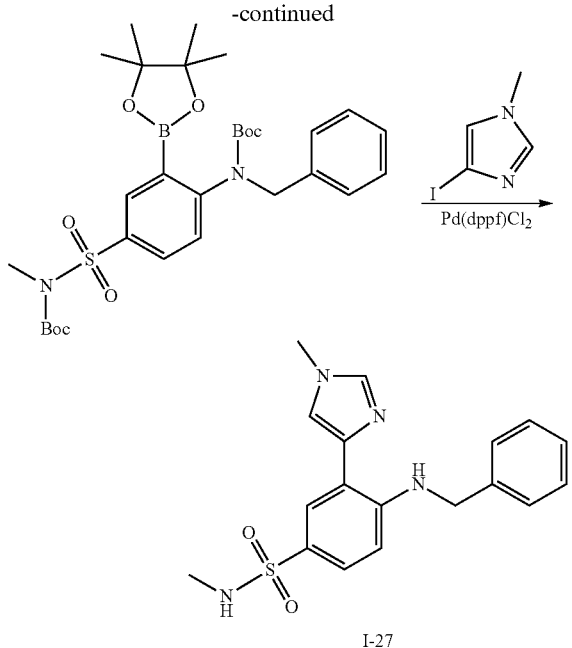

Step 1: 4-(Benzylamino)-3-bromo-N-methyl-benzenesulfonamide

To a stirred solution of 3-bromo-4-fluoro-N-methyl-benzenesulfonamide (1.5 g, 5.32 mmol, 1 eq) in DMSO (10 mL) was added phenylmethanamine (1.14 g, 10.63 mmol, 1.16 mL, 2 eq). The reaction mixture was stirred at 140° C. for 1 h under $N_2$ atmosphere. The reaction mixture was diluted with $H_2O$ (30 mL) and extracted with EtOAc (30 mL×3). The combined organic layers were washed with brine (30 mL), dried over $Na_2SO_4$, filtered and concentrated under reduced pressure to yield a residue which was purified by flash silica gel chromatography (from PE/EtOAc=100/1 to 10/1, TLC: PE/EtOAc=10/1, $R_f$=0.45) to yield 4-(benzylamino)-3-bromo-N-methyl-benzenesulfonamide (1.88 g, 5.24 mmol, 98.6% yield, 99.0% purity) as a white solid. $^1$H NMR (400 MHz, DMSO-$d_6$) δ ppm 7.74 (d, J=2.2 Hz, 1H), 7.43 (dd, J=2.0, 8.6 Hz, 1H), 7.33 (d, J=4.4 Hz, 4H), 7.26-7.21 (m, 1H), 7.14 (q, J=5.1 Hz, 1H), 6.78 (t, J=6.1 Hz, 1H), 6.63 (d, J=8.8 Hz, 1H), 4.49 (d, J=6.1 Hz, 2H), 2.33 (d, J=5.1 Hz, 3H); ES-LCMS m/z 354.8, 356.8 [M+H]$^+$.

Step 2: tert-Butyl N-benzyl-N-[2-bromo-4-[tert-butoxycarbonyl(methyl)sulfamoyl]phenyl]carbamate To a stirred solution of 4-(benzylamino)-3-bromo-N-methyl-benzenesulfonamide (300 mg, 836.03 μmol, 1 eq) and (Boc)$_2$O (1.09 g, 5.02 mmol, 1.15 mL, 6 eq) in THF (2 mL) was added DMAP (10.21 mg, 83.60 μmol, 0.1 eq) and DIEA (324.15 mg, 2.51 mmol, 436.85 μL, 3 eq). The reaction mixture was stirred at 25° C. for 12 h. The reaction mixture was concentrated under reduced pressure to remove THF. The residue was diluted with $H_2O$ (10 mL) and extracted with EtOAc (20 mL×3). The combined organic layers were washed with brine (15 mL), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.44) to yield tert-butyl N-benzyl-N-[2-bromo-4-[tert-butoxycarbonyl(methyl)sulfamoyl]phenyl]carbamate (460 mg, 687.33 μmol, 82.2% yield, 83.0% purity) as colourless oil. $^1$H NMR (400 MHz, DMSO-$d_6$) δ ppm 8.10 (s, 1H), 7.84 (d, J=9.0 Hz, 1H), 7.35 (d, J=7.8 Hz, 1H), 7.31-7.24 (m, 4H), 7.20 (s, 1H), 4.69-4.35 (m, 2H), 3.27 (s, 3H), 1.38 (s, 18H); ES-LCMS m/z 444.9, 446.9 [M-2(t-Bu)+H]$^+$.

Step 3: N-Benzyl-N-[4-[tert-butoxycarbonyl(methyl)sulfamoyl]-2-(4,4,5,5-tetramethyl-1,3,2-dioxaborolan-2-yl)phenyl]carbamate To a stirred solution of tert-butyl N-benzyl-N-[2-bromo-4-[tert-butoxycarbonyl(methyl)sulfamoyl]phenyl]carbamate (400 mg, 597.68 μmol, 1 eq) and 4,4,5,5-tetramethyl-2-(4,4,5,5-tetramethyl-1,3,2-dioxaborolan-2-yl)-1,3,2-dioxaborolane (455.32 mg, 1.79 mmol, 3 eq) in 1,4-dioxane (8 mL) was added KOAc (117.31 mg, 1.20 mmol, 2 eq) and Pd(dppf)Cl$_2$ (43.73 mg, 59.77 μmol, 0.1 eq). The reaction mixture was stirred at 90° C. for 3 h under $N_2$ atmosphere. The reaction mixture was diluted with $H_2O$ (15 mL) and extracted with EtOAc (40 mL×3). The combined organic layers were washed with brine (30 mL), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.45) to yield N-benzyl-N-[4-[tert-butoxycarbonyl(methyl)sulfamoyl]-2-(4,4,5,5-tetramethyl-1,3,2-dioxaborolan-2-yl)phenyl]carbamate (0.22 g, 292.09 μmol, 48.9% yield, 80.0% purity) as colorless oil. $^1$H NMR (400 MHz, DMSO-$d_6$) δ ppm 8.28-8.24 (m, 1H), 7.96 (d, J=2.2 Hz, 1H), 7.83 (d, J=2.7 Hz, 1H), 7.36-7.30 (m, 4H), 7.17 (s, 1H), 4.96 (s, 2H), 3.25 (s, 3H), 1.40 (s, 12H), 1.16 (s, 18H); ES-LCMS m/z 603.2 [M+H]$^+$.

Step 4: 4-(Benzylamino)-N-methyl-3-(1-methylimidazol-4-yl)benzenesulfonamide

To a stirred solution of tert-butyl N-benzyl-N-[4-[tert-butoxycarbonyl(methyl)sulfamoyl]-2-(4,4,5,5-tetramethyl-1,3,2-dioxaborolan-2-yl)phenyl]carbamate (200 mg, 265.54 μmol, 1 eq) and 4-iodo-1-methyl-imidazole (66.28 mg, 318.65 μmol, 1.2 eq) in 1,4-dioxane (8 mL) and $H_2O$ (4 mL) was added Cs$_2$CO$_3$ (173.04 mg, 531.08 μmol, 2 eq) and Pd(dppf)Cl$_2$ (19.43 mg, 26.55 μmol, 0.1 eq). The reaction mixture was stirred at 100° C. for 12 h under $N_2$ atmosphere. The reaction mixture was diluted with $H_2O$ (10 mL) and extracted with EtOAc (30 mL×3). The combined organic layers were washed with brine (20 mL), dried over $Na_2SO_4$, filtered and concentrated under reduced pressure to yield a residue which was purified by flash silica gel chromatography (from PE/EtOAc=100/1 to 1/1, TLC: PE/EtOAc=1/1, $R_f$=0.45) to yield the crude product which was purified by preparative HPLC (column: Agela DuraShell C18 150*25 mm*5 μm; mobile phase: [water (0.05% NH$_3$·H$_2$O+10 mM NH$_4$HCO$_3$)-ACN]; B %: 31%-61%, 10 min) to yield 4-(benzylamino)-N-methyl-3-(1-methylimidazol-4-yl)benzenesulfonamide (10.04 mg, 27.65 μmol, 10.4% yield, 98.2% purity) as a white solid. $^1$H NMR (400 MHz, DMSO-$d_6$) δ ppm 9.20 (t, J=5.7 Hz, 1H), 7.79 (s, 2H), 7.68 (s, 1H), 7.39-7.31 (m, 5H), 7.26 (d, J=6.3 Hz, 1H), 6.99 (d, J=5.1 Hz, 1H), 6.69 (d, J=8.6 Hz, 1H), 4.51 (d, J=5.5 Hz, 2H), 3.74 (s, 3H), 2.35 (d, J=5.1 Hz, 3H); ES-LCMS m/z 357.0 [M+H]$^+$.

I-28

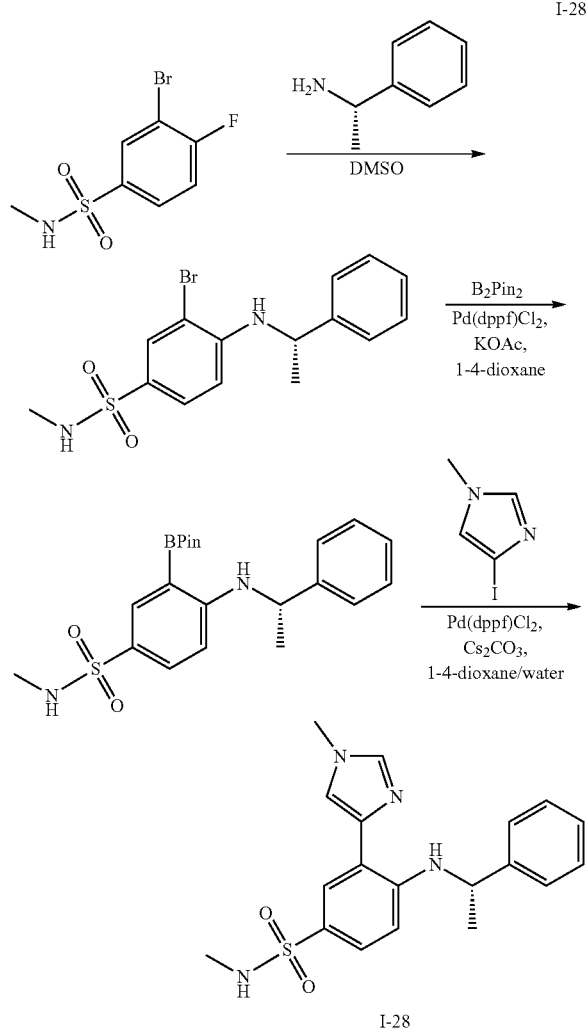

I-28

Step 1: 3-Bromo-N-methyl-4-[[(1S)-1-phenylethyl]amino]benzenesulfonamide

To a stirred solution of 3-bromo-4-fluoro-N-methyl-benzenesulfonamide (290 mg, 1.08 mmol, 1 eq) in DMSO (3 mL) was added (1S)-1-phenylethanamine (262.15 mg, 2.16 mmol, 275.37 µL, 2 eq). The reaction mixture was stirred at 140° C. for 12 h. The mixture was filtered through a celite pad, and the filtrate was concentrated to yield a residue which was purified by flash silica gel chromatography (from PE/EtOAc=100/1 to 3/1, TLC: PE/EtOAc=3/1, $R_f$=0.45) to yield 3-bromo-N-methyl-4-[[(1S)-1-phenylethyl]amino]benzenesulfonamide (380 mg, 895.27 µmol, 82.7% yield, 87.0% purity) as yellow oil. $^1$H NMR (400 MHz, DMSO-$d_6$) δ ppm 7.74 (d, J=2.2 Hz, 1H), 7.40 (d, J=8.1 Hz, 3H), 7.32 (t, J=7.6 Hz, 2H), 7.24-7.19 (m, 1H), 7.15 (q, J=5.1 Hz, 1H), 6.60 (d, J=8.8 Hz, 1H), 5.94 (d, J=7.1 Hz, 1H), 4.689-4.757 (m, 1H), 2.32 (d, J=5.1 Hz, 3H), 1.55 (d, J=6.8 Hz, 3H); ES-LCMS m/z 368.9, 370.9 [M+H]$^+$.

Step 2: N-methyl-4-[[(1S)-1-phenylethyl]amino]-3-(4,4,5,5-tetramethyl-1,3,2-dioxaborolan-2-yl)benzenesulfonamide To a stirred solution of 3-bromo-N-methyl-4-[[(1S)-1-phenylethyl]amino]benzenesulfonamide (380 mg, 895.27 µmol, 1 eq) and 4,4,5,5-tetramethyl-2-(4,4,5,5-tetramethyl-1,3,2-dioxaborolan-2-yl)-1,3,2-dioxaborolane (1.14 g, 4.48 mmol, 5 eq) in 1,4-dioxane (6 mL) was added Pd(dppf)Cl$_2$ (65.51 mg, 89.53 µmol, 0.1 eq) and KOAc (263.59 mg, 2.69 mmol, 3 eq). The reaction mixture was stirred at 110° C. for 12 h. The mixture was filtered through a celite pad, and the filtrate was concentrated to yield a residue which was purified by flash silica gel chromatography (from PE/EtOAc=100/1 to 3/1, TLC: PE/EtOAc=3/1, $R_f$=0.45) to yield N-methyl-4-[[(1S)-1-phenylethyl]amino]-3-(4,4,5,5-tetramethyl-1,3,2-dioxaborolan-2-yl)benzenesulfonamide (600 mg, crude) as yellow oil. $^1$H NMR (400 MHz, DMSO-$d_6$) δ ppm 7.94 (s, 2H), 7.81 (d, J=2.4 Hz, 1H), 7.47 (dd, J=2.4, 8.8 Hz, 1H), 7.35 (s, 1H), 7.34 (d, J=1.5 Hz, 1H), 7.26-7.21 (m, 1H), 7.02 (q, J=5.1 Hz, 1H), 6.83 (d, J=6.6 Hz, 1H), 6.48 (d, J=9.0 Hz, 1H), 4.68 (t, J=6.6 Hz, 1H), 2.28 (d, J=5.1 Hz, 3H), 1.47 (d, J=6.6 Hz, 3H), 1.07 (s, 12H); ES-LCMS m/z 417.2 [M+H]$^+$.

Step 3: N-Methyl-3-(1-methylimidazol-4-yl)-4-[[(1S)-1-phenylethyl]amino]benzenesulfonamide To a stirred solution of N-methyl-4-[[(1S)-1-phenylethyl]amino]-3-(4,4,5,5-tetramethyl-1,3,2-dioxaborolan-2-yl)benzenesulfonamide (580 mg, 1.39 mmol, 1 eq) and 4-iodo-1-methyl-imidazole (304.25 mg, 1.46 mmol, 1.05 eq) in 1,4-dioxane (3 mL) and water (1 mL) was added Pd(dppf)Cl$_2$ (101.93 mg, 139.31 µmol, 0.1 eq) and Cs$_2$CO$_3$ (1.36 g, 4.18 mmol, 3 eq). The reaction mixture bubbled with N$_2$ for 1 min then stirred at 100° C. for 30 min under microwave. TLC (PE/EtOAc=1:1, $R_f$=0.25) showed starting material was remained and one new spot was detected. The mixture was filtered through a celite pad, and the filtrate was concentrated to yield a residue which was purified by flash silica gel chromatography (from PE/EtOAc=100/1 to 1/1, TLC: PE/EtOAc=1/1, $R_f$=0.25) to yield N-methyl-3-(1-methyl-imidazol-4-yl)-4-[[(1S)-1-phenylethyl]amino]benzenesulfonamide (125 mg, 337.41 µmol, 24.2% yield, 100% purity, $[α]^{28.1}_D$=+170.59 (MeOH, c=0.034 g/100 mL)) as white solid. $^1$H NMR (400 MHz, CDCl$_3$) δ ppm 9.09 (s, 1H), 7.82 (d, J=2.2 Hz, 1H), 7.53 (s, 1H), 7.38 (s, 1H), 7.36 (d, J=1.0 Hz, 2H), 7.34-7.28 (m, 3H), 7.25-7.20 (m, 1H), 6.43 (d, J=8.8 Hz, 1H), 4.62 (d, J=5.4 Hz, 1H), 4.11 (q, J=5.3 Hz, 1H), 3.79 (s, 3H), 2.58 (d, J=5.4 Hz, 3H), 1.63 (d, J=6.8 Hz, 3H); ES-LCMS m/z 371.2 [M+H]$^+$.

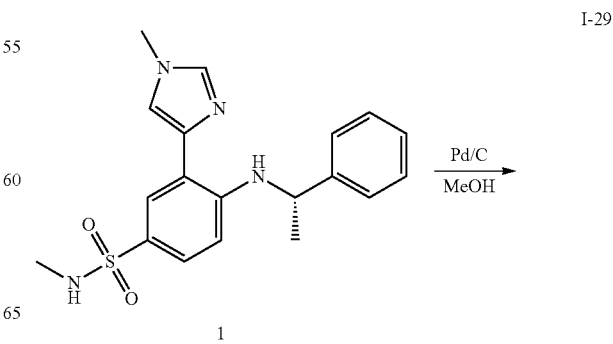

I-29

-continued

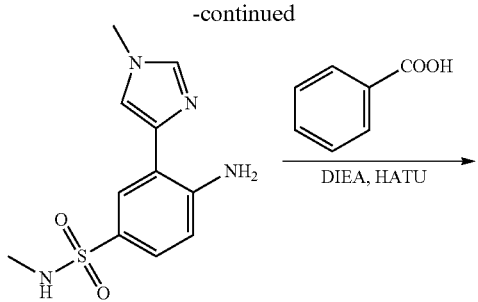

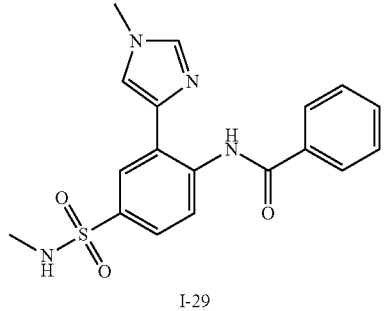

I-29

Step 1: 4-Amino-N-methyl-3-(1-methylimidazol-4-yl)benzenesulfonamide

To a solution of N-methyl-3-(1-methylimidazol-4-yl)-4-[[(1S)-1-phenylethyl]amino]benzenesulfonamide (70 mg, 188.95 μmol, 1 eq) in MeOH (10 mL) was added Pd/C (100 mg, 10% purity) under $N_2$ atmosphere. The suspension was degassed under vacuum and purged with $H_2$ several times. The mixture was stirred under $H_2$ (50 psi) at 50° C. for 24 h. The reaction mixture was filtered through a pad of celite and the filter was concentrated to yield the residue which was purified by preparative TLC (PE/EtOAc=0/1, TLC: PE/EtOAc=0/1, $R_f$=0.30) to yield 4-amino-N-methyl-3-(1-methylimidazol-4-yl)benzenesulfonamide (20 mg, 60.08 μmol, 31.8% yield, 80% purity) as yellow oil. $^1$H NMR (500 MHz, CDCl$_3$) δ ppm 7.66 (d, J=2.1 Hz, 1H), 7.28 (d, J=2.3 Hz, 1H), 7.05 (d, J=1.1 Hz, 1H), 6.51 (d, J=8.5 Hz, 1H), 6.00 (s, 2H), 5.15-5.06 (m, 1H), 4.26 (d, J=5.0 Hz, 1H), 3.58-3.48 (m, 3H), 2.41 (d, J=5.2 Hz, 3H); ES-LCMS m/z 266.9 [M+H]$^+$.

Step 2: N-[2-(1-Methylimidazol-4-yl)-4-(methylsulfamoyl)phenyl]benzamide

To a solution of 4-amino-N-methyl-3-(1-methylimidazol-4-yl)benzenesulfonamide (20 mg, 60.08 μmol, 1 eq) and benzoic acid (8.80 mg, 72.09 μmol, 11.01 μL, 1.2 eq) in DMF (1 mL) was added HATU (34.27 mg, 90.12 μmol, 1.5 eq) and DIEA (15.53 mg, 120.16 μmol, 20.93 μL, 2 eq). The mixture was stirred at 25° C. for 12 h. To the mixture was added water (30 mL) and extracted with ethyl acetate (30 mL×3). The combined organic phase was washed with brine (20 mL), dried over anhydrous Na$_2$SO$_4$, filtered and concentrated in vacuum to yield a residue which was purified by preparative HPLC (column: Agela DuraShell C18 150*25 mm*5 μm; mobile phase: [water (0.05% NH$_3$.H$_2$O+10 mM NH$_4$HCO$_3$)-ACN]; B %: 30%-60%, 10 min), followed by lyophilization to yield N-[2-(1-methylimidazol-4-yl)-4-(methylsulfamoyl)phenyl]benzamide (9.9 mg, 26.73 μmol, 44.5% yield, 100% purity) as a white solid. $^1$H NMR (400 MHz, CDCl$_3$) δ ppm 13.32 (s, 1H), 9.06 (d, J=8.6 Hz, 1H), 8.19-8.14 (m, 2H), 8.04 (d, J=2.3 Hz, 1H), 7.75 (dd, J=2.3, 8.6 Hz, 1H), 7.62 (s, 1H), 7.58-7.49 (m, 3H), 7.40 (d, J=1.2 Hz, 1H), 4.36 (d, J=5.5 Hz, 1H), 3.81 (s, 3H), 2.69 (d, J=5.5 Hz, 3H); ES-LCMS m/z 371.1 [M+H]$^+$.

I-30

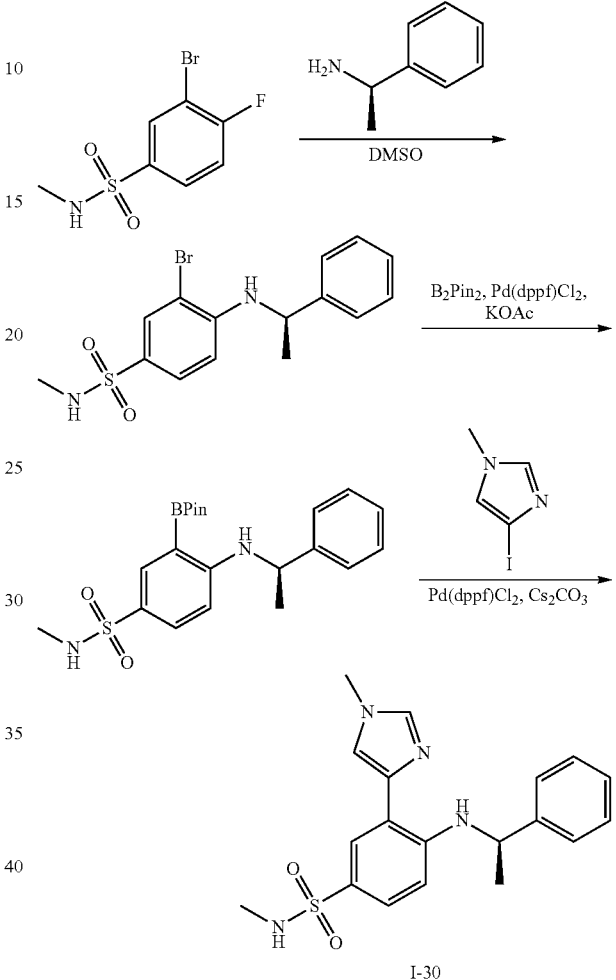

I-30

Step 1: 3-Bromo-N-methyl-4-[[(1R)-1-phenylethyl]amino]benzenesulfonamide

A mixture of 3-bromo-4-fluoro-N-methyl-benzenesulfonamide (220 mg, 779.55 μmol, 1 eq) and (1R)-1-phenylethanamine (285 mg, 2.35 mmol, 303.19 μL, 3.02 eq) in DMSO (5 mL) was degassed and purged with N$_2$ for 3 times and then the mixture was stirred under N$_2$ atmosphere at 140° C. for 12 h. TLC (PE/EtOAc=3/1, $R_f$=0.45) indicated Reactant 1 was consumed completely and two new spot formed. The mixture was diluted with water (20 mL) and extracted with EtOAc (20 mL×3). The combined organic layers were dried over Na$_2$SO$_4$, filtered and concentrated under reduced pressure to yield a residue which was purified by flash silica gel chromatography (from PE/EtOAc=100/1 to 2/1, TLC: PE/EtOAc=3/1, $R_f$=0.45) to yield 3-bromo-N-methyl-4-[[(1R)-1-phenylethyl]amino]benzenesulfonamide (200 mg, 433.28 μmol, 55.6% yield, 80.0% purity) as a yellow oil. $^1$H NMR (400 MHz, DMSO-d$_6$) δ ppm 7.71 (d, J=2.0 Hz, 1H), 7.37 (d, J=8.1 Hz, 3H), 7.29 (t, J=7.6 Hz, 2H), 7.22-7.15 (m, 1H), 7.13-7.09 (m, 1H), 6.57 (d, J=8.8 Hz, 1H), 5.90 (d, J=7.1 Hz, 1H), 4.69 (t, J=6.8 Hz, 1H), 1.95 (s, 3H), 1.52 (d, J=6.6 Hz, 3H); ES-LCMS m/z 369.0 [M+H]$^+$.

Step 2: N-Methyl-4-[[(1R)-1-phenylethyl]amino]-3-(4,4,5,5-tetramethyl-1,3,2-dioxaborolan-2-yl)benzenesulfonamide A mixture of 3-bromo-N-methyl-4-[[(1R)-1-phenylethyl]amino]benzenesulfonamide (185 mg, 400.78 µmol, 1 eq), 4,4,5,5-tetramethyl-2-(4,4,5,5-tetramethyl-1,3,2-dioxaborolan-2-yl)-1,3,2-dioxaborolane (122 mg, 480.43 µmol, 1.2 eq), KOAc (118 mg, 1.20 mmol, 3.00 eq) and Pd(dppf)Cl$_2$ (50 mg, 68.33 µmol, 0.17 eq) in 1,4-dioxane (6 mL) was degassed and purged with N$_2$ for 3 times and then the mixture was stirred under N$_2$ atmosphere at 110° C. for 12 h. TLC (PE/EtOAc=3/1, R$_f$=0.40) indicated Reactant 1 was consumed completely and three new spots formed. The mixture was diluted with water (20 mL) and extracted with EtOAc (20 mL×3). The combined organic layers were dried over Na$_2$SO$_4$, filtered and concentrated under reduced pressure to yield a residue which was purified by preparative TLC (PE/EtOAc=3/1, R$_f$=0.30) to yield N-methyl-4-[[(1R)-1-phenylethyl]amino]-3-(4,4,5,5-tetramethyl-1,3,2-dioxaborolan-2-yl)benzenesulfonamide (85 mg, 136.79 µmol, 34.1% yield, 67.0% purity) as a yellow oil. $^1$H NMR (500 MHz, DMSO-d$_6$) δ ppm 7.81 (br s, 1H), 7.43-7.49 (m, 1H), 7.30-7.38 (m, 3H), 7.18-7.28 (m, 1H), 6.92-7.13 (m, 1H), 6.80-6.87 (m, 1H), 6.43-6.52 (m, 1H), 4.68 (br s, 1H), 3.63-3.66 (m, 1H), 2.28 (br s, 3H), 1.42-1.58 (m, 3H), 1.06 (d, J=2.9 Hz, 12H); ES-LCMS m/z 417.2 [M+H]$^+$.

Step 3: N-Methyl-3-(1-methylimidazol-4-yl)-4-[[(1R)-1-phenylethyl]amino]benzenesulfonamide To a solution of N-methyl-4-[[(1R)-1-phenylethyl]amino]-3-(4,4,5,5-tetramethyl-1,3,2-dioxaborolan-2-yl)benzenesulfonamide (85 mg, 136.79 µmol, 1 eq) and 4-iodo-1-methyl-imidazole (30 mg, 144.23 µmol, 1.05 eq) in 1,4-dioxane (3 mL) and water (1 mL) was added Pd(dppf)Cl$_2$ (10 mg, 13.67 µmol, 9.99e-2 eq) and Cs$_2$CO$_3$ (134 mg, 411.27 µmol, 3.01 eq). The reaction mixture was bubbled with N$_2$ for 3 min then stirred at 100° C. for 30 min under microwave. The mixture was diluted with water (10 mL) and extracted with EtOAc (10 mL×3). The combined organic layers were dried over Na$_2$SO$_4$, filtered and concentrated under reduced pressure to yield a residue which was purified by preparative HPLC (column: Agela DuraShell C18 150*25 mm*5 um; mobile phase: [water (0.05% NH$_3$.H$_2$O+10 mM NH$_4$HCO$_3$)-ACN]; B %: 39%-54%, 14 min), followed by lyophilization to yield N-methyl-3-(1-methylimidazol-4-yl)-4-[[(1R)-1-phenylethyl]amino]benzenesulfonamide (15.11 mg, 39.60 µmol, 29.0% yield, 97.1% purity) as a white solid. $^1$H NMR (400 MHz, CDCl$_3$) δ ppm 9.08 (d, J=5.6 Hz, 1H), 7.80 (d, J=2.0 Hz, 1H), 7.50 (s, 1H), 7.36 (s, 1H), 7.34 (s, 2H), 7.32-7.26 (m, 3H), 7.23-7.17 (m, 1H), 6.40 (d, J=8.8 Hz, 1H), 4.60 (t, J=6.4 Hz, 1H), 4.03 (d, J=5.4 Hz, 1H), 3.77 (s, 3H), 2.56 (d, J=5.6 Hz, 3H), 1.60 (d, J=6.8 Hz, 3H); ES-LCMS m/z 371.2 [M+H]$^+$.

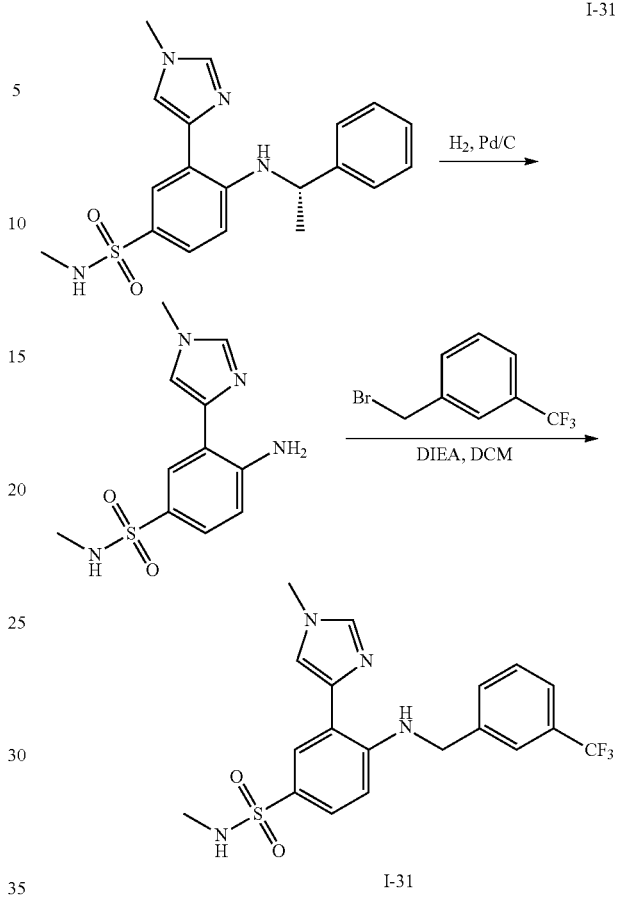

I-31

Step 1: 4-Amino-N-methyl-3-(1-methylimidazol-4-yl)benzenesulfonamide

To a solution of N-methyl-3-(1-methylimidazol-4-yl)-4-[[(1S)-1-phenylethyl]amino]benzenesulfonamide (600 mg, 1.46 mmol, 1 eq) in MeOH (10 mL) was added Pd/C (300 mg, 10% purity). The mixture was stirred under H$_2$ (50 psi) at 50° C. for 16 h. TLC (PE/EtOAc=1/, R$_f$=0.4) showed the reaction was completed. The mixture was filtered and concentrated to yield 4-amino-N-methyl-3-(1-methylimidazol-4-yl)benzenesulfonamide (400 mg, 1.35 mmol, 92.7% yield, 90.0% purity) as a yellow solid, which was used in the next step directly without further purification. $^1$H NMR (400 MHz, CDCl$_3$) δ ppm 7.78 (d, J=2.20 Hz, 1H), 7.34-7.44 (m, 2H), 7.17 (d, J=0.98 Hz, 1H), 6.63 (d, J=8.56 Hz, 1H), 6.13 (s, 2H), 4.31 (d, J=5.14 Hz, 1H), 3.66 (s, 3H), 2.54 (d, J=5.38 Hz, 3H); ES-LCMS m/z 267.2 [M+H]$^+$.

Step 2: N-Methyl-3-(1-methyl-1H-imidazol-4-yl)-4-((3-(trifluoromethyl)benzyl)amino)benzenesulfonamide To a solution of 4-amino-N-methyl-3-(1-methylimidazol-4-yl)benzenesulfonamide (50 mg, 168.97 µmol, 1 eq) in DCM (5 mL) was added DIEA (26.21 mg, 202.76 µmol, 35.32 µL, 1.2 eq), 1-(bromomethyl)-3-(trifluoromethyl)benzene (40.39 mg, 168.97 µmol, 25.73 µL, 1 eq). The mixture was stirred at 40° C. for 32 h. TLC (PE/EtOAc=1/1, R$_f$=0.4) showed the reaction was completed. The mixture was filtered and concentrated to give residue which was purified by preparative HPLC (column: Welch Xtimate C18 150*25 mm*5 um; mobile phase: [water (10 mM NH₄HCO₃)-ACN]; B %: 37%-67%, 10 min) and then lyophilized to yield N-methyl-3-(1-methylimidazol-4-yl)-4-[[3-(trifluoromethyl)phenyl]methylamino]benzenesulfonamide (20.38 mg, 47.54 μmol, 28.1% yield, 99.0% purity) as a white solid. $^1$H NMR (400 MHz, CDCl₃) δ ppm 9.25 (s, 1H), 7.88 (d, J=2.35 Hz, 1H), 7.60 (d, J=8.22 Hz, 1H), 7.50 (d, J=6.26 Hz, 5H), 7.32 (d, J=1.17 Hz, 1H), 6.55 (d, J=9.00 Hz, 1H), 4.61 (d, J=5.87 Hz, 2H), 4.12 (s, 1H), 3.79 (s, 3H), 2.63 (d, J=5.48 Hz, 3H); ES-LCMS m/z 425.1 [M+H]⁺.

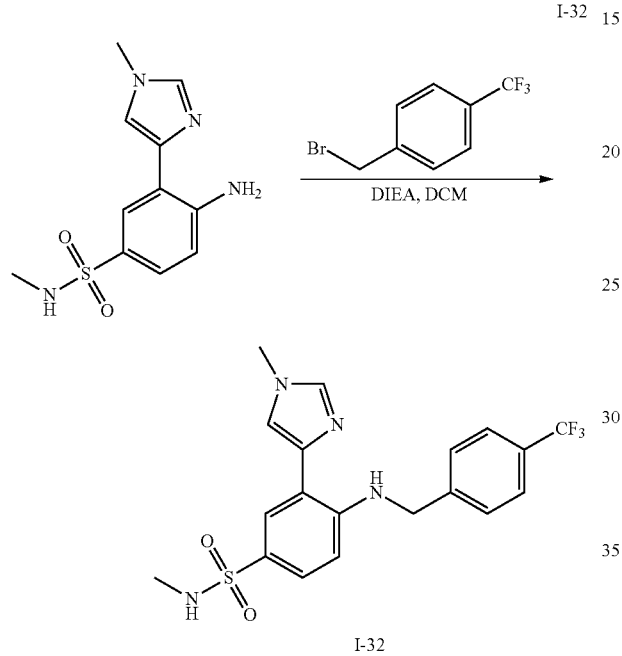

I-32

Step 1: N-Methyl-3-(1-methyl-1H-imidazol-4-yl)-4-((4-(trifluoromethyl)benzyl)amino)benzenesulfonamide To a solution of 4-amino-N-methyl-3-(1-methylimidazol-4-yl)benzenesulfonamide (50 mg, 168.97 μmol, 1 eq) in MeOH (3 mL) was added NaBH₃CN (84.95 mg, 1.35 mmol, 8.0 eq), 4-(trifluoromethyl)benzaldehyde (35.31 mg, 202.76 μmol, 27.16 μL, 1.2 eq). The mixture was stirred at 20° C. for 16 h. The mixture was concentrated, diluted with water (10 mL) and extracted with EtOAc (10 mL×3). The combined organic layers were washed with brine (10 mL), dried over Na₂SO₄, filtered and concentrated to yield a residue which was purified by preparative HPLC (column: Welch Xtimate C18 150*25 mm*5 um; mobile phase: [water (10 mM NH₄HCO3)-ACN]; B %: 38%-68%, 10 min) and then lyophilized to yield N-Methyl-3-(1-methyl-1H-imidazol-4-yl)-4-((4-(trifluoromethyl)benzyl)amino)benzenesulfonamide (18.06 mg, 42.55 μmol, 25.2% yield, 100.0% purity) as a white solid. $^1$H NMR (400 MHz, CDCl₃) δ ppm 9.25 (s, 1H), 7.88 (d, J=2.35 Hz, 1H), 7.60 (d, J=8.22 Hz, 2H), 7.50 (d, J=6.26 Hz, 4H), 7.32 (d, J=1.17 Hz, 1H), 6.55 (d, J=9.00 Hz, 1H), 4.61 (d, J=5.87 Hz, 2H), 4.12 (s, 1H), 3.79 (s, 3H), 2.63 (d, J=5.48 Hz, 3H); ES-LCMS m/z 425.2 [M+H]⁺.

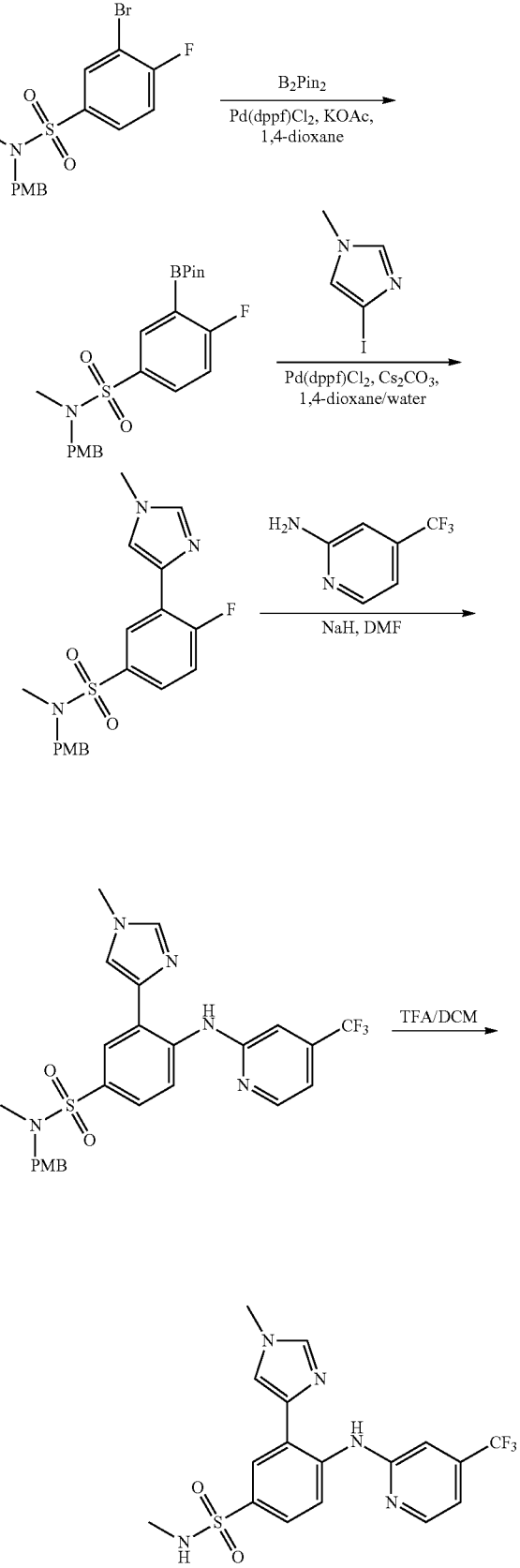

Step 1: 4-Fluoro-N-[(4-methoxyphenyl)methyl]-N-methyl-3-(4,4,5,5-tetramethyl-1,3,2-dioxaborolan-2-yl)benzenesulfonamide

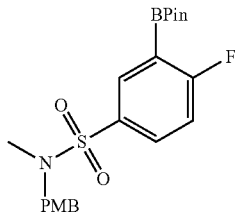

A mixture of 3-bromo-4-fluoro-N-[(4-methoxyphenyl)methyl]-N-methyl-benzenesulfonamide (500 mg, 1.16 mmol, 1 eq), 4,4,5,5-tetramethyl-2-(4,4,5,5-tetramethyl-1,3,2-dioxaborolan-2-yl)-1,3,2-dioxaborolane (882.97 mg, 3.48 mmol, 3 eq), Pd(dppf)Cl$_2$ (84.81 mg, 115.90 umol, 0.1 eq), KOAc (341.25 mg, 3.48 mmol, 3 eq) in 1,4-dioxane (10 mL) was degassed and purged with N$_2$ for 3 times, and then the mixture was stirred under N$_2$ atmosphere at 110° C. for 12 h. TLC (PE/EtOAc=3/1, R$_f$=0.28) indicated the starting material was consumed completely. The reaction mixture was concentrated, quenched by addition of water (200 mL) and extracted with EtOAc (200 mL×3). The combined organic layers were washed with brine (50 mL), dried over Na$_2$SO$_4$, filtered and concentrated under reduced pressure to yield crude 4-fluoro-N-[(4-methoxyphenyl)methyl]-N-methyl-3-(4,4,5,5-tetramethyl-1,3,2-dioxaborolan-2-yl)benzenesulfonamide (504 mg, 1.16 mmol, 99.8% yield, N/A purity) as black brown oil, which was used in the next step without further purification.

Step 2: 4-Fluoro-N-[(4-methoxyphenyl)methyl]-N-methyl-3-(1-methylimidazol-4-yl)benzenesulfonamide

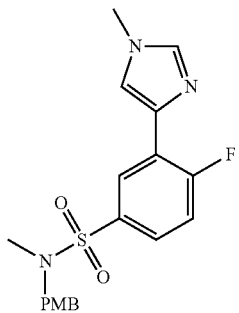

To a solution of 4-fluoro-N-[(4-methoxyphenyl)methyl]-N-methyl-3-(4,4,5,5-tetramethyl-1,3,2-dioxaborolan-2-yl)benzenesulfonamide (504 mg, 1.16 mmol, 1 eq), 4-iodo-1-methyl-imidazole (240.82 mg, 1.16 mmol, 1 eq), Cs$_2$CO$_3$ (754.46 mg, 2.32 mmol, 2 eq) in 1,4-dioxane (10 mL) and H$_2$O (2 mL) was added Pd(dppf)Cl$_2$ (84.72 mg, 115.78 umol, 0.1 eq) under N$_2$ atmosphere. The mixture was stirred under N$_2$ atmosphere at 110° C. for 12 h. The reaction mixture was quenched by addition of water (100 mL), extracted with EtOAc (100 mL×3). The combined organic layers were washed with brine (30 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.27) to yield 4-fluoro-N-[(4-methoxyphenyl)methyl]-N-methyl-3-(1-methylimidazol-4-yl)benzenesulfonamide (150 mg, 385.17 μmol, 33.3% yield, 100.0% purity) as colorless oil. ES-LCMS m/z 390.2 [M+H]$^+$.

Step 3: N-[(4-Methoxyphenyl)methyl]-N-methyl-3-(1-methylimidazol-4-yl)-4-[[4-(trifluoromethyl)-2-pyridyl]amino]benzenesulfonamide

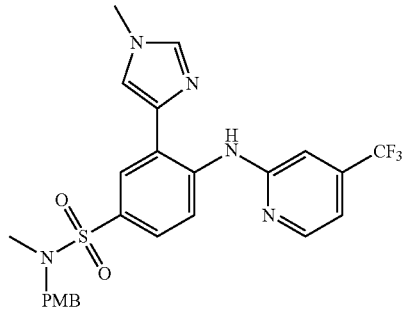

To a stirred solution of 4-(trifluoromethyl)pyridin-2-amine (149.86 mg, 924.40 μmol, 3 eq) in DMF (10 mL) was added NaH (110.93 mg, 2.77 mmol, 60%, 9 eq). The reaction mixture was stirred at 0° C. for 0.5 h. 4-Fluoro-N-[(4-methoxyphenyl)methyl]-N-methyl-3-(1-methylimidazol-4-yl)benzenesulfonamide (120 mg, 308.13 μmol, 1 eq) was added and the mixture was stirred under N$_2$ atmosphere at 120° C. for 11.5 h. The reaction mixture was diluted with H$_2$O (10 mL) and extracted with EtOAc (30 mL×3). The combined organic layers were washed with brine (20 mL), dried over Na$_2$SO$_4$, filtered and concentrated under reduced pressure to yield a residue which was purified by flash silica gel chromatography (from PE/EtOAc=100/1 to 5/1, TLC: PE/EtOAc=5/1, R$_f$=0.41) to yield N-[(4-methoxyphenyl)methyl]-N-methyl-3-(1-methylimidazol-4-yl)-4-[[4-(trifluoromethyl)-2-pyridyl]amino]benzenesulfonamide (170 mg, 287.84 μmol, 93.4% yield, 90.0% purity) as yellow oil. $^1$H NMR (400 MHz, CDCl$_3$) δ ppm 12.18 (s, 1H), 8.93 (d, J=8.8 Hz, 1H), 8.45 (d, J=5.4 Hz, 1H), 7.94 (d, J=2.2 Hz, 1H), 7.69 (dd, J=2.2, 8.8 Hz, 1H), 7.61 (s, 1H), 7.37 (d, J=1.2 Hz, 1H), 7.24 (d, J=8.6 Hz, 2H), 7.09 (s, 1H), 6.99 (d, J=5.1 Hz, 1H), 6.87 (d, J=8.6 Hz, 2H), 4.09 (s, 2H), 3.82 (s, 3H), 3.80 (s, 3H), 2.59 (s, 3H); ES-LCMS m/z 532.2 [M+H]$^+$.

Step 4: N-Methyl-3-(1-methylimidazol-4-yl)-4-[[4-(trifluoromethyl)-2-pyridyl]amino]benzenesulfonamide

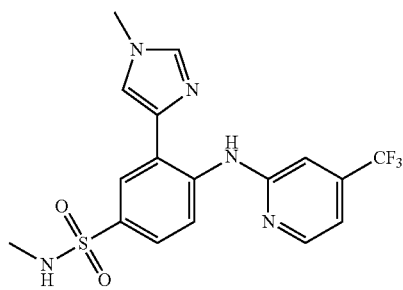 [SMILES: CNS(=O)(=O)c1ccc(Nc2cc(C(F)(F)F)ccn2)c(-c2cn(C)cn2)c1]

To a stirred solution of N-[(4-methoxyphenyl)methyl]-N-methyl-3-(1-methylimidazol-4-yl)-4-[[4-(trifluoromethyl)-2-pyridyl]amino]benzenesulfonamide (160 mg, 270.91 µmol, 1 eq) in DCM (25 mL) was added TFA (3.85 g, 33.77 mmol, 2.5 mL, 124.64 eq) at 0° C. The reaction mixture was stirred under N$_2$ atmosphere at 25° C. for 12 h. The reaction mixture was concentrated under reduced pressure to yield a residue which was purified by preparative HPLC (column: Agela DuraShell C18 150*25 mm*5 um; mobile phase: [water (0.05% NH$_3$.H$_2$O+10 mM NH$_4$HCO$_3$)-ACN]; B %: 39%-69%, 10 min) to yield N-methyl-3-(1-methylimidazol-4-yl)-4-[[4-(trifluoromethyl)-2-pyridyl]amino]benzenesulfonamide (47.29 mg, 114.95 µmol, 42.4% yield, 100.0% purity) as a light yellow solid. $^1$H NMR (500 MHz, DMSO-d$_6$) δ ppm 12.12 (s, 1H), 8.68 (d, J=8.7 Hz, 1H), 8.49 (d, J=5.2 Hz, 1H), 8.02 (d, J=2.1 Hz, 1H), 7.95 (s, 1H), 7.83 (d, J=0.9 Hz, 1H), 7.59 (dd, J=2.1, 8.7 Hz, 1H), 7.28 (s, 1H), 7.19-7.15 (m, 2H), 3.77 (s, 3H), 2.43 (s, 3H); ES-LCMS m/z 412.0 [M+H]$^+$.

I-34

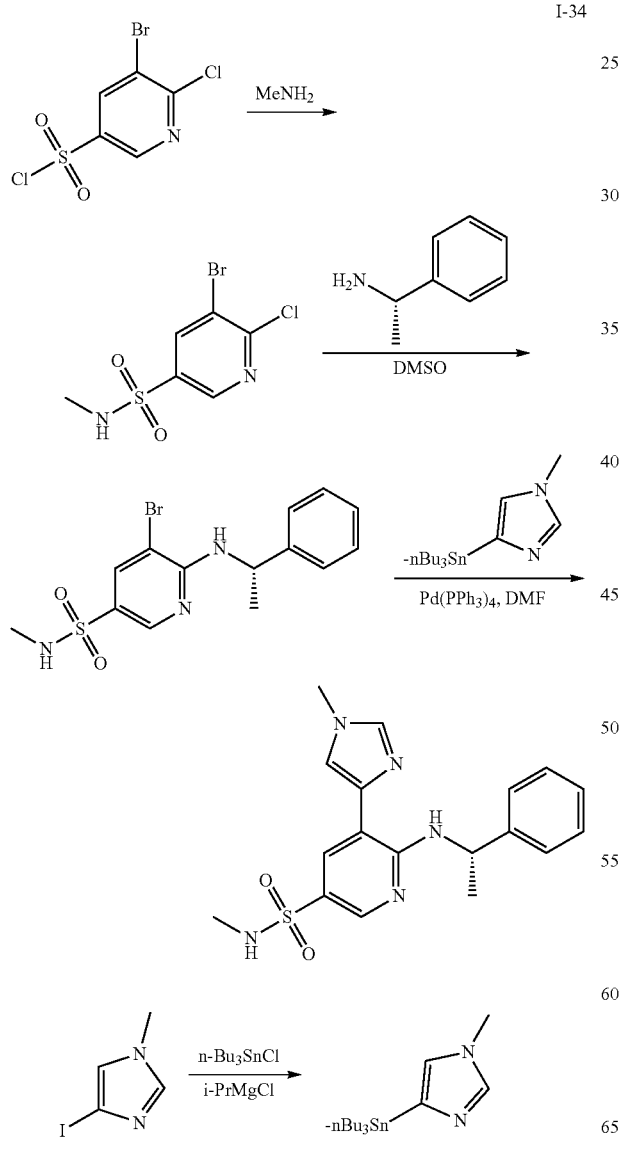

Step 1: 5-Bromo-6-chloro-N-methyl-pyridine-3-sulfonamide

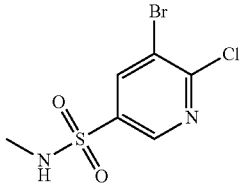

To a solution of 5-bromo-6-chloro-pyridine-3-sulfonyl chloride (4 g, 13.75 mmol, 1 eq) in DCM (5 mL) was added MeNH$_2$ (2.85 g, 27.50 mmol, 30% purity, 2 eq) (the solution of EtOH) at 0° C. under N$_2$ atmosphere. The mixture was stirred at 25° C. for 2 h. TLC (PE/EtOAc=5:1, R$_f$=0.29) showed the reaction was completed. The mixture was concentrated and then water (80 mL) was added. The mixture was extracted with EtOAc (50 mL×3). The combined organic layers were washed with brine (50 mL), dried over Na$_2$SO$_4$, filtered and concentrated to yield 5-bromo-6-chloro-N-methyl-pyridine-3-sulfonamide (3.07 g, 10.71 mmol, 77.9% yield, 99.6% purity) as a white solid, which was used in the next step without further purification. $^1$H NMR (400 MHz, CDCl$_3$) δ ppm 2.77 (d, J=5.48 Hz, 3H), 4.64 (d, J=5.09 Hz, 1H), 8.36 (d, J=2.35 Hz, 1H), 8.77 (d, J=1.96 Hz, 1H); ES-LCMS m/z 284.8, 286.8 [M+H]$^+$.

Step 2: 5-Bromo-N-methyl-6-[[(1S)-1-phenylethyl]amino]pyridine-3-sulfonamide

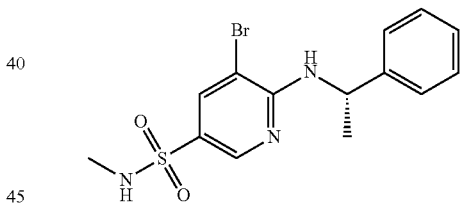

To a solution of 5-bromo-6-chloro-N-methyl-pyridine-3-sulfonamide (1 g, 3.50 mmol, 1 eq) in DMSO (10 mL) was added (1S)-1-phenylethanamine (976.07 mg, 8.05 mmol, 1.03 mL, 2.3 eq) under N$_2$ atmosphere. The mixture was stirred at 140° C. for 12 h. The mixture was diluted with water (80 mL) and extracted with EtOAc (50 mL×3). The combined organic layers were washed with brine (50 mL), dried over Na$_2$SO$_4$, filtered and concentrated to yield a residue which was purified by flash silica gel chromatography (From PE/EtOAc=1/0 to 5/1, R$_f$=0.52) to yield 5-bromo-N-methyl-6-[[(1S)-1-phenylethyl]amino]pyridine-3-sulfonamide (1.28 g, 3.28 mmol, 93.7% yield, 94.9% purity) as red oil. $^1$H NMR (400 MHz, CDCl$_3$) δ ppm 1.61 (d, J=7.04 Hz, 3H), 2.66 (d, J=5.48 Hz, 3H), 4.40 (d, J=5.09 Hz, 1H), 5.32-5.33 (m, 1H), 5.76 (d, J=7.04 Hz, 1H), 7.26-7.32 (m, 1H), 7.32-7.41 (m, 4H), 8.00 (d, J=1.96 Hz, 1H), 8.47 (d, J=1.96 Hz, 1H); ES-LCMS m/z 370.1, 372.1 [M+H]$^+$.

Step 3: N-Methyl-5-(1-methylimidazol-4-yl)-6-[[(1S)-1-phenylethyl]amino]pyridine-3-sulfonamide

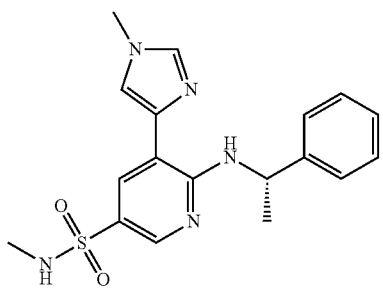 [SMILES: CNS(=O)(=O)c1cnc(N[C@@H](C)c2ccccc2)c(-c2cn(C)cn2)c1]

A mixture of 5-bromo-N-methyl-6-[[(1S)-1-phenylethyl]amino]pyridine-3-sulfonamide (50 mg, 128.15 μmol, 1 eq), tributyl-(1-methylimidazol-4-yl)stannane (50 mg, 126.23 μmol, 9.85e-1 eq) and Pd(PPh$_3$)$_4$ (10 mg, 8.65 μmol, 6.75e-2 eq) in DMF (2 mL) was stirred under N$_2$ atmosphere at 130° C. for 12 h. The reaction mixture was diluted with H$_2$O (50 mL) and extracted with EtOAc (50 mL×3). The organic layer was dried over Na$_2$SO$_4$, filtered and concentrated under reduced pressure to yield a residue which was purified by preparative HPLC (column: Phenomenex Synergi C18 150*30 mm*4 um; mobile phase: [water (0.05% HCl)-ACN]; B %: 30%-50%, 9 min). The desired fraction was basified with saturated aqueous NaHCO$_3$ until pH=8 and extracted with EtOAc (50 mL×3). The organic layer was dried over Na$_2$SO$_4$, filtered and concentrated under reduced pressure to yield a residue which was dissolved in MeCN (15 mL) and water (15 mL) and lyophilized to yield N-methyl-5-(1-methylimidazol-4-yl)-6-[[(1S)-1-phenylethyl]amino]pyridine-3-sulfonamide (22.85 mg, 61.51 μmol, 48.0% yield, 100.0% purity, $[\alpha]^{24.8}_D$=+24.00 (DMSO, c=0.025 g/100 mL)) as an off-white solid. $^1$H NMR (500 MHz, CDCl$_3$) δ ppm 9.75 (d, J=7.5 Hz, 1H), 8.43 (d, J=2.3 Hz, 1H), 7.89 (d, J=2.3 Hz, 1H), 7.50 (s, 1H), 7.43 (d, J=7.6 Hz, 2H), 7.35-7.29 (m, 3H), 7.25-7.21 (m, 1H), 5.50 (q, J=7.1 Hz, 1H), 4.27 (q, J=5.4 Hz, 1H), 3.76 (s, 3H), 2.65 (d, J=5.5 Hz, 3H), 1.63 (d, J=6.9 Hz, 3H); ES-LCMS m/z 372.2 [M+H]$^+$.

Step 4: Tributyl-(1-methylimidazol-4-yl)stannane

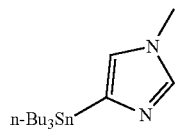

To a solution of 4-iodo-1-methyl-imidazole (200 mg, 961.54 μmol, 1 eq) in THF (2 mL) was added i-PrMgCl (2 M, 720 μL, 1.5 eq) under N$_2$ atmosphere at −10° C. The mixture was stirred under N$_2$ atmosphere at −10° C. for 1 h. Tributyl(chloro)stannane (330 mg, 1.01 mmol, 272.73 μL, 1.05 eq) was added. The mixture was stirred under N$_2$ atmosphere at 20° C. for 11 h. TLC (PE/EtOAc=0/1, R$_f$=0.35) showed the starting material was consumed completely. The reaction mixture was quenched with aqueous KF (10 mL, 2M) and extracted with EtOAc (10 mL×3). The organic layer was washed with water (20 mL×2) and brine (20 mL), dried over Na$_2$SO$_4$, filtered and concentrated under reduced pressure to yield tributyl-(1-methylimidazol-4-yl)stannane (350 mg, 883.61 μmol, 91.9% yield, 93.7% purity) as colorless oil, which was used in the next step without further purification. $^1$H NMR (400 MHz, CDCl$_3$) δ ppm 7.64 (s, 1H), 6.87 (d, J=0.8 Hz, 1H), 3.69 (s, 3H), 1.58-1.51 (m, 6H), 1.36-1.32 (m, 6H), 1.10-1.00 (m, 6H), 0.91-0.87 (m, 9H); ES-LCMS m/z 373.2 [M+H]$^+$.

I-35

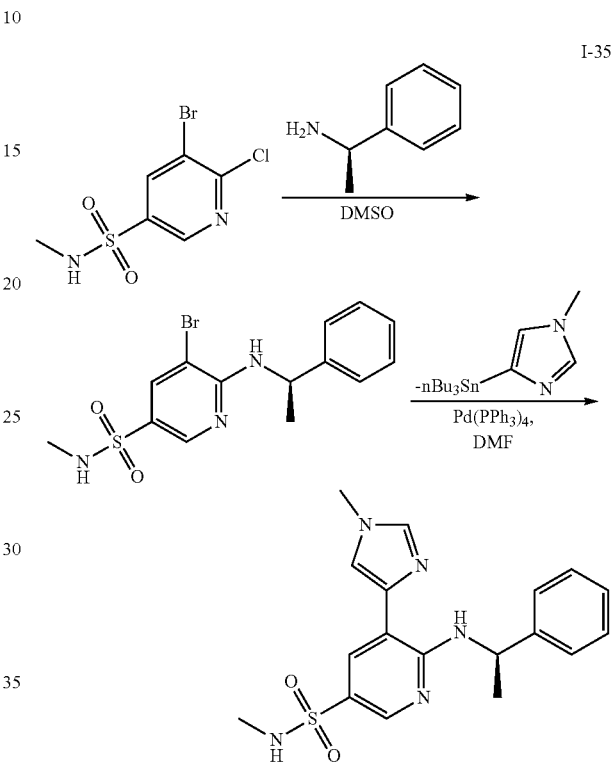

Step 1: 5-Bromo-N-methyl-6-[[(1R)-1-phenylethyl]amino]pyridine-3-sulfonamide

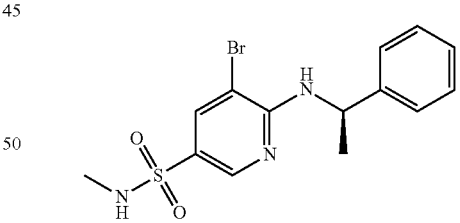

A mixture of 5-bromo-6-chloro-N-methyl-pyridine-3-sulfonamide (200 mg, 700.41 μmol, 1 eq) and (1R)-1-phenylethanamine (200 mg, 1.65 mmol, 212.77 μL, 2.36 eq) in DMSO (3 mL) was stirred at 140° C. for 2 h. The reaction mixture was diluted with H$_2$O (20 mL) and extracted with EtOAc (20 mL×3). The organic layer was dried over Na$_2$SO$_4$, filtered and concentrated under reduced pressure to yield a residue which was purified by flash silica gel chromatography (from PE/EtOAc=100/1 to 6/1, TLC: PE/EtOAc=3/1, R$_f$=0.60) to yield 5-bromo-N-methyl-6-[[(1R)-1-phenylethyl]amino]pyridine-3-sulfonamide (240 mg, 648.19 μmol, 92.5% yield, 100.0% purity) as a colorless gum. $^1$H NMR (400 MHz, CDCl$_3$) δ ppm 8.48 (d, J=2.0 Hz, 1H), 8.00 (d, J=2.0 Hz, 1H), 7.39-7.34 (m, 4H), 7.30 (dd, J=2.7, 5.9 Hz, 1H), 5.77 (d, J=6.7 Hz, 1H), 5.38 (q, J=6.9 Hz, 1H), 4.27 (d, J=5.5 Hz, 1H), 2.68 (d, J=5.1 Hz, 3H), 1.62 (d, J=6.7 Hz, 3H); ES-LCMS m/z 370.0, 372.0 [M+H]+.

Step 2: N-Methyl-5-(1-methylimidazol-4-yl)-6-[[(1R)-1-phenylethyl]amino]pyridine-3-sulfonamide

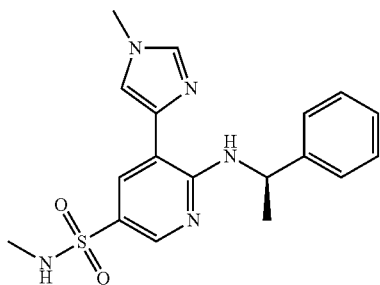 [SMILES: CNS(=O)(=O)c1cnc(N[C@H](C)c2ccccc2)c(-c2cn(C)cn2)c1]

A mixture of 5-bromo-N-methyl-6-[[(1R)-1-phenylethyl]amino]pyridine-3-sulfonamide (50 mg, 135.04 μmol, 1 eq), tributyl-(1-methylimidazol-4-yl)stannane (130 mg, 140.11 μmol, 1.04 eq) and Pd(PPh₃)₄ (10 mg, 8.65 μmol, 6.41e-2 eq) in DMF (2 mL) was stirred under N₂ atmosphere at 130° C. for 12 h. The reaction mixture was diluted with H₂O (50 mL) and extracted with EtOAc (50 mL×3). The organic layer was dried over Na₂SO₄, filtered and concentrated under reduced pressure to yield a residue which was purified by preparative HPLC (column: Phenomenex Synergi C18 150*30 mm*4 um; mobile phase: [water (0.05% HCl)-ACN]; B %: 27%-47%, 9 min). The desired fraction was basified with saturated aqueous NaHCO₃ until pH=8 and extracted with EtOAc (50 mL×3). The organic layer was dried over Na₂SO₄, filtered and concentrated under reduced pressure to yield a residue which was dissolved in MeCN (15 mL) and water (15 mL) and lyophilized to yield N-methyl-5-(1-methylimidazol-4-yl)-6-[[(1R)-1-phenylethyl]amino]pyridine-3-sulfonamide (15.25 mg, 41.05 μmol, 30.4% yield, 100.0% purity, $[\alpha]^{24.8}_D$=−31.58 (DMSO, c=0.019 g/100 mL)) as an off-white solid. ¹H NMR (500 MHz, CDCl₃) δ ppm 9.74 (d, J=7.5 Hz, 1H), 8.43 (d, J=2.3 Hz, 1H), 7.88 (d, J=2.4 Hz, 1H), 7.51 (s, 1H), 7.44 (d, J=7.3 Hz, 2H), 7.35-7.29 (m, 3H), 7.25-7.21 (m, 1H), 5.50 (q, J=7.1 Hz, 1H), 4.19 (q, J=5.1 Hz, 1H), 3.78 (s, 3H), 2.65 (d, J=5.5 Hz, 3H), 1.63 (d, J=7.0 Hz, 3H); ES-LCMS m/z 372.2 [M+H]+.

I-36

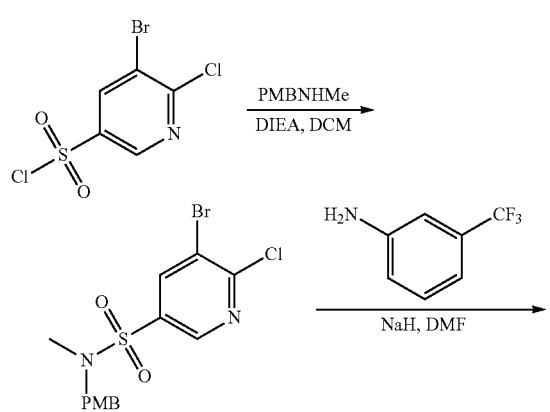

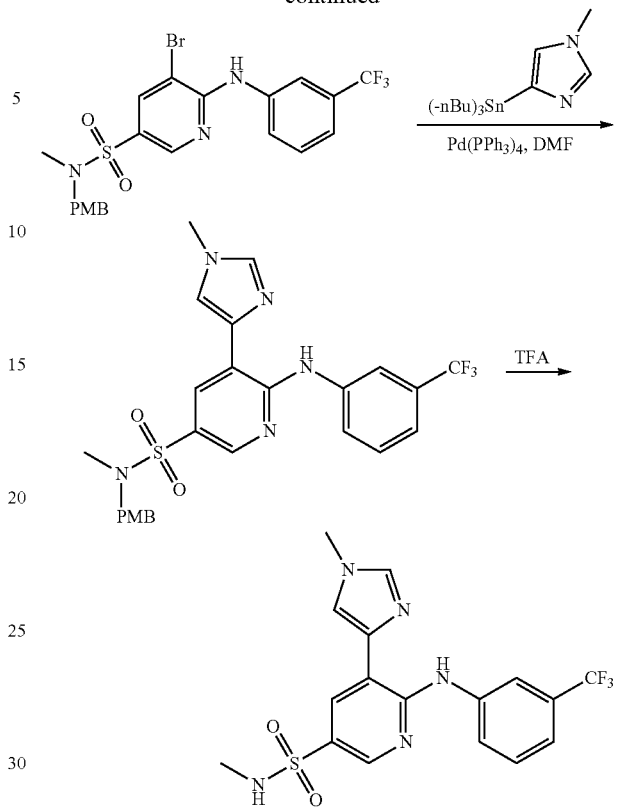

Step 1: 5-Bromo-6-chloro-N-[(4-methoxyphenyl)methyl]-N-methyl-pyridine-3-sulfonamide

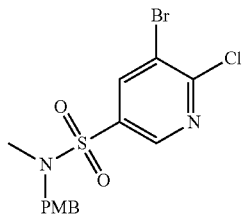

To a solution of 5-bromo-6-chloro-pyridine-3-sulfonyl chloride (150 mg, 515.55 μmol, 1 eq) in DCM (5 mL) was added DIEA (333.16 mg, 2.58 mmol, 449.00 μL, 5 eq) and 1-(4-methoxyphenyl)-N-methyl-methanamine (80.00 mg, 529.08 μmol, 1.03 eq). The mixture was stirred at 20° C. for 2 h. TLC (PE/EtOAc=4/1, R$_f$=0.30) showed the starting material was consumed completely. The mixture was concentrated under reduced pressure to yield a residue which was purified by flash silica gel chromatography (from PE/EtOAc=100/1 to 4/1, TLC: PE/EtOAc=4/1, R$_f$=0.30) to yield 5-bromo-6-chloro-N-[(4-methoxyphenyl)methyl]-N-methyl-pyridine-3-sulfonamide (170 mg, 398.50 μmol, 77.3% yield, 95.1% purity) as an off-white solid. H NMR (400 MHz, CDCl₃) δ ppm 8.72 (d, J=2.0 Hz, 1H), 8.24 (d, J=2.0 Hz, 1H), 7.22 (d, J=8.6 Hz, 2H), 6.89 (d, J=8.6 Hz, 2H), 4.19 (s, 2H), 3.82 (s, 3H), 2.71 (s, 3H); ES-LCMS m/z 405.0, 407.0, 409.0 [M+H]+.

Step 2: 5-Bromo-N-[(4-methoxyphenyl)methyl]-N-methyl-6-[3-(trifluoromethyl)anilino]pyridine-3-sulfonamide

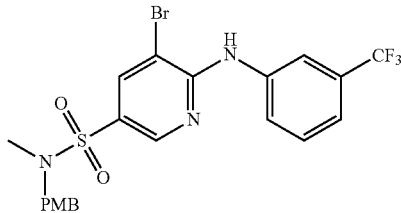

To a solution of 3-(trifluoromethyl)aniline (100 mg, 620.64 μmol, 1.77 eq) in DMF (2 mL) was added NaH (70 mg, 1.75 mmol, 60% purity, 4.98 eq). The mixture was stirred at 20° C. for 0.5 h. 5-Bromo-6-chloro-N-[(4-methoxyphenyl)methyl]-N-methyl-pyridine-3-sulfonamide (150 mg, 351.62 μmol, 1 eq) was added. The mixture was stirred at 20° C. for 2 h. TLC (PE/EtOAc=4/1, $R_f$=0.24) showed the starting material was consumed completely. The reaction mixture was quenched with $H_2O$ (10 mL) and extracted with EtOAc (10 mL×3). The organic layer was dried over $Na_2SO_4$, filtered and concentrated under reduced pressure to yield a residue which was purified by preparative HPLC (column: Phenomenex Synergi C18 150*30 mm*4 um; mobile phase: [water (0.1% TFA)-ACN]; B %: 73%-93%, 9 min). The desired fraction was basified with saturated aqueous $NaHCO_3$ until pH=8 and extracted with EtOAc (50 mL×3). The organic layer was dried over $Na_2SO_4$, filtered and concentrated under reduced pressure to yield 5-bromo-N-[(4-methoxyphenyl)methyl]-N-methyl-6-[3-(trifluoromethyl)anilino]pyridine-3-sulfonamide (110 mg, 207.41 μmol, 59.0% yield, 100.0% purity) as a white solid. $^1$H NMR (500 MHz, $CDCl_3$) δ ppm 8.61 (d, J=2.1 Hz, 1H), 8.12 (d, J=2.0 Hz, 1H), 8.00 (s, 1H), 7.86 (d, J=7.9 Hz, 1H), 7.52 (t, J=8.0 Hz, 1H), 7.48-7.45 (m, 1H), 7.42 (d, J=7.9 Hz, 1H), 7.24 (d, J=8.7 Hz, 2H), 6.89 (d, J=8.7 Hz, 2H), 4.15 (s, 2H), 3.82 (s, 3H), 2.66 (s, 3H); ES-LCMS m/z 530.0, 532.0 $[M+H]^+$.

Step 3: N-[(4-Methoxyphenyl)methyl]-N-methyl-5-(1-methylimidazol-4-yl)-6-[3-(trifluoromethyl)anilino]pyridine-3-sulfonamide

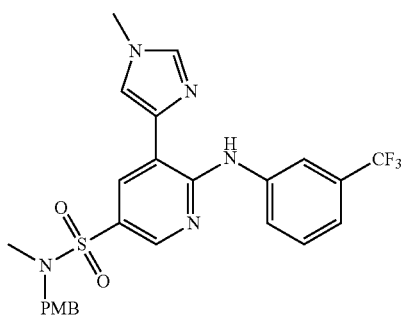

A mixture of 5-bromo-N-[(4-methoxyphenyl)methyl]-N-methyl-6-[3-(trifluoromethyl)anilino]pyridine-3-sulfonamide (100 mg, 188.55 μmol, 1 eq), tributyl-(1-methylimidazol-4-yl)stannane (80 mg, 209.08 μmol, 1.11 eq) and Pd(PPh$_3$)$_4$ (10 mg, 8.65 μmol, 4.59e-2 eq) in DMF (2 mL) was stirred under $N_2$ atmosphere at 140° C. for 12 h. TLC (PE/EtOAc=2/1, $R_f$=0.15) showed the starting material was consumed completely. The reaction mixture was diluted with $H_2O$ (20 mL) and extracted with EtOAc (20 mL×3). The organic layer was dried over $Na_2SO_4$, filtered and concentrated under reduced pressure to yield a residue which was purified by flash silica gel chromatography (from PE/EtOAc=100/1 to 1/1, TLC: PE/EtOAc=2/1, $R_f$=0.15) to yield N-[(4-methoxyphenyl)methyl]-N-methyl-5-(1-methylimidazol-4-yl)-6-[3-(trifluoromethyl)anilino]pyridine-3-sulfonamide (65 mg, 113.60 μmol, 60.3% yield, 92.9% purity) as a white solid. $^1$H NMR (500 MHz, $CDCl_3$) δ ppm 11.92 (s, 1H), 8.58 (d, J=2.4 Hz, 1H), 8.10 (s, 1H), 8.06 (d, J=8.1 Hz, 1H), 8.01 (d, J=2.3 Hz, 1H), 7.61 (s, 1H), 7.47 (t, J=7.9 Hz, 1H), 7.40 (d, J=1.1 Hz, 1H), 7.30 (d, J=7.8 Hz, 1H), 7.24 (d, J=8.7 Hz, 2H), 6.87 (d, J=8.7 Hz, 2H), 4.12 (s, 2H), 3.83 (s, 3H), 3.80 (s, 3H), 2.62 (s, 3H); ES-LCMS m/z 532.2 $[M+H]^+$.

Step 4: N-Methyl-5-(1-methylimidazol-4-yl)-6-[3-(trifluoromethyl)anilino]pyridine-3-sulfonamide

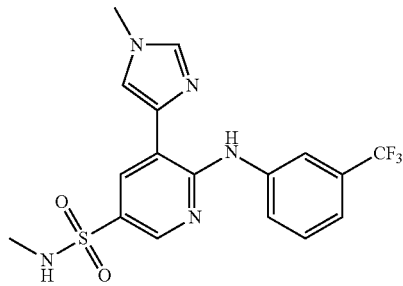 [SMILES: CNS(=O)(=O)c1cnc(Nc2cccc(C(F)(F)F)c2)c(-c2cn(C)cn2)c1]

To a solution of N-[(4-methoxyphenyl)methyl]-N-methyl-5-(1-methylimidazol-4-yl)-6-[3-(trifluoromethyl)anilino]pyridine-3-sulfonamide (60 mg, 104.86 μmol, 1 eq) in DCM (10 mL) was added TFA (3.08 g, 27.01 mmol, 2 mL, 257.59 eq). The mixture was stirred at 30° C. for 4 h. The mixture was concentrated under reduced pressure to yield a residue which was purified by preparative HPLC (column: Phenomenex Synergi C18 150*30 mm*4 um; mobile phase: [water (0.1% TFA)-ACN]; B %: 41%-61%, 9 min). The desired fraction was basified with saturated aqueous $NaHCO_3$ until pH=8 and extracted with EtOAc (50 mL×3). The organic layer was dried over $Na_2SO_4$, filtered and concentrated under reduced pressure to yield a residue which was dissolved in MeCN (15 mL) and $H_2O$ (15 mL) and lyophilized to yield N-methyl-5-(1-methylimidazol-4-yl)-6-[3-(trifluoromethyl)anilino]pyridine-3-sulfonamide (35.75 mg, 86.51 μmol, 82.5% yield, 99.5% purity) as a white solid. $^1$H NMR (500 MHz, $CDCl_3$) δ ppm 11.94 (s, 1H), 8.60 (d, J=2.4 Hz, 1H), 8.10 (s, 1H), 8.07 (d, J=2.3 Hz, 1H), 8.03 (d, J=8.2 Hz, 1H), 7.58 (s, 1H), 7.46 (t, J=8.0 Hz, 1H), 7.39 (d, J=1.2 Hz, 1H), 7.30 (d, J=7.8 Hz, 1H), 4.41 (q, J=5.4 Hz, 1H), 3.82 (s, 3H), 2.71 (d, J=5.5 Hz, 3H); ES-LCMS m/z 412.2 $[M+H]^+$.

I-37

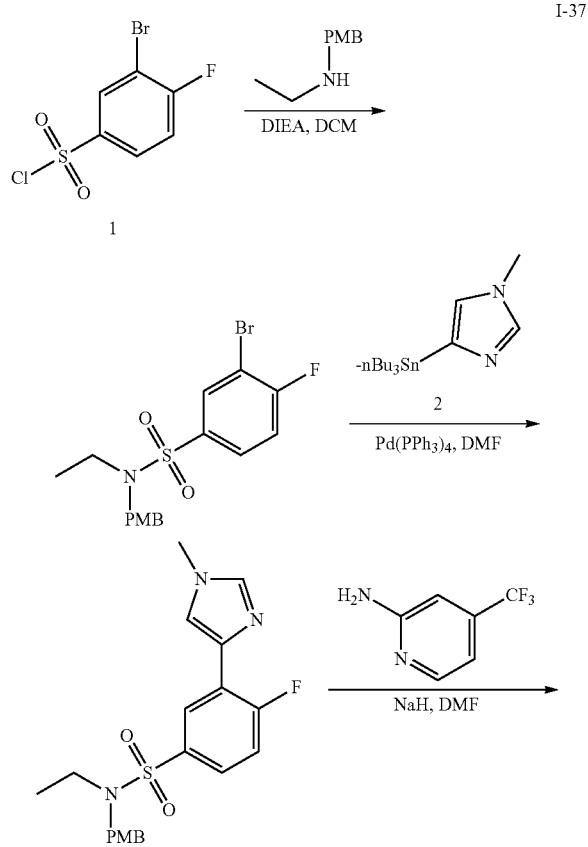

Step 1: 3-Bromo-1-ethyl-4-fluoro-N-[(4-methoxyphenyl)methyl]benzenesulfonamide A mixture of 3-bromo-4-fluoro-benzenesulfonyl chloride (1 g, 3.66 mmol, 1 eq), N-[(4-methoxyphenyl)methyl]ethanamine (755.15 mg, 4.57 mmol, 1.25 eq), DIEA (2.36 g, 18.28 mmol, 3.18 mL, 5 eq) in DCM (20 mL). The mixture was stirred at 15° C. under $N_2$ atmosphere for 12 h. TLC (PE/EtOAc=5:1, $R_f$=0.70) showed starting material was remained and one new spot was detected. The reaction mixture was quenched by addition of water (50 mL), extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 5/1, TLC: PE/EtOAc=5/1, $R_f$=0.50) to yield 3-bromo-N-ethyl-4-fluoro-N-[(4-methoxyphenyl)methyl]benzenesulfonamide (1.2 g, 2.83 mmol, 77.5% yield, 95.0% purity) as a yellow solid. $^1$H NMR (400 MHz, $CDCl_3$) δ ppm 8.04 (dd, J=2.2, 6.4 Hz, 1H), 7.80 (ddd, J=2.3, 4.5, 8.6 Hz, 1H), 7.29 (d, J=2.9 Hz, 1H), 7.24 (d, J=8.8 Hz, 2H), 6.89 (d, J=8.6 Hz, 2H), 4.34 (s, 2H), 3.84 (s, 3H), 3.24 (q, J=7.1 Hz, 2H), 1.01 (t, J=7.2 Hz, 3H); ES-LCMS no desired m/z was found.

Step 2: N-Ethyl-4-fluoro-N-[(4-methoxyphenyl)methyl]-3-(1-methylimidazol-4-yl)benzenesulfonamide

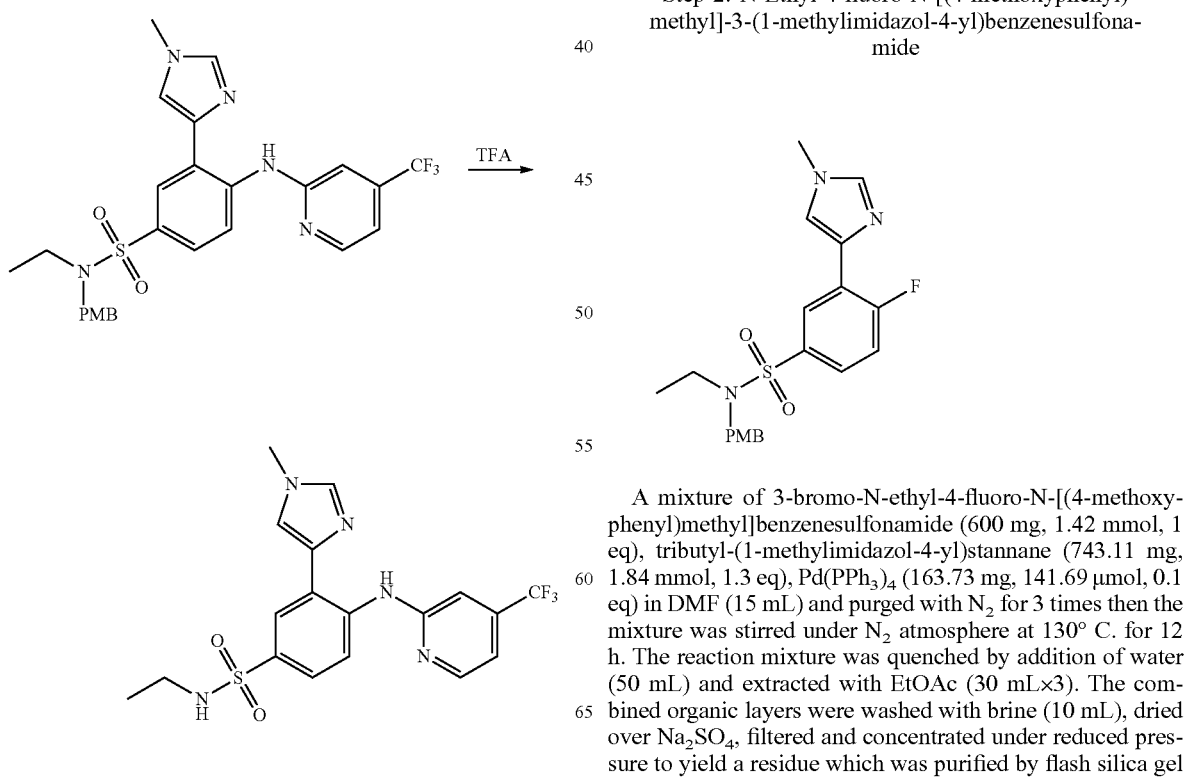

A mixture of 3-bromo-N-ethyl-4-fluoro-N-[(4-methoxyphenyl)methyl]benzenesulfonamide (600 mg, 1.42 mmol, 1 eq), tributyl-(1-methylimidazol-4-yl)stannane (743.11 mg, 1.84 mmol, 1.3 eq), Pd(PPh$_3$)$_4$ (163.73 mg, 141.69 μmol, 0.1 eq) in DMF (15 mL) and purged with $N_2$ for 3 times then the mixture was stirred under $N_2$ atmosphere at 130° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 1/1, TLC: PE/EtOAc=1/1, R$_f$=0.40) to yield N-ethyl-4-fluoro-N-[(4-methoxyphenyl)methyl]-3-(1-methylimidazol-4-yl)benzenesulfonamide (380 mg, 609.36 μmol, 43.0% yield, 64.7% purity) as a white gum. $^1$H NMR (400 MHz, CDCl$_3$) δ ppm 8.66 (dd, J=2.4, 7.1 Hz, 1H), 7.72-7.70 (m, 1H), 7.54 (s, 1H), 7.50-7.47 (m, 2H), 7.44 (dd, J=1.1, 4.0 Hz, 1H), 7.25 (s, 1H), 6.85 (d, J=8.8 Hz, 2H), 4.34 (s, 2H), 3.80 (s, 3H), 3.78 (s, 3H), 3.22 (q, J=7.1 Hz, 2H), 0.93 (t, J=7.1 Hz, 3H); ES-LCMS m/z 404.2, 405.2 [M+H]$^+$.

Step 3: N-Ethyl-N-[(4-methoxyphenyl)methyl]-3-(1-methylimidazol-4-yl)-4-[[4-(trifluoromethyl)-2-pyridyl]amino]benzenesulfonamide

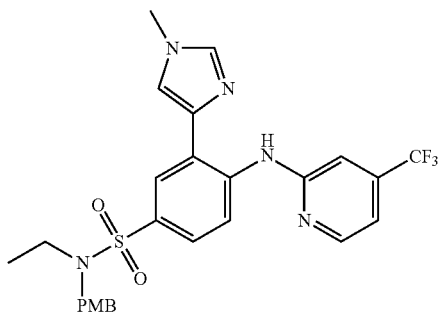

To a stirred solution of 4-(trifluoromethyl)pyridin-2-amine (193.26 mg, 1.19 mmol, 2 eq) in DMF (5 mL) was added NaH (119.20 mg, 2.98 mmol, 60% purity, 5 eq) slowly at 0° C. under ice-water bath. The mixture was stirred at 0° C. for 1 h. N-Ethyl-4-fluoro-N-[(4-methoxyphenyl)methyl]-3-(1-methylimidazol-4-yl)benzenesulfonamide (370 mg, 596.08 μmol, 1 eq) was added. The mixture was stirred at 120° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, R$_f$=0.50) to yield N-ethyl-N-[(4-methoxyphenyl)methyl]-3-(1-methylimidazol-4-yl)-4-[[4-(trifluoromethyl)-2-pyridyl]amino]benzenesulfonamide (150 mg, 247.45 μmol, 41.5% yield, 90.0% purity) as green oil. $^1$H NMR (400 MHz, CDCl$_3$) δ ppm 12.15 (s, 1H), 8.89 (d, J=8.8 Hz, 1H), 8.44 (d, J=5.4 Hz, 1H), 7.95 (d, J=2.2 Hz, 1H), 7.69 (dd, J=2.2, 8.8 Hz, 1H), 7.60 (s, 1H), 7.33 (d, J=1.2 Hz, 1H), 7.24 (s, 1H), 7.08 (s, 1H), 6.98 (d, J=5.1 Hz, 1H), 6.86 (d, J=8.6 Hz, 2H), 4.30 (s, 2H), 3.81 (s, 3H), 3.80 (s, 3H), 1.56 (s, 2H), 0.99-0.95 (m, 3H); ES-LCMS m/z 546.3 [M+H]$^+$.

Step 4: N-Ethyl-3-(1-methylimidazol-4-yl)-4-[[4-(trifluoromethyl)-2-pyridyl]amino]benzenesulfonamide

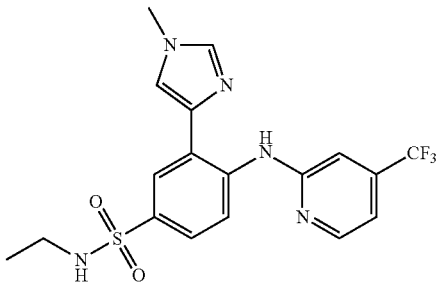 [SMILES: CCNS(=O)(=O)c1ccc(Nc2cc(C(F)(F)F)ccn2)c(-c2cn(C)cn2)c1]

To a solution of N-ethyl-N-[(4-methoxyphenyl)methyl]-3-(1-methylimidazol-4-yl)-4-[[4-(trifluoromethyl)-2-pyridyl]amino]benzenesulfonamide (150 mg, 247.45 μmol, 1 eq) in DCM (10 mL) was added TFA (1.54 g, 13.51 mmol, 1 mL, 54.58 eq). The mixture was stirred at 25° C. for 12 h. The mixture was quenched with sat. aq. NaOH (50 mL) and extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 46%-76%, 10 min). The desired fraction was lyophilized to yield N-ethyl-3-(1-methylimidazol-4-yl)-4-[[4-(trifluoromethyl)-2-pyridyl]amino]benzenesulfonamide (34.56 mg, 80.42 μmol, 32.5% yield, 99.0% purity) as a white solid. $^1$H NMR (400 MHz, CDCl$_3$) δ ppm 12.16 (s, 1H), 8.87 (d, J=9.0 Hz, 1H), 8.43 (d, J=5.1 Hz, 1H), 8.00 (d, J=2.2 Hz, 1H), 7.71 (dd, J=2.2, 8.8 Hz, 1H), 7.60 (s, 1H), 7.37 (d, J=1.2 Hz, 1H), 7.08 (s, 1H), 7.02-6.94 (m, 1H), 4.24 (t, J=6.1 Hz, 1H), 3.81 (s, 3H), 3.07-2.99 (m, 2H), 1.13 (t, J=7.2 Hz, 3H); ES-LCMS m/z 426.2 [M+H]$^+$.

I-38

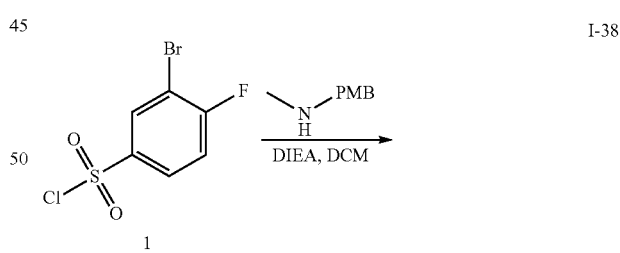

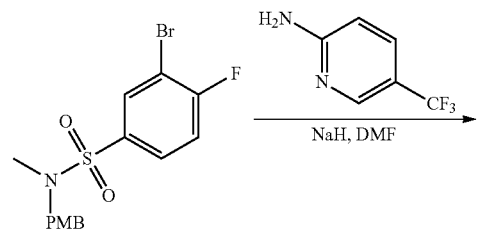

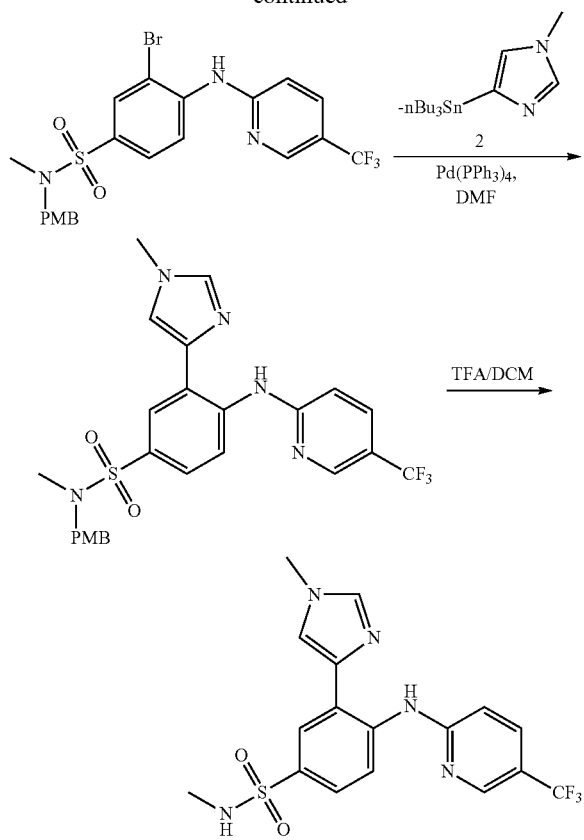

Step 1: 3-Bromo-4-fluoro-N-[(4-methoxyphenyl)methyl]-N-methyl-benzenesulfonamide

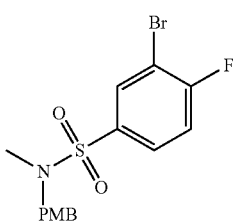

To a stirred solution of 3-bromo-4-fluoro-benzenesulfonyl chloride (8 g, 24.86 mmol, 1 eq) in DCM (150 mL) was added DIEA (16.07 g, 124.31 mmol, 21.65 mL, 5 eq) and 1-(4-methoxyphenyl)-N-methyl-methanamine (4.51 g, 29.83 mmol, 1.2 eq). The reaction mixture was stirred under $N_2$ atmosphere at 25° C. for 2 h. The reaction mixture was diluted with $H_2O$ (50 mL) and extracted with DCM (50 mL×3). The combined organic layers were washed with brine (50 mL), dried over $Na_2SO_4$, filtered and concentrated under reduced pressure to yield a residue which was purified by flash silica gel chromatography (from PE/EtOAc=100/1 to 3/1, TLC: PE/EtOAc=1/1, $R_f$=0.36) to yield 3-bromo-4-fluoro-N-[(4-methoxyphenyl)methyl]-N-methyl-benzenesulfonamide (9 g, 23.18 mmol, 93.2% yield, 100.0% purity) as a white solid. $^1H$ NMR (500 MHz, $CDCl_3$) δ ppm 8.04 (dd, J=2.3, 6.3 Hz, 1H), 7.79-7.76 (m, 1H), 7.29 (t, J=8.3 Hz, 1H), 7.22 (d, J=8.5 Hz, 2H), 6.88 (d, J=8.5 Hz, 2H), 4.12 (s, 2H), 3.82 (s, 3H), 2.63 (s, 3H); ES-LCMS no desired m/z was detected.

Step 2: 3-Bromo-N-[(4-methoxyphenyl)methyl]-N-methyl-4-[[5-(trifluoromethyl)-2-pyridyl]amino]benzenesulfonamide

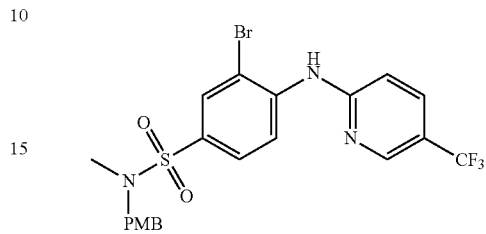

To a stirred solution of 5-(trifluoromethyl)pyridin-2-amine (125.26 mg, 772.70 μmol, 1 eq) in DMF (10 mL) was added NaH (92.71 mg, 2.32 mmol, 60%, 3 eq). The reaction mixture was stirred at 0° C. for 0.5 h. 3-Bromo-4-fluoro-N-[(4-methoxyphenyl)methyl]-N-methyl-benzenesulfonamide (300 mg, 772.70 μmol, 1 eq) was added and the mixture was stirred under $N_2$ atmosphere at 25° C. for 3.5 h. TLC (PE/EtOAc=3/1, $R_f$=0.28) showed starting material was consumed completely and one new spot was detected. The reaction mixture was diluted with $H_2O$ (10 mL) and extracted with EtOAc (30 mL×3). The combined organic layers were washed with brine (20 mL), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.28) to yield 3-bromo-N-[(4-methoxyphenyl)methyl]-N-methyl-4-[[5-(trifluoromethyl)-2-pyridyl]amino]benzenesulfonamide (330 mg, 609.78 μmol, 78.9% yield, 98.0% purity) as yellow oil. $^1H$ NMR (500 MHz, $CDCl_3$) δ ppm 8.67 (d, J=8.7 Hz, 1H), 8.60 (s, 1H), 8.05 (d, J=2.1 Hz, 1H), 7.84 (dd, J=2.3, 8.7 Hz, 1H), 7.78 (dd, J=2.1, 8.8 Hz, 1H), 7.41 (s, 1H), 7.24 (d, J=8.5 Hz, 2H), 6.98 (d, J=8.7 Hz, 1H), 6.90-6.86 (m, 2H), 4.16-4.08 (m, 2H), 3.82 (s, 3H), 2.62 (s, 3H); ES-LCMS m/z 530.1, 532.1 [M+H]⁺.

Step 3: N-[(4-Methoxyphenyl)methyl]-N-methyl-3-(1-methylimidazol-4-yl)-4-[[5-(trifluoromethyl)-2-pyridyl]amino]benzenesulfonamide

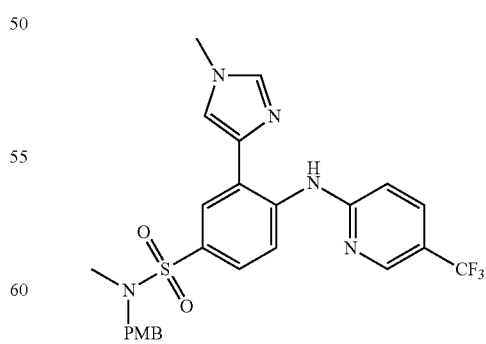

To a stirred solution of 3-bromo-N-[(4-methoxyphenyl)methyl]-N-methyl-4-[[5-(trifluoromethyl)-2-pyridyl]amino]benzenesulfonamide (330 mg, 609.78 μmol, 1 eq) and tributyl-(1-methylimidazol-4-yl)stannane (462.82 mg, 1.22 mmol, 2 eq) in DMF (20 mL) was added Pd(PPh$_3$)$_4$ (70.46 mg, 60.98 μmol, 0.1 eq). The reaction mixture was bubbled with N$_2$ for 3 times and stirred under N$_2$ atmosphere at 130° C. for 12 h. The reaction mixture was diluted with H$_2$O (20 mL) and extracted with EtOAc (40 mL×3). The combined organic layers were washed with brine (30 mL), dried over Na$_2$SO$_4$, filtered and concentrated under reduced pressure to yield a residue which was purified by flash silica gel chromatography (from PE/EtOAc=100/1 to 3/1, TLC: PE/EtOAc=3/1, R$_f$=0.28) to yield N-[(4-methoxyphenyl)methyl]-N-methyl-3-(1-methylimidazol-4-yl)-4-[[5-(trifluoromethyl)-2-pyridyl]amino]benzenesulfonamide (240 mg, 447.00 μmol, 73.3% yield, 99.0% purity) as yellow oil. $^1$H NMR (500 MHz, CDCl$_3$) δ ppm 12.22 (s, 1H), 8.95 (d, J=8.9 Hz, 1H), 8.56 (s, 1H), 8.03 (s, 1H), 7.95 (d, J=2.1 Hz, 1H), 7.74-7.68 (m, 2H), 7.59 (s, 1H), 7.37 (d, J=1.2 Hz, 1H), 7.23 (s, 1H), 6.95 (d, J=8.7 Hz, 1H), 6.89-6.84 (m, 2H), 4.11-4.07 (m, 2H), 3.81 (s, 3H), 3.80 (s, 3H), 2.59 (s, 3H); ES-LCMS m/z 532.2 [M+H]$^+$.

Step 4: N-Methyl-3-(1-methylimidazol-4-yl)-4-[[5-(trifluoromethyl)-2-pyridyl]amino]benzenesulfonamide To a stirred solution of N-[(4-methoxyphenyl)methyl]-N-methyl-3-(1-methylimidazol-4-yl)-4-[[5-(trifluoromethyl)-2-pyridyl]amino]benzenesulfonamide (240 mg, 447.00 μmol, 1 eq) in DCM (20 mL) was added TFA (3.08 g, 27.01 mmol, 2 mL, 60.43 eq). The reaction mixture was stirred under N$_2$ atmosphere at 25° C. for 12 h. The reaction mixture was concentrated under reduced pressure to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 43%-73%, 10 min) to yield N-methyl-3-(1-methylimidazol-4-yl)-4-[[5-(trifluoromethyl)-2-pyridyl]amino]benzenesulfonamide (48.32 mg, 117.45 μmol, 26.3% yield, 100.0% purity) as a white solid. $^1$H NMR (500 MHz, DMSO-d$_6$) δ ppm 12.26 (s, 1H), 8.70 (d, J=8.7 Hz, 1H), 8.60 (s, 1H), 8.04 (d, J=2.1 Hz, 1H), 7.96 (dd, J=2.4, 8.8 Hz, 1H), 7.94 (s, 1H), 7.85 (d, J=1.1 Hz, 1H), 7.59 (dd, J=2.2, 8.8 Hz, 1H), 7.29 (d, J=5.5 Hz, 1H), 7.07 (d, J=8.9 Hz, 1H), 3.77 (s, 3H), 2.42 (s, 3H); ES-LCMS m/z 412.2 [M+H]$^+$.

I-39

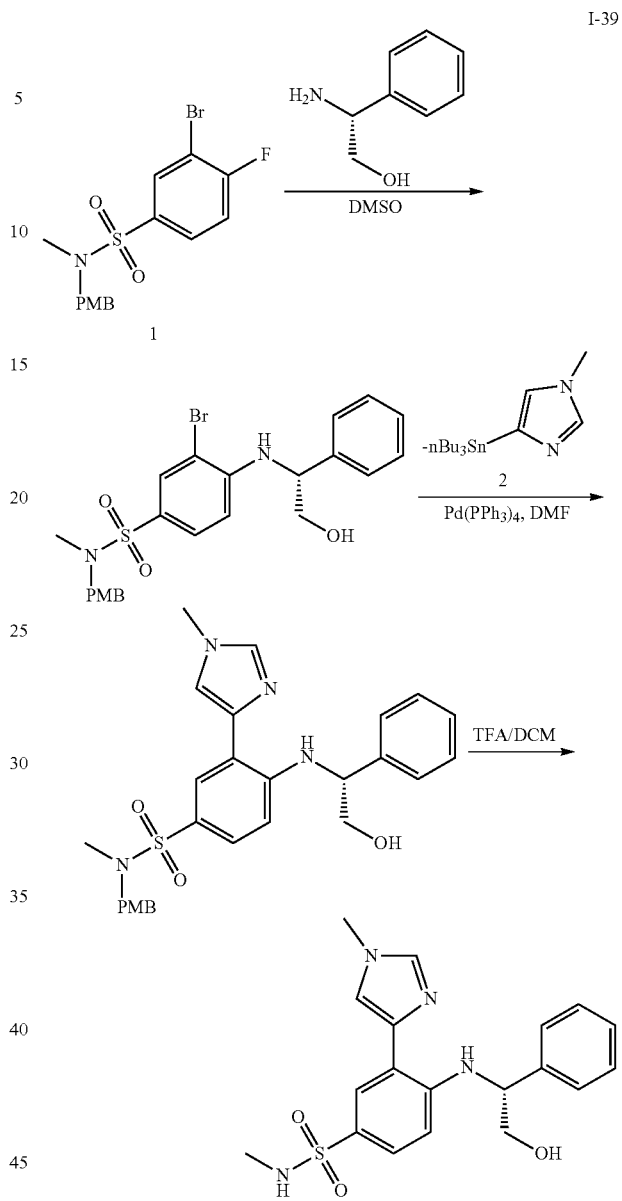

Step 1: 3-Bromo-4-[[(1S)-2-hydroxy-1-phenylethyl]amino]-N-[(4-methoxyphenyl)methyl]-N-methyl-benzenesulfonamide

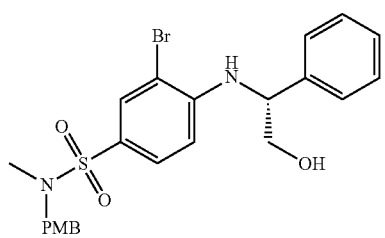

To a stirred solution of 3-bromo-4-fluoro-N-[(4-methoxyphenyl)methyl]-N-methyl-benzenesulfonamide (200 mg, 515.13 μmol, 1 eq) in DMSO (5 mL) was added (2R)-2- amino-2-phenyl-ethanol (141.33 mg, 1.03 mmol, 2 eq). The reaction mixture was stirred under $N_2$ atmosphere at 140° C. for 12 h. The reaction mixture was diluted with $H_2O$ (15 mL) and extracted with EtOAc (30 mL×3). The combined organic layers were washed with brine (30 mL), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.21) to yield 3-bromo-4-[[(1S)-2-hydroxy-1-phenyl-ethyl]amino]-N-[(4-methoxyphenyl)methyl]-N-methyl-benzenesulfonamide (110 mg, 174.11 μmol, 33.8% yield, 80.0% purity) as yellow oil. $^1$H NMR (500 MHz, $CDCl_3$) δ ppm 7.90 (d, J=2.1 Hz, 1H), 7.45 (dd, J=1.8, 8.7 Hz, 1H), 7.40 (d, J=7.3 Hz, 2H), 7.37-7.34 (m, 3H), 7.20 (d, J=8.5 Hz, 2H), 6.87-6.83 (m, 2H), 6.44 (d, J=8.7 Hz, 1H), 4.66-4.56 (m, 1H), 4.11-4.05 (m, 1H), 4.02 (s, 2H), 3.94-3.89 (m, 1H), 3.80 (s, 3H), 2.52 (s, 3H); ES-LCMS m/z 505.1, 507.1 $[M+H]^+$.

Step 2: 4-[[(1S)-2-Hydroxy-1-phenyl-ethyl]amino]-N-[(4-methoxyphenyl)methyl]-N-methyl-3-(1-methylimidazol-4-yl)benzenesulfonamide

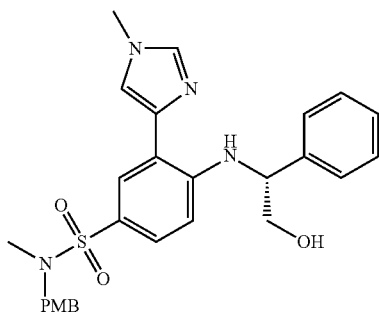

To a stirred solution of 3-bromo-4-[[(1S)-2-hydroxy-1-phenyl-ethyl]amino]-N-[(4-methoxyphenyl)methyl]-N-methyl-benzenesulfonamide (100 mg, 158.28 μmol, 1 eq) and tributyl-(1-methylimidazol-4-yl)stannane (120.14 mg, 316.57 μmol, 2 eq) in DMF (10 mL) was added $Pd(PPh_3)_4$ (18.29 mg, 15.83 μmol, 0.1 eq). The reaction mixture was bubbled with $N_2$ for 3 times and stirred under $N_2$ atmosphere at 130° C. for 12 h. The reaction mixture was diluted with $H_2O$ (20 mL) and extracted with EtOAc (30 mL×3). The combined organic layers were washed with brine (30 mL), dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.23) to yield 4-[[(1S)-2-hydroxy-1-phenyl-ethyl]amino]-N-[(4-methoxyphenyl)methyl]-N-methyl-3-(1-methylimidazol-4-yl)benzenesulfonamide (80 mg, 151.59 μmol, 95.8% yield, 96.0% purity) as yellow oil. $^1$H NMR (500 MHz, $CDCl_3$) δ ppm 8.99 (s, 1H), 7.78 (d, J=2.1 Hz, 1H), 7.56 (s, 1H), 7.44-7.38 (m, 3H), 7.36 (t, J=7.6 Hz, 2H), 7.31-7.28 (m, 2H), 7.20 (d, J=8.5 Hz, 2H), 6.86-6.82 (m, 2H), 6.55 (d, J=8.7 Hz, 1H), 4.73-4.67 (m, 1H), 4.00 (s, 2H), 3.94-3.87 (m, 1H), 3.79 (s, 6H), 3.73-3.70 (m, 2H), 2.50 (s, 3H); ES-LCMS m/z 507.2 $[M+H]^+$.

Step 3: 4-[[(1S)-2-Hydroxy-1-phenyl-ethyl]amino]-N-methyl-3-(1-methylimidazol-4-yl)benzenesulfonamide

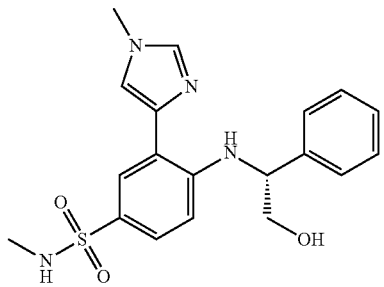 [SMILES: CNS(=O)(=O)c1ccc(N[C@@H](CO)c2ccccc2)c(-c2cn(C)cn2)c1]

To a stirred solution of 4-[[(1S)-2-hydroxy-1-phenyl-ethyl]amino]-N-[(4-methoxyphenyl)methyl]-N-methyl-3-(1-methylimidazol-4-yl)benzenesulfonamide (80 mg, 151.59 μmol, 1 eq) in DCM (10 mL) was added TFA (1.54 g, 13.51 mmol, 1 mL, 89.10 eq). The reaction mixture was stirred under $N_2$ atmosphere at 25° C. for 12 h. The reaction mixture was concentrated under reduced pressure to yield a residue which was purified by preparative HPLC (column: Agela DuraShell C18 150*25 mm*5 um; mobile phase: [water (0.04% $NH_3.H_2O$+10 mM $NH_4HCO_3$)-ACN]; B %: 25%-55%, 10 min) to yield 4-[[(1S)-2-hydroxy-1-phenyl-ethyl]amino]-N-methyl-3-(1-methylimidazol-4-yl)benzenesulfonamide (17.98 mg, 46.22 μmol, 30.5% yield, 99.4% purity, $[α]^{17.7}_D$=+128.571 (MeOH, c=0.028 g/100 mL)) as a white solid. $^1$H NMR (500 MHz, MeOD) δ ppm 7.79 (d, J=2.3 Hz, 1H), 7.74 (s, 1H), 7.48 (d, J=1.4 Hz, 1H), 7.40 (d, J=7.3 Hz, 2H), 7.36-7.29 (m, 3H), 7.26-7.21 (m, 1H), 6.50 (d, J=8.9 Hz, 1H), 4.63 (dd, J=4.4, 7.2 Hz, 1H), 3.86 (dd, J=4.4, 11.3 Hz, 1H), 3.83 (s, 3H), 3.75 (dd, J=7.2, 11.2 Hz, 1H), 2.45 (s, 3H); ES-LCMS m/z 387.2 $[M+H]^+$.

I-40

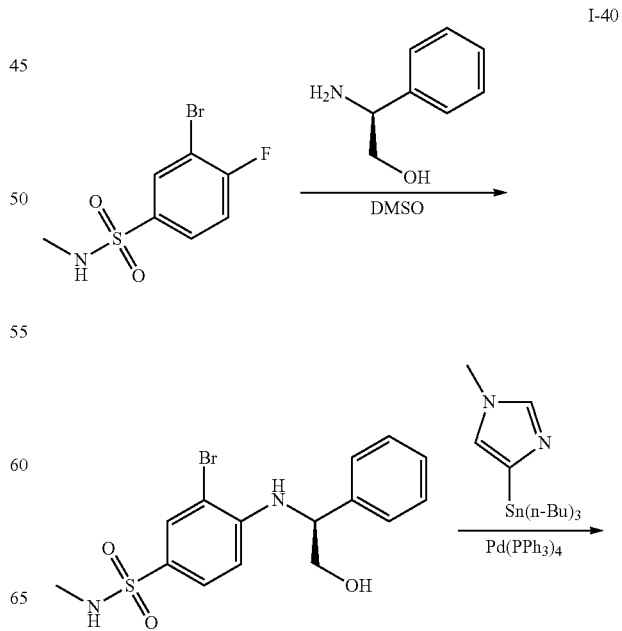

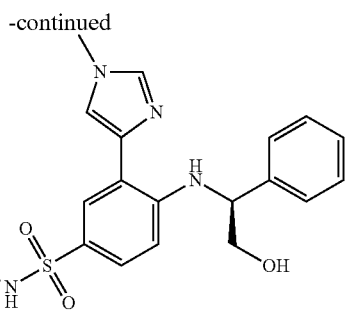

Step 1: 3-Bromo-4-[[(1S)-2-hydroxy-1-phenyl-ethyl]amino]-N-methyl-benzenesulfonamide

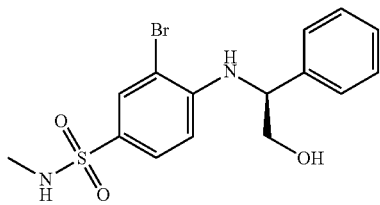 [SMILES: CNS(=O)(=O)c1ccc(N[C@H](CO)c2ccccc2)c(Br)c1]

To a solution of 3-bromo-4-fluoro-N-methyl-benzenesulfonamide (200 mg, 641.54 μmol, 1 eq) in DMSO (4 mL) was added (2S)-2-amino-2-phenyl-ethanol (176.01 mg, 1.28 mmol, 2 eq). The mixture was stirred at 140° C. for 12 h. TLC (PE/EtOAc=3/1, $R_f$=0.35) showed starting material was consumed and one major new spot was detected. The mixture was diluted with H$_2$O (5 mL) and filtered. The filtered cake was collected to yield a residue which was purified by preparative TLC (PE/EtOAc=3/1, TLC: PE/EtOAc=3/1, $R_f$=0.35) to yield 3-bromo-4-[[(1S)-2-hydroxy-1-phenyl-ethyl]amino]-N-methyl-benzenesulfonamide (60 mg, 132.37 μmol, 20.6% yield, 85.0% purity) as a yellow solid. $^1$H NMR (500 MHz, DMSO-d$_6$) δ ppm 7.77 (d, J=2.0 Hz, 1H), 7.40-7.32 (m, 5H), 7.27-7.23 (m, 1H), 7.19-7.12 (m, 1H), 6.52 (d, J=9.0 Hz, 1H), 6.02 (d, J=6.0 Hz, 1H), 5.32 (t, J=5.5 Hz, 1H), 4.65-4.57 (m, 1H), 3.79 (td, J=4.5, 11.0 Hz, 1H), 3.65 (td, J=6.5, 11.0 Hz, 1H), 2.32 (d, J=5.0 Hz, 3H).

Step 2: 4-[[(1S)-2-Hydroxy-1-phenyl-ethyl]amino]-N-methyl-3-(1-methylimidazol-4-yl)benzenesulfonamide

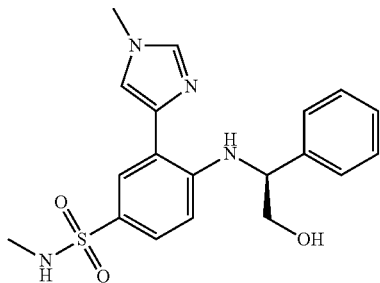 [SMILES: CNS(=O)(=O)c1ccc(N[C@H](CO)c2ccccc2)c(-c2cn(C)cn2)c1]

To a solution of 3-bromo-4-[[(1S)-2-hydroxy-1-phenyl-ethyl]amino]-N-methyl-benzenesulfonamide (60 mg, 132.37 μmol, 1 eq) in DMF (1 mL) was added tributyl-(1-methylimidazol-4-yl)stannane (100.47 mg, 264.75 μmol, 2 eq) and Pd(PPh$_3$)$_4$ (30.59 mg, 26.47 μmol, 0.2 eq) under N$_2$ atmosphere. The mixture was stirred under N$_2$ atmosphere at 100° C. for 12 h. The reaction mixture was concentrated to yield a residue which was purified by preparative HPLC (column: Phenomenex Synergi C18 150*30 mm*4 μm; mobile phase: [water (0.1% TFA)-ACN]; B %: 15%-35%, 9 min). The desired fraction was basified with sat. aq. NaHCO$_3$ (adjusted pH to 9) and extracted with EtOAc (20 mL×3). The combine organic layers were dried over anhydrous Na$_2$SO$_4$, filtered and concentrated to yield a residue which was dissolved in MeCN (5 mL) and H$_2$O (10 mL) and lyophilized to yield 4-[[(1S)-2-hydroxy-1-phenyl-ethyl]amino]-N-methyl-3-(1-methylimidazol-4-yl)benzenesulfonamide (12.44 mg, 30.57 μmol, 23.1% yield, 95.0% purity, $[\alpha]^{17.7}_D$=−150.129 (MeOH, c=0.021 g/100 mL) as a white solid. $^1$H NMR (500 MHz, CD$_3$OD) δ ppm 7.79 (d, J=2.0 Hz, 1H), 7.75 (s, 1H), 7.48 (d, J=1.0 Hz, 1H), 7.40 (d, J=7.5 Hz, 2H), 7.35-7.29 (m, 3H), 7.26-7.21 (m, 1H), 6.50 (d, J=9.0 Hz, 1H), 4.63 (dd, J=4.5, 7.2 Hz, 1H), 3.86 (dd, J=4.5, 11.3 Hz, 1H), 3.83 (s, 3H), 3.75 (dd, J=7.5, 11.3 Hz, 1H), 2.45 (s, 3H); ES-LCMS m/z 387.0 [M+H]$^+$.

I-41

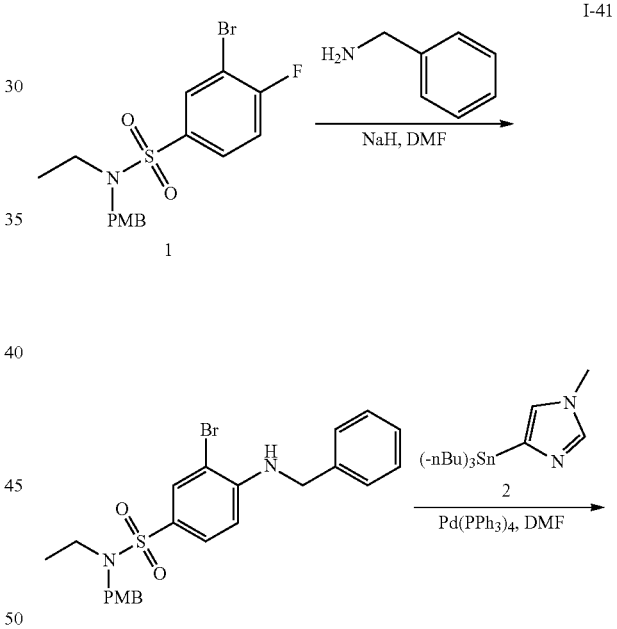

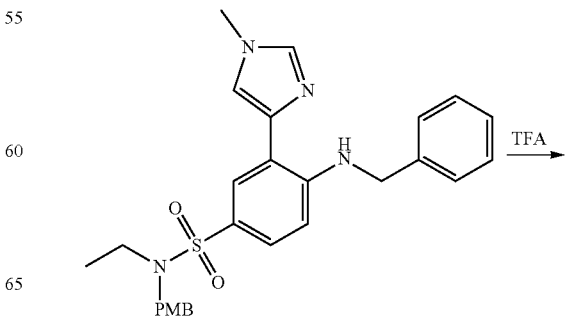

-continued

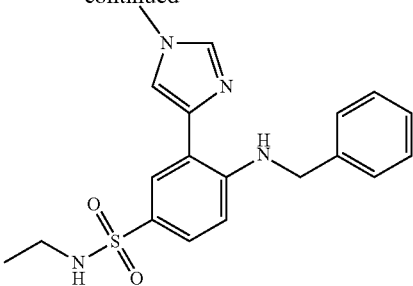

Step 1: 4-(Benzylamino)-3-bromo-N-ethyl-N-[(4-methoxyphenyl)methyl]benzenesulfonamide

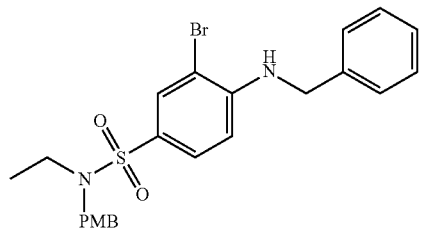

To a solution of 3-bromo-N-ethyl-4-fluoro-N-[(4-methoxyphenyl)methyl]benzenesulfonamide (520 mg, 1.23 mmol, 1 eq) in DMSO (15 mL) was added phenylmethanamine (263.17 mg, 2.46 mmol, 267.72 μL, 2 eq). The mixture was stirred at 140° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.25) to yield 4-(benzylamino)-3-bromo-N-ethyl-N-[(4-methoxyphenyl)methyl]benzenesulfonamide (425 mg, 785.87 μmol, 64.0% yield, 90.5% purity) as white oil. $^1$H NMR (400 MHz, CDCl$_3$) δ ppm 7.90 (d, J=2.2 Hz, 1H), 7.59 (dd, J=2.0, 8.6 Hz, 1H), 7.42-7.31 (m, 5H), 7.22 (d, J=8.6 Hz, 2H), 6.85 (d, J=8.6 Hz, 2H), 6.62 (d, J=8.8 Hz, 1H), 4.48 (d, J=5.6 Hz, 2H), 4.26-4.24 (m, 1H), 4.25 (s, 1H), 3.81 (s, 3H), 3.15 (q, J=7.1 Hz, 2H), 0.95 (t, J=7.1 Hz, 3H); ES-LCMS m/z 489.1, 491.1 [M+H]$^+$.

Step 2: 4-(Benzylamino)-N-ethyl-N-[(4-methoxyphenyl)methyl]-3-(1-methylimidazol-4-yl)benzenesulfonamide

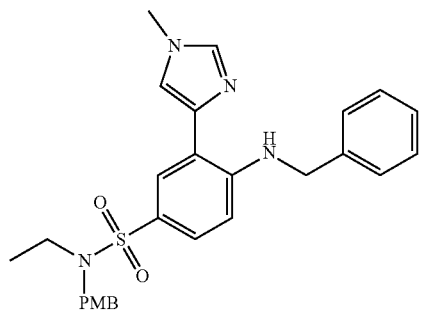

A mixture of 4-(benzylamino)-3-bromo-N-ethyl-N-[(4-methoxyphenyl)methyl]benzenesulfonamide (200 mg, 369.82 μmol, 1 eq), tributyl-(1-methylimidazol-4-yl)stannane (421.90 mg, 1.11 mmol, 3 eq), Pd(PPh$_3$)$_4$ (42.74 mg, 36.98 μmol, 0.1 eq) in DMF (5 mL) and purged with N$_2$ for 3 times and the mixture was stirred under N$_2$ atmosphere at 130° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, R$_f$=0.50) to yield 4-(benzylamino)-N-ethyl-N-[(4-methoxyphenyl)methyl]-3-(1-methylimidazol-4-yl)benzenesulfonamide (175 mg, 337.43 μmol, 91.2% yield, 94.6% purity) as a white solid. $^1$H NMR (400 MHz, CDCl$_3$) δ ppm 9.04 (t, J=5.5 Hz, 1H), 7.82 (d, J=2.2 Hz, 1H), 7.52-7.46 (m, 2H), 7.42-7.32 (m, 4H), 7.29 (s, 1H), 7.26-7.24 (m, 2H), 7.22 (s, 1H), 6.84 (d, J=8.8 Hz, 2H), 6.63 (d, J=8.8 Hz, 1H), 4.55 (d, J=5.6 Hz, 2H), 4.24 (s, 2H), 3.78 (d, J=10.5 Hz, 6H), 3.13 (q, J=7.2 Hz, 2H), 0.95-0.91 (m, 3H); ES-LCMS m/z 491.3 [M+H]$^+$.

Step 3: 4-(Benzylamino)-N-ethyl-3-(1-methylimidazol-4-yl)benzenesulfonamide

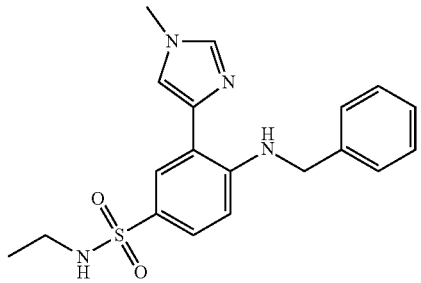 [SMILES: CCNS(=O)(=O)c1ccc(NCc2ccccc2)c(-c2cn(C)cn2)c1]

To a solution of 4-(benzylamino)-N-ethyl-N-[(4-methoxyphenyl)methyl]-3-(1-methylimidazol-4-yl)benzenesulfonamide (175 mg, 337.43 μmol, 1 eq) in DCM (10 mL) was added TFA (1.54 g, 13.51 mmol, 1 mL, 40.03 eq). The mixture was stirred at 25° C. for 12 h. The mixture was quenched with sat. aq. NaOH (50 mL) and extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 35%-65%, 10 min). The desired fraction was lyophilized to yield 4-(benzylamino)-N-ethyl-3-(1-methylimidazol-4-yl)benzenesulfonamide (74.92 mg, 202.23 μmol, 59.9% yield, 100.0% purity) as a white solid. $^1$H NMR (400 MHz, CDCl$_3$) δ ppm 9.08 (t, J=5.4 Hz, 1H), 7.86 (d, J=2.4 Hz, 1H), 7.53-7.45 (m, 2H), 7.40-7.32 (m, 4H), 7.28 (d, J=1.2 Hz, 2H), 6.62 (d, J=8.8 Hz, 1H), 4.54 (d, J=5.6 Hz, 2H), 4.12 (t, J=6.1 Hz, 1H), 3.76 (s, 3H), 3.02-2.93 (m, 2H), 1.09 (t, J=7.2 Hz, 3H); ES-LCMS m/z 371.3 [M+H]$^+$.

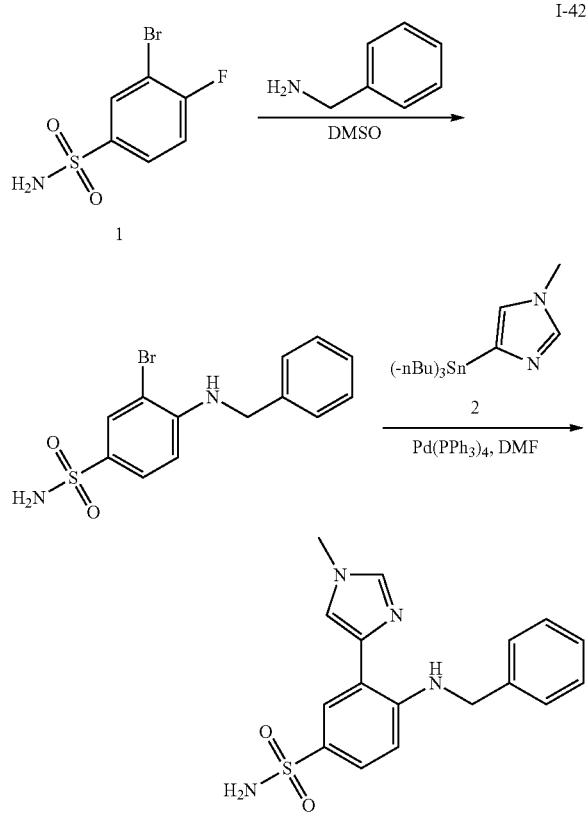

Step 1:
4-(Benzylamino)-3-bromo-benzenesulfonamide

To a solution of 3-bromo-4-fluoro-benzenesulfonamide (100 mg, 373.90 μmol, 1 eq) in DMSO (5 mL) was added phenylmethanamine (92.15 mg, 859.98 μmol, 93.74 μL, 2.3 eq). The mixture was stirred under $N_2$ atmosphere at 140° C. for 6 h. The mixture was diluted with water (80 mL) and extracted with EtOAc (50 mL×3). The combined organic layers were washed with brine (50 mL), dried over $Na_2SO_4$, filtered and concentrated to yield a residue which was purified by flash silica gel chromatography (From PE/EtOAc=1/0 to 5/1, $R_f$=0.44) to yield 4-(benzylamino)-3-bromo-benzenesulfonamide (100 mg, 217.16 μmol, 58.1% yield, 74.1% purity) as a yellow solid. $^1$H NMR (400 MHz, $CDCl_3$) δ ppm 8.01 (d, J=2.0 Hz, 1H), 7.67 (dd, J=1.8, 8.8 Hz, 1H), 7.41-7.36 (m, 2H), 7.36-7.29 (m, 3H), 6.62 (d, J=8.6 Hz, 1H), 4.70 (s, 2H), 4.49 (d, J=5.9 Hz, 2H); ES-LCMS m/z 340.8, 342.8 [M+H]$^+$.

Step 2: 4-(Benzylamino)-3-(1-methylimidazol-4-yl)benzenesulfonamide

To a solution of 4-(benzylamino)-3-bromo-benzenesulfonamide (100 mg, 217.16 μmol, 1 eq) in DMF (4 mL) were added tributyl-(1-methylimidazol-4-yl)stannane (164.82 mg, 434.32 μmol, 2 eq) and $Pd(PPh_3)_4$ (20.08 mg, 17.37 μmol, 0.08 eq). The mixture was stirred under $N_2$ atmosphere at 130° C. for 12 h. The mixture was added sat. aq. KF (80 mL) and stirred for 1 h. The mixture was extracted with EtOAc (50 mL×3). The combined organic layers were washed with brine (50 mL), dried over $Na_2SO_4$, filtered and concentrated to yield a residue which was purified by preparative HPLC (column: Agela DuraShell C18 150*25 mm*5 μm; mobile phase: [water (0.04% $NH_3 \cdot H_2O$+10 mM $NH_4HCO_3$)-ACN]; B %: 32%-47%, 14 min) to yield 4-(benzylamino)-3-(1-methylimidazol-4-yl)benzenesulfonamide (24.52 mg, 69.75 μmol, 32.1% yield, 97.4% purity) as a white solid. $^1$H NMR (400 MHz, $CDCl_3$) δ ppm 9.16 (s, 1H), 7.93 (d, J=2.3 Hz, 1H), 7.56 (dd, J=2.3, 9.0 Hz, 1H), 7.47 (s, 1H), 7.37-7.34 (m, 4H), 7.29-7.27 (m, 2H), 6.61 (d, J=8.6 Hz, 1H), 4.60 (s, 2H), 4.55 (d, J=5.5 Hz, 2H), 3.77 (s, 3H); ES-LCMS m/z 343.2 [M+H]$^+$.

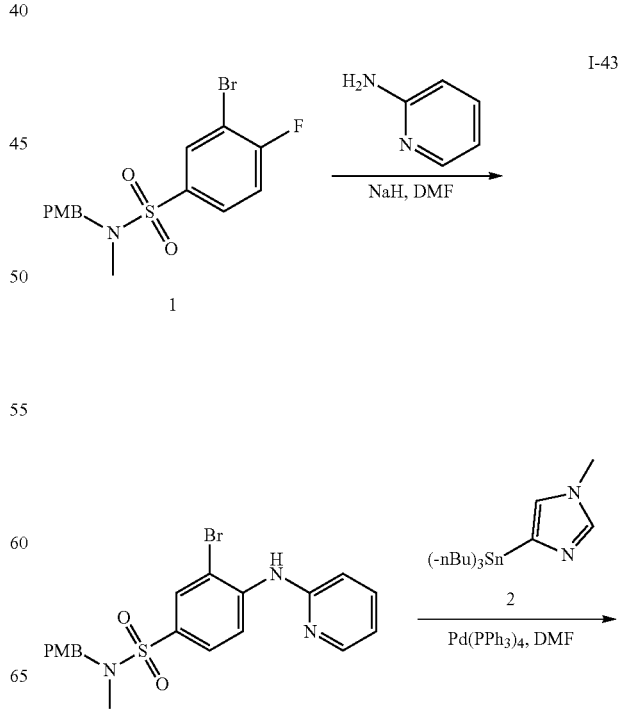

-continued

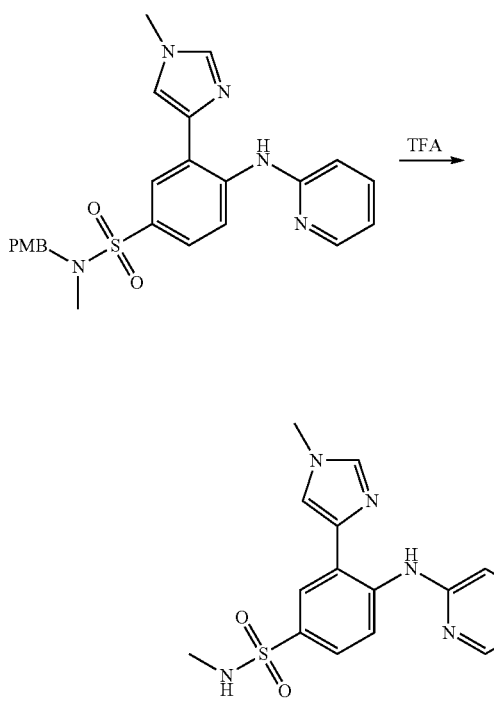

Step 1: 3-Bromo-N-[(4-methoxyphenyl)methyl]-N-methyl-4-(2-pyridylamino)benzenesulfonamide

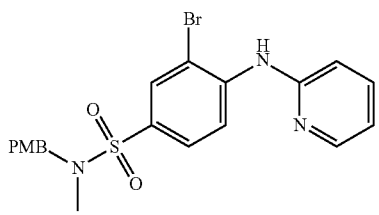

To a solution of pyridin-2-amine (163.62 mg, 1.74 mmol, 1.5 eq) in DMF (12 mL) was added NaH (139.07 mg, 3.48 mmol, 60% purity, 3 eq) under N₂ atmosphere. The mixture was stirred under N₂ atmosphere at 0° C. for 1 h. 3-Bromo-4-fluoro-N-[(4-methoxyphenyl)methyl]-N-methyl-benzenesulfonamide (500 mg, 1.16 mmol, 1 eq) was added and the mixture was stirred at 25° C. for 5 h. The mixture was concentrated and water (80 mL) was added. The mixture was extracted with EtOAc (50 mL×3). The combined organic layers were washed with brine (50 mL), dried over Na₂SO₄, filtered and concentrated to yield a residue which was purified by flash silica gel chromatography (From PE/EtOAc=1/0 to 5/1, R$_f$=0.22) to yield 3-bromo-N-[(4-methoxyphenyl)methyl]-N-methyl-4-(2-pyridylamino)benzenesulfonamide (300 mg, 555.41 µmol, 47.9% yield, 85.6% purity) as a white solid. $^1$H NMR (400 MHz, DMSO-d$_6$) δ ppm 8.55 (s, 1H), 8.36 (d, J=8.6 Hz, 1H), 8.21 (d, J=3.5 Hz, 1H), 7.93 (d, J=2.3 Hz, 1H), 7.76-7.66 (m, 2H), 7.26-7.19 (m, 3H), 6.96-6.88 (m, 3H), 4.06 (s, 2H), 3.72 (s, 3H), 2.51 (s, 3H); ES-LCMS m/z 462.1, 464.1 [M+H]⁺.

Step 2: N-[(4-Methoxyphenyl)methyl]-N-methyl-3-(1-methylimidazol-4-yl)-4-(2-pyridylamino)benzenesulfonamide

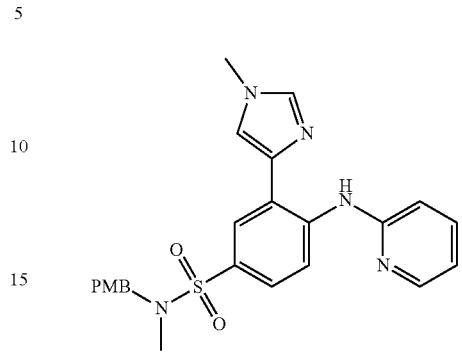

To a solution of 3-bromo-N-[(4-methoxyphenyl)methyl]-N-methyl-4-(2-pyridylamino)benzenesulfonamide (300 mg, 555.41 µmol, 1 eq) in DMF (8 mL) were added tributyl-(1-methylimidazol-4-yl)stannane (421.55 mg, 1.11 mmol, 2 eq) and Pd(PPh₃)₄ (64.18 mg, 55.54 µmol, 0.1 eq). The mixture was stirred under N₂ atmosphere at 130° C. for 12 h. TLC (PE/EtOAc=5/1, R$_f$=0.27) indicated starting material was consumed completely and one new spot formed. The mixture was added sat. aq. KF (80 mL) stirred for 1 h. The mixture was extracted with EtOAc (50 mL×3). The combined organic layers were washed with brine (50 mL), dried over Na₂SO₄, filtered and concentrated to yield a residue which was purified by flash silica gel chromatography (From PE/EtOAc=1/0 to 5/1, R$_f$=0.27) to yield N-[(4-methoxyphenyl)methyl]-N-methyl-3-(1-methylimidazol-4-yl)-4-(2-pyridylamino)benzenesulfonamide (500 mg, 539.31 µmol, 97.1% yield, 50.0% purity) as colorless oil. $^1$H NMR (400 MHz, CDCl₃) δ ppm 11.70 (s, 1H), 8.84 (d, J=9.0 Hz, 1H), 8.33-8.29 (m, 1H), 7.91 (d, J=2.3 Hz, 1H), 7.77-7.73 (m, 1H), 7.59-7.53 (m, 3H), 7.50-7.43 (m, 3H), 7.33 (d, J=1.2 Hz, 1H), 6.93 (d, J=8.6 Hz, 1H), 6.84-6.80 (m, 1H), 4.07 (s, 2H), 3.80 (s, 6H), 2.56 (s, 3H); ES-LCMS m/z 464.2 [M+H]⁺.

Step 3: N-Methyl-3-(1-methylimidazol-4-yl)-4-(2-pyridylamino)benzenesulfonamide

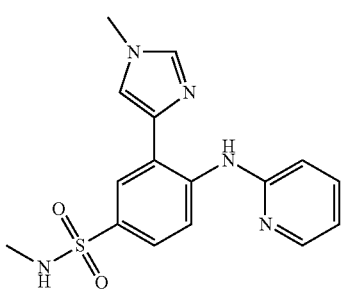 [SMILES: CNS(=O)(=O)c1ccc(Nc2ccccn2)c(-c2cn(C)cn2)c1]

To a solution of N-[(4-methoxyphenyl)methyl]-N-methyl-3-(1-methylimidazol-4-yl)-4-(2-pyridylamino)benzenesulfonamide (500 mg, 539.31 µmol, 1 eq) in DCM (10 mL) was added TFA (4.98 mL) under N₂ atmosphere at 0° C. The mixture was stirred at 25° C. for 4 h. The reaction mixture was concentrated under reduced pressure to yield a residue which was purified by preparative HPLC (column:

Agela DuraShell C18 150*25 mm*5 um; mobile phase: [water (0.04% NH$_3$.H$_2$O+10 mM NH$_4$HCO$_3$)-ACN]; B %: 26%-56%, 10 min) to yield N-methyl-3-(1-methylimidazol-4-yl)-4-(2-pyridylamino)benzenesulfonamide (18.65 mg, 53.66 μmol, 9.9% yield, 98.8% purity) as a white solid. $^1$H NMR (400 MHz, CDCl$_3$) δ ppm 11.68 (s, 1H), 8.79 (d, J=8.6 Hz, 1H), 8.31 (d, J=4.3 Hz, 1H), 7.97 (s, 1H), 7.67 (d, J=8.6 Hz, 1H), 7.6-7.52 (m, 2H), 7.33 (s, 1H), 6.92 (d, J=8.2 Hz, 1H), 6.82 (t, J=6.3 Hz, 1H), 4.33 (d, J=5.9 Hz, 1H), 3.78 (s, 3H), 2.66 (d, J=5.5 Hz, 3H); ES-LCMS m/z 344.1 [M+H]$^+$.

I-44

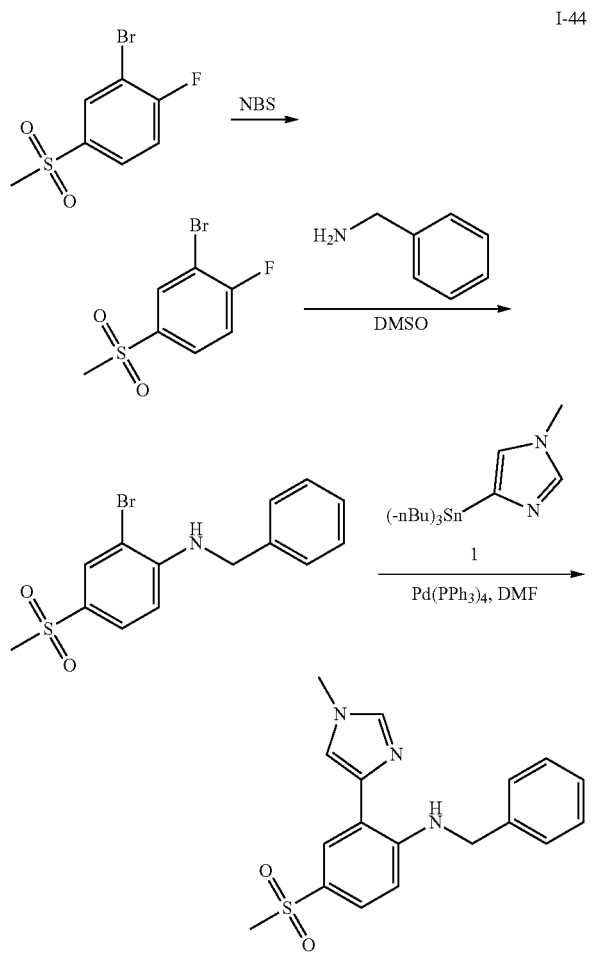

Step 1: 2-Bromo-1-fluoro-4-methylsulfonyl-benzene

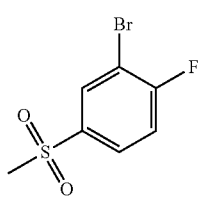

To a solution of 1-fluoro-4-methylsulfonyl-benzene (500 mg, 2.87 mmol, 1 eq) in H$_2$SO$_4$ (5 mL) was added NBS (766.32 mg, 4.31 mmol, 1.5 eq) in portions at 0° C. The mixture was stirred at 15° C. for 16 h. The mixture was poured into ice water (50 mL) and the precipitated solid was filtered, collected and dried to yield 2-bromo-1-fluoro-4-methylsulfonyl-benzene (720 mg, 2.70 mmol, 94.2% yield, 95.0% purity) as a white solid, which was used in the next step without further purification. $^1$H NMR (500 MHz, DMSO-d$_6$) δ ppm 8.35-8.20 (m, 1H), 8.02-7.99 (m, 1H), 7.68 (t, J=8.6 Hz, 1H), 3.31 (s, 3H).

Step 2: N-Benzyl-2-bromo-4-methylsulfonyl-aniline

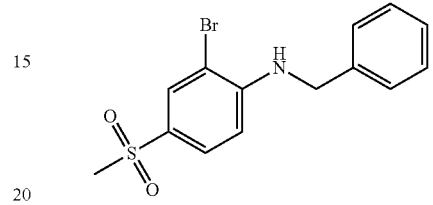

A mixture of 2-bromo-1-fluoro-4-methylsulfonyl-benzene (200 mg, 750.73 μmol, 1 eq) and phenylmethanamine (160.88 mg, 1.50 mmol, 163.67 μL, 2 eq) in DMSO (3 mL) was stirred at 140° C. for 5 h. TLC (PE/EtOAc=1/1, R$_f$=0.56) indicated the starting material was consumed completely and one new spot formed. The reaction mixture was poured into water (20 mL) and extracted with EtOAc (20 mL×2). The combined organic layers were washed with brine (20 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=3/1, R$_f$=0.56) to yield N-benzyl-2-bromo-4-methylsulfonyl-aniline (195 mg, 573.13 μmol, 76.3% yield, 100.0% purity) as a white solid. $^1$H NMR (500 MHz, CDCl$_3$) δ ppm 8.00 (d, J=2.1 Hz, 1H), 7.66 (dd, J=2.1, 8.6 Hz, 1H), 7.41-7.36 (m, 2H), 7.35-7.31 (m, 3H), 6.64 (d, J=8.7 Hz, 1H), 5.35 (br s, 1H), 4.49 (d, J=5.5 Hz, 2H), 3.01 (s, 3H); ES-LCMS m/z 340.1, 342.1 [M+H]$^+$.

Step 3: N-Benzyl-2-(1-methylimidazol-4-yl)-4-methylsulfonyl-aniline

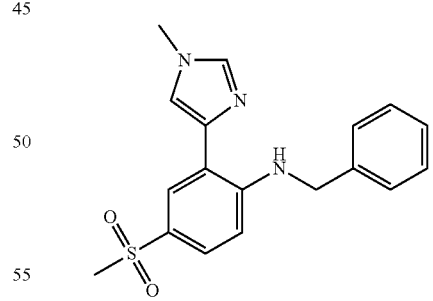

To a solution of N-benzyl-2-bromo-4-methylsulfonyl-aniline (165 mg, 484.96 μmol, 1 eq) and tributyl-(1-methylimidazol-4-yl)stannane (382.96 mg, 969.92 μmol, 2 eq) in DMF (10 mL) was added Pd(PPh$_3$)$_4$ (56.04 mg, 48.50 μmol, 0.1 eq) and the mixture was stirred under N$_2$ atmosphere at 130° C. for 3 h. TLC (PE/EtOAc=1/1, R$_f$=0.21) indicated the starting material was consumed completely and one new spot formed. The reaction mixture was quenched by 15% KF (15 mL), diluted with water (30 mL) and extracted with EtOAc (30 mL×2). The combined organic layers were washed with brine (20 mL), dried over Na$_2$SO$_4$, filtered and concentrated under reduced pressure to yield a residue which was purified by flash silica gel chromatography (from PE/EtOAc=1/1 to 0/1) and preparative HPLC (column: Agela DuraShell C18 150*25 mm*5 µm; mobile phase: [water (0.04% NH$_3$.H$_2$O+10 mM NH$_4$HCO$_3$)-ACN]; B %: 33%-63%, 10 min), followed by lyophilization to yield N-benzyl-2-(1-methylimidazol-4-yl)-4-methylsulfonyl-aniline (129.49 mg, 379.26 µmol, 78.2% yield, 100.0% purity) as a white solid. $^1$H NMR (400 MHz, CDCl$_3$) δ ppm 9.23 (br s, 1H), 7.89 (d, J=2.2 Hz, 1H), 7.54 (dd, J=2.2, 8.6 Hz, 1H), 7.46 (s, 1H), 7.40-7.29 (m, 5H), 7.28 (br s, 1H), 6.63 (d, J=8.8 Hz, 1H), 4.54 (d, J=4.4 Hz, 2H), 3.77 (s, 3H), 3.00 (s, 3H); ES-LCMS m/z 342.2 [M+H]$^+$.

I-45

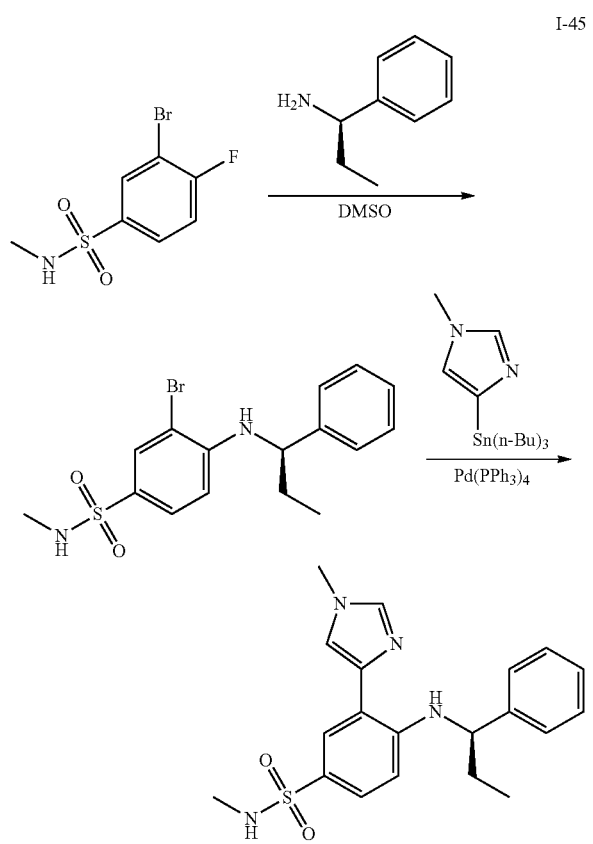

Step 1: 3-Bromo-N-methyl-4-[[(1R)-1-phenylpropyl]amino]benzenesulfonamide

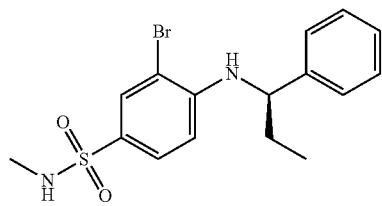 [SMILES: CC[C@@H](Nc1ccc(S(=O)(=O)NC)cc1Br)c1ccccc1]

To a solution of 3-bromo-4-fluoro-N-methyl-benzenesulfonamide (200 mg, 745.98 µmol, 1 eq) in DMSO (1 mL) was added (1R)-1-phenylpropan-1-amine (201.72 mg, 1.49 mmol, 214.14 µL, 2 eq). The mixture was stirred at 140° C. for 12 h. The mixture was diluted with H$_2$O (5 mL) and filtered. The filtered cake was collected to yield a residue which was purified by preparative TLC (PE/EtOAc=3/1, TLC: PE/EtOAc=3/1, R$_f$=0.55) to yield 3-bromo-N-methyl-4-[[(1R)-1-phenylpropyl]amino]benzenesulfonamide (210 mg, 438.30 µmol, 58.7% yield, 80.0% purity) as yellow oil. $^1$H NMR (500 MHz, DMSO-d$_6$) δ ppm 7.73 (d, J=2.0 Hz, 1H), 7.43-7.38 (m, 3H), 7.32 (t, J=7.5 Hz, 2H), 7.25-7.20 (m, 1H), 7.14 (q, J=5.0 Hz, 1H), 6.63 (d, J=9.0 Hz, 1H), 5.92 (d, J=7.5 Hz, 1H), 4.46 (q, J=7.5 Hz, 1H), 2.31 (d, J=5.0 Hz, 3H), 2.04-1.98 (m, 1H), 1.81 (q, J=7.0, 13.9 Hz, 1H), 0.91 (t, J=7.5 Hz, 3H); ES-LCMS m/z 765.1, 767.1 [2M+H]$^+$.

Step 2: N-Methyl-3-(1-methylimidazol-4-yl)-4-[[(1R)-1-phenylpropyl]amino]benzenesulfonamide

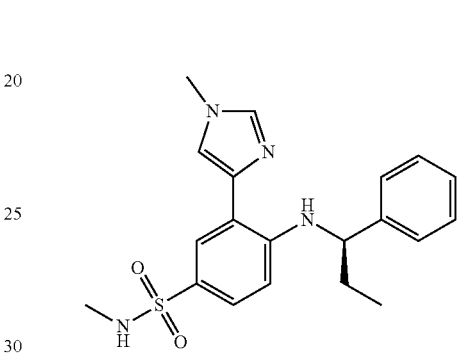

To a solution of 3-bromo-N-methyl-4-[[(1R)-1-phenylpropyl]amino]benzenesulfonamide (210 mg, 438.30 µmol, 1 eq) and tributyl-(1-methylimidazol-4-yl)stannane (346.11 mg, 876.59 µmol, 2 eq) in DMF (5 mL) was added Pd(PPh$_3$)$_4$ (50.65 mg, 43.83 µmol, 0.1 eq) under N$_2$ atmosphere. The mixture was stirred under N$_2$ atmosphere at 140° C. for 12 h. The reaction mixture was concentrated to yield a residue which was purified by preparative HPLC (column: Phenomenex Synergi C18 150*30 mm*4 µm; mobile phase: [water (0.1% TFA)-ACN]; B %: 27%-47%, 9 min). The desired fraction was basified with sat. aq. NaHCO$_3$ (adjusted pH to 9) and extracted with EtOAc (30 mL×3). The combined organic layers were dried over anhydrous Na$_2$SO$_4$, filtered and concentrated to yield a residue which was dissolved in MeCN (20 mL) and H$_2$O (40 mL) and lyophilized to yield N-methyl-3-(1-methylimidazol-4-yl)-4-[[(1R)-1-phenylpropyl]amino]benzenesulfonamide (97.37 mg, 253.24 µmol, 57.8% yield, 100.0% purity, [α]$^{25D}$=-119.014 (MeOH, c=0.093 g/100 mL) as a white solid. $^1$H NMR (500 MHz, DMSO-d$_6$) δ ppm 9.44 (d, J=6.7 Hz, 1H), 7.86 (s, 1H), 7.76 (d, J=2.0 Hz, 1H), 7.69 (s, 1H), 7.35-7.29 (m, 4H), 7.25-7.18 (m, 2H), 6.94 (q, J=4.8 Hz, 1H), 6.48 (d, J=8.9 Hz, 1H), 4.52 (q, J=6.4 Hz, 1H), 3.76 (s, 3H), 2.32 (d, J=5.0 Hz, 3H), 1.83 (q, J=7.1 Hz, 2H), 0.95 (t, J=7.3 Hz, 3H); ES-LCMS m/z 407.3 [M+Na]$^+$.

I-46

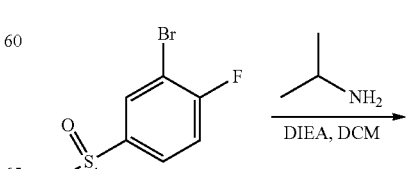

Step 2: 4-(Benzylamino)-3-bromo-N-isopropyl-benzenesulfonamide

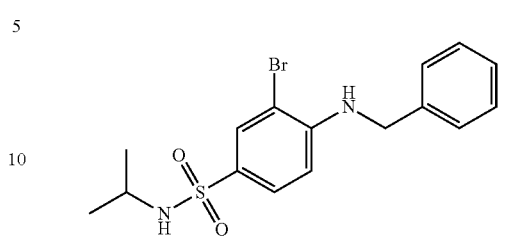

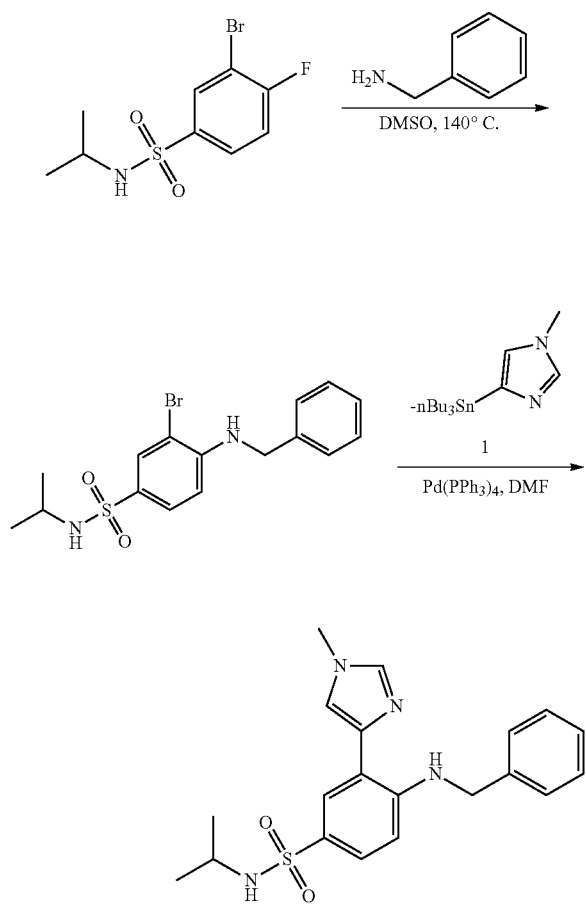

To a solution of 3-bromo-4-fluoro-N-isopropyl-benzenesulfonamide (200 mg, 654.92 μmol, 1 eq) in DMSO (15 mL) was added phenylmethanamine (140.35 mg, 1.31 mmol, 142.78 μL, 2 eq). The mixture was stirred at 140° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.43) to yield 4-(benzylamino)-3-bromo-N-isopropyl-benzenesulfonamide (220 mg, 514.78 μmol, 78.6% yield, 89.6% purity) as yellow oil. $^1$H NMR (500 MHz, $CD_3OD$) δ ppm 7.86 (d, J=2.1 Hz, 1H), 7.51 (dd, J=2.1, 8.7 Hz, 1H), 7.35-7.30 (m, 4H), 7.27-7.22 (m, 1H), 6.62 (d, J=8.7 Hz, 1H), 4.53 (d, J=5.5 Hz, 2H), 3.26 (td, J=6.6, 13.1 Hz, 1H), 1.00 (d, J=6.6 Hz, 6H); ES-LCMS m/z 385.0 $[M+H]^+$.

Step 3: 4-(Benzylamino)-N-isopropyl-3-(1-methylimidazol-4-yl) benzenesulfonamide

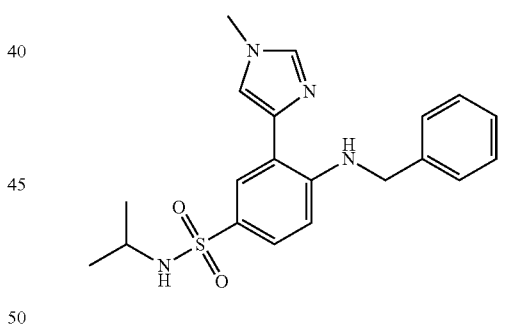

To a solution of 4-(benzylamino)-3-bromo-N-isopropyl-benzenesulfonamide (150 mg, 348.29 μmol, 1 eq) in DMF (5 mL) was added tributyl-(1-methylimidazol-4-yl)stannane (287.26 mg, 696.58 μmol, 2 eq) and $Pd(PPh_3)_4$ (20.12 mg, 17.41 μmol, 0.05 eq). The mixture was stirred under $N_2$ atmosphere at 130° C. for 2 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by preparative HPLC (column: Agela DuraShell C18 150*25 mm*5 μm; mobile phase: [water (0.04% $NH_3.H_2O$+10 mM $NH_4HCO_3$)-ACN]; B %: 44%-74%, 10 min), followed by lyophilization to yield 4-(benzylamino)-N-isopropyl-3-(1-methylimidazol-4-yl)benzenesulfonamide (47.35 mg, 123.15 μmol, 35.3% yield, 100.0% purity) as a white solid. $^1$H NMR (500 MHz, $CD_3OD$) δ ppm

Step 1: 3-Bromo-4-fluoro-N-isopropyl-benzenesulfonamide

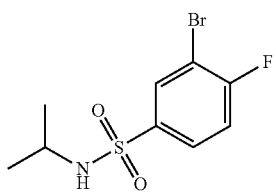

To a solution of 3-bromo-4-fluoro-benzenesulfonyl chloride (1.2 g, 3.51 mmol, 1 eq) in DCM (15 mL) was added DIEA (1.81 g, 14.04 mmol, 2.45 mL, 4 eq) and propan-2-amine (207.47 mg, 3.51 mmol, 301.56 μL, 1 eq). The mixture was stirred at 25° C. for 2 h. The reaction mixture was concentrated to yield a residue which was purified by flash silica gel chromatography (from PE/EtOAc=1/0 to 5/1, TLC: PE/EtOAc=3/1, $R_f$=0.56) to yield 3-bromo-4-fluoro-N-isopropyl-benzenesulfonamide (0.9 g, 2.95 mmol, 83.9% yield, 96.9% purity) as a yellow solid. $^1$H NMR (500 MHz, CDCl3) δ ppm 8.12 (dd, J=2.3, 6.3 Hz, 1H), 7.83 (ddd, J=2.3, 4.4, 8.5 Hz, 1H), 7.25 (d, J=8.5 Hz, 1H), 4.41 (d, J=6.7 Hz, 1H), 3.56-3.46 (m, 1H), 1.13 (d, J=6.6 Hz, 6H); ES-LCMS m/z 297.9 $[M+H]^+$.

7.83 (d, J=2.3 Hz, 1H), 7.66 (s, 1H), 7.48 (dd, J=2.1, 8.7 Hz, 1H), 7.44 (d, J=1.2 Hz, 1H), 7.39-7.36 (m, 2H), 7.31 (t, J=7.6 Hz, 2H), 7.26-7.22 (m, 1H), 6.67 (d, J=8.7 Hz, 1H), 4.49 (s, 2H), 3.79 (s, 3H), 1.01 (d, J=6.6 Hz, 6H); ES-LCMS m/z 385.1 [M+H]⁺.

I-47

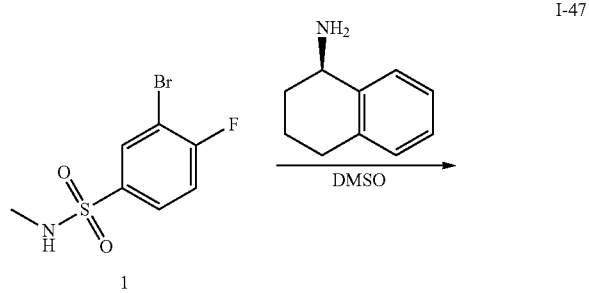

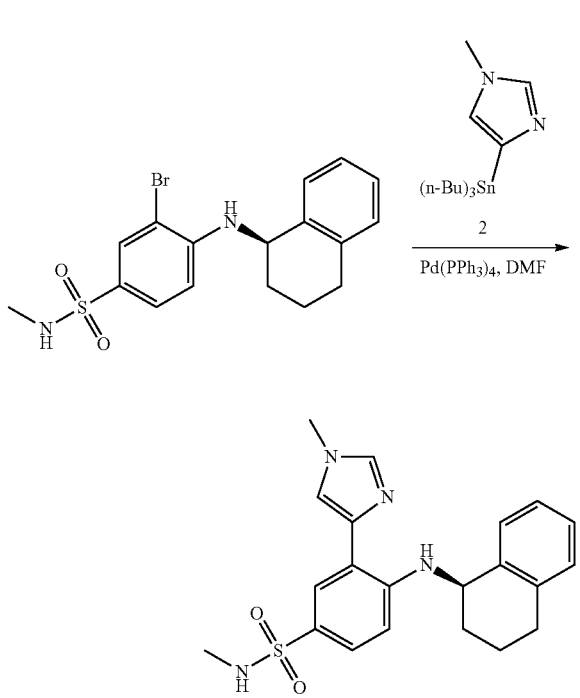

Step 1: 3-Bromo-N-methyl-4-[[(1R)-tetralin-1-yl]amino]benzenesulfonamide

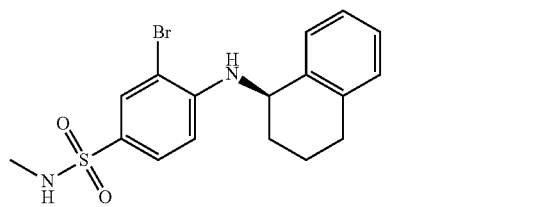 [SMILES: CNS(=O)(=O)c1ccc(N[C@@H]2CCCc3ccccc32)c(Br)c1]

To a solution of 3-bromo-4-fluoro-N-methyl-benzenesulfonamide (200 mg, 745.98 µmol, 1 eq) in DMSO (5 mL) was added (1R)-tetralin-1-amine (219.64 mg, 1.49 mmol, 2.0 eq). The mixture was stirred at 140° C. for 2 h. TLC (PE/EtOAc=3/1, $R_f$=0.6) showed that new point was formed and start material was consumed completely. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to yield a residue which was purified by flash silica gel chromatography (from PE/EtOAc=100/1 to 3/1, TLC: PE/EtOAc=3/1, $R_f$=0.6) to yield 3-bromo-N-methyl-4-[[(1R)-tetralin-1-yl]amino]benzenesulfonamide (200 mg, 303.56 µmol, 40.7% yield, 60.0% purity) as a white solid. ES-LCMS m/z 395.1, 397.1 [M+H]⁺.

Step 2: N-Methyl-3-(1-methylimidazol-4-yl)-4-[[(1R)-tetralin-1-yl]amino]benzenesulfonamide

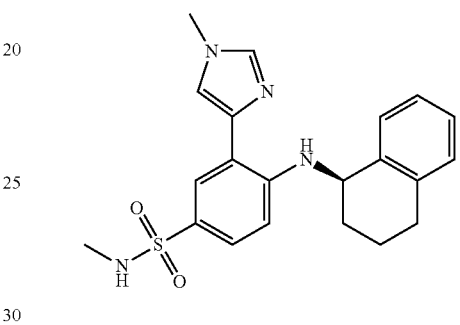

To a solution of 3-bromo-N-methyl-4-[[(1R)-tetralin-1-yl]amino]benzenesulfonamide (150 mg, 265.61 µmol, 1 eq) and tributyl-(1-methylimidazol-4-yl)stannane (98.58 mg, 265.61 µmol, 1 eq) in DMF (5 mL) was added Pd(PPh₃)₄ (30.69 mg, 26.56 µmol, 0.1 eq) under N₂ atmosphere. The mixture was stirred under N₂ atmosphere at 100° C. for 4 h. The reaction mixture was quenched by addition of H₂O (20 mL) and extracted with EtOAc (30 mL×3). The combined organic layers were washed with brine (30 mL), dried over Na₂SO₄, filtered and concentrated under reduced pressure to yield a residue which was purified by preparative HPLC (column: Welch Xtimate C18 150*25 mm*5 µm; mobile phase: [water (10 mM NH₄HCO₃)-ACN]; B %: 42%-72%, 10 min) and lyophilized to yield N-methyl-3-(1-methylimidazol-4-yl)-4-[[(1R)-tetralin-1-yl]amino]benzenesulfonamide (56.15 mg, 141.61 µmol, 53.3% yield, 100.0% purity) as a white solid. ¹H NMR (400 MHz, DMSO-d₆) δ ppm 9.08 (d, J=8.3 Hz, 1H), 7.78 (d, J=2.2 Hz, 1H), 7.64 (d, J=9.0 Hz, 2H), 7.44 (dd, J=2.0, 8.8 Hz, 1H), 7.27 (d, J=7.6 Hz, 1H), 7.20-7.11 (m, 3H), 7.05-6.98 (m, 2H), 4.85 (d, J=7.3 Hz, 1H), 3.69 (s, 3H), 2.87-2.69 (m, 2H), 2.39 (d, J=5.1 Hz, 3H), 2.01 (d, J=4.9 Hz, 1H), 1.81 (s, 3H); ES-LCMS m/z 397.2 [M+H]⁺.

I-48

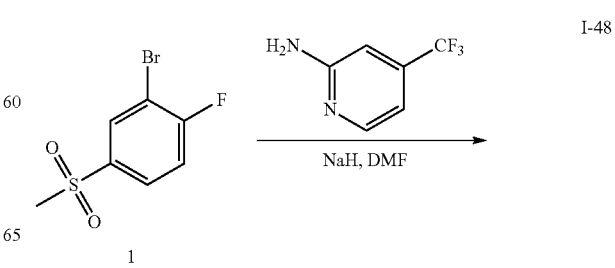

Step 2: N-[2-(1-Methylimidazol-4-yl)-4-methylsulfonyl-phenyl]-4-(trifluoromethyl)pyridin-2-amine

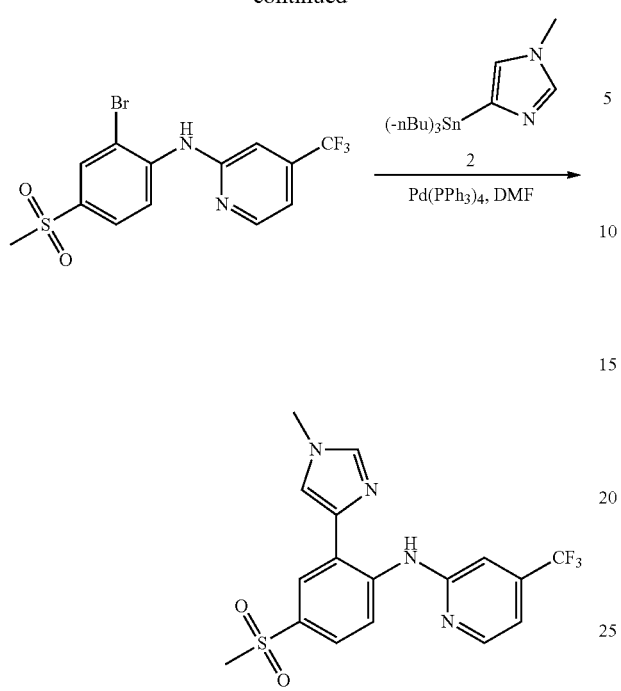

To a solution of N-(2-bromo-4-methylsulfonyl-phenyl)-4-(trifluoromethyl)pyridin-2-amine (210 mg, 531.38 µmol, 1 eq) and tributyl-(1-methylimidazol-4-yl)stannane (419.62 mg, 1.06 mmol, 2 eq) in DMF (12 mL) was added Pd(PPh$_3$)$_4$ (61.40 mg, 53.14 µmol, 0.1 eq) and the mixture was stirred under N$_2$ atmosphere at 130° C. for 3 h. The reaction mixture was quenched by 15% KF (15 mL), treated with water (20 mL) and extracted with EtOAc (20 mL×2). The combined organic layers were washed with brine (20 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, R$_f$=0.32) and preparative HPLC (column: Agela DuraShell C18 150*25 mm*5 um; mobile phase: [water (0.04% NH$_3$.H$_2$O+10 mM NH$_4$HCO$_3$)-ACN]; B %: 39%-69%, 10 min), followed by lyophilization to yield N-[2-(1-methylimidazol-4-yl)-4-methylsulfonyl-phenyl]-4-(trifluoromethyl)pyridin-2-amine (57.7 mg, 145.57 µmol, 27.4% yield, 100.0% purity) as a white solid. $^1$H NMR (500 MHz, CDCl$_3$) δ ppm 12.25 (s, 1H), 8.91 (d, J=9.0 Hz, 1H), 8.43 (d, J=5.2 Hz, 1H), 8.04 (d, J=2.1 Hz, 1H), 7.76 (dd, J=2.2, 8.9 Hz, 1H), 7.60 (s, 1H), 7.39 (d, J=1.1 Hz, 1H), 7.08 (s, 1H), 6.99 (d, J=5.2 Hz, 1H), 3.81 (s, 3H), 3.06 (s, 3H); ES-LCMS m/z 397.1 [M+H]$^+$.

Step 1: N-(2-Bromo-4-methylsulfonyl-phenyl)-4-(trifluoromethyl)pyridin-2-amine

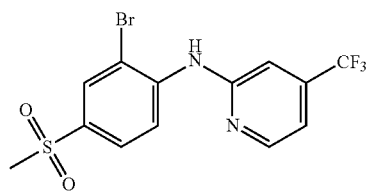 [SMILES: CS(=O)(=O)c1ccc(Nc2cc(C(F)(F)F)ccn2)c(Br)c1]

To a solution of 4-(trifluoromethyl)pyridin-2-amine (121.70 mg, 750.73 µmol, 1.0 eq) in DMF (10 mL) was added NaH (90.08 mg, 2.25 mmol, 60% purity, 3.0 eq) at 0° C. and the mixture was stirred for 30 min. 2-Bromo-1-fluoro-4-methylsulfonyl-benzene (200 mg, 750.73 µmol, 1.0 eq) was added and the mixture was stirred at 15° C. for 2 h. TLC (PE/EtOAc=1/1, R$_f$=0.75) indicated the starting material was consumed completely and one new spot formed. The reaction mixture was poured into water (30 mL) and extracted with EtOAc (20 mL×2). The combined organic layers were washed with brine (30 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=1/1, R$_f$=0.75) to yield N-(2-bromo-4-methylsulfonyl-phenyl)-4-(trifluoromethyl)pyridin-2-amine (230 mg, 552.89 µmol, 73.7% yield, 95.0% purity) as a white solid. $^1$H NMR (500 MHz, CDCl$_3$) δ ppm 8.66 (d, J=8.9 Hz, 1H), 8.50 (d, J=5.2 Hz, 1H), 8.15 (d, J=2.1 Hz, 1H), 7.87 (dd, J=1.9, 8.8 Hz, 1H), 7.40 (s, 1H), 7.15 (d, J=5.2 Hz, 1H), 7.11 (s, 1H), 3.07 (s, 3H); ES-LCMS m/z 395.0, 397.0 [M+H]$^+$.

I-49

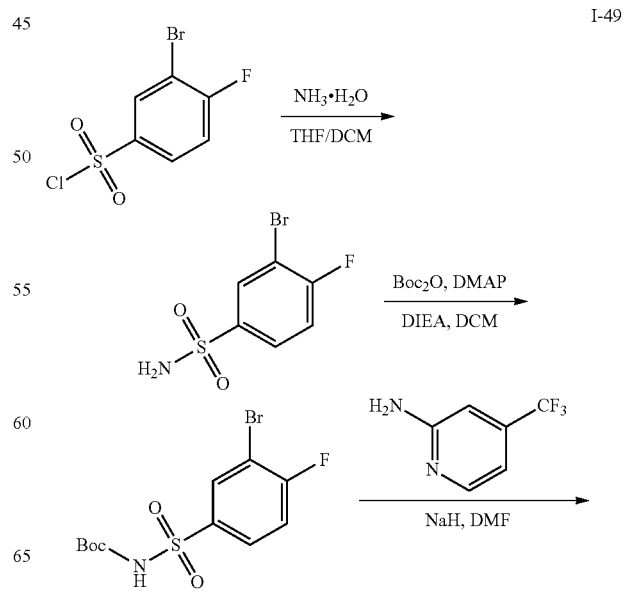

-continued

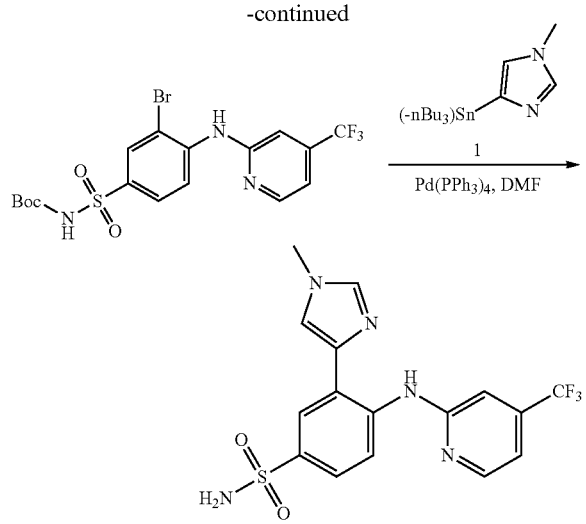

Step 1: 3-Bromo-4-fluoro-benzenesulfonamide

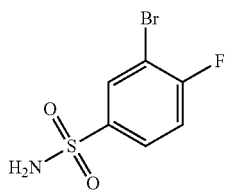 [SMILES: NS(=O)(=O)c1ccc(F)c(Br)c1]

To a solution of 3-bromo-4-fluoro-benzenesulfonyl chloride (1.0 g, 3.11 mmol, 1 eq) in THF (30 mL) and DCM (10 mL) was added NH₃·H₂O (1.17 g, 9.32 mmol, 1.28 mL, 28%, 3 eq) dropwise at 0° C. and the mixture was stirred at 0° C. for 2 h. TLC (PE/EtOAc=3/1, $R_f$=0.42) indicated the starting material was consumed completely and one new spot formed. The solvent was concentrated, diluted with water (30 mL) and extracted with EtOAc (30 mL×2). The organic phases were washed with brine (20 mL), dried over anhydrous Na₂SO₄, filtered and concentrated to yield 3-bromo-4-fluoro-benzenesulfonamide (785 mg, 2.94 mmol, 94.4% yield, 95.0% purity) as a yellow solid, which was used in next step without further purification. ¹H NMR (500 MHz, DMSO-d₆) δ ppm 8.12 (dd, J=2.3, 6.4 Hz, 1H), 7.89-7.85 (m, 1H), 7.60 (t, J=8.6 Hz, 1H), 7.54 (s, 2H).

Step 2: tert-Butyl N-(3-bromo-4-fluoro-phenyl)sulfonylcarbamate

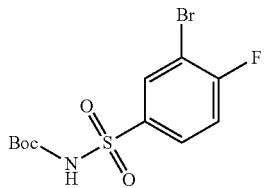

To a solution of 3-bromo-4-fluoro-benzenesulfonamide (400 mg, 1.50 mmol, 1 eq) in DCM (15 mL) were added DMAP (18.27 mg, 149.56 μmol, 0.1 eq), Et₃N (227.01 mg, 2.24 mmol, 312.25 μL, 1.5 eq) and Boc₂O (391.70 mg, 1.79 mmol, 412.31 μL, 1.2 eq). The mixture was stirred at 15° C. for 2 h. TLC (PE/EtOAc=3/1, $R_f$=0.78) indicated the starting material was consumed completely and one new spot formed. The mixture was diluted with water (50 mL) and extracted with DCM (30 mL×2). The combined organic phases were washed with brine (30 mL), dried over anhydrous Na₂SO₄, filtered and concentrated to yield a residue which was purified by flash silica gel chromatography (from PE/EtOAc=1/0 to 3/1, TLC: PE/EtOAc=3/1, $R_f$=0.78) to yield tert-butyl N-(3-bromo-4-fluoro-phenyl)sulfonylcarbamate (71.0 mg, 200.46 μmol, 13.4% yield, 100.0% purity) as light yellow gum. ¹H NMR (500 MHz, CDCl₃) δ ppm 8.33 (dd, J=2.3, 6.3 Hz, 1H), 8.00-7.97 (m, 1H), 7.22 (t, J=8.3 Hz, 1H), 1.47 (s, 9H).

Step 3: tert-Butyl N-[3-bromo-4-[[4-(trifluoromethyl)-2-pyridyl]amino]phenyl]sulfonylcarbamate

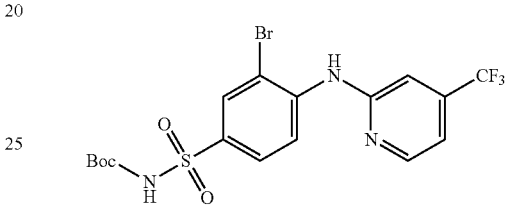

To a solution of 4-(trifluoromethyl)pyridin-2-amine (32.04 mg, 197.63 μmol, 1 eq) in DMF (5 mL) was added NaH (23.71 mg, 592.90 μmol, 60% purity, 3 eq) at 0° C. and the mixture was stirred for 30 min. tert-Butyl N-(3-bromo-4-fluoro-phenyl)sulfonylcarbamate (70 mg, 197.63 μmol, 1 eq) was added and the mixture was stirred at 15° C. for 2 h. TLC (PE/EtOAc=3/1, $R_f$=0.78) indicated the starting material was consumed completely and one new spot formed. The reaction mixture was poured into water (20 mL) slowly and extracted with EtOAc (20 mL×2). The combined organic layers were washed with brine (20 mL), dried over Na₂SO₄, filtered and concentrated under reduced pressure to yield a residue which was purified by preparative TLC (PE/EtOAc=3/1, $R_f$=0.78) to yield tert-butyl N-[3-bromo-4-[[4-(trifluoromethyl)-2-pyridyl]amino]phenyl]sulfonylcarbamate (75 mg, 123.92 μmol, 62.7% yield, 82.0% purity) as a light yellow solid. ¹H NMR (500 MHz, CDCl₃) δ ppm 8.54 (d, J=8.9 Hz, 1H), 8.50-8.45 (m, 1H), 8.29 (d, J=2.1 Hz, 1H), 7.96 (dd, J=2.1, 9.0 Hz, 1H), 7.34 (s, 1H), 7.12 (d, J=5.3 Hz, 1H), 7.09 (s, 1H), 1.50 (s, 9H); ES-LCMS m/z 496.0, 498.0 [M+H]⁺.

Step 4: 3-(1-Methylimidazol-4-yl)-4-[[4-(trifluoromethyl)-2-pyridyl]amino]benzenesulfonamide

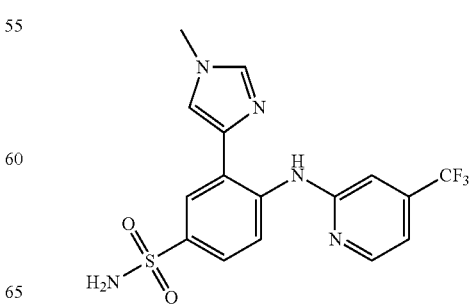

To a solution of tert-butyl N-[3-bromo-4-[[4-(trifluoromethyl)-2-pyridyl]amino]phenyl]sulfonylcarbamate (70 mg, 115.66 μmol, 1 eq) and tributyl-(1-methylimidazol-4-yl)stannane (91.33 mg, 231.31 μmol, 2 eq) in DMF (3 mL) was added Pd(PPh$_3$)$_4$ (13.36 mg, 11.57 μmol, 0.1 eq). The mixture was stirred under N$_2$ atmosphere at 130° C. for 3 h. The reaction mixture was quenched by 15% KF (15 mL), treated with water (20 mL) and extracted with EtOAc (20 mL×2). The combined organic layers were washed with brine (20 mL), dried over Na$_2$SO$_4$, filtered and concentrated under reduced pressure to yield a residue which was purified by preparative TLC (from PE/EtOAc=0/1) and preparative HPLC (column: Agela DuraShell C18 150*25 mm*5 um; mobile phase: [water (0.04% NH$_3$.H$_2$O+10 mM NH$_4$HCO$_3$)-ACN]; B %: 34%-64%, 10 min), followed by lyophilization to yield 3-(1-methylimidazol-4-yl)-4-[[4-(trifluoromethyl)-2-pyridyl]amino]benzenesulfonamide (10.19 mg, 24.82 μmol, 21.5% yield, 96.8% purity) as a white solid. $^1$H NMR (500 MHz, CD$_3$OD) δ ppm 8.72 (d, J=8.9 Hz, 1H), 8.41 (d, J=5.3 Hz, 1H), 8.12 (d, J=2.3 Hz, 1H), 7.78 (s, 1H), 7.72 (dd, J=2.3, 8.9 Hz, 1H), 7.59 (d, J=1.1 Hz, 1H), 7.09 (s, 1H), 7.04 (d, J=5.2 Hz, 1H), 3.82 (s, 3H); ES-LCMS m/z 398.0 [M+H]$^+$.

I-50

Step 1: 4-(Benzylamino)-3-(1-isopropylimidazol-4-yl)-N-methyl-benzenesulfonamide

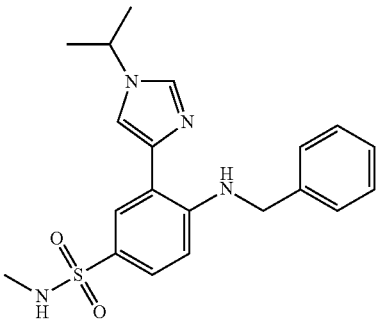 [SMILES: CNS(=O)(=O)c1ccc(NCc2ccccc2)c(-c2cn(C(C)C)cn2)c1]

4-(Benzylamino)-N-methyl-3-(4,4,5,5-tetramethyl-1,3,2-dioxaborolan-2-yl)benzenesulfonamide (150 mg, 372.84 μmol, 1 eq), 4-bromo-1-isopropyl-imidazole (70.49 mg, 372.84 μmol, 1 eq), Cs$_2$CO$_3$ (364.44 mg, 1.12 mmol, 3 eq) and Pd(dppf)Cl$_2$ (27.28 mg, 37.28 μmol, 0.1 eq) were taken up into a microwave tube in 1,4-dioxane (3 mL) and water (1 mL) was bubbled with N$_2$ for 3 times. The sealed tube was heated under microwave at 100° C. for 1 h. The reaction mixture was diluted with water (10 mL) and extracted with EtOAc (10 mL×3). The combined organic layers were dried over Na$_2$SO$_4$, filtered and the filtrate was concentrated to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 45%-75%, 10 min) to yield 4-(benzylamino)-3-(1-isopropylimidazol-4-yl)-N-methyl-benzenesulfonamide (20 mg, 51.67 μmol, 13.9% yield, 99.3% purity) as a white solid. $^1$H NMR (400 MHz, DMSO-d$_6$) δ ppm 9.30 (t, J=5.5 Hz, 1H), 7.89 (s, 1H), 7.83 (d, J=2.4 Hz, 2H), 7.41-7.31 (m, 5H), 7.28-7.22 (m, 1H), 6.95 (d, J=4.9 Hz, 1H), 6.69 (d, J=8.8 Hz, 1H), 4.50 (d, J=5.6 Hz, 2H), 3.30 (s, 1H), 2.34 (d, J=5.1 Hz, 3H), 1.46 (d, J=6.8 Hz, 6H); ES-LCMS m/z 385.3 [M+H]$^+$.

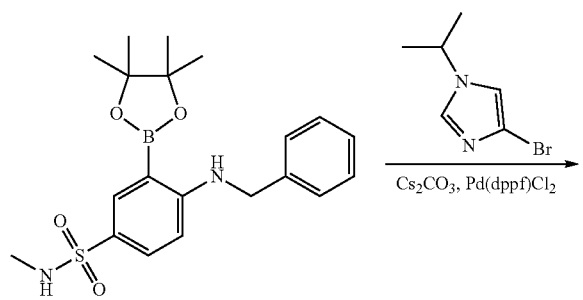

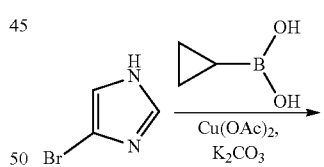

I-51

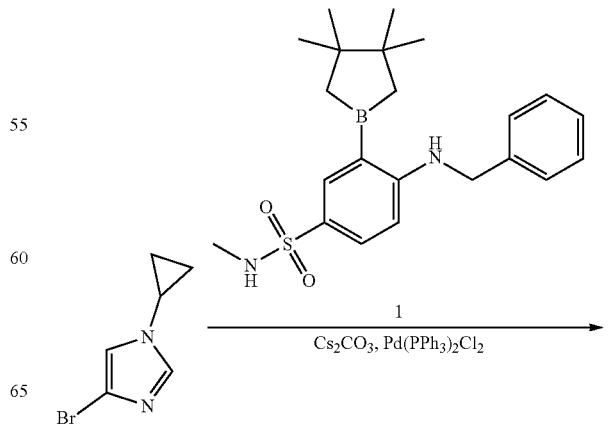

-continued

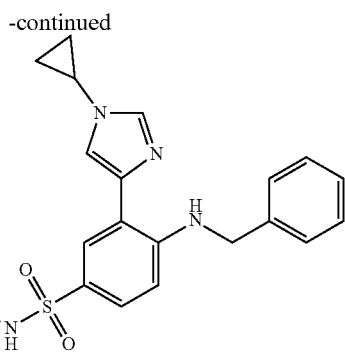

Step 1: 4-Bromo-1-cyclopropyl-imidazole

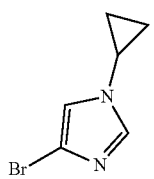

To a solution of 4-bromo-1H-imidazole (3 g, 20.41 mmol, 1 eq) in 1,2-dichloroethane (40 mL) was added 2-(2-pyridyl)pyridine (3.19 g, 20.41 mmol, 1 eq), Cu(OAc)$_2$ (3.71 g, 20.41 mmol, 1 eq), K$_2$CO$_3$ (5.64 g, 40.82 mmol, 2 eq) and cyclopropylboronic acid (2.98 g, 34.70 mmol, 1.7 eq). The mixture was stirred under N$_2$ atmosphere at 20° C. for 16 h. The reaction mixture was filtered through a pad of celite and the filtrate was concentrated to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 12%-42%, 10 min) to yield 4-bromo-1-cyclopropyl-imidazole (800 mg, 4.19 mmol, 20.5% yield, 98.0% purity) as brown oil. $^1$H NMR (400 MHz, DMSO-d$_6$) δ ppm 7.69 (s, 1H), 7.35 (d, J=1.2 Hz, 1H), 3.53-3.46 (m, 1H), 1.01-0.85 (m, 4H); ES-LCMS m/z 187.0, 189.0 [M+H]$^+$.

Step 2: 4-(Benzylamino)-3-(1-cyclopropylimidazol-4-yl)-N-methyl-benzenesulfonamide

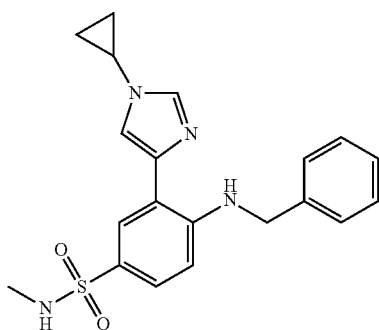 [SMILES: CNS(=O)(=O)c1ccc(NCc2ccccc2)c(-c2cn(C3CC3)cn2)c1]

4-(Benzylamino)-N-methyl-3-(4,4,5,5-tetramethyl-1,3,2-dioxaborolan-2-yl)benzenesulfonamide (200 mg, 497.12 μmol, 1 eq), 4-bromo-1-cyclopropyl-imidazole (92.98 mg, 497.12 μmol, 1 eq), Cs$_2$CO$_3$ (485.92 mg, 1.49 mmol, 3 eq) and Pd(PPh$_3$)$_2$Cl$_2$ (34.89 mg, 49.71 μmol, 0.1 eq) were taken up into a microwave tube in 1,4-dioxane (3 mL) and water (1 mL) and bubbled with N$_2$ for 3 times. The sealed tube was heated under microwave at 100° C. for 1 h. The reaction mixture was diluted with water (10 mL) and extracted with EtOAc (10 mL×3). The combined organic layers were dried over Na$_2$SO$_4$, filtered and the filtrate was concentrated to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 40%-70%, 10 min). The desired fraction was lyophilized to yield 4-(benzylamino)-3-(1-cyclopropylimidazol-4-yl)-N-methyl-benzenesulfonamide (22.61 mg, 57.05 μmol, 11.5% yield, 96.5% purity) as a white solid. $^1$H NMR (400 MHz, DMSO-d$_6$) δ ppm 9.13 (t, J=5.9 Hz, 1H), 7.90 (s, 1H), 7.82 (d, J=2.2 Hz, 1H), 7.74 (d, J=1.2 Hz, 1H), 7.39-7.32 (m, 5H), 7.29-7.21 (m, 1H), 6.94 (s, 1H), 6.69 (d, J=8.8 Hz, 1H), 4.50 (d, J=5.9 Hz, 2H), 3.60 (tt, J=3.8, 7.3 Hz, 1H), 2.35 (d, J=2.9 Hz, 3H), 1.09-1.03 (m, 2H), 1.02-0.95 (m, 2H); ES-LCMS m/z 383.1 [M+H]$^+$.

I-52

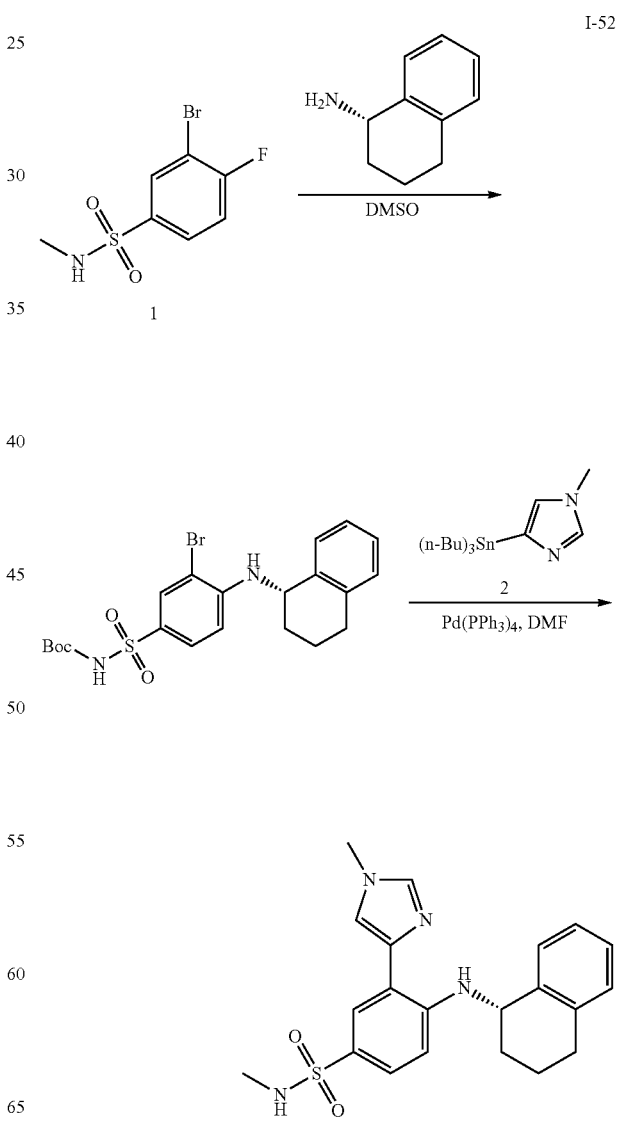

Step 1: 3-Bromo-N-methyl-4-[[(1S)-tetralin-1-yl]amino]benzenesulfonamide

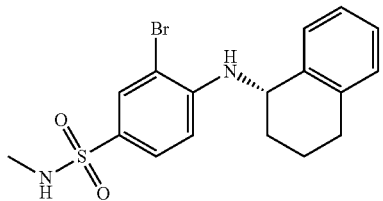 [SMILES: CNS(=O)(=O)c1ccc(N[C@H]2CCCc3ccccc32)c(Br)c1]

To a solution of 3-bromo-4-fluoro-N-methyl-benzenesulfonamide (300 mg, 1.12 mmol, 1 eq) in DMSO (5 mL) was added (1S)-tetralin-1-amine (165 mg, 1.12 mmol, 1 eq). The mixture was stirred at 140° C. for 12 h. TLC (PE/EtOAc=2/1, $R_f$=0.50) indicated starting material was consumed completely and one new spot formed. The mixture was diluted with water (5 mL) and extracted with EtOAc (5 mL×3). The combined organic layers were dried over $Na_2SO_4$, filtered and concentrated under reduced pressure to yield a residue which was purified by flash silica gel chromatography (from PE/EtOAc=100/1 to 4/1, TLC: PE/EtOAc=2/1, $R_f$=0.50) to yield 3-bromo-N-methyl-4-[[(1S)-tetralin-1-yl]amino]benzenesulfonamide (350 mg, 619.76 μmol, 55.4% yield, 70.0% purity) as a black brown oil. $^1$H NMR (400 MHz, DMSO-$d_6$) δ ppm 7.78 (d, J=2.0 Hz, 1H), 7.63 (s, 1H), 7.55 (dd, J=2.0, 8.6 Hz, 1H), 7.24-7.19 (m, 2H), 7.19-7.16 (m, 1H), 7.16-7.13 (m, 1H), 7.01 (d, J=9.0 Hz, 1H), 5.68 (d, J=8.6 Hz, 1H), 4.94-4.82 (m, 1H), 2.89-2.65 (m, 2H), 2.43 (d, J=4.7 Hz, 3H), 2.38 (d, J=5.1 Hz, 2H), 1.93-1.79 (m, 2H).

Step 2: N-Methyl-3-(1-methylimidazol-4-yl)-4-[[(1S)-tetralin-1-yl]amino]benzenesulfonamide

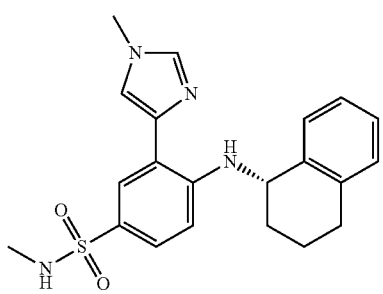 [SMILES: CNS(=O)(=O)c1ccc(N[C@H]2CCCc3ccccc32)c(-c2cn(C)cn2)c1]

A mixture of 3-bromo-N-methyl-4-[[(1S)-tetralin-1-yl]amino]benzenesulfonamide (240 mg, 424.98 μmol, 1 eq), tributyl-(1-methylimidazol-4-yl)stannane (325.75 mg, 848.72 μmol, 2 eq), Pd(PPh$_3$)$_4$ (50 mg, 43.27 μmol, 1.02e-1 eq) in DMF (7 mL) was degassed and purged with $N_2$ for 3 times. The mixture was stirred under $N_2$ atmosphere at 120° C. for 30 h. The reaction mixture was filtered and concentrated to yield a residue which was purified by preparative HPLC (column: Welch Xtimate C18 150*25 mm*5 um; mobile phase: [water (10 mM NH$_4$HCO$_3$)-ACN]; B %: 41%-71%, 10 min) followed by lyophilization to yield N-methyl-3-(1-methylimidazol-4-yl)-4-[[(1S)-tetralin-1-yl]amino]benzenesulfonamide (38.3 mg, 96.59 μmol, 22.7% yield, 100.0% purity, $[α]^{25.7}_D$=+15.777 (MeOH, c=0.052 g/100 mL)) as a white solid. $^1$H NMR (400 MHz, DMSO-$d_6$) δ ppm 9.08 (d, J=8.2 Hz, 1H), 7.78 (d, J=2.3 Hz, 1H), 7.65 (s, 1H), 7.63 (s, 1H), 7.44 (dd, J=2.0, 8.6 Hz, 1H), 7.27 (d, J=7.4 Hz, 1H), 7.19-7.11 (m, 3H), 7.00 (d, J=9.0 Hz, 2H), 4.90-4.80 (m, 1H), 3.68 (s, 3H), 2.84-2.67 (m, 2H), 2.39 (d, J=5.1 Hz, 3H), 2.06-1.97 (m, 1H), 1.85-1.78 (m, 3H); ES-LCMS m/z 397.2 [M+H]$^+$.

I-53

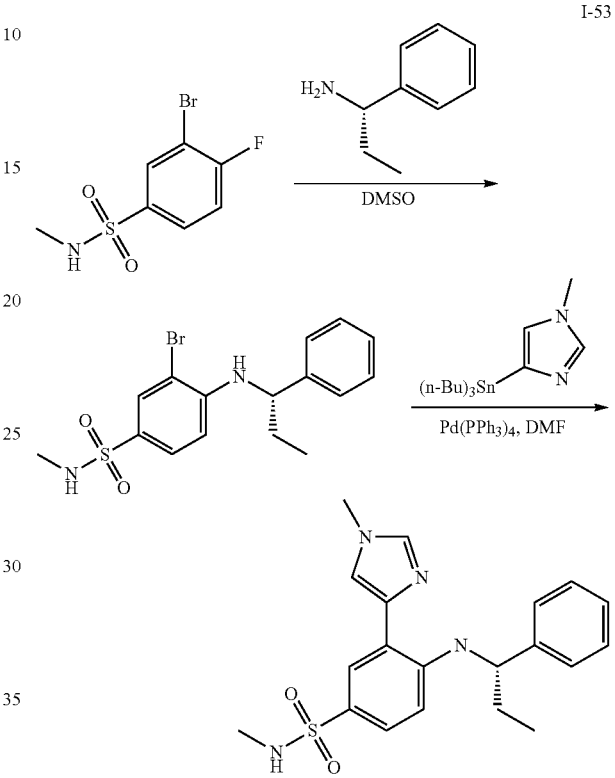

Step 1: 3-Bromo-N-methyl-4-[[(1S)-1-phenylpropyl]amino]benzenesulfonamide

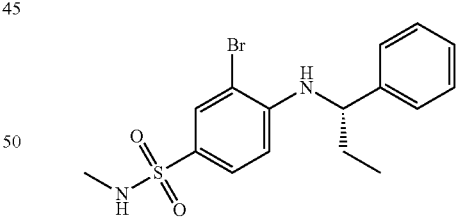

To a solution of 3-bromo-4-fluoro-N-methyl-benzenesulfonamide (200 mg, 745.98 mol, 1 eq) in DMSO (1.5 mL) was added (1S)-1-phenylpropan-1-amine (150 mg, 1.11 mmol, 159.57 μL, 1.49 eq) under $N_2$ atmosphere. The mixture was stirred at 140° C. for 1 h. The reaction mixture was diluted with $H_2O$ (20 mL) and extracted with EtOAc (20 mL×3). The combined organic layers dried over $Na_2SO_4$, filtered and concentrated under reduced pressure to yield a residue which was purified by preparative HPLC (column: Phenomenex Synergi C18 150×30 mm×4 m; mobile phase: [water (0.05% HCl)-ACN]; B %: 57%-77%, 9 min) to yield 3-bromo-N-methyl-4-[[(1S)-1-phenylpropyl]amino]benzenesulfonamide (130 mg, 336.17 μmol, 45.1% yield, 99.1% purity) as an off-white solid. ¹H NMR (400 MHz, CDCl₃) δ ppm 7.91 (d, J=2.3 Hz, 1H), 7.46 (dd, J=2.0, 8.6 Hz, 1H), 7.38-7.27 (m, 5H), 6.41 (d, J=8.6 Hz, 1H), 5.26 (d, J=5.1 Hz, 1H), 4.33 (q, J=6.3 Hz, 1H), 4.17 (d, J=5.1 Hz, 1H), 2.60 (d, J=5.5 Hz, 3H), 1.98-1.90 (m, 2H), 1.02 (t, J=7.4 Hz, 3H); ES-LCMS m/z 385.1 [M+H]⁺.

Step 2: N-Methyl-3-(1-methylimidazol-4-yl)-4-[[(1S)-1-phenylpropyl]amino]benzenesulfonamide

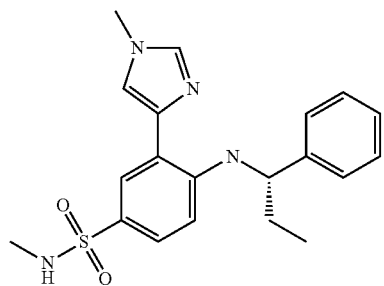 [SMILES: CC[C@H](Nc1ccc(S(=O)(=O)NC)cc1-c1cn(C)cn1)c1ccccc1]

To a solution of 3-bromo-N-methyl-4-[[(1S)-1-phenylpropyl]amino]benzenesulfonamide (100 mg, 258.28 μmol, 1 eq) in DMF (2 mL) was added Pd(PPh₃)₄ (30 mg, 25.96 μmol, 1.01e⁻¹ eq) and tributyl-(1-methylimidazol-4-yl)stannane (100 mg, 255.96 μmol, 9.91e⁻¹ eq) under N₂ atmosphere. The mixture was stirred under N₂ atmosphere at 130° C. for 1 h. The reaction mixture was diluted with H₂O (30 mL) and extracted with EtOAc (30 mL×3). The combined organic layers dried over Na₂SO₄, filtered and concentrated under reduced pressure to yield a residue which was purified by preparative HPLC (column: Phenomenex Synergi C18 150×30 mm×4 um; mobile phase: [water (0.05% HCl)-ACN]; B %: 30%-50%, 9 min). The desired fraction was basified with saturated aqueous NaHCO₃ until pH=8 and extracted with EtOAc (50 mL×3). The organic layer was dried over Na₂SO₄, filtered and concentrated under reduced pressure to yield a residue which was dissolved in MeCN (10 mL) and water (10 mL) and lyophilized to yield N-methyl-3-(1-methylimidazol-4-yl)-4-[[(1S)-1-phenylpropyl]amino]benzenesulfonamide (24.46 mg, 62.21 μmol, 24.1% yield, 99.7% purity, [α]$^{25.0}_D$=+111.1 (MeOH, c=0.045 g/100 mL)) as a white solid. ¹H NMR (400 MHz, DMSO-d₆) δ ppm 9.44 (d, J=6.7 Hz, 1H), 7.86 (s, 1H), 7.75 (d, J=2.3 Hz, 1H), 7.69 (d, J=0.8 Hz, 1H), 7.36-7.27 (m, 4H), 7.24-7.17 (m, 2H), 6.94 (q, J=5.0 Hz, 1H), 6.47 (d, J=8.6 Hz, 1H), 4.52 (q, J=6.5 Hz, 1H), 3.76 (s, 3H), 2.31 (d, J=5.5 Hz, 3H), 1.86-1.78 (m, 2H), 0.95 (t, J=7.4 Hz, 3H); ES-LCMS m/z 385.0 [M+H]⁺.

I-54

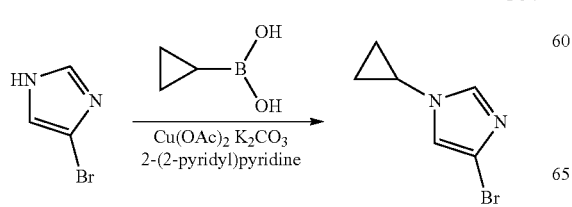

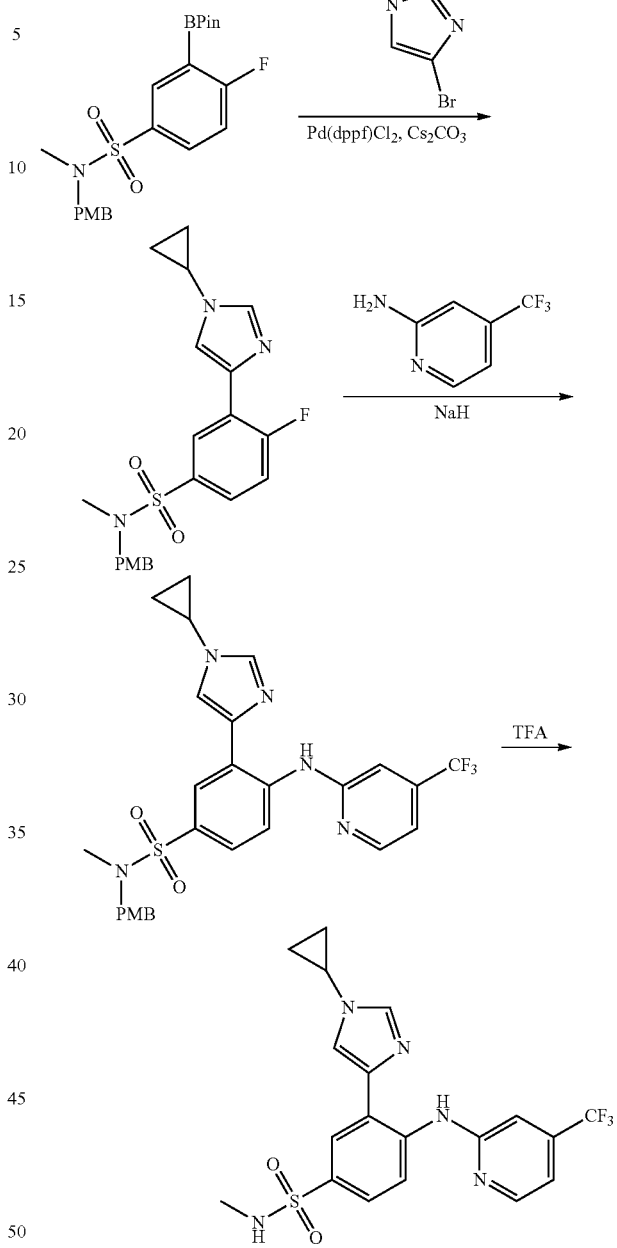

Step 1: 4-Bromo-1-cyclopropyl-imidazole

To a solution of 4-bromo-1H-imidazole (1 g, 6.80 mmol, 1 eq) in 1,2-dichloroethane (30 mL) was added 2-(2-pyridyl)

pyridine (1.06 g, 6.80 mmol, 1 eq), Cu(OAc)$_2$ (1.24 g, 6.80 mmol, 1 eq), K$_2$CO$_3$ (1.88 g, 13.61 mmol, 2 eq) and cyclopropylboronic acid (993.55 mg, 11.57 mmol, 1.7 eq). The mixture was stirred under N$_2$ atmosphere at 70° C. for 16 h. The reaction mixture was diluted with water (50 mL) and extracted with EtOAc (100 mL×2). The combined organic layers were washed with brine (50 mL), dried over Na$_2$SO$_4$, filtered and concentrated under reduced pressure to yield a residue which was purified by preparative HPLC (column: Agela DuraShell Cis 150*25 mm*5 um; mobile phase: [water (0.05% NH$_3$.H$_2$O+10 mM NH$_4$HCO$_3$)-ACN]; B %: 13%-43%, 10 min), followed by lyophilization to yield 4-bromo-1-cyclopropyl-imidazole (190 mg, 839.09 μmol, 12.3% yield, 82.6% purity) as a white solid. $^1$H NMR (400 MHz, CDCl$_3$) δ ppm 7.37 (s, 1H), 6.90 (s, 1H), 3.29-3.23 (m, 1H), 0.99-0.82 (m, 4H); ES-LCMS m/z 187.1 [M+H]$^+$.

Step 2: 3-(1-Cyclopropylimidazol-4-yl)-4-fluoro-N-[(4-methoxyphenyl)methyl]-N-methyl-benzenesulfonamide

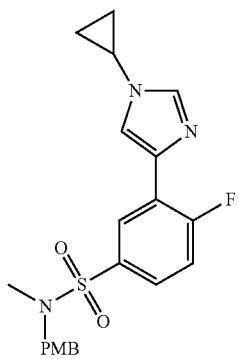

To a solution of 4-fluoro-N-[(4-methoxyphenyl)methyl]-N-methyl-3-(4,4,5,5-tetramethyl-1,3,2-dioxaborolan-2-yl)benzenesulfonamide (500 mg, 1.09 mmol, 1 eq) in 1,4-dioxane (5 mL) and H$_2$O (1 mL) were added Pd(dppf)Cl$_2$ (39.92 mg, 54.56 μmol, 0.05 eq), Cs$_2$CO$_3$ (711.04 mg, 2.18 mmol, 2 eq) and 4-bromo-1-cyclopropyl-imidazole (208.25 mg, 1.09 mmol, 1 eq). The mixture was degassed and purged with N$_2$ for three times and stirred under N$_2$ atmosphere at 90° C. for 6 h. The reaction mixture was diluted with water (30 mL) and extracted with EtOAc (50 mL×2). The combined organic layers were washed with brine (50 mL), dried over Na$_2$SO$_4$, filtered and concentrated under reduced pressure to yield a residue which was purified by silica gel chromatography (from PE/EtOAc=1/0 to 1/1, TLC: PE/EtOAc=1/1, R$_f$=0.23) to yield 3-(1-cyclopropylimidazol-4-yl)-4-fluoro-N-[(4-methoxyphenyl)methyl]-N-methyl-benzenesulfonamide (160 mg, 385.10 μmol, 35.3% yield, 100.0% purity) as colorless oil. $^1$H NMR (500 MHz, CDCl$_3$) δ ppm 8.62 (dd, J=2.4, 7.0 Hz, 1H), 7.70-7.63 (m, 2H), 7.52 (dd, J=1.1, 4.1 Hz, 1H), 7.25-7.19 (m, 3H), 6.88-6.82 (m, 2H), 4.11 (s, 2H), 3.79 (s, 3H), 3.45-3.38 (m, 1H), 2.60 (s, 3H), 1.12-0.98 (m, 4H); ES-LCMS m/z 416.2 [M+H]$^+$.

Step 3: 3-(1-Cyclopropylimidazol-4-yl)-N-[(4-methoxyphenyl)methyl]-N-methyl-4-[[4-(trifluoromethyl)-2-pyridyl]amino]benzenesulfonamide

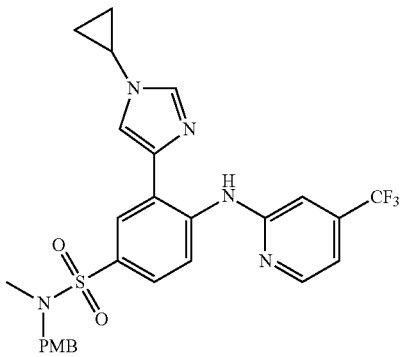

To a solution of 4-(trifluoromethyl)pyridin-2-amine (117.05 mg, 722.06 μmol, 2 eq) in DMF (3 mL) was added NaH (72.20 mg, 1.81 mmol, 60% purity, 5 eq) at 0° C. and the mixture was stirred for 0.5 h. 3-(1-Cyclopropylimidazol-4-yl)-4-fluoro-N-[(4-methoxyphenyl)methyl]-N-methyl-benzenesulfonamide (150 mg, 361.03 μmol, 1 eq) was added at 0° C. The resulting mixture was stirred at 60° C. for 6 h. The reaction mixture was quenched by addition of water (20 mL) and extracted with EtOAc (40 mL×2). The combined organic layers were washed with brine (50 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.43) to yield 3-(1-cyclopropylimidazol-4-yl)-N-[(4-methoxyphenyl)methyl]-N-methyl-4-[[4-(trifluoromethyl)-2-pyridyl]amino]benzenesulfonamide (260 mg, 326.41 μmol, 90.4% yield, 70.0% purity) as yellow oil. $^1$H NMR (400 MHz, CDCl$_3$) δ ppm 12.15 (s, 1H), 8.91 (d, J=9.0 Hz, 1H), 8.44 (d, J=5.5 Hz, 1H), 7.94 (d, J=2.3 Hz, 1H), 7.72 (s, 1H), 7.68 (dd, J=2.0, 9.0 Hz, 1H), 7.45 (d, J=1.2 Hz, 1H), 7.24 (d, J=8.6 Hz, 2H), 7.07 (s, 1H), 6.98 (d, J=5.5 Hz, 1H), 6.86 (d, J=8.6 Hz, 2H), 4.08 (s, 2H), 3.80 (s, 3H), 3.46 (t, J=3.7, 7.2 Hz, 1H), 2.58 (s, 3H), 1.13-1.06 (m, 4H); ES-LCMS m/z 558.2 [M+H]$^+$.

Step 4: 3-(1-Cyclopropylimidazol-4-yl)-N-methyl-4-[[4-(trifluoromethyl)-2-pyridyl]amino]benzenesulfonamide

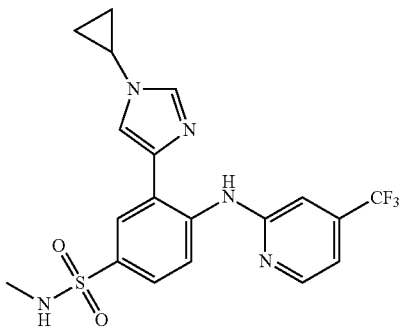 [SMILES: CNS(=O)(=O)c1ccc(Nc2cc(C(F)(F)F)ccn2)c(-c2cn(C3CC3)cn2)c1]

To a solution of 3-(1-cyclopropylimidazol-4-yl)-N-[(4-methoxyphenyl)methyl]-N-methyl-4-[[4-(trifluoromethyl)-2-pyridyl]amino]benzenesulfonamide (200 mg, 251.08 μmol, 1 eq) in DCM (3 mL) was added TFA (0.6 mL). The mixture was stirred at 20° C. for 16 h. The reaction mixture was filtered to yield a residue which was purified by preparative HPLC (column: Agela DuraShell $C_{18}$ 150*25 mm*5 um; mobile phase: [water (0.04% $NH_3 \cdot H_2O$+10 mM $NH_4HCO_3$)-ACN]; B %: 46%-76%, 10 min), followed by lyophilization to yield 3-(1-cyclopropylimidazol-4-yl)-N-methyl-4-[[4-(trifluoromethyl)-2-pyridyl]amino]benzenesulfonamide (27.74 mg, 61.58 μmol, 24.5% yield, 97.1% purity) as a white solid. $^1$H NMR (400 MHz, DMSO-$d_6$) δ ppm 12.08 (s, 1H), 8.66 (d, J=8.8 Hz, 1H), 8.48 (d, J=5.1 Hz, 1H), 8.11-8.03 (m, 2H), 7.90 (d, J=1.0 Hz, 1H), 7.59 (dd, J=2.2, 8.8 Hz, 1H), 7.25 (q, J=4.8 Hz, 1H), 7.20-7.12 (m, 2H), 3.71-3.59 (m, 1H), 2.43 (d, J=4.9 Hz, 3H), 1.11-0.97 (m, 4H); ES-LCMS m/z 438.2 [M+H]$^+$.

I-55

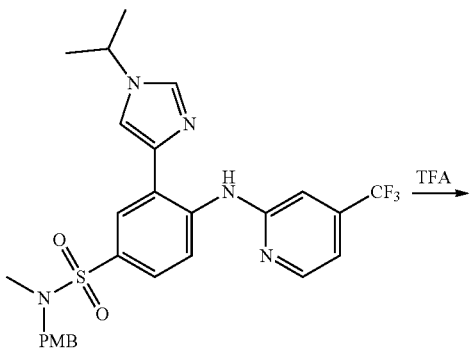

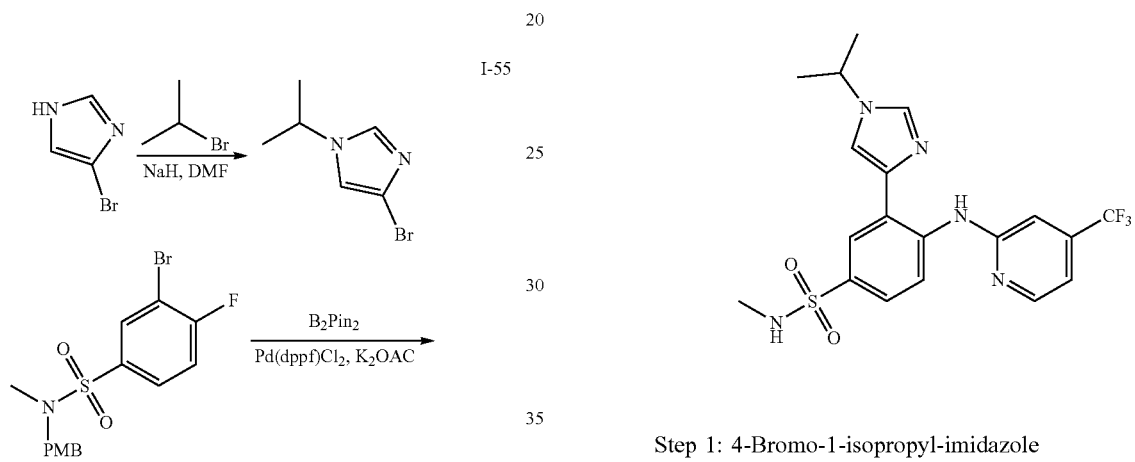

Step 1: 4-Bromo-1-isopropyl-imidazole

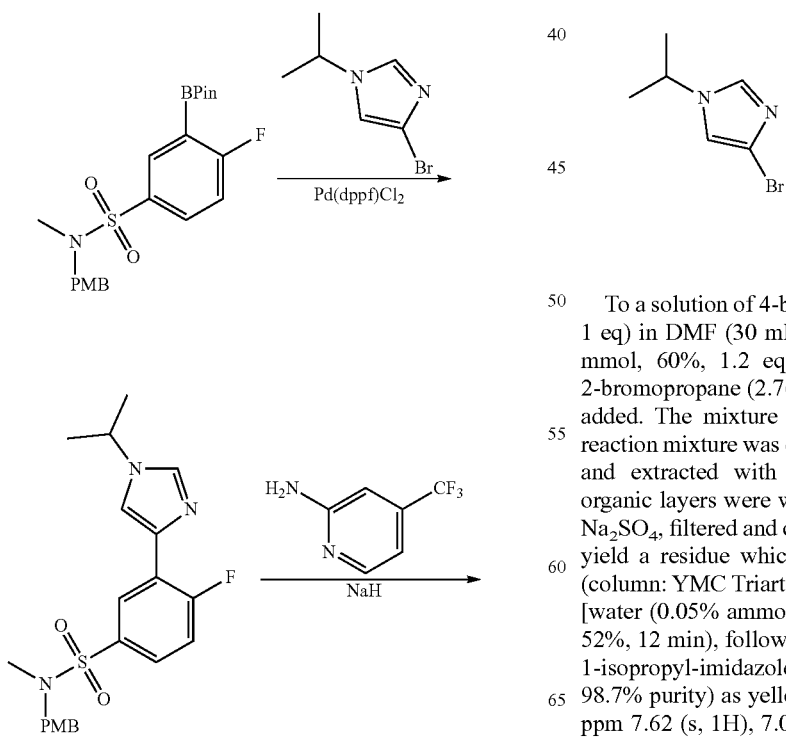

To a solution of 4-bromo-1H-imidazole (3 g, 20.41 mmol, 1 eq) in DMF (30 mL) was added NaH (979.68 mg, 24.49 mmol, 60%, 1.2 eq) at 0° C. After stirring for 0.5 h, 2-bromopropane (2.76 g, 22.45 mmol, 2.11 mL, 1.1 eq) was added. The mixture was stirred at 25° C. for 12 h. The reaction mixture was quenched by addition of water (50 mL) and extracted with EtOAc (50 mL×3). The combined organic layers were washed with brine (30 mL), dried over $Na_2SO_4$, filtered and concentrated under reduced pressure to yield a residue which was purified by preparative HPLC (column: YMC Triart C18 250*50 mm*7 μm; mobile phase: [water (0.05% ammonia hydroxide v/v)-ACN]; B %: 12%-52%, 12 min), followed by lyophilization to yield 4-bromo-1-isopropyl-imidazole (1.3 g, 6.79 mmol, 33.2% yield, 98.7% purity) as yellow oil. $^1$H NMR (500 MHz, CDCl$_3$) δ ppm 7.62 (s, 1H), 7.01 (s, 1H), 4.45-4.34 (m, 1H), 1.49 (d, J=6.9 Hz, 6H); ES-LCMS m/z 189.1, 192.1 [M+H]$^+$.

Step 2: 4-Fluoro-N-[(4-methoxyphenyl)methyl]-N-methyl-3-(4,4,5,5-tetramethyl-1,3,2-dioxaborolan-2-yl)benzenesulfonamide

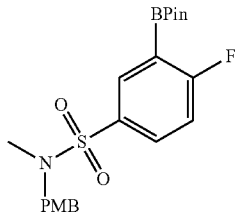

To a solution of 3-bromo-4-fluoro-N-[(4-methoxyphenyl)methyl]-N-methyl-benzenesulfonamide (1 g, 2.32 mmol, 1 eq) and 4,4,5,5-tetramethyl-2-(4,4,5,5-tetramethyl-1,3,2-dioxaborolan-2-yl)-1,3,2-dioxaborolane (1.77 g, 6.95 mmol, 3 eq) in 1,4-dioxane (10 mL) was added KOAc (682.51 mg, 6.95 mmol, 3 eq) and Pd(dppf)Cl$_2$ (84.81 mg, 115.90 µmol, 0.05 eq) under N$_2$ atmosphere. The mixture was stirred under N$_2$ atmosphere at 110° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by re-crystallization from PE (100 mL) at 25° C. to yield 4-fluoro-N-[(4-methoxyphenyl)methyl]-N-methyl-3-(4,4,5,5-tetramethyl-1,3,2-dioxaborolan-2-yl)benzenesulfonamide (800 mg, 1.75 mmol, 75.3% yield, 95.0% purity) as a white solid. $^1$H NMR (500 MHz, CDCl$_3$) δ ppm 8.24 (dd, J=2.4, 5.3 Hz, 1H), 7.91 (ddd, J=2.4, 5.0, 8.6 Hz, 1H), 7.25-7.18 (m, 3H), 6.89-6.85 (m, 2H), 4.10 (s, 2H), 3.81 (s, 3H), 2.60 (s, 3H), 1.38 (s, 12H).

Step 3: 4-Fluoro-3-(1-isopropylimidazol-4-yl)-N-[(4-methoxyphenyl)methyl]-N-methyl-benzenesulfonamide

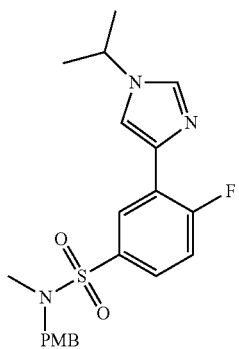

To a solution of 4-bromo-1-isopropyl-imidazole (200 mg, 1.04 mmol, 1 eq), 4-fluoro-N-[(4-methoxyphenyl)methyl]-N-methyl-3-(4,4,5,5-tetramethyl-1,3,2-dioxaborolan-2-yl)benzenesulfonamide (718.27 mg, 1.57 mmol, 1.5 eq) and Cs$_2$CO$_3$ (680.96 mg, 2.09 mmol, 2 eq) in 1,4-dioxane (8 mL) and H$_2$O (2 mL) was added Pd(dppf)Cl$_2$ (76.46 mg, 104.50 µmol, 0.1 eq) under N$_2$ atmosphere. The mixture was stirred under N$_2$ atmosphere at 110° C. for 4 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/2, TLC: PE/EtOAc=3/1, R$_f$=0.32) to yield 4-fluoro-3-(1-isopropylimidazol-4-yl)-N-[(4-methoxyphenyl)methyl]-N-methyl-benzenesulfonamide (300 mg, 625.87 µmol, 59.8% yield, 87.1% purity) as colorless oil. $^1$H NMR (500 MHz, CD$_3$OD) δ ppm 8.48 (dd, J=2.3, 7.0 Hz, 1H), 7.89 (s, 1H), 7.76-7.69 (m, 2H), 7.41 (dd, J=8.6, 10.9 Hz, 1H), 7.24 (d, J=8.7 Hz, 2H), 6.90-6.87 (m, 2H), 4.54 (spt, J=6.7 Hz, 1H), 4.14 (s, 2H), 3.77 (s, 3H), 2.61 (s, 3H), 1.55 (d, J=6.7 Hz, 6H); ES-LCMS m/z 418.4 [M+H]$^+$.

Step 4: 3-(1-Isopropylimidazol-4-yl)-N-[(4-methoxyphenyl)methyl]-N-methyl-4-[[4-(trifluoromethyl)-2-pyridyl]amino]benzenesulfonamide

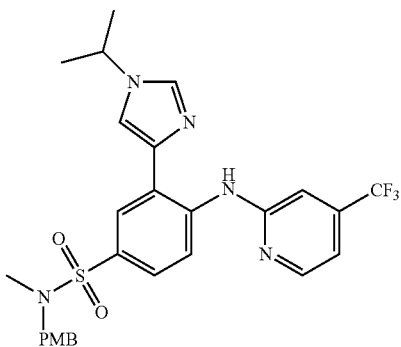

To a solution of 4-(trifluoromethyl)pyridin-2-amine (405.85 mg, 2.50 mmol, 4 eq) in DMF (10 mL) was added NaH (200.28 mg, 5.01 mmol, 60%, 8 eq) and 4-fluoro-3-(1-isopropylimidazol-4-yl)-N-[(4-methoxyphenyl)methyl]-N-methyl-benzenesulfonamide (300 mg, 625.87 µmol, 1 eq). The mixture was stirred at 25° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.14) to yield 3-(1-isopropylimidazol-4-yl)-N-[(4-methoxyphenyl)methyl]-N-methyl-4-[[4-(trifluoromethyl)-2-pyridyl]amino]benzenesulfonamide (430 mg, 603.81 µmol, 96.4% yield, 78.5% purity) as yellow oil. $^1$H NMR (400 MHz, CD$_3$OD) δ ppm 8.83 (d, J=8.8 Hz, 1H), 8.44 (d, J=5.1 Hz, 1H), 8.04 (d, J=2.0 Hz, 1H), 7.92 (s, 1H), 7.78 (s, 1H), 7.69-7.63 (m, 1H), 7.24 (d, J=8.3 Hz, 2H), 7.12 (s, 1H), 7.07 (d, J=4.9 Hz, 1H), 6.88 (d, J=8.6 Hz, 2H), 4.57-4.48 (m, 1H), 4.13-4.12 (m, 2H), 3.77 (s, 3H), 2.60 (s, 3H), 1.56 (d, J=6.6 Hz, 6H); ES-LCMS m/z 560.6 [M+H]$^+$.

Step 5: 3-(1-Isopropylimidazol-4-yl)-N-methyl-4-[[4-(trifluoromethyl)-2-pyridyl]amino]benzenesulfonamide

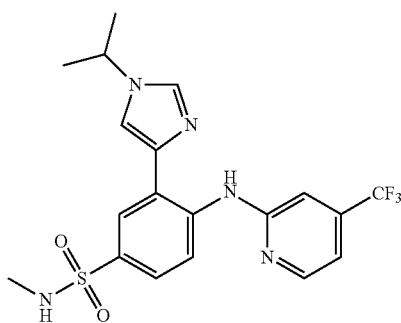 [SMILES: CNS(=O)(=O)c1ccc(Nc2cc(C(F)(F)F)ccn2)c(-c2cn(C(C)C)cn2)c1]

To a solution of 3-(1-isopropylimidazol-4-yl)-N-[(4-methoxyphenyl)methyl]-N-methyl-4-[[4-(trifluoromethyl)-2-pyridyl]amino]benzenesulfonamide (430 mg, 603.81 μmol, 78.58% purity, 1 eq) in DCM (15 mL) was added TFA (10.41 g, 91.27 mmol, 6.76 mL, 151.16 eq). The mixture was stirred at 25° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by preparative HPLC (column: Agela DuraShell C18 150*25 mm*5 μm; mobile phase: [water (0.04% NH$_3$H$_2$O+10 mM NH$_4$HCO$_3$)-ACN]; B %: 54%-69%, 14 min), followed by lyophilization to yield 3-(1-isopropylimidazol-4-yl)-N-methyl-4-[[4-(trifluoromethyl)-2-pyridyl]amino]benzenesulfonamide (100.52 mg, 228.74 μmol, 37.8% yield, 100.0% purity) as a white solid. $^1$H NMR (500 MHz, DMSO-d$_6$) δ ppm 12.34 (s, 1H), 8.71 (d, J=8.7 Hz, 1H), 8.49 (d, J=5.2 Hz, 1H), 8.09 (d, J=0.9 Hz, 1H), 8.06 (d, J=2.1 Hz, 1H), 8.01 (d, J=1.1 Hz, 1H), 7.59 (dd, J=2.3, 8.9 Hz, 1H), 7.25 (q, J=5.0 Hz, 1H), 7.19-7.14 (m, 2H), 4.58-4.50 (m, 1H), 2.43 (d, J=5.0 Hz, 3H), 1.49 (d, J=6.7 Hz, 6H); ES-LCMS m/z 440.1 [M+H]$^+$.

I-56

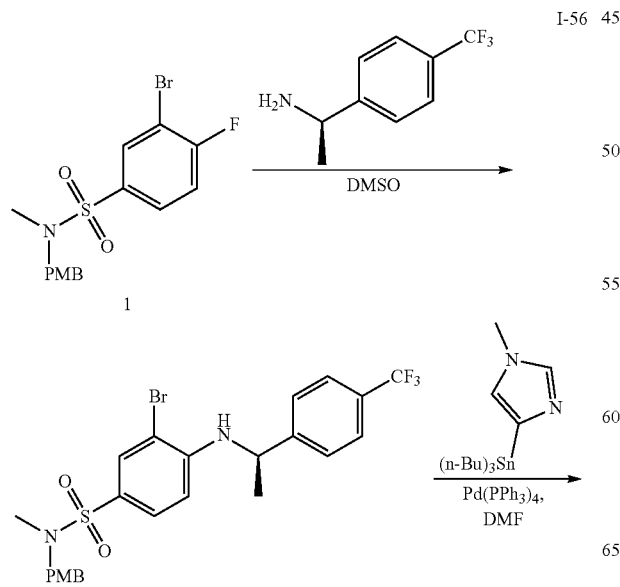

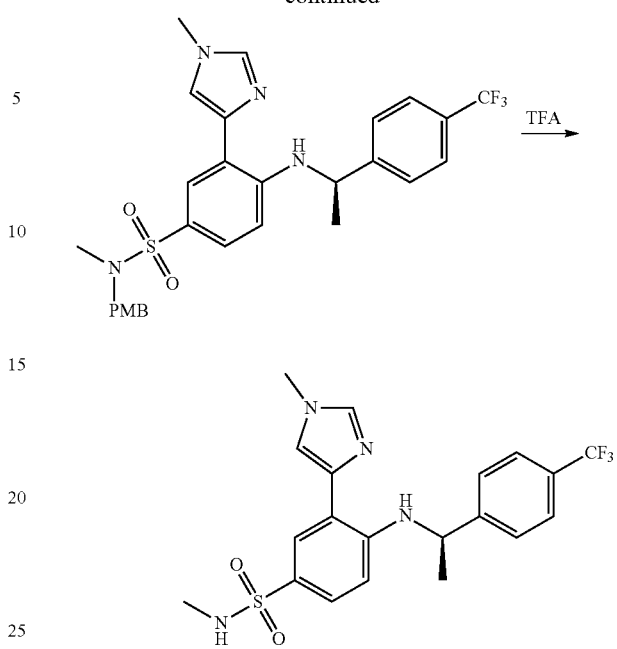

Step 1: 3-Bromo-N-[(4-methoxyphenyl)methyl]-N-methyl-4-[[(1R)-1-[4-(trifluoromethyl)phenyl]ethyl]amino]benzenesulfonamide

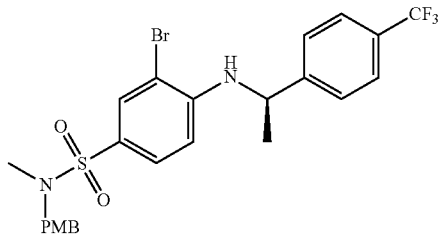

To a stirred solution of 3-bromo-4-fluoro-N-[(4-methoxyphenyl)methyl]-N-methyl-benzenesulfonamide (300 mg, 695.43 μmol, 1 eq) in DMSO (5 mL) was added (1R)-1-[4-(trifluoromethyl)phenyl]ethanamine (144.71 mg, 764.97 μmol, 1.1 eq). The reaction mixture was stirred at 140° C. for 12 h. The reaction mixture was diluted with water (50 mL), adjusted pH to 9-10 by saturated NaHCO$_3$ solution then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 3/1, TLC: PE/EtOAc=3/1, R$_f$=0.35) to yield 3-bromo-N-[(4-methoxyphenyl)methyl]-N-methyl-4-[[(1R)-1-[4-(trifluoromethyl)phenyl]ethyl]amino]benzenesulfonamide (140 mg, 220.52 μmol, 31.7% yield, 87.8% purity) as yellow oil. $^1$H NMR (500 MHz, DMSO-d$_6$) δ ppm 7.78 (d, J=2.1 Hz, 1H), 7.74-7.71 (m, 2H), 7.69-7.64 (m, 2H), 7.49 (dd, J=2.1, 8.8 Hz, 1H), 7.18 (d, J=8.5 Hz, 2H), 6.89 (d, J=8.7 Hz, 2H), 6.61 (d, J=8.9 Hz, 1H), 6.22 (d, J=7.2 Hz, 1H), 4.87 (q, J=6.8 Hz, 1H), 3.97 (s, 2H), 3.73 (s, 3H), 2.42 (s, 3H), 1.59 (d, J=6.9 Hz, 3H); ES-LCMS m/z 557.1, 559.1 [M+H]$^+$.

Step 2: N-[(4-Methoxyphenyl)methyl]-N-methyl-3-(1-methylimidazol-4-yl)-4-[[(1R)-1-[4-(trifluoromethyl)phenyl]ethyl]amino]benzenesulfonamide

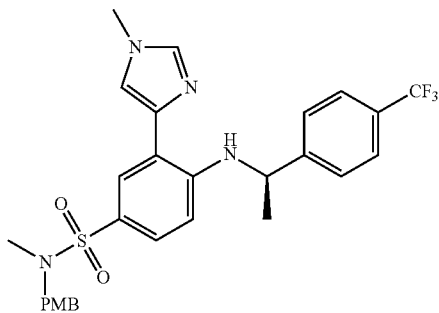

To a stirred solution of 3-bromo-N-[(4-methoxyphenyl)methyl]-N-methyl-4-[[(1R)-1-[4-(trifluoromethyl)phenyl]ethyl]amino]benzenesulfonamide (110 mg, 173.26 µmol, 1 eq) in DMF (4 mL) was added tributyl-(1-methylimidazol-4-yl)stannane (136.82 mg, 346.52 µmol, 2 eq) and Pd(PPh$_3$)$_4$ (10.01 mg, 8.66 µmol, 0.05 eq). The reaction mixture was stirred at 130° C. for 12 h. The reaction mixture was diluted with water (30 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 1/1, TLC: PE/EtOAc=1/1, R$_f$=0.45) to yield N-[(4-methoxyphenyl)methyl]-N-methyl-3-(1-methylimidazol-4-yl)-4-[[(1R)-1-[4-(trifluoromethyl)phenyl]ethyl]amino]benzenesulfonamide (60 mg, 95.92 µmol, 55.4% yield, 89.3% purity) as yellow oil. $^1$H NMR (500 MHz, CDCl$_3$) δ ppm 9.20 (d, J=5.5 Hz, 1H), 7.80 (d, J=2.1 Hz, 1H), 7.59 (d, J=8.2 Hz, 2H), 7.55 (s, 1H), 7.51 (d, J=8.1 Hz, 2H), 7.37 (dd, J=2.1, 8.7 Hz, 1H), 7.31 (s, 1H), 7.20 (d, J=8.5 Hz, 2H), 6.84 (d, J=8.5 Hz, 2H), 6.38 (d, J=8.7 Hz, 1H), 4.69 (q, J=6.4 Hz, 1H), 4.03-3.98 (m, 2H), 3.79 (d, J=3.2 Hz, 6H), 2.53-2.48 (m, 3H), 1.65 (d, J=6.7 Hz, 3H); ES-LCMS m/z 559.2 [M+H]$^+$.

Step 3: N-Methyl-3-(1-methylimidazol-4-yl)-4-[[(1R)-1-[4-(trifluoromethyl)phenyl]ethyl]amino]benzenesulfonamide

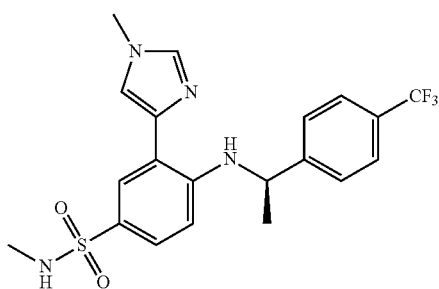 [SMILES: CNS(=O)(=O)c1ccc(N[C@H](C)c2ccc(C(F)(F)F)cc2)c(-c2cn(C)cn2)c1]

To a stirred solution of N-[(4-methoxyphenyl)methyl]-N-methyl-3-(1-methylimidazol-4-yl)-4-[[(1R)-1-[4-(trifluoromethyl)phenyl]ethyl]amino]benzenesulfonamide (60 mg, 95.92 µmol, 89.3% purity, 1 eq) in DCM (10 mL) was added TFA (1.54 g, 13.51 mmol, 1 mL, 140.81 eq). The reaction mixture was stirred at 15° C. for 12 h. The reaction mixture was diluted with saturated NaHCO$_3$ solution (20 mL) then extracted with DCM (20 mL×2). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 44%-74%, 10 min). The desired fraction was lyophilized to yield N-methyl-3-(1-methylimidazol-4-yl)-4-[[(1R)-1-[4-(trifluoromethyl)phenyl]ethyl]amino]benzenesulfonamide (19.66 mg, 44.84 µmol, 46.8% yield, 100.0% purity, [α]$^{21.9}_D$=~152.0 (MeOH, c=0.025 g/100 mL)) as a white solid. $^1$H NMR (400 MHz, CDCl$_3$) δ ppm 9.22 (d, J=5.1 Hz, 1H), 7.84 (d, J=2.2 Hz, 1H), 7.61-7.55 (m, 2H), 7.53 (s, 1H), 7.52-7.46 (m, 2H), 7.38 (dd, J=2.2, 8.6 Hz, 1H), 7.31 (d, J=1.2 Hz, 1H), 6.34 (d, J=8.8 Hz, 1H), 4.68 (t, J=6.4 Hz, 1H), 4.09 (q, J=5.5 Hz, 1H), 3.80 (s, 3H), 2.60 (d, J=5.6 Hz, 3H), 1.64 (d, J=6.8 Hz, 3H); ES-LCMS m/z 439.2 [M+H]$^+$.

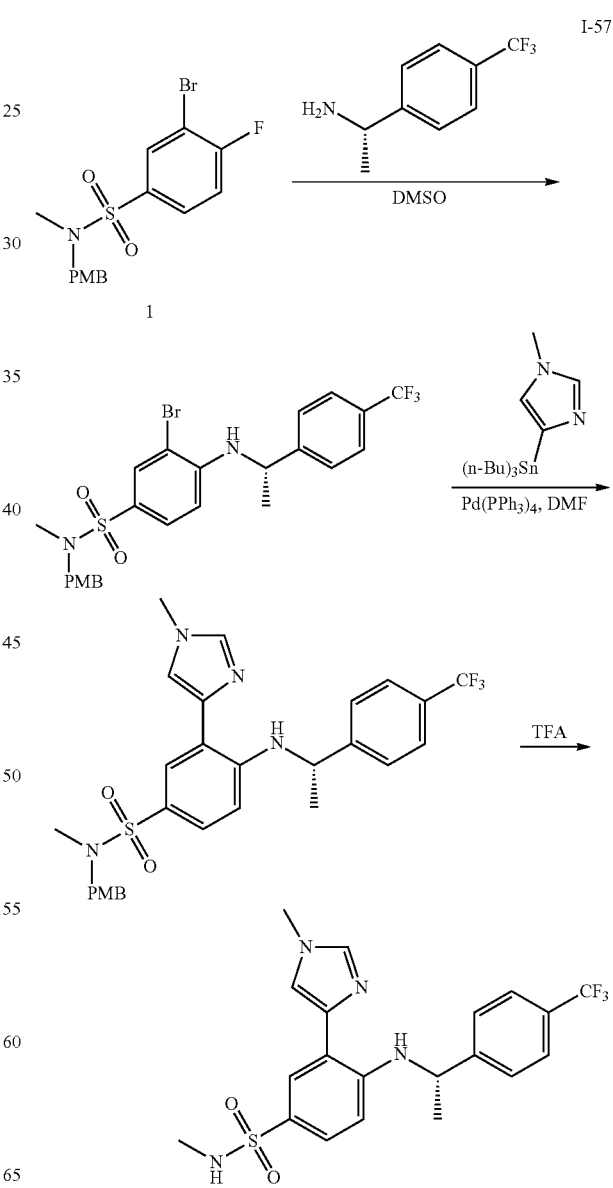

I-57

Step 1: 3-Bromo-N-[(4-methoxyphenyl)methyl]-N-methyl-4-[[(1S)-1-[4-(trifluoromethyl)phenyl]ethyl]amino]benzenesulfonamide

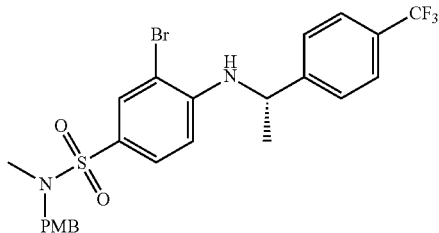

To a stirred solution of 3-bromo-4-fluoro-N-[(4-methoxyphenyl)methyl]-N-methyl-benzenesulfonamide (300 mg, 772.70 μmol, 1 eq) in DMSO (5 mL) was added DIEA (199.73 mg, 1.55 mmol, 269.17 μL, 2 eq) and (1S)-1-[4-(trifluoromethyl)phenyl]ethanamine (174.35 mg, 772.70 μmol, 1 eq, HCl). The reaction mixture was stirred at 140° C. for 12 h. The reaction mixture was diluted with water (50 mL), adjusted pH to 9-10 by saturated NaHCO$_3$ solution and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 3/1, TLC: PE/EtOAc=3/1, R$_f$=0.35) to yield 3-bromo-N-[(4-methoxyphenyl)methyl]-N-methyl-4-[[(1S)-1-[4-(trifluoromethyl)phenyl]ethyl]amino]benzenesulfonamide (80 mg, 121.13 μmol, 15.8% yield, 84.4% purity) as yellow oil. $^1$H NMR (500 MHz, DMSO-d$_6$) δ ppm 7.78 (d, J=2.1 Hz, 1H), 7.74-7.71 (m, 2H), 7.68-7.65 (m, 2H), 7.49 (dd, J=2.1, 8.8 Hz, 1H), 7.18 (d, J=8.5 Hz, 2H), 6.89 (d, J=8.5 Hz, 2H), 6.61 (d, J=8.9 Hz, 1H), 6.22 (d, J=7.0 Hz, 1H), 4.87 (quin, J=6.7 Hz, 1H), 3.97 (s, 2H), 3.73 (s, 3H), 2.42 (s, 3H), 1.59 (d, J=6.9 Hz, 3H); ES-LCMS m/z 557.1, 559.1 [M+H]$^+$.

Step 2: N-[(4-Methoxyphenyl)methyl]-N-methyl-3-(1-methylimidazol-4-yl)-4-[[(1S)-1-[4-(trifluoromethyl)phenyl]ethyl]amino]benzenesulfonamide

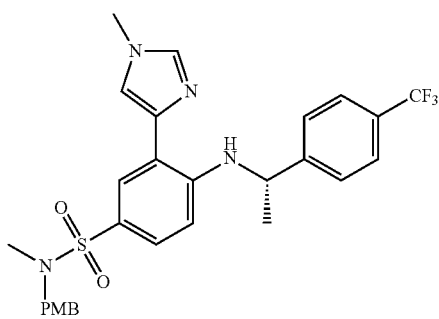

To a stirred solution of 3-bromo-N-[(4-methoxyphenyl)methyl]-N-methyl-4-[[(1S)-1-[4-(trifluoromethyl)phenyl]ethyl]amino]benzenesulfonamide (80 mg, 121.13 μmol, 1 eq) in DMF (4 mL) was added tributyl-(1-methylimidazol-4-yl)stannane (95.65 mg, 242.26 μmol, 2 eq) and Pd(PPh$_3$)$_4$ (7.00 mg, 6.06 μmol, 0.05 eq). The reaction mixture was stirred at 130° C. for 12 h. The reaction mixture was diluted with water (30 mL) then extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=1/1, R$_f$=0.45) to yield N-[(4-methoxyphenyl)methyl]-N-methyl-3-(1-methylimidazol-4-yl)-4-[[(1S)-1-[4-(trifluoromethyl)phenyl]ethyl]amino]benzenesulfonamide (50 mg, 89.51 μmol, 73.9% yield, 100.0% purity) as yellow oil. $^1$H NMR (500 MHz, CDCl$_3$) δ ppm 9.22 (d, J=5.5 Hz, 1H), 7.81 (d, J=2.1 Hz, 1H), 7.62-7.57 (m, 2H), 7.54 (s, 1H), 7.53-7.50 (m, 2H), 7.37 (dd, J=2.1, 8.9 Hz, 1H), 7.31 (d, J=1.1 Hz, 1H), 7.20 (d, J=8.7 Hz, 2H), 6.84 (d, J=8.7 Hz, 2H), 6.38 (d, J=8.7 Hz, 1H), 4.69 (quin, J=6.4 Hz, 1H), 4.05-3.96 (m, 2H), 3.81-3.76 (m, 6H), 2.54-2.46 (m, 3H), 1.65 (d, J=6.7 Hz, 3H); ES-LCMS m/z 559.2 [M+H]$^+$.

Step 3: N-Methyl-3-(1-methylimidazol-4-yl)-4-[[(1S)-1-[4-(trifluoromethyl)phenyl]ethyl]amino]benzenesulfonamide

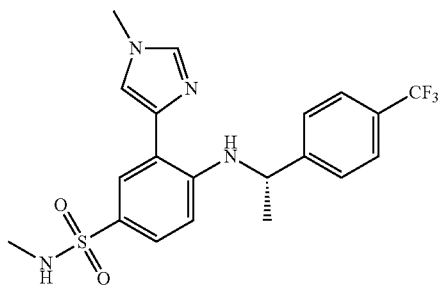 [SMILES: CNS(=O)(=O)c1ccc(N[C@@H](C)c2ccc(C(F)(F)F)cc2)c(-c2cn(C)cn2)c1]

To a stirred solution of N-[(4-methoxyphenyl)methyl]-N-methyl-3-(1-methylimidazol-4-yl)-4-[[(1S)-1-[4-(trifluoromethyl)phenyl]ethyl]amino]benzenesulfonamide (50 mg, 89.51 μmol, 100% purity, 1 eq) in DCM (10 mL) was added TFA (1.54 g, 13.51 mmol, 1 mL, 150.89 eq). The reaction mixture was stirred at 15° C. for 12 h. The reaction mixture was diluted with saturated NaHCO$_3$ solution (20 mL) then extracted with DCM (20 mL×2). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 44%-74%, 10 min). The desired fraction was lyophilized to yield N-methyl-3-(1-methylimidazol-4-yl)-4-[[(1S)-1-[4-(trifluoromethyl)phenyl]ethyl]amino]benzenesulfonamide (12.90 mg, 29.42 μmol, 32.9% yield, 100.0% purity, [α]$^{21.9}_D$=+34.8 (MeOH, c=0.023 g/100 mL)) as a white solid. $^1$H NMR (400 MHz, CDCl$_3$) δ ppm 9.22 (d, J=5.4 Hz, 1H), 7.84 (d, J=2.2 Hz, 1H), 7.62-7.55 (m, 2H), 7.54 (s, 1H), 7.52-7.46 (m, 2H), 7.38 (dd, J=2.1, 8.7 Hz, 1H), 7.31 (d, J=1.0 Hz, 1H), 6.35 (d, J=8.8 Hz, 1H), 4.68 (q, J=6.5 Hz, 1H), 4.08 (q, J=5.2 Hz, 1H), 3.80 (s, 3H), 2.60 (d, J=5.6 Hz, 3H), 1.64 (d, J=6.8 Hz, 3H); ES-LCMS m/z 439.2 [M+H]$^+$.

I-58 & I-59

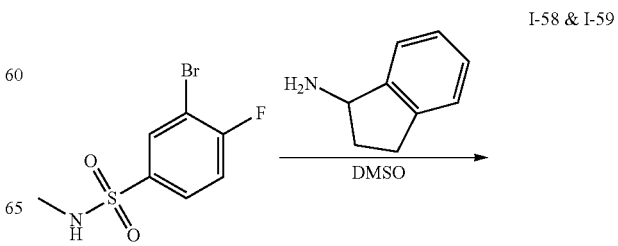

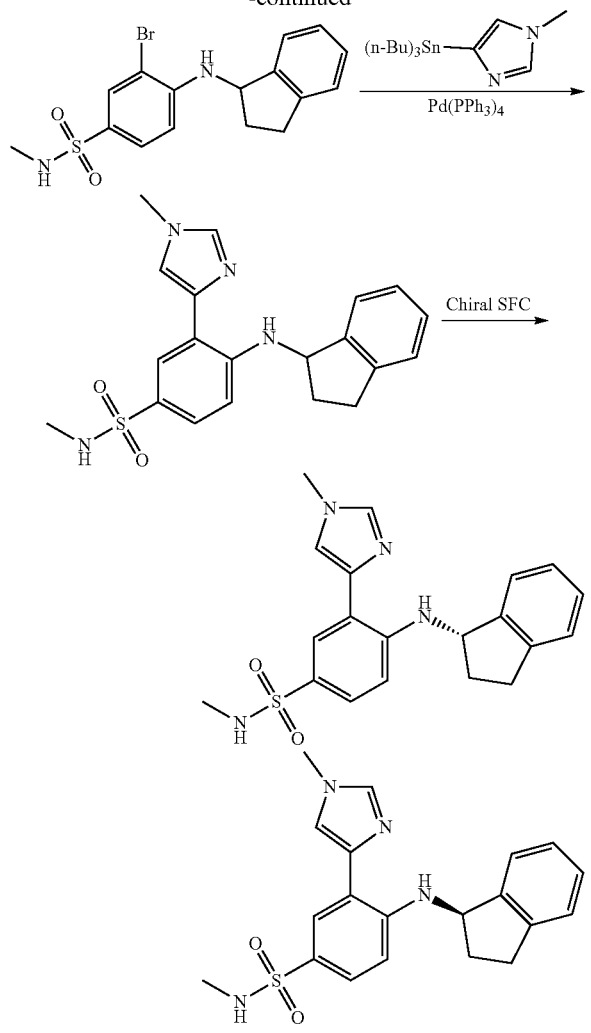

Step 1: 3-Bromo-4-(indan-1-ylamino)-N-methyl-benzenesulfonamide

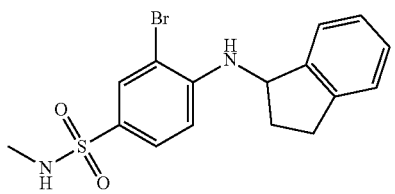 [SMILES: CNS(=O)(=O)c1ccc(NC2CCc3ccccc32)c(Br)c1]

A mixture of 3-bromo-4-fluoro-N-methyl-benzenesulfonamide (300 mg, 962.32 μmol, 1 eq), indan-1-amine (256.34 mg, 1.92 mmol, 246.48 μL, 2 eq) in DMSO (10 mL) was degassed and purged with $N_2$ for 3 times and stirred under $N_2$ atmosphere at 140° C. for 3 h. The reaction mixture was quenched by addition of water (50 mL) and extracted with EtOAc (50 mL×3). The organic layer was washed with brine (20 mL), dried over $Na_2SO_4$, filtered and concentrated under reduced pressure to yield a residue which was purified by flash silica gel chromatography (from PE/EtOAc=1/0 to 5/1, TLC: PE/EtOAc=5/1, $R_f$=0.46) and preparative HPLC (column: Agela DuraShell C18 150*25 mm*5 μm; mobile phase: [water (0.04% $NH_3.H_2O$+10 mM $NH_4HCO_3$)-ACN]; B %: 45%-75%, 10 min), followed by lyophilization to yield 3-bromo-4-(indan-1-ylamino)-N-methyl-benzenesulfonamide (140 mg, 367.18 μmol, 64.3% yield, 100.0% purity) as a white solid. $^1$H NMR (400 MHz, $CDCl_3$) δ ppm 7.96 (d, J=2.0 Hz, 1H), 7.71 (dd, J=2.3, 8.6 Hz, 1H), 7.37 (d, J=7.0 Hz, 1H), 7.33 (d, J=3.9 Hz, 2H), 7.31-7.25 (m, 2H), 6.88 (d, J=8.6 Hz, 1H), 3.13-3.06 (m, 1H), 3.01-2.92 (m, 1H), 2.68 (s, 3H), 2.01-1.91 (m, 1H), 1.61 (s, 1H), 1.27 (s, 1H); ES-LCMS m/z 381.3, 383.3 $[M+H]^+$.

Step 2: 4-[[(1S)-Indan-1-yl]amino]-N-methyl-3-(1-methylimidazol-4-yl)benzenesulfonamide and 4-[[(1R)-indan-1-yl]amino]-N-methyl-3-(1-methyl-imidazol-4-yl)benzenesulfonamide

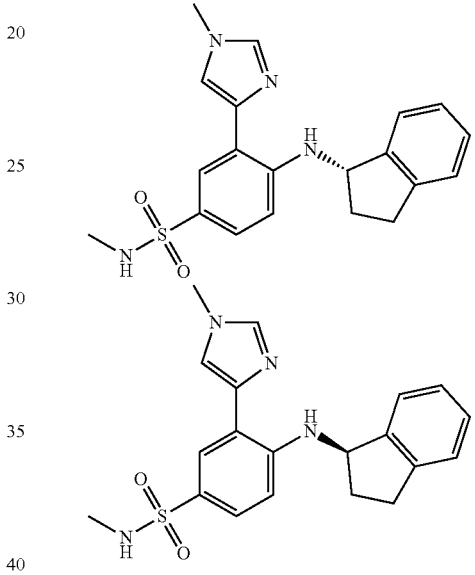

To a solution of 3-bromo-4-(indan-1-ylamino)-N-methyl-benzenesulfonamide (115 mg, 301.61 μmol, 100%, 1 eq), tributyl-(1-methylimidazol-4-yl)stannane (416.80 mg, 1.06 mmol, 94%, 3.5 eq) in DMF (10 mL) was added $Pd(PPh_3)_4$ (34.85 mg, 30.16 μmol, 0.1 eq). The mixture was stirred under $N_2$ atmosphere at 140° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated to yield a residue which was purified by preparative HPLC (column: DAICEL CHIRALPAK IG (250 mm*30 mm, 10 μm); mobile phase: [0.1% $NH_3.H_2O$/EtOH]; B %: 50%-50%), followed by lyophilization to yield product which was separated by SFC (column: DAICEL CHIRALPAK IG (250 mm*30 mm, 10 μm); mobile phase: [0.1% $NH_3.H_2O$ EtOH]; B %: 50%-50%) to yield peak 1 (2.745) and peak 2 (3.263). Peak 1 was purified by preparative HPLC (column: Agela DuraShell C18 150*25 mm*5 μm; mobile phase: [water (0.05% $NH_3.H_2O$+ 10 mM $NH_4HCO_3$)-ACN]; B %: 38%-68%, 10 min), followed by lyophilization to yield 4-[[(1S)-indan-1-yl]amino]-N-methyl-3-(1-methylimidazol-4-yl)benzenesulfonamide (13.44 mg, 35.14 μmol, 11.6% yield, 100.0% purity, SFC: Rt=2.745, ee=100%, $[α]^{19.6}_D$=+30.43 (MeOH, c=0.046 g/100 mL)) as a white solid. $^1$H NMR (400 MHz, DMSO-$d_6$) δ ppm 9.15 (d, J=7.0 Hz, 1H), 7.78 (d, J=2.3 Hz, 1H), 7.68

(s, 1H), 7.64 (s, 1H), 7.45 (d, J=10.6 Hz, 1H), 7.33-7.17 (m, 4H), 7.05-6.99 (m, 2H), 5.15 (d, J=7.8 Hz, 1H), 3.69 (s, 3H), 2.97 (s, 1H), 2.93-2.83 (m, 1H), 2.66 (s, 1H), 2.38 (d, J=5.1 Hz, 3H), 1.87-1.74 (m, 1H); ES-LCMS m/z 383.1 [M+H]+.

Peak 2 was concentrated under reduced pressure to yield a residue which was dissolved in MeCN (20 mL) and H$_2$O (10 mL) and lyophilized to yield 4-[[(1R)-indan-1-yl]amino]-N-methyl-3-(1-methylimidazol-4-yl)benzenesulfonamide (23.24 mg, 60.76 μmol, 20.1% yield, 100.0% purity, SFC: Rt=3.263, ee=100%, [α]$^{19.7}_D$=−42.55 (MeOH, c=0.047 g/100 mL)) as a white solid. $^1$H NMR (400 MHz, DMSO-d$_6$) δ ppm 9.15 (d, J=7.1 Hz, 1H), 7.79 (d, J=2.2 Hz, 1H), 7.68 (s, 1H), 7.64 (d, J=1.2 Hz, 1H), 7.46 (dd, J=2.1, 8.7 Hz, 1H), 7.33-7.19 (m, 4H), 7.05-6.99 (m, 2H), 5.16 (q, J=7.1 Hz, 1H), 3.70 (s, 3H), 3.03-2.94 (m, 1H), 2.94-2.83 (m, 1H), 2.69-2.64 (m, 1H), 2.39 (d, J=5.1 Hz, 3H), 1.84-1.73 (m, 1H); ES-LCMS m/z 383.1 [M+H]+.

I-60

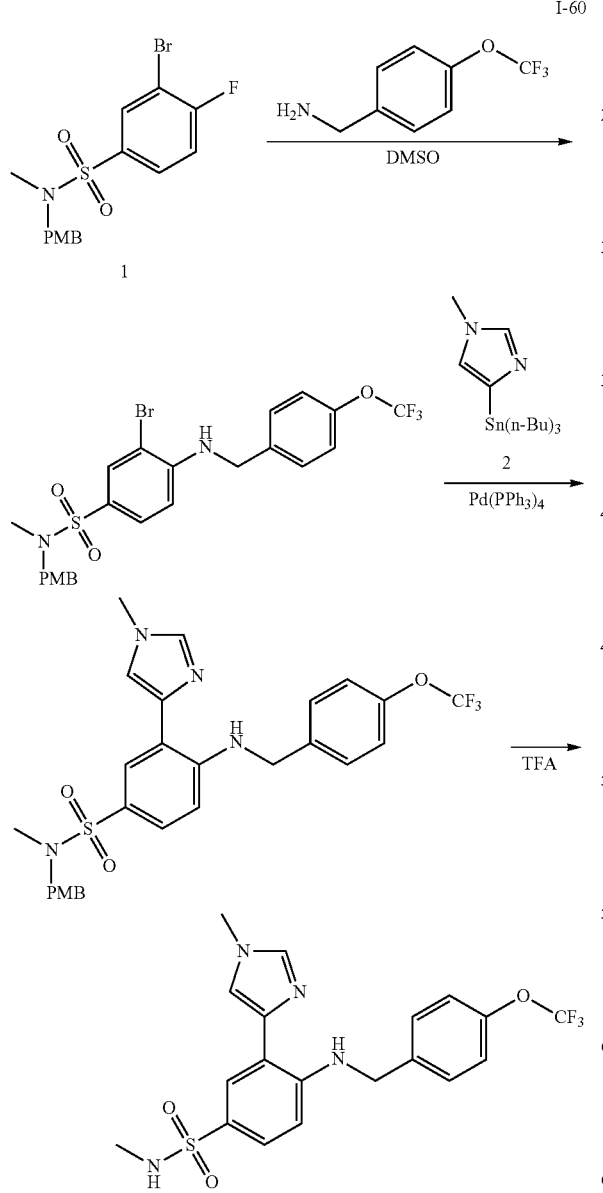

Step 1: 3-Bromo-N-(4-methoxybenzyl)-N-methyl-4-((4-(trifluoromethoxy)benzyl)amino)benzenesulfonamide

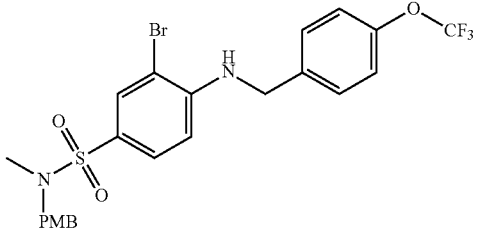

A solution of [4-(trifluoromethoxy)phenyl]methanamine (280.63 mg, 1.47 mmol, 224.50 μL, 2 eq) and 3-bromo-4-fluoro-N-[(4-methoxyphenyl)methyl]-N-methyl-benzenesulfonamide (300 mg, 734.06 μmol, 95% purity, 1 eq) in DMSO (5 mL) was stirred at 140° C. for 16 h. The reaction mixture was diluted with water (20 ml) and extracted with EtOAc (10 ml×3). The combined organic layers was washed with brine (20 mL), dried over Na$_2$SO$_4$, filtered and concentrated to yield a residue which was purified by silica gel column chromatography (from PE/EtOAc=10/1 to 3/1, TLC: PE/EtOAc=3/1, R$_f$=0.5) to yield 3-bromo-N-[(4-methoxyphenyl)methyl]-N-methyl-4-[[4-(trifluoromethoxy)phenyl]methylamino]benzenesulfonamide (340 mg, 547.02 μmol, 74.5% yield, 90.0% purity) as colorless oil. $^1$H NMR (400 MHz, CDCl$_3$) δ ppm 7.92 (d, J=2.0 Hz, 1H), 7.60 (dd, J=1.7, 8.6 Hz, 1H), 7.39 (d, J=8.6 Hz, 2H), 7.24 (t, J=9.0 Hz, 4H), 6.87 (d, J=8.6 Hz, 2H), 6.61-6.60 (m, 1H), 6.62 (d, J=8.8 Hz, 1H), 4.50 (d, J=5.6 Hz, 2H), 4.06 (s, 2H), 3.81 (s, 3H), 2.57 (s, 3H).

Step 2: N-(4-Methoxybenzyl)-N-methyl-3-(1-methyl-1H-imidazol-4-yl)-4-((4-(trifluoromethoxy)benzyl)amino)benzenesulfonamide

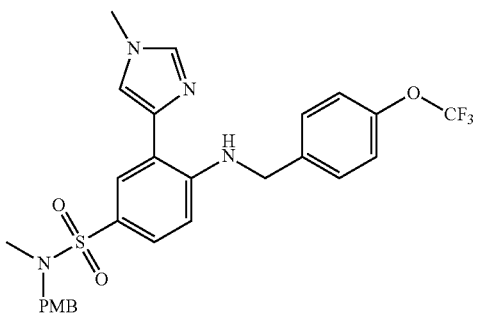

To a solution of 3-bromo-N-[(4-methoxyphenyl)methyl]-N-methyl-4-[[4-(trifluoromethoxy)phenyl]methylamino]benzenesulfonamide (340 mg, 547.02 μmol, 90% purity, 1 eq) and tributyl-(1-methylimidazol-4-yl)stannane (431.97 mg, 1.09 mmol, 94% purity, 2 eq) in DMF (5 mL) was added Pd(dppf)Cl$_2$ (40.03 mg, 54.70 μmol, 0.1 eq). The resulting mixture was stirred under N$_2$ atmosphere at 140° C. for 2 h. The reaction mixture was diluted with water (10 mL) and extracted with EtOAc (10 mL×3), washed with brine (20 mL), dried over Na$_2$SO$_4$, filtered and concentrated to yield a residue which was purified by silica gel column chromatography (from PE/EtOAc=5/1 to 1/1, TLC: PE/EtOAc=5/1, R$_f$=0.3) to yield N-[(4-methoxyphenyl)methyl]-N-methyl-3-(1-methylimidazol-4-yl)-4-[[4-(trifluoromethoxy)phenyl]methylamino]benzenesulfonamide (260 mg, 440.61 μmol, 80.6% yield, 95.0% purity) as yellow oil. $^1$H NMR (400 MHz, DMSO-d$_6$) δ ppm 9.39 (t, J=5.7 Hz, 1H), 7.87-7.78 (m, 3H), 7.50 (d, J=8.8 Hz, 2H), 7.42 (dd, J=2.1, 8.7 Hz, 1H), 7.36 (d, J=7.8 Hz, 2H), 7.22 (d, J=8.8 Hz, 2H), 6.90 (d, J=8.6 Hz, 2H), 6.73 (d, J=8.8 Hz, 1H), 4.59 (d, J=5.9 Hz, 2H), 3.97 (s, 2H), 3.74 (s, 6H), 2.44 (s, 3H); ES-LCMS m/z 561.2 [M+H]$^+$.

Step 3: N-Methyl-3-(1-methyl-1H-imidazol-4-yl)-4-((4-(trifluoromethoxy)benzyl)amino)benzenesulfonamide

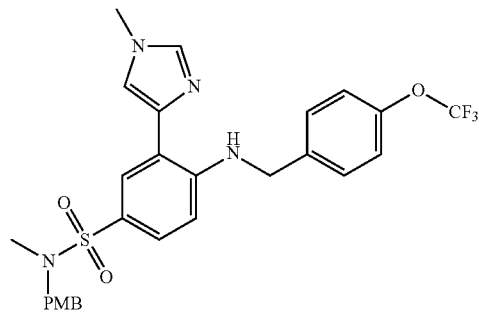

A solution of N-[(4-methoxyphenyl)methyl]-N-methyl-3-(1-methylimidazol-4-yl)-4-[[4-(trifluoromethoxy)phenyl]methylamino]benzenesulfonamide (90 mg, 152.52 μmol, 95% purity, 1 eq) and TFA (1.54 g, 13.51 mmol, 1 mL, 88.56 eq) in DCM (3 mL) was stirred at 15° C. for 2 h. The reaction mixture was concentrated to yield a residue which was purified by preparative HPLC (column: Welch Xtimate C18 150*25 mm*5 um; mobile phase: [water (10 mM NH$_4$HCO$_3$)-ACN]; B %: 40%-70%, 10 min) to yield N-methyl-3-(1-methylimidazol-4-yl)-4-[[4-(trifluoromethoxy)phenyl]methylamino]benzenesulfonamide (25.45 mg, 57.78 μmol, 37.9% yield, 100.0% purity) as a white solid. $^1$H NMR (400 MHz, DMSO-d$_6$) δ ppm 9.24 (t, J=5.9 Hz, 1H), 7.80 (s, 2H), 7.69 (d, J=1.2 Hz, 1H), 7.47 (d, J=8.6 Hz, 2H), 7.39-7.30 (m, 3H), 6.99 (d, J 5.1 Hz, 1H), 6.68 (d, J=8.8 Hz, 1H), 4.57 (d, J=5.9 Hz, 2H), 3.75 (s, 3H), 2.36 (d, J=5.1 Hz, 3H). ES-LCMS m/z 441.2 [M+H]$^+$.

I-61

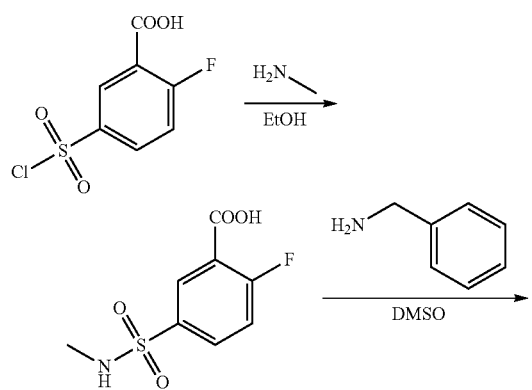

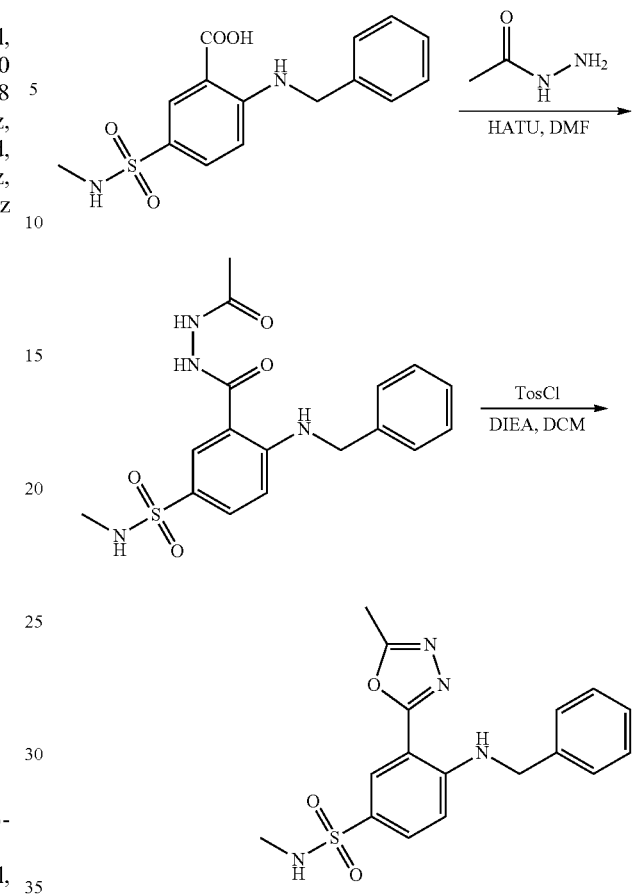

Step 1: 2-Fluoro-5-(methylsuLfamoyl)benzoic Acid

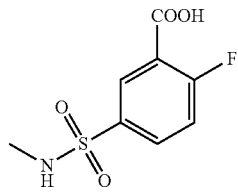

To a solution of 5-chlorosulfonyl-2-fluoro-benzoic acid (4.50 g, 18.86 mmol, 1 eq) in THF (100 mL) was added methanamine (4.44 g, 47.15 mmol, 10 mL, 33% purity, 2.5 eq). The mixture was stirred at −70° C. for 2 h. TLC (EtOAc, R$_f$=0.15) indicated starting material was consumed completely and one new spot formed. The mixture was adjusted to pH 3-4 with 1 N HCl, diluted with water (200 mL) and extracted with EtOAc (150 mL×3). The combined organic layers were washed with brine (50 mL), dried over Na$_2$SO$_4$, filtered and concentrated under reduced pressure to yield a 2-fluoro-5-(methylsulfamoyl)benzoic acid (3.9 g, 15.05 mmol, 79.8% yield, 90.0% purity) as a white solid. $^1$H NMR (400 MHz, DMSO-d$_6$) δ ppm 13.73 (s, 1H), 8.24 (dd, J=2.5, 6.8 Hz, 1H), 7.99 (ddd, J=2.3, 4.3, 8.6 Hz, 1H), 7.62 (q, J=4.7 Hz, 1H), 7.55 (dd, J=8.8, 10.4 Hz, 1H), 2.40 (d, J=4.7 Hz, 3H).

Step 2: 2-(Benzylamino)-5-(methylsulfamoyl)benzoic Acid

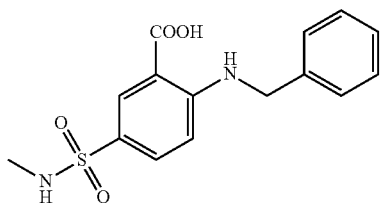 [SMILES: CNS(=O)(=O)c1ccc(NCc2ccccc2)c(C(=O)O)c1]

To a solution of 2-fluoro-5-(methylsulfamoyl)benzoic acid (3.9 g, 15.05 mmol, 1 eq) in DMSO (60 mL) was added phenylmethanamine (1.94 g, 18.06 mmol, 1.97 mL, 1.2 eq). The mixture was stirred at 140° C. for 4 h. The reaction mixture was quenched by addition of water (500 mL), extracted with EtOAc (500 mL×3). The combined organic layers were washed with brine (300 mL), dried over $Na_2SO_4$, filtered and concentrated under reduced pressure to give a residue which was added PE/EA (2/1, 250 mL) and stirred at 15° C. for 2 h. The slurry was filtered, rinsed with PE (50 mL) to yield 2-(benzylamino)-5-(methylsulfamoyl)benzoic acid (4.8 g, 14.68 mmol, 97.6% yield, 98.0% purity) as a white solid. $^1$H NMR (400 MHz, DMSO-$d_6$) δ ppm 13.21 (s, 1H), 8.75 (s, 1H), 8.19 (d, J=2.3 Hz, 1H), 7.60 (dd, J=2.3, 9.0 Hz, 1H), 7.38-7.31 (m, 4H), 7.29-7.22 (m, 1H), 7.15 (q, J=5.1 Hz, 1H), 6.82 (d, J=9.0 Hz, 1H), 4.53 (d, J=4.7 Hz, 2H), 2.32 (d, J=5.1 Hz, 3H); ES-LCMS m/z 320.7 [M+H]$^+$.

Step 3: 3-(Acetamidocarbamoyl)-4-(benzylamino)-N-methyl-benzenesulfonamide

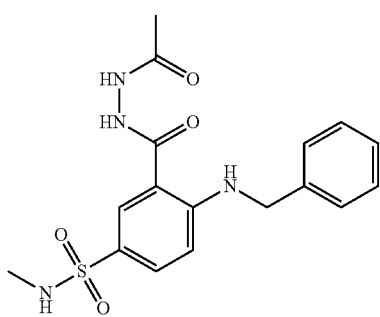 [SMILES: CNS(=O)(=O)c1ccc(NCc2ccccc2)c(C(=O)NNC(C)=O)c1]

To a solution of 2-(benzylamino)-5-(methylsulfamoyl)benzoic acid (1 g, 3.06 mmol, 98% purity, 1 eq) in DMF (20 mL) was added acetohydrazide (271.94 mg, 3.67 mmol, 1.2 eq), DIEA (1.19 g, 9.18 mmol, 1.60 mL, 3 eq) and HATU (2.09 g, 5.51 mmol, 1.8 eq). The mixture was stirred under $N_2$ atmosphere at 15° C. for 2 h. The reaction mixture was quenched by addition of water (250 mL) and extracted with EtOAc (150 mL×3). The combined organic layers were washed with brine (100 mL), dried over $Na_2SO_4$, filtered and concentrated under reduced pressure to yield a residue which was purified by flash silica gel chromatography (from PE/EtOAc=3/1 to 0/1, TLC:PE/EtOAc=0/1, $R_f$=0.32) to yield 3-(acetamidocarbamoyl)-4-(benzylamino)-N-methyl-benzenesulfonamide (500 mg, 1.20 mmol, 39.1% yield, 90.0% purity) as a white solid. $^1$H NMR (400 MHz, CDCl$_3$) δ ppm 9.46 (s, 1H), 8.48-8.38 (m, 2H), 8.10 (d, J=2.0 Hz, 1H), 7.63 (dd, J=2.0, 9.0 Hz, 1H), 7.38-7.27 (m, 5H), 6.62 (d, J=9.0 Hz, 1H), 5.17 (q, J=5.2 Hz, 1H), 4.41 (d, J=5.5 Hz, 2H), 2.52 (d, J=5.5 Hz, 3H), 2.03 (s, 3H).

Step 4: 4-(Benzylamino)-N-methyl-3-(5-methyl-1,3,4-oxadiazol-2-yl)benzenesulfonamide

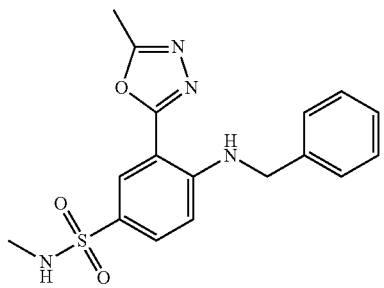 [SMILES: CNS(=O)(=O)c1ccc(NCc2ccccc2)c(-c2nnc(C)o2)c1]

To a solution of 3-(acetamidocarbamoyl)-4-(benzylamino)-N-methyl-benzenesulfonamide (100 mg, 239.09 µmol, 90% purity, 1 eq) in DCM (5 mL) was added TosCl (68.37 mg, 358.63 µmol, 1.5 eq) and DIEA (92.70 mg, 717.27 µmol, 124.9, 3 eq). The mixture was stirred under $N_2$ atmosphere at 15° C. for 2 h. The reaction mixture was concentrated under reduced pressure to yield a yellow solid (100 mg) which was added MeOH (10 mL) and stirred at 15° C. for 12 h. The suspension was filtered and the solid was collected, washed with MeOH (5 mL×2) and dried under reduced pressure to yield 4-(benzylamino)-N-methyl-3-(5-methyl-1,3,4-oxadiazol-2-yl)benzenesulfonamide (40.67 mg, 112.68 µmol, 47.1% yield, 99.3% purity) as a white solid. $^1$H NMR (500 MHz, DMSO-$d_6$) δ ppm 8.42 (t, J=5.7 Hz, 1H), 8.11 (d, J=2.3 Hz, 1H), 7.66 (dd, J=2.1, 9.0 Hz, 1H), 7.42-7.35 (m, 4H), 7.33-7.20 (m, 2H), 7.01 (d, J=9.2 Hz, 1H), 4.68 (d, J=5.6 Hz, 2H), 2.63 (s, 3H), 2.37 (d, J=5.0 Hz, 3H); ES-LCMS m/z 359.1 [M+H]$^+$.

I-62

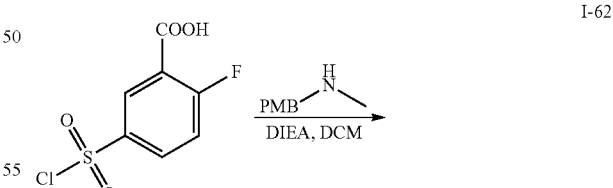

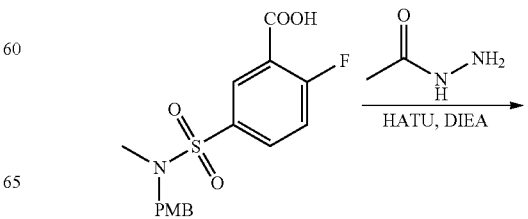

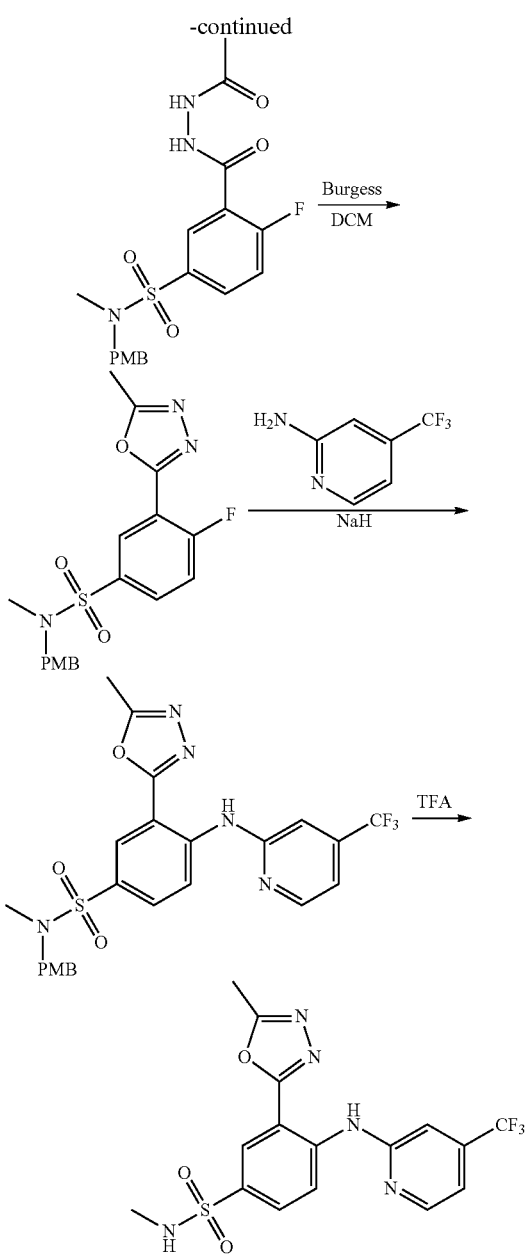

Step 1: 2-Fluoro-5-[(4-methoxyphenyl)methyl-methyl-sulfamoyl]benzoic acid

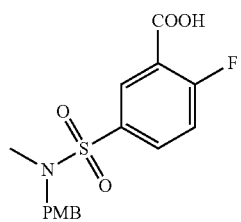

To a solution of 5-chlorosulfonyl-2-fluoro-benzoic acid (2 g, 8.38 mmol, 1 eq) in DCM (20 mL) was added DIEA (5.42 g, 41.91 mmol, 7.30 mL, 5 eq) and 1-(4-methoxyphenyl)-N-methyl-methanamine (1.58 g, 10.48 mmol, 1.25 eq) at −78° C. The mixture was stirred under $N_2$ atmosphere at −78° C. for 2 h. The mixture was quenched with HCl (1 M, 50 mL) and extracted with DCM (50 mL×2). The combined organic phase was washed with brine (20 mL), dried over anhydrous $Na_2SO_4$, filtered and concentrated in vacuum to yield 2-fluoro-5-[(4-methoxyphenyl)methyl-methyl-sulfamoyl]benzoic acid (2.2 g, 4.98 mmol, 59.4% yield, 80.0% purity) as a yellow solid, which was used in the next step without further purification. $^1$H NMR (500 MHz, $CDCl_3$) δ ppm 8.55 (dd, J=2.4, 6.5 Hz, 1H), 8.12-8.09 (m, 1H), 7.42 (t, J=9.3 Hz, 1H), 7.29 (s, 1H), 6.93 (d, J=8.5 Hz, 2H), 4.20 (s, 2H), 3.87 (s, 3H), 2.70 (s, 3H); ES-LCMS m/z 376.0 $[M+Na]^+$.

Step 2: 3-(Acetamidocarbamoyl)-4-fluoro-N-[(4-methoxyphenyl)methyl]-N-methyl-benzenesulfonamide

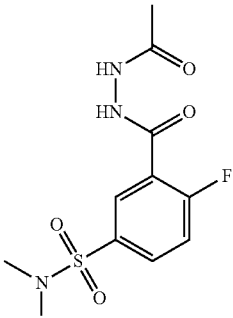

To a solution of 2-fluoro-5-[(4-methoxyphenyl)methyl-methyl-sulfamoyl]benzoic acid (400 mg, 905.58 μmol, 80%, 1 eq) and acetohydrazide (335.43 mg, 4.53 mmol, 5 eq) in DMF (10 mL) was added DIEA (351.11 mg, 2.72 mmol, 473.20 μL, 3 eq) and HATU (619.79 mg, 1.63 mmol, 1.8 eq). The mixture was stirred at 25° C. for 0.5 h. The mixture was quenched with water (100 mL) and extracted with EtOAc (100 mL×3). The combined organic phase was washed with brine (20 mL), dried over anhydrous $Na_2SO_4$, filtered and concentrated in vacuum to yield a residue which was purified by flash silica gel chromatography (from DCM/MeOH=100/1 to 10/1, TLC: DCM/MeOH=10/1, $R_f$=0.42) to yield 3-(acetamidocarbamoyl)-4-fluoro-N-[(4-methoxyphenyl)methyl]-N-methyl-benzenesulfonamide (350 mg, 692.42 μmol, 76.5% yield, 81.0% purity) as a yellow solid. $^1$H NMR (400 MHz, $CDCl_3$) δ ppm 9.29 (s, 1H), 8.58 (d, J=6.7 Hz, 1H), 8.47 (d, J=4.7 Hz, 1H), 8.01 (d, J=5.5 Hz, 1H), 7.41-7.35 (m, 1H), 7.22 (d, J=8.6 Hz, 2H), 6.88 (d, J=8.6 Hz, 2H), 4.13 (s, 2H), 3.81 (s, 3H), 2.63 (s, 3H), 2.17 (s, 3H); ES-LCMS m/z 410.2 $[M+H]^+$.

Step 3: 4-Fluoro-N-[(4-methoxyphenyl)methyl]-N-methyl-3-(5-methyl-1,3,4-oxadiazol-2-yl)benzenesulfonamide

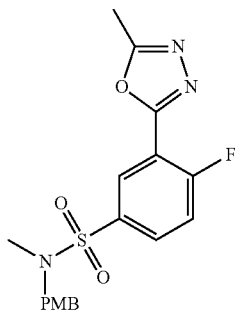

3-(Acetamidocarbamoyl)-4-fluoro-N-[(4-methoxyphenyl)methyl]-N-methyl-benzenesulfonamide (300 mg, 593.51 μmol, 81%, 1 eq) and burgess reagent (565.74 mg, 2.37 mmol, 4 eq) were taken up into a microwave tube in DCM (3 mL). The sealed tube was heated at 90° C. for 3 h under microwave. The reaction mixture was concentrated under reduced pressure to yield 4-fluoro-N-[(4-methoxyphenyl)methyl]-N-methyl-3-(5-methyl-1,3,4-oxadiazol-2-yl)benzenesulfonamide (200 mg, 398.55 μmol, 67.2% yield, 78.0% purity) as a yellow solid, which was used in the next step without further purification. $^1$H NMR (400 MHz, CDCl$_3$) δ ppm 8.49 (dd, J=2.3, 6.7 Hz, 1H), 8.00-7.97 (m, 1H), 7.44 (t, J=9.4 Hz, 1H), 7.22 (d, J=8.6 Hz, 2H), 6.89-6.85 (m, 2H), 4.16 (s, 2H), 3.80 (s, 3H), 2.69 (s, 3H), 2.66 (s, 3H); ES-LCMS m/z 392.2 [M+H]$^+$.

Step 4: N-[(4-Methoxyphenyl)methyl]-N-methyl-3-(5-methyl-1,3,4-oxadiazol-2-yl)-4-[[4-(trifluoromethyl)-2-pyridyl]amino]benzenesulfonamide

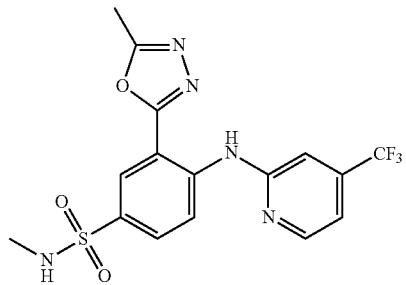

To a solution of 4-(trifluoromethyl)pyridin-2-amine (129.22 mg, 797.11 μmol, 2 eq) in DMF (10 mL) was added NaH (47.82 mg, 1.20 mmol, 60%, 3 eq) at 0° C. The mixture was stirred at 25° C. for 0.5 h. 4-Fluoro-N-[(4-methoxyphenyl)methyl]-N-methyl-3-(5-methyl-1,3,4-oxadiazol-2-yl)benzenesulfonamide (200 mg, 398.55 μmol, 78%, 1 eq) was added into the above mixture. The mixture was stirred at 25° C. for 0.5 h. TLC (PE/EtOAc=0/1, R$_f$=0.32) indicated the starting material was consumed completely and two new spots formed. The mixture was diluted with water (30 mL) and extracted with EtOAc (30 mL×3). The combined organic phase was washed with brine (20 mL), dried over anhydrous Na$_2$SO$_4$, filtered and concentrated in vacuum to yield N-[(4-methoxyphenyl)methyl]-N-methyl-3-(5-methyl-1,3,4-oxadiazol-2-yl)-4-[[4-(trifluoromethyl)-2-pyridyl]amino]benzenesulfonamide (200 mg, 277.40 μmol, 69.6% yield, 74.0% purity) as a yellow solid, which was used in the next step without further purification. $^1$H NMR (400 MHz, CDCl$_3$) δ ppm 11.07 (s, 1H), 9.22 (d, J=9.0 Hz, 1H), 8.53 (d, J=5.1 Hz, 1H), 8.38 (d, J=2.3 Hz, 1H), 7.92 (dd, J=2.2, 9.2 Hz, 1H), 7.24 (d, J=8.6 Hz, 3H), 7.15 (d, J=4.7 Hz, 1H), 6.89-6.86 (m, 2H), 4.14 (s, 2H), 3.81 (s, 3H), 2.71 (s, 3H), 2.63 (s, 3H); ES-LCMS m/z 534.1 [M+H]$^+$.

Step 5: N-Methyl-3-(5-methyl-1,3,4-oxadiazol-2-yl)-4-[[4-(trifluoromethyl)-2-pyridyl]amino]benzenesulfonamide

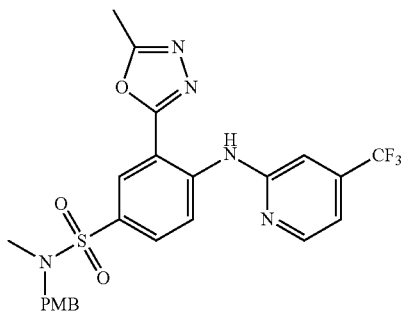

A solution of N-[(4-methoxyphenyl)methyl]-N-methyl-3-(5-methyl-1,3,4-oxadiazol-2-yl)-4-[[4-(trifluoromethyl)-2-pyridyl]amino]benzenesulfonamide (180 mg, 249.66 μmol, 74%, 1 eq) in DCM (6 mL) and TFA (2.05 g, 17.99 mmol, 1.33 mL, 72.06 eq) was stirred at 25° C. for 1 h. The reaction mixture was concentrated under reduced pressure. The residue was basified with sat. aq. NaHCO$_3$ (30 mL) and extracted with EtOAc (30 mL×3). The combined organic phase was washed with brine (20 mL), dried over anhydrous Na$_2$SO$_4$, filtered and concentrated in vacuum to yield a residue which was purified by preparative HPLC (column: Agela DuraShell C18 150*25 mm*5 μm; mobile phase: [water (0.04% NH$_3$.H$_2$O+10 mM NH$_4$HCO$_3$)-ACN]; B %: 48%-68%, 10 min), followed by lyophilization to yield N-methyl-3-(5-methyl-1,3,4-oxadiazol-2-yl)-4-[[4-(trifluoromethyl)-2-pyridyl]amino]benzenesulfonamide (94.9 mg, 217.87 μmol, 87.3% yield, 94.9% purity) as a white solid. $^1$H NMR (500 MHz, CDCl$_3$) δ ppm 11.05 (s, 1H), 9.19 (d, J=9.2 Hz, 1H), 8.52 (d, J=5.2 Hz, 1H), 8.43 (d, J=2.3 Hz, 1H), 7.94 (dd, J=2.3, 9.2 Hz, 1H), 7.24 (s, 1H), 7.15 (d, J=5.2 Hz, 1H), 4.39-4.30 (m, 1H), 2.73-2.70 (m, 6H); ES-LCMS m/z 414.0 [M+H]$^+$.

I-63

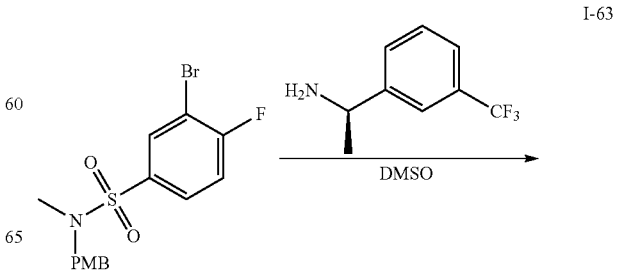

227
-continued

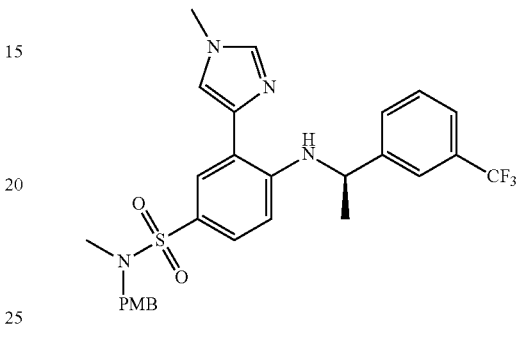

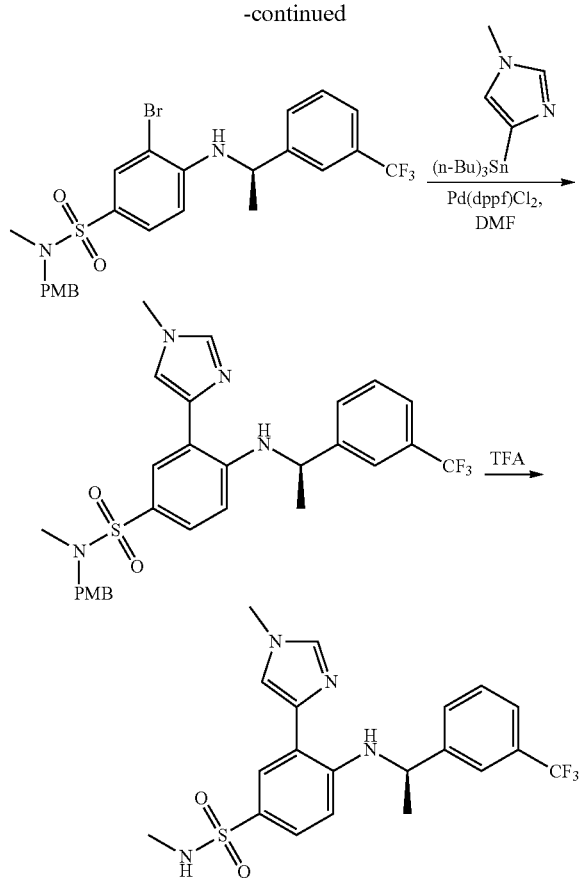

Step 1: 3-Bromo-N-[(4-methoxyphenyl)methyl]-N-methyl-4-[[(1R)-1-[3-(trifluoromethyl)phenyl]ethyl]amino]benzenesulfonamide

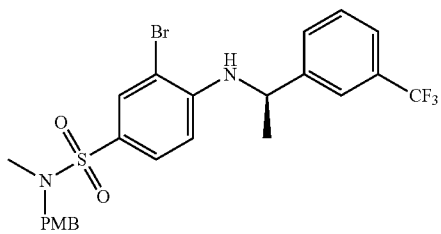

A mixture of 3-bromo-4-fluoro-N-[(4-methoxyphenyl)methyl]-N-methyl-benzenesulfonamide (250 mg, 611.72 μmol, 95% purity, 1 eq), (1R)-1-[3-(trifluoromethyl)phenyl]ethanamine (145 mg, 642.62 μmol, 1.05 eq, HCl) and DIEA (80 mg, 618.99 μmol, 107.82 μL, 1.01 eq) in DMSO (1 mL) was stirred at 140° C. for 2 h. The reaction mixture was filtered. The filtrate was purified by preparative HPLC (column: Phenomenex Synergi C18 150*30 mm*4 um; mobile phase: [water (0.1% TFA)-ACN]; B %: 74%-94%, 9 min). The desired fraction was basified with saturated aqueous NaHCO₃ until pH=8 and extracted with EtOAc (50 mL×3). The organic layer was dried over Na₂SO₄, filtered and concentrated under reduced pressure to yield 3-bromo-N-[(4-methoxyphenyl)methyl]-N-methyl-4-[[(1R)-1-[3-(trifluoromethyl)phenyl]ethyl]amino]benzenesulfonamide (80 mg, 143.52 μmol, 23.5% yield, 100.0% purity) as an off-white solid. $^1$H NMR (500 MHz, CDCl$_3$) δ ppm 7.91 (d, J=2.0 Hz, 1H), 7.59 (s, 1H), 7.58-7.46 (m, 4H), 7.20 (d, J=8.7 Hz, 2H), 6.85 (d, J=8.7 Hz, 2H), 6.37 (d, J=8.7 Hz, 1H), 5.19 (d, J=5.2 Hz, 1H), 4.65 (q, J=6.3 Hz, 1H), 4.03 (s, 2H), 3.80 (s, 3H), 2.53 (s, 3H), 1.67 (d, J=6.7 Hz, 3H); ES-LCMS m/z 557.1, 559.1 [M+H]$^+$.

Step 2: N-[(4-Methoxyphenyl)methyl]-N-methyl-3-(1-methylimidazol-4-yl)-4-[[(1R)-1-[3-(trifluoromethyl)phenyl]ethyl]amino]benzenesulfonamide

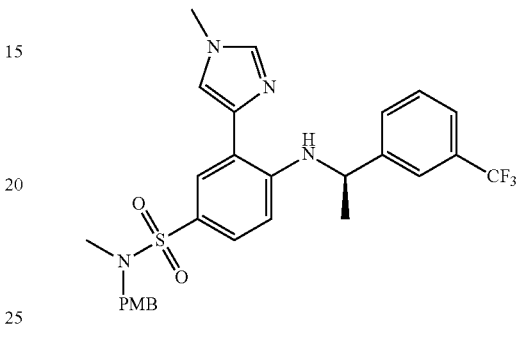

A mixture of 3-bromo-N-[(4-methoxyphenyl)methyl]-N-methyl-4-[[(1R)-1-[3-(trifluoromethyl)phenyl]ethyl]amino]benzenesulfonamide (70 mg, 125.58 μmol, 100% purity, 1 eq), tributyl-(1-methylimidazol-4-yl)stannane (140 mg, 371.17 μmol, 98.4% purity, 2.96 eq) and Pd(dppf)Cl$_2$ (10 mg, 13.67 μmol, 1.09e-1 eq) in DMF (3 mL) was stirred under N$_2$ atmosphere at 130° C. for 12 h. TLC (PE/EtOAc=1/1, R$_f$=0.14) showed the starting material was consumed completely. The reaction mixture was concentrated under reduced pressure to yield a residue which was purified by flash silica gel chromatography (from PE/EtOAc=10/1 to 1/1, TLC: PE/EtOAc=1/1, R$_f$=0.14) to yield N-[(4-methoxyphenyl)methyl]-N-methyl-3-(1-methylimidazol-4-yl)-4-[[(1R)-1-[3-(trifluoromethyl)phenyl]ethyl]amino]benzenesulfonamide (50 mg, 87.72 μmol, 69.9% yield, 98.0% purity) as a colorless gum. $^1$H NMR (500 MHz, CDCl$_3$) δ ppm 9.20 (br s, 1H), 7.80 (d, J=2.1 Hz, 1H), 7.65 (s, 1H), 7.58 (d, J=7.6 Hz, 1H), 7.54 (s, 1H), 7.53-7.50 (m, 1H), 7.47-7.42 (m, 1H), 7.38 (dd, J=2.2, 8.8 Hz, 1H), 7.31 (d, J=1.1 Hz, 1H), 7.20 (d, J=8.5 Hz, 2H), 6.84 (d, J=8.7 Hz, 2H), 6.39 (d, J=8.9 Hz, 1H), 4.69 (d, J=6.1 Hz, 1H), 4.00 (s, 2H), 3.80 (s, 3H), 3.79 (s, 3H), 2.50 (s, 3H), 1.66 (d, J=6.7 Hz, 3H); ES-LCMS m/z 559.2 [M+H]$^+$.

Step 3: N-Methyl-3-(1-methylimidazol-4-yl)-4-[[(1R)-1-[3-(trifluoromethyl)phenyl]ethyl]amino]benzenesulfonamide

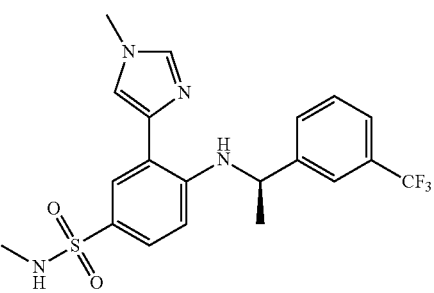 [SMILES: CNS(=O)(=O)c1ccc(N[C@H](C)c2cccc(C(F)(F)F)c2)c(-c2cn(C)cn2)c1]

To a solution of N-[(4-methoxyphenyl)methyl]-N-methyl-3-(1-methylimidazol-4-yl)-4-[[(1R)-1-[3-(trifluoromethyl)phenyl]ethyl]amino]benzenesulfonamide (50 mg, 87.72 μmol, 98.0% purity, 1 eq) in DCM (3 mL) was added TFA (770.00 mg, 6.75 mmol, 0.5 mL, 76.99 eq). The mixture was stirred at 15° C. for 12 h. The reaction mixture was concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 40%-70%, 10 min) and lyophilized to yield N-methyl-3-(1-methylimidazol-4-yl)-4-[[(1R)-1-[3-(trifluoromethyl)phenyl]ethyl]amino]benzenesulfonamide (18.57 mg, 41.37 μmol, 47.2% yield, 97.7% purity, SFC: Rt=4.154, ee=100.000%, [α]$^{20.6}_D$=−168.00 (MeOH, c=0.100 g/100 mL)) as a white solid. $^1$H NMR (500 MHz, CD$_3$OD) δ ppm 7.83 (d, J=2.1 Hz, 1H), 7.75 (s, 1H), 7.70 (s, 1H), 7.67 (d, J=6.7 Hz, 1H), 7.55-7.49 (m, 3H), 7.37 (dd, J=2.2, 8.8 Hz, 1H), 6.46 (d, J=8.9 Hz, 1H), 4.80 (q, J=6.6 Hz, 1H), 3.85 (s, 3H), 2.47 (s, 3H), 1.61 (d, J=6.7 Hz, 3H); ES-LCMS m/z 439.2 [M+H]$^+$.

To a solution of 3-bromo-4-fluoro-N-methyl-benzenesulfonamide (600 mg, 2.24 mmol, 100% purity, 1 eq) in DMSO (2 mL) was added 1,3-benzodioxol-5-ylmethanamine (676.59 mg, 4.48 mmol, 559.16 μL, 2 eq). The mixture was stirred under N$_2$ atmosphere at 140° C. for 12 h. The reaction mixture was diluted with water (30 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=2/1, R$_f$=0.45) to yield 4-(1,3-benzodioxol-5-ylmethylamino)-3-bromo-N-methyl-benzenesulfonamide (890 mg, 2.17 mmol, 96.9% yield, 97.2% purity) as a yellow solid. $^1$H NMR (500 MHz, DMSO-d$_6$) δ ppm 7.73 (d, J=2.1 Hz, 1H), 7.44 (dd, J=2.0, 8.7 Hz, 1H), 7.14 (q, J=5.0 Hz, 1H), 6.91 (d, J=1.1 Hz, 1H), 6.87-6.80 (m, 2H), 6.71 (t, J=6.2 Hz, 1H), 6.67 (d, J=8.7 Hz, 1H), 5.97 (s, 2H), 4.37 (d, J=6.3 Hz, 2H), 2.33 (d, J=5.2 Hz, 3H).

Step 2: 4-(1,3-Benzodioxol-5-ylmethylamino)-N-methyl-3-(1-methylimidazol-4-yl)benzenesulfonamide

I-64

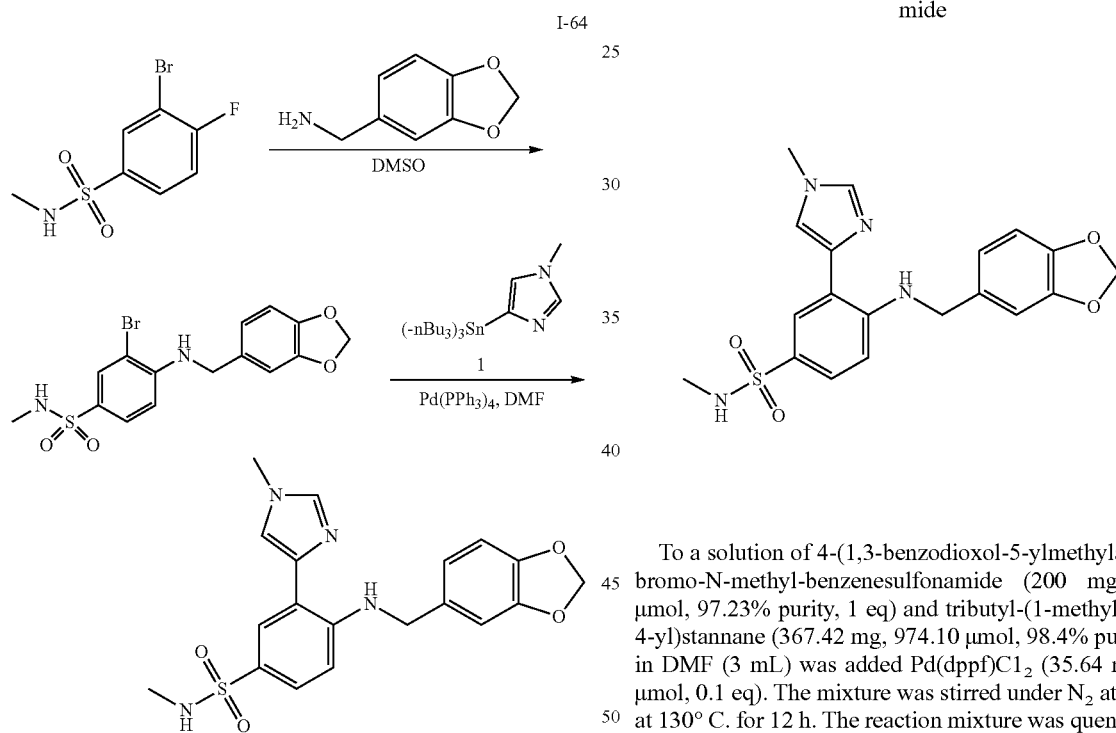

Step 1: 4-(1,3-Benzodioxol-5-ylmethylamino)-3-bromo-N-methyl-benzenesulfonamide

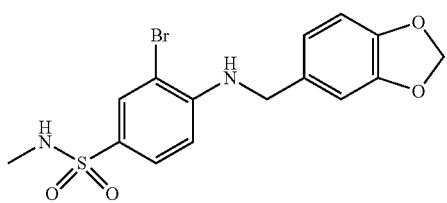 [SMILES: CNS(=O)(=O)c1ccc(NCc2ccc3c(c2)OCO3)c(Br)c1]

To a solution of 4-(1,3-benzodioxol-5-ylmethylamino)-3-bromo-N-methyl-benzenesulfonamide (200 mg, 487.05 μmol, 97.23% purity, 1 eq) and tributyl-(1-methylimidazol-4-yl)stannane (367.42 mg, 974.10 μmol, 98.4% purity, 2 eq) in DMF (3 mL) was added Pd(dppf)Cl$_2$ (35.64 mg, 48.71 μmol, 0.1 eq). The mixture was stirred under N$_2$ atmosphere at 130° C. for 12 h. The reaction mixture was quenched with aqueous KF (10 mL, 2M) and extracted with EtOAc (20 mL×3). The organic layer was washed with water (20 mL×2) and brine (20 mL), dried over Na$_2$SO$_4$, filtered and concentrated under reduced pressure to yield a residue which was purified by preparative HPLC (column: Welch Xtimate C18 150*25 mm*5 μm; mobile phase: [water (10 mM NH$_4$HCO$_3$)-ACN]; B %: 30%-60%, 10 min) to yield 4-(1,3-benzodioxol-5-ylmethylamino)-N-methyl-3-(1-methylimidazol-4-yl)benzenesulfonamide (50 mg, 121.86 μmol, 25.0% yield, 97.8% purity) as a white solid. $^1$H NMR (400 MHz, CDCl$_3$) δ ppm 9.04 (t, J=5.1 Hz, 1H), 7.85 (d, J=2.2 Hz, 1H), 7.54-7.45 (m, 2H), 7.28 (d, J=1.2 Hz, 1H), 6.88-6.82 (m, 2H), 6.80-6.76 (m, 1H), 6.62 (d, J=8.8 Hz, 1H), 5.95 (s, 2H), 4.44 (d, J=5.6 Hz, 2H), 4.15 (q, J=5.3 Hz, 1H), 3.77 (s, 3H), 2.62 (d, J=5.6 Hz, 3H); ES-LCMS m/z 401.2 [M+H]$^+$.

I-65

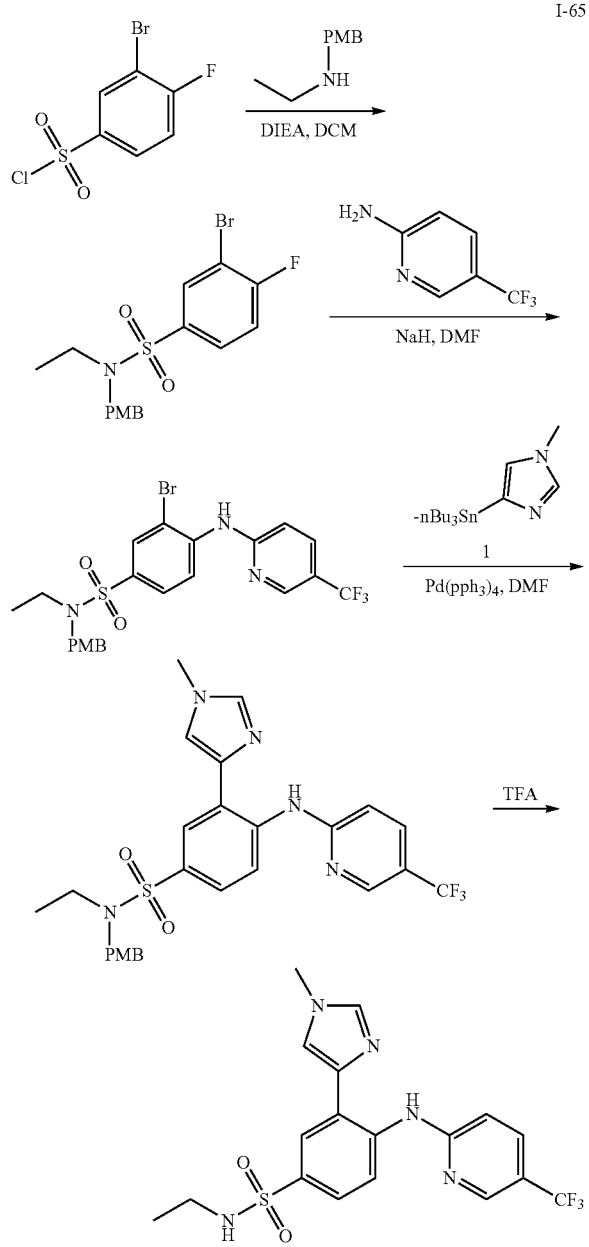

Step 1: 3-Bromo-N-ethyl-4-fluoro-N-[(4-methoxyphenyl)methyl]benzenesulfonamide

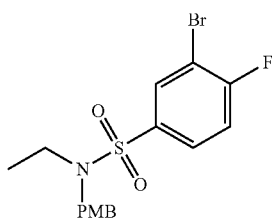

To a solution of 3-bromo-4-fluoro-benzenesulfonyl chloride (1.5 g, 5.48 mmol, 1 eq) and N-[(4-methoxyphenyl)methyl]ethanamine (1.13 g, 6.86 mmol, 1.25 eq) in DCM (10 mL) was added DIEA (3.54 g, 27.42 mmol, 4.78 mL, 5 eq). The mixture was stirred under N₂ atmosphere at 15° C. for 2 h. The reaction mixture was acidified with aqueous HCl (1 M) until pH=5, diluted with water (30 mL) and extracted with DCM (10 mL×3). The organic layer was washed with brine (30 mL), dried over Na₂SO₄, filtered and the filtrate was concentrated. To the residue was added PE (20 mL). The mixture was stirred at 15° C. for 0.5 h and filtered. The solid was washed with PE (30 mL×2), dried under vacuum to yield 3-bromo-N-ethyl-4-fluoro-N-[(4-methoxyphenyl)methyl]benzenesulfonamide (1.8 g, 4.39 mmol, 80.1% yield, 98.2% purity) as a yellow solid. ¹H NMR (500 MHz, DMSO-d₆) δ ppm 8.09 (dd, J=2.3, 6.4 Hz, 1H), 7.92 (ddd, J=2.3, 4.6, 8.7 Hz, 1H), 7.62 (t, J=8.6 Hz, 1H), 7.23 (d, J=8.5 Hz, 2H), 6.90 (d, J=8.5 Hz, 2H), 4.29 (s, 2H), 3.74 (s, 3H), 3.14 (q, J=7.2 Hz, 2H), 0.86 (t, J=7.1 Hz, 3H).

Step 2: 3-Bromo-N-ethyl-N-[(4-methoxyphenyl)methyl]-4-[[5-(trifluoromethyl)-2-pyridyl]amino]benzenesulfonamide

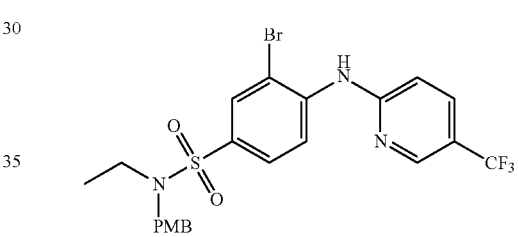

To a solution of 5-(trifluoromethyl)pyridin-2-amine (197.87 mg, 1.22 mmol, 1 eq) in DMF (2 mL) was added NaH (146.45 mg, 3.66 mmol, 60% purity, 3 eq) at 0° C. under N₂. After being stirred for 30 min, 3-bromo-N-ethyl-4-fluoro-N-[(4-methoxyphenyl)methyl]benzenesulfonamide (500 mg, 1.22 mmol, 98.2% purity, 1 eq) was added at 0° C. The mixture was stirred at 15° C. for 4 h. The reaction mixture was diluted with water (50 mL) and extracted with EtOAc (30 mL×3). The combined organic layers were washed with brine (10 mL), dried over Na₂SO₄, filtered and concentrated under reduced pressure to yield a residue which was purified by flash silica gel chromatography (from PE/EtOAc=100/1 to 2/1, TLC: PE/EtOAc=2/1, R_f=0.65) to yield 3-bromo-N-ethyl-N-[(4-methoxyphenyl)methyl]-4-[[5-(trifluoromethyl)-2-pyridyl]amino]benzenesulfonamide (670 mg, 1.20 mmol, 98.3% yield, 97.5% purity) as a yellow solid. ¹H NMR (500 MHz, DMSO-d₆) δ ppm 9.25 (s, 1H), 8.51 (s, 1H), 8.17 (d, J=8.7 Hz, 1H), 8.03-7.96 (m, 2H), 7.81 (dd, J=2.1, 8.7 Hz, 1H), 7.29-7.23 (m, 3H), 6.91 (d, J=8.7 Hz, 2H), 4.29 (s, 2H), 3.74 (s, 3H), 3.13 (q, J=7.1 Hz, 2H), 0.86 (t, J=7.1 Hz, 3H); ES-LCMS m/z 544.0, 546.0 [M+H]⁺.

Step 3: N-Ethyl-N-[(4-methoxyphenyl)methyl]-3-(1-methylimidazol-4-yl)-4-[[5-(trifluoromethyl)-2-pyridyl]amino]benzenesulfonamide

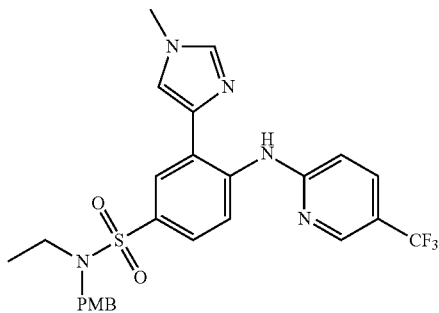

To a solution of 3-bromo-N-ethyl-N-[(4-methoxyphenyl)methyl]-4-[[5-(trifluoromethyl)-2-pyridyl]amino]benzenesulfonamide (400 mg, 716.41 μmol, 97.5% purity, 1 eq) in DMF (10 mL) was added tributyl-(1-methylimidazol-4-yl)stannane (810.65 mg, 2.15 mmol, 98.4% purity, 3 eq) and Pd(dppf)Cl$_2$ (52.42 mg, 71.64 μmol, 0.1 eq). The mixture was stirred under N$_2$ atmosphere at 130° C. for 12 h. The reaction mixture was quenched with aqueous KF (5 mL, 2M) and extracted with EtOAc (10 mL×3). The organic layers were washed with water (10 mL×2) and brine (10 mL), dried over Na$_2$SO$_4$, filtered and concentrated under reduced pressure to yield a residue which was purified by flash silica gel chromatography (from PE/EtOAc=100/1 to 2/1, TLC: PE/EtOAc=0/1, R$_f$=0.45) to yield N-ethyl-N-[(4-methoxyphenyl)methyl]-3-(1-methylimidazol-4-yl)-4-[[5-(trifluoromethyl)-2-pyridyl]amino]benzenesulfonamide (350 mg, 637.03 μmol, 88.9% yield, 99.3% purity) as a yellow oil. $^1$H NMR (500 MHz, DMSO-d$_6$) δ ppm 12.47 (s, 1H), 8.79 (d, J=8.9 Hz, 1H), 8.61 (s, 1H), 8.04 (d, J=2.1 Hz, 1H), 7.97 (dd, J=2.3, 8.9 Hz, 1H), 7.95 (s, 2H), 7.67 (dd, J=2.2, 8.8 Hz, 1H), 7.27 (d, J=8.5 Hz, 2H), 7.08 (d, J=8.9 Hz, 1H), 6.91 (d, J=8.7 Hz, 2H), 4.27 (s, 2H), 3.80-3.74 (m, 3H), 3.73 (s, 3H), 3.11 (q, J=7.1 Hz, 2H), 0.84 (t, J=7.1 Hz, 3H); ES-LCMS m/z 546.6 [M+H]$^+$.

Step 4: N-ethyl-3-(1-methylimidazol-4-yl)-4-[[5-(trifluoromethyl)-2-pyridyl]amino]benzenesulfonamide

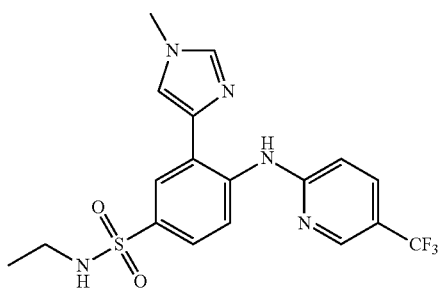 [SMILES: CCNS(=O)(=O)c1ccc(Nc2ccc(C(F)(F)F)cn2)c(-c2cn(C)cn2)c1]

To a solution of N-ethyl-N-[(4-methoxyphenyl)methyl]-3-(1-methylimidazol-4-yl)-4-[[5-(trifluoromethyl)-2-pyridyl]amino]benzenesulfonamide (200 mg, 366.59 μmol, 1 eq) in DCM (3 mL) was added TFA (1 mL). The mixture was stirred under N$_2$ atmosphere at 15° C. for 2 h. The reaction mixture was concentrated to yield a residue which was purified by preparative HPLC (column: Welch Xtimate C18 150*25 mm*5 μm; mobile phase: [water (10 mM NH$_4$HCO$_3$)-ACN]; B %: 40%-70%, 10 min). The desired fraction was lyophilized to yield N-ethyl-3-(1-methylimidazol-4-yl)-4-[[5-(trifluoromethyl)-2-pyridyl]amino]benzenesulfonamide (34.87 mg, 81.23 μmol, 22.2% yield, 99.1% purity) as a white solid. $^1$H NMR (500 MHz, DMSO-d$_6$) δ ppm 12.25 (s, 1H), 8.69 (d, J=8.9 Hz, 1H), 8.60 (s, 1H), 8.05 (d, J=2.3 Hz, 1H), 7.99-7.94 (m, 2H), 7.84 (s, 1H), 7.60 (dd, J=2.2, 8.8 Hz, 1H), 7.40 (t, J=5.7 Hz, 1H), 7.08 (s, 1H), 3.78 (s, 3H), 2.83-2.76 (m, 2H), 0.99 (t, J=7.2 Hz, 3H); ES-LCMS m/z 426.2 [M+H]$^+$.

I-66

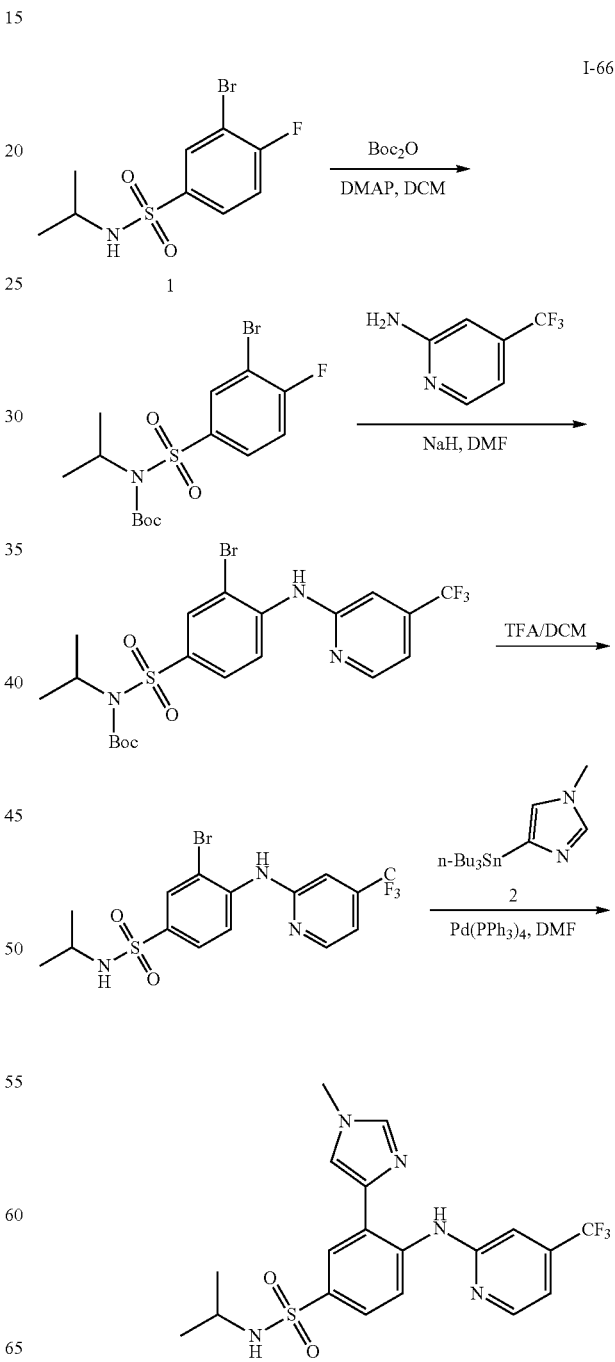

Step 1: tert-Butyl N-(3-bromo-4-fluoro-phenyl)sulfonyl-N-isopropyl-carbamate

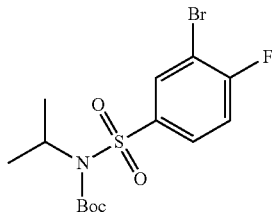 [SMILES: CC(C)N(C(=O)OC(C)(C)C)S(=O)(=O)c1ccc(F)c(Br)c1]

To a solution of 3-bromo-4-fluoro-N-isopropyl-benzenesulfonamide (200 mg, 654.92 µmol, 1 eq) in DCM (5 mL) was added DMAP (240.03 mg, 1.96 mmol, 3 eq) and tert-butoxycarbonyl tert-butyl carbonate (214.40 mg, 982.39 µmol, 225.69 µL, 1.5 eq). The mixture was stirred at 25° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 10/1, TLC: PE/EtOAc=3/1, $R_f$=0.49) to yield tert-butyl N-(3-bromo-4-fluoro-phenyl)sulfonyl-N-isopropyl-carbamate (250 mg, 605.14 µmol, 92.4% yield, 95.9% purity) as yellow oil. $^1$H NMR (500 MHz, $CDCl_3$) δ ppm 8.19 (dd, J=2.4, 6.3 Hz, 1H), 7.93 (ddd, J=2.3, 4.4, 8.7 Hz, 1H), 7.46 (t, J=8.5 Hz, 1H), 4.74 (td, J=6.9, 13.7 Hz, 1H), 1.44 (d, J=6.9 Hz, 6H), 1.40 (s, 9H); ES-LCMS m/z 340.0, 342.0 [M-t-Bu+H]$^+$.

Step 2: tert-Butyl N-[3-bromo-4-[[4-(trifluoromethyl)-2-pyridyl]amino]phenyl]sulfonyl-N-isopropyl-carbamate

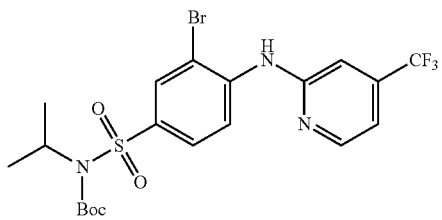 [SMILES: CC(C)N(C(=O)OC(C)(C)C)S(=O)(=O)c1ccc(Nc2cc(C(F)(F)F)ccn2)c(Br)c1]

To a solution of 4-(trifluoromethyl)pyridin-2-amine (184.09 mg, 1.14 mmol, 1.5 eq) in DMF (10 mL) was added NaH (90.84 mg, 2.27 mmol, 60%, 3 eq) and tert-butyl N-(3-bromo-4-fluoro-phenyl)sulfonyl-N-isopropyl-carbamate (312.76 mg, 757.06 µmol, 95.9%, 1 eq). The mixture was stirred at 25° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.49) to yield tert-butyl N-[3-bromo-4-[[4-(trifluoromethyl)-2-pyridyl]amino]phenyl]sulfonyl-N-isopropyl-carbamate (200 mg, 275.31 µmol, 36.4% yield, 74.1% purity) as a white solid. $^1$H NMR (500 MHz, $CDCl_3$) δ ppm 8.61 (d, J=8.9 Hz, 1H), 8.50 (d, J=5.2 Hz, 1H), 8.16 (d, J=2.3 Hz, 1H), 7.82 (dd, J=2.1, 8.9 Hz, 1H), 7.39 (s, 1H), 7.14 (d, J=5.2 Hz, 1H), 7.11 (s, 1H), 4.76 (spt, J=6.9 Hz, 1H), 1.48 (d, J=6.9 Hz, 6H), 1.43 (s, 9H); ES-LCMS m/z 538.0, 540.0 [M+H]$^+$.

Step 3: 3-Bromo-N-isopropyl-4-[[4-(trifluoromethyl)-2-pyridyl]amino]benzenesulfonamide

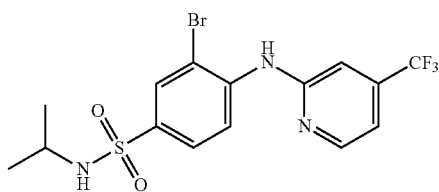 [SMILES: CC(C)NS(=O)(=O)c1ccc(Nc2cc(C(F)(F)F)ccn2)c(Br)c1]

To a solution of tert-butyl N-[3-bromo-4-[[4-(trifluoromethyl)-2-pyridyl]amino]phenyl]sulfonyl-N-isopropyl-carbamate (200 mg, 371.49 µmol, 1 eq) in DCM (5 mL) was added TFA (3.08 g, 27.01 mmol, 2 mL, 72.71 eq). The mixture was stirred at 25° C. for 12 h. The reaction mixture was quenched by addition of water (50 mL) and extracted with DCM (30 mL×3). The combined organic layers were washed with brine (10 mL), dried over $Na_2SO_4$, filtered and concentrated under reduced pressure to yield a residue which was purified by flash silica gel chromatography (from PE/EtOAc=1/0 to 5/1, TLC: PE/EtOAc=5/1, $R_f$=0.68) to yield 3-bromo-N-isopropyl-4-[[4-(trifluoromethyl)-2-pyridyl]amino]benzenesulfonamide (160 mg, 321.52 µmol, 86.6% yield, 88.1% purity) as a white solid. $^1$H NMR (400 MHz, $CD_3OD$) δ ppm 8.45-8.38 (m, 2H), 8.07 (d, J=2.2 Hz, 1H), 7.78 (dd, J=2.1, 8.7 Hz, 1H), 7.40 (s, 1H), 7.14 (d, J=5.1 Hz, 1H), 3.38 (td, J=6.6, 13.0 Hz, 1H), 1.07 (d, J=6.6 Hz, 6H); ES-LCMS m/z 439.7, 441.7 [M+H]$^+$.

Step 4: N-Isopropyl-3-(1-methylimidazol-4-yl)-4-[[4-(trifluoromethyl)-2-pyridyl]amino]benzenesulfonamide

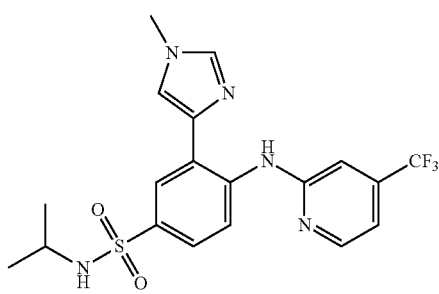

To a solution of 3-bromo-N-isopropyl-4-[[4-(trifluoromethyl)-2-pyridyl]amino]benzenesulfonamide (160 mg, 321.52 µmol, 88.07%, 1 eq) in DMF (10 mL) was added tributyl-(1-methylimidazol-4-yl)stannane (265.18 mg, 643.05 µmol, 90%, 2 eq) and Pd(PPh$_3$)$_4$ (18.58 mg, 16.08 µmol, 0.05 eq). The mixture was degassed and purged with $N_2$ for 3 times and stirred at 130° C. for 4 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by preparative HPLC (column: Agela DuraShell C18 150*25 mm*5p m; mobile phase:

[water (0.04% NH$_3$.H$_2$O+10 mM NH$_4$HCO$_3$)-ACN]; B %: 47%-77%, 10 min), followed by lyophilization to yield N-isopropyl-3-(1-methylimidazol-4-yl)-4-[[4-(trifluoromethyl)-2-pyridyl]amino]benzenesulfonamide (34.32 mg, 78.10 μmol, 24.3% yield, 100.0% purity) as a white solid. $^1$H NMR (500 MHz, DMSO-d$_6$) δ ppm 12.13 (s, 1H), 8.69 (d, J=8.9 Hz, 1H), 8.49 (d, J=5.8 Hz, 1H), 8.07 (d, J=2.1 Hz, 1H), 7.96 (s, 1H), 7.82 (s, 1H), 7.62 (dd, J=2.2, 8.8 Hz, 1H), 7.41 (d, J=7.2 Hz, 1H), 7.20-7.15 (m, 2H), 3.81-3.75 (m, 3H), 3.26 (qd, J=6.6, 13.3 Hz, 1H), 0.97 (d, J=6.6 Hz, 6H); ES-LCMS m/z 440.1 [M+H]$^+$.

I-67

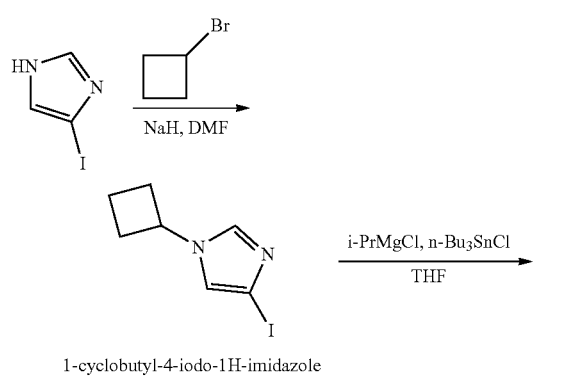

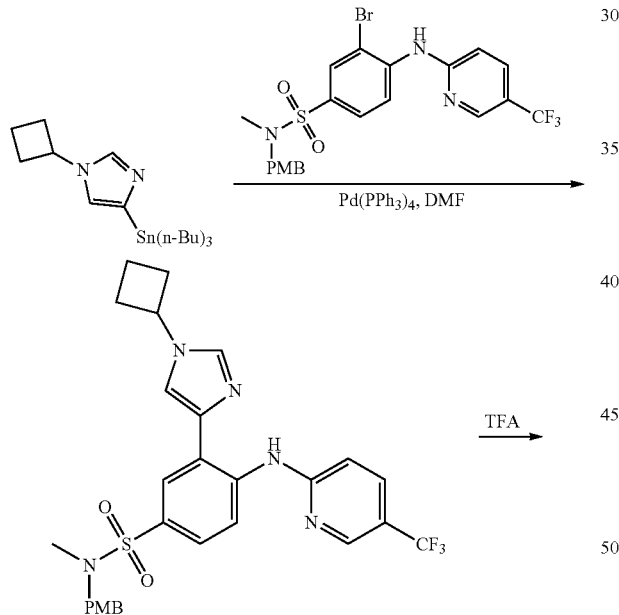

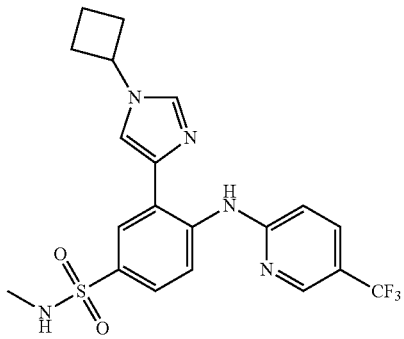

Step 1: 1-Cyclobutyl-4-iodo-imidazole

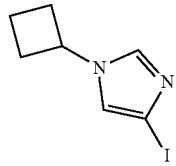

To a solution of bromocyclobutane (1 g, 7.41 mmol, 699.30 μL, 1 eq) in DMF (20 mL) was added NaH (325.89 mg, 8.15 mmol, 123.45 μL, 60.0% purity, 1.1 eq) at 15° C. The mixture was stirred for 15 minutes. 4-Iodo-1H-imidazole (2.87 g, 14.81 mmol, 2.01 mL, 2 eq) was added and the mixture was stirred at 80° C. for 16 h. The reaction was quenched with water (20 mL) and extracted with EtOAc (50 mL×3). The combined organic layers were washed with brine (50 mL), dried over Na$_2$SO$_4$, filtered and concentrated to yield a residue which was purified by silica gel column chromatography (from PE/EtOAc=5/1 to 0/1, TLC: PE/EtOAc=0/1, R$_f$=0.65) to yield 1-cyclobutyl-4-iodo-imidazole (939 mg, 3.41 mmol, 46.0% yield, 90.0% purity) as a yellow solid. $^1$H NMR (400 MHz, CDCl$_3$) δ ppm 7.41 (d, J=1.0 Hz, 1H), 7.09 (d, J=1.2 Hz, 1H), 4.58 (t, J=8.4 Hz, 1H), 2.53-2.46 (m, 2H), 2.33 (dt, J=2.7, 9.8 Hz, 2H), 1.93-1.88 (m, 2H); ES-LCMS m/z 249.1 [M+H]$^+$.

Step 2: Tributyl-(1-cyclobutylimidazol-4-yl)stannane

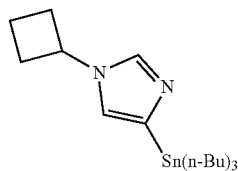

To a solution of 1-cyclobutyl-4-iodo-imidazole (555.56 mg, 2.02 mmol, 90.0% purity, 1 eq) in THF (5 mL) was added chloro(isopropyl)magnesium (2 M, 3.02 mL, 3 eq) under N$_2$ atmosphere at −10° C. The mixture was stirred under N$_2$ atmosphere at −10° C. for 1 h. Tributyl(chloro)stannane (3.69 g, 11.34 mmol, 3.05 mL, 5.62 eq) was added. The resulting mixture was stirred under N$_2$ atmosphere at 10° C. for 16 h. The reaction mixture was quenched by addition of sat.aq KF (50 mL) and extracted with EtOAc (50 mL×3). The combined organic layers were washed with brine (50 mL), dried over Na$_2$SO$_4$, filtered and concentrated to yield tributyl-(1-cyclobutylimidazol-4-yl)stannane (1 g, 1.22 mmol, 60.3% yield, 54.9% purity) as a yellow oil. ES-LCMS m/z 412.9 [M+H]$^+$.

Step 3: 3-(1-Cyclobutyl-1H-imidazol-4-yl)-N-(4-methoxybenzyl)-N-methyl-4-((5-(trifluoromethyl)pyridin-2-yl)amino)benzenesulfonamide

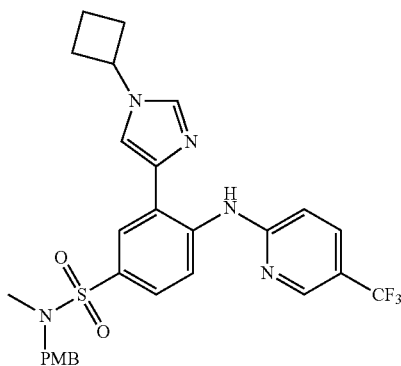

To a solution of 3-bromo-N-[(4-methoxyphenyl)methyl]-N-methyl-4-[[5-(trifluoromethyl)-2-pyridyl]amino]benzenesulfonamide (140 mg, 250.77 µmol, 95.0% purity, 1 eq) and tributyl-(1-cyclobutylimidazol-4-yl)stannane (300 mg, 364.78 µmol, 50.0% purity, 1.45 eq) in DMF (10 mL) was added Pd(dppf)Cl$_2$ (18.35 mg, 25.08 µmol, 0.1 eq) under N$_2$ atmosphere. The resulting mixture was stirred under N$_2$ atmosphere at 140° C. for 2 h. The reaction mixture was diluted with water (10 mL) and extracted with EtOAc (20 mL×3). The combined organic layer was washed with brine (30 mL), dried over Na$_2$SO$_4$, filtered and concentrated to yield a residue which was purified by silica gel column chromatography (from PE/EtOAc=5/1 to 0/1, TLC: PE/EtOAc=0/1, R$_f$=0.42) to yield 3-(1-cyclobutylimidazol-4-yl)-N-[(4-methoxyphenyl)methyl]-N-methyl-4-[[5-(trifluoromethyl)-2-pyridyl]amino]benzenesulfonamide (60 mg, 98.67 µmol, 39.3% yield, 94.0% purity) as a yellow solid. ES-LCMS m/z 572.2 [M+H]$^+$.

Step 4: 3-(1-Cyclobutylimidazol-4-yl)-N-methyl-4-[[5-(trifluoromethyl)-2-pyridyl]amino]benzenesulfonamide

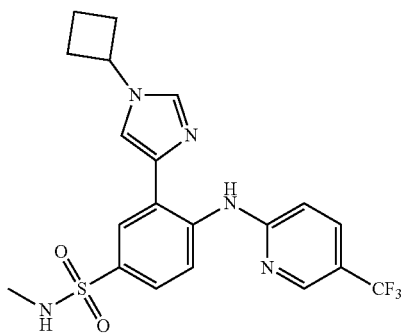 [SMILES: CNS(=O)(=O)c1ccc(Nc2ccc(C(F)(F)F)cn2)c(-c2cn(C3CCC3)cn2)c1]

To a solution of 3-(1-cyclobutylimidazol-4-yl)-N-[(4-methoxyphenyl)methyl]-N-methyl-4-[[5-(trifluoromethyl)-2-pyridyl]amino]benzenesulfonamide (60 mg, 98.67 µmol, 94.0% purity, 1 eq) in DCM (5 mL) was added TFA (1.54 g, 13.51 mmol, 1 mL, 136.89 eq). The resulting mixture was stirred at 15° C. for 16 h. The mixture was concentrated to yield a residue which was purified by preparative HPLC (column: Welch Xtimate C18 150*25 mm*5 um; mobile phase: [water (10 mM NH$_4$HCO$_3$)-ACN]; B %: 45%-75%, 10 min) to yield 3-(1-cyclobutylimidazol-4-yl)-N-methyl-4-[[5-(trifluoromethyl)-2-pyridyl]amino]benzenesulfonamide (19.78 mg, 42.94 µmol, 43.5% yield, 98.1% purity) as a white solid. $^1$H NMR (400 MHz, CDCl$_3$) δ ppm 12.23 (s, 1H), 8.89 (d, J=9.0 Hz, 1H), 8.52 (s, 1H), 8.00 (d, J=2.4 Hz, 1H), 7.72-7.66 (m, 2H), 7.62 (s, 1H), 7.47 (d, J=1.2 Hz, 1H), 6.91 (d, J=8.6 Hz, 1H), 4.67 (t, J=8.4 Hz, 1H), 4.19 (d, J=5.1 Hz, 1H), 2.66 (d, J=5.6 Hz, 3H), 2.63-2.53 (m, 2H), 2.48-2.38 (m, 2H), 2.01-1.90 (m, 2H). ES-LCMS m/z 452.0 [M+H]$^+$.

I-68

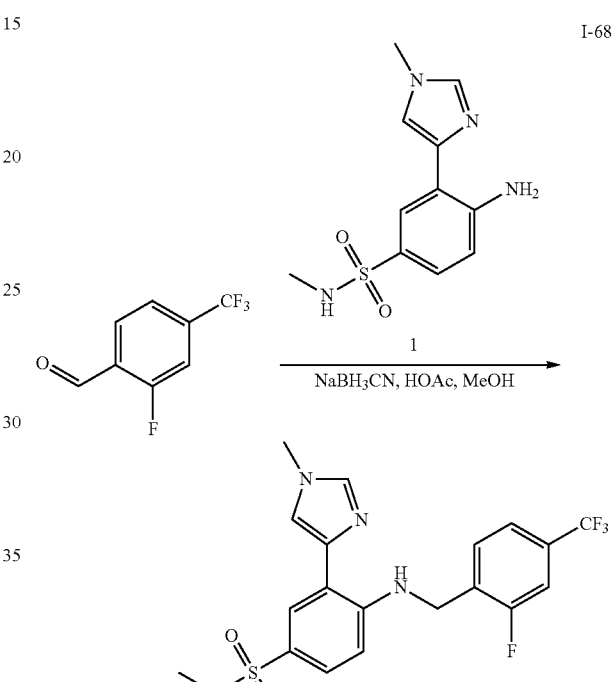

Step 1: 4-[[2-Fluoro-4-(trifluoromethyl)phenyl]methylamino]-N-methyl-3-(1-methylimidazol-4-yl)benzenesulfonamide

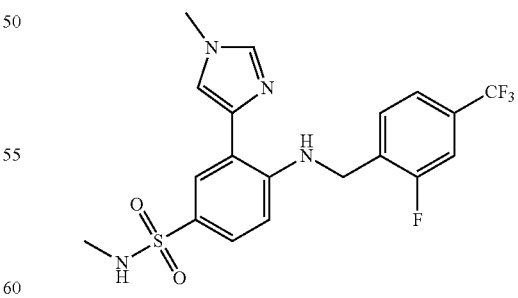

To a solution of 2-fluoro-4-(trifluoromethyl)benzaldehyde (60 mg, 312.32 µmol, 1 eq) and HOAc (18.76 mg, 312.32 µmol, 17.86 µL, 1 eq) in MeOH (5 mL) was added 4-amino-N-methyl-3-(1-methylimidazol-4-yl)benzenesulfonamide (100 mg, 337.94 µmol, 90.0% purity, 1.08 eq). The mixture was stirred at 15° C. for 1 h. NaBH$_3$CN (98.13 mg, 1.56 mmol, 5 eq) was added and the resulting mixture was stirred at 15° C. for 2 h. The reaction mixture was concentrated to yield a residue which was purified by preparative HPLC (column: Welch Xtimate C18 150*25 mm*5 um; mobile phase: [water (10 mM NH$_4$HCO$_3$)-ACN]; B %: 38%-68%, 10 min) to yield 4-[[2-fluoro-4-(trifluoromethyl)phenyl]methylamino]-N-methyl-3-(1-methylimidazol-4-yl)benzenesulfonamide (18.58 mg, 42.00 μmol, 13.5% yield, 100.0% purity) as a white solid. $^1$H NMR (400 MHz, CDCl$_3$) δ ppm 9.27 (s, 1H), 7.90 (d, J=2.0 Hz, 1H), 7.53-7.46 (m, 3H), 7.36 (s, 1H), 7.33 (d, J=3.1 Hz, 2H), 6.55 (d, J=9.0 Hz, 1H), 4.65 (d, J=5.5 Hz, 2H), 4.28 (d, J=5.5 Hz, 1H), 3.78 (s, 3H), 2.63 (d, J=5.5 Hz, 3H). ES-LCMS m/z 443.2 [M+H]$^+$.

NaBH$_3$CN (53.09 mg, 844.85 μmol, 5 eq) was added. The resulting mixture was stirred at 15° C. for 2 h. The reaction mixture was concentrated to yield a residue which was purified by preparative HPLC (column: Welch Xtimate C18 150*25 mm*5 um; mobile phase: [water (10 mM NH$_4$HCO$_3$)-ACN]; B %: 38%-68%, 10 min) to yield N-methyl-3-(1-methylimidazol-4-yl)-4-[[3-(trifluoromethoxy)phenyl]methylamino]benzenesulfonamide (36.59 mg, 83.08 μmol, 49.2% yield, 100.0% purity) as a white solid. $^1$H NMR (400 MHz, CDCl$_3$) δ ppm 9.23 (t, J=5.4 Hz, 1H), 7.87 (d, J=2.2 Hz, 1H), 7.51 (dd, J=2.0, 8.8 Hz, 1H), 7.48 (s, 1H), 7.39-7.34 (m, 1H), 7.33-7.29 (m, 2H), 7.24 (s, 1H), 7.12 (d, J=7.8 Hz, 1H), 6.57 (d, J=8.8 Hz, 1H), 4.56 (d, J=5.6 Hz, 2H), 4.14 (q, J=5.5 Hz, 1H), 3.78 (s, 3H), 2.63 (d, J=5.6 Hz, 3H). ES-LCMS m/z 441.2 [M+H]$^+$.

I-69

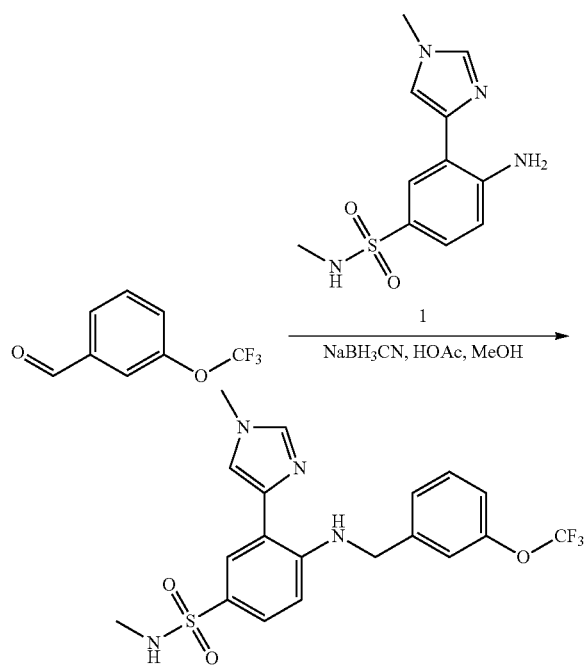

Step 1: N-Methyl-3-(1-methylimidazol-4-yl)-4-[[3-(trifluoromethoxy)phenyl]methylamino]benzenesulfonamide

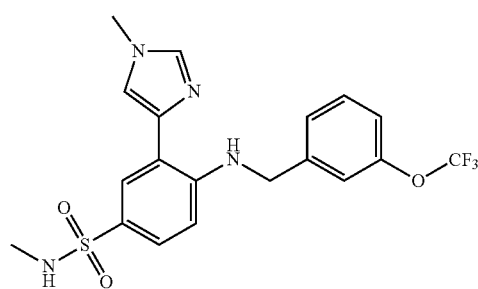 [SMILES: CNS(=O)(=O)c1ccc(NCc2cccc(OC(F)(F)F)c2)c(-c2cn(C)cn2)c1]

A solution of 3-(trifluoromethoxy)benzaldehyde (45.00 mg, 236.69 μmol, 1.40 eq), HOAc (10.15 mg, 168.97 μmol, 9.66 μL, 1 eq) and 4-amino-N-methyl-3-(1-methylimidazol-4-yl)benzenesulfonamide (50 mg, 168.97 μmol, 90.0% purity, 1 eq) in MeOH (3 mL) was stirred at 15° C. for 1 h.

I-70

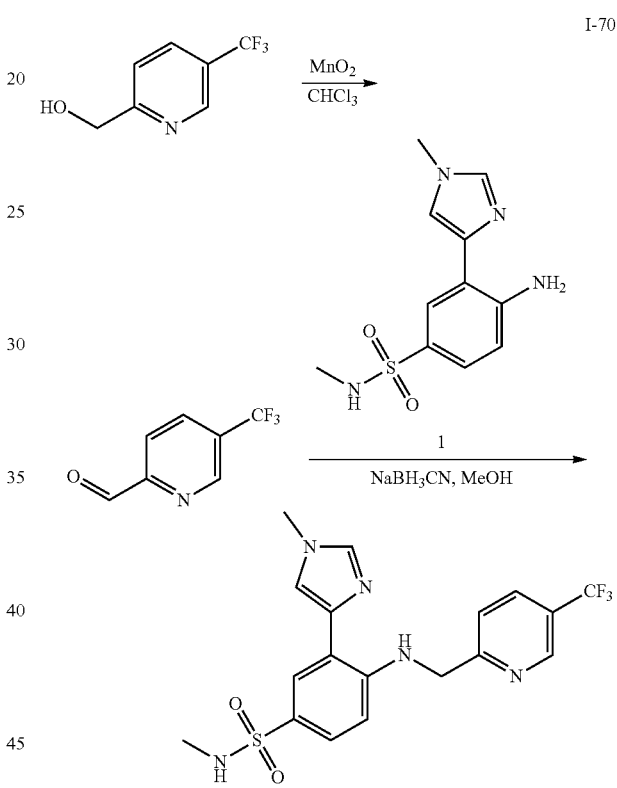

Step 1: 5-(Trifluoromethyl)pyridine-2-carbaldehyde

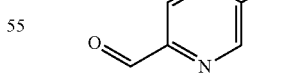

To a solution of [5-(trifluoromethyl)-2-pyridyl]methanol (150 mg, 846.87 μmol, 1 eq) in CHCl$_3$ (2 mL) was added MnO$_2$ (588.99 mg, 6.77 mmol, 8 eq). The mixture was stirred under N$_2$ atmosphere at 90° C. for 12 h. TLC (PE/EtOAc=1/1, R$_f$=0.4) indicated starting material was consumed completely and one new spot formed. The reaction mixture was filtered and concentrated under reduced pressure to yield 5-(trifluoromethyl)pyridine-2-carbaldehyde (60 mg, 274.12 μmol, 32.4% yield, 80.0% purity) as Step 2: N-Methyl-3-(1-methylimidazol-4-yl)-4-[[5-(trifluoromethyl)-2-pyridyl]methylamino]benzenesulfonamide

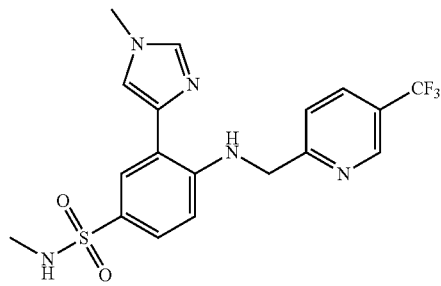 [SMILES: CNS(=O)(=O)c1ccc(NCc2ccc(C(F)(F)F)cn2)c(-c2cn(C)cn2)c1]

To a solution of 4-amino-N-methyl-3-(1-methylimidazol-4-yl)benzenesulfonamide (50 mg, 168.97 μmol, 90% purity, 1 eq) in MeOH (10 mL) was added 5-(trifluoromethyl)pyridine-2-carbaldehyde (36.99 mg, 168.97 μmol, 80% purity, 1 eq). After addition, the mixture was stirred at 15° C. for 2 h. NaBH$_3$CN (10.62 mg, 168.97 μmol, 1 eq) was added. The resulting mixture was stirred at 50° C. for 12 h. The reaction mixture was concentrated under reduced pressure to yield a residue which was purified by preparative HPLC (column: Welch Xtimate C18 150*25 mm*5 um; mobile phase: [water (10 mM NH$_4$HCO$_3$)-ACN]; B %: 29%-59%, 10 min) and lyophilized to yield N-methyl-3-(1-methylimidazol-4-yl)-4-[[5-(trifluoromethyl)-2-pyridyl]methylamino]benzenesulfonamide (16.22 mg, 37.97 μmol, 22.5% yield, 99.6% purity) as a white solid. $^1$H NMR (500 MHz, DMSO-d$_6$) δ ppm 9.38 (d, J=5.5 Hz, 1H), 8.96 (s, 1H), 8.18 (d, J=7.8 Hz, 1H), 7.83 (d, J=4.3 Hz, 2H), 7.71 (s, 1H), 7.56 (d, J=8.1 Hz, 1H), 7.35 (d, J=8.1 Hz, 1H), 7.02 (d, J=4.9 Hz, 1H), 6.63 (d, J=8.7 Hz, 1H), 4.75 (d, J=5.3 Hz, 2H), 3.76 (s, 3H), 2.36 (d, J=4.7 Hz, 3H); ES-LCMS m/z 426.2 [M+H]$^+$.

I-71

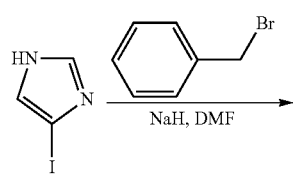

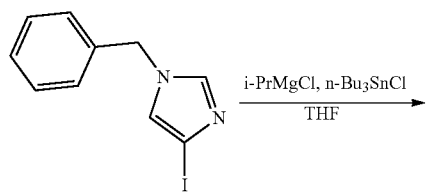

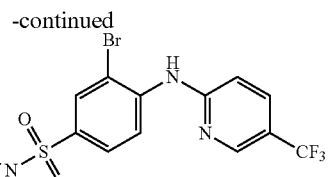

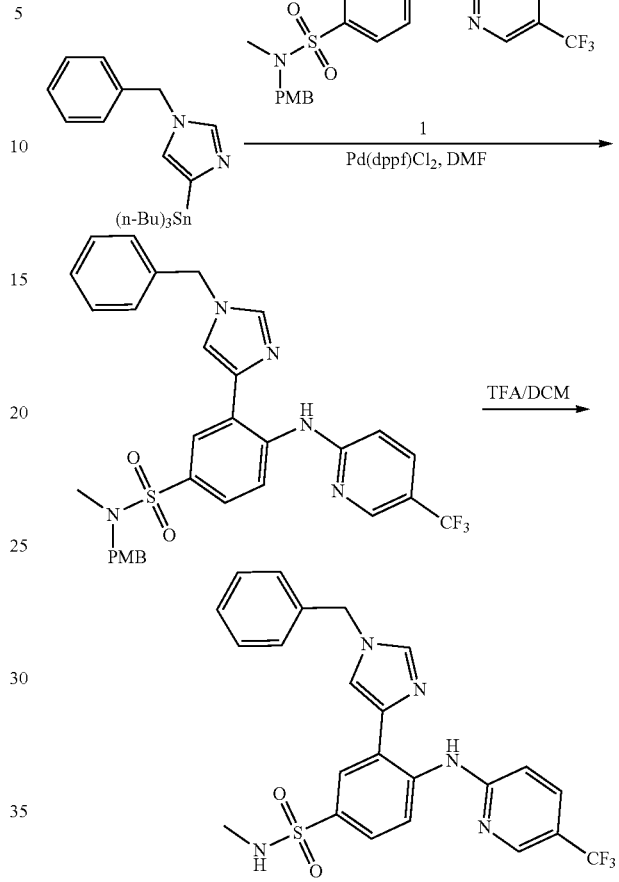

Step 1: 1-Benzyl-4-iodo-imidazole

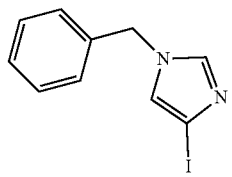 [SMILES: Ic1cn(Cc2ccccc2)cn1]

To a solution of 4-iodo-1H-imidazole (3.3 g, 17.01 mmol, 1 eq) in DMF (30 mL) was added NaH (1.02 g, 25.52 mmol, 60% purity, 1.5 eq). The mixture was stirred under N$_2$ atmosphere at 0° C. for 1 h. Bromomethylbenzene (2.91 g, 17.01 mmol, 2.02 mL, 1 eq) was added to the mixture. The mixture was stirred under N$_2$ atmosphere at 75° C. for 12 h. The reaction mixture was quenched by addition of water (300 mL) and extracted with EtOAc (300 mL×3). The combined organic layers were washed with brine (100 mL), dried over Na$_2$SO$_4$, filtered and concentrated under reduced pressure to yield a residue which was purified by flash silica gel chromatography (from PE/EtOAc=1/0 to 5/1, TLC: PE/EtOAc=3/1, R$_f$=0.47) to yield 1-benzyl-4-iodo-imidazole (3 g, 10.03 mmol, 59.0% yield, 95.0% purity) as a yellow solid. $^1$H NMR (400 MHz, CDCl$_3$) δ ppm 7.43 (d, J=1.2 Hz, 1H), 7.40-7.32 (m, 3H), 7.20-7.13 (m, 2H), 6.97 (d, J=1.6 Hz, 1H), 5.08 (s, 2H); ES-LCMS m/z 285.1 [M+H]⁺.

Step 2: (1-Benzylimidazol-4-yl)-tributyl-stannane

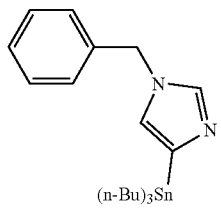

To a solution of 1-benzyl-4-iodo-imidazole (300 mg, 1.06 mmol, 1 eq) in THE (10 mL) was added i-PrMgCl (2 M, 580.79 μL, 1.1 eq) dropwise under N₂ atmosphere at −10° C. The mixture was stirred under N₂ atmosphere at −10° C. for 2 h. Tributyl(chloro)stannane (378.10 mg, 1.16 mmol, 312.48 μL, 1.1 eq) was added under N₂ atmosphere at −10° C. The mixture was warmed to 20° C. slowly and stirred under N₂ atmosphere at 20° C. for 1.5 h. The reaction mixture was quenched water (60 mL) and extracted with EtOAc (50 mL×3). The organic layer was washed with brine (40 mL), dried over Na₂SO₄, filtered and concentrated under reduced pressure to yield (1-benzylimidazol-4-yl)-tributyl-stannane (424 mg, 635.18 μmol, 60.2% yield, 67.0% purity) as red oil. ¹H NMR (500 MHz, CDCl₃) δ ppm 7.46 (s, 1H), 7.28-7.24 (m, 3H), 7.07 (d, J=7.2 Hz, 2H), 7.01 (s, 1H), 5.04 (s, 2H), 1.52-1.39 (m, 6H), 1.27-1.23 (m, 6H), 1.04-0.87 (m, 6H), 0.85-0.80 (m, 9H); ES-LCMS m/z 477.2 [M+H]⁺.

Step 3: 3-(1-Benzylimidazol-4-yl)-N-[(4-methoxyphenyl)methyl]-N-methyl-4-[[5-(trifluoromethyl)-2-pyridyl]amino]benzenesulfonamide

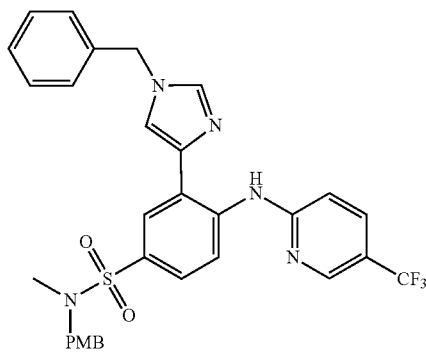

To a solution of 3-bromo-N-[(4-methoxyphenyl)methyl]-N-methyl-4-[[5-(trifluoromethyl)-2-pyridyl]amino]benzenesulfonamide (100 mg, 169.70 μmol, 90% purity, 1 eq) in DMF (4 mL) was added (1-benzylimidazol-4-yl)-tributyl-stannane (203.90 mg, 305.45 μmol, 67% purity, 1.8 eq) and Pd(dppf)Cl₂ (12.42 mg, 16.97 μmol, 0.1 eq). The mixture was stirred under N₂ atmosphere at 100° C. for 5 h. TLC (PE/EtOAc=3/1, R_f=0.45) indicated starting material was consumed completely and one new spot formed. The reaction mixture was quenched by addition of water (50 mL) and extracted with EtOAc (50 mL×3). The combined organic layers were washed with brine (30 mL), dried over Na₂SO₄, filtered and concentrated under reduced pressure to yield a residue which was purified by flash silica gel chromatography (from PE/EtOAc=1/0 to 3/1, TLC: PE/EtOAc=3/1, R_f=0.45) to yield 3-(1-benzylimidazol-4-yl)-N-[(4-methoxyphenyl)methyl]-N-methyl-4-[[5-(trifluoromethyl)-2-pyridyl]amino]benzenesulfonamide (75 mg, 98.74 μmol, 58.2% yield, 80.0% purity) as yellow oil. ¹H NMR (400 MHz, CDCl₃) δ ppm 12.26 (s, 1H), 8.94 (d, J=9.0 Hz, 1H), 8.55 (s, 1H), 7.91 (d, J=2.0 Hz, 1H), 7.83-7.75 (m, 1H), 7.72-7.66 (m, 3H), 7.44-7.34 (m, 4H), 7.24-7.19 (m, 3H), 6.91-6.83 (m, 3H), 5.19 (s, 2H), 4.07 (s, 2H), 3.79 (s, 3H); ES-LCMS m/z 608.1 [M+H]⁺.

Step 4: 3-(1-Benzylimidazol-4-yl)-N-methyl-4-[[5-(trifluoromethyl)-2-pyridyl]amino]benzenesulfonamide

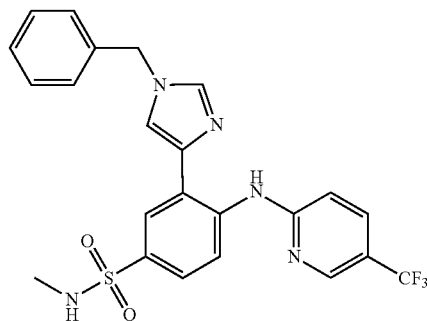 [SMILES: CNS(=O)(=O)c1ccc(Nc2ccc(C(F)(F)F)cn2)c(-c2cn(Cc3ccccc3)cn2)c1]

To a solution of 3-(1-benzylimidazol-4-yl)-N-[(4-methoxyphenyl)methyl]-N-methyl-4-[[5-(trifluoromethyl)-2-pyridyl]amino]benzenesulfonamide (70 mg, 92.2 μmol, 80% purity, 1 eq) in DCM (6 mL) was added TFA (2 mL). The mixture was stirred at 15° C. for 1 h. TLC (PE/EtOAc=3/1, R_f=0.20) indicated starting material was consumed completely and one new spot formed. The reaction mixture was quenched by addition of NaHCO₃ (50 mL) and extracted with EtOAc (50 mL×3). The combined organic layers were washed with brine (40 mL), dried over Na₂SO₄, filtered and concentrated under reduced pressure to yield a residue which was purified by flash silica gel chromatography (from PE/EtOAc=1/0 to 2/1, TLC:PE/EtOAc=3/1, R_f=0.20) to yield 3-(1-benzylimidazol-4-yl)-N-methyl-4-[[5-(trifluoromethyl)-2-pyridyl]amino]benzenesulfonamide (15.22 mg, 31.22 μmol, 33.9% yield, 100.0% purity) as a white solid. H NMR (500 MHz, CDCl₃) δ ppm 12.25 (s, 1H), 8.89 (d, J=8.4 Hz, 1H), 8.54 (s, 1H), 7.96 (s, 1H), 7.77-7.61 (m, 3H), 7.47-7.31 (m, 4H), 7.24 (d, J=7.3 Hz, 2H), 6.93 (d, J=8.2 Hz, 1H), 5.18 (s, 2H), 4.32 (d, J=4.6 Hz, 1H), 2.65 (d, J=4.7 Hz, 3H); ES-LCMS m/z 488.2 [M+H]⁺.

I-72

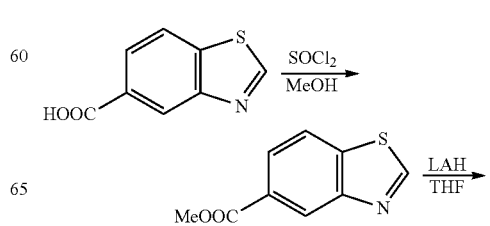

-continued

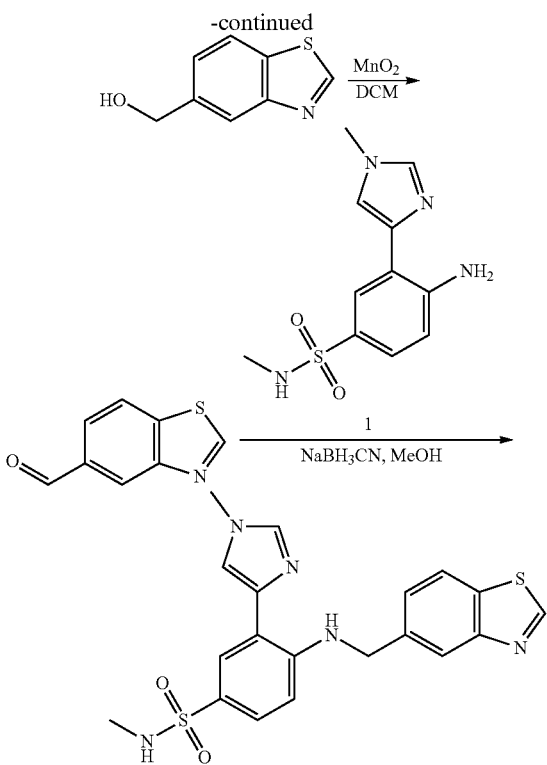

Step 1: Methyl 1,3-benzothiazole-5-carboxylate

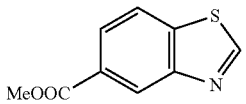

To a solution of 1,3-benzothiazole-5-carboxylic acid (120 mg, 669.66 μmol, 1 eq) in MeOH (3 mL) was added SOCl₂ (398.35 mg, 3.35 mmol, 242.89 μL, 5 eq). The mixture was stirred under N₂ atmosphere at 60° C. for 2 h. The reaction mixture was concentrated under reduced pressure. The residue was diluted with water (30 mL) and extracted with EtOAc (30 mL×3). The combined organic phase was washed with brine (20 mL), dried over anhydrous Na₂SO₄, filtered and concentrated in vacuum to yield methyl 1,3-benzothiazole-5-carboxylate (120 mg, 565.15 μmol, 84.4% yield, 91.0% purity) as a white solid. H NMR (500 MHz, DMSO-d₆) δ ppm 9.53 (s, 1H), 8.60 (d, J=1.2 Hz, 1H), 8.34 (d, J=8.4 Hz, 1H), 8.05 (dd, J=1.4, 8.5 Hz, 1H), 3.92 (s, 3H); ES-LCMS m/z 194.2 [M+H]⁺.

Step 2: 1,3-Benzothiazol-5-ylmethanol

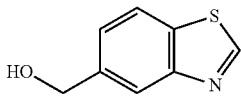 [SMILES: OCc1ccc2scnc2c1]

To a solution of methyl 1,3-benzothiazole-5-carboxylate (120 mg, 565.15 umol, 91%, 1 eq) in THF (6 mL) was added LiAlH₄ (32.17 mg, 847.73 μmol, 1.5 eq) at 0° C. The mixture was stirred at 0° C. for 2 min. TLC (PE/EtOAc=1/1, R𝑓=0.22) indicated the starting material was consumed completely and two new spots formed. The reaction mixture was quenched by addition of THF (6 mL), H₂O (0.04 mL), 15% NaOH solution (0.04 mL) and H₂O (0.12 mL) at 0° C. in turn and filtered. The filtrate was concentrated under reduced pressure to yield a residue which was purified by flash silica gel chromatography (from PE/EtOAc=100/1 to 1/1, TLC: PE/EtOAc=1/1, R𝑓=0.22) to yield 1,3-benzothiazol-5-ylmethanol (50 mg, 275.40 μmol, 48.7% yield, 91.0% purity) as a yellow solid. ¹H NMR (500 MHz, CDCl₃) δ ppm 9.03 (s, 1H), 8.15 (s, 1H), 7.97 (d, J=8.2 Hz, 1H), 7.50 (d, J=8.2 Hz, 1H), 4.89 (d, J=6.0 Hz, 2H), 1.84 (t, J=6.0 Hz, 1H); ES-LCMS m/z 166.2 [M+H]⁺.

Step 3: 1,3-Benzothiazole-5-carbaldehyde

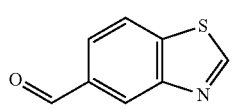 [SMILES: O=Cc1ccc2scnc2c1]

To a solution of 1,3-benzothiazol-5-ylmethanol (50 mg, 275.40 μmol, 91%, 1 eq) in DCM (5 mL) was added MnO₂ (239.43 mg, 2.75 mmol, 10 eq). The mixture was stirred at 25° C. for 12 h. The reaction mixture was filtered and concentrated under reduced pressure to yield 1,3-benzothiazole-5-carbaldehyde (35 mg, 214.47 μmol, 77.9% yield, 100.0% purity) as a yellow solid, which was used in the next step without further purification. ¹H NMR (400 MHz, CDCl₃) δ ppm 10.19 (s, 1H), 9.14 (s, 1H), 8.62 (d, J=1.2 Hz, 1H), 8.13 (d, J=8.6 Hz, 1H), 8.04-8.00 (m, 1H); ES-LCMS m/z 163.7 [M+H]⁺.

Step 4: 4-(1,3-Benzothiazol-5-ylmethylamino)-N-methyl-3-(1-methylimidazol-4-yl)benzenesulfonamide

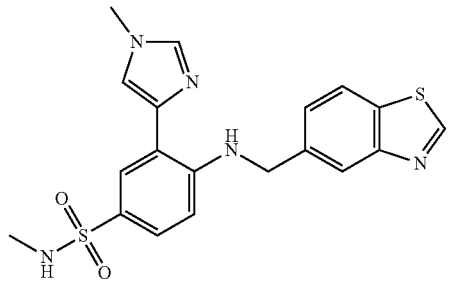 [SMILES: CNS(=O)(=O)c1ccc(NCc2ccc3scnc3c2)c(-c2cn(C)cn2)c1]

To a solution of 1,3-benzothiazole-5-carbaldehyde (35 mg, 195.16 μmol, 91%, 1 eq) and 4-amino-N-methyl-3-(1-methylimidazol-4-yl)benzenesulfonamide (75.08 mg, 253.71 μmol, 90% purity, 1.3 eq) in MeOH (3 mL) was added HOAc (11.72 mg, 195.16 μmol, 11.16 μL, 1 eq). The mixture was stirred at 25° C. for 1 h. NaBH₃CN (61.32 mg, 975.82 μmol, 5 eq) was added and the mixture was stirred at 25° C. for 1 h. The reaction mixture was filtered and the filtrate was purified by preparative HPLC (column: Agela DuraShell C18 150*25 mm*5 μm; mobile phase: [water (0.04% NH₃.H₂O+10 mM NH₄HCO₃)-ACN]; B %: 28%-58%, 10 min), followed by lyophilization to yield 4-(1,3- benzothiazol-5-ylmethylamino)-N-methyl-3-(1-methylimidazol-4-yl)benzenesulfonamide (21.36 mg, 51.65 µmol, 26.5% yield, 100.0% purity) as a white solid. ¹H NMR (400 MHz, DMSO-d₆) δ ppm 9.38 (s, 1H), 9.32 (t, J=6.1 Hz, 1H), 8.13 (d, J=8.2 Hz, 1H), 8.05 (s, 1H), 7.80 (s, 2H), 7.70 (d, J=0.8 Hz, 1H), 7.50 (d, J=8.6 Hz, 1H), 7.34 (dd, J=2.0, 8.6 Hz, 1H), 6.98 (q, J=4.7 Hz, 1H), 6.74 (d, J=8.6 Hz, 1H), 4.70 (d, J=5.9 Hz, 2H), 3.75 (s, 3H), 2.36-2.33 (m, 1H); ES-LCMS m/z 414.1 [M+H]⁺.

I-73

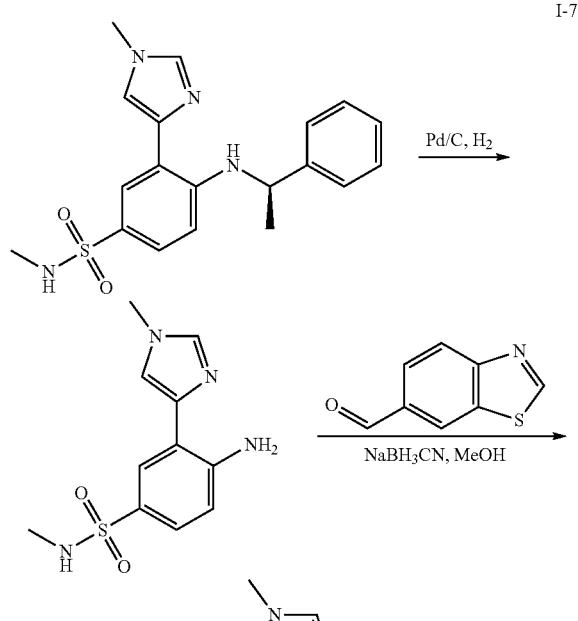

Step 1: 4-Amino-N-methyl-3-(1-methyl-1H-imidazol-4-yl)benzenesulfonamide

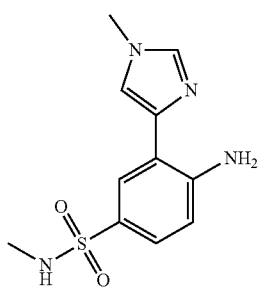 [SMILES: CNS(=O)(=O)c1ccc(N)c(-c2cn(C)cn2)c1]

To a solution of N-methyl-3-(1-methylimidazol-4-yl)-4-[[(1R)-1-phenylethyl]amino]benzenesulfonamide (3.7 g, 8.99 mmol, 90% purity, 1 eq) in MeOH (350 mL) was added Pd/C (0.8 g, 10% purity). The mixture was stirred at 50° C. under H₂ (50 psi) for 28 h. TLC (EtOAc, R_f=0.06) showed the starting material remained and desired product was formed. The mixture was filtered and concentrated to yield a crude material which was purified by silica gel column chromatography (from PE/EtOAc=5/1 to 0/1, TLC: PE/EtOAc=0/1, R_f=0.06) to yield 4-amino-N-methyl-3-(1-methylimidazol-4-yl)benzenesulfonamide (1.0 g, 3.38 mmol, 37.6% yield, 90.0% purity) as a yellow solid. ¹H NMR (400 MHz, CDCl₃) δ ppm 7.85 (d, J=2.2 Hz, 1H), 7.53-7.42 (m, 2H), 7.28-7.24 (m, 2H), 6.72 (d, J=8.6 Hz, 1H), 4.26 (d, J=4.6 Hz, 1H), 3.81-3.71 (m, 3H), 2.63 (d, J=5.4 Hz, 3H).

Step 2: 4-(1,3-Benzothiazol-6-ylmethylamino)-N-methyl-3-(1-methylimidazol-4-yl)benzenesulfonamide

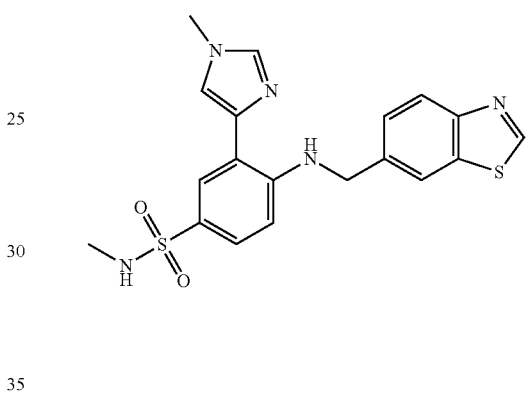

A solution of 4-amino-N-methyl-3-(1-methylimidazol-4-yl)benzenesulfonamide (50 mg, 168.97 µmol, 90% purity, 1 eq), 1,3-benzothiazole-6-carbaldehyde (30 mg, 183.83 µmol, 1.09 eq) in MeOH (3 mL) and AcOH (0.1 mL) was stirred at 15° C. for 2 h. NaBH₃CN (55 mg, 875.21 µmol, 5.18 eq) was added. The mixture was stirred at 15° C. for 10 h. The mixture was concentrated under reduced pressure to yield a residue which was purified by preparative HPLC (column: Welch Xtimate C18 150*25 mm*5 um; mobile phase: [water (10 mM NH₄HCO₃)-ACN]; B %: 26%-56%, 10 min) and lyophilized to yield 4-(1,3-benzothiazol-6-ylmethylamino)-N-methyl-3-(1-methylimidazol-4-yl)benzenesulfonamide (24.57 mg, 59.42 µmol, 35.2% yield, 100.0% purity) as a white solid. ¹H NMR (500 MHz, CD₃OD) δ ppm 9.22 (s, 1H), 8.10 (s, 1H), 8.05 (d, J=8.4 Hz, 1H), 7.84 (d, J=2.3 Hz, 1H), 7.70 (s, 1H), 7.62 (d, J=8.5 Hz, 1H), 7.50 (d, J=1.2 Hz, 1H), 7.47 (dd, J=2.2, 8.8 Hz, 1H), 6.71 (d, J=8.9 Hz, 1H), 4.71 (s, 2H), 3.82 (s, 3H), 2.49 (s, 3H); ES-LCMS m/z 414.2 [M+H]⁺.

I-74

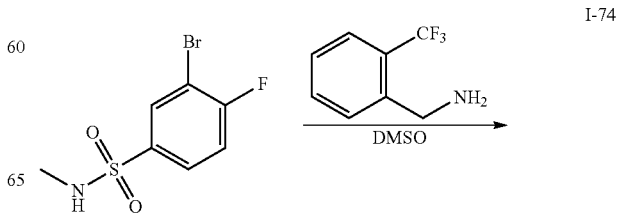

Step 2: N-Methyl-3-(1-methylimidazol-4-yl)-4-[[2-(trifluoromethyl)phenyl]methylamino]benzenesulfonamide

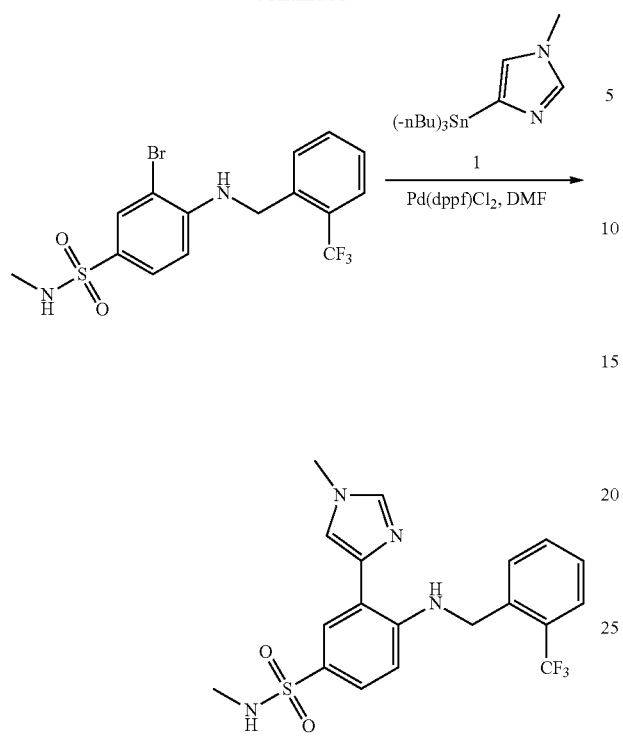

To a solution of 3-bromo-N-methyl-4-[[2-(trifluoromethyl)phenyl]methylamino]benzenesulfonamide (300 mg, 496.16 μmol, 70% purity, 1 eq) and tributyl-(1-methylimidazol-4-yl)stannane (561.43 mg, 1.49 mmol, 98.4% purity, 3 eq) in DMF (3 mL) was added Pd(dppf)Cl$_2$ (36.30 mg, 49.62 μmol, 0.1 eq). The mixture was stirred under N$_2$ atmosphere at 130° C. for 12 h. The reaction mixture was quenched with aqueous KF (10 mL, 2M) and extracted with EtOAc (10 mL×3). The organic layer was washed with water (10 mL×2) and brine (10 mL), dried over Na$_2$SO$_4$, filtered and concentrated under reduced pressure to yield a residue which was purified by preparative HPLC (column: Welch Xtimate C18 150*25 mm*5 μm; mobile phase: [water (10 mM NH$_4$HCO$_3$)-ACN]; B %: 38%-68%, 10 min). The desired fraction was lyophilized to yield N-methyl-3-(1-methylimidazol-4-yl)-4-[[2-(trifluoromethyl)phenyl]methylamino]benzenesulfonamide (60 mg, 141.36 μmol, 28.5% yield, 100.0% purity) as a white solid. $^1$H NMR (400 MHz, DMSO-d$_6$) δ ppm 9.29 (t, J=5.9 Hz, 1H), 7.83 (d, J=2.0 Hz, 1H), 7.80 (s, 1H), 7.78 (d, J=7.8 Hz, 1H), 7.71 (s, 1H), 7.66-7.60 (m, 1H), 7.57-7.53 (m, 1H), 7.52-7.46 (m, 1H), 7.36 (dd, J=2.1, 8.7 Hz, 1H), 7.01 (q, J=5.1 Hz, 1H), 6.54 (d, J=8.8 Hz, 1H), 4.70 (d, J=5.5 Hz, 2H), 3.75 (s, 3H), 2.36 (d, J=5.3 Hz, 3H); ES-LCMS m/z 425.2 [M+H]$^+$.

Step 1: 3-Bromo-N-methyl-4-[[2-(trifluoromethyl)phenyl]methylamino]benzenesulfonamide

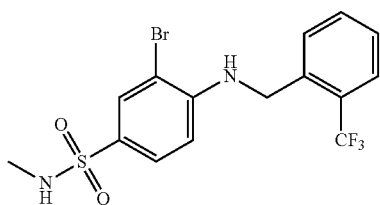 [SMILES: CNS(=O)(=O)c1ccc(NCc2ccccc2C(F)(F)F)c(Br)c1]

To a solution of 3-bromo-4-fluoro-N-methyl-benzenesulfonamide (400 mg, 1.49 mmol, 100.0% purity, 1 eq) in DMSO (3 mL) was added [2-(trifluoromethyl)phenyl]methanamine (522.64 mg, 2.98 mmol, 418.11 μL, 2 eq). The mixture was stirred under N$_2$ atmosphere at 140° C. for 12 h. The reaction mixture was diluted with water (30 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 2/1, TLC: PE/EtOAc=2/1, R$_f$=0.55) to yield 3-bromo-N-methyl-4-[[2-(trifluoromethyl)phenyl]methylamino]benzenesulfonamide (570 mg, 942.71 μmol, 63.2% yield, 70.0% purity) as a yellow solid. $^1$H NMR (400 MHz, DMSO-d$_6$) δ ppm 7.79 (d, J=2.2 Hz, 1H), 7.77 (d, J=7.8 Hz, 1H), 7.63 (s, 1H), 7.51-7.44 (m, 2H), 7.18 (q, J=4.9 Hz, 1H), 6.85 (t, J=6.0 Hz, 1H), 6.88-6.82 (m, 1H), 6.42 (d, J=8.8 Hz, 1H), 4.66 (d, J=5.6 Hz, 2H), 2.35 (d, J=5.1 Hz, 3H); ES-LCMS m/z 423.0, 425.0 [M+H]$^+$.

I-75

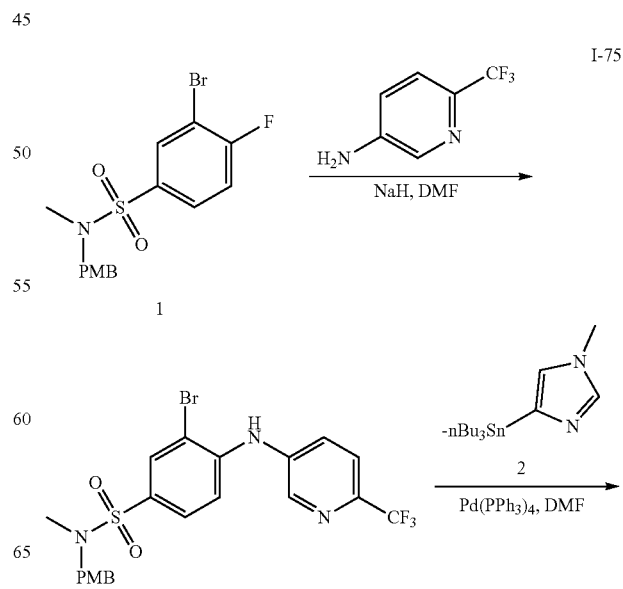

-continued

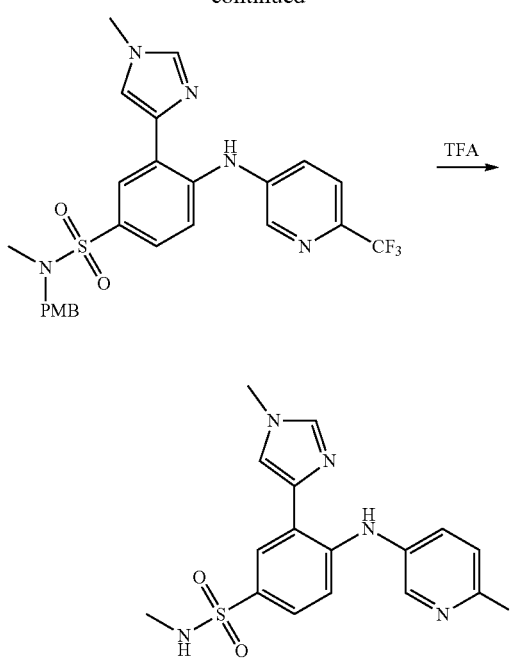

Step 1: 3-Bromo-N-[(4-methoxyphenyl)methyl]-N-methyl-4-[[6-(trifluoromethyl)-3-pyridyl]amino]benzenesulfonamide

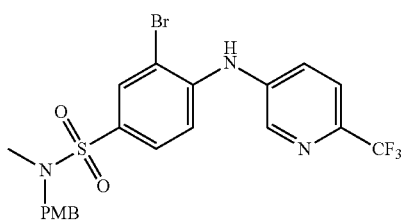

To a solution of 6-(trifluoromethyl)pyridin-3-amine (178.50 mg, 1.10 mmol, 1.5 eq) in DMF (5 mL) was added NaH (117.44 mg, 2.94 mmol, 60% purity, 4 eq) at 0° C. The mixture was stirred at 0° C. for 0.5 h. 3-Bromo-4-fluoro-N-[(4-methoxyphenyl)methyl]-N-methyl-benzenesulfonamide (300 mg, 734.06 μmol, 95% purity, 1 eq) was added. The mixture was stirred at 20° C. for 3 h. The reaction mixture was quenched by addition of water (30 mL) and extracted with EtOAc (50 mL×2). The combined organic layers were washed with brine (50 mL), dried over $Na_2SO_4$, filtered and concentrated under reduced pressure to yield a residue which was purified by flash silica gel chromatography (from PE/EtOAc=1/0 to 3/1, TLC: PE/EtOAc=3/1, $R_f$=0.43) to yield 3-bromo-N-[(4-methoxyphenyl)methyl]-N-methyl-4-[[6-(trifluoromethyl)-3-pyridyl]amino]benzenesulfonamide (350 mg, 593.94 μmol, 80.9% yield, 90.0% purity) as yellow oil. $^1$H NMR (400 MHz, $CDCl_3$) δ ppm 8.62 (s, 1H), 8.03 (d, J=2.0 Hz, 1H), 7.69 (d, J=1.2 Hz, 2H), 7.66 (dd, J=1.8, 8.7 Hz, 1H), 7.34 (d, J=8.6 Hz, 1H), 7.22 (d, J=8.6 Hz, 2H), 6.87 (d, J=8.6 Hz, 2H), 6.74 (s, 1H), 4.11 (s, 2H), 3.80 (s, 3H), 2.62 (s, 3H); ES-LCMS m/z 532.1 [M+H]$^+$.

Step 2: N-[(4-Methoxyphenyl)methyl]-N-methyl-3-(1-methylimidazol-4-yl)-4-[[6-(trifluoromethyl)-3-pyridyl]amino]benzenesulfonamide

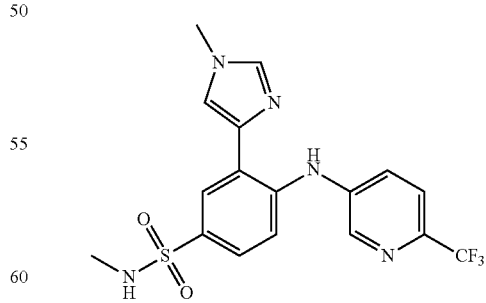

To a solution of 3-bromo-N-[(4-methoxyphenyl)methyl]-N-methyl-4-[[6-(trifluoromethyl)-3-pyridyl]amino]benzenesulfonamide (350 mg, 593.94 μmol, 90% purity, 1 eq) in DMF (3 mL) was added tributyl-(1-methylimidazol-4-yl)stannane (448.05 mg, 1.19 mmol, 98.4% purity, 2 eq) and Pd(dppf)Cl$_2$ (21.73 mg, 29.70 μmol, 0.05 eq). The mixture was degassed and purged with $N_2$ for three times and stirred under $N_2$ atmosphere at 130° C. for 2 h. The reaction mixture was quenched by addition of sat. aq. KF (30 mL) and extracted with EtOAc (50 mL×2). The combined organic layers were washed with brine (50 mL), dried over $Na_2SO_4$, filtered and concentrated under reduced pressure to yield a residue which was purified by flash silica gel chromatography (from PE/EtOAc=1/0 to 1/2, TLC: PE/EtOAc=0/1, $R_f$=0.51) to yield N-[(4-methoxyphenyl)methyl]-N-methyl-3-(1-methylimidazol-4-yl)-4-[[6-(trifluoromethyl)-3-pyridyl]amino]benzenesulfonamide (380 mg, 569.77 μmol, 95.9% yield, 79.7% purity) as black brown gum. $^1$H NMR (400 MHz, DMSO-$d_6$) δ ppm 11.06 (s, 1H), 8.62 (d, J=2.3 Hz, 1H), 8.08 (d, J=1.6 Hz, 1H), 7.95 (d, J=0.8 Hz, 1H), 7.90 (s, 1H), 7.85-7.80 (m, 1H), 7.80-7.76 (m, 1H), 7.63-7.56 (m, 2H), 7.24 (d, J=9.0 Hz, 2H), 6.92 (d, J=9.0 Hz, 2H), 4.07 (s, 2H), 3.74 (d, J=3.9 Hz, 6H), 2.52 (s, 3H); ES-LCMS m/z 532.2 [M+H]$^+$.

Step 3: N-Methyl-3-(1-methylimidazol-4-yl)-4-[[6-(trifluoromethyl)-3-pyridyl]amino]benzenesulfonamide To a solution of N-[(4-methoxyphenyl)methyl]-N-methyl-3-(1-methylimidazol-4-yl)-4-[[6-(trifluoromethyl)-3-pyridyl]amino]benzenesulfonamide (380 mg, 569.77 μmol, 79.7% purity, 1 eq) in DCM (3 mL) was added TFA (797.00 μL). The mixture was stirred at 20° C. for 3 h. The reaction mixture was filtered to yield a residue which was purified by preparative HPLC (column: Agela DuraShell C$_{18}$ 150*25 mm*5 um; mobile phase: [water (0.04% NH$_3$.H$_2$O+ 10 mM NH$_4$HCO$_3$)-ACN]; B %: 37%-67%, 10 min), followed by lyophilization to yield N-methyl-3-(1-methylimidazol-4-yl)-4-[[6-(trifluoromethyl)-3-pyridyl]amino]benzenesulfonamide (51.27 mg, 123.63 μmol, 21.7% yield, 99.2% purity) as a white solid. $^1$H NMR (400 MHz, CDCl$_3$) δ ppm 11.20 (s, 1H), 8.63 (d, J=2.4 Hz, 1H), 8.00 (d, J=2.2 Hz, 1H), 7.72 (dd, J=2.4, 8.6 Hz, 1H), 7.63-7.59 (m, 2H), 7.57-7.52 (m, 1H), 7.47 (d, J=8.8 Hz, 1H), 7.37 (d, J=1.2 Hz, 1H), 4.24 (d, J=5.4 Hz, 1H), 3.81 (s, 3H), 2.70 (d, J=5.6 Hz, 3H); ES-LCMS m/z 412.1 [M+H]$^+$.

I-76

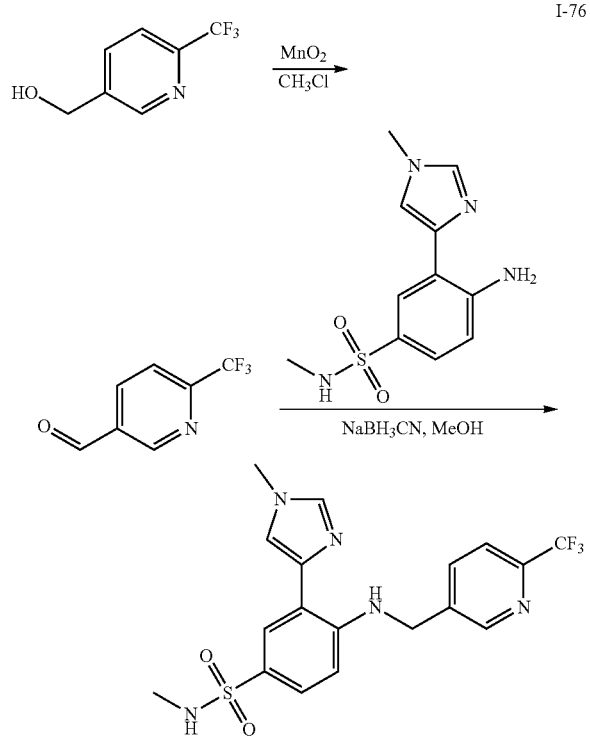

Step 1: 6-(Trifluoromethyl)nicotinaldehyde

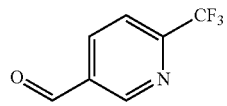

To a solution of [6-(trifluoromethyl)-3-pyridyl]methanol (50 mg, 282.29 μmol, 1 eq) in CHCl$_3$ (3 mL) was added MnO$_2$ (134.98 mg, 1.55 mmol, 5.5 eq). The mixture was stirred at 80° C. for 16 h. The mixture was filtered and concentrated to yield 6-(trifluoromethyl)pyridine-3-carbaldehyde (40 mg, 228.43 μmol, 80.9% yield, 100.0% purity) as a yellow solid, which was used in the next step without further purification. $^1$H NMR (400 MHz, CDCl$_3$) δ ppm 10.23 (s, 1H), 9.21 (s, 1H), 8.42-8.33 (m, 1H), 7.90 (d, J=8.2 Hz, 1H); ES-LCMS m/z 176.3 [M+H]$^+$.

Step 2: N-Methyl-3-(1-methyl-1H-imidazol-4-yl)-4-(((6-(trifluoromethyl)pyridin-3-yl)methyl)amino)benzenesulfonamide

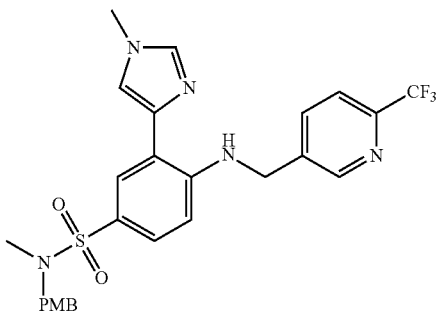

To a solution of 4-amino-N-methyl-3-(1-methylimidazol-4-yl)benzenesulfonamide (50 mg, 168.97 μmol, 90% purity, 0.74 eq) in MeOH (3 mL) was added 6-(trifluoromethyl)pyridine-3-carbaldehyde (40 mg, 228.43 μmol, 100% purity, 1 eq) and a drop of AcOH at 20° C. The mixture was stirred under N$_2$ atmosphere at 20° C. for 1 h. NaBH$_3$CN (71.78 mg, 1.14 mmol, 5.0 eq) was added. The mixture was stirred at 20° C. for 11 h. The mixture was quenched with H$_2$O (1 mL) and concentrated to yield a residue which was purified preparative HPLC (column: Welch Xtimate C18 150*25 mm*5 um; mobile phase: [water (10 mM NH$_4$HCO$_3$)-ACN]; B %: 28%-58%, 10 min) and lyophilized to yield N-methyl-3-(1-methylimidazol-4-yl)-4-[[6-(trifluoromethyl)-3-pyridyl]methylamino]benzenesulfonamide (20.38 mg, 47.90 μmol, 20.9% yield, 100.0% purity) as a white solid. $^1$H NMR (400 MHz, CDCl$_3$) δ ppm 9.35 (t, J=5.5 Hz, 1H), 8.75 (s, 1H), 7.93-7.82 (m, 2H), 7.64 (d, J=8.1 Hz, 1H), 7.54-7.46 (m, 2H), 7.31 (d, J=1.0 Hz, 1H), 6.53 (d, J=8.6 Hz, 1H), 4.64 (d, J=5.6 Hz, 2H), 4.18 (q, J=5.4 Hz, 1H), 3.77 (s, 3H), 2.62 (d, J=5.4 Hz, 3H); ES-LCMS m/z 426.1 [M+H]$^+$.

I-77

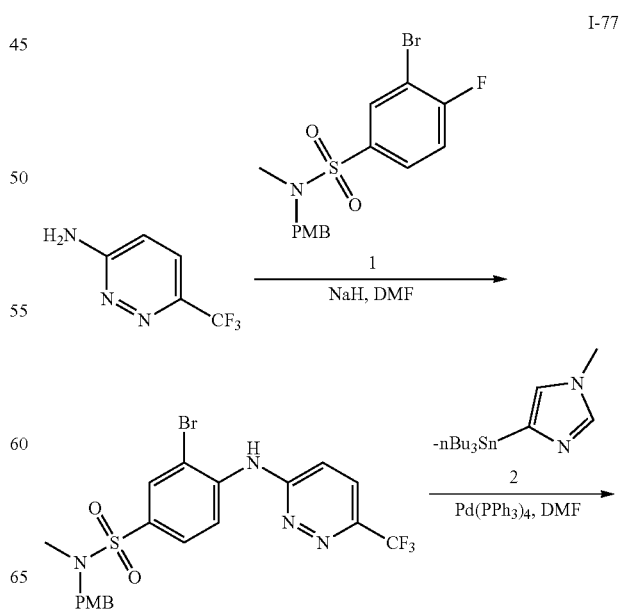

-continued

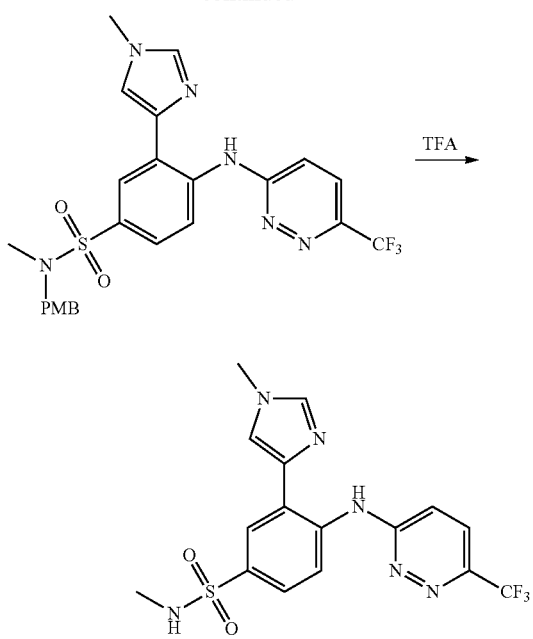

Step 1: 3-Bromo-N-[(4-methoxyphenyl)methyl]-N-methyl-4-[[6-(trifluoromethyl)pyridazin-3-yl]amino]benzenesulfonamide

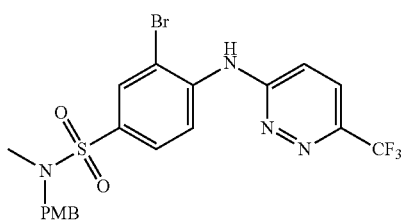

To a stirred solution of 6-(trifluoromethyl)pyridazin-3-amine (100 mg, 613.12 μmol, 94.81 μL, 1 eq) in DMF (5 mL) was added NaH (73.86 mg, 1.85 mmol, 60% purity, 3 eq) at 0° C. The reaction mixture was stirred at 0° C. for 15 min and at 20° C. for 45 min. 3-Bromo-4-fluoro-N-[(4-methoxyphenyl)methyl]-N-methyl-benzenesulfonamide (250 mg, 615.58 μmol, 95.6% purity, 1 eq) was added. The mixture was stirred at 20° C. for 12 h. The reaction mixture was diluted with water (50 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 1/1, TLC: PE/EtOAc=1/1, R$_f$=0.20) to yield 3-bromo-N-[(4-methoxyphenyl)methyl]-N-methyl-4-[[6-(trifluoromethyl)pyridazin-3-yl]amino]benzenesulfonamide (300 mg, 536.37 μmol, 87.1% yield, 95.0% purity) as a yellow solid. $^1$H NMR (400 MHz, CDCl$_3$) δ ppm 8.71 (d, J=8.8 Hz, 1H), 8.08 (d, J=2.0 Hz, 1H), 7.81 (dd, J=2.1, 8.7 Hz, 1H), 7.73 (d, J=9.3 Hz, 1H), 7.51 (s, 1H), 7.24 (d, J=8.3 Hz, 3H), 6.88 (d, J=8.8 Hz, 2H), 4.14 (s, 2H), 3.81 (s, 3H), 2.64 (s, 3H); ES-LCMS m/z 531.0, 533.0 [M+H]$^+$.

Step 2: N-[(4-Methoxyphenyl)methyl]-N-methyl-3-(1-methylimidazol-4-yl)-4-[[6-(trifluoromethyl)pyridazin-3-yl]amino]benzenesulfonamide

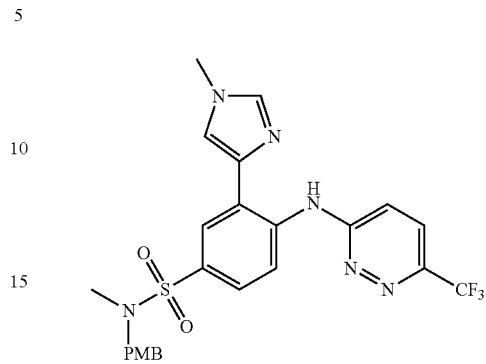

To a stirred solution of 3-bromo-N-[(4-methoxyphenyl)methyl]-N-methyl-4-[[6-(trifluoromethyl)pyridazin-3-yl]amino]benzenesulfonamide (300 mg, 536.37 μmol, 95% purity, 1 eq) in DMF (6 mL) was added Pd(PPh$_3$)$_4$ (61.98 mg, 53.64 μmol, 0.1 eq) and tributyl-(1-methylimidazol-4-yl)stannane (442.39 mg, 1.07 mmol, 90% purity, 2 eq). The reaction mixture was degassed and purged with N$_2$ for three times and stirred under N$_2$ atmosphere at 130° C. for 12 h. The reaction mixture was diluted with 2 M KF solution (50 mL), stirred at 20° C. for 15 min and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 4/3, TLC: PE/EtOAc=1/1, R$_f$=0.10) to yield N-[(4-methoxyphenyl)methyl]-N-methyl-3-(1-methylimidazol-4-yl)-4-[[6-(trifluoromethyl)pyridazin-3-yl]amino]benzenesulfonamide (200 mg, 338.00 μmol, 63.0% yield, 90.0% purity) as a yellow solid. $^1$H NMR (500 MHz, DMSO-d$_6$) δ ppm 12.56 (s, 1H), 8.78 (d, J=8.7 Hz, 1H), 8.09 (d, J=2.1 Hz, 1H), 8.05 (s, 1H), 7.99 (d, J=9.3 Hz, 1H), 7.95 (s, 1H), 7.72 (dd, J=2.1, 8.8 Hz, 1H), 7.51 (d, J=9.3 Hz, 1H), 7.25 (d, J=8.7 Hz, 2H), 6.92 (d, J=8.7 Hz, 2H), 4.09 (s, 2H), 3.77 (s, 3H), 3.74 (s, 3H), 2.54 (s, 3H).

Step 3: N-Methyl-3-(1-methylimidazol-4-yl)-4-[[6-(trifluoromethyl)pyridazin-3-yl]amino]benzenesulfonamide

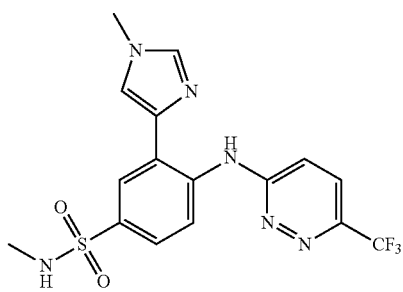 [SMILES: CNS(=O)(=O)c1ccc(Nc2ccc(C(F)(F)F)nc2)c(-c2cn(C)cn2)c1]

To a stirred solution of N-[(4-methoxyphenyl)methyl]-N-methyl-3-(1-methylimidazol-4-yl)-4-[[6-(trifluoromethyl)pyridazin-3-yl]amino]benzenesulfonamide (200 mg, 338.00 μmol, 90% purity, 1 eq) in DCM (5 mL) was added TFA (1.54 g, 13.51 mmol, 1 mL, 39.96 eq). The reaction mixture was stirred at 15° C. for 12 h. The reaction mixture was basified with saturated aqueous NaHCO$_3$ solution (30 mL) and extracted with DCM (20 mL×3). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 40%-70%, 10 min). The desired fraction was lyophilized to yield N-methyl-3-(1-methylimidazol-4-yl)-4-[[6-(trifluoromethyl)pyridazin-3-yl]amino] benzenesulfonamide (61.91 mg, 146.22 μmol, 43.3% yield, 97.4% purity) as a white solid. $^1$H NMR (400 MHz, DMSO-d$_6$) δ ppm 12.32 (s, 1H), 8.67 (d, J=8.6 Hz, 1H), 8.10 (d, J=2.0 Hz, 1H), 8.01-7.92 (m, 2H), 7.87 (d, J=1.2 Hz, 1H), 7.65 (dd, J=2.3, 8.7 Hz, 1H), 7.48 (d, J=9.3 Hz, 1H), 7.36 (d, J=4.9 Hz, 1H), 3.77 (s, 3H), 2.44 (d, J=4.4 Hz, 3H); ES-LCMS m/z 413.2 [M+H]$^+$.

I-78

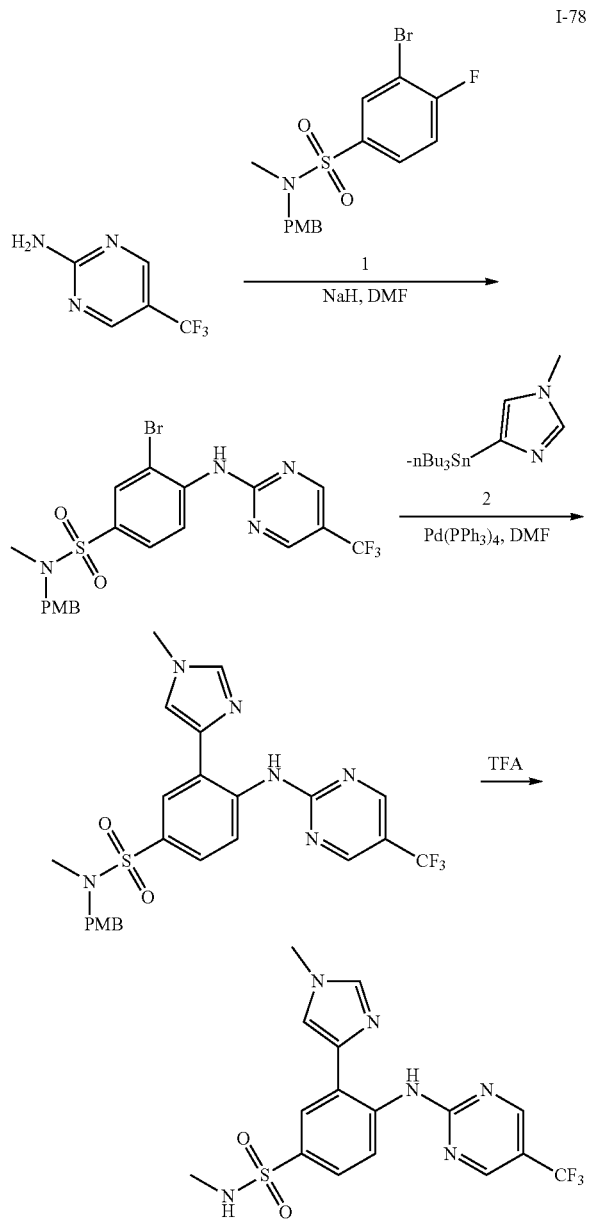

Step 1: 3-Bromo-N-[(4-methoxyphenyl)methyl]-N-methyl-4-[[5-(trifluoromethyl)pyrimidin-2-yl]amino] benzenesulfonamide

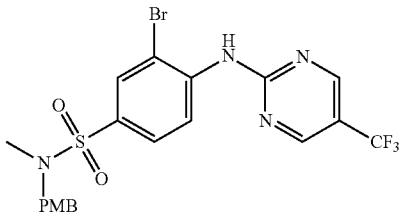

To a stirred solution of 5-(trifluoromethyl)pyrimidin-2-amine (80 mg, 490.50 μmol, 94.81 μL, 1 eq) in DMF (3 mL) was added NaH (58.86 mg, 1.47 mmol, 60% purity, 3 eq) at 0° C. The reaction mixture was stirred at 0° C. for 15 min and at 20° C. for 45 min. 3-Bromo-4-fluoro-N-[(4-methoxyphenyl)methyl]-N-methyl-benzenesulfonamide (200 mg, 492.46 μmol, 95.6% purity, 1 eq) was added and the reaction mixture was stirred at 30° C. for 12 h. The reaction mixture was diluted with water (50 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 1/1, TLC: PE/EtOAc=1/1, R$_f$=0.20) to yield 3-bromo-N-[(4-methoxyphenyl)methyl]-N-methyl-4-[[5-(trifluoromethyl)pyrimidin-2-yl]amino] benzenesulfonamide (230 mg, 389.58 μmol, 79.4% yield, 90.0% purity) as a yellow solid. $^1$H NMR (400 MHz, CDCl$_3$) δ ppm 8.84 (d, J=8.8 Hz, 1H), 8.77 (s, 2H), 8.16 (s, 1H), 8.08-8.05 (m, 1H), 7.82 (dd, J=2.0, 8.8 Hz, 1H), 7.24 (d, J=8.6 Hz, 2H), 6.88 (d, J=8.6 Hz, 2H), 4.12 (d, J=1.7 Hz, 2H), 3.81 (s, 3H), 2.63 (s, 3H); ES-LCMS m/z 531.0, 533.0 [M+H]$^+$.

Step 2: N-[(4-Methoxyphenyl)methyl]-N-methyl-3-(1-methylimidazol-4-yl)-4-[[5-(trifluoromethyl)pyrimidin-2-yl]amino]benzenesulfonamide

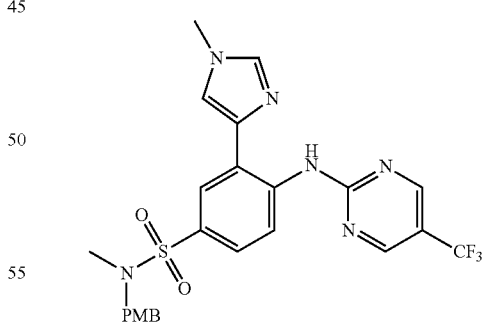

To a stirred solution of 3-bromo-N-[(4-methoxyphenyl)methyl]-N-methyl-4-[[5-(trifluoromethyl)pyrimidin-2-yl]amino]benzenesulfonamide (230 mg, 389.58 μmol, 90% purity, 1 eq) in DMF (6 mL) was added Pd(PPh$_3$)$_4$ (45.02 mg, 38.96 μmol, 0.1 eq) and tributyl-(1-methylimidazol-4-yl)stannane (321.31 mg, 779.15 μmol, 90% purity, 2 eq). The reaction mixture was degassed and purged with N$_2$ for three times and stirred under N$_2$ atmosphere at 130° C. for 12 h. The reaction mixture was diluted with 2 M KF solution (50 mL), stirred at 20° C. for 15 min and extracted with EtOAc (30 mL×3). The combined organic layers were dried over Na₂SO₄, filtered and the filtrate was concentrated to yield a residue which was purified by flash silica gel chromatography (from PE/EtOAc=100/1 to 4/3, TLC: PE/EtOAc=1/1, R$_f$=0.15) to yield N-[(4-methoxyphenyl)methyl]-N-methyl-3-(1-methylimidazol-4-yl)-4-[[5-(trifluoromethyl)pyrimidin-2-yl]amino]benzenesulfonamide (150 mg, 253.50 μmol, 65.1% yield, 90.0% purity) as a yellow solid. ¹H NMR (500 MHz, DMSO-d₆) δ ppm 13.18 (s, 1H), 8.97 (s, 2H), 8.92 (d, J=8.9 Hz, 1H), 8.08 (s, 1H), 8.05 (d, J=2.1 Hz, 1H), 8.00 (s, 1H), 7.71 (dd, J=2.1, 8.8 Hz, 1H), 7.25 (d, J=8.7 Hz, 2H), 6.92 (d, J=8.5 Hz, 2H), 4.08 (s, 2H), 3.77 (s, 3H), 3.74 (s, 3H), 2.53 (s, 3H); ES-LCMS m/z 533.2 [M+H]⁺.

Step 3: N-Methyl-3-(1-methylimidazol-4-yl)-4-[[5-(trifluoromethyl)pyrimidin-2-yl]amino]benzenesulfonamide

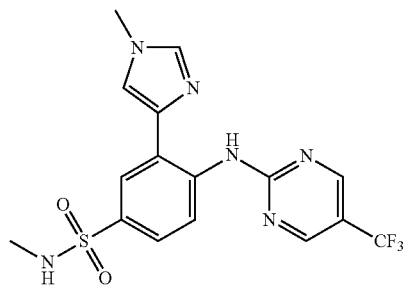

To a stirred solution of N-[(4-methoxyphenyl)methyl]-N-methyl-3-(1-methylimidazol-4-yl)-4-[[5-(trifluoromethyl)pyrimidin-2-yl]amino]benzenesulfonamide (150 mg, 253.50 μmol, 90% purity, 1 eq) in DCM (5 mL) was added TFA (1.54 g, 13.51 mmol, 1 mL, 53.28 eq). The reaction mixture was stirred at 15° C. for 12 h. The reaction mixture was basified with saturated aqueous NaHCO₃ solution (30 mL) and extracted with DCM (20 mL×3). The combined organic layers were dried over Na₂SO₄, filtered and the filtrate was concentrated to yield a residue which was purified by preparative HPLC (column: Agela DuraShell C18 150*25 mm*5 um; mobile phase: [water (0.04% NH₃.H₂O+10 mM NH₄HCO₃)-ACN]; B %: 45%-75%, 10 min). The desired fraction was lyophilized to yield N-methyl-3-(1-methylimidazol-4-yl)-4-[[5-(trifluoromethyl)pyrimidin-2-yl]amino]benzenesulfonamide (42.14 mg, 102.19 μmol, 40.3% yield, 100.0% purity) as white solid. ¹H NMR (400 MHz, DMSO-d₆) δ ppm 13.02 (s, 1H), 8.95 (s, 2H), 8.83 (d, J=8.8 Hz, 1H), 8.04 (d, J=2.0 Hz, 1H), 7.99 (s, 1H), 7.90 (d, J=1.0 Hz, 1H), 7.64 (dd, J=2.0, 8.8 Hz, 1H), 7.33 (d, J=5.1 Hz, 1H), 3.78 (s, 3H), 2.43 (d, J=4.9 Hz, 3H); ES-LCMS m/z 413.1 [M+H]⁺.

I-79

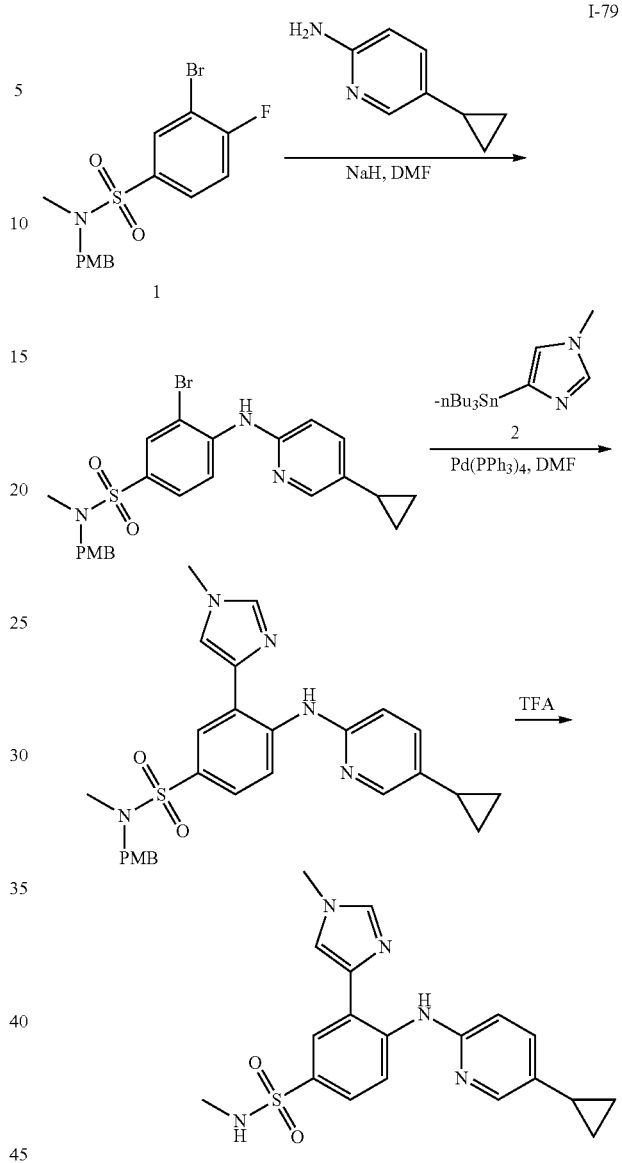

Step 1: 3-Bromo-4-[(5-cyclopropyl-2-pyridyl)amino]-N-[(4-methoxyphenyl)methyl]-N-methyl-benzenesulfonamide

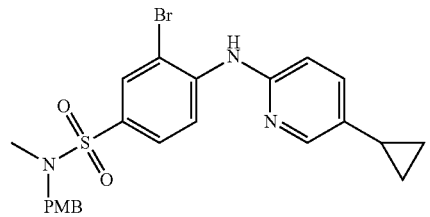

To a stirred solution of 5-cyclopropylpyridin-2-amine (100 mg, 745.28 μmol, 94.81 L, 1.01 eq) in DMF (5 mL) was added NaH (88.64 mg, 2.22 mmol, 60% purity, 3 eq) at 0° C. The reaction mixture was stirred at 0° C. for 15 min and at 20° C. for 45 min 3-Bromo-4-fluoro-N-[(4-methoxyphenyl)methyl]-N-methyl-benzenesulfonamide (300 mg, 738.70 μmol, 95.6% purity, 1 eq) was added and the mixture was stirred at 30° C. for 12 h. The reaction mixture was diluted with water (50 mL) and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 1/1, TLC: PE/EtOAc=1/1, R$_f$=0.55) to yield 3-bromo-4-[(5-cyclopropyl-2-pyridyl)amino]-N-[(4-methoxyphenyl)methyl]-N-methyl-benzenesulfonamide (250 mg, 447.83 μmol, 60.6% yield, 90.0% purity) as a yellow solid. $^1$H NMR (400 MHz, CDCl$_3$) δ ppm 8.45 (d, J=8.8 Hz, 1H), 8.18 (d, J=2.4 Hz, 1H), 8.03-7.97 (m, 1H), 7.71 (dd, J=2.0, 8.8 Hz, 1H), 7.32 (dd, J=2.4, 8.3 Hz, 1H), 7.24 (d, J=8.6 Hz, 2H), 7.13 (s, 1H), 6.90-6.85 (m, 3H), 4.09 (s, 2H), 3.81 (s, 3H), 2.59 (s, 3H), 1.95-1.85 (m, 1H), 1.06-0.97 (m, 2H), 0.74-0.65 (m, 2H); ES-LCMS m/z 501.8, 503.8 [M+H]$^+$.

Step 2: 4-[(5-Cyclopropyl-2-pyridyl)amino]-N-[(4-methoxyphenyl)methyl]-N-methyl-3-(1-methylimidazol-4-yl)benzenesulfonamide

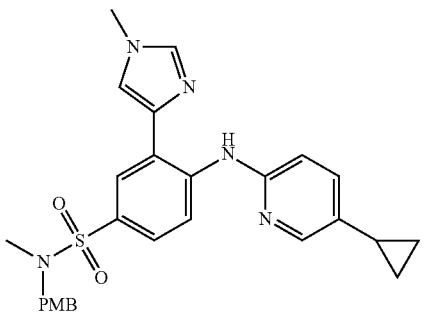

To a stirred solution of 3-bromo-4-[(5-cyclopropyl-2-pyridyl)amino]-N-[(4-methoxyphenyl)methyl]-N-methyl-benzenesulfonamide (250 mg, 447.83 μmol, 90% purity, 1 eq) in DMF (6 mL) was added Pd(PPh$_3$)$_4$ (51.75 mg, 44.78 μmol, 0.1 eq) and tributyl-(1-methylimidazol-4-yl)stannane (369.36 mg, 895.66 μmol, 90% purity, 2 eq). The reaction mixture was degassed and purged with N$_2$ for three times and stirred under N$_2$ atmosphere at 130° C. for 12 h. The reaction mixture was diluted with 2 M KF solution (50 mL), stirred at 20° C. for 15 min and extracted with EtOAc (30 mL×3). The combined organic layers were dried over Na$_2$SO$_4$, filtered and the filtrate was concentrated to yield a residue which was purified by flash silica gel chromatography (from PE/EtOAc=100/1 to 4/3, TLC: PE/EtOAc=1/1, R$_f$=0.15) to yield 4-[(5-cyclopropyl-2-pyridyl)amino]-N-[(4-methoxyphenyl)methyl]-N-methyl-3-(1-methylimidazol-4-yl)benzenesulfonamide (180 mg, 321.67 μmol, 71.8% yield, 90.0% purity) as a yellow solid. $^1$H NMR (500 MHz, DMSO-d$_6$) δ ppm 12.00 (s, 1H), 8.76 (d, J=8.9 Hz, 1H), 8.12 (d, J=2.1 Hz, 1H), 7.97 (s, 1H), 7.94 (d, J=2.3 Hz, 1H), 7.92 (s, 1H), 7.58 (dd, J=2.1, 8.9 Hz, 1H), 7.36 (dd, J=2.3, 8.5 Hz, 1H), 7.24 (d, J=8.5 Hz, 2H), 6.94-6.86 (m, 3H), 4.04 (s, 2H), 3.76 (s, 3H), 3.74 (s, 3H), 2.50 (s, 3H), 1.95-1.86 (m, 1H), 0.94-0.92 (m, 2H), 0.70-0.63 (m, 2H).

Step 3: 4-[(5-Cyclopropyl-2-pyridyl)amino]-N-methyl-3-(1-methylimidazol-4-yl)benzenesulfonamide

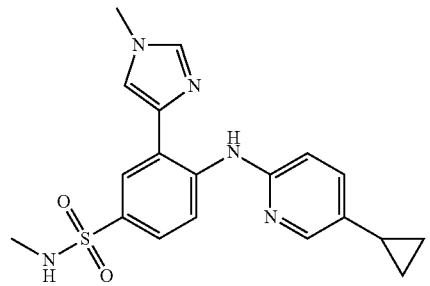 [SMILES: CNS(=O)(=O)c1ccc(Nc2ccc(C3CC3)cn2)c(-c2cn(C)cn2)c1]

To a stirred solution of 4-[(5-cyclopropyl-2-pyridyl)amino]-N-[(4-methoxyphenyl)methyl]-N-methyl-3-(1-methylimidazol-4-yl)benzenesulfonamide (180 mg, 321.67 μmol, 90% purity, 1 eq) in DCM (5 mL) was added TFA (1.54 g, 13.51 mmol, 1 mL, 41.99 eq). The reaction mixture was stirred at 15° C. for 12 h. The reaction mixture was basified with saturated aqueous NaHCO$_3$ solution (30 mL) and extracted with DCM (30 mL×3). The combined organic layers were dried over Na$_2$SO$_4$, filtered and the filtrate was concentrated to yield a residue which was purified by preparative HPLC (column: Agela DuraShell C18 150*25 mm*5 um; mobile phase: [water (0.04% NH$_3$.H$_2$O+10 mM NH$_4$HCO$_3$)-ACN]; B %: 45%-75%, 10 min). The desired fraction was lyophilized to yield 4-[(5-cyclopropyl-2-pyridyl)amino]-N-methyl-3-(1-methylimidazol-4-yl)benzenesulfonamide (48.08 mg, 123.88 μmol, 38.5% yield, 98.8% purity) as a white solid. $^1$H NMR (400 MHz, DMSO-d$_6$) δ ppm 11.84 (s, 1H), 8.66 (d, J=8.8 Hz, 1H), 8.10 (d, J=2.4 Hz, 1H), 7.98-7.89 (m, 2H), 7.80 (d, J=1.0 Hz, 1H), 7.52 (dd, J=2.2, 8.8 Hz, 1H), 7.35 (dd, J=2.4, 8.6 Hz, 1H), 7.19 (d, J=5.1 Hz, 1H), 6.86 (d, J=8.6 Hz, 1H), 3.77 (s, 3H), 2.41 (d, J=4.9 Hz, 3H), 1.95-1.83 (m, 1H), 0.97-0.87 (m, 2H), 0.71-0.61 (m, 2H); ES-LCMS m/z 384.2 [M+H]$^+$.

I-80

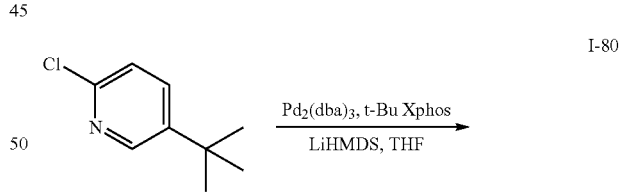

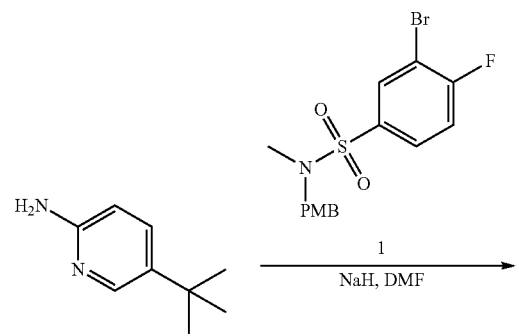

-continued

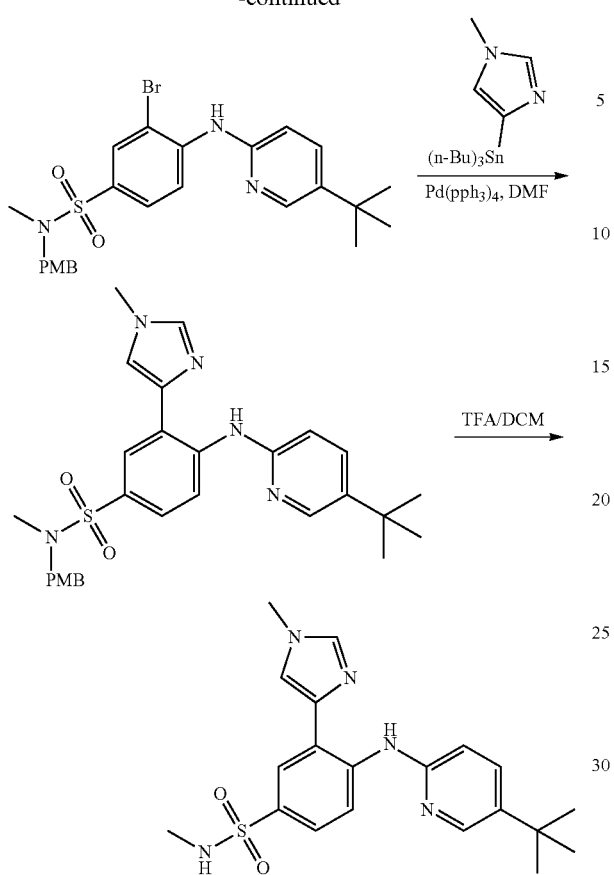

Step 1: 5-tert-Butylpyridin-2-amine

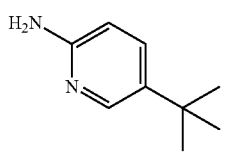

A mixture of 5-tert-butyl-2-chloro-pyridine (400 mg, 2.36 mmol, 1 eq), Pd$_2$(dba)$_3$ (215.91 mg, 235.78 µmol, 0.1 eq), t-Bu Xphos (200.24 mg, 471.56 µmol, 0.2 eq) and LiHMNDS (1 M, 11.79 mL, 5 eq) in THF (15 mL) was degassed and purged with N$_2$ for 3 times and stirred under N$_2$ atmosphere at 80° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=0/1, R$_f$=0.45) to yield 5-tert-butylpyridin-2-amine (350 mg, 2.28 mmol, 96.8% yield, 98.0% purity) as a yellow solid. $^1$H NMR (400 MHz, DMSO-d$_6$) δ ppm 7.89 (d, J=2.2 Hz, 1H), 7.40 (dd, J=2.7, 8.6 Hz, 1H), 6.38 (d, J=8.6 Hz, 1H), 5.63 (s, 2H), 1.21 (s, 9H); ES-LCMS m/z 151.4 [M+H]$^+$.

Step 2: 3-Bromo-4-[(5-tert-butyl-2-pyridyl)amino]-N-[(4-methoxyphenyl)methyl]-N-methyl-benzene-sulfonamide

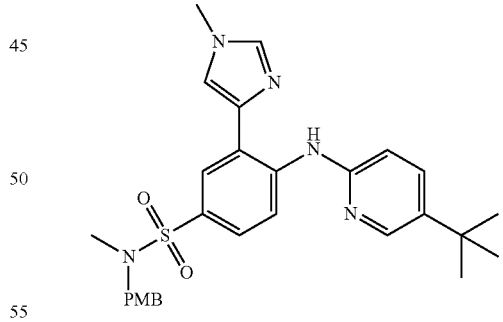

To a solution of 3-bromo-4-fluoro-N-[(4-methoxyphenyl)methyl]-N-methyl-benzenesulfonamide (893.16 mg, 2.19 mmol, 95%, 1 eq) in DMF (25 mL) was added NaH (262.23 mg, 6.56 mmol, 60%, 3 eq) and 5-tert-butylpyridin-2-amine (335 mg, 2.19 mmol, 98%, 1 eq). The mixture was stirred at 20° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.7) to yield 3-bromo-4-[(5-tert-butyl-2-pyridyl)amino]-N-[(4-methoxyphenyl)methyl]-N-methyl-benzenesulfonamide (600 mg, 1.15 mmol, 52.7% yield, 99.5% purity) as a yellow solid. $^1$H NMR (400 MHz, CDCl$_3$) δ ppm 8.50 (d, J=8.8 Hz, 1H), 8.38 (d, J=2.2 Hz, 1H), 8.00 (d, J=2.0 Hz, 1H), 7.73-7.67 (m, 2H), 7.24 (d, J=8.6 Hz, 2H), 7.15 (s, 1H), 6.93-6.86 (m, 3H), 4.09 (s, 2H), 3.81 (s, 3H), 2.59 (s, 3H), 1.36 (s, 9H); ES-LCMS m/z 520.1, 522.1 [M+H]$^+$.

Step 3: 4-[(5-tert-Butyl-2-pyridyl)amino]-N-[(4-methoxyphenyl)methyl]-N-methyl-3-(1-methylimidazol-4-yl)benzenesulfonamide A mixture of 3-bromo-4-[5-tert-butyl-2-pyridyl)amino]-N-[(4-methoxyphenyl)methyl]-N-methyl-benzenesulfonamide (300 mg, 575.74 µmol, 99.5%, 1 eq), tributyl-(1-methylimidazol-4-yl)stannane (308.65 mg, 748.46 µmol, 90%, 1.3 eq), Pd(dppf)Cl$_2$ (42.13 mg, 57.57 µmol, 0.1 eq) in DMF (12 mL) was degassed and purged with N$_2$ for 3 times and stirred under N$_2$ atmosphere at 130° C. for 12 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 1/1, TLC: PE/EtOAc=1/1, $R_f$=0.40) to yield 4-[(5-tert-butyl-2-pyridyl)amino]-N-[(4-methoxyphenyl)methyl]-N-methyl-3-(1-methylimidazol-4-yl)benzenesulfonamide (275 mg, 522.32 µmol, 90.7% yield, 98.7% purity) as a yellow solid. $^1$H NMR (400 MHz, DMSO-$d_6$) δ ppm 12.01 (s, 1H), 8.80 (d, J=8.8 Hz, 1H), 8.31 (d, J=2.4 Hz, 1H), 7.98 (s, 1H), 7.96-7.93 (m, 1H), 7.96-7.92 (m, 1H), 7.75 (dd, J=2.7, 8.6 Hz, 1H), 7.59 (dd, J=2.2, 9.0 Hz, 1H), 7.24 (d, J=8.8 Hz, 2H), 6.92 (dd, J=2.7, 8.8 Hz, 3H), 4.04 (s, 2H), 3.77 (s, 3H), 3.73 (s, 3H), 2.51-2.51 (m, 3H), 1.30 (s, 9H); ES-LCMS m/z 520.2 [M+H]$^+$.

Step 4: 4-[(5-tert-Butyl-2-pyridyl)amino]-N-methyl-3-(1-methylimidazol-4-yl)benzenesulfonamide

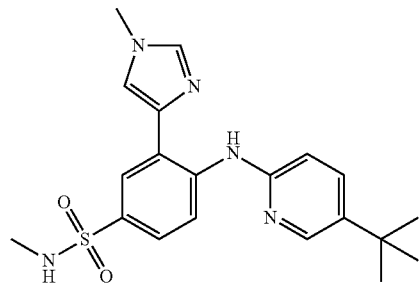 [SMILES: CNS(=O)(=O)c1ccc(Nc2ccc(C(C)(C)C)cn2)c(-c2cn(C)cn2)c1]

To a solution of 4-[(5-tert-butyl-2-pyridyl)amino]-N-[(4-methoxyphenyl)methyl]-N-methyl-3-(1-methylimidazol-4-yl)benzenesulfonamide (275 mg, 523.90 µmol, 99%, 1 eq) in DCM (6 mL) was added TFA (4.62 g, 40.52 mmol, 3 mL, 77.34 eq). The mixture was stirred at 20° C. for 12 h. The mixture was diluted with DCM (20 mL×4) and concentrated under reduced pressure to yield a residue which was purified by preparative HPLC (column: Agela DuraShell C18 150*25 mm*5 µm; mobile phase: [water (0.04% $NH_3$·$H_2O$+ 10 mM $NH_4HCO_3$)-ACN]; B %: 50%-80%, 10 min) and lyophilized to yield 4-[(5-tert-butyl-2-pyridyl)amino]-N-methyl-3-(1-methylimidazol-4-yl)benzenesulfonamide (18.01 mg, 44.90 µmol, 8.6% yield, 99.6% purity) as a white solid. $^1$H NMR (400 MHz, $CD_3OD$) δ ppm 8.42 (d, J=8.8 Hz, 1H), 8.25 (d, J=2.2 Hz, 1H), 7.99 (d, J=2.4 Hz, 1H), 7.78-7.71 (m, 2H), 7.61 (dd, J=2.3, 8.9 Hz, 1H), 7.56 (d, J=1.2 Hz, 1H), 6.98 (d, J=8.6 Hz, 1H), 3.81 (s, 3H), 2.54 (s, 3H), 1.35 (s, 9H); ES-LCMS m/z 400.2 [M+H]$^+$.

I-81

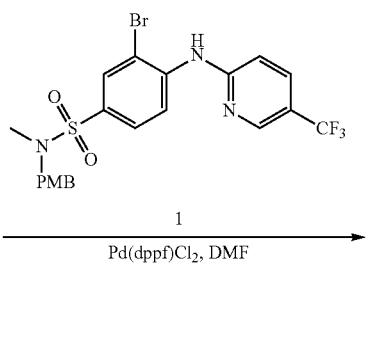

Step 1: 1-[(2-Fluorophenyl)methyl]-4-iodo-imidazole

To a solution of 4-iodo-1H-imidazole (2.01 g, 10.38 mmol, 1 eq) in DMF (20 mL) was added NaH (585.00 mg, 14.63 mmol, 60% purity, 1.41 eq) at 20° C. The mixture was stirred at 20° C. for 0.5 h. 1-(Chloromethyl)-2-fluoro-benzene (1.5 g, 10.38 mmol, 1.23 mL, 1 eq) was added into the mixture. The mixture stirred under $N_2$ atmosphere at 20° C. for 11.5 h. TLC (PE/EtOAc=1/1, $R_f$=0.47) showed the starting material was consumed completely. The reaction mixture was diluted with $H_2O$ (30 mL) and extracted with EtOAc (50 mL×3). The combined organic layers dried over $Na_2SO_4$, filtered and concentrated under reduced pressure to yield a residue which was purified by flash silica gel chromatography (from PE/EtOAc=100/1 to 1/1, TLC: PE/EtOAc=1/1, $R_f$=0.47) to yield 1-[(2-fluorophenyl)methyl]-4-iodo-imidazole (2 g, 5.30 mmol, 51.1% yield, 80.0% purity) as a white solid. $^1$H NMR (500 MHz, CDCl$_3$) δ ppm 7.47-7.41 (m, 1H), 7.37-7.28 (m, 1H), 7.17-7.09 (m, 1H), 7.03-6.95 (m, 3H), 5.15-5.09 (m, 2H); ES-LCMS m/z 302.8 [M+H]$^+$.

Step 2: Tributyl-[1-[(2-fluorophenyl)methyl]imidazol-4-yl]stannane

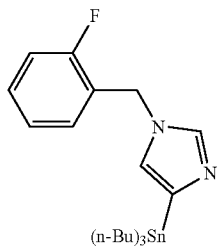

To a solution of 1-[(2-fluorophenyl)methyl]-4-iodo-imidazole (750 mg, 2.48 mmol, 1 eq) in THF (8 mL) was added i-PrMgCl (2.0 M, 1.86 mL, 1.5 eq). The mixture was stirred under $N_2$ atmosphere at −10° C. for 1 h. Tributyl(chloro)stannane (1.21 g, 3.72 mmol, 1 mL, 1.50 eq) was added dropwise at −10° C. The mixture was stirred under $N_2$ atmosphere at −10° C. for 1 h and at 20° C. for 2 h. The reaction mixture was quenched by addition of saturated aqueous KF (20 mL) and extracted with EtOAc (50 mL×3). The combined organic layers were washed with brine (50 mL), dried over $Na_2SO_4$, filtered and concentrated under reduced pressure to yield tributyl-[1-[(2-fluorophenyl)methyl]imidazol-4-yl]stannane (1.5 g, 2.26 mmol, 90.9% yield, 70.0% purity) as colorless oil, which was used in the next step without further purification. $^1$H NMR (400 MHz, CDCl$_3$) δ ppm 7.76 (s, 1H), 7.38-7.28 (m, 2H), 7.12 (d, J=7.4 Hz, 2H), 6.96 (s, 1H), 5.18 (s, 2H), 1.96-1.74 (m, 12H), 1.60-1.55 (m, 6H), 1.24-1.15 (m, 9H); ES-LCMS m/z 466.7 [M+H]$^+$.

Step 3: 3-[1-[(2-Fluorophenyl)methyl]imidazol-4-yl]-N-[(4-methoxyphenyl)methyl]-N-methyl-4-[[5-(trifluoromethyl)-2-pyridyl]amino]benzenesulfonamide

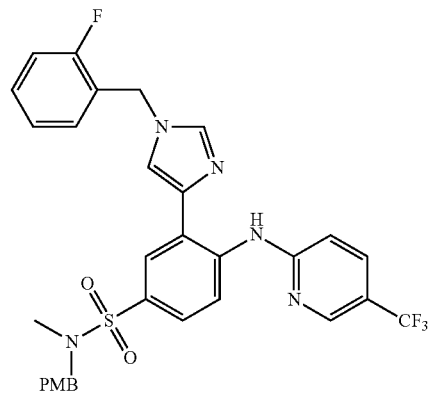

To a solution of 3-bromo-N-[(4-methoxyphenyl)methyl]-N-methyl-4-[[5-(trifluoromethyl)-2-pyridyl]amino]benzenesulfonamide (200.00 mg, 358.25 μmol, 95% purity, 1 eq) in DMF (2 mL) was added Pd(PPh$_3$)$_4$ (45 mg, 38.94 μmol, 1.09e-1 eq) and tributyl-[1-[(2-fluorophenyl)methyl]imidazol-4-yl]stannane (300 mg, 451.39 μmol, 70% purity, 1.26 eq). The mixture was stirred under $N_2$ atmosphere at 145° C. for 12 h. TLC (PE/EtOAc=3/1, $R_f$=0.40) showed the starting material was consumed completely. The reaction mixture was quenched with $H_2O$ (20 mL) and extracted with EtOAc (50 mL×3). The combined organic layers dried over $Na_2SO_4$, filtered and concentrated under reduced pressure to yield a residue which was purified by flash silica gel chromatography (from PE/EtOAc=100/1 to 3/1, TLC: PE/EtOAc=10/1, $R_f$=0.40) to yield 3-[1-[(2-fluorophenyl)methyl]imidazol-4-yl]-N-[(4-methoxyphenyl)methyl]-N-methyl-4-[[5-(trifluoromethyl)-2-pyridyl]amino]benzenesulfonamide (150 mg, 215.78 μmol, 60.2% yield, 90.0% purity) as brown oil. $^1$H NMR (400 MHz, CDCl$_3$) δ ppm 12.23 (s, 1H), 8.94 (d, J=9.0 Hz, 1H), 8.55 (s, 1H), 7.92 (d, J=2.2 Hz, 1H), 7.75-7.67 (m, 3H), 7.43-7.37 (m, 2H), 7.26-7.14 (m, 5H), 6.95 (d, J=8.8 Hz, 1H), 6.89-6.85 (m, 2H), 5.25 (s, 2H), 4.08 (s, 2H), 3.80 (s, 3H), 2.59-2.57 (m, 3H); ES-LCMS m/z 626.1 [M+H]$^+$.

Step 4: 3-[1-[(2-Fluorophenyl)methyl]imidazol-4-yl]-N-methyl-4-[[5-(trifluoromethyl)-2-pyridyl]amino]benzenesulfonamide

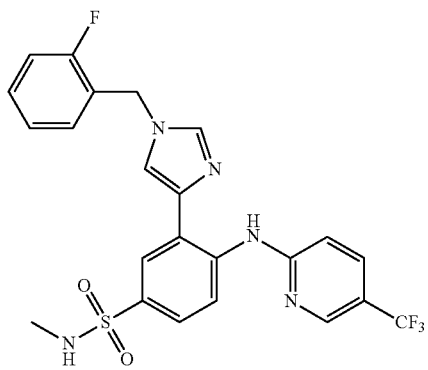 [SMILES: CNS(=O)(=O)c1ccc(Nc2ccc(C(F)(F)F)cn2)c(-c2cn(Cc3ccccc3F)cn2)c1]

To a solution of 3-[1-[(2-fluorophenyl)methyl]imidazol-4-yl]-N-[(4-methoxyphenyl)methyl]-N-methyl-4-[[5-(trifluoromethyl)-2-pyridyl]amino]benzenesulfonamide (100 mg, 159.84 μmol, 100% purity, 1 eq) in DCM (3 mL) was added TFA (1 g, 8.77 mmol, 649.35 μL, 54.87 eq). The mixture was stirred at 20° C. for 12 h. The reaction mixture was diluted with H$_2$O (20 mL), basified with saturated aqueous NaHCO$_3$ until pH=8 and extracted with EtOAc (50 mL×3). The combined organic layers dried over Na$_2$SO$_4$, filtered and concentrated under reduced pressure to yield a residue which was purified by preparative HPLC (column: Phenomenex Synergi C18 150×30 mm×4 um; mobile phase: [water (0.05% HCl)-ACN]; B %: 41%-61%, 9 min). The desired fraction was lyophilized to yield 3-[1-[(2-fluorophenyl)methyl]imidazol-4-yl]-N-methyl-4-[[5-(trifluoromethyl)-2-pyridyl]amino]benzenesulfonamide (55.12 mg, 109.04 μmol, 68.2% yield, 100.0% purity) as a white solid. $^1$H NMR (400 MHz, CDCl$_3$) δ ppm 12.22 (s, 1H), 8.90 (d, J=9.0 Hz, 1H), 8.54 (s, 1H), 7.98 (d, J=2.2 Hz, 1H), 7.74-7.66 (m, 3H), 7.44-7.35 (m, 2H), 7.27-7.11 (m, 3H), 6.93 (d, J=8.8 Hz, 1H), 5.24 (s, 2H), 4.33 (q, J=5.3 Hz, 1H), 2.66 (d, J=5.4 Hz, 3H); ES-LCMS m/z 506.1 [M+H]$^+$.

I-82

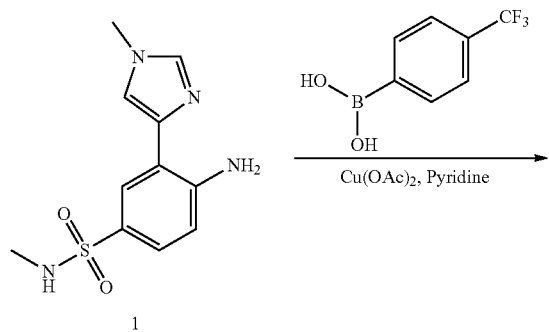

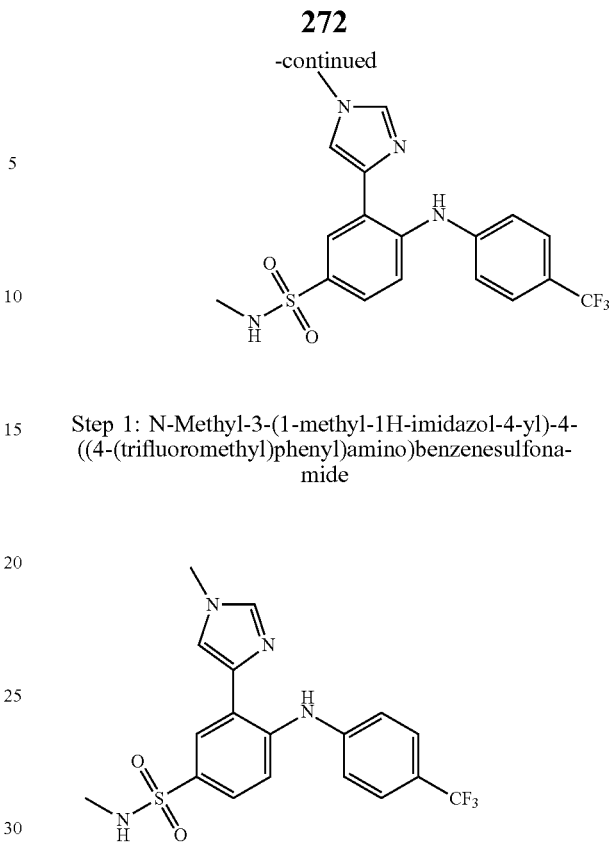

Step 1: N-Methyl-3-(1-methyl-1H-imidazol-4-yl)-4-((4-(trifluoromethyl)phenyl)amino)benzenesulfonamide To a solution of 4-amino-N-methyl-3-(1-methylimidazol-4-yl)benzenesulfonamide (20 mg, 67.59 μmol, 90% purity, 1 eq) in DCM (2 mL) was added pyridine (16.04 mg, 202.76 μmol, 16.37 μL, 3 eq), Cu(OAc)$_2$ (18.41 mg, 101.38 μmol, 1.5 eq) and [4-(trifluoromethyl)phenyl]boronic acid (15.40 mg, 81.11 μmol, 1.2 eq) under O$_2$ (15 Psi). The mixture was stirred at 10° C. for 12 h. The reaction mixture was quenched by addition of H$_2$O (20 mL) and extracted with EtOAc (30 mL×3). The combined organic layers were washed with brine (30 mL), dried over Na$_2$SO$_4$, filtered and concentrated under reduced pressure to give a residue which was purified by preparative HPLC (column: column: Agela DuraShell C18 150*25 mm*5 μm; mobile phase: [water (0.04% NH$_3$.H$_2$O+10 mM NH$_4$HCO$_3$)-ACN]; B %: 47%-77%, 10 min), followed by lyophilization to yield N-methyl-3-(1-methylimidazol-4-yl)-4-[4-(trifluoromethyl)anilino]benzenesulfonamide (12.48 mg, 29.47 μmol, 43.6% yield, 96.9% purity) as a white solid. $^1$H NMR (400 MHz, CDCl$_3$) δ ppm 10.89 (br s, 1H), 7.98 (br s, 1H), 7.62-7.51 (m, 4H), 7.5-7.47 (m, 1H), 7.35-7.32 (m, 2H), 7.27-7.20 (m, 1H), 4.27 (s, 1H), 3.80 (s, 3H), 2.68 (d, J=5.2 Hz, 3H); ES-LCMS m/z 411.0 [M+H]$^+$.

I-83

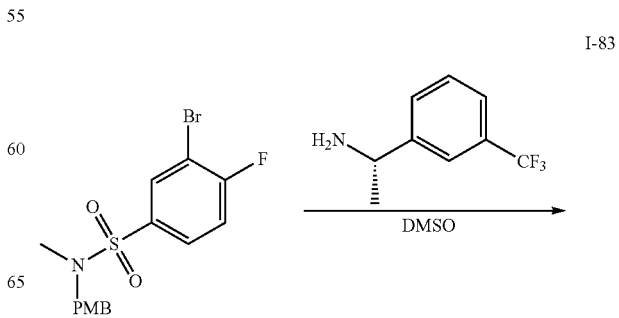

-continued

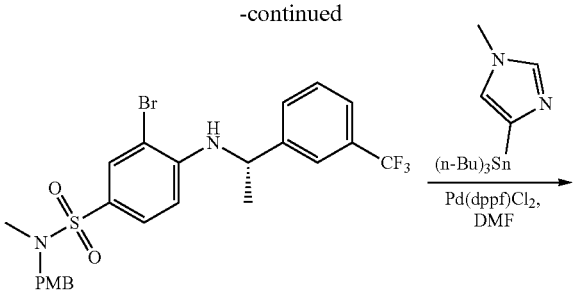

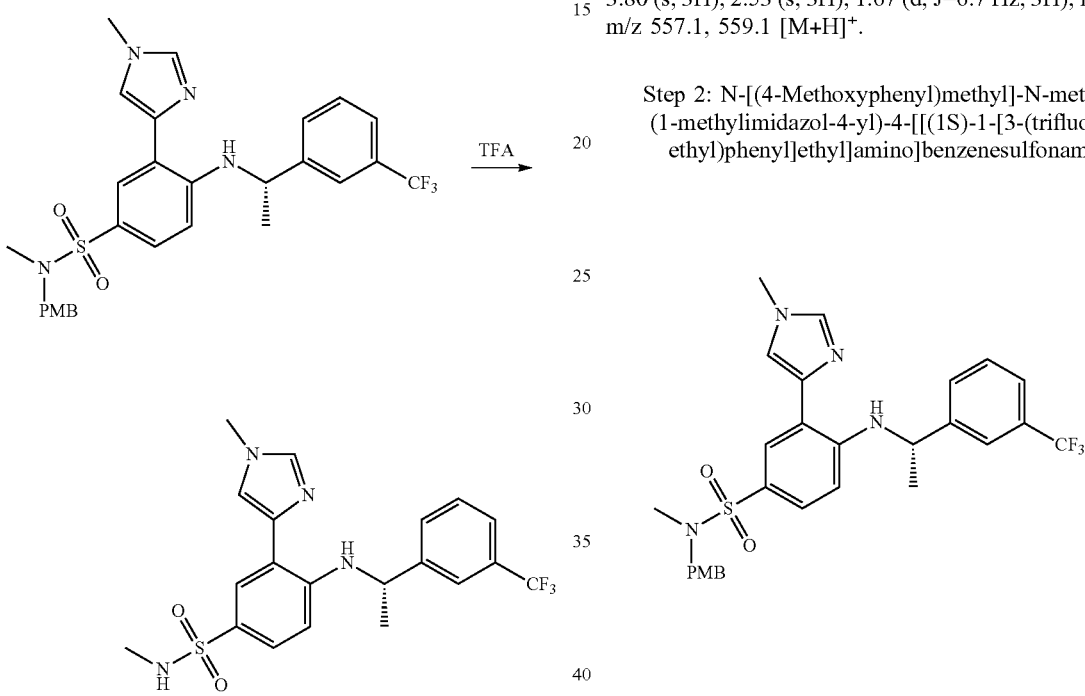

Step 1: 3-Bromo-N-[(4-methoxyphenyl)methyl]-N-methyl-4-[[(1S)-1-[3-(trifluoromethyl)phenyl]ethyl]amino]benzenesulfonamide

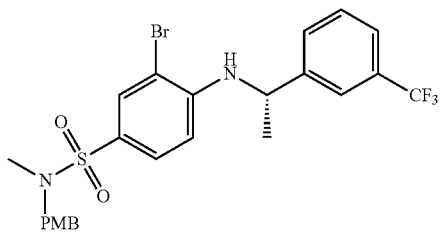

A mixture of 3-bromo-4-fluoro-N-[(4-methoxyphenyl)methyl]-N-methyl-benzenesulfonamide (210 mg, 513.84 µmol, 95% purity, 1 eq) and (1S)-1-[3-(trifluoromethyl)phenyl]ethanamine (100 mg, 528.60 µmol, 1.03 eq) in DMSO (2 mL) was stirred at 140° C. for 2 h. The mixture was filtered and the filtrate was purified by preparative HPLC (column: Phenomenex Synergi C18 150*30 mm*4 um; mobile phase: [water (0.1% TFA)-ACN]; B %: 72%-92%, 9 min). The desired fraction was basified with saturated aqueous NaHCO$_3$ until pH=8 and extracted with EtOAc (50 mL×3). The organic layer was dried over Na$_2$SO$_4$, filtered and concentrated under reduced pressure to yield 3-bromo-N-[(4-methoxyphenyl)methyl]-N-methyl-4-[[(1S)-1-[3-(trifluoromethyl)phenyl]ethyl]amino]benzenesulfonamide (50 mg, 80.73 µmol, 15.7% yield, 90.0% purity) as a yellow gum. $^1$H NMR (500 MHz, CDCl$_3$) δ ppm 7.91 (d, J=2.0 Hz, 1H), 7.59 (s, 1H), 7.58-7.46 (m, 4H), 7.20 (d, J=8.5 Hz, 2H), 6.85 (d, J=8.5 Hz, 2H), 6.37 (d, J=8.9 Hz, 1H), 5.19 (d, J=5.0 Hz, 1H), 4.70-4.60 (m, 1H), 4.03 (s, 2H), 3.80 (s, 3H), 2.53 (s, 3H), 1.67 (d, J=6.7 Hz, 3H); ES-LCMS m/z 557.1, 559.1 [M+H]$^+$.

Step 2: N-[(4-Methoxyphenyl)methyl]-N-methyl-3-(1-methylimidazol-4-yl)-4-[[(1S)-1-[3-(trifluoromethyl)phenyl]ethyl]amino]benzenesulfonamide A mixture of 3-bromo-N-[(4-methoxyphenyl)methyl]-N-methyl-4-[[(1S)-1-[3-(trifluoromethyl)phenyl]ethyl]amino]benzenesulfonamide (50 mg, 80.73 µmol, 90% purity, 1 eq), tributyl-(1-methylimidazol-4-yl)stannane (102.04 mg, 269.43 µmol, 98% purity, 3.34 eq) and Pd(dppf)Cl$_2$ (5 mg, 6.83 µmol, 8.46e-2 eq) in DMF (1 mL) was stirred under N$_2$ atmosphere at 130° C. for 12 h. TLC (PE/EtOAc=1/1, R$_f$=0.30) showed the starting material was consumed completely. The mixture was diluted with aqueous KF (20 mL), stirred at 15° C. for 1 h and extracted with EtOAc (20 mL×3). The organic layer was dried over Na$_2$SO$_4$, filtered and concentrated under reduced pressure to yield a residue which was purified by flash silica gel chromatography (from PE/EtOAc=10/1 to 1/1, TLC: PE/EtOAc=1/1, R$_f$=0.30) to yield N-[(4-methoxyphenyl)methyl]-N-methyl-3-(1-methylimidazol-4-yl)-4-[[(1S)-1-[3-(trifluoromethyl)phenyl]ethyl]amino]benzenesulfonamide (40 mg, 53.70 µmol, 66.5% yield, 75.0% purity) as a colorless gum. $^1$H NMR (500 MHz, CDCl$_3$) δ ppm 9.19 (d, J=4.7 Hz, 1H), 7.79 (d, J=2.0 Hz, 1H), 7.64 (s, 1H), 7.58 (d, J=7.6 Hz, 1H), 7.54 (s, 1H), 7.52-7.48 (m, 1H), 7.47-7.42 (m, 1H), 7.37 (dd, J=2.1, 8.7 Hz, 1H), 7.30 (s, 1H), 7.19 (d, J=8.5 Hz, 2H), 6.83 (d, J=8.5 Hz, 2H), 6.38 (d, J=8.7 Hz, 1H), 4.68 (q, J=6.3 Hz, 1H), 3.99 (s, 2H), 3.79 (d, J=6.3 Hz, 6H), 2.49 (s, 3H), 1.65 (d, J=6.7 Hz, 3H); ES-LCMS m/z 559.3 [M+H]$^+$.

Step 3: N-Methyl-3-(1-methylimidazol-4-yl)-4-[[(1S)-1-[3-(trifluoromethyl)phenyl]ethyl]amino]benzenesulfonamide

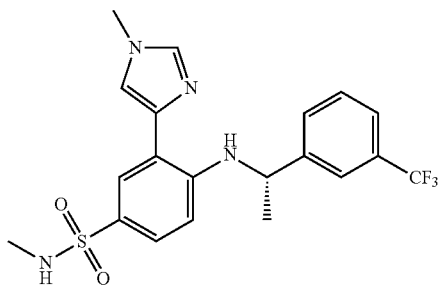 [SMILES: CNS(=O)(=O)c1ccc(N[C@@H](C)c2cccc(C(F)(F)F)c2)c(-c2cn(C)cn2)c1]

To a solution of N-[(4-methoxyphenyl)methyl]-N-methyl-3-(1-methylimidazol-4-yl)-4-[[(1S)-1-[3-(trifluoromethyl)phenyl]ethyl]amino]benzenesulfonamide (40 mg, 53.70 µmol, 75% purity, 1 eq) in DCM (3 mL) was added TFA (770.00 mg, 6.75 mmol, 0.5 mL, 125.74 eq). The mixture was stirred at 15° C. for 12 h. The reaction mixture was concentrated under reduced pressure to yield a residue which was purified by preparative HPLC (column: Agela DuraShell C18 150*25 mm*5 um; mobile phase: [water (0.05% $NH_3 \cdot H_2O$+10 mM $NH_4HCO_3$)-ACN]; B %: 46%-76%, 10 min) and lyophilized to yield N-methyl-3-(1-methylimidazol-4-yl)-4-[[(1S)-1-[3-(trifluoromethyl)phenyl]ethyl]amino]benzenesulfonamide (5.38 mg, 12.27 µmol, 22.9% yield, 100.0% purity, SFC1: Rt=5.290, ee=99.56%, SFC2: Rt=3.680, ee=99.58%, $[\alpha]^{23.0}_D$=+98.00 (MeOH, c=0.100 g/100 mL)) as a white solid. $^1$H NMR (500 MHz, $CD_3OD$) δ ppm 7.83 (d, J=2.1 Hz, 1H), 7.76 (s, 1H), 7.70 (s, 1H), 7.67 (d, J=6.6 Hz, 1H), 7.56-7.49 (m, 3H), 7.37 (dd, J=2.1, 8.7 Hz, 1H), 6.46 (d, J=8.7 Hz, 1H), 4.80 (q, J=6.8 Hz, 1H), 3.85 (s, 3H), 2.47 (s, 3H), 1.61 (d, J=6.7 Hz, 3H); ES-LCMS m/z 439.1 [M+H]$^+$.

I-84

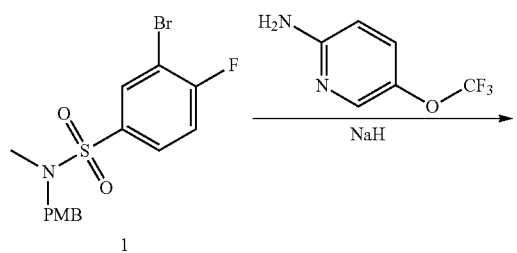

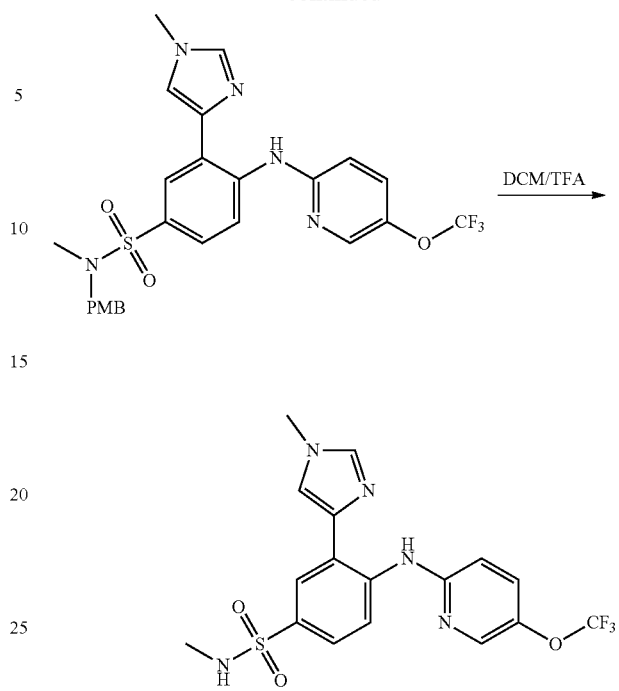

Step 1: 3-Bromo-N-[(4-methoxyphenyl)methyl]-N-methyl-4-[[5-(trifluoromethoxy)-2-pyridyl]amino]benzenesulfonamide

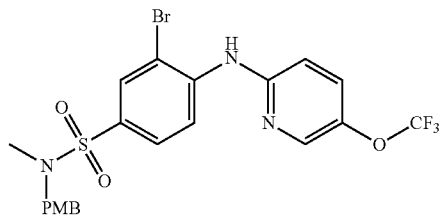

To a solution of 5-(trifluoromethoxy)pyridin-2-amine (43.60 mg, 244.82 µmol, 1 eq) in DMF (3 mL) was added NaH (29.36 mg, 734.06 mol, 60%, 3 eq) at 0° C. The mixture was stirred at 25° C. for 0.5 h. 3-Bromo-4-fluoro-N-[(4-methoxyphenyl)methyl]-N-methyl-benzenesulfonamide (100 mg, 244.69 mol, 95%, 1 eq) was added. The mixture was stirred at 60° C. for 12 h. The reaction mixture was concentrated under reduced pressure to yield a residue which was purified by flash silica gel chromatography (from PE/EtOAc=100/1 to 3/1, TLC: PE/EtOAc=3/1, $R_f$=0.42) to yield 3-bromo-N-[(4-methoxyphenyl)methyl]-N-methyl-4-[[5-(trifluoromethoxy)-2-pyridyl]amino]benzenesulfonamide (120 mg, 204.26 µmol, 83.5% yield, 93.0% purity) as a white solid. $^1$H NMR (400 MHz, $CDCl_3$) δ ppm 8.56 (d, J=8.6 Hz, 1H), 8.29 (d, J=2.7 Hz, 1H), 8.03 (d, J=2.0 Hz, 1H), 7.75 (dd, J=2.0, 9.0 Hz, 1H), 7.60-7.50 (m, 1H), 7.29 (s, 1H), 7.24 (d, J=8.6 Hz, 2H), 6.96 (d, J=9.0 Hz, 1H), 6.88 (d, J=8.6 Hz, 2H), 4.11 (s, 2H), 3.81 (s, 3H), 2.61 (s, 3H); ES-LCMS m/z 546.0, 548.0 [M+H]$^+$.

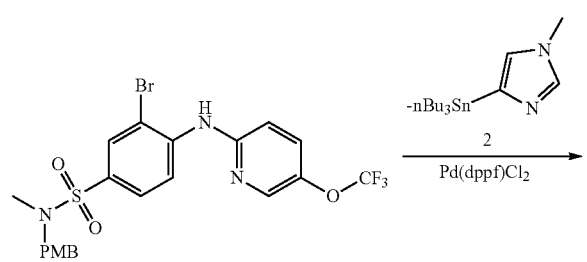

Step 2: N-[(4-Methoxyphenyl)methyl]-N-methyl-3-(1-methylimidazol-4-yl)-4-[[5-(trifluoromethoxy)-2-pyridyl]amino]benzenesulfonamide

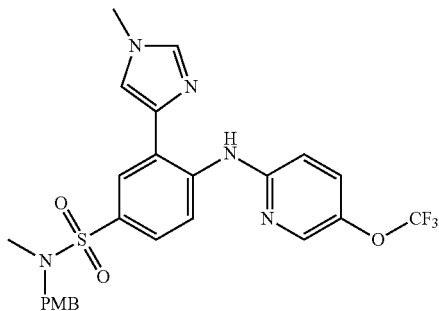

To a solution of 3-bromo-N-[(4-methoxyphenyl)methyl]-N-methyl-4-[[5-(trifluoromethoxy)-2-pyridyl]amino]benzenesulfonamide (100 mg, 170.22 μmol, 93%, 1 eq) and tributyl-(1-methylimidazol-4-yl)stannane (128.93 mg, 340.44 μmol, 98%, 2 eq) in DMF (3 mL) was added Pd(PPh$_3$)$_4$ (19.67 mg, 17.02 μmol, 0.1 eq). The mixture was stirred at 130° C. for 12 h. TLC (PE/EtOAc=1/1, R$_f$=0.31) indicated the starting material was consumed completely and one new spots formed. The mixture was diluted with water (100 mL) and extracted with EtOAc (100 mL×3). The combined organic phase was washed with brine (20 mL), dried over anhydrous Na$_2$SO$_4$, filtered and concentrated in vacuum to yield a residue which was purified by flash silica gel chromatography (from PE/EtOAc=100/1 to 1/1, TLC: PE/EtOAc=1/1, R$_f$=0.31) to yield N-[(4-methoxyphenyl)methyl]-N-methyl-3-(1-methylimidazol-4-yl)-4-[[5-(trifluoromethoxy)-2-pyridyl]amino]benzenesulfonamide (80 mg, 144.64 μmol, 85.0% yield, 99.0% purity) as yellow oil. $^1$H NMR (400 MHz, CDCl$_3$) δ ppm 11.99 (s, 1H), 8.83 (d, J=8.6 Hz, 1H), 8.25 (s, 1H), 7.93 (d, J=2.0 Hz, 1H), 7.69-7.65 (m, 1H), 7.57 (s, 1H), 7.46 (d, J=9.0 Hz, 1H), 7.36 (d, J=1.6 Hz, 1H), 7.24 (d, J=8.6 Hz, 2H), 6.94 (d, J=8.6 Hz, 1H), 6.87 (d, J=8.6 Hz, 2H), 4.09 (s, 2H), 3.81 (d, J=2.0 Hz, 6H), 2.58 (s, 3H); ES-LCMS m/z 548.2 [M+H]$^+$.

Step 3: N-Methyl-3-(1-methylimidazol-4-yl)-4-[[5-(trifluoromethoxy)-2-pyridyl]amino]benzenesulfonamide

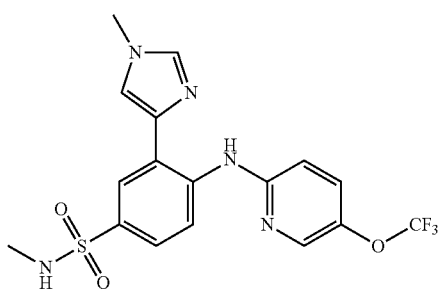 [SMILES: CNS(=O)(=O)c1ccc(Nc2ccc(OC(F)(F)F)cn2)c(-c2cn(C)cn2)c1]

To a solution of N-[(4-methoxyphenyl)methyl]-N-methyl-3-(1-methylimidazol-4-yl)-4-[[5-(trifluoromethoxy)-2-pyridyl]amino]benzenesulfonamide (80 mg, 144.64 μmol, 99%, 1 eq) in DCM (6 mL) was added TFA (3.08 g, 27.01 mmol, 2 mL, 186.75 eq) at 0° C. The mixture was stirred at 25° C. for 2 h. The mixture was basified with sat. aq. NaHCO$_3$ (30 mL) at 0° C. and extracted with DCM (30 mL×3). The combined organic phase was washed with brine (20 mL), dried over anhydrous Na$_2$SO$_4$, filtered and concentrated in vacuum to yield a residue which was purified by preparative HPLC (column: Agela DuraShell C18 150*25 mm*5 μm; mobile phase: [water (0.05% NH$_3$.H$_2$O+10 mM NH$_4$HCO$_3$)-ACN]; B %: 49%-79%, 10 min), followed by lyophilization to yield N-methyl-3-(1-methylimidazol-4-yl)-4-[[5-(trifluoromethoxy)-2-pyridyl]amino] benzenesulfonamide (43.95 mg, 102.83 μmol, 71.1% yield, 100.0% purity) as a white solid. $^1$H NMR (400 MHz, CDCl$_3$) δ ppm 11.97 (s, 1H), 8.78 (d, J=9.0 Hz, 1H), 8.23 (d, J=2.3 Hz, 1H), 7.99 (d, J=2.0 Hz, 1H), 7.69 (dd, J=2.3, 9.0 Hz, 1H), 7.56 (s, 1H), 7.47-7.42 (m, 1H), 7.36 (d, J=1.2 Hz, 1H), 6.93 (d, J=9.0 Hz, 1H), 4.34 (q, J=5.2 Hz, 1H), 3.80 (s, 3H), 2.67 (d, J=5.5 Hz, 3H); ES-LCMS m/z 428.1 [M+H]$^+$.

I-85

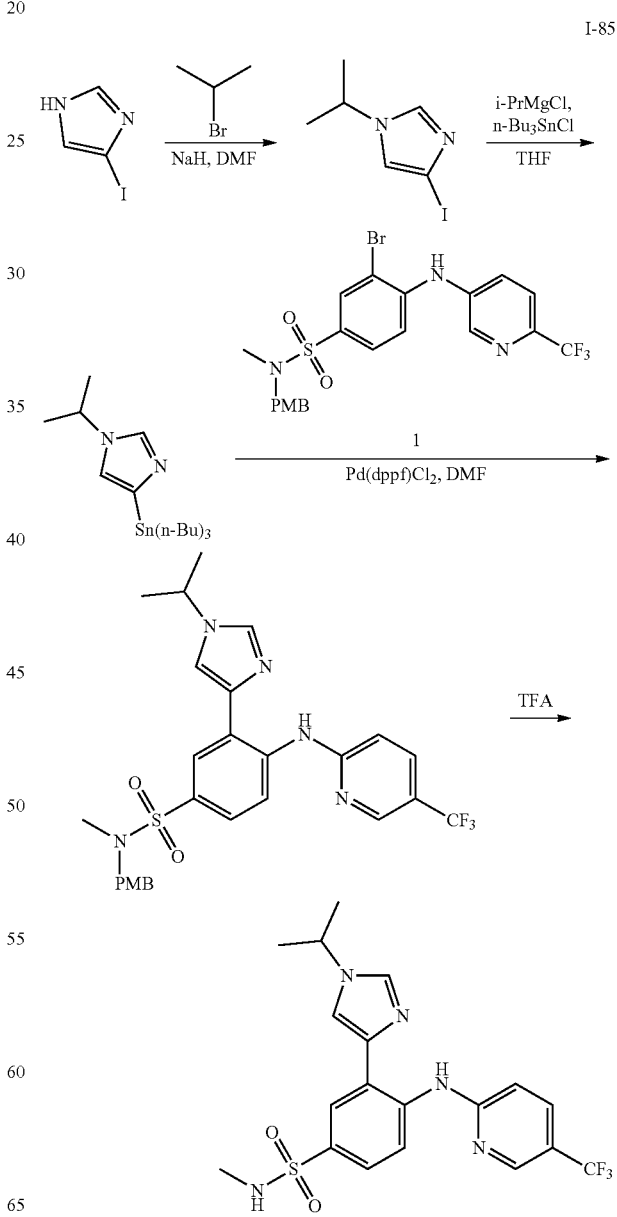

Step 1: 4-Iodo-1-isopropyl-imidazole

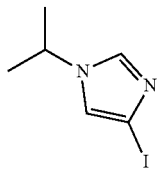

To a solution of 4-iodo-1H-imidazole (2 g, 10.31 mmol, 1 eq) in DMF (30 mL) was added NaH (494.87 mg, 12.37 mmol, 60%, 1.2 eq) at 0° C. After stirring for 0.5 h, 2-bromopropane (1.39 g, 11.34 mmol, 1.06 mL, 1.1 eq) was added. The mixture was stirred at 25° C. for 12 h. The reaction mixture was quenched by addition of water (50 mL), extracted with EtOAc (50 mL×3). The combined organic layers were washed with brine (30 mL), dried over Na$_2$SO$_4$, filtered and concentrated under reduced pressure to yield a residue which was purified by preparative HPLC (column: Phenomenex Genimi NX C18 150*40 mm*5 µm; mobile phase: [water (0.04% NH$_3$.H$_2$O+10 mM NH$_4$HCO$_3$)-ACN]; B %: 11%-41%, 10 min), followed by lyophilization to yield 4-iodo-1-isopropyl-imidazole (1.6 g, 6.77 mmol, 65.6% yield, 99.8% purity) as yellow oil. $^1$H NMR (500 MHz, CDCl$_3$) δ ppm 7.42 (s, 1H), 7.04 (s, 1H), 4.36-4.26 (m, 1H), 1.47 (s, 3H), 1.45 (s, 3H); ES-LCMS m/z 237.1 [M+H]$^+$.

Step 2: tert-Butyl tributyl-(1-isopropylimidazol-4-yl)stannane

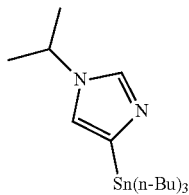

To a solution of 4-iodo-1-isopropyl-imidazole (200 mg, 845.74 µmol, 99.8%, 1 eq) in THF (15 mL) was added i-PrMgBr (2 M, 465.16 µL, 1.1 eq) at −10° C. under N$_2$ atmosphere. After being stirred at −10° C. for 1 h, tributyl (chloro)stannane (300.07 mg, 921.86 µmol, 247.99 µL, 1.09 eq) was added. The mixture was stirred at 20° C. for 1.5 h. The reaction mixture was quenched with aqueous KF (50 mL, 2M) and extracted with EtOAc (50 mL×3). The organic layer was washed with water (20 mL×2) and brine (30 mL), dried over Na$_2$SO$_4$, filtered and concentrated under reduced pressure to yield tributyl-(1-isopropylimidazol-4-yl)stannane (480 mg, 444.89 µmol, 52.6% yield, 37.0% purity) as colorless oil, which was used in the next step without further purification. $^1$H NMR (500 MHz, CDCl$_3$) δ ppm 7.53 (s, 1H), 7.05 (s, 1H), 4.35 (td, J=6.7, 13.4 Hz, 1H), 1.67-1.62 (m, 6H), 1.50 (d, J=6.7 Hz, 6H), 1.36 (d, J=7.3 Hz, 6H), 1.31 (d, J=7.8 Hz, 6H), 0.92-0.88 (m, 9H); ES-LCMS m/z 401.2 [M+H]$^+$.

Step 3: 3-(1-Isopropylimidazol-4-yl)-N-[(4-methoxyphenyl)methyl]-N-methyl-4-[[5-(trifluoromethyl)-2-pyridyl]amino]benzenesulfonamide

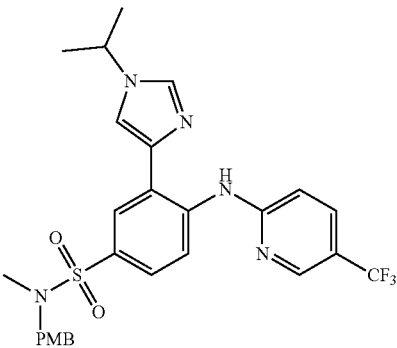

To a solution of 3-bromo-N-[(4-methoxyphenyl)methyl]-N-methyl-4-[[5-(trifluoromethyl)-2-pyridyl]amino]benzenesulfonamide (120 mg, 214.95 µmol, 95%, 1 eq) in DMF (10 mL) was added tributyl-(1-isopropylimidazol-4-yl)stannane (463.83 mg, 429.90 µmol, 37%, 2 eq) and Pd(dppf)Cl$_2$ (15.73 mg, 21.49 µmol, 0.1 eq) was degassed and purged with N$_2$ for 3 times. The mixture was stirred at 130° C. for 4 h. The reaction mixture was quenched by addition of water (50 mL) and extracted with EtOAc (30 mL×3). The combined organic layers were washed with brine (10 mL), dried over Na$_2$SO$_4$, filtered and concentrated under reduced pressure to yield a residue which was purified by flash silica gel chromatography (from PE/EtOAc=1/0 to 3/1, TLC: PE/EtOAc=3/1, R$_f$=0.49) to yield 3-(1-isopropylimidazol-4-yl)-N-[(4-methoxyphenyl)methyl]-N-methyl-4-[[5-(trifluoromethyl)-2-pyridyl]amino]benzenesulfonamide (100 mg, 53.54 µmol, 24.9% yield, 30.0% purity) as a white solid. $^1$H NMR (500 MHz, CDCl$_3$) δ ppm 12.28 (br s, 1H), 8.94 (d, J=8.9 Hz, 1H), 8.56-8.56 (m, 1H), 7.98 (d, J=2.1 Hz, 1H), 7.80 (d, J=2.4 Hz, 2H), 7.78 (d, J=2.3 Hz, 2H), 7.69 (br s, 1H), 7.43 (s, 1H), 6.96 (d, J=8.9 Hz, 1H), 6.89-6.89 (m, 1H), 6.87-6.87 (m, 1H), 4.45 (td, J=6.7, 13.4 Hz, 1H), 4.15 (s, 1H), 4.12 (s, 2H), 3.81 (s, 3H), 2.60 (s, 3H), 1.59 (d, J=6.7 Hz, 6H); ES-LCMS m/z 560.2 [M+H]$^+$.

Step 4: N-Isopropyl-3-(1-methylimidazol-4-yl)-4-[[4-(trifluoromethyl)-2-pyridyl]amino]benzenesulfonamide

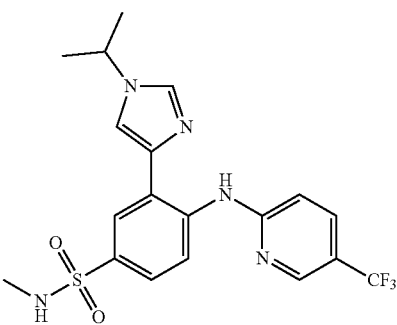 [SMILES: CNS(=O)(=O)c1ccc(Nc2ccc(C(F)(F)F)cn2)c(-c2cn(C(C)C)cn2)c1]

To a solution of 3-(1-isopropylimidazol-4-yl)-N-[(4-methoxyphenyl)methyl]-N-methyl-4-[[5-(trifluoromethyl)-

2-pyridyl]amino]benzenesulfonamide (300.00 mg, 160.61 µmol, 30.0%, 1 eq) in DCM (15 mL) was added TFA (1.54 g, 13.51 mmol, 1 mL, 84.09 eq). The mixture was stirred at 25° C. for 12 h. The reaction mixture was quenched by addition of water (50 mL) and extracted with EtOAc (30 mL×3). The combined organic layers were washed with brine (10 mL), dried over $Na_2SO_4$, filtered and concentrated under reduced pressure to yield a residue which was purified by preparative HPLC (column: Agela DuraShell C18 150*25 mm*5 µm; mobile phase: [water (0.05% $NH_3.H_2O$+ 10 mM $NH_4HCO_3$)-ACN]; B %: 55%-85%, 10 min), followed by lyophilization to yield 3-(1-isopropylimidazol-4-yl)-N-methyl-4-[[5-(trifluoromethyl)-2-pyridyl]amino] benzenesulfonamide (15.3 mg, 34.40 µmol, 21.4% yield, 98.8% purity) as a white solid. $^1$H NMR (500 MHz, $CDCl_3$) δ ppm 12.31 (s, 1H), 8.91 (d, J=8.9 Hz, 1H), 8.55 (s, 1H), 8.05 (d, J=1.8 Hz, 1H), 7.75-7.69 (m, 2H), 7.66 (s, 1H), 7.47 (d, J=0.8 Hz, 1H), 6.94 (d, J=8.7 Hz, 1H), 4.47-4.33 (m, 2H), 2.68 (d, J=5.5 Hz, 3H), 1.58 (d, J=6.6 Hz, 6H); ES-LCMS m/z 440.1 [M+H]$^+$.

I-86

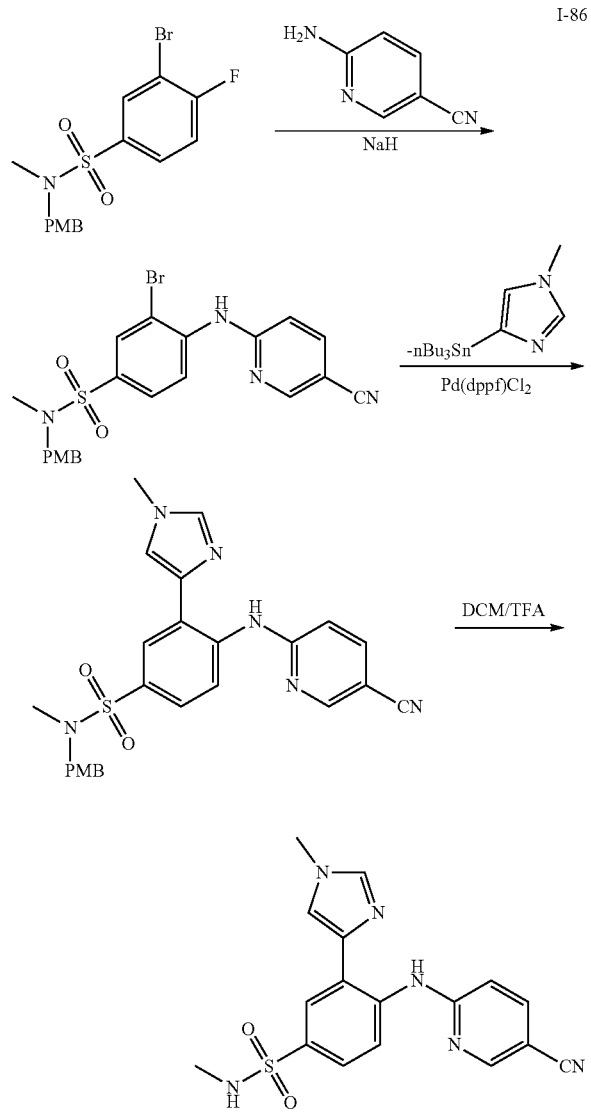

Step 1: 3-Bromo-4-[(5-cyano-2-pyridyl)amino]-N-[(4-methoxyphenyl)methyl]-N-methyl-benzenesulfonamide

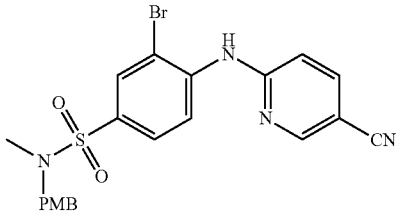

To a solution of 6-aminopyridine-3-carbonitrile (200 mg, 1.68 mmol, 1.37 eq) in DMF (10 mL) was added NaH (150 mg, 3.75 mmol, 60% purity, 3.07 eq). The mixture was stirred at 0° C. for 1 h. 3-Bromo-4-fluoro-N-[(4-methoxyphenyl)methyl]-N-methyl-benzenesulfonamide (500 mg, 1.22 mmol, 95% purity, 1 eq) was added into the mixture at 0° C. The mixture was stirred under $N_2$ atmosphere at 0° C. for 1 h and at 20° C. for 10 h. TLC (PE/EtOAc=3/1, $R_f$=0.47) showed the starting material was consumed completely. The reaction mixture was diluted with $H_2O$ (30 mL) and extracted with EtOAc (50 mL×3). The combined organic layers dried over $Na_2SO_4$, filtered and concentrated under reduced pressure to yield a residue which was purified by flash silica gel chromatography (from PE/EtOAc=100/1 to 3/1, TLC: PE/EtOAc=3/1, $R_f$=0.47) to yield 3-bromo-4-[(5-cyano-2-pyridyl)amino]-N-[(4-methoxyphenyl)methyl]-N-methyl-benzenesulfonamide (500 mg, 974.62 µmol, 79.7% yield, 95.0% purity) as a yellow solid. $^1$H NMR (400 MHz, $CDCl_3$) δ ppm 8.65-8.58 (m, 2H), 8.04 (d, J=2.0 Hz, 1H), 7.86-7.77 (m, 2H), 7.47 (s, 1H), 7.23 (d, J=8.6 Hz, 2H), 6.95 (d, J=8.6 Hz, 1H), 6.88 (d, J=8.8 Hz, 2H), 4.12 (s, 2H), 3.81 (s, 3H), 2.62 (s, 3H); ES-LCMS m/z 489.0 [M+H]$^+$.

Step 2: 4-[(5-Cyano-2-pyridyl)amino]-N-[(4-methoxyphenyl)methyl]-N-methyl-3-(1-methylimidazol-4-yl)benzenesulfonamide

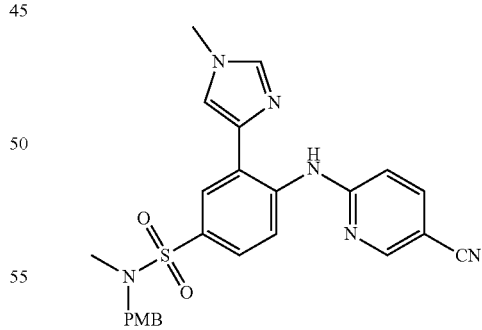

To a solution of 3-bromo-4-[(5-cyano-2-pyridyl)amino]-N-[(4-methoxyphenyl)methyl]-N-methyl-benzenesulfonamide (210 mg, 409.34 µmol, 95% purity, 1 eq) in DMF (2 mL) was added Pd(PPh$_3$)$_4$ (50 mg, 43.27 µmol, 1.06 e$^{-1}$ eq) and tributyl-(1-methylimidazol-4-yl)stannane (230 mg, 607.31 µmol, 98% purity, 1.48 eq). The mixture was stirred under $N_2$ atmosphere at 130° C. for 12 h. The reaction mixture was quenched with $H_2O$ (20 mL) and extracted with EtOAc (20 mL×3). The combined organic layers dried over Na₂SO₄, filtered and concentrated under reduced pressure to yield a residue which was purified by flash silica gel chromatography (from PE/EtOAc=100/1 to 1/2, TLC: PE/EtOAc=1/2, R_f=0.29) to yield 4-[(5-cyano-2-pyridyl)amino]-N-[(4-methoxyphenyl)methyl]-N-methyl-3-(1-methylimidazol-4-yl)benzenesulfonamide (150 mg, 307.02 μmol, 75.0% yield, 100.0% purity) as a white solid. ¹H NMR (400 MHz, CDCl₃) δ ppm 12.48 (s, 1H), 8.93 (d, J=8.8 Hz, 1H), 8.58 (d, J=2.0 Hz, 1H), 7.95 (d, J=2.2 Hz, 1H), 7.70 (dt, J=2.2, 8.7 Hz, 3H), 7.61-7.45 (m, 3H), 7.38 (s, 1H), 7.24 (d, J=8.6 Hz, 2H), 6.95-6.84 (m, 3H), 4.10 (s, 2H), 3.82 (s, 3H), 2.61-2.56 (m, 3H); ES-LCMS m/z 489.2 [M+H]⁺.

Step 3: 4-[(5-Cyano-2-pyridyl)amino]-N-methyl-3-(1-methylimidazol-4-yl)benzenesulfonamide

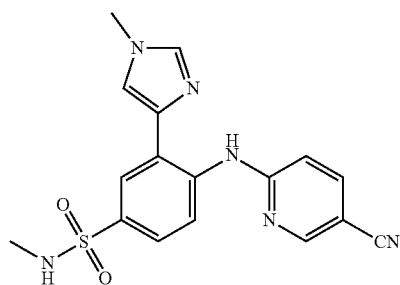 [SMILES: CNS(=O)(=O)c1ccc(Nc2ccc(C#N)cn2)c(-c2cn(C)cn2)c1]

To a solution of 4-[(5-cyano-2-pyridyl)amino]-N-[(4-methoxyphenyl)methyl]-N-methyl-3-(1-methylimidazol-4-yl)benzenesulfonamide (100 mg, 204.68 μmol, 100% purity, 1 eq) in DCM (3 mL) was added TFA (1.54 g, 13.51 mmol, 1 mL, 65.99 eq). The mixture was stirred at 20° C. for 12 h. The reaction mixture was concentrated under reduced pressure to yield a residue which was purified by preparative HPLC (column: Welch Xtimate C18 150×25 mm×5 um; mobile phase: [water (10 mM NH₄HCO₃)-ACN]; B %: 29%-59%, 10 min). The desired fraction was lyophilized to yield 4-[(5-cyano-2-pyridyl)amino]-N-methyl-3-(1-methylimidazol-4-yl)benzenesulfonamide (25.38 mg, 68.89 μmol, 33.7% yield, 100.0% purity) as a white solid. ¹H NMR (400 MHz, CDCl₃) δ ppm 12.47 (s, 1H), 8.89 (d, J=8.8 Hz, 1H), 8.57 (d, J=2.0 Hz, 1H), 8.01 (d, J=2.2 Hz, 1H), 7.75-7.69 (m, 2H), 7.57 (s, 1H), 7.39 (d, J=1.2 Hz, 1H), 6.91 (d, J=8.6 Hz, 1H), 4.26 (q, J=5.1 Hz, 1H), 3.82 (s, 3H), 2.69 (d, J=5.4 Hz, 3H; ES-LCMS m/z 369.2 [M+H]⁺.

I-87

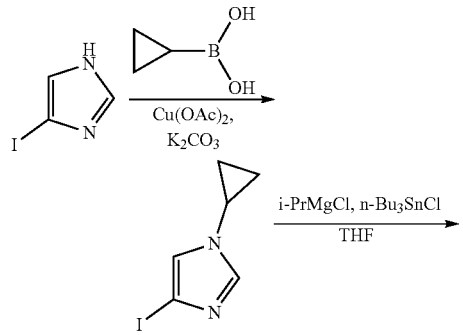

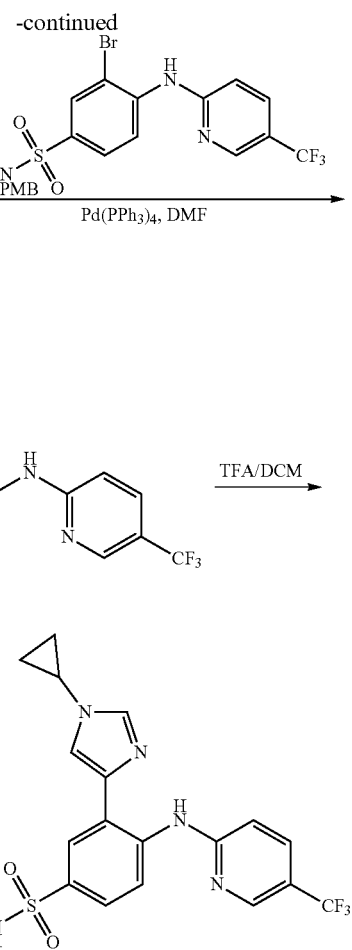

Step 1: 1-Cyclopropyl-4-iodo-imidazole

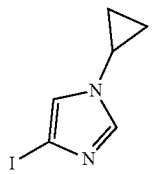

To a solution of 4-iodo-1H-imidazole (1.5 g, 7.73 mmol, 1 eq) in 1,2-dichloroethane (25 mL) was added 2-(2-pyridyl)pyridine (1.21 g, 7.73 mmol, 1 eq), Cu(OAc)₂ (1.40 g, 7.73 mmol, 1 eq), K₂CO₃ (2.14 g, 15.47 mmol, 2 eq) and cyclopropylboronic acid (1.13 g, 13.15 mmol, 1.7 eq). The mixture was stirred under N₂ atmosphere at 50° C. for 16 h. The reaction mixture was filtered through a pad of celite and the filtrate was concentrated to yield a residue which was purified by preparative HPLC column: Welch Xtimate C18 150*25 mm*5 μm; mobile phase: [water (10 mM NH₄HCO₃)-ACN]; B %: 16%-46%, 10 min) to yield 1-cyclopropyl-4-iodo-imidazole (600 mg, 1.03 mmol, 13.3% yield, 40.0% purity) as a yellow solid. ¹H NMR (400 MHz, DMSO-d₆) δ ppm 7.67 (d, J=1.0 Hz, 1H), 7.39 (d, J=1.2 Hz, 1H), 3.54-3.44 (m, 1H), 0.95-0.91 (m, 4H); ES-LCMS m/z 235.1 [M+H]⁺.

Step 2: Tributyl-(1-cyclopropylimidazol-4-yl)stannane

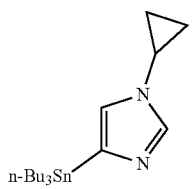

To a solution of 1-cyclopropyl-4-iodo-imidazole (300 mg, 512.74 μmol, 40% purity, 1 eq) in THF (10 mL) was added chloro(isopropyl)magnesium (2 M, 282.01 μL, 1.1 eq) dropwise under N₂ atmosphere at −10° C. The mixture was stirred under N₂ atmosphere at −10° C. for 1 h. Tributyl (chloro)stannane (183.59 mg, 564.01 μmol, 151.73 μL, 1.1 eq) was added under N₂ atmosphere at −10° C. The mixture was warmed to 15° C. slowly and stirred under N₂ atmosphere at 15° C. for 1.5 h. The reaction mixture was quenched with aqueous KF (50 mL, 2M) and extracted with EtOAc (30 mL×3). The organic layer was washed with water (20 mL×2) and brine (40 mL), dried over Na₂SO₄, filtered and concentrated under reduced pressure to yield tributyl-(1-cyclopropylimidazol-4-yl)stannane (100 mg, 251.77 μmol, 49.1% yield, N/A purity) as yellow oil. ¹H NMR (400 MHz, CDCl₃) δ ppm 8.06 (d, J=10.5 Hz, 1H), 7.75 (s, 1H), 7.55 (s, 1H), 3.35-3.30 (m, 2H), 3.01 (d, J=6.9, 13.9 Hz, 2H), 1.54-1.50 (m, 6H), 1.40-1.37 (m, 6H), 1.18-1.15 (m, 6H), 0.93 (d, J=2.0 Hz, 9H); ES-LCMS m/z 399.2 [M+H]⁺.

Step 3 3-(1-Cyclopropylimidazol-4-yl)-N-[(4-methoxyphenyl)methyl]-N-methyl-4-[[5-(trifluoromethyl)-2-pyridyl]amino]benzenesulfonamide

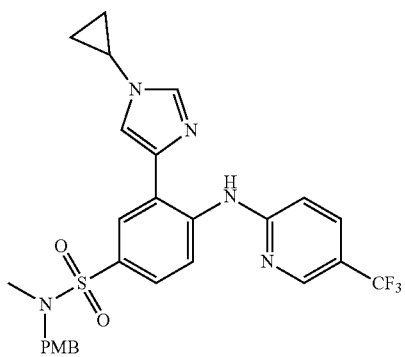

To a solution of tributyl-(1-cyclopropylimidazol-4-yl)stannane (100 mg, 251.77 μmol, 1 eq) and 3-bromo-N-[(4-methoxyphenyl)methyl]-N-methyl-4-[[5-(trifluoromethyl)-2-pyridyl]amino]benzenesulfonamide (136.53 mg, 251.77 μmol, 97.8% purity, 1 eq) in DMF (2 mL) was added Pd(dppf)Cl₂ (18.42 mg, 25.18 μmol, 0.1 eq). The mixture was stirred under N₂ atmosphere at 130° C. for 12 h. The reaction mixture was diluted with water (10 mL) and extracted with EtOAc (10 mL×3). The combined organic layers were dried over Na₂SO₄, filtered and the filtrate was concentrated to yield a residue which was purified by preparative TLC (PE/EtOAc=1/1, R_f=0.65) to yield 3-(1-cyclopropylimidazol-4-yl)-N-[(4-methoxyphenyl)methyl]-N-methyl-4-[[5-(trifluoromethyl)-2-pyridyl]amino]benzenesulfonamide (70 mg, 125.54 μmol, 49.9% yield) as yellow oil. ES-LCMS m/z 558.2 [M+H]⁺.

Step 4 3-(1-Cyclopropylimidazol-4-yl)-N-methyl-4-[[5-(trifluoromethyl)-2-pyridyl]amino]benzenesulfonamide

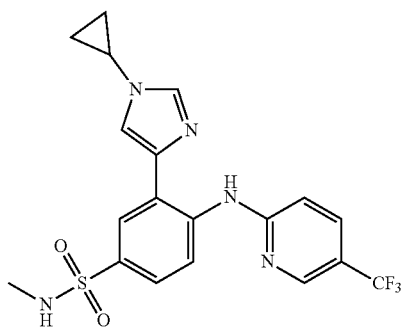 [SMILES: CNS(=O)(=O)c1ccc(Nc2ccc(C(F)(F)F)cn2)c(-c2cn(C3CC3)cn2)c1]

To a solution of 3-(1-cyclopropylimidazol-4-yl)-N-[(4-methoxyphenyl)methyl]-N-methyl-4-[[5-(trifluoromethyl)-2-pyridyl]amino]benzenesulfonamide (70 mg, 49.24 μmol, 39.22% purity, 1 eq) in DCM (3 mL) was added TFA (5.61 mg, 49.24 μmol, 3.65 μL, 1 eq). The mixture was stirred under N₂ atmosphere at 15° C. for 2 h. The reaction mixture was diluted with water (10 mL) and extracted with EtOAc (10 mL×3). The combined organic layers were dried over Na₂SO₄, filtered and the filtrate was concentrated to yield a residue which was purified by preparative HPLC (column: Welch Xtimate C18 150*25 mm*5 μm mobile phase: [water (10 mM NH₄HCO₃)-ACN]; B %: 48%-78%, 10 min) to yield 3-(1-cyclopropylimidazol-4-yl)-N-methyl-4-[[5-(trifluoromethyl)-2-pyridyl]amino]benzenesulfonamide (7.58 mg, 16.6 μmol, 33.8% yield, 96.0% purity) as a white solid. ¹H NMR (500 MHz, CDCl₃) δ ppm 12.14 (s, 1H), 8.87 (d, J=9.0 Hz, 1H), 8.54 (s, 1H), 8.00 (d, J=2.3 Hz, 1H), 7.75-7.68 (m, 3H), 7.47 (d, J=8.7 Hz, 1H), 6.96-6.92 (m, 1H), 4.29 (d, J=5.3 Hz, 1H), 3.50-3.43 (m, 1H), 2.68 (d, J=5.5 Hz, 3H), 1.14-1.10 (m, 2H), 1.10-1.06 (m, 2H); ES-LCMS m/z 438.2 [M+H]⁺.

I-88

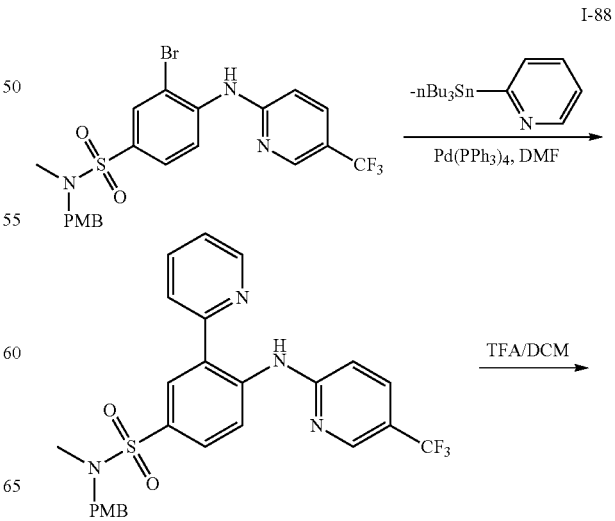

Step 2: N-Methyl-3-(2-pyridyl)-4-[[5-(trifluoromethyl)-2-pyridyl]amino]benzenesulfonamide

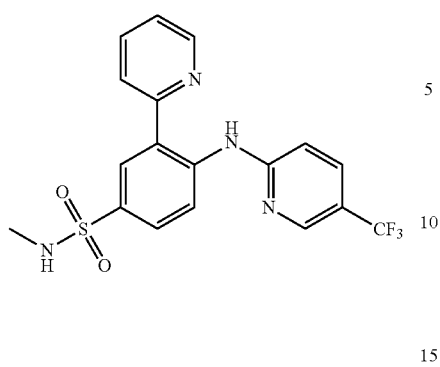

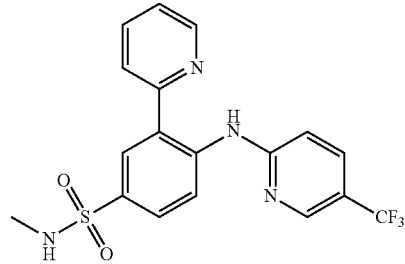

To a solution of N-[(4-methoxyphenyl)methyl]-N-methyl-3-(2-pyridyl)-4-[[5-(trifluoromethyl)-2-pyridyl]amino]benzenesulfonamide (140 mg, 261.67 μmol, 98.79% purity, 1 eq) in DCM (1.5 mL) was added TFA (770.00 mg, 6.75 mmol, 0.5 mL, 25.81 eq). The mixture was stirred under N₂ atmosphere at 15° C. for 2 h. The pH was adjusted to around 9 by progressively adding solid NaHCO₃. The reaction mixture was diluted with water (10 mL) and extracted with EtOAc (10 mL×3). The combined organic layers were dried over Na₂SO₄, filtered and the filtrate was concentrated to yield a residue which was purified by preparative HPLC (column: Welch Xtimate C18 150*25 mm*5 μm; mobile phase: [water (10 mM NH₄HCO₃)-ACN]; B %: 47%-77%, min) to yield N-methyl-3-(2-pyridyl)-4-[[5-(trifluoromethyl)-2-pyridyl]amino]benzenesulfonamide (21.54 mg, 52.74 μmol, 20.2% yield, 100.0% purity) as a white solid. $^1$H NMR (400 MHz, DMSO-d₆) δ ppm 11.71 (s, 1H), 8.80 (d, J=3.9 Hz, 1H), 8.56-8.50 (m, 2H), 8.13 (d, J=2.2 Hz, 1H), 8.04-7.98 (m, 1H), 7.97-7.88 (m, 2H), 7.79 (dd, J=2.1, 8.7 Hz, 1H), 7.49 (dd, J=5.0, 6.5 Hz, 1H), 7.40 (s, 1H), 7.15 (d, J=8.8 Hz, 1H), 2.45 (s, 3H); ES-LCMS m/z 409.2 [M+H]⁺.

Step 1: N-[(4-Methoxyphenyl)methyl]-N-methyl-3-(2-pyridyl)-4-[[5-(trifluoromethyl)-2-pyridyl]amino]benzenesulfonamide

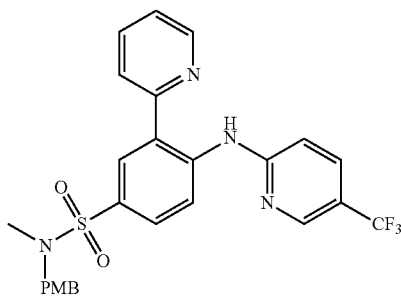

To a solution of 3-bromo-N-[(4-methoxyphenyl)methyl]-N-methyl-4-[[5-(trifluoromethyl)-2-pyridyl]amino]benzenesulfonamide (200 mg, 368.81 μmol, 97.8% purity, 1 eq) and tributyl(2-pyridyl)stannane (271.55 mg, 737.62 μmol, 2 eq) in DMF (2 mL) was added Pd(dppf)Cl₂ (26.99 mg, 36.88 umol, 0.1 eq). The mixture was stirred under N₂ atmosphere at 130° C. for 12 h. The reaction mixture was diluted with water (10 mL) and extracted with EtOAc (10 mL×3). The combined organic layers were dried over Na₂SO₄, filtered and the filtrate was concentrated to yield a residue which was purified by flash silica gel chromatography (from PE/EtOAc=100/1 to 2/1, TLC: PE/EtOAc=2/1, R$_f$=0.55) to yield N-[(4-methoxyphenyl)methyl]-N-methyl-3-(2-pyridyl)-4-[[5-(trifluoromethyl)-2-pyridyl]amino]benzenesulfonamide (140 mg, 261.67 μmol, 71.0% yield, 98.8% purity) as a white solid. $^1$H NMR (400 MHz, DMSO-d₆) δ ppm 11.94 (s, 1H), 8.81 (d, J=4.6 Hz, 1H), 8.66 (d, J=9.0 Hz, 1H), 8.57 (s, 1H), 8.11 (d, J=2.2 Hz, 1H), 8.03-7.96 (m, 3H), 7.87 (dd, J=2.1, 8.7 Hz, 1H), 7.53-7.48 (m, 1H), 7.25 (d, J=8.6 Hz, 2H), 7.20 (d, J=8.8 Hz, 1H), 6.92 (d, J=8.8 Hz, 2H), 4.12 (s, 2H), 3.73 (s, 3H), 2.56 (s, 3H); ES-LCMS m/z 529.2 [M+H]⁺.

I-89

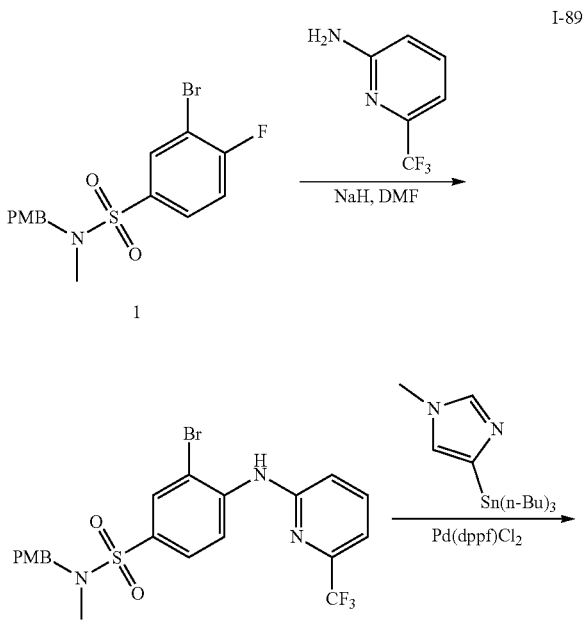

-continued

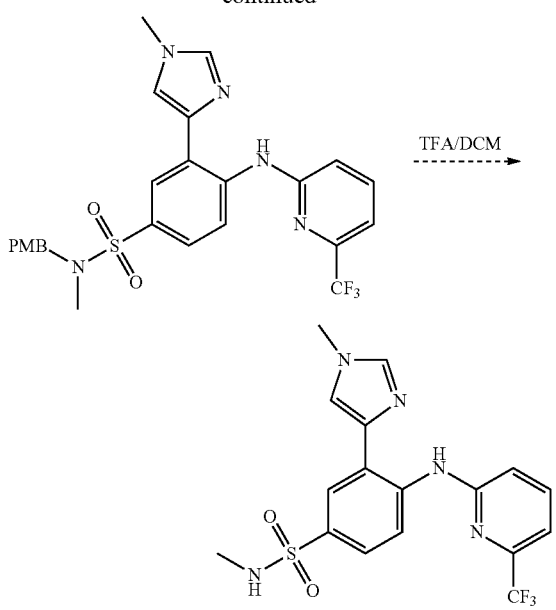

Step 1: 3-Bromo-N-[(4-methoxyphenyl)methyl]-N-methyl-4-[[6-(trifluoromethyl)-2-pyridyl]amino]benzenesulfonamide

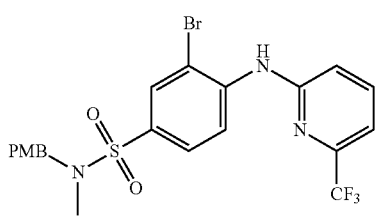

To a solution of 6-(trifluoromethyl)pyridin-2-amine (218.17 mg, 1.35 mmol, 1.1 eq) in DMF (15 mL) was added NaH (146.80 mg, 3.67 mmol, 60%, 3 eq). After being stirred for 30 min, 3-bromo-4-fluoro-N-[(4-methoxyphenyl)methyl]-N-methyl-benzenesulfonamide (500 mg, 1.22 mmol, 95%, 1 eq) was added at 0° C. The mixture was stirred under $N_2$ atmosphere at 20° C. for 12 h. The reaction mixture was quenched by addition of water (30 mL) and extracted with EtOAc (30 mL×3). The combined organic layers were washed with brine (10 mL), dried over $Na_2SO_4$, filtered and concentrated to yield a residue which was purified by preparative HPLC (column: Agela DuraShell C18 150*25 mm*5 μm; mobile phase: [water (0.05% $NH_3 \cdot H_2O$+10 mM $NH_4HCO_3$)-ACN]; B %: 62%-92%, 10 min), followed by lyophilization to yield 3-bromo-N-[(4-methoxyphenyl)methyl]-N-methyl-4-[[6-(trifluoromethyl)-2-pyridyl]amino]benzenesulfonamide (530 mg, 999.33 μmol, 81.6% yield, 100.0% purity) as a white solid. $^1H$ NMR (500 MHz, $CDCl_3$) δ ppm 8.74 (d, J=8.9 Hz, 1H), 8.04 (d, J=2.1 Hz, 1H), 7.82-7.77 (m, 2H), 7.41 (s, 1H), 7.32 (d, J=7.5 Hz, 1H), 7.26-7.25 (m, 1H), 7.24 (s, 1H), 7.08 (d, J=8.4 Hz, 1H), 6.90-6.86 (m, 2H), 4.12 (s, 2H), 3.82 (s, 3H), 2.62 (s, 3H); ES-LCMS m/z 530.1, 532.1 [M+H]⁺.

Step 2: N-[(4-Methoxyphenyl)methyl]-N-methyl-3-(1-methylimidazol-4-yl)-4-[[6-(trifluoromethyl)-2-pyridyl]amino]benzenesulfonamide

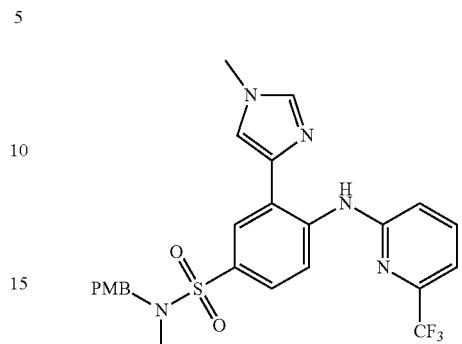

To a solution of 3-bromo-N-[(4-methoxyphenyl)methyl]-N-methyl-4-[[6-(trifluoromethyl)-2-pyridyl]amino]benzenesulfonamide (200 mg, 377.10 μmol, 100%, 1 eq), tributyl-(1-methylimidazol-4-yl)stannane (282.75 mg, 754.21 μmol, 99%, 2 eq) in DMF (10 mL) was added $Pd(dppf)Cl_2$ (27.59 mg, 37.71 μmol, 0.1 eq). The mixture was stirred under $N_2$ atmosphere at 130° C. for 12 h. The reaction mixture was quenched by addition of aqueous KF (50 mL, 2M) and extracted with EtOAc (50 mL×3). The combined organic layers were washed with brine (10 mL), dried over $Na_2SO_4$, filtered and concentrated to yield a residue which was purified by flash silica gel chromatography (from PE/EtOAc=1/0 to 1/1, TLC: PE/EtOAc=1/1, $R_f$=0.22) to yield N-[(4-methoxyphenyl)methyl]-N-methyl-3-(1-methylimidazol-4-yl)-4-[[6-(trifluoromethyl)-2-pyridyl]amino]benzenesulfonamide (190 mg, 357.45 μmol, 94.7% yield, 100.0% purity) as colorless oil. $^1H$ NMR (400 MHz, $CDCl_3$) δ ppm 12.12 (s, 1H), 9.04 (d, J=8.8 Hz, 1H), 7.93 (s, 1H), 7.75-7.64 (m, 2H), 7.60 (s, 1H), 7.36 (s, 1H), 7.26 (s, 1H), 7.24 (s, 1H), 7.17 (d, J=7.3 Hz, 1H), 7.06 (d, J=8.3 Hz, 1H), 6.87 (d, J=8.3 Hz, 2H), 4.10 (s, 2H), 3.82 (s, 3H), 3.80 (s, 3H), 2.59 (s, 3H); ES-LCMS m/z 532.2 [M+H]⁺.

Step 3: N-Methyl-3-(1-methylimidazol-4-yl)-4-[[6-(trifluoromethyl)-2-pyridyl]amino]benzenesulfonamide

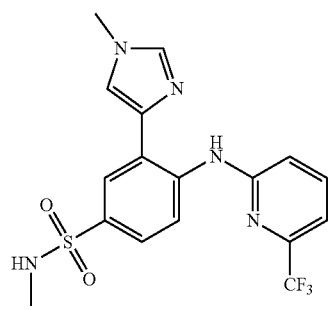 [SMILES: CNS(=O)(=O)c1ccc(Nc2cccc(C(F)(F)F)n2)c(-c2cn(C)cn2)c1]

To a solution of N-[(4-methoxyphenyl)methyl]-N-methyl-3-(1-methylimidazol-4-yl)-4-[[6-(trifluoromethyl)-2-pyridyl]amino]benzenesulfonamide (70 mg, 131.69 μmol, 100%, 1 eq) in DCM (3 mL) was added TFA (1.54 g, 13.51 mmol, 1 mL, 102.56 eq). The mixture was stirred at 20° C. for 12 h. The reaction mixture was concentrated, diluted with water (10 mL) and extracted with EtOAc (10 mL×3). The combined organic layers were washed with brine (10 mL), dried over $Na_2SO_4$, filtered and concentrated to yield a residue which was purified by preparative HPLC (column: Agela DuraShell C18 150*25 mm*5 µm; mobile phase: [water (0.05% $NH_3.H_2O$+10 mM $NH_4HCO_3$)-ACN]; B %: 46%-76%, 10 min), followed by lyophilization to yield N-methyl-3-(1-methylimidazol-4-yl)-4-[[6-(trifluoromethyl)-2-pyridyl]amino]benzenesulfonamide (48.44 mg, 115.51 µmol, 87.7% yield, 98.1% purity) as a white solid. $^1$H NMR (400 MHz, DMSO-$d_6$) δ ppm 12.30 (s, 1H), 8.70 (d, J=9.0 Hz, 1H), 8.02 (d, J=2.0 Hz, 1H), 7.95 (s, 1H), 7.93-7.89 (m, 1H), 7.88-7.86 (m, 1H), 7.58 (d, J=10.6 Hz, 1H), 7.34 (d, J=7.4 Hz, 1H), 7.26 (d, J=5.5 Hz, 1H), 7.21 (d, J=8.2 Hz, 1H), 3.78 (s, 3H), 2.43 (d, J=5.1 Hz, 3H); ES-LCMS m/z 412.2 $[M+H]^+$.

Example 2. TEAD Inhibition Assay

TEAD inhibition can be assayed using Hippo Pathway TEAD Reporter—MCF7 Cell Line (BPS Bioscience, Catalog #: 60618).

BACKGROUND

The Hippo pathway regulates cell proliferation and cell death. It is activated by high cell density and cell stress to stop cell proliferation and induce apoptosis. The mammalian Hippo pathway comprises MST kinases and LATS kinases. When the Hippo pathway is activated, MST kinases phosphorylate LATS kinases, which phosphorylate transcriptional co-activators YAP and TAZ. Unphosphorylated YAP and TAZ remain in nucleus and interact with TEAD/TEF transcriptional factors to turn on cell cycle-promoting gene transcription. However, when phosphorylated, YAP and TAZ are recruited from the nucleus to the cytosol, so that the YAP and TAZ-dependent gene transcription is turned off. Dysfunction of the Hippo pathway is frequently detected in human cancer and its down-regulation correlates with the aggressive properties of cancer cells and poor prognosis.
Description
The TEAD Reporter—MCF7 cell line contains the firefly luciferase gene under the control of TEAD responsive elements stably integrated into the human breast cancer cell line, MCF7. Inside the cells, basal unphosphorylated YAP/TAZ remains in the nucleus and induces the constitutive expression of luciferase reporter. The cell line is validated for the inhibition of the expression of luciferase reporter by the activators of the Hippo pathway.
Application
   Monitor Hippo pathway activity.
   Screen for activators or inhibitors of the Hippo pathway.
Format
   Each vial contains ~1.5×106 cells in 1 ml of 10% DMSO.
Storage
   Immediately upon receipt, store in liquid nitrogen.
General Culture Conditions
   Thaw Medium 1 (BPS Bioscience #60187)+10 µg/ml of Insulin (Sigma-Aldrich #I0516): MEM medium (Hyclone #SH30024.01) supplemented with 10% FBS (Invitrogen #26140-079), 1% non-essential amino acids (Hyclone #SH30238.01), 1 mM Na pyruvate (Hyclone #SH30239.01), 1% Penicillin/Streptomycin (Hyclone SV30010.01), plus 10 µg/ml of insulin (Sigma-Aldrich #I0516)
   Growth Medium 1B (BPS Bioscience #79531)+10 µg/ml of Insulin (Sigma-Aldrich #I0516): Thaw Medium 1 (BPS Cat. #60187)+10 µg/ml of insulin (Sigma-Aldrich #I0516), and 400 µg/ml of Geneticin (invitrogen #11811031).

Cells should be grown at 37° C. with 5% $CO_2$ using Growth Medium 1B with 10 µg/ml of Insulin. It may be necessary to adjust the percentage of $CO_2$ in the incubator depending on the $NaHCO_3$ level in the basal medium.

To thaw the cells, it is recommended to quickly thaw the frozen cells from liquid nitrogen in a 37° C. water-bath, transfer to a tube containing 10 ml of Thaw Medium 1+Insulin (no Geneticin), spin down cells, resuspend cells in pre-warmed Thaw Medium 1+Insulin (no Geneticin), transfer resuspended cells to a T25 flask and culture in a $CO_2$ incubator at 37° C. overnight. The next day, replace the medium with fresh Thaw Medium 1+Insulin (no Geneticin), and continue growing culture in a $CO_2$ incubator at 37° C. until the cells are ready to be split. At first passage, switch to Growth Medium 1B+10 µg/ml of Insulin (includes Thaw Medium 1, Insulin, and Geneticin). Cells should be split before they reach complete confluence.

To passage the cells, rinse cells with phosphate buffered saline (PBS), and detach cells from the culture vessel with 0.25% Trypsin/EDTA. Add Growth Medium 1B+10 µg/ml of Insulin (Includes Thaw Medium 1, Insulin, and Geneticin) and transfer to a tube, spin down the cells, then, resuspend cells and seed appropriate aliquots of cell suspension into new culture vessels. Subcultivation ration: 1:5 to 1:10 weekly.

To freeze down the cells, rinse cells with phosphate buffered saline (PBS), and detach cells from culture vessel with Trypsin/EDTA. Add Growth Medium 1B+10 µg/ml of Insulin (Includes Thaw Medium 1, Insulin, and Geneticin) and transfer to a tube, spin down cells, and resuspend in freezing medium (10% DMSO+90% FBS). Place at −80° C. overnight and place in liquid nitrogen the next day. Alternatively, vials may be placed directly in liquid nitrogen.
Functional Validation and Assay Performance The following assays are designed for 96-well format. To perform the assay in different tissue culture formats, the cell number and reagent volume should be scaled appropriately.
Materials Required but Not Supplied for Cell Culture
   Thaw Medium 1 (BPS Bioscience #60187)+10 µg/ml of insulin
   Growth Medium 1B (BPS Bioscience #79531)+10 µg/ml of insulin
   Insulin Solution from Bovine Pancreas (Sigma-Aldrich #: I0516)
Materials Required but Not Supplied for Cellular Assay
   $H_2O_2$: activator of Hippo pathway (activate MST kinases)
   Insulin
   Assay Medium: Thaw Medium 1 (BPS Cat. #60187)+10 µg/ml of insulin
   Insulin Solution from Bovine Pancreas (Sigma-Aldrich Cat #: 10516)
   Okadaic acid (BPS bioscience #27047): activator of Hippo pathway (activate MST kinases). Prepare 10 mM stock in DMSO.
   96-well tissue culture plate or 96-well tissue culture-treated white clear-bottom assay plate
   ONE-Step™ Luciferase Assay System (BPS, Cat. #60690)
   Luminometer
Mycoplasma Testing The cell line has been screened using the PCR-based VenorGeM Mycoplasma Detection kit (Sigma-Aldrich) to confirm the absence of Mycoplasma species.

Inhibition of TEAD Reporter Activity by Activator of Hippo Pathway in TEAD Reporter—MCF7 cells 1) Harvest TEAD Reporter—MCF7 cells from culture in growth medium and seed cells at a density of 35,000 cells per well into white clear-bottom 96-well microplate in 45 µl of assay medium.
2) Incubate cells at 37° C. in a $CO_2$ incubator for overnight.
3) Dilute the activators ($H_2O_2$ or okadaic acid) stock in assay medium. Add 5 µl of diluted activators to the wells. The final concentration of DMSO in assay medium is 0.1%.
4) Add 5 µl of assay medium with same concentration of DMSO without activator to control wells.
5) Add 50 µl of assay medium with DMSO to cell-free control wells (for determining background luminescence).
6) Set up each treatment in at least triplicate.
7) Incubate cells at 37° C. in a $CO_2$ incubator for 5-6 hours.
8) Perform luciferase assay using the ONE-Step™ Luciferase Assay System following the protocol provided: Add 100 µl of ONE-Step™ Luciferase reagent per well and rock at room temperature for ~15 minutes. Measure luminescence using a luminometer.
9) Data Analysis: Obtain the background-subtracted luminescence by subtracting the average background luminescence (cell-free control wells) from the luminescence reading of all wells.

Certain compounds were tested in TEAD reporter assay, and in H226 and H28. The data are listed in Table 2 below. A: EC50<0.1 uM; B: 0.1 uM≤EC50≤0.5 uM; C: EC50>0.5 uM.

TABLE 2

In vitro Data of Certain Exemplary Compounds.

| Compound | TEAD Reporter Assay EC50 (uM) | H226 EC50 (uM) | H28 EC50 (uM) |
|---|---|---|---|
| I-16 | B | C | C |
| I-17 | C | C | C |
| I-18 | | C | |
| I-19 | | C | |
| I-20 | | C | |
| I-21 | | C | |
| I-22 | C | C | |
| I-23 | C | C | |
| I-24 | C | C | |
| I-25 | C | | |
| I-26 | C | C | |
| I-27 | A | A | C |
| I-28 | C | C | |
| I-29 | C | C | |
| I-30 | A | A | |
| I-31 | A | A | |
| I-32 | A | A | |
| I-33 | A | A | |
| I-34 | C | C | |
| I-35 | B | B | |
| I-36 | A | A | |
| I-37 | A | A | |
| I-38 | A | A | |
| I-39 | C | C | |
| I-40 | C | C | |
| I-41 | B | A | |
| I-42 | C | B | |
| I-43 | C | C | |
| I-44 | C | B | |
| I-45 | B | B | |
| I-46 | C | B | |
| I-47 | B | B | |
| I-48 | C | B | |
| I-49 | C | B | |
| I-50 | B | B | |
| I-51 | A | A | |
| I-52 | C | C | |
| I-53 | C | C | |
| I-54 | A | A | |
| I-55 | B | A | |
| I-56 | B | B | |
| I-57 | C | C | |
| I-58 | C | C | |
| I-59 | A | A | |
| I-60 | B | B | |
| I-61 | C | B | |
| I-62 | B | B | |
| I-63 | B | B | |
| I-64 | B | B | |
| I-65 | A | A | |
| I-66 | C | B | |
| I-67 | A | A | |
| I-68 | A | A | |
| I-69 | B | A | |
| I-70 | B | A | |
| I-71 | B | B | |
| I-72 | A | B | |
| I-73 | C | B | |
| I-74 | A | A | |
| I-75 | A | A | |
| I-76 | C | B | |
| I-77 | C | B | |
| I-78 | A | A | |
| I-79 | B | A | |
| I-80 | A | A | |
| I-81 | A | A | |
| I-82 | A | A | |
| I-83 | B | A | |
| I-84 | A | A | |
| I-85 | A | A | |
| I-86 | C | B | |
| I-87 | A | | |

Example 3: Mouse Pharmacokinetics Study

Formulated compounds were administered intravenously or orally via gavage to BALB/c mice. Typically, at 0.167, 0.5, 1, 2, 4, 6, 12, and 24 hours post-dose, blood was collected and processed to plasma by centrifugation and stored at −80° C. until analysis. Internal standard was added to each sample prior to protein precipitation with acetonitrile or TCA. The precipitates were filtered through a filter plate and the samples were analyzed by LC/MS/MS. A standard curve was prepared in plasma from typically from 1.0 ng/mL to 3000 ng/mL and processed in the same manner as the samples. Sample analysis was typically performed on a suitable LC/MS/MS system fitted with an analytical UPLC column and compounds eluted from the analytical column with a gradient from 30-95% 0.1% formic acid (v/v) in ACN: 0.1% formic acid (v/v) in water. Mass spectrometric detection of test compound and the internal standard was performed by MRM in positive mode. The pharmacokinetics of each compound were analyzed by Phoenix WinNonlin software (Pharsight, St. Louis, Mo.) via noncompartmental analysis. Compounds in Table 3 were dosed in 50% DMS/95% PEG400 at 10 mg/kg by oral gavage with Cmax and $AUC_{0-last}$ summarized in Table 3.

TABLE 3

Summary of Cmax and AUC$_{0\text{-}last}$ Data

| | Cmax (ng/mL) | AUC 0-last (ng*h/mL) |
|---|---|---|
| P-14 | 210 | 622 |
| P-12 | 558 | 2333 |
| I-27 | 1037 | 2252 |
| I-30 | 882 | 887 |
| I-31 | 774 | 2519 |
| I-32 | 1088 | 4581 |
| I-33 | 420 | 731 |
| I-36 | 213 | 595 |
| I-37 | 351 | 521 |
| I-38 | 1621 | 25942 |

Example 4. CTGF Data Analysis

NU/NU nude female mice obtained from Charles River Laboratories and were subcutaneously injected with NCI-H226 (ATCC) human mesothelioma cells. Once tumors grew to an average size of 350-400 mm$^3$, mice were randomized into each treatment group. NCI-H226 tumor bearing mice were treated by oral gavage with Vehicle (5% DMSO/95% PEG 400) or a TEAD inhibitor for a total of 3 administrations. 4 hours post-third administration, mice were euthanized and tumors were collected for isolation of RNA for pharmacodynamic (PD) analysis.

RNA was extracted from the tumors utilizing the QIAZOL (Qiagen) lysis reagent, tissues were then homogenized for 10 minutes using TissueLyser II (Qiagen). Once sample disruption and digestion was complete, chloroform was added to each sample, the homogenate was separated into aqueous and organic phases by centrifugation.

RNA was then isolated from samples using the KingFisher Flex automated extraction system and MagMAX mirvana total RNA isolation kit. Manufacturer's recommended protocol for high-throughput isolation of RNA from tissue samples was followed for RNA extraction.

Expression of the YAP/TEAD-regulated gene, CCN2 that encodes CTFG (Connective Tissue Growth Factor), and the housekeeping gene, human glyceraldehyde 3-phosphate dehydrogenase (GAPDH), were quantified by qRT-PCR analysis using the TaqMan Gene Expression Master Mix and TaqMan probes. CTGF and GAPDH cycle threshold (Ct) values for tumor cDNA samples were determined, and CTGF expression was normalized to GAPDH as an internal control.

The relative CTGF mRNA expression levels for each treatment group from tumor tissues were normalized to the vehicle control group. For comparisons between vehicle control and TEAD inhibitor treatment groups, an independent sample t-test was used for statistical analysis.

Figure 2:
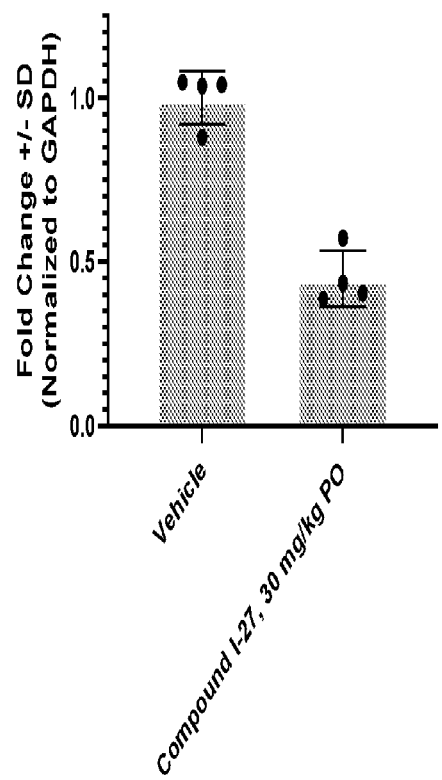
FIG. 2 depicts pharmacodynamic (PD) properties of compound I-27 using real-time PCR.

FIG. 2 depicts pharmacodynamic (PD) properties of compound I-27 using real-time PCR.

Example 5. Anti-Proliferation Assay

Individual cell lines were grown in medium according to supplier instructions and seeded into 96-well plates at a density that ensured logarithmic growth over 72 hours. TEAD inhibitor compounds were administered to cells at a top concentration of 10 μm and subsequently a 10 point 3-fold serial dilution was conducted. After 72 hours, proliferation was quantified using Cell TITERGLO™ (Promega, Inc.) and compared to vehicle control. IC50 and EC50 values were generated using XLFit curve fitting software.

Example 6. In Vivo Inhibition of Tumor Growth

NCI-11226 In Vivo Efficacy Studies 6-8 week old nu/nu nude mice (CRL) were inoculated subcutaneously with 5×10$^6$ NCI-H226 human mesothelioma tumor cells in the right flank. Tumor growth was monitored twice per week using vernier calipers and mean tumor volume (MTV) was calculated using the formula V=W2× L/2.

When the MTV reached approximately 150-200 mm$^3$, animals were randomized into treatment groups (n=8-10/group) and dosed per os (PO) on a once everyday (QD) schedule for 27-40 days with either Vehicle (5% DMSO+ 95% PEG 400) or TEAD inhibitors, such as compound I-27.

Randomization and treatments started on Day 0 and % Tumor Growth Inhibition was calculated on the last day of the study (when the control MTV reaches maximum allowable tumor volume), the following calculation was performed.

% TGI=100−[MTV treated/MTV control]×100

Tumor growth and body weight change were measured twice per week.

For comparisons between vehicle control and TEAD inhibitor treatment groups, an independent sample t-test was used for statistical analysis.

MSTO-211H In Vivo Efficacy Studies 6-8 week old SCID mice (CRL) were inoculated subcutaneously with 5×10$^6$ MSTO-211H human mesothelioma tumor cells in the right flank. Tumor growth was monitored twice per week using vernier calipers and mean tumor volume (MTV) was calculated using the formula V=W2× L/2.

When the MTV reached approximately 150-200 mm$^3$, animals were randomized into treatment groups (n=6-8/group) and dosed per os (PO) on a once everyday (QD) schedule for 22-25 days with either Vehicle (5% DMSO+ 95% PEG 400) or TEAD inhibitors, such as compound I-27.

Randomization and treatments started on Day 0 and % Tumor Growth Inhibition was calculated on the last day of the study (when the control MTV reaches maximum allowable tumor volume), the following calculation was performed.

% TGI=100−[MTV treated/MTV control]×100

Tumor growth and body weight change were measured twice per week.

For comparisons between vehicle control and TEAD inhibitor treatment groups, an independent sample t-test was used for statistical analysis.

Example 7. TEAD Selectivity Assays

The TEAD targeting selectivity profiles of the TEAD inhibitor compounds described herein can be determined by either or both of two exemplary assays provided herein designed to monitor the interaction of TEAD isoforms or variants, e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4), and YAP1 or TAZ. While co-immunoprecipitation techniques can be used to monitor protein-protein interactions, it is difficult to increase the throughput based on the basic methodology required. Accordingly, alternative but complementary assays are employed to monitor the interaction of the different TEAD isoforms or variants, e.g., human TEAD1 (UniProt KB ID P28347-1 (SEQ ID NO: 1)), human TEAD2 (UniProtKB ID Q15562 (SEQ ID NO: 2)), human TEAD3 (UniProtKB ID Q99594 (SEQ ID NO: 3)), and human TEAD4 (UniProtKB ID Q15561 (SEQ ID NO: 4), and YAP1 (or TAZ).

The first exemplary assay is an in vitro biochemical fluorescent polarization assay using recombinantly expressed and purified YAP-binding domains of individual TEAD isoforms and a fluorescently labeled peptide derived from the primary sequence of YAP1. (Bum-Erdene et al., Cell Chem Biol. 2019 Mar. 21; 26(3):378-389. e13, the contents of which are herein incorporated by reference in their entireties). Compounds are incubated with individual TEAD isoform proteins and the fluorescent peptide and potency is determined by quantifying the displacement of the peptide.

The second exemplary assay is a cell-based assay employing the split luciferase reporter system (Hall et al, ACS Chem. Biol. 2012, 7, 11, 1848-1857, the contents of which are herein incorporated by reference in their entireties). Briefly, the YAP-binding domain of each TEAD isoform is transiently co-expressed with the TEAD-binding domain or either YAP1 or TAZ in HEK293 cells and the proximity of the two chimeric gene fusion products is monitored by luciferase activity (Nouri et al. Cancers (Basel). 2019 Oct. 19; 11(10), the contents of which are herein incorporated by reference in their entireties). Compounds that interfere with the interaction of a TEAD isoform and YAP1 (or TAZ) decrease the resulting luciferase activity relative to vehicle treated controls. Similar in process to the fluorescent polarization assay, these chimeric gene fusions are recombinantly expressed in bacteria or insect cells and employed as an in vitro biochemical assay with a similar luciferase readout as the cell-based assay.

Example 8. Inhibition of Malignant Mesothelioma Tumor Cell Growth

The tumor cell growth inhibitory activity of the TEAD inhibitors described herein is evaluated in NCI-H2052 mesothelioma cell line harboring a NF2 mutation. This cell line is selected, in part, based on its mutational status and the ability of a siRNA directed against YAP, TAZ or TEAD1-TEAD4 to inhibit cell proliferation. The nuclear localization of YAP at confluence is also taken into account. 10,000 cells/well were plated in a 96-well black plate with clear flat bottom TC-Treated Imaging plate in regular medium with serum, which was replaced the day after with starvation medium containing 1% serum. After one day growth in the starvation medium, cells are incubated with TEAD inhibitor compounds. The starting concentration is 30 µM and serial dilutions in DMSO and medium are performed until 0.1 µM to achieve a final DMSO concentration of 0.5%. The cells are then allowed to grow for 3 days, and then, EdU (Invitrogen, Molecular Probe) is added in each well at a final concentration of 10 mM and the cells are returned to the incubator for an additional 24 h. The starvation medium is removed and 100 µl of PFA 4% containing Hoechst dye is added in each well to fix the cells. Plates are then incubated at room temperature for 15 min, washed twice with PBS, and the cells permeabilized by adding 100 µl per well of triton-100 containing 0.3% BSA. After 20 min, cells are washed with PBS and EdU detection is performed according to the instructions of the manufacturer. Image acquisition is performed, for example, using the ImageXpress Micro and analyzed using the MetaXpress software (Molecular Device).

While we have described a number of embodiments of this invention, it is apparent that our basic examples may be altered to provide other embodiments that utilize the compounds and methods of this invention. Therefore, it will be appreciated that the scope of this invention is to be defined by the application and appended claims rather than by the specific embodiments that have been represented by way of example.

What is claimed is:

1. A method for treating mesothelioma in a patient, comprising administering to the patient a compound of Formula I:

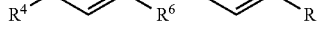

or a pharmaceutically acceptable salt thereof, wherein:
$L^1$ is —NH—CH$_2$— or —NH—C(O)—;
Ring A is phenyl, optionally substituted 1-2 times by halogen, —CN, —NO$_2$, or —C$_{1-6}$ aliphatic substituted 0-6 times by halogen, —CN, or —NO$_2$;
$R^2$ is an optionally substituted 5-membered heteroaryl ring having 2 nitrogen atoms;
$R^3$ is —H;
$R^4$ is halogen, —S(O)$_2$N(R)$_2$, —S(O)N(R)$_2$, or —C(O)N(R)$_2$;
$R^6$ is —H or —C$_{1-6}$ aliphatic substituted 0-6 times by halogen, —CN, or —NO$_2$; and
each R is independently —H or optionally substituted —C$_{1-6}$ aliphatic.

2. The method of claim 1, wherein $L^1$ is —NH—CH$_2$—.

3. The method of claim 1, wherein Ring A is phenyl, optionally substituted 1-2 times by —C$_{1-6}$ aliphatic substituted 0-6 times by halogen.

4. The method of claim 1, wherein $R^2$ is

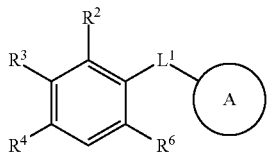

and R is unsubstituted —C$_{1-6}$ aliphatic.

5. The method of claim 1, wherein $R^1$ is —S(O)$_2$NHR.

6. The method of claim 1, wherein $R^6$ is —H.

7. The method of claim 1, wherein the compound is of Formulas (IXa-1), (IXa-2), (Xa-1), or (Xa-2):

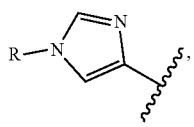

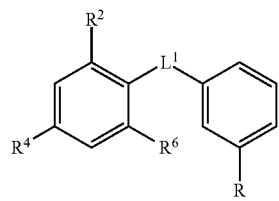

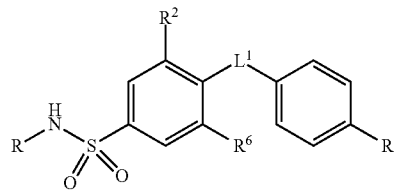

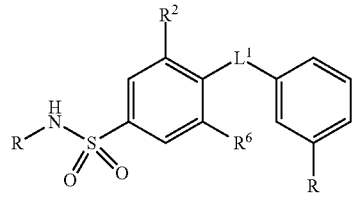

wherein $L^1$ is —NH—CH$_2$—, and each R is independently —H or —C$_{1-6}$ aliphatic substituted 0-6 times by halogen, —CN, or —NO$_2$.

8. The method of claim 1, wherein the compound is of Formula (XIa-1) or (XIa-2):

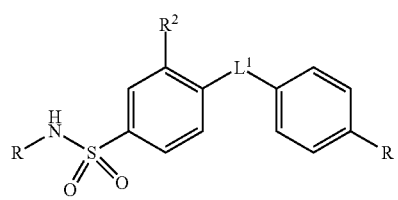

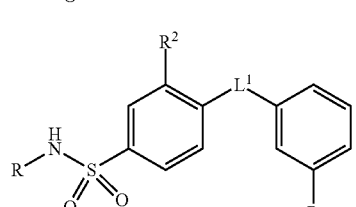

wherein $L^1$ is —NH—CH$_2$—, and each R is independently —H or —C$_{1-6}$ aliphatic substituted 0-6 times by halogen, —CN, or —NO$_2$.

9. The method of claim 1, wherein the compound is of Formula (XIIa-1) or (XIIa-2):

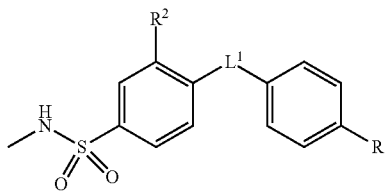
XIIa-1

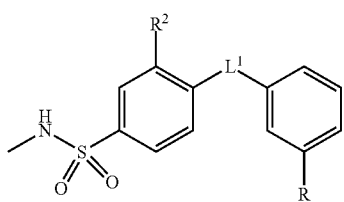
XIIa-2 wherein L¹ is —NH—CH₂—, and R is —C$_{1-3}$ aliphatic substituted 1, 2, 3, 4, 5, or 6 times by —F.

10. The method of claim 1, wherein the compound is of Formula (XIIIa-1) or (XIIIa-2):

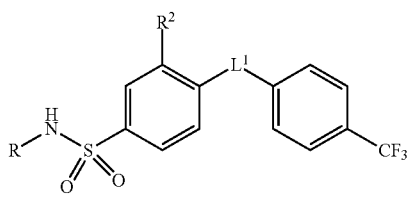
XIIIa-1

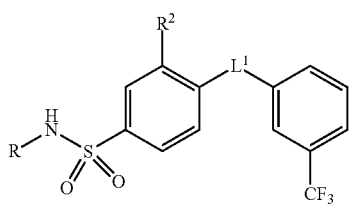
XIIIa-2 wherein L¹ is —NH—CH₂—, and R is optionally substituted —C$_{1-6}$ aliphatic.

11. The method of claim 1, wherein the compound is of Formula (XIVa-1) or (XIVa-2):

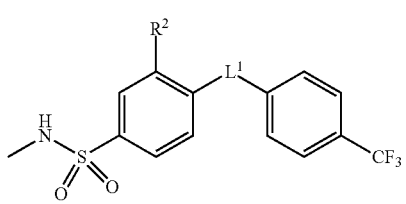
XIVa-1

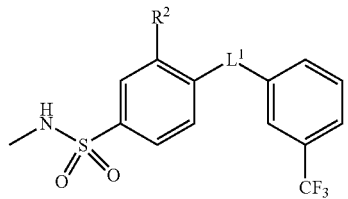
XIVa-2 wherein L¹ is —NH—CH₂—.

12. The method of claim 1, wherein the compound is of Formulas (XVa-1), or (XVa-2):

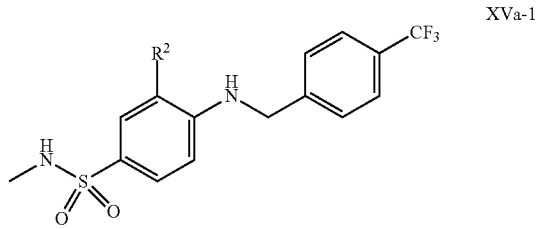
XVa-1

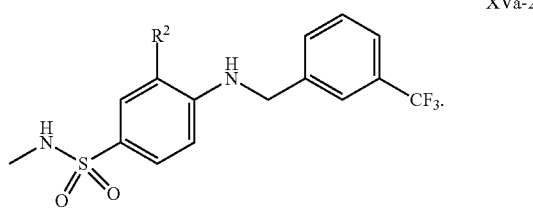
XVa-2

13. The method of claim 1, wherein the compound is of Formulas (XVIa-1), or (XVIa-2):

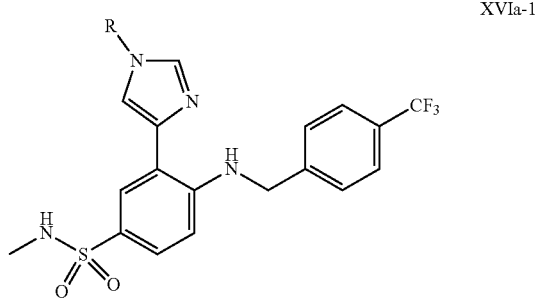
XVIa-1

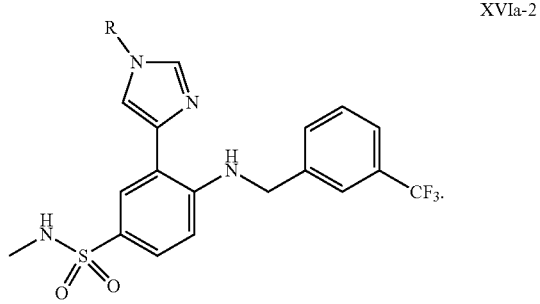
XVIa-2

14. The method of claim 1, wherein the compound is of Formula (II):
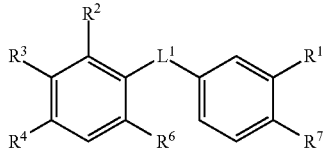
(II)
wherein $L^1$ is —NH—CH$_2$—, Ie is —H, -halogen, —CN, —NO$_2$, or —C$_{1-6}$ aliphatic, and $R^7$ is —H, -halogen, —CN, —NO$_2$, or —C1-6 aliphatic.
15. The method of claim 1, wherein $R^2$ is
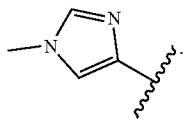
16. The method of claim 1, wherein $R^4$ is —S(O)$_2$NH—CH$_3$.
17. The method of claim 1, wherein the compound is selected from:
I-27
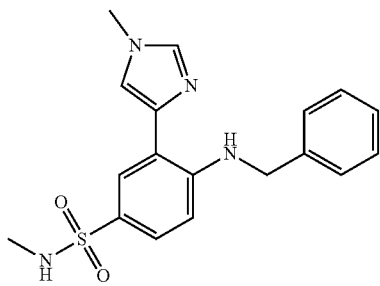
I-29
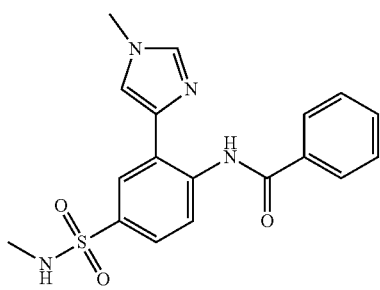
I-31
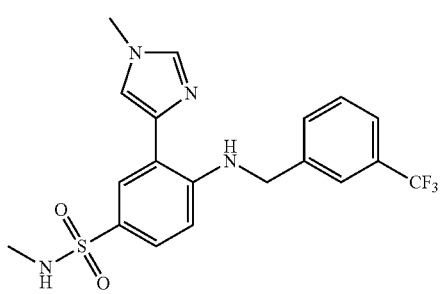
I-32
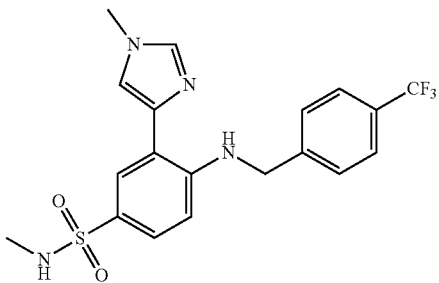
I-41
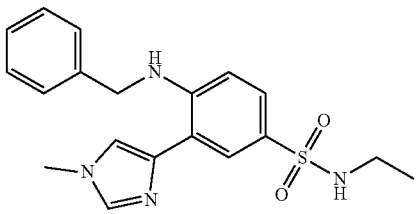
I-42
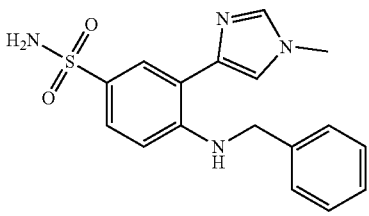
I-46
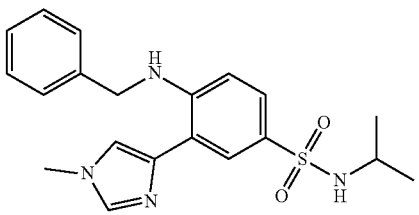
I-50
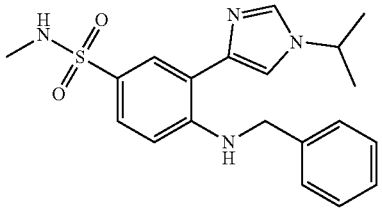
I-51

-continued

I-68

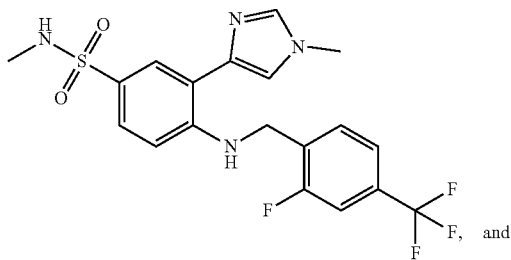

, and

I-74

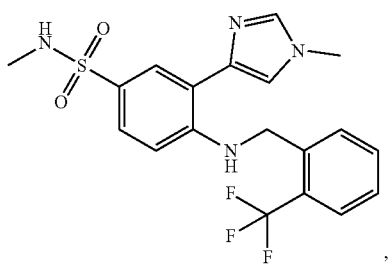

, or a pharmaceutically acceptable salt thereof.

18. The method of claim 1, wherein the compound is:

I-68

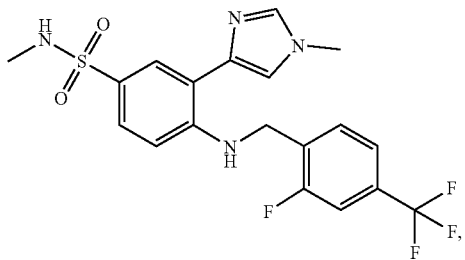

or a pharmaceutically acceptable salt thereof.

19. The method of claim 1, wherein the compound is:

I-31

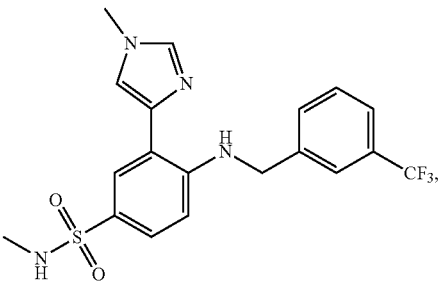

or a pharmaceutically acceptable salt thereof.

20. The method of claim 1, wherein the compound is:

I-32

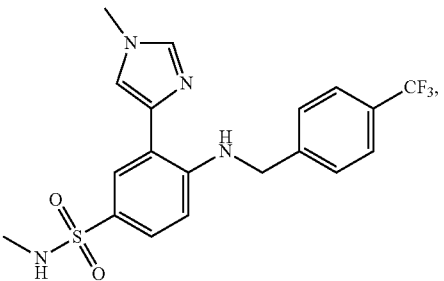

or a pharmaceutically acceptable salt thereof.

21. The method of claim 1, wherein the compound is:

I-74

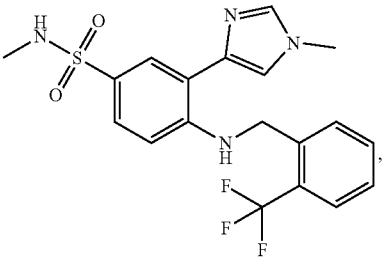

or a pharmaceutically acceptable salt thereof.

* * * * *